United States Patent
Ihori et al.

(10) Patent No.: US 10,111,437 B2
(45) Date of Patent: Oct. 30, 2018

(54) SUBSTITUTED GUANIDINES AS FUNGICIDES

(71) Applicant: Nippon Soda Co., Ltd., Chiyoda-ku, Tokyo (JP)

(72) Inventors: Yoichi Ihori, Odawara (JP); Shuuji Inoue, Odawara (JP); Kotaro Shibayama, Odawara (JP); Chang-Kyung Kang, Odawara (JP); Yasuyuki Shiinoki, Odawara (JP); Takuya Kamada, Odawara (JP); Hiroaki Naito, Odawara (JP); Satoshi Nishimura, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 15/576,425

(22) PCT Filed: Jun. 3, 2016

(86) PCT No.: PCT/JP2016/066603
§ 371 (c)(1),
(2) Date: Nov. 22, 2017

(87) PCT Pub. No.: WO2016/195077
PCT Pub. Date: Dec. 8, 2016

(65) Prior Publication Data
US 2018/0146677 A1 May 31, 2018

(30) Foreign Application Priority Data
Jun. 3, 2015 (JP) ................................. 2015-113376

(51) Int. Cl.
*A61K 31/155* (2006.01)
*C07C 291/00* (2006.01)
(Continued)

(52) U.S. Cl.
CPC ............. *A01N 47/40* (2013.01); *A01N 43/50* (2013.01); *A01N 43/52* (2013.01); *A01N 47/12* (2013.01); *A01N 47/28* (2013.01); *A01N 47/44* (2013.01); *A01N 51/00* (2013.01); *C07C 279/08* (2013.01); *C07C 279/12* (2013.01); *C07C 279/24* (2013.01); *C07C 335/02* (2013.01); *C07D 213/64* (2013.01); *C07D 213/78* (2013.01); *C07D 233/46* (2013.01); *C07D 233/48* (2013.01); *C07D 233/52* (2013.01); *C07D 233/88* (2013.01); *C07D 235/30* (2013.01); *C07D 237/14* (2013.01); *C07D 237/24* (2013.01); *C07D 239/06* (2013.01); *C07D 243/04* (2013.01); *C07D 277/28* (2013.01); *C07D 277/56* (2013.01);
(Continued)

(58) Field of Classification Search
CPC ........................... A61K 31/155; C07C 291/00
USPC .......................................... 514/638; 564/248
See application file for complete search history.

(56) References Cited

U.S. PATENT DOCUMENTS 3,113,151 A 12/1963 McKay et al.
3,468,898 A 9/1969 Cutler et al.
(Continued)

FOREIGN PATENT DOCUMENTS

EP 3305759 * 4/2018
WO WO 03/074476 A1 9/2003
(Continued)

OTHER PUBLICATIONS

J.ordan, V. C. Nature Reviews: Drug Discovery, 2, 2003, 205.*
(Continued)

*Primary Examiner* — Douglas M Willis
(74) *Attorney, Agent, or Firm* — Foley & Lardner LLP

(57) ABSTRACT

A novel guanidine compound having excellent fungicidal activity is represented by formula [I]. (In the formula, Y represents a divalent group represented by formula [II] (wherein each of $R^7$-$R^9$ independently represents a hydrogen atom or the like) or the like; each of X and Z independently represents an unsubstituted or substituted alkylene group or the like; each of $Q^1$ and $Q^2$ independently represents a single bond or the like; each of $A^1$ and $A^2$ independently represents an unsubstituted or substituted divalent heterocyclic compound residue or the like; and each of $R^1$-$R^6$ independently represents a hydrogen atom or the like.)

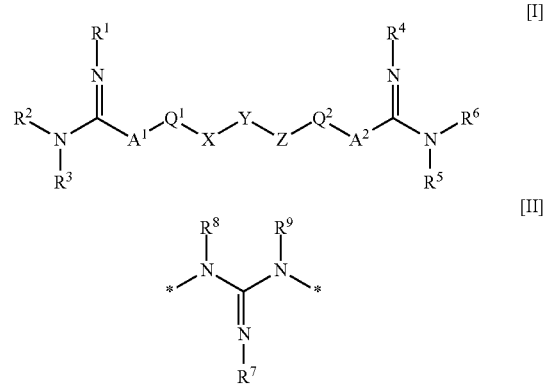

3 Claims, No Drawings

(51) Int. Cl.

| | | |
|---|---|---|
| *A01N 47/40* | (2006.01) | |
| *C07D 401/14* | (2006.01) | |
| *A01N 43/50* | (2006.01) | |
| *A01N 43/52* | (2006.01) | |
| *A01N 47/12* | (2006.01) | |
| *A01N 47/44* | (2006.01) | |
| *A01N 51/00* | (2006.01) | |
| *C07C 279/08* | (2006.01) | |
| *C07C 279/12* | (2006.01) | |
| *C07C 279/24* | (2006.01) | |
| *C07D 333/22* | (2006.01) | |
| *C07D 233/46* | (2006.01) | |
| *C07D 233/52* | (2006.01) | |
| *C07D 233/88* | (2006.01) | |
| *C07D 235/30* | (2006.01) | |
| *C07D 237/14* | (2006.01) | |
| *C07D 277/28* | (2006.01) | |
| *C07D 213/64* | (2006.01) | |
| *C07D 307/81* | (2006.01) | |
| *A01N 47/28* | (2006.01) | |
| *C07C 335/02* | (2006.01) | |
| *C07D 213/78* | (2006.01) | |
| *C07D 233/48* | (2006.01) | |
| *C07D 237/24* | (2006.01) | |
| *C07D 239/06* | (2006.01) | |
| *C07D 243/04* | (2006.01) | |
| *C07D 277/56* | (2006.01) | |
| *C07D 333/38* | (2006.01) | |
| *C07D 401/04* | (2006.01) | |
| *C07D 401/12* | (2006.01) | |
| *C07D 403/12* | (2006.01) | |
| *C07D 403/14* | (2006.01) | |
| *C07D 405/04* | (2006.01) | |

(52) U.S. Cl.
CPC ......... *C07D 307/81* (2013.01); *C07D 333/22* (2013.01); *C07D 333/38* (2013.01); *C07D 401/04* (2013.01); *C07D 401/12* (2013.01); *C07D 401/14* (2013.01); *C07D 403/12* (2013.01); *C07D 403/14* (2013.01); *C07D 405/04* (2013.01)

(56) References Cited

U.S. PATENT DOCUMENTS

| 4,694,086 A | 9/1987 | Morimoto et al. |
| 4,945,112 A | 7/1990 | Zipplies et al. |
| 5,116,838 A | 5/1992 | Ishikawa et al. |
| 5,242,948 A | 9/1993 | Mueller et al. |
| 2005/0113424 A1 | 5/2005 | Hayashi et al. |
| 2010/0016602 A1 | 1/2010 | Hayashi |

FOREIGN PATENT DOCUMENTS

| WO | WO 2006/011499 A1 | 2/2006 |
| WO | WO 2007/074868 A1 | 7/2007 |
| WO | WO 2008/029810 A1 | 3/2008 |
| WO | WO 2013/062024 A1 | 5/2013 |
| WO | WO 2015/087857 A1 | 6/2015 |

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface.*
International Search Report dated Jul. 19, 2016, in PCT/JP2016/066603.

* cited by examiner

SUBSTITUTED GUANIDINES AS FUNGICIDES

TECHNICAL FIELD

The present invention relates to a guanidine compound and a fungicide. More particularly, the present invention relates to a novel guanidine compound which has excellent fungicidal activity, is safe to use, and can be industrially advantageously synthesized, as well as a fungicide or a plant disease-controlling agent containing the guanidine compound as an active ingredient thereof.

CROSS-REFERENCE TO RELATED APPLICATIONS

The present invention is a National Stage application of PCT/JP2016/066603, filed Jun. 3, 2016, which claims priority on the basis of Japanese Patent Application No. 2015-113376 filed in Japan on Jun. 3, 2015, the contents of which are incorporated herein by reference.

BACKGROUND OF THE INVENTION

Patent Document 1, 2, 3, and 4 disclose that some arylamidine compounds have controlling effects against fungi or disease pathogens. In addition, fungicides or plant disease-controlling agents containing the arylamidine compounds as active ingredients thereof have been proposed.

DOCUMENTS OF RELATED ART

Patent Documents

Patent Document 1: WO 2013/062024 A1
Patent Document 2: WO 2006/011499 A1
Patent Document 3: WO 2007/074868 A1
Patent Document 4: WO 2003/074476 A1

SUMMARY OF THE INVENTION

Problems to be Solved by the Invention

The present invention aims to provide a novel guanidine compound which has excellent fungicidal activity, is safe to use, and can be industrially advantageously synthesized, as well as a fungicide or a plant disease-controlling agent containing the guanidine compounds as an active ingredient thereof.

Means to Solve the Problems

The present invention encompasses the following aspects.
[1] A compound represented by formula [I] or a salt thereof.

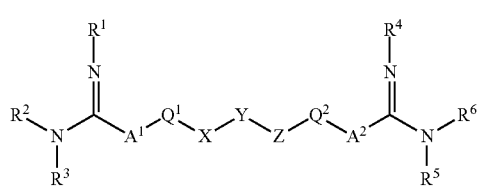

In the formula [I],
Y represents a divalent group represented by formula [II], [IIa], or [IIb].

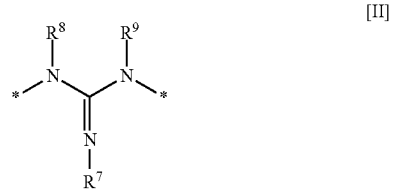

In the formula [II], $R^7$ to $R^9$ each independently represents a hydrogen atom, a nitro group, a cyano group, an unsubstituted or substituted hydrocarbon group, an unsubstituted or substituted heterocyclyl group, a hydroxyl group, an unsubstituted or substituted alkoxy group, an unsubstituted or substituted alkoxycarbonyl group, an unsubstituted or substituted aryloxy group, an unsubstituted or substituted amino group, an unsubstituted or substituted alkylsulfonyl group, an unsubstituted or substituted arylsulfonyl group, an unsubstituted or substituted heterocyclylsulfonyl group, an unsubstituted or substituted alkylcarbonyl group, an unsubstituted or substituted arylcarbonyl group, or an unsubstituted or substituted heterocyclylcarbonyl group. Both $R^8$ and $R^9$, both $R^7$ and $R^8$, or both $R^7$ and $R^9$ may be bonded together to form a divalent organic group. Both $R^8$ and a substituent on X may be bonded together to form a divalent organic group. * represents a binding site.

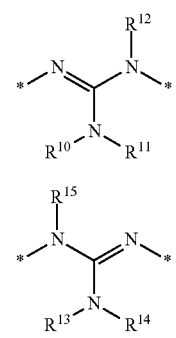

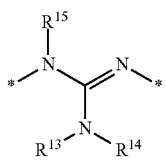

In the formula [IIa] and formula [IIb], $R^{10}$ to $R^{15}$ each independently represents a hydrogen atom, a nitro group, a cyano group, an unsubstituted or substituted hydrocarbon group, an unsubstituted or substituted heterocyclyl group, a hydroxyl group, an unsubstituted or substituted alkoxy group, an unsubstituted or substituted alkoxycarbonyl group, an unsubstituted or substituted aryloxy group, an unsubstituted or substituted amino group, an unsubstituted or substituted alkylsulfonyl group, an unsubstituted or substituted arylsulfonyl group, an unsubstituted or substituted heterocyclylsulfonyl group, an unsubstituted or substituted alkylcarbonyl group, an unsubstituted or substituted arylcarbonyl group, or an unsubstituted or substituted heterocyclylcarbonyl group. Both $R^{10}$ and $R^{11}$, both $R^{10}$ and $R^{12}$, both $R^{13}$ and $R^{14}$, or both $R^{14}$ and $R^{15}$ may be bonded together to form a divalent organic group. * represents a binding site.

X and Z each independently represents an unsubstituted or substituted alkylene group, an unsubstituted or substituted alkenylene group, an unsubstituted or substituted alkynylene group, -T$^a$-O-T$^b$-, -T$^a$-S-T$^b$-, or -T$^a$-N(R$^{21}$)-T$^b$-. T$^a$ and T$^b$ each independently represents a single bond or an unsubstituted or substituted alkylene group, R$^{21}$ represents a hydrogen atom, an unsubstituted or substituted hydrocarbon group, an unsubstituted or substituted heterocyclyl group, a hydroxyl group, an unsubstituted or substituted alkoxy group, an unsubstituted or substituted alkoxycarbonyl group, an unsubstituted or substituted aryloxy group, an unsubstituted or substituted amino group, an unsubstituted or substituted alkylsulfonyl group, an unsubstituted or substituted arylsulfonyl group, an unsubstituted or substituted heterocyclylsulfonyl group, an unsubstituted or substituted alkylcarbonyl group, an unsubstituted or substituted arylcarbonyl group, or an unsubstituted or substituted heterocyclylcarbonyl group.

Q$^1$ and Q$^2$ each independently represents a single bond, an unsubstituted or substituted phenylene group, —CH═CH—, —C≡C—, —O—, —S—, —SO—, —SO$_2$—, or —N(R$^{22}$)—. R$^{22}$ represents a hydrogen atom, an unsubstituted or substituted hydrocarbon group, an unsubstituted or substituted heterocyclyl group, a hydroxyl group, an unsubstituted or substituted alkoxy group, an unsubstituted or substituted alkoxycarbonyl group, an unsubstituted or substituted aryloxy group, an unsubstituted or substituted amino group, an unsubstituted or substituted alkylsulfonyl group, an unsubstituted or substituted arylsulfonyl group, an unsubstituted or substituted heterocyclylsulfonyl group, an unsubstituted or substituted alkylcarbonyl group, an unsubstituted or substituted arylcarbonyl group, or an unsubstituted or substituted heterocyclylcarbonyl group.

A$^1$ and A$^2$ each independently represents an unsubstituted or substituted divalent heterocyclic compound residue, an unsubstituted or substituted divalent aromatic hydrocarbon residue, or —N(R$^{23}$)—. R$^{23}$ represents a hydrogen atom, an unsubstituted or substituted hydrocarbon group, an unsubstituted or substituted heterocyclyl group, a hydroxyl group, an unsubstituted or substituted alkoxy group, an unsubstituted or substituted alkoxycarbonyl group, an unsubstituted or substituted aryloxy group, an unsubstituted or substituted amino group, an unsubstituted or substituted alkylsulfonyl group, an unsubstituted or substituted arylsulfonyl group, an unsubstituted or substituted heterocyclylsulfonyl group, an unsubstituted or substituted alkylcarbonyl group, an unsubstituted or substituted arylcarbonyl group, or an unsubstituted or substituted heterocyclylcarbonyl group.

R$^1$ to R$^6$ each independently represents a hydrogen atom, an unsubstituted or substituted hydrocarbon group, an unsubstituted or substituted heterocyclyl group, a hydroxyl group, an unsubstituted or substituted alkoxy group, an unsubstituted or substituted alkoxycarbonyl group, an unsubstituted or substituted aryloxy group, an unsubstituted or substituted amino group, an unsubstituted or substituted alkylsulfonyl group, an unsubstituted or substituted arylsulfonyl group, an unsubstituted or substituted heterocyclylsulfonyl group, an unsubstituted or substituted alkylcarbonyl group, an unsubstituted or substituted arylcarbonyl group, or an unsubstituted or substituted heterocyclylcarbonyl group. R$^1$ and R$^2$ may be bonded together to form a 4- to 8-membered ring with two nitrogen atoms binding therewith and a carbon atom binding with the two nitrogen atoms, R$^2$ and R$^3$ may be bonded together to form a 4- to 8-membered ring with a nitrogen atom binding therewith, R$^4$ and R$^5$ may be bonded together to form a 4- to 8-membered ring with two nitrogen atoms binding therewith and a carbon atom binding with the two nitrogen atoms, or R$^5$ and R$^6$ may be bonded together to form a 4- to 8-membered ring with a nitrogen atom binding therewith.

[2] The compound or the salt thereof according to [1], wherein Y in the formula [I]represents a divalent group represented by formula [II], and the divalent group represented by formula [II] represents a divalent group represented by formula [III].

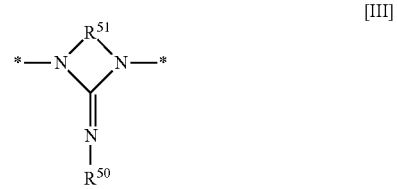

[III]

In the formula [III], R$^{51}$ represents an unsubstituted or substituted alkylene group, an unsubstituted or substituted alkenylene group, or an unsubstituted or substituted phenylene group. R$^{50}$ each independently represents a hydrogen atom, a nitro group, a cyano group, an unsubstituted or substituted hydrocarbon group, an unsubstituted or substituted heterocyclyl group, a hydroxyl group, an unsubstituted or substituted alkoxy group, an unsubstituted or substituted alkoxycarbonyl group, an unsubstituted or substituted aryloxy group, an unsubstituted or substituted amino group, an unsubstituted or substituted alkylsulfonyl group, an unsubstituted or substituted arylsulfonyl group, an unsubstituted or substituted heterocyclylsulfonyl group, an unsubstituted or substituted alkylcarbonyl group, an unsubstituted or substituted arylcarbonyl group, or an unsubstituted or substituted heterocyclylcarbonyl group. * represents a binding site.

[3] A fungicide containing at least one selected from the compound and the salt thereof according to [1] as an active ingredient thereof.

[4] A plant disease-controlling agent containing at least one selected from the compound and the salt thereof according to [1] as an active ingredient thereof.

Effects of the Invention

The guanidine compound (the compound of formula [I] or the salt thereof) according to the present invention has excellent fungicidal activity, is safe to use, and can be industrially advantageously synthesized. The fungicide or the plant disease-controlling agent containing the guanidine compound as an active ingredient thereof is particularly excellent in controlling plant diseases such as apple scab disease, cucumber gray mold disease, wheat powdery mildew disease, tomato late blight disease, or wheat leaf rust disease.

EMBODIMENTS FOR CARRYING OUT THE INVENTION

First, in the present invention, the term "unsubstituted" refers to a group consisting of a mother nucleus. In the case where only a name of a group serving as a mother nucleus is provided without being indicated with the term "substituted", this refers to "unsubstituted" unless specifically indicated otherwise.

On the other hand, the term "substituted" refers to any hydrogen atom of a group serving as a mother nucleus being substituted with a group having a structure that is the same as or different from the mother nucleus. Thus, a "substituent" is another group bound to a group serving as the mother nucleus. There may be one substituent or two or more substituents. Two or more substituents may be the same or different.

The term "C1-6", for example, indicates that the number of carbon atoms of the group serving as the mother nucleus is 1 to 6. The number of carbon atoms does not include the number of carbon atoms present in substituents. For example, a butyl group having an ethoxy group as a substituent thereof is classified as a C2 alkoxy C4 alkyl group.

There are no particular limitations on "substituents" provided that they are chemically available and achieve the effects of the present invention. Examples of groups that can be "substituents" include the following groups.

C1-6 alkyl groups such as a methyl group, an ethyl group, a n-propyl group, an i-propyl group, a n-butyl group, a s-butyl group, an i-butyl group, a t-butyl group, a n-pentyl group, and a n-hexyl group;

C2-6 alkenyl groups such as a vinyl group, a 1-propenyl group, a 2-propenyl group (allyl group), a 1-butenyl group, a 2-butenyl group, a 3-butenyl group, a 1-methyl-2-propenyl group, and a 2-methyl-2-propenyl group;

C2-6 alkynyl groups such as an ethynyl group, a 1-propynyl group, a 2-propynyl group, a 1-butynyl group, a 2-butynyl group, a 3-butynyl group, and a 1-methyl-2-propynyl group;

C3-8 cycloalkyl groups such as a cyclopropyl group, a cyclobutyl group, a cyclopentyl group, and a cyclohexyl group;

C4-8 cycloalkenyl groups such as a 2-cyclopentenyl group, a 3-cyclohexenyl group, and a 4-cyclooctenyl group;

C6-10 aryl groups such as a phenyl group and naphthyl group;

C7-11 aralkyl groups such as a benzyl group and a phenethyl group;

3- to 6-membered heterocyclyl groups;

C1-7 acyl groups such as a formyl group, an acetyl group, a propionyl group, a benzoyl group, and a cyclohexylcarbonyl group;

a hydroxyl group;

C1-6 alkoxy groups such as a methoxy group, an ethoxy group, a n-propoxy group, an i-propoxy group, a n-butoxy group, a s-butoxy group, an i-butoxy group, and a t-butoxy group;

C2-6 alkenyloxy groups such as a vinyloxy group, an allyloxy group, a propenyloxy group, and a butenyloxy group;

C2-6 alkynyloxy groups such as an ethynyloxy group and a propargyloxy group;

C6-10 aryloxy groups such as a phenoxy group and a naphthoxy group;

C7-11 aralkyloxy groups such as a benzyloxy group and a phenethyloxy group;

C1-7 acyloxy groups such as a formyloxy group, an acetyloxy group, a propionyloxy group, a benzoyloxy group, and a cyclohexylcarbonyloxy group;

C1-6 alkoxycarbonyl groups such as a methoxycarbonyl group, an ethoxycarbonyl group, a n-propoxycarbonyl group, an i-propoxycarbonyl group, a n-butoxycarbonyl group, and a t-butoxycarbonyl group;

C1-6 alkoxycarbonyloxy groups such as a methoxycarbonyloxy group, an ethoxycarbonyloxy group, a n-propoxycarbonyloxy group, an i-propoxycarbonyloxy group, a n-butoxycarbonyloxy group, and a t-butoxycarbonyloxy group;

a carboxyl group;

halogeno groups such as a fluoro group, a chloro group, a bromo group, and an iodo group;

C1-6 haloalkyl groups such as a chloromethyl group, a chloroethyl group, a trifluoromethyl group, a 1,2-dichloro-n-propyl group, 1-fluoro-n-butyl group, and a perfluoro-n-pentyl group;

C2-6 haloalkenyl groups such as a 2-chloro-1-propenyl group, and a 2-fluoro-1-butenyl group;

C2-6 haloalkynyl groups such as a 4,4-dichloro-1-butynyl group, a 4-fluoro-1-pentynyl group, and a 5-bromo-2-pentynyl group;

C6-10 haloaryl groups such as a 4-chlorophenyl group, a 4-fluorophenyl group, and a 2,4-dichlorophenyl group;

C1-6 haloalkoxy groups such as a trifluoromethoxy group, a 2-chloro-n-propoxy group, and a 2,3-dichlorobutoxy group;

C2-6 haloalkenyloxy groups such as a 2-chloropropenyloxy group and a 3-bromobutenyloxy group;

C6-10 haloaryloxy groups such as a 4-fluorophenyloxy group and a 4-chloro-1-naphthoxy group;

C1-7 haloacyl groups such as a chloroacetyl group, a trifluoroacetyl group, a trichloroacetyl group and a 4-chlorobenzoyl group;

an amino group (a group represented by $NH_2$);

C1-6 alkyl substituted-amino groups such as a methylamino group, a dimethylamino group and a diethylamino group;

C6-10 arylamino groups such as an anilino group and a naphthylamino group;

C7-11 aralkylamino groups such as a benzylamino group and a phenethylamino group;

C1-7 acylamino groups such as a formylamino group, an acetylamino group, a propanoylamino group, a butyrylamino group, an i-propylcarbonylamino group, and a benzoylamino group;

C1-6 alkoxycarbonylamino groups such as a methoxycarbonylamino group, an ethoxycarbonylamino group, a n-propoxycarbonylamino group, and an i-propoxycarbonylamino group;

unsubstituted or substituted aminocarbonyl groups such as an aminocarbonyl group, a dimethylaminocarbonyl group, a phenylaminocarbonyl group, and a N-phenyl-N-methylaminocarbonyl group;

imino C1-6 alkyl groups such as an iminomethyl group, a (1-imino)ethyl group, and a (1-imino)-n-propyl group;

an unsubstituted or substituted N-hydroxyimino C1-6 alkyl groups such as a N-hydroxy-iminomethyl group, a (1-(N-hydroxy)-imino)ethyl group, a (1-(N-hydroxy)-imino)propyl group, an N-methoxy-iminomethyl group, and a (1-(N-methoxy)-imino)ethyl group;

a mercapto group;

C1-6 alkylthio groups such as a methylthio group, an ethylthio group, a n-propylthio group, an i-propylthio group, a n-butylthio group, an i-butylthio group, a s-butylthio group, and a t-butylthio group;

C6-10 arylthio groups such as a phenylthio group and a naphthylthio group;

heteroarylthio groups such as a thiazolylthio group and a pyridylthio group;

C7-11 aralkylthio groups such as a benzylthio group and a phenethylthio group;

C1-6 alkylsulfinyl groups such as a methylsulfinyl group, an ethylsulfinyl group, and a t-butylsulfinyl group;

C6-10 arylsulfinyl groups such as a phenylsulfinyl group;

heteroarylsulfinyl groups such as a thiazolylsulfinyl group and a pyridylsulfinyl group;

C7-11 aralkylsulfinyl groups such as a benzylsulfinyl group and a phenethylsulfinyl group;

C1-6 alkylsulfonyl groups such as a methylsulfonyl group, an ethylsulfonyl group, and a t-butylsulfonyl group;

C6-10 arylsulfonyl groups such as a phenylsulfonyl group;

heteroarylsulfonyl groups such as a thiazolylsulfonyl group and a pyridylsulfonyl group;

C7-11 aralkylsulfonyl group such as a benzylsulfonyl group and a phenethylsulfonyl group;

an aminocarbonyloxy group;

C1-6 alkyl-substituted aminocarbonyloxy groups such as an ethylaminocarbonyloxy group and a dimethylaminocarbonyloxy group;

tri C1-6 alkyl-substituted silyl groups such as a trimethylsilyl group, a triethylsilyl group, and a t-butyldimethylsilyl group;

triaryl-substited silyl groups such as a triphenyl silyl group;

a cyano group; a nitro group; and an oxo group.

In addition, any hydrogen atoms in these "substituents" may also be substituted with other "substituents" having a different structure.

The "3- to 6-membered heterocyclyl group" contains as constituent atoms of its ring 1 to 4 heteroatoms selected from the group consisting of a nitrogen atom, an oxygen atom and sulfur atom. The heterocyclyl group may be monocyclic or polycyclic. As long as at least one of rings of a polycyclicheterocyclyl group is a hetero ring, the remaining rings may be saturated alicyclic rings, unsaturated alicyclic rings, or aromatic rings. Examples of the "3- to 6-membered heterocyclyl group" include: 3- to 6-membered saturated heterocyclyl groups, 5- to 6-membered heteroaryl groups, and 5- to 6-membered partially unsaturated heterocyclyl groups.

Examples of the 3- to 6-membered saturated heterocyclyl groups include an aziridinyl group, an epoxy group, a pyrrolidinyl group, a tetrahydrofuranyl group, a thiazolidinyl group, a piperidyl group, a piperazinyl group, a morpholinyl group, a dioxolanyl group, and a dioxanyl group.

Examples of 5-membered heteroaryl groups include a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, and a tetrazolyl group.

Examples of 6-membered heteroaryl groups include a pyridyl group, a pyrazinyl group, a pyrimidinyl group, a pyridazinyl group, and a triazinyl group.

A guanidine compound according to the present invention is a compound represented by formula [I] (which, hereinafter, may be abbreviated as compound [I]) or a salt thereof.

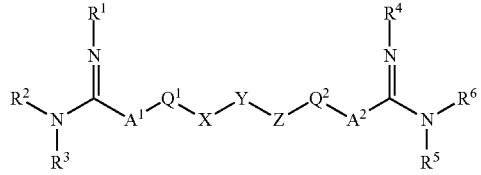

In the formula [I], Y represents a divalent group represented by formula [II], formula [IIa], or formula [IIb], and preferably represents a divalent group represented by formula [II].

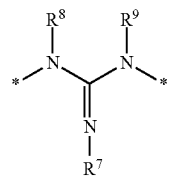

In the formula [II], $R^7$ to $R^9$ each independently represents a hydrogen atom, a nitro group, a cyano group, an unsubstituted or substituted hydrocarbon group, an unsubstituted or substituted heterocyclyl group, a hydroxyl group, an unsubstituted or substituted alkoxy group, an unsubstituted or substituted alkoxycarbonyl group, an unsubstituted or substituted aryloxy group, an unsubstituted or substituted amino group, an unsubstituted or substituted alkylsulfonyl group, an unsubstituted or substituted arylsulfonyl group, an unsubstituted or substituted heterocyclylsulfonyl group, an unsubstituted or substituted alkylcarbonyl group, an unsubstituted or substituted arylcarbonyl group, or an unsubstituted or substituted heterocyclylcarbonyl group.

In the formula [II], * represents a binding site.

The "hydrocarbon group" for $R^7$ to $R^9$ is a group formed by removing a hydrogen atom from a hydrocarbon compound. Examples of the hydrocarbon compound include: saturated hydrocarbon compounds such as a methane, an ethane, a propane, a butane, a pentane, a hexane, and a heptane; unsaturated hydrocarbon compounds such as an ethylene, an acetylene, and a propylene; alicyclic hydrocarbon compounds such as a cyclopentane, a cyclohexane, and a cyclohexene; and aromatic hydrocarbon compounds such as a benzene and a naphthalene. Among these, the "hydrocarbon group" is preferably a C1-6 alkyl group or a C6-10 aryl group, and more preferably a C1-6 alkyl group or a phenyl group.

The "heterocyclyl group" for $R^7$ to $R^9$ is a group formed by formed by removing a hydrogen atom from a heterocyclic compound. Examples of the heterocyclyl group include an aziridinyl group, an epoxy group, a pyrrolidinyl group, a tetrahydrofuranyl group, a thiazolidinyl group, a piperidyl group, a piperazinyl group, a morpholinyl group, a dioxolanyl group, a dioxanyl group; a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, a tetrazolyl group, a pyridyl group, a pyrazinyl group, a pyrimidinyl group, a pyridazinyl group, and a triazinyl group.

Examples of the "alkoxy group" for $R^7$ to $R^9$ include a methoxy group, an ethoxy group, a n-propoxy group, an i-propoxy group, a n-butoxy group, a s-butoxy group, an i-butoxy group, and a t-butoxy group, and a C1-6 alkoxy group is preferable.

Examples of the "alkoxycarbonyl group" for $R^7$ to $R^9$ include a methoxycarbonyl group, an ethoxycarbonyl group, a n-propoxycarbonyl group, an i-propoxycarbonyl group, a n-butoxycarbonyl group, a s-butoxycarbonyl group, an i-butoxycarbonyl group, and a t-butoxycarbonyl group, and a C1-6 alkoxycarbonyl group is preferable.

Examples of the "aryloxy group" for $R^7$ to $R^9$ include a phenoxy group and a naphthoxy group, and a phenoxy group is preferable.

Examples of the "unsubstituted or substituted amino group" for $R^7$ to $R^9$ include an amino group (represented by $NH_2$); C1-6 alkyl-substituted amino groups such as a methylamino group, a dimethylamino group, and a diethylamino group; C6-10 arylamino groups such as an anilino group and a naphthylamino group; C7-11 aralkylamino groups such as a benzylamino group and a phenethylamino group; C1-7 acylamino groups such as a formylamino group, an acetylamino group, a propanoylamino group, a butyrylamino group, an i-propylcarbonylamino group, and a benzoylamino group; C1-6 alkoxycarbonylamino groups such as a methoxycarbonylamino group, an ethoxycarbonylamino group, a n-propoxycarbonylamino group, and an i-propoxycarbonylamino group.

Examples of the "alkylsulfonyl group" for $R^7$ to $R^9$ include a methylsulfonyl group, an ethylsulfonyl group, a n-propylsulfonyl group, an i-propylsulfonyl group, a n-butylsulfonyl group, a s-butylsulfonyl group, an i-butylsulfonyl group, and a t-butylsulfonyl group, and a C1-6 alkylsulfonyl group is preferable.

Examples of the "arylsulfonyl group" for $R^7$ to $R^9$ include a phenylsulfonyl group and a naphthylsulfonyl group, and a phenylsulfonyl group is preferable.

Examples of the "heterocyclylsulfonyl group" for $R^7$ to $R^9$ include an aziridinylsulfonyl group, an epoxysulfonyl group, a pyrrolidinylsulfonyl group, a tetrahydrofuranylsulfonyl group, a thiazolidinylsulfonyl group, a piperidylsulfonyl group, a piperazinylsulfonyl group, a morpholinylsulfonyl group, a dioxolanylsulfonyl group, a dioxanylsulfonyl group; a pyrrolylsulfonyl group, a furylsulfonyl group, a thienylsulfonyl group, an imidazolylsulfonyl group, a pyrazolylsulfonyl group, an oxazolylsulfonyl group, an isoxazolylsulfonyl group, a thiazolylsulfonyl group, an isothiazolylsulfonyl group, a triazolylsulfonyl group, an oxadiazolylsulfonyl group, a thiadiazolylsulfonyl group, a tetrazolylsulfonyl group, a pyridylsulfonyl group, a pyrazinylsulfonyl group, a pyrimidinylsulfonyl group, a pyridazinylsulfonyl group, and a triazinylsulfonyl group.

Examples of the "alkylcarbonyl group" for $R^7$ to $R^9$ include a methylcarbonyl group, an ethylcarbonyl group, a n-propylcarbonyl group, an i-propylcarbonyl group, a n-butylcarbonyl group, a s-butylcarbonyl group, an i-butylcarbonyl group, and a t-butylcarbonyl group, and a C1-6 alkylcarbonyl group is preferable. As a substituent thereof, a halogeno group is preferable among the above-mentioned substituents.

Examples of the "arylcarbonyl group" for $R^7$ to $R^9$ include a phenylcarbonyl group and a naphthylcarbonyl group, and a phenylcarbonyl group is preferable.

Examples of the "heterocyclylcarbonyl group" for $R^7$ to $R^9$ include an aziridinylcarbonyl group, an epoxycarbonyl group, a pyrrolidinylcarbonyl group, a tetrahydrofuranylcarbonyl group, a thiazolidinylcarbonyl group, a piperidylcarbonyl group, a piperazinylcarbonyl group, a morpholinylcarbonyl group, a dioxolanylcarbonyl group, a dioxanylcarbonyl group; a pyrrolylcarbonyl group, a furylcarbonyl group, a thienylcarbonyl group, an imidazolylcarbonyl group, a pyrazolylcarbonyl group, an oxazolylcarbonyl group, an isoxazolylcarbonyl group, a thiazolylcarbonyl group, an isothiazolylcarbonyl group, a triazolylcarbonyl group, an oxadiazolylcarbonyl group, a thiadiazolylcarbonyl group, a tetrazolylcarbonyl group, a pyridylcarbonyl group, a pyrazinylcarbonyl group, a pyrimidinylcarbonyl group, a pyridazinylcarbonyl group, and a triazinylcarbonyl group.

Among these, it is preferable that $R^7$ to $R^9$ in formula [II] each independently represents a hydrogen atom, a nitro group, a cyano group, an unsubstituted or substituted hydrocarbon group, an unsubstituted or substituted alkoxycarbonyl group, or an unsubstituted or substituted alkylcarbonyl group.

In formula [II], $R^8$ and $R^9$, $R^7$ and $R^8$, or $R^7$ and $R^9$ may be bonded together to form a divalent organic group. In the case where $R^8$ and $R^9$ are bonded together to form a divalent organic group, examples thereof include a divalent organic group represented by formula [III].

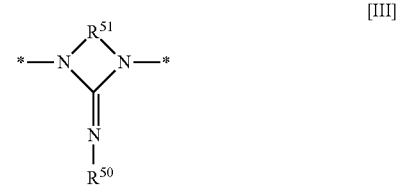

[III]

In the formula [III], $R^{51}$ represents an unsubstituted or substituted alkylene group, an unsubstituted or substituted alkenylene group, or an unsubstituted or substituted phenylene group.

Examples of the "alkylene group" for $R^{51}$ include a methylene group, an ethylene group, a propane-1,3-diyl group (another name: trimethylene group), a propane-1,2-diyl group (another name: propylene group), a butane-1,4-diyl group, a butane-1,3-diyl group, a butane-1,2-diyl group, a pentane-1,5-diyl group, a hexane-1,6-diyl group, a heptane-1,7-diyl group, and an octane-1,8-diyl group, and an ethylene group is preferable.

Examples of the "alkenylene group" for $R^{51}$ include an ethene-1,2-diyl group (—CH=CH—) group, a propenylene group and 2-butenylene group, and an ethene-1,2-diyl group is preferable.

Examples of the "phenylene group" for $R^{51}$ include a 1,2-phenylene group.

Preferable examples of a substituent on the "alkylene group" or "alkenylene group" for $R^{51}$ include a C1-6 alkyl group, a C6-10 aryl group, a hydroxyl group, a C1-6 alkoxy group, a C6-10 aryloxy group, a carboxyl group, a halogeno group, a C1-6 haloalkyl group, a C6-10 haloaryl group, a C1-6 haloalkoxy group, an amino group (represented by $NH_2$), a C1-6 alkyl-substituted amino group, a C6-10 arylamino group, a C1-7 acylamino group, a C1-6 alkylthio group, a C6-10 arylthio group, a heteroarylthio group, a C1-6 alkylsulfinyl group, a C1-6 alkylsulfonyl group, a C6-10 arylsulfonyl group, a heteroarylsulfonyl group, a cyano group, and an oxo group, and a C1-6 alkyl group or a C6-10 aryl group (phenyl group) is more preferable.

Examples of substituents on the "phenylene group" for $R^{51}$ include C1-6 alkyl groups, C3 to 8 cycloalkyl groups, C6-10 aryl groups, 3- to 6-membered heterocyclyl groups, a hydroxyl group, C1-6 alkoxy groups, C6-10 aryloxy groups, a carboxyl group, halogeno groups, C1-6 haloalkyl groups, C6-10 haloaryl groups, C1-6 haloalkoxy groups, an amino group (represented by $NH_2$), C1-6 alkyl-substituted amino group, C6-10 arylamino groups, C1-7 acylamino groups, C1-6 alkoxycarbonylamino groups, C1-6 alkyl thio groups, C6-10 arylthio groups, heteroarylthio groups, C7-11 aralkylthio groups, C1-6 alkylsulfinyl groups, C6-10 arylsulfinyl groups, heteroarylsulfinyl groups, C7-11 aralkyl sulfinyl groups, C1-6 alkylsulfonyl groups, C6-10 arylsulfonyl groups, heteroarylsulfonyl groups, a cyano group, and a nitro group.

In the formula [III], $R^{50}$ each independently represents a hydrogen atom, a nitro group, a cyano group, an unsubstituted or substituted hydrocarbon group, an unsubstituted or substituted heterocyclyl group, a hydroxyl group, an unsubstituted or substituted alkoxy group, an unsubstituted or substituted alkoxycarbonyl group, an unsubstituted or substituted aryloxy group, an unsubstituted or substituted amino group, an unsubstituted or substituted alkylsulfonyl group, an unsubstituted or substituted arylsulfonyl group, an unsubstituted or substituted heterocyclylsulfonyl group, an unsubstituted or substituted alkylcarbonyl group, an unsubstituted or substituted arylcarbonyl group, or an unsubstituted or substituted heterocyclylcarbonyl group.

Examples of the "hydrocarbon group", "heterocyclyl group", "alkoxy group", "alkoxycarbonyl group", "aryloxy group", "unsubstituted or substituted amino group", "alkylsulfonyl group", "arylsulfonyl group", "heterocyclylsulfonyl group", "alkylcarbonyl group", "arylcarbonyl group", or "heterocyclylcarbonyl group" for $R^{50}$ in formula [III] include the same groups as those exemplified for $R^7$ to $R^9$ in the formula [II]. Among these, $R^{50}$ preferably represents a hydrogen atom, a nitro group, or an unsubstituted or substituted alkylcarbonyl group, and more preferably represents a hydrogen atom, a nitro group, a C1-6 alkylcarbonyl group, or a C1-6 haloalkylcarbonyl group.

In the formula [III], * represents a binding site.

$R^8$ and a substituent on X may be bonded together to form a divalent organic group (such as a C1-3 alkylene group).

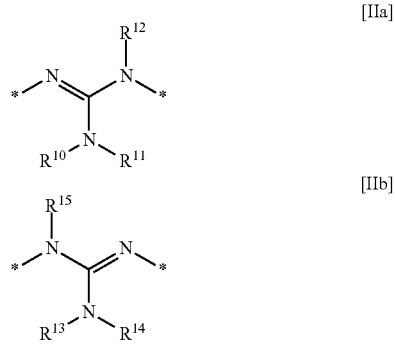

In the formula [IIa] and formula [IIb], $R^{10}$ to $R^{15}$ each independently represents a hydrogen atom, a nitro group, a cyano group, an unsubstituted or substituted hydrocarbon group, an unsubstituted or substituted heterocyclyl group, a hydroxyl group, an unsubstituted or substituted alkoxy group, an unsubstituted or substituted alkoxycarbonyl group, an unsubstituted or substituted aryloxy group, an unsubstituted or substituted amino group, an unsubstituted or substituted alkylsulfonyl group, an unsubstituted or substituted arylsulfonyl group, an unsubstituted or substituted heterocyclylsulfonyl group, an unsubstituted or substituted alkylcarbonyl group, an unsubstituted or substituted arylcarbonyl group, or an unsubstituted or substituted heterocyclylcarbonyl group.

In the formula [IIa] and formula [IIb], * represents a binding site.

The "hydrocarbon group" for $R^{10}$ to $R^{15}$ is a group formed by removing a hydrogen atom from a hydrocarbon compound. Examples of the hydrocarbon compound include: saturated hydrocarbon compounds such as methane, ethane, propane, butane, pentane, hexane, and heptane; unsaturated hydrocarbon compounds such as ethylene, acetylene, and propylene; alicyclic hydrocarbon compounds such as cyclopentane, cyclohexane, and cyclohexene; and aromatic hydrocarbon compounds such as benzene and naphthalene.

The "heterocyclyl group" for $R^{10}$ to $R^{15}$ is a group formed by removing a hydrogen atom from a heterocyclic compound. Examples of the heterocyclyl group include an aziridinyl group, an epoxy group, a pyrrolidinyl group, a tetrahydrofuranyl group, a thiazolidinyl group, a piperidyl group, a piperazinyl group, a morpholinyl group, a dioxolanyl group, a dioxanyl group; a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, a tetrazolyl group, a pyridyl group, a pyrazinyl group, a pyrimidinyl group, a pyridazinyl group, and a triazinyl group.

Examples of the "alkoxy group" for $R^{10}$ to $R^{15}$ include a methoxy group, an ethoxy group, a n-propoxy group, an i-propoxy group, a n-butoxy group, a s-butoxy group, an i-butoxy group, and a t-butoxy group.

Examples of the "alkoxycarbonyl group" for $R^{10}$ to $R^{15}$ include a methoxycarbonyl group, an ethoxycarbonyl group, n-propoxycarbonyl group, i-propoxycarbonyl group, n-butoxycarbonyl group, a s-butoxycarbonyl group, an i-butoxycarbonyl group, and a t-butoxycarbonyl group.

Examples of the "aryloxy group" for $R^{10}$ to $R^{15}$ include a phenoxy group and a naphthoxy group.

Examples of the "unsubstituted or substituted amino group" for $R^{10}$ to $R^{15}$ include: an amino group (represented by $NH_2$); C1-6 alkyl-substituted amino groups such as a methylamino group, a dimethylamino group, and a diethylamino group; C6-10 arylamino groups such as an anilino group and a naphthylamino group; C7-11 aralkyl amino groups such as a benzylamino group and a phenethylamino group; C1-7 acylamino groups such as a formylamino group, an acetylamino group, a propanoylamino group, a butyrylamino group, an i-propylcarbonylamino group, and a benzoylamino group; C1-6 alkoxycarbonylamino groups such as a methoxycarbonylamino group, an ethoxycarbonylamino group, a n-propoxycarbonylamino group, and an i-propoxycarbonylamino group.

Examples of the "alkylsulfonyl group" for $R^{10}$ to $R^{15}$ include a methylsulfonyl group, an ethylsulfonyl group, a n-propylsulfonyl group, an i-propylsulfonyl group, a n-butylsulfonyl group, a s-butylsulfonyl group, an i-butylsulfonyl group, and a t-butylsulfonyl group.

Examples of the "arylsulfonyl group" for $R^{10}$ to $R^{15}$ include a phenylsulfonyl group and a naphthylsulfonyl group.

Examples of the "heterocyclylsulfonyl group" for $R^{10}$ to $R^{15}$ include an aziridinylsulfonyl group, an epoxysulfonyl group, a pyrrolidinylsulfonyl group, a tetrahydrofuranylsulfonyl group, a thiazolidinylsulfonyl group, a piperidylsulfonyl group, a piperazinylsulfonyl group, a morpholinylsulfonyl group, a dioxolanylsulfonyl group, a dioxanylsulfonyl group; a pyrrolylsulfonyl group, a furylsulfonyl group, a thienylsulfonyl group, an imidazolylsulfonyl group, a pyrazolylsulfonyl group, an oxazolylsulfonyl group, an isoxazolylsulfonyl group, a thiazolylsulfonyl group, an isothiazolylsulfonyl group, a triazolylsulfonyl group, an oxadiazolylsulfonyl group, a thiadiazolylsulfonyl group, a tetrazolylsulfonyl group, a pyridylsulfonyl group, a pyrazinylsulfonyl group, a pyrimidinylsulfonyl group, a pyridazinyl sulfonyl group, and a triazinylsulfonyl group.

Examples of the "alkylcarbonyl group" for $R^{10}$ to $R^{15}$ include a methylcarbonyl group, an ethylcarbonyl group, a n-propylcarbonyl group, an i-propylcarbonyl group, a n-butylcarbonyl group, a s-butylcarbonyl group, an i-butylcarbonyl group, and a t-butylcarbonyl group.

Examples of the "arylcarbonyl group" for $R^{10}$ to $R^{15}$ include a phenylcarbonyl group and a naphthylcarbonyl group.

Examples of the "heterocyclylcarbonyl group" for $R^{10}$ to $R^{15}$ include an aziridinylcarbonyl group, an epoxycarbonyl group, a pyrrolidinylcarbonyl group, a tetrahydrofuranylcarbonyl group, a thiazolidinylcarbonyl group, a piperidylcarbonyl group, a piperazinylcarbonyl group, a morpholinylcarbonyl group, a dioxolanylcarbonyl group, a dioxanylcarbonyl group; a pyrrolylcarbonyl group, a furylcarbonyl group, a thienylcarbonyl group, an imidazolylcarbonyl group, a pyrazolylcarbonyl group, an oxazolylcarbonyl group, an isoxazolylcarbonyl group, a thiazolylcarbonyl group, an isothiazolylcarbonyl group, a triazolylcarbonyl group, an oxadiazolylcarbonyl group, a thiadiazolylcarbonyl group, a tetrazolylcarbonyl group, a pyridylcarbonyl group, a pyrazinylcarbonyl group, a pyrimidinylcarbonyl group, a pyridazinylcarbonyl group, and a triazinylcarbonyl group.

In the formula [IIa] and formula [IIb], both $R^{10}$ and $R^{11}$, both $R^{10}$ and $R^{12}$, both $R^{13}$ and $R^{14}$, or both $R^{14}$ and $R^{15}$ may be bonded together to form a divalent organic group.

Among these, it is preferable that $R^{10}$ to $R^{15}$ each independently represents a hydrogen atom, a C1-6 alkyl group, or a phenyl group.

In the formula [I], X and Z each independently represents an unsubstituted or substituted alkylene group, an unsubstituted or substituted alkenylene group, an unsubstituted or substituted alkynylene group, $-T^a-O-T^b-$, $-T^a-S-T^b-$, or $-T^a-N(R^{21})-T^b-$. $T^a$ and $T^b$ each independently represents a single bond or an unsubstituted or substituted alkylene group, and $R^{21}$ represents a hydrogen atom, an unsubstituted or substituted hydrocarbon group, an unsubstituted or substituted heterocyclyl group, a hydroxyl group, an unsubstituted or substituted alkoxy group, an unsubstituted or substituted alkoxycarbonyl group, an unsubstituted or substituted aryloxy group, an unsubstituted or substituted amino group, an unsubstituted or substituted alkylsulfonyl group, an unsubstituted or substituted arylsulfonyl group, an unsubstituted or substituted heterocyclylsulfonyl group, an unsubstituted or substituted alkylcarbonyl group, an unsubstituted or substituted arylcarbonyl group or an unsubstituted or substituted heterocyclylcarbonyl group.

Examples of the "hydrocarbon group", "heterocyclyl group", "alkoxy group", "alkoxycarbonyl group", "aryloxy group", "unsubstituted or substituted amino group", "alkylsulfonyl group", "arylsulfonyl group", "heterocyclylsulfonyl group", "alkylcarbonyl group", "arylcarbonyl group", or "heterocyclylcarbonyl group" for $R^{21}$ include the same groups as those exemplified for $R^7$ to $R^9$ in the formula [II].

Examples of the "alkylene group" for X and Z include the same groups as those exemplified for $R^{51}$ in the formula [III] and a C1-10 alkylene group is preferable.

Examples of the "alkenylene group" for X and Z include the same groups as those exemplified for $R^{51}$ in the formula [III].

Examples of the "alkynylene group" for X and Z include an ethynylene group and a 2-butynylene group.

Examples fo a substituent on the "alkylene group", "alkenylene group", or "alkynylene group" for X or Z include C1-6 alkyl groups, C6-10 aryl groups, a hydroxyl group, C1-6 alkoxy groups, C6-10 aryloxy groups, a carboxyl group, halogeno groups, C1-6 haloalkyl groups, C6-10 haloaryl groups, C1-6 haloalkoxy groups, an amino group (represented by $NH_2$), C1-6 alkyl-substituted amino groups, C6-10 arylamino groups, C1-7 acylamino groups, C1-6 alkylthio groups, C6-10 arylthio groups, heteroarylthio groups, C1-6 alkylsulfinyl groups, C1-6 alkylsulfinyl groups, C6-10 arylsulfonyl groups, heteroarylsulfonyl groups, a cyano group, and an oxo group.

Among these, it is preferable that X and Y each independently represents an unsubstituted or substituted alkylene group or $-T^a-O-T^b-$ (wherein $T^a$ and $T^b$ each independently represents a single bond or an unsubstituted or substituted C1-6 alkylene group).

In the formula [I], $Q^1$ and $Q^2$ each independently represents a single bond, an unsubstituted or substituted phenylene group, an ethene-1,2-diyl group (—CH=CH—), an ethyne-1,2-diyl group (—C≡C—), an oxy group (—O—), a thio group (—S—), a sulfinyl group (—SO—), a sulfonyl group (—$SO_2$—), or an unsubstituted or N-substituted imino group (—N($R^{22}$)—).

Examples of a substituent on the "phenylene group" for $Q^1$ or $Q^2$ include the same groups as those exemplified for the substituent on the phenylene group for $R^{51}$ in the formula [III].

$R^{22}$ represents a hydrogen atom, an unsubstituted or substituted hydrocarbon group, an unsubstituted or substituted heterocyclyl group, a hydroxyl group, an unsubstituted or substituted alkoxy group, an unsubstituted or substituted alkoxycarbonyl group, an unsubstituted or substituted aryloxy group, an unsubstituted or substituted amino group, an unsubstituted or substituted alkylsulfonyl group, an unsubstituted or substituted arylsulfonyl group, an unsubstituted or substituted heterocyclylsulfonyl group, an unsubstituted or substituted alkylcarbonyl group, an unsubstituted or substituted arylcarbonyl group, or an unsubstituted or substituted heterocyclylcarbonyl group.

Examples of the "hydrocarbon group", "heterocyclyl group", "alkoxy group", "alkoxycarbonyl group", "aryloxy group", "unsubstituted or substituted amino group", "alkylsulfonyl group", "arylsulfonyl group", "heterocyclylsulfonyl group", "alkylcarbonyl group", "arylcarbonyl group", "heterocyclylcarbonyl group" for $R^{22}$ include the same groups as those exemplified for $R^7$ to $R^9$ in the formula [II].

Among these, it is preferable that $Q^1$ and $Q^2$ each independently represents a single bond, an ethene-1,2-diyl group (—CH=CH—), an ethyne-1,2-diyl group (—C≡C—), an oxy group (—O—), or a thio group (—S—).

In the formula [I], $A^1$ and $A^2$ each independently represents an unsubstituted or substituted divalent heterocyclic compound residue, an unsubstituted or substituted divalent aromatic hydrocarbon residue, or —N($R^{23}$)—. $R^{23}$ represents a hydrogen atom, an unsubstituted or substituted hydrocarbon group, an unsubstituted or substituted heterocyclyl group, a hydroxyl group, an unsubstituted or substituted alkoxy group, an unsubstituted or substituted alkoxycarbonyl group, an unsubstituted or substituted aryloxy group, an unsubstituted or substituted amino group, an unsubstituted or substituted alkylsulfonyl group, an unsubstituted or substituted arylsulfonyl group, an unsubstituted or substituted heterocyclylsulfonyl group, an unsubstituted or substituted alkylcarbonyl group, an unsubstituted or substituted arylcarbonyl group, or an unsubstituted or substituted heterocyclylcarbonyl group.

The "divalent heterocyclic compound residue" for $A^1$ or $A^2$ is a group formed by removing two hydrogen atoms from a heterocyclic compound. The heterocyclic compound may be either a monocyclic heterocyclic compound or a polycyclic heterocyclic compound. Examples of the monocyclic heterocyclic compound include five-membered heterocyclic compounds and six-membered heterocyclic compounds. In the case where at least one ring of the polycyclic heterocyclic compound is heterocycle, the remaining rings may be any of saturated alicycle, unsaturated alicycle and aromatic rings.

The "heterocyclic compound" is a cyclic compound containing at least 1 to 4 heteroatoms selected from the group consisting of a nitrogen atom, an oxygen atom and a sulfur atom as constituent atoms thereof.

Examples of the "monocyclic heterocyclic compound" include: 5-membered aromatic heterocyclic compounds such as imidazole, pyrazole, oxazole, thiazole, triazole, tetrazole, pyrrole, furan, and thiophene (preferably thiazole or thiophene); 6-membered aromatic heterocyclic compounds such as pyridine, pyrazine, pyrimidine, pyridazine, and triazine (preferably pyridine or pyridazine); 5-membered saturated heterocyclic compounds such as pyrrolidine, tetrahydrofuran, tetrahydrothiophene, and thiazoline; 6-membered saturated heterocyclic compounds such as piperidine, tetrahydropyran, and tetrahydrothiopyran; and 5-membered partially unsaturated heterocyclic compounds such as pyrroline, imidazoline, pyrazoline, oxazoline, and isoxazoline.

Examples of the "polycyclic heterocyclic compound" include benzofuran, benzothiophene, indole, isoindole, benzimidazole, purine, quinoline, isoquinoline, quinoxaline, cinnoline, pteridine, chromene, and isochromene, and benzofuran is preferable.

Among these, 5-membered aromatic heterocyclic compounds, 6-membered aromatic heterocyclic compounds, or polycyclic heterocyclic compounds are preferable, 6-membered aromatic heterocyclic compounds or polycyclic heterocyclic compounds are more preferable, and pyridine or benzofuran is even more preferable.

The "divalent aromatic hydrocarbon residue" for $A^1$ or $A^2$ is a group formed by removing two hydrogen atoms from an aromatic hydrocarbon. The aromatic hydrocarbon may be a monocycle or a polycycle. In the case where at least one ring of the polycyclic aromatic hydrocarbon is an aromatic ring, the remaining rings thereof may be any of saturated alicycles, unsaturated alicycles and aromatic rings.

Examples of the "aromatic hydrocarbon" include benzene, naphthalene, azulene, indene, indane, and tetralin. Among these, benzene or naphthalene is preferable, and benzene is more preferable.

Preferable examples of a substituent on the "divalent heterocyclic compound residue" or the "divalent aromatic hydrocarbon residue" include C1-6 alkyl groups, C3-8 cycloalkyl groups, C6-10 aryl groups, 3- to 6-membered heterocyclyl groups, a hydroxyl group, C1-6 alkoxy groups, C6-10 aryloxy groups, a carboxyl group, halogeno groups, C1-6 haloalkyl groups, C6-10 haloaryl groups, C1-6 haloalkoxy groups, an amino group (represented by $NH_2$), C1-6 alkyl-substituted amino groups, C6-10 arylamino groups, C1-7 acylamino groups, C1-6 alkoxycarbonylamino groups, C1-6 alkylthio groups, C6-10 arylthio groups, heteroarylthio groups, C7-11 aralkylthio groups, C1-6 alkylsulfinyl groups, C6-10 arylsulfinyl groups, heteroarylsulfinyl groups, C7-11 aralkylsulfinyl groups, C1-6 alkylsulfonyl groups, C6-10 arylsulfonyl groups, heteroarylsulfonyl groups, a cyano group, and a nitro group, and a C1-6 alkyl group or a halogeno groups is more preferable.

Examples of the "hydrocarbon group", "heterocyclyl group", "alkoxy group", "alkoxycarbonyl group", "aryloxy group", "unsubstituted or substituted amino group", "alkylsulfonyl group", "arylsulfonyl group", "heterocyclylsulfonyl group", "alkylcarbonyl group", "arylcarbonyl group", or "heterocyclylcarbonyl group" for $R^{23}$ include the same groups as those exemplified for $R^7$ to $R^9$ in the formula [II]. Among these, $R^{23}$ preferably represents a hydrogen atom.

$R^1$ to $R^6$ each independently represents a hydrogen atom, an unsubstituted or substituted hydrocarbon group, an unsubstituted or substituted heterocyclyl group, a hydroxyl group, an unsubstituted or substituted alkoxy group, an unsubstituted or substituted alkoxycarbonyl group, an unsubstituted or substituted aryloxy group, an unsubstituted or substituted amino group, an unsubstituted or substituted alkylsulfonyl group, an unsubstituted or substituted arylsulfonyl group, an unsubstituted or substituted heterocyclylsulfonyl group, an unsubstituted or substituted alkylcarbonyl group, an unsubstituted or substituted arylcarbonyl group, or an unsubstituted or substituted heterocyclylcarbonyl group. $R^1$ and $R^2$ may be bonded together to form a 4- to 8-membered ring with two nitrogen atoms binding therewith and a carbon atom binding with the two nitrogen atoms, $R^2$ and $R^3$ may be bonded together to form a 4- to 8-membered ring with a nitrogen atom binding therewith, $R^4$ and $R^5$ may be bonded together to form a 4- to 8-membered ring with two nitrogen atoms binding therewith and a carbon atom binding with the two nitrogen atoms, or $R^5$ and $R^6$ may be bonded together to form a 4- to 8-membered ring with a nitrogen atom binding therewith.

In the case where $R^1$ and $R^2$ are bonded together to form a 4- to 8-membered ring with two nitrogen atoms binding therewith and a carbon atom binding with the two nitrogen atoms, the 4- to 8-membered ring may be specifically represented by formula [IV-1], formula [IV-2], or formula [IV-3].

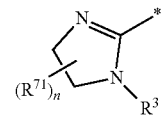

IV-1

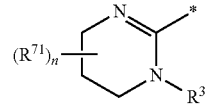

IV-2

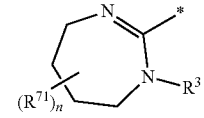

IV-3

In the formula [IV-1], formula [IV-2], and formula [IV-3], $R^3$ is mentioned above.

In the formula [IV-1], formula [IV-2], and formula [IV-3], $R^{71}$ each independently represents an unsubstituted or substituted hydrocarbon group, an unsubstituted or substituted heterocyclyl group, a hydroxyl group, an unsubstituted or substituted alkoxy group, an unsubstituted or substituted alkoxycarbonyl group, an unsubstituted or substituted aryloxy group, an unsubstituted or substituted amino group, an unsubstituted or substituted alkylsulfonyl group, an unsubstituted or substituted arylsulfonyl group, an unsubstituted or substituted heterocyclylsulfonyl group, an unsubstituted or substituted alkylcarbonyl group, an unsubstituted or substituted arylcarbonyl group, or an unsubstituted or substituted heterocyclylcarbonyl group.

Examples of the "hydrocarbon group", "heterocyclyl group", "alkoxy group", "alkoxycarbonyl group", "aryloxy group", "unsubstituted or substituted amino group", "alkylsulfonyl group", "arylsulfonyl group", "heterocyclylsulfonyl group", "alkylcarbonyl group", "arylcarbonyl group", or "heterocyclylcarbonyl group" for $R^{71}$ include the same groups as those exemplified for $R^7$ to $R^9$ in the formula [II].

Among these, it is preferable that $R^{71}$ each independently represents an unsubstituted or substituted C1-6 alkyl group, an unsubstituted or substituted C1-6 alkoxycarbonyl group, or an unsubstituted or substituted amino group (preferably unsubstituted amino group).

In the formula [IV-1], formula [IV-2], and formula [IV-3], n indicates the number of the substituent $R^{71}$ and represents an integer of 0 to 4, and preferably represents an integer of 0 to 2.

In the formula [IV-1], formula [IV-2], and formula [IV-3], * represents a binding portion with $A^1$.

In the case where $R^4$ and $R^5$ are bonded together to form a 4- to 8-membered ring with two nitrogen atoms binding therewith and a carbon atom binding with the two nitrogen atoms, the 4- to 8-membered ring may be specifically represented by formula [V-1], formula [V-2], or formula [V-3].

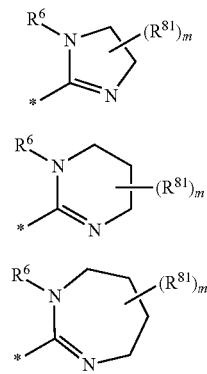

In the formula [V-1], formula [V-2], and formula [V-3], $R^6$ is described above.

In the formula [V-1], formula [V-2], and formula [V-3], $R^{81}$ each independently represents an unsubstituted or substituted hydrocarbon group, an unsubstituted or substituted heterocyclyl group, a hydroxyl group, an unsubstituted or substituted alkoxy group, an unsubstituted or substituted alkoxycarbonyl group, an unsubstituted or substituted aryloxy group, an unsubstituted or substituted amino group, an unsubstituted or substituted alkylsulfonyl group, an unsubstituted or substituted arylsulfonyl group, an unsubstituted or substituted heterocyclylsulfonyl group, an unsubstituted or substituted alkylcarbonyl group, an unsubstituted or substituted arylcarbonyl group, or an unsubstituted or substituted heterocyclylcarbonyl group.

Examples of the "hydrocarbon group", "heterocyclyl group", "alkoxy group", "alkoxycarbonyl group", "aryloxy group", "unsubstituted or substituted amino group", "alkylsulfonyl group", "arylsulfonyl group", "heterocyclylsulfonyl group", "alkylcarbonyl group", "arylcarbonyl group", or "heterocyclylcarbonyl group" for $R^{81}$ include the same groups as those for the substituent $R^{71}$.

In the formula [V-1], formula [V-2], and formula [V-3], m represents the number of the substituent $R^{81}$ and is an integer of 0 to 4 and preferably an integer of 0 to 2.

In the formula [V-1], formula [V-2], and formula [V-3], * represents a binding portion with $A^2$.

Examples of the "hydrocarbon group", "heterocyclyl group", "alkoxy group", "alkoxycarbonyl group", "aryloxy group", "unsubstituted or substituted amino group", "alkylsulfonyl group", "arylsulfonyl group", "heterocyclylsulfo- nyl group", "alkylcarbonyl group", "arylcarbonyl group", or "heterocyclylcarbonyl group" for $R^1$ to $R^6$ include the same groups as those exemplified for $R^7$ to $R^9$ in the formula [II].

Among these, it is preferable that $R^1$ to $R^6$ each independently represents a hydrogen atom, an unsubstituted or substituted hydrocarbon group (C1-6 alkyl group which is unsubstituted or substituted with a C1-6 alkyl-substituted amino group), an unsubstituted or substituted C1-6 alkoxycarbonyl group, or an unsubstituted or substituted C1-6 alkylcarbonyl group, or that both $R^1$ and $R^2$ or both $R^4$ and $R^5$ be bonded together to form a 4- to 8-membered ring with two nitrogen atoms binding therewith and a carbon atom binding with the two nitrogen atoms.

In the case where $A^1$ and/or $A^2$ represent —N($R^{23}$)—, $R^{23}$ and $R^2$, or $R^{23}$ and $R^5$ may be bonded together to form a 4- to 6-membered ring (preferably 5-membered ring) with two nitrogen atoms binding therewith and a carbon atom binding with the two nitrogen atoms.

Specific examples of the compound represented by the formula [I] include the following compounds.

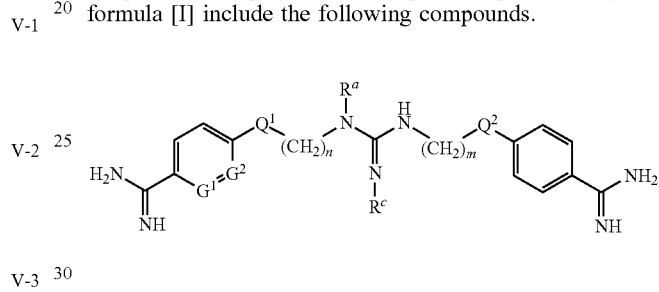

TABLE 1

| Compound No. | $G^1$ | $G^2$ | n | m | $R^a$ | $R^c$ | $Q^1$ | $Q^2$ |
|---|---|---|---|---|---|---|---|---|
| A-1 | CH | CH | 3 | 3 | Me | H | —O— | —O— |
| A-2 | CH | CH | 3 | 3 | Me | H | —O— | —S— |
| A-3 | CH | CH | 3 | 3 | Me | H | —O— | —OCH$_2$— |
| A-4 | CH | CH | 3 | 3 | Me | H | —O— | singlebond |
| A-5 | CH | CH | 3 | 3 | Me | H | —S— | —O— |
| A-6 | CH | CH | 3 | 3 | Me | H | —CH$_2$O— | —O— |
| A-7 | CH | CH | 3 | 3 | Me | H | singlebond | —O— |
| A-8 | CH | CH | 3 | 3 | Me | H | —S— | —S— |
| A-9 | CH | CH | 3 | 3 | Me | H | —CH$_2$O— | —OCH$_2$— |
| A-10 | CH | CH | 3 | 3 | Me | H | singlebond | singlebond |
| A-11 | CH | CH | 3 | 3 | H | Me | —O— | —O— |
| A-12 | CH | CH | 3 | 3 | H | Me | —O— | —S— |
| A-13 | CH | CH | 3 | 3 | H | Me | —O— | —OCH$_2$— |
| A-14 | CH | CH | 3 | 3 | H | Me | —O— | singlebond |
| A-15 | CH | CH | 3 | 3 | H | Me | —S— | —O— |
| A-16 | CH | CH | 3 | 3 | H | Me | —CH$_2$O— | —O— |
| A-17 | CH | CH | 3 | 3 | H | Me | singlebond | —O— |
| A-18 | CH | CH | 3 | 3 | H | Me | —S— | —S— |
| A-19 | CH | CH | 3 | 3 | H | Me | —CH$_2$O— | —OCH$_2$— |
| A-20 | CH | CH | 3 | 3 | H | Me | singlebond | singlebond |
| A-21 | CH | CH | 3 | 3 | Ph | H | —O— | —O— |
| A-22 | CH | CH | 3 | 3 | Ph | H | —O— | —S— |
| A-23 | CH | CH | 3 | 3 | Ph | H | —O— | —OCH$_2$— |
| A-24 | CH | CH | 3 | 3 | Ph | H | —O— | singlebond |
| A-25 | CH | CH | 3 | 3 | Ph | H | —S— | —O— |
| A-26 | CH | CH | 3 | 3 | Ph | H | —CH$_2$O— | —O— |
| A-27 | CH | CH | 3 | 3 | Ph | H | singlebond | —O— |
| A-28 | CH | CH | 3 | 3 | Ph | H | —S— | —S— |
| A-29 | CH | CH | 3 | 3 | Ph | H | —CH$_2$O— | —OCH$_2$— |
| A-30 | CH | CH | 3 | 3 | Ph | H | singlebond | singlebond |
| A-31 | CH | CH | 3 | 3 | H | Ph | —O— | —O— |
| A-32 | CH | CH | 3 | 3 | H | Ph | —O— | —S— |
| A-33 | CH | CH | 3 | 3 | H | Ph | —O— | —OCH$_2$— |
| A-34 | CH | CH | 3 | 3 | H | Ph | —O— | singlebond |
| A-35 | CH | CH | 3 | 3 | H | Ph | —S— | —O— |
| A-36 | CH | CH | 3 | 3 | H | Ph | —CH$_2$O— | —O— |
| A-37 | CH | CH | 3 | 3 | H | Ph | singlebond | —O— |
| A-38 | CH | CH | 3 | 3 | H | Ph | —S— | —S— |
| A-39 | CH | CH | 3 | 3 | H | Ph | —CH$_2$O— | —OCH$_2$— |

TABLE 1-continued

| Compound No. | G¹ | G² | n | m | $R^a$ | $R^c$ | Q¹ | Q² |
|---|---|---|---|---|---|---|---|---|
| A-40 | CH | CH | 3 | 3 | H | Ph | singlebond | singlebond |
| A-41 | CH | CH | 3 | 4 | Me | H | —O— | —O— |
| A-42 | CH | CH | 3 | 4 | Me | H | —O— | —S— |
| A-43 | CH | CH | 3 | 4 | Me | H | —O— | —OCH₂— |
| A-44 | CH | CH | 3 | 4 | Me | H | —O— | singlebond |
| A-45 | CH | CH | 3 | 4 | Me | H | —S— | —O— |
| A-46 | CH | CH | 3 | 4 | Me | H | —CH₂O— | —O— |
| A-47 | CH | CH | 3 | 4 | Me | H | singlebond | —O— |
| A-48 | CH | CH | 3 | 4 | Me | H | —S— | —S— |
| A-49 | CH | CH | 3 | 4 | Me | H | —CH₂O— | —OCH₂— |
| A-50 | CH | CH | 3 | 4 | Me | H | singlebond | singlebond |
| A-51 | CH | CH | 3 | 4 | H | Me | —O— | —O— |
| A-52 | CH | CH | 3 | 4 | H | Me | —O— | —S— |
| A-53 | CH | CH | 3 | 4 | H | Me | —O— | —OCH₂— |
| A-54 | CH | CH | 3 | 4 | H | Me | —O— | singlebond |
| A-55 | CH | CH | 3 | 4 | H | Me | —S— | —O— |
| A-56 | CH | CH | 3 | 4 | H | Me | —CH₂O— | —O— |
| A-57 | CH | CH | 3 | 4 | H | Me | singlebond | —O— |
| A-58 | CH | CH | 3 | 4 | H | Me | —S— | —S— |
| A-59 | CH | CH | 3 | 4 | H | Me | —CH₂O— | —OCH₂— |
| A-60 | CH | CH | 3 | 4 | H | Me | singlebond | singlebond |
| A-61 | CH | CH | 3 | 4 | Ph | H | —O— | —O— |
| A-62 | CH | CH | 3 | 4 | Ph | H | —O— | —S— |
| A-63 | CH | CH | 3 | 4 | Ph | H | —O— | —OCH₂— |
| A-64 | CH | CH | 3 | 4 | Ph | H | —O— | singlebond |
| A-65 | CH | CH | 3 | 4 | Ph | H | —S— | —O— |
| A-66 | CH | CH | 3 | 4 | Ph | H | —CH₂O— | —O— |
| A-67 | CH | CH | 3 | 4 | Ph | H | singlebond | —O— |
| A-68 | CH | CH | 3 | 4 | Ph | H | —S— | —S— |
| A-69 | CH | CH | 3 | 4 | Ph | H | —CH₂O— | —OCH₂— |
| A-70 | CH | CH | 3 | 4 | Ph | H | singlebond | singlebond |
| A-71 | CH | CH | 3 | 4 | H | Ph | —O— | —O— |
| A-72 | CH | CH | 3 | 4 | H | Ph | —O— | —S— |
| A-73 | CH | CH | 3 | 4 | H | Ph | —O— | —OCH₂— |
| A-74 | CH | CH | 3 | 4 | H | Ph | —O— | singlebond |
| A-75 | CH | CH | 3 | 4 | H | Ph | —S— | —O— |
| A-76 | CH | CH | 3 | 4 | H | Ph | —CH₂O— | —O— |
| A-77 | CH | CH | 3 | 4 | H | Ph | singlebond | —O— |
| A-78 | CH | CH | 3 | 4 | H | Ph | —S— | —S— |
| A-79 | CH | CH | 3 | 4 | H | Ph | —CH₂O— | —OCH₂— |
| A-80 | CH | CH | 3 | 4 | H | Ph | singlebond | singlebond |
| A-81 | CH | CH | 4 | 3 | Me | H | —O— | —O— |
| A-82 | CH | CH | 4 | 3 | Me | H | —O— | —S— |
| A-83 | CH | CH | 4 | 3 | Me | H | —O— | —OCH₂— |
| A-84 | CH | CH | 4 | 3 | Me | H | —O— | singlebond |
| A-85 | CH | CH | 4 | 3 | Me | H | —S— | —O— |
| A-86 | CH | CH | 4 | 3 | Me | H | —CH₂O— | —O— |
| A-87 | CH | CH | 4 | 3 | Me | H | singlebond | —O— |
| A-88 | CH | CH | 4 | 3 | Me | H | —S— | —S— |
| A-89 | CH | CH | 4 | 3 | Me | H | —CH₂O— | —OCH₂— |
| A-90 | CH | CH | 4 | 3 | Me | H | singlebond | singlebond |
| A-91 | CH | CH | 4 | 3 | H | Me | —O— | —O— |
| A-92 | CH | CH | 4 | 3 | H | Me | —O— | —S— |
| A-93 | CH | CH | 4 | 3 | H | Me | —O— | —OCH₂— |
| A-94 | CH | CH | 4 | 3 | H | Me | —O— | singlebond |
| A-95 | CH | CH | 4 | 3 | H | Me | —S— | —O— |
| A-96 | CH | CH | 4 | 3 | H | Me | —CH₂O— | —O— |
| A-97 | CH | CH | 4 | 3 | H | Me | singlebond | —O— |
| A-98 | CH | CH | 4 | 3 | H | Me | —S— | —S— |
| A-99 | CH | CH | 4 | 3 | H | Me | —CH₂O— | —OCH₂— |
| A-100 | CH | CH | 4 | 3 | H | Me | singlebond | singlebond |
| A-101 | CH | CH | 4 | 3 | Ph | H | —O— | —O— |
| A-102 | CH | CH | 4 | 3 | Ph | H | —O— | —S— |
| A-103 | CH | CH | 4 | 3 | Ph | H | —O— | —OCH₂— |
| A-104 | CH | CH | 4 | 3 | Ph | H | —O— | singlebond |
| A-105 | CH | CH | 4 | 3 | Ph | H | —S— | —O— |
| A-106 | CH | CH | 4 | 3 | Ph | H | —CH₂O— | —O— |
| A-107 | CH | CH | 4 | 3 | Ph | H | singlebond | —O— |
| A-108 | CH | CH | 4 | 3 | Ph | H | —S— | —S— |
| A-109 | CH | CH | 4 | 3 | Ph | H | —CH₂O— | —OCH₂— |
| A-110 | CH | CH | 4 | 3 | Ph | H | singlebond | singlebond |

TABLE 2

| Compound No. | G¹ | G² | n | m | $R^a$ | $R^c$ | Q¹ | Q² |
|---|---|---|---|---|---|---|---|---|
| A-111 | CH | CH | 4 | 3 | H | Ph | —O— | —O— |
| A-112 | CH | CH | 4 | 3 | H | Ph | —O— | —S— |
| A-113 | CH | CH | 4 | 3 | H | Ph | —O— | —OCH₂— |
| A-114 | CH | CH | 4 | 3 | H | Ph | —O— | singlebond |
| A-115 | CH | CH | 4 | 3 | H | Ph | —S— | —O— |
| A-116 | CH | CH | 4 | 3 | H | Ph | —CH₂O— | —O— |
| A-117 | CH | CH | 4 | 3 | H | Ph | singlebond | —O— |
| A-118 | CH | CH | 4 | 3 | H | Ph | —S— | —S— |
| A-119 | CH | CH | 4 | 3 | H | Ph | —CH₂O— | —OCH₂— |
| A-120 | CH | CH | 4 | 3 | H | Ph | singlebond | singlebond |
| A-121 | CH | CH | 4 | 4 | Me | H | —O— | —O— |
| A-122 | CH | CH | 4 | 4 | Me | H | —O— | —S— |
| A-123 | CH | CH | 4 | 4 | Me | H | —O— | —OCH₂— |
| A-124 | CH | CH | 4 | 4 | Me | H | —O— | singlebond |
| A-125 | CH | CH | 4 | 4 | Me | H | —S— | —O— |
| A-126 | CH | CH | 4 | 4 | Me | H | —CH₂O— | —O— |
| A-127 | CH | CH | 4 | 4 | Me | H | singlebond | —O— |
| A-128 | CH | CH | 4 | 4 | Me | H | —S— | —S— |
| A-129 | CH | CH | 4 | 4 | Me | H | —CH₂O— | —OCH₂— |
| A-130 | CH | CH | 4 | 4 | Me | H | singlebond | singlebond |
| A-131 | CH | CH | 4 | 4 | H | Me | —O— | —O— |
| A-132 | CH | CH | 4 | 4 | H | Me | —O— | —S— |
| A-133 | CH | CH | 4 | 4 | H | Me | —O— | —OCH₂— |
| A-134 | CH | CH | 4 | 4 | H | Me | —O— | singlebond |
| A-135 | CH | CH | 4 | 4 | H | Me | —S— | —O— |
| A-136 | CH | CH | 4 | 4 | H | Me | —CH₂O— | —O— |
| A-137 | CH | CH | 4 | 4 | H | Me | singlebond | —O— |
| A-138 | CH | CH | 4 | 4 | H | Me | —S— | —S— |
| A-139 | CH | CH | 4 | 4 | H | Me | —CH₂O— | —OCH₂— |
| A-140 | CH | CH | 4 | 4 | H | Me | singlebond | singlebond |
| A-141 | CH | CH | 4 | 4 | Ph | H | —O— | —O— |
| A-142 | CH | CH | 4 | 4 | Ph | H | —O— | —S— |
| A-143 | CH | CH | 4 | 4 | Ph | H | —O— | —OCH₂— |
| A-144 | CH | CH | 4 | 4 | Ph | H | —O— | singlebond |
| A-145 | CH | CH | 4 | 4 | Ph | H | —S— | —O— |
| A-146 | CH | CH | 4 | 4 | Ph | H | —CH₂O— | —O— |
| A-147 | CH | CH | 4 | 4 | Ph | H | singlebond | —O— |
| A-148 | CH | CH | 4 | 4 | Ph | H | —S— | —S— |
| A-149 | CH | CH | 4 | 4 | Ph | H | —CH₂O— | —OCH₂— |
| A-150 | CH | CH | 4 | 4 | Ph | H | singlebond | singlebond |
| A-151 | CH | CH | 4 | 4 | H | Ph | —O— | —O— |
| A-152 | CH | CH | 4 | 4 | H | Ph | —O— | —S— |
| A-153 | CH | CH | 4 | 4 | H | Ph | —O— | —OCH₂— |
| A-154 | CH | CH | 4 | 4 | H | Ph | —O— | singlebond |
| A-155 | CH | CH | 4 | 4 | H | Ph | —S— | —O— |
| A-156 | CH | CH | 4 | 4 | H | Ph | —CH₂O— | —O— |
| A-157 | CH | CH | 4 | 4 | H | Ph | singlebond | —O— |
| A-158 | CH | CH | 4 | 4 | H | Ph | —S— | —S— |
| A-159 | CH | CH | 4 | 4 | H | Ph | —CH₂O— | —OCH₂— |
| A-160 | CH | CH | 4 | 4 | H | Ph | singlebond | singlebond |
| A-161 | N | CH | 3 | 3 | Me | H | —O— | —O— |
| A-162 | N | CH | 3 | 3 | Me | H | —O— | —S— |
| A-163 | N | CH | 3 | 3 | Me | H | —O— | —OCH₂— |
| A-164 | N | CH | 3 | 3 | Me | H | —O— | singlebond |
| A-165 | N | CH | 3 | 3 | Me | H | —S— | —O— |
| A-166 | N | CH | 3 | 3 | Me | H | —CH₂O— | —O— |
| A-167 | N | CH | 3 | 3 | Me | H | singlebond | —O— |
| A-168 | N | CH | 3 | 3 | Me | H | —S— | —S— |
| A-169 | N | CH | 3 | 3 | Me | H | —CH₂O— | —OCH₂— |
| A-170 | N | CH | 3 | 3 | Me | H | singlebond | singlebond |
| A-171 | N | CH | 3 | 3 | H | Me | —O— | —O— |
| A-172 | N | CH | 3 | 3 | H | Me | —O— | —S— |
| A-173 | N | CH | 3 | 3 | H | Me | —O— | —OCH₂— |
| A-174 | N | CH | 3 | 3 | H | Me | —O— | singlebond |
| A-175 | N | CH | 3 | 3 | H | Me | —S— | —O— |
| A-176 | N | CH | 3 | 3 | H | Me | —CH₂O— | —O— |
| A-177 | N | CH | 3 | 3 | H | Me | singlebond | —O— |
| A-178 | N | CH | 3 | 3 | H | Me | —S— | —S— |
| A-179 | N | CH | 3 | 3 | H | Me | —CH₂O— | —OCH₂— |
| A-180 | N | CH | 3 | 3 | H | Me | singlebond | singlebond |
| A-181 | N | CH | 3 | 3 | Ph | H | —O— | —O— |
| A-182 | N | CH | 3 | 3 | Ph | H | —O— | —S— |
| A-183 | N | CH | 3 | 3 | Ph | H | —O— | —OCH₂— |
| A-184 | N | CH | 3 | 3 | Ph | H | —O— | singlebond |
| A-185 | N | CH | 3 | 3 | Ph | H | —S— | —O— |
| A-186 | N | CH | 3 | 3 | Ph | H | —CH₂O— | —O— |
| A-187 | N | CH | 3 | 3 | Ph | H | singlebond | —O— |

TABLE 2-continued

| Compound No. | G¹ | G² | n | m | $R^a$ | $R^c$ | Q¹ | Q² |
|---|---|---|---|---|---|---|---|---|
| A-188 | N | CH | 3 | 3 | Ph | H | —S— | —S— |
| A-189 | N | CH | 3 | 3 | Ph | H | —CH₂O— | —OCH₂— |
| A-190 | N | CH | 3 | 3 | Ph | H | singlebond | singlebond |
| A-191 | N | CH | 3 | 3 | H | Ph | —O— | —O— |
| A-192 | N | CH | 3 | 3 | H | Ph | —O— | —S— |
| A-193 | N | CH | 3 | 3 | H | Ph | —O— | —OCH₂— |
| A-194 | N | CH | 3 | 3 | H | Ph | —O— | singlebond |
| A-195 | N | CH | 3 | 3 | H | Ph | —S— | —O— |
| A-196 | N | CH | 3 | 3 | H | Ph | —CH₂O— | —O— |
| A-197 | N | CH | 3 | 3 | H | Ph | singlebond | —O— |
| A-198 | N | CH | 3 | 3 | H | Ph | —S— | —S— |
| A-199 | N | CH | 3 | 3 | H | Ph | —CH₂O— | —OCH₂— |
| A-200 | N | CH | 3 | 3 | H | Ph | singlebond | singlebond |
| A-201 | N | CH | 3 | 4 | Me | H | —O— | —O— |
| A-202 | N | CH | 3 | 4 | Me | H | —O— | —S— |
| A-203 | N | CH | 3 | 4 | Me | H | —O— | —OCH₂— |
| A-204 | N | CH | 3 | 4 | Me | H | —O— | singlebond |
| A-205 | N | CH | 3 | 4 | Me | H | —S— | —O— |
| A-206 | N | CH | 3 | 4 | Me | H | —CH₂O— | —O— |
| A-207 | N | CH | 3 | 4 | Me | H | singlebond | —O— |
| A-208 | N | CH | 3 | 4 | Me | H | —S— | —S— |
| A-209 | N | CH | 3 | 4 | Me | H | —CH₂O— | —OCH₂— |
| A-210 | N | CH | 3 | 4 | Me | H | singlebond | singlebond |
| A-211 | N | CH | 3 | 4 | H | Me | —O— | —O— |
| A-212 | N | CH | 3 | 4 | H | Me | —O— | —S— |
| A-213 | N | CH | 3 | 4 | H | Me | —O— | —OCH₂— |
| A-214 | N | CH | 3 | 4 | H | Me | —O— | singlebond |
| A-215 | N | CH | 3 | 4 | H | Me | —S— | —O— |
| A-216 | N | CH | 3 | 4 | H | Me | —CH₂O— | —O— |
| A-217 | N | CH | 3 | 4 | H | Me | singlebond | —O— |
| A-218 | N | CH | 3 | 4 | H | Me | —S— | —S— |
| A-219 | N | CH | 3 | 4 | H | Me | —CH₂O— | —OCH₂— |
| A-220 | N | CH | 3 | 4 | H | Me | singlebond | singlebond |

TABLE 3

| Compound No. | G¹ | G² | n | m | $R^a$ | $R^c$ | Q¹ | Q² |
|---|---|---|---|---|---|---|---|---|
| A-221 | N | CH | 3 | 4 | Ph | H | —O— | —O— |
| A-222 | N | CH | 3 | 4 | Ph | H | —O— | —S— |
| A-223 | N | CH | 3 | 4 | Ph | H | —O— | —OCH₂— |
| A-224 | N | CH | 3 | 4 | Ph | H | —O— | singlebond |
| A-225 | N | CH | 3 | 4 | Ph | H | —S— | —O— |
| A-226 | N | CH | 3 | 4 | Ph | H | —CH₂O— | —O— |
| A-227 | N | CH | 3 | 4 | Ph | H | singlebond | —O— |
| A-228 | N | CH | 3 | 4 | Ph | H | —S— | —S— |
| A-229 | N | CH | 3 | 4 | Ph | H | —CH₂O— | —OCH₂— |
| A-230 | N | CH | 3 | 4 | Ph | H | singlebond | singlebond |
| A-231 | N | CH | 3 | 4 | H | Ph | —O— | —O— |
| A-232 | N | CH | 3 | 4 | H | Ph | —O— | —S— |
| A-233 | N | CH | 3 | 4 | H | Ph | —O— | —OCH₂— |
| A-234 | N | CH | 3 | 4 | H | Ph | —O— | singlebond |
| A-235 | N | CH | 3 | 4 | H | Ph | —S— | —O— |
| A-236 | N | CH | 3 | 4 | H | Ph | —CH₂O— | —O— |
| A-237 | N | CH | 3 | 4 | H | Ph | singlebond | —O— |
| A-238 | N | CH | 3 | 4 | H | Ph | —S— | —S— |
| A-239 | N | CH | 3 | 4 | H | Ph | —CH₂O— | —OCH₂— |
| A-240 | N | CH | 3 | 4 | H | Ph | singlebond | singlebond |
| A-241 | N | CH | 4 | 3 | Me | H | —O— | —O— |
| A-242 | N | CH | 4 | 3 | Me | H | —O— | —S— |
| A-243 | N | CH | 4 | 3 | Me | H | —O— | —OCH₂— |
| A-244 | N | CH | 4 | 3 | Me | H | —O— | singlebond |
| A-245 | N | CH | 4 | 3 | Me | H | —S— | —O— |
| A-246 | N | CH | 4 | 3 | Me | H | —CH₂O— | —O— |
| A-247 | N | CH | 4 | 3 | Me | H | singlebond | —O— |
| A-248 | N | CH | 4 | 3 | Me | H | —S— | —S— |
| A-249 | N | CH | 4 | 3 | Me | H | —CH₂O— | —OCH₂— |
| A-250 | N | CH | 4 | 3 | Me | H | singlebond | singlebond |
| A-251 | N | CH | 4 | 3 | H | Me | —O— | —O— |
| A-252 | N | CH | 4 | 3 | H | Me | —O— | —S— |
| A-253 | N | CH | 4 | 3 | H | Me | —O— | —OCH₂— |
| A-254 | N | CH | 4 | 3 | H | Me | —O— | singlebond |
| A-255 | N | CH | 4 | 3 | H | Me | —S— | —O— |
| A-256 | N | CH | 4 | 3 | H | Me | —CH₂O— | —O— |
| A-257 | N | CH | 4 | 3 | H | Me | singlebond | —O— |
| A-258 | N | CH | 4 | 3 | H | Me | —S— | —S— |
| A-259 | N | CH | 4 | 3 | H | Me | —CH₂O— | —OCH₂— |
| A-260 | N | CH | 4 | 3 | H | Me | singlebond | singlebond |
| A-261 | N | CH | 4 | 3 | Ph | H | —O— | —O— |
| A-262 | N | CH | 4 | 3 | Ph | H | —O— | —S— |
| A-263 | N | CH | 4 | 3 | Ph | H | —O— | —OCH₂— |
| A-264 | N | CH | 4 | 3 | Ph | H | —O— | singlebond |
| A-265 | N | CH | 4 | 3 | Ph | H | —S— | —O— |
| A-266 | N | CH | 4 | 3 | Ph | H | —CH₂O— | —O— |
| A-267 | N | CH | 4 | 3 | Ph | H | singlebond | —O— |
| A-268 | N | CH | 4 | 3 | Ph | H | —S— | —S— |
| A-269 | N | CH | 4 | 3 | Ph | H | —CH₂O— | —OCH₂— |
| A-270 | N | CH | 4 | 3 | Ph | H | singlebond | singlebond |
| A-271 | N | CH | 4 | 3 | H | Ph | —O— | —O— |
| A-272 | N | CH | 4 | 3 | H | Ph | —O— | —S— |
| A-273 | N | CH | 4 | 3 | H | Ph | —O— | —OCH₂— |
| A-274 | N | CH | 4 | 3 | H | Ph | —O— | singlebond |
| A-275 | N | CH | 4 | 3 | H | Ph | —S— | —O— |
| A-276 | N | CH | 4 | 3 | H | Ph | —CH₂O— | —O— |
| A-277 | N | CH | 4 | 3 | H | Ph | singlebond | —O— |
| A-278 | N | CH | 4 | 3 | H | Ph | —S— | —S— |
| A-279 | N | CH | 4 | 3 | H | Ph | —CH₂O— | —OCH₂— |
| A-280 | N | CH | 4 | 3 | H | Ph | singlebond | singlebond |
| A-281 | N | CH | 4 | 4 | Me | H | —O— | —O— |
| A-282 | N | CH | 4 | 4 | Me | H | —O— | —S— |
| A-283 | N | CH | 4 | 4 | Me | H | —O— | —OCH₂— |
| A-284 | N | CH | 4 | 4 | Me | H | —O— | singlebond |
| A-285 | N | CH | 4 | 4 | Me | H | —S— | —O— |
| A-286 | N | CH | 4 | 4 | Me | H | —CH₂O— | —O— |
| A-287 | N | CH | 4 | 4 | Me | H | singlebond | —O— |
| A-288 | N | CH | 4 | 4 | Me | H | —S— | —S— |
| A-289 | N | CH | 4 | 4 | Me | H | —CH₂O— | —OCH₂— |
| A-290 | N | CH | 4 | 4 | Me | H | singlebond | singlebond |
| A-291 | N | CH | 4 | 4 | H | Me | —O— | —O— |
| A-292 | N | CH | 4 | 4 | H | Me | —O— | —S— |
| A-293 | N | CH | 4 | 4 | H | Me | —O— | —OCH₂— |
| A-294 | N | CH | 4 | 4 | H | Me | —O— | singlebond |
| A-295 | N | CH | 4 | 4 | H | Me | —S— | —O— |
| A-296 | N | CH | 4 | 4 | H | Me | —CH₂O— | —O— |
| A-297 | N | CH | 4 | 4 | H | Me | singlebond | —O— |
| A-298 | N | CH | 4 | 4 | H | Me | —S— | —S— |
| A-299 | N | CH | 4 | 4 | H | Me | —CH₂O— | —OCH₂— |
| A-300 | N | CH | 4 | 4 | H | Me | singlebond | singlebond |
| A-301 | N | CH | 4 | 4 | Ph | H | —O— | —O— |
| A-302 | N | CH | 4 | 4 | Ph | H | —O— | —S— |
| A-303 | N | CH | 4 | 4 | Ph | H | —O— | —OCH₂— |
| A-304 | N | CH | 4 | 4 | Ph | H | —O— | singlebond |
| A-305 | N | CH | 4 | 4 | Ph | H | —S— | —O— |
| A-306 | N | CH | 4 | 4 | Ph | H | —CH₂O— | —O— |
| A-307 | N | CH | 4 | 4 | Ph | H | singlebond | —O— |
| A-308 | N | CH | 4 | 4 | Ph | H | —S— | —S— |
| A-309 | N | CH | 4 | 4 | Ph | H | —CH₂O— | —OCH₂— |
| A-310 | N | CH | 4 | 4 | Ph | H | singlebond | singlebond |
| A-311 | N | CH | 4 | 4 | H | Ph | —O— | —O— |
| A-312 | N | CH | 4 | 4 | H | Ph | —O— | —S— |
| A-313 | N | CH | 4 | 4 | H | Ph | —O— | —OCH₂— |
| A-314 | N | CH | 4 | 4 | H | Ph | —O— | singlebond |
| A-315 | N | CH | 4 | 4 | H | Ph | —S— | —O— |
| A-316 | N | CH | 4 | 4 | H | Ph | —CH₂O— | —O— |
| A-317 | N | CH | 4 | 4 | H | Ph | singlebond | —O— |
| A-318 | N | CH | 4 | 4 | H | Ph | —S— | —S— |
| A-319 | N | CH | 4 | 4 | H | Ph | —CH₂O— | —OCH₂— |
| A-320 | N | CH | 4 | 4 | H | Ph | singlebond | singlebond |
| A-321 | CH | N | 3 | 3 | Me | H | —O— | —O— |
| A-322 | CH | N | 3 | 3 | Me | H | —O— | —S— |
| A-323 | CH | N | 3 | 3 | Me | H | —O— | —OCH₂— |
| A-324 | CH | N | 3 | 3 | Me | H | —O— | singlebond |
| A-325 | CH | N | 3 | 3 | Me | H | —S— | —O— |
| A-326 | CH | N | 3 | 3 | Me | H | —CH₂O— | —O— |
| A-327 | CH | N | 3 | 3 | Me | H | singlebond | —O— |
| A-328 | CH | N | 3 | 3 | Me | H | —S— | —S— |
| A-329 | CH | N | 3 | 3 | Me | H | —CH₂O— | —OCH₂— |
| A-330 | CH | N | 3 | 3 | Me | H | singlebond | singlebond |

TABLE 4

| Compound No. | G$^1$ | G$^2$ | n | m | R$^a$ | R$^c$ | Q$^1$ | Q$^2$ |
|---|---|---|---|---|---|---|---|---|
| A-331 | CH | N | 3 | 3 | H | Me | —O— | —O— |
| A-332 | CH | N | 3 | 3 | H | Me | —O— | —S— |
| A-333 | CH | N | 3 | 3 | H | Me | —O— | —OCH$_2$— |
| A-334 | CH | N | 3 | 3 | H | Me | —O— | singlebond |
| A-335 | CH | N | 3 | 3 | H | Me | —S— | —O— |
| A-336 | CH | N | 3 | 3 | H | Me | —CH$_2$O— | —O— |
| A-337 | CH | N | 3 | 3 | H | Me | singlebond | —O— |
| A-338 | CH | N | 3 | 3 | H | Me | —S— | —S— |
| A-339 | CH | N | 3 | 3 | H | Me | —CH$_2$O— | —OCH$_2$— |
| A-340 | CH | N | 3 | 3 | H | Me | singlebond | singlebond |
| A-341 | CH | N | 3 | 3 | Ph | H | —O— | —O— |
| A-342 | CH | N | 3 | 3 | Ph | H | —O— | —S— |
| A-343 | CH | N | 3 | 3 | Ph | H | —O— | —OCH$_2$— |
| A-344 | CH | N | 3 | 3 | Ph | H | —O— | singlebond |
| A-345 | CH | N | 3 | 3 | Ph | H | —S— | —O— |
| A-346 | CH | N | 3 | 3 | Ph | H | —CH$_2$O— | —O— |
| A-347 | CH | N | 3 | 3 | Ph | H | singlebond | —O— |
| A-348 | CH | N | 3 | 3 | Ph | H | —S— | —S— |
| A-349 | CH | N | 3 | 3 | Ph | H | —CH$_2$O— | —OCH$_2$— |
| A-350 | CH | N | 3 | 3 | Ph | H | singlebond | singlebond |
| A-351 | CH | N | 3 | 3 | H | Ph | —O— | —O— |
| A-352 | CH | N | 3 | 3 | H | Ph | —O— | —S— |
| A-353 | CH | N | 3 | 3 | H | Ph | —O— | —OCH$_2$— |
| A-354 | CH | N | 3 | 3 | H | Ph | —O— | singlebond |
| A-355 | CH | N | 3 | 3 | H | Ph | —S— | —O— |
| A-356 | CH | N | 3 | 3 | H | Ph | —CH$_2$O— | —O— |
| A-357 | CH | N | 3 | 3 | H | Ph | singlebond | —O— |
| A-358 | CH | N | 3 | 3 | H | Ph | —S— | —S— |
| A-359 | CH | N | 3 | 3 | H | Ph | —CH$_2$O— | —OCH$_2$— |
| A-360 | CH | N | 3 | 3 | H | Ph | singlebond | singlebond |
| A-361 | CH | N | 3 | 4 | Me | H | —O— | —O— |
| A-362 | CH | N | 3 | 4 | Me | H | —O— | —S— |
| A-363 | CH | N | 3 | 4 | Me | H | —O— | —OCH$_2$— |
| A-364 | CH | N | 3 | 4 | Me | H | —O— | singlebond |
| A-365 | CH | N | 3 | 4 | Me | H | —S— | —O— |
| A-366 | CH | N | 3 | 4 | Me | H | —CH$_2$O— | —O— |
| A-367 | CH | N | 3 | 4 | Me | H | singlebond | —O— |
| A-368 | CH | N | 3 | 4 | Me | H | —S— | —S— |
| A-369 | CH | N | 3 | 4 | Me | H | —CH$_2$O— | —OCH$_2$— |
| A-370 | CH | N | 3 | 4 | Me | H | singlebond | singlebond |
| A-371 | CH | N | 3 | 4 | H | Me | —O— | —O— |
| A-372 | CH | N | 3 | 4 | H | Me | —O— | —S— |
| A-373 | CH | N | 3 | 4 | H | Me | —O— | —OCH$_2$— |
| A-374 | CH | N | 3 | 4 | H | Me | —O— | singlebond |
| A-375 | CH | N | 3 | 4 | H | Me | —S— | —O— |
| A-376 | CH | N | 3 | 4 | H | Me | —CH$_2$O— | —O— |
| A-377 | CH | N | 3 | 4 | H | Me | singlebond | —O— |
| A-378 | CH | N | 3 | 4 | H | Me | —S— | —S— |
| A-379 | CH | N | 3 | 4 | H | Me | —CH$_2$O— | —OCH$_2$— |
| A-380 | CH | N | 3 | 4 | H | Me | singlebond | singlebond |
| A-381 | CH | N | 3 | 4 | Ph | H | —O— | —O— |
| A-382 | CH | N | 3 | 4 | Ph | H | —O— | —S— |
| A-383 | CH | N | 3 | 4 | Ph | H | —O— | —OCH$_2$— |
| A-384 | CH | N | 3 | 4 | Ph | H | —O— | singlebond |
| A-385 | CH | N | 3 | 4 | Ph | H | —S— | —O— |
| A-386 | CH | N | 3 | 4 | Ph | H | —CH$_2$O— | —O— |
| A-387 | CH | N | 3 | 4 | Ph | H | singlebond | —O— |
| A-388 | CH | N | 3 | 4 | Ph | H | —S— | —S— |
| A-389 | CH | N | 3 | 4 | Ph | H | —CH$_2$O— | —OCH$_2$— |
| A-390 | CH | N | 3 | 4 | Ph | H | singlebond | singlebond |
| A-391 | CH | N | 3 | 4 | H | Ph | —O— | —O— |
| A-392 | CH | N | 3 | 4 | H | Ph | —O— | —S— |
| A-393 | CH | N | 3 | 4 | H | Ph | —O— | —OCH$_2$— |
| A-394 | CH | N | 3 | 4 | H | Ph | —O— | singlebond |
| A-395 | CH | N | 3 | 4 | H | Ph | —S— | —O— |
| A-396 | CH | N | 3 | 4 | H | Ph | —CH$_2$O— | —O— |
| A-397 | CH | N | 3 | 4 | H | Ph | singlebond | —O— |
| A-398 | CH | N | 3 | 4 | H | Ph | —S— | —S— |
| A-399 | CH | N | 3 | 4 | H | Ph | —CH$_2$O— | —OCH$_2$— |
| A-400 | CH | N | 3 | 4 | H | Ph | singlebond | singlebond |
| A-401 | CH | N | 4 | 3 | Me | H | —O— | —O— |
| A-402 | CH | N | 4 | 3 | Me | H | —O— | —S— |
| A-403 | CH | N | 4 | 3 | Me | H | —O— | —OCH$_2$— |
| A-404 | CH | N | 4 | 3 | Me | H | —O— | singlebond |
| A-405 | CH | N | 4 | 3 | Me | H | —S— | —O— |
| A-406 | CH | N | 4 | 3 | Me | H | —CH$_2$O— | —O— |
| A-407 | CH | N | 4 | 3 | Me | H | singlebond | —O— |
| A-408 | CH | N | 4 | 3 | Me | H | —S— | —S— |
| A-409 | CH | N | 4 | 3 | Me | H | —CH$_2$O— | —OCH$_2$— |
| A-410 | CH | N | 4 | 3 | Me | H | singlebond | singlebond |
| A-411 | CH | N | 4 | 3 | H | Me | —O— | —O— |
| A-412 | CH | N | 4 | 3 | H | Me | —O— | —S— |
| A-413 | CH | N | 4 | 3 | H | Me | —O— | —OCH$_2$— |
| A-414 | CH | N | 4 | 3 | H | Me | —O— | singlebond |
| A-415 | CH | N | 4 | 3 | H | Me | —S— | —O— |
| A-416 | CH | N | 4 | 3 | H | Me | —CH$_2$O— | —O— |
| A-417 | CH | N | 4 | 3 | H | Me | singlebond | —O— |
| A-418 | CH | N | 4 | 3 | H | Me | —S— | —S— |
| A-419 | CH | N | 4 | 3 | H | Me | —CH$_2$O— | —OCH$_2$— |
| A-420 | CH | N | 4 | 3 | H | Me | singlebond | singlebond |
| A-421 | CH | N | 4 | 3 | Ph | H | —O— | —O— |
| A-422 | CH | N | 4 | 3 | Ph | H | —O— | —S— |
| A-423 | CH | N | 4 | 3 | Ph | H | —O— | —OCH$_2$— |
| A-424 | CH | N | 4 | 3 | Ph | H | —O— | singlebond |
| A-425 | CH | N | 4 | 3 | Ph | H | —S— | —O— |
| A-426 | CH | N | 4 | 3 | Ph | H | —CH$_2$O— | —O— |
| A-427 | CH | N | 4 | 3 | Ph | H | singlebond | —O— |
| A-428 | CH | N | 4 | 3 | Ph | H | —S— | —S— |
| A-429 | CH | N | 4 | 3 | Ph | H | —CH$_2$O— | —OCH$_2$— |
| A-430 | CH | N | 4 | 3 | Ph | H | singlebond | singlebond |
| A-431 | CH | N | 4 | 3 | H | Ph | —O— | —O— |
| A-432 | CH | N | 4 | 3 | H | Ph | —O— | —S— |
| A-433 | CH | N | 4 | 3 | H | Ph | —O— | —OCH$_2$— |
| A-434 | CH | N | 4 | 3 | H | Ph | —O— | singlebond |
| A-435 | CH | N | 4 | 3 | H | Ph | —S— | —O— |
| A-436 | CH | N | 4 | 3 | H | Ph | —CH$_2$O— | —O— |
| A-437 | CH | N | 4 | 3 | H | Ph | singlebond | —O— |
| A-438 | CH | N | 4 | 3 | H | Ph | —S— | —S— |
| A-439 | CH | N | 4 | 3 | H | Ph | —CH$_2$O— | —OCH$_2$— |
| A-440 | CH | N | 4 | 3 | H | Ph | singlebond | singlebond |

TABLE 5

| Compound No. | G$^1$ | G$^2$ | n | m | R$^a$ | R$^c$ | Q$^1$ | Q$^2$ |
|---|---|---|---|---|---|---|---|---|
| A-441 | CH | N | 4 | 4 | Me | H | —O— | —O— |
| A-442 | CH | N | 4 | 4 | Me | H | —O— | —S— |
| A-443 | CH | N | 4 | 4 | Me | H | —O— | —OCH$_2$— |
| A-444 | CH | N | 4 | 4 | Me | H | —O— | singlebond |
| A-445 | CH | N | 4 | 4 | Me | H | —S— | —O— |
| A-446 | CH | N | 4 | 4 | Me | H | —CH$_2$O— | —O— |
| A-447 | CH | N | 4 | 4 | Me | H | | —O— |
| A-448 | CH | N | 4 | 4 | Me | H | —S— | —S— |
| A-449 | CH | N | 4 | 4 | Me | H | —CH$_2$O— | —OCH$_2$— |
| A-450 | CH | N | 4 | 4 | Me | H | singlebond | singlebond |
| A-451 | CH | N | 4 | 4 | H | Me | —O— | —O— |
| A-452 | CH | N | 4 | 4 | H | Me | —O— | —S— |
| A-453 | CH | N | 4 | 4 | H | Me | —O— | —OCH$_2$— |
| A-454 | CH | N | 4 | 4 | H | Me | —O— | singlebond |
| A-455 | CH | N | 4 | 4 | H | Me | —S— | —O— |
| A-456 | CH | N | 4 | 4 | H | Me | —CH$_2$O— | —O— |
| A-457 | CH | N | 4 | 4 | H | Me | singlebond | —O— |
| A-458 | CH | N | 4 | 4 | H | Me | —S— | —S— |
| A-459 | CH | N | 4 | 4 | H | Me | —CH$_2$O— | —OCH$_2$— |
| A-460 | CH | N | 4 | 4 | H | Me | singlebond | singlebond |
| A-461 | CH | N | 4 | 4 | Ph | H | —O— | —O— |
| A-462 | CH | N | 4 | 4 | Ph | H | —O— | —S— |
| A-463 | CH | N | 4 | 4 | Ph | H | —O— | —OCH$_2$— |
| A-464 | CH | N | 4 | 4 | Ph | H | —O— | singlebond |
| A-465 | CH | N | 4 | 4 | Ph | H | —S— | —O— |
| A-466 | CH | N | 4 | 4 | Ph | H | —CH$_2$O— | —O— |
| A-467 | CH | N | 4 | 4 | Ph | H | singlebond | —O— |
| A-468 | CH | N | 4 | 4 | Ph | H | —S— | —S— |
| A-469 | CH | N | 4 | 4 | Ph | H | —CH$_2$O— | —OCH$_2$— |
| A-470 | CH | N | 4 | 4 | Ph | H | singlebond | singlebond |
| A-471 | CH | N | 4 | 4 | H | Ph | —O— | —O— |
| A-472 | CH | N | 4 | 4 | H | Ph | —O— | —S— |
| A-473 | CH | N | 4 | 4 | H | Ph | —O— | —OCH$_2$— |
| A-474 | CH | N | 4 | 4 | H | Ph | —O— | singlebond |
| A-475 | CH | N | 4 | 4 | H | Ph | —S— | —O— |

TABLE 5-continued

| Compound No. | G¹ | G² | n | m | $R^a$ | $R^c$ | Q¹ | Q² |
|---|---|---|---|---|---|---|---|---|
| A-476 | CH | N | 4 | 4 | H | Ph | —CH₂O— | —O— |
| A-477 | CH | N | 4 | 4 | H | Ph | singlebond | —O— |
| A-478 | CH | N | 4 | 4 | H | Ph | —S— | —S— |
| A-479 | CH | N | 4 | 4 | H | Ph | —CH₂O— | —OCH₂— |
| A-480 | CH | N | 4 | 4 | H | Ph | singlebond | singlebond |
| A-481 | CH | CH | 2 | 5 | H | H | —O— | —O— |
| A-482 | CH | CH | 3 | 5 | H | H | —O— | —O— |
| A-483 | CH | CH | 5 | 2 | H | H | —O— | —O— |
| A-484 | CH | CH | 5 | 3 | H | H | —O— | —O— |

TABLE 6

| Compound No. | G¹ | G² | n | m | $R^a$ | $R^c$ | Q¹ | Q² |
|---|---|---|---|---|---|---|---|---|
| B-1 | CH | CH | 3 | 3 | Me | H | —O— | —O— |
| B-2 | CH | CH | 3 | 3 | Me | H | —O— | —S— |
| B-3 | CH | CH | 3 | 3 | Me | H | —O— | —OCH₂— |
| B-4 | CH | CH | 3 | 3 | Me | H | —O— | singlebond |
| B-5 | CH | CH | 3 | 3 | Me | H | —S— | —O— |
| B-6 | CH | CH | 3 | 3 | Me | H | —CH₂O— | —O— |
| B-7 | CH | CH | 3 | 3 | Me | H | singlebond | —O— |
| B-8 | CH | CH | 3 | 3 | Me | H | —S— | —S— |
| B-9 | CH | CH | 3 | 3 | Me | H | —CH₂O— | —OCH₂— |
| B-10 | CH | CH | 3 | 3 | Me | H | singlebond | singlebond |
| B-11 | CH | CH | 3 | 3 | H | Me | —O— | —O— |
| B-12 | CH | CH | 3 | 3 | H | Me | —O— | —S— |
| B-13 | CH | CH | 3 | 3 | H | Me | —O— | —OCH₂— |
| B-14 | CH | CH | 3 | 3 | H | Me | —O— | singlebond |
| B-15 | CH | CH | 3 | 3 | H | Me | —S— | —O— |
| B-16 | CH | CH | 3 | 3 | H | Me | —CH₂O— | —O— |
| B-17 | CH | CH | 3 | 3 | H | Me | singlebond | —O— |
| B-18 | CH | CH | 3 | 3 | H | Me | —S— | —S— |
| B-19 | CH | CH | 3 | 3 | H | Me | —CH₂O— | —OCH₂— |
| B-20 | CH | CH | 3 | 3 | H | Me | singlebond | singlebond |
| B-21 | CH | CH | 3 | 3 | Ph | H | —O— | —O— |
| B-22 | CH | CH | 3 | 3 | Ph | H | —O— | —S— |
| B-23 | CH | CH | 3 | 3 | Ph | H | —O— | —OCH₂— |
| B-24 | CH | CH | 3 | 3 | Ph | H | —O— | singlebond |
| B-25 | CH | CH | 3 | 3 | Ph | H | —S— | —O— |
| B-26 | CH | CH | 3 | 3 | Ph | H | —CH₂O— | —O— |
| B-27 | CH | CH | 3 | 3 | Ph | H | singlebond | —O— |
| B-28 | CH | CH | 3 | 3 | Ph | H | —S— | —S— |
| B-29 | CH | CH | 3 | 3 | Ph | H | —CH₂O— | —OCH₂— |
| B-30 | CH | CH | 3 | 3 | Ph | H | singlebond | singlebond |
| B-31 | CH | CH | 3 | 3 | H | Ph | —O— | —O— |
| B-32 | CH | CH | 3 | 3 | H | Ph | —O— | —S— |
| B-33 | CH | CH | 3 | 3 | H | Ph | —O— | —OCH₂— |
| B-34 | CH | CH | 3 | 3 | H | Ph | —O— | singlebond |
| B-35 | CH | CH | 3 | 3 | H | Ph | —S— | —O— |
| B-36 | CH | CH | 3 | 3 | H | Ph | —CH₂O— | —O— |
| B-37 | CH | CH | 3 | 3 | H | Ph | singlebond | —O— |
| B-38 | CH | CH | 3 | 3 | H | Ph | —S— | —S— |
| B-39 | CH | CH | 3 | 3 | H | Ph | —CH₂O— | —OCH₂— |
| B-40 | CH | CH | 3 | 3 | H | Ph | singlebond | singlebond |
| B-41 | CH | CH | 3 | 4 | Me | H | —O— | —O— |
| B-42 | CH | CH | 3 | 4 | Me | H | —O— | —S— |
| B-43 | CH | CH | 3 | 4 | Me | H | —O— | —OCH₂— |
| B-44 | CH | CH | 3 | 4 | Me | H | —O— | singlebond |
| B-45 | CH | CH | 3 | 4 | Me | H | —S— | —O— |
| B-46 | CH | CH | 3 | 4 | Me | H | —CH₂O— | —O— |
| B-47 | CH | CH | 3 | 4 | Me | H | singlebond | —O— |
| B-48 | CH | CH | 3 | 4 | Me | H | —S— | —S— |
| B-49 | CH | CH | 3 | 4 | Me | H | —CH₂O— | —OCH₂— |
| B-50 | CH | CH | 3 | 4 | Me | H | singlebond | singlebond |
| B-51 | CH | CH | 3 | 4 | H | Me | —O— | —O— |
| B-52 | CH | CH | 3 | 4 | H | Me | —O— | —S— |
| B-53 | CH | CH | 3 | 4 | H | Me | —O— | —OCH₂— |
| B-54 | CH | CH | 3 | 4 | H | Me | —O— | singlebond |
| B-55 | CH | CH | 3 | 4 | H | Me | —S— | —O— |
| B-56 | CH | CH | 3 | 4 | H | Me | —CH₂O— | —O— |
| B-57 | CH | CH | 3 | 4 | H | Me | singlebond | —O— |
| B-58 | CH | CH | 3 | 4 | H | Me | —S— | —S— |
| B-59 | CH | CH | 3 | 4 | H | Me | —CH₂O— | —OCH₂— |
| B-60 | CH | CH | 3 | 4 | H | Me | singlebond | singlebond |
| B-61 | CH | CH | 3 | 4 | Ph | H | —O— | —O— |
| B-62 | CH | CH | 3 | 4 | Ph | H | —O— | —S— |
| B-63 | CH | CH | 3 | 4 | Ph | H | —O— | —OCH₂— |
| B-64 | CH | CH | 3 | 4 | Ph | H | —O— | singlebond |
| B-65 | CH | CH | 3 | 4 | Ph | H | —S— | —O— |
| B-66 | CH | CH | 3 | 4 | Ph | H | —CH₂O— | —O— |
| B-67 | CH | CH | 3 | 4 | Ph | H | singlebond | —O— |
| B-68 | CH | CH | 3 | 4 | Ph | H | —S— | —S— |
| B-69 | CH | CH | 3 | 4 | Ph | H | —CH₂O— | —OCH₂— |
| B-70 | CH | CH | 3 | 4 | Ph | H | singlebond | singlebond |
| B-71 | CH | CH | 3 | 4 | H | Ph | —O— | —O— |
| B-72 | CH | CH | 3 | 4 | H | Ph | —O— | —S— |
| B-73 | CH | CH | 3 | 4 | H | Ph | —O— | —OCH₂— |
| B-74 | CH | CH | 3 | 4 | H | Ph | —O— | singlebond |
| B-75 | CH | CH | 3 | 4 | H | Ph | —S— | —O— |
| B-76 | CH | CH | 3 | 4 | H | Ph | —CH₂O— | —O— |
| B-77 | CH | CH | 3 | 4 | H | Ph | singlebond | —O— |
| B-78 | CH | CH | 3 | 4 | H | Ph | —S— | —S— |
| B-79 | CH | CH | 3 | 4 | H | Ph | —CH₂O— | —OCH₂— |
| B-80 | CH | CH | 3 | 4 | H | Ph | singlebond | singlebond |
| B-81 | CH | CH | 4 | 3 | Me | H | —O— | —O— |
| B-82 | CH | CH | 4 | 3 | Me | H | —O— | —S— |
| B-83 | CH | CH | 4 | 3 | Me | H | —O— | —OCH₂— |
| B-84 | CH | CH | 4 | 3 | Me | H | —O— | singlebond |
| B-85 | CH | CH | 4 | 3 | Me | H | —S— | —O— |
| B-86 | CH | CH | 4 | 3 | Me | H | —CH₂O— | —O— |
| B-87 | CH | CH | 4 | 3 | Me | H | singlebond | —O— |
| B-88 | CH | CH | 4 | 3 | Me | H | —S— | —S— |
| B-89 | CH | CH | 4 | 3 | Me | H | —CH₂O— | —OCH₂— |
| B-90 | CH | CH | 4 | 3 | Me | H | singlebond | singlebond |
| B-91 | CH | CH | 4 | 3 | H | Me | —O— | —O— |
| B-92 | CH | CH | 4 | 3 | H | Me | —O— | —S— |
| B-93 | CH | CH | 4 | 3 | H | Me | —O— | —OCH₂— |
| B-94 | CH | CH | 4 | 3 | H | Me | —O— | singlebond |
| B-95 | CH | CH | 4 | 3 | H | Me | —S— | —O— |
| B-96 | CH | CH | 4 | 3 | H | Me | —CH₂O— | —O— |
| B-97 | CH | CH | 4 | 3 | H | Me | singlebond | —O— |
| B-98 | CH | CH | 4 | 3 | H | Me | —S— | —S— |
| B-99 | CH | CH | 4 | 3 | H | Me | —CH₂O— | —OCH₂— |
| B-100 | CH | CH | 4 | 3 | H | Me | singlebond | singlebond |
| B-101 | CH | CH | 4 | 3 | Ph | H | —O— | —O— |
| B-102 | CH | CH | 4 | 3 | Ph | H | —O— | —S— |
| B-103 | CH | CH | 4 | 3 | Ph | H | —O— | —OCH₂— |
| B-104 | CH | CH | 4 | 3 | Ph | H | —O— | singlebond |
| B-105 | CH | CH | 4 | 3 | Ph | H | —S— | —O— |
| B-106 | CH | CH | 4 | 3 | Ph | H | —CH₂O— | —O— |
| B-107 | CH | CH | 4 | 3 | Ph | H | singlebond | —O— |
| B-108 | CH | CH | 4 | 3 | Ph | H | —S— | —S— |
| B-109 | CH | CH | 4 | 3 | Ph | H | —CH₂O— | —OCH₂— |
| B-110 | CH | CH | 4 | 3 | Ph | H | singlebond | singlebond |

TABLE 7

| Compound No. | G¹ | G² | n | m | $R^a$ | $R^c$ | Q¹ | Q² |
|---|---|---|---|---|---|---|---|---|
| B-111 | CH | CH | 4 | 3 | H | Ph | —O— | —O— |
| B-112 | CH | CH | 4 | 3 | H | Ph | —O— | —S— |
| B-113 | CH | CH | 4 | 3 | H | Ph | —O— | —OCH₂— |
| B-114 | CH | CH | 4 | 3 | H | Ph | —O— | singlebond |
| B-115 | CH | CH | 4 | 3 | H | Ph | —S— | —O— |

TABLE 7-continued

| Compound No. | G¹ | G² | n | m | $R^a$ | $R^c$ | Q¹ | Q² |
|---|---|---|---|---|---|---|---|---|
| B-116 | CH | CH | 4 | 3 | H | Ph | —CH$_2$O— | —O— |
| B-117 | CH | CH | 4 | 3 | H | Ph | singlebond | —O— |
| B-118 | CH | CH | 4 | 3 | H | Ph | —S— | —S— |
| B-119 | CH | CH | 4 | 3 | H | Ph | —CH$_2$O— | —OCH$_2$— |
| B-120 | CH | CH | 4 | 3 | H | Ph | singlebond | singlebond |
| B-121 | CH | CH | 4 | 4 | Me | H | —O— | —O— |
| B-122 | CH | CH | 4 | 4 | Me | H | —O— | —S— |
| B-123 | CH | CH | 4 | 4 | Me | H | —O— | —OCH$_2$— |
| B-124 | CH | CH | 4 | 4 | Me | H | —O— | singlebond |
| B-125 | CH | CH | 4 | 4 | Me | H | —S— | —O— |
| B-126 | CH | CH | 4 | 4 | Me | H | —CH$_2$O— | —O— |
| B-127 | CH | CH | 4 | 4 | Me | H | singlebond | —O— |
| B-128 | CH | CH | 4 | 4 | Me | H | —S— | —S— |
| B-129 | CH | CH | 4 | 4 | Me | H | —CH$_2$O— | —OCH$_2$— |
| B-130 | CH | CH | 4 | 4 | Me | H | singlebond | singlebond |
| B-131 | CH | CH | 4 | 4 | H | Me | —O— | —O— |
| B-132 | CH | CH | 4 | 4 | H | Me | —O— | —S— |
| B-133 | CH | CH | 4 | 4 | H | Me | —O— | —OCH$_2$— |
| B-134 | CH | CH | 4 | 4 | H | Me | —O— | singlebond |
| B-135 | CH | CH | 4 | 4 | H | Me | —S— | —O— |
| B-136 | CH | CH | 4 | 4 | H | Me | —CH$_2$O— | —O— |
| B-137 | CH | CH | 4 | 4 | H | Me | singlebond | —O— |
| B-138 | CH | CH | 4 | 4 | H | Me | —S— | —S— |
| B-139 | CH | CH | 4 | 4 | H | Me | —CH$_2$O— | —OCH$_2$— |
| B-140 | CH | CH | 4 | 4 | H | Me | singlebond | singlebond |
| B-141 | CH | CH | 4 | 4 | Ph | H | —O— | —O— |
| B-142 | CH | CH | 4 | 4 | Ph | H | —O— | —S— |
| B-143 | CH | CH | 4 | 4 | Ph | H | —O— | —OCH$_2$— |
| B-144 | CH | CH | 4 | 4 | Ph | H | —O— | singlebond |
| B-145 | CH | CH | 4 | 4 | Ph | H | —S— | —O— |
| B-146 | CH | CH | 4 | 4 | Ph | H | —CH$_2$O— | —O— |
| B-147 | CH | CH | 4 | 4 | Ph | H | singlebond | —O— |
| B-148 | CH | CH | 4 | 4 | Ph | H | —S— | —S— |
| B-149 | CH | CH | 4 | 4 | Ph | H | —CH$_2$O— | —OCH$_2$— |
| B-150 | CH | CH | 4 | 4 | Ph | H | singlebond | singlebond |
| B-151 | CH | CH | 4 | 4 | H | Ph | —O— | —O— |
| B-152 | CH | CH | 4 | 4 | H | Ph | —O— | —S— |
| B-153 | CH | CH | 4 | 4 | H | Ph | —O— | —OCH$_2$— |
| B-154 | CH | CH | 4 | 4 | H | Ph | —O— | singlebond |
| B-155 | CH | CH | 4 | 4 | H | Ph | —S— | —O— |
| B-156 | CH | CH | 4 | 4 | H | Ph | —CH$_2$O— | —O— |
| B-157 | CH | CH | 4 | 4 | H | Ph | singlebond | —O— |
| B-158 | CH | CH | 4 | 4 | H | Ph | —S— | —S— |
| B-159 | CH | CH | 4 | 4 | H | Ph | —CH$_2$O— | —OCH$_2$— |
| B-160 | CH | CH | 4 | 4 | H | Ph | singlebond | singlebond |
| B-161 | N | CH | 3 | 3 | Me | H | —O— | —O— |
| B-162 | N | CH | 3 | 3 | Me | H | —O— | —S— |
| B-163 | N | CH | 3 | 3 | Me | H | —O— | —OCH$_2$— |
| B-164 | N | CH | 3 | 3 | Me | H | —O— | singlebond |
| B-165 | N | CH | 3 | 3 | Me | H | —S— | —O— |
| B-166 | N | CH | 3 | 3 | Me | H | —CH$_2$O— | —O— |
| B-167 | N | CH | 3 | 3 | Me | H | singlebond | —O— |
| B-168 | N | CH | 3 | 3 | Me | H | —S— | —S— |
| B-169 | N | CH | 3 | 3 | Me | H | —CH$_2$O— | —OCH$_2$— |
| B-170 | N | CH | 3 | 3 | Me | H | singlebond | singlebond |
| B-171 | N | CH | 3 | 3 | H | Me | —O— | —O— |
| B-172 | N | CH | 3 | 3 | H | Me | —O— | —S— |
| B-173 | N | CH | 3 | 3 | H | Me | —O— | —OCH$_2$— |
| B-174 | N | CH | 3 | 3 | H | Me | —O— | singlebond |
| B-175 | N | CH | 3 | 3 | H | Me | —S— | —O— |
| B-176 | N | CH | 3 | 3 | H | Me | —CH$_2$O— | —O— |
| B-177 | N | CH | 3 | 3 | H | Me | singlebond | —O— |
| B-178 | N | CH | 3 | 3 | H | Me | —S— | —S— |
| B-179 | N | CH | 3 | 3 | H | Me | —CH$_2$O— | —OCH$_2$— |
| B-180 | N | CH | 3 | 3 | H | Me | singlebond | singlebond |
| B-181 | N | CH | 3 | 3 | Ph | H | —O— | —O— |
| B-182 | N | CH | 3 | 3 | Ph | H | —O— | —S— |
| B-183 | N | CH | 3 | 3 | Ph | H | —O— | —OCH$_2$— |
| B-184 | N | CH | 3 | 3 | Ph | H | —O— | singlebond |
| B-185 | N | CH | 3 | 3 | Ph | H | —S— | —O— |
| B-186 | N | CH | 3 | 3 | Ph | H | —CH$_2$O— | —O— |
| B-187 | N | CH | 3 | 3 | Ph | H | singlebond | —O— |
| B-188 | N | CH | 3 | 3 | Ph | H | —S— | —S— |
| B-189 | N | CH | 3 | 3 | Ph | H | —CH$_2$O— | —OCH$_2$— |
| B-190 | N | CH | 3 | 3 | Ph | H | singlebond | singlebond |
| B-191 | N | CH | 3 | 3 | H | Ph | —O— | —O— |
| B-192 | N | CH | 3 | 3 | H | Ph | —O— | —S— |
| B-193 | N | CH | 3 | 3 | H | Ph | —O— | —OCH$_2$— |
| B-194 | N | CH | 3 | 3 | H | Ph | —O— | singlebond |
| B-195 | N | CH | 3 | 3 | H | Ph | —S— | —O— |
| B-196 | N | CH | 3 | 3 | H | Ph | —CH$_2$O— | —O— |
| B-197 | N | CH | 3 | 3 | H | Ph | singlebond | —O— |
| B-198 | N | CH | 3 | 3 | H | Ph | —S— | —S— |
| B-199 | N | CH | 3 | 3 | H | Ph | —CH$_2$O— | —OCH$_2$— |
| B-200 | N | CH | 3 | 3 | H | Ph | singlebond | singlebond |
| B-201 | N | CH | 3 | 4 | Me | H | —O— | —O— |
| B-202 | N | CH | 3 | 4 | Me | H | —O— | —S— |
| B-203 | N | CH | 3 | 4 | Me | H | —O— | —OCH$_2$— |
| B-204 | N | CH | 3 | 4 | Me | H | —O— | singlebond |
| B-205 | N | CH | 3 | 4 | Me | H | —S— | —O— |
| B-206 | N | CH | 3 | 4 | Me | H | —CH$_2$O— | —O— |
| B-207 | N | CH | 3 | 4 | Me | H | singlebond | —O— |
| B-208 | N | CH | 3 | 4 | Me | H | —S— | —S— |
| B-209 | N | CH | 3 | 4 | Me | H | —CH$_2$O— | —OCH$_2$— |
| B-210 | N | CH | 3 | 4 | Me | H | singlebond | singlebond |
| B-211 | N | CH | 3 | 4 | H | Me | —O— | —O— |
| B-212 | N | CH | 3 | 4 | H | Me | —O— | —S— |
| B-213 | N | CH | 3 | 4 | H | Me | —O— | —OCH$_2$— |
| B-214 | N | CH | 3 | 4 | H | Me | —O— | singlebond |
| B-215 | N | CH | 3 | 4 | H | Me | —S— | —O— |
| B-216 | N | CH | 3 | 4 | H | Me | —CH$_2$O— | —O— |
| B-217 | N | CH | 3 | 4 | H | Me | | —O— |
| B-218 | N | CH | 3 | 4 | H | Me | —S— | —S— |
| B-219 | N | CH | 3 | 4 | H | Me | —CH$_2$O— | —OCH$_2$— |
| B-220 | N | CH | 3 | 4 | H | Me | singlebond | singlebond |

TABLE 8

| Compound No. | G¹ | G² | n | m | $R^a$ | $R^c$ | Q¹ | Q² |
|---|---|---|---|---|---|---|---|---|
| B-221 | N | CH | 3 | 4 | Ph | H | —O— | —O— |
| B-222 | N | CH | 3 | 4 | Ph | H | —O— | —S— |
| B-223 | N | CH | 3 | 4 | Ph | H | —O— | —OCH$_2$— |
| B-224 | N | CH | 3 | 4 | Ph | H | —O— | singlebond |
| B-225 | N | CH | 3 | 4 | Ph | H | —S— | —O— |
| B-226 | N | CH | 3 | 4 | Ph | H | —CH$_2$O— | —O— |
| B-227 | N | CH | 3 | 4 | Ph | H | singlebond | —O— |
| B-228 | N | CH | 3 | 4 | Ph | H | —S— | —S— |
| B-229 | N | CH | 3 | 4 | Ph | H | —CH$_2$O— | —OCH$_2$— |
| B-230 | N | CH | 3 | 4 | Ph | H | singlebond | singlebond |
| B-231 | N | CH | 3 | 4 | H | Ph | —O— | —O— |
| B-232 | N | CH | 3 | 4 | H | Ph | —O— | —S— |
| B-233 | N | CH | 3 | 4 | H | Ph | —O— | —OCH$_2$— |
| B-234 | N | CH | 3 | 4 | H | Ph | —O— | singlebond |
| B-235 | N | CH | 3 | 4 | H | Ph | —S— | —O— |
| B-236 | N | CH | 3 | 4 | H | Ph | —CH$_2$O— | —O— |
| B-237 | N | CH | 3 | 4 | H | Ph | singlebond | —O— |
| B-238 | N | CH | 3 | 4 | H | Ph | —S— | —S— |
| B-239 | N | CH | 3 | 4 | H | Ph | —CH$_2$O— | —OCH$_2$— |
| B-240 | N | CH | 3 | 4 | H | Ph | singlebond | singlebond |
| B-241 | N | CH | 4 | 3 | Me | H | —O— | —O— |
| B-242 | N | CH | 4 | 3 | Me | H | —O— | —S— |
| B-243 | N | CH | 4 | 3 | Me | H | —O— | —OCH$_2$— |
| B-244 | N | CH | 4 | 3 | Me | H | —O— | singlebond |
| B-245 | N | CH | 4 | 3 | Me | H | —S— | —O— |
| B-246 | N | CH | 4 | 3 | Me | H | —CH$_2$O— | —O— |
| B-247 | N | CH | 4 | 3 | Me | H | singlebond | —O— |
| B-248 | N | CH | 4 | 3 | Me | H | —S— | —S— |
| B-249 | N | CH | 4 | 3 | Me | H | —CH$_2$O— | —OCH$_2$— |
| B-250 | N | CH | 4 | 3 | Me | H | singlebond | singlebond |
| B-251 | N | CH | 4 | 3 | H | Me | —O— | —O— |
| B-252 | N | CH | 4 | 3 | H | Me | —O— | —S— |
| B-253 | N | CH | 4 | 3 | H | Me | —O— | —OCH$_2$— |
| B-254 | N | CH | 4 | 3 | H | Me | —O— | singlebond |
| B-255 | N | CH | 4 | 3 | H | Me | —S— | —O— |
| B-256 | N | CH | 4 | 3 | H | Me | —CH$_2$O— | —O— |
| B-257 | N | CH | 4 | 3 | H | Me | singlebond | —O— |
| B-258 | N | CH | 4 | 3 | H | Me | —S— | —S— |
| B-259 | N | CH | 4 | 3 | H | Me | —CH$_2$O— | —OCH$_2$— |

TABLE 8-continued

| Compound No. | G¹ | G² | n | m | $R^a$ | $R^e$ | Q¹ | Q² |
|---|---|---|---|---|---|---|---|---|
| B-260 | N | CH | 4 | 3 | H | Me | singlebond | singlebond |
| B-261 | N | CH | 4 | 3 | Ph | H | —O— | —O— |
| B-262 | N | CH | 4 | 3 | Ph | H | —O— | —S— |
| B-263 | N | CH | 4 | 3 | Ph | H | —O— | —OCH₂— |
| B-264 | N | CH | 4 | 3 | Ph | H | —O— | singlebond |
| B-265 | N | CH | 4 | 3 | Ph | H | —S— | —O— |
| B-266 | N | CH | 4 | 3 | Ph | H | —CH₂O— | —O— |
| B-267 | N | CH | 4 | 3 | Ph | H | singlebond | —O— |
| B-268 | N | CH | 4 | 3 | Ph | H | —S— | —S— |
| B-269 | N | CH | 4 | 3 | Ph | H | —CH₂O— | —OCH₂— |
| B-270 | N | CH | 4 | 3 | Ph | H | singlebond | singlebond |
| B-271 | N | CH | 4 | 3 | H | Ph | —O— | —O— |
| B-272 | N | CH | 4 | 3 | H | Ph | —O— | —S— |
| B-273 | N | CH | 4 | 3 | H | Ph | —O— | —OCH₂— |
| B-274 | N | CH | 4 | 3 | H | Ph | —O— | singlebond |
| B-275 | N | CH | 4 | 3 | H | Ph | —S— | —O— |
| B-276 | N | CH | 4 | 3 | H | Ph | —CH₂O— | —O— |
| B-277 | N | CH | 4 | 3 | H | Ph | singlebond | —O— |
| B-278 | N | CH | 4 | 3 | H | Ph | —S— | —S— |
| B-279 | N | CH | 4 | 3 | H | Ph | —CH₂O— | —OCH₂— |
| B-280 | N | CH | 4 | 3 | H | Ph | singlebond | singlebond |
| B-281 | N | CH | 4 | 4 | Me | H | —O— | —O— |
| B-282 | N | CH | 4 | 4 | Me | H | —O— | —S— |
| B-283 | N | CH | 4 | 4 | Me | H | —O— | —OCH₂— |
| B-284 | N | CH | 4 | 4 | Me | H | —O— | singlebond |
| B-285 | N | CH | 4 | 4 | Me | H | —S— | —O— |
| B-286 | N | CH | 4 | 4 | Me | H | —CH₂O— | —O— |
| B-287 | N | CH | 4 | 4 | Me | H | singlebond | —O— |
| B-288 | N | CH | 4 | 4 | Me | H | —S— | —S— |
| B-289 | N | CH | 4 | 4 | Me | H | —CH₂O— | —OCH₂— |
| B-290 | N | CH | 4 | 4 | Me | H | singlebond | singlebond |
| B-291 | N | CH | 4 | 4 | H | Me | —O— | —O— |
| B-292 | N | CH | 4 | 4 | H | Me | —O— | —S— |
| B-293 | N | CH | 4 | 4 | H | Me | —O— | —OCH₂— |
| B-294 | N | CH | 4 | 4 | H | Me | —O— | singlebond |
| B-295 | N | CH | 4 | 4 | H | Me | —S— | —O— |
| B-296 | N | CH | 4 | 4 | H | Me | —CH₂O— | —O— |
| B-297 | N | CH | 4 | 4 | H | Me | singlebond | —O— |
| B-298 | N | CH | 4 | 4 | H | Me | —S— | —S— |
| B-299 | N | CH | 4 | 4 | H | Me | —CH₂O— | —OCH₂— |
| B-300 | N | CH | 4 | 4 | H | Me | singlebond | singlebond |
| B-301 | N | CH | 4 | 4 | Ph | H | —O— | —O— |
| B-302 | N | CH | 4 | 4 | Ph | H | —O— | —S— |
| B-303 | N | CH | 4 | 4 | Ph | H | —O— | —OCH₂— |
| B-304 | N | CH | 4 | 4 | Ph | H | —O— | singlebond |
| B-305 | N | CH | 4 | 4 | Ph | H | —S— | —O— |
| B-306 | N | CH | 4 | 4 | Ph | H | —CH₂O— | —O— |
| B-307 | N | CH | 4 | 4 | Ph | H | singlebond | —O— |
| B-308 | N | CH | 4 | 4 | Ph | H | —S— | —S— |
| B-309 | N | CH | 4 | 4 | Ph | H | —CH₂O— | —OCH₂— |
| B-310 | N | CH | 4 | 4 | Ph | H | singlebond | singlebond |
| B-311 | N | CH | 4 | 4 | H | Ph | —O— | —O— |
| B-312 | N | CH | 4 | 4 | H | Ph | —O— | —S— |
| B-313 | N | CH | 4 | 4 | H | Ph | —O— | —OCH₂— |
| B-314 | N | CH | 4 | 4 | H | Ph | —O— | singlebond |
| B-315 | N | CH | 4 | 4 | H | Ph | —S— | —O— |
| B-316 | N | CH | 4 | 4 | H | Ph | —CH₂O— | —O— |
| B-317 | N | CH | 4 | 4 | H | Ph | singlebond | —O— |
| B-318 | N | CH | 4 | 4 | H | Ph | —S— | —S— |
| B-319 | N | CH | 4 | 4 | H | Ph | —CH₂O— | —OCH₂— |
| B-320 | N | CH | 4 | 4 | H | Ph | singlebond | singlebond |
| B-321 | CH | N | 3 | 3 | Me | H | —O— | —O— |
| B-322 | CH | N | 3 | 3 | Me | H | —O— | —S— |
| B-323 | CH | N | 3 | 3 | Me | H | —O— | —OCH₂— |
| B-324 | CH | N | 3 | 3 | Me | H | —O— | singlebond |
| B-325 | CH | N | 3 | 3 | Me | H | —S— | —O— |
| B-326 | CH | N | 3 | 3 | Me | H | —CH₂O— | —O— |
| B-327 | CH | N | 3 | 3 | Me | H | singlebond | —O— |
| B-328 | CH | N | 3 | 3 | Me | H | —S— | —S— |
| B-329 | CH | N | 3 | 3 | Me | H | —CH₂O— | —OCH₂— |
| B-330 | CH | N | 3 | 3 | Me | H | singlebond | singlebond |

TABLE 9

| Compound No. | G¹ | G² | n | m | $R^a$ | $R^e$ | Q¹ | Q² |
|---|---|---|---|---|---|---|---|---|
| B-331 | CH | N | 3 | 3 | H | Me | —O— | —O— |
| B-332 | CH | N | 3 | 3 | H | Me | —O— | —S— |
| B-333 | CH | N | 3 | 3 | H | Me | —O— | —OCH₂— |
| B-334 | CH | N | 3 | 3 | H | Me | —O— | singlebond |
| B-335 | CH | N | 3 | 3 | H | Me | —S— | —O— |
| B-336 | CH | N | 3 | 3 | H | Me | —CH₂O— | —O— |
| B-337 | CH | N | 3 | 3 | H | Me | singlebond | —O— |
| B-338 | CH | N | 3 | 3 | H | Me | —S— | —S— |
| B-339 | CH | N | 3 | 3 | H | Me | —CH₂O— | —OCH₂— |
| B-340 | CH | N | 3 | 3 | H | Me | singlebond | singlebond |
| B-341 | CH | N | 3 | 3 | Ph | H | —O— | —O— |
| B-342 | CH | N | 3 | 3 | Ph | H | —O— | —S— |
| B-343 | CH | N | 3 | 3 | Ph | H | —O— | —OCH₂— |
| B-344 | CH | N | 3 | 3 | Ph | H | —O— | singlebond |
| B-345 | CH | N | 3 | 3 | Ph | H | —S— | —O— |
| B-346 | CH | N | 3 | 3 | Ph | H | —CH₂O— | —O— |
| B-347 | CH | N | 3 | 3 | Ph | H | singlebond | —O— |
| B-348 | CH | N | 3 | 3 | Ph | H | —S— | —S— |
| B-349 | CH | N | 3 | 3 | Ph | H | —CH₂O— | —OCH₂— |
| B-350 | CH | N | 3 | 3 | Ph | H | singlebond | singlebond |
| B-351 | CH | N | 3 | 3 | H | Ph | —O— | —O— |
| B-352 | CH | N | 3 | 3 | H | Ph | —O— | —S— |
| B-353 | CH | N | 3 | 3 | H | Ph | —O— | —OCH₂— |
| B-354 | CH | N | 3 | 3 | H | Ph | —O— | singlebond |
| B-355 | CH | N | 3 | 3 | H | Ph | —S— | —O— |
| B-356 | CH | N | 3 | 3 | H | Ph | —CH₂O— | —O— |
| B-357 | CH | N | 3 | 3 | H | Ph | singlebond | —O— |
| B-358 | CH | N | 3 | 3 | H | Ph | —S— | —S— |
| B-359 | CH | N | 3 | 3 | H | Ph | —CH₂O— | —OCH₂— |
| B-360 | CH | N | 3 | 3 | H | Ph | singlebond | singlebond |
| B-361 | CH | N | 3 | 4 | Me | H | —O— | —O— |
| B-362 | CH | N | 3 | 4 | Me | H | —O— | —S— |
| B-363 | CH | N | 3 | 4 | Me | H | —O— | —OCH₂— |
| B-364 | CH | N | 3 | 4 | Me | H | —O— | singlebond |
| B-365 | CH | N | 3 | 4 | Me | H | —S— | —O— |
| B-366 | CH | N | 3 | 4 | Me | H | —CH₂O— | —O— |
| B-367 | CH | N | 3 | 4 | Me | H | singlebond | —O— |
| B-368 | CH | N | 3 | 4 | Me | H | —S— | —S— |
| B-369 | CH | N | 3 | 4 | Me | H | —CH₂O— | —OCH₂— |
| B-370 | CH | N | 3 | 4 | Me | H | singlebond | singlebond |
| B-371 | CH | N | 3 | 4 | H | Me | —O— | —O— |
| B-372 | CH | N | 3 | 4 | H | Me | —O— | —S— |
| B-373 | CH | N | 3 | 4 | H | Me | —O— | —OCH₂— |
| B-374 | CH | N | 3 | 4 | H | Me | —O— | singlebond |
| B-375 | CH | N | 3 | 4 | H | Me | —S— | —O— |
| B-376 | CH | N | 3 | 4 | H | Me | —CH₂O— | —O— |
| B-377 | CH | N | 3 | 4 | H | Me | singlebond | —O— |
| B-378 | CH | N | 3 | 4 | H | Me | —S— | —S— |
| B-379 | CH | N | 3 | 4 | H | Me | —CH₂O— | —OCH₂— |
| B-380 | CH | N | 3 | 4 | H | Me | singlebond | singlebond |
| B-381 | CH | N | 3 | 4 | Ph | H | —O— | —O— |
| B-382 | CH | N | 3 | 4 | Ph | H | —O— | —S— |
| B-383 | CH | N | 3 | 4 | Ph | H | —O— | —OCH₂— |
| B-384 | CH | N | 3 | 4 | Ph | H | —O— | singlebond |
| B-385 | CH | N | 3 | 4 | Ph | H | —S— | —O— |
| B-386 | CH | N | 3 | 4 | Ph | H | —CH₂O— | —O— |
| B-387 | CH | N | 3 | 4 | Ph | H | singlebond | —O— |
| B-388 | CH | N | 3 | 4 | Ph | H | —S— | —S— |
| B-389 | CH | N | 3 | 4 | Ph | H | —CH₂O— | —OCH₂— |
| B-390 | CH | N | 3 | 4 | Ph | H | singlebond | singlebond |
| B-391 | CH | N | 3 | 4 | H | Ph | —O— | —O— |
| B-392 | CH | N | 3 | 4 | H | Ph | —O— | —S— |
| B-393 | CH | N | 3 | 4 | H | Ph | —O— | —OCH₂— |
| B-394 | CH | N | 3 | 4 | H | Ph | —O— | singlebond |
| B-395 | CH | N | 3 | 4 | H | Ph | —S— | —O— |
| B-396 | CH | N | 3 | 4 | H | Ph | —CH₂O— | —O— |
| B-397 | CH | N | 3 | 4 | H | Ph | singlebond | —O— |
| B-398 | CH | N | 3 | 4 | H | Ph | —S— | —S— |
| B-399 | CH | N | 3 | 4 | H | Ph | —CH₂O— | —OCH₂— |
| B-400 | CH | N | 3 | 4 | H | Ph | singlebond | singlebond |
| B-401 | CH | N | 4 | 3 | Me | H | —O— | —O— |
| B-402 | CH | N | 4 | 3 | Me | H | —O— | —S— |
| B-403 | CH | N | 4 | 3 | Me | H | —O— | —OCH₂— |
| B-404 | CH | N | 4 | 3 | Me | H | —O— | singlebond |
| B-405 | CH | N | 4 | 3 | Me | H | —S— | —O— |
| B-406 | CH | N | 4 | 3 | Me | H | —CH₂O— | —O— |

TABLE 9-continued

| Compound No. | G¹ | G² | n | m | $R^a$ | $R^c$ | Q¹ | Q² |
|---|---|---|---|---|---|---|---|---|
| B-407 | CH | N | 4 | 3 | Me | H | singlebond | —O— |
| B-408 | CH | N | 4 | 3 | Me | H | —S— | —S— |
| B-409 | CH | N | 4 | 3 | Me | H | —CH₂O— | —OCH₂— |
| B-410 | CH | N | 4 | 3 | Me | H | singlebond | singlebond |
| B-411 | CH | N | 4 | 3 | H | Me | —O— | —O— |
| B-412 | CH | N | 4 | 3 | H | Me | —O— | —S— |
| B-413 | CH | N | 4 | 3 | H | Me | —O— | —OCH₂— |
| B-414 | CH | N | 4 | 3 | H | Me | —O— | singlebond |
| B-415 | CH | N | 4 | 3 | H | Me | —S— | —O— |
| B-416 | CH | N | 4 | 3 | H | Me | —CH₂O— | —O— |
| B-417 | CH | N | 4 | 3 | H | Me | singlebond | —O— |
| B-418 | CH | N | 4 | 3 | H | Me | —S— | —S— |
| B-419 | CH | N | 4 | 3 | H | Me | —CH₂O— | —OCH₂— |
| B-420 | CH | N | 4 | 3 | H | Me | singlebond | singlebond |
| B-421 | CH | N | 4 | 3 | Ph | H | —O— | —O— |
| B-422 | CH | N | 4 | 3 | Ph | H | —O— | —S— |
| B-423 | CH | N | 4 | 3 | Ph | H | —O— | —OCH₂— |
| B-424 | CH | N | 4 | 3 | Ph | H | —O— | singlebond |
| B-425 | CH | N | 4 | 3 | Ph | H | —S— | —O— |
| B-426 | CH | N | 4 | 3 | Ph | H | —CH₂O— | —O— |
| B-427 | CH | N | 4 | 3 | Ph | H | singlebond | —O— |
| B-428 | CH | N | 4 | 3 | Ph | H | —S— | —S— |
| B-429 | CH | N | 4 | 3 | Ph | H | —CH₂O— | —OCH₂— |
| B-430 | CH | N | 4 | 3 | Ph | H | singlebond | singlebond |
| B-431 | CH | N | 4 | 3 | H | Ph | —O— | —O— |
| B-432 | CH | N | 4 | 3 | H | Ph | —O— | —S— |
| B-433 | CH | N | 4 | 3 | H | Ph | —O— | —OCH₂— |
| B-434 | CH | N | 4 | 3 | H | Ph | —O— | singlebond |
| B-435 | CH | N | 4 | 3 | H | Ph | —S— | —O— |
| B-436 | CH | N | 4 | 3 | H | Ph | —CH₂O— | —O— |
| B-437 | CH | N | 4 | 3 | H | Ph | singlebond | —O— |
| B-438 | CH | N | 4 | 3 | H | Ph | —S— | —S— |
| B-439 | CH | N | 4 | 3 | H | Ph | —CH₂O— | —OCH₂— |
| B-440 | CH | N | 4 | 3 | H | Ph | singlebond | singlebond |

TABLE 10

| Compound No. | G¹ | G² | n | m | $R^a$ | $R^c$ | Q¹ | Q² |
|---|---|---|---|---|---|---|---|---|
| B-441 | CH | N | 4 | 4 | Me | H | —O— | —O— |
| B-442 | CH | N | 4 | 4 | Me | H | —O— | —S— |
| B-443 | CH | N | 4 | 4 | Me | H | —O— | —OCH₂— |
| B-444 | CH | N | 4 | 4 | Me | H | —O— | singlebond |
| B-445 | CH | N | 4 | 4 | Me | H | —S— | —O— |
| B-446 | CH | N | 4 | 4 | Me | H | —CH₂O— | —O— |
| B-447 | CH | N | 4 | 4 | Me | H | singlebond | —O— |
| B-448 | CH | N | 4 | 4 | Me | H | —S— | —S— |
| B-449 | CH | N | 4 | 4 | Me | H | —CH₂O— | —OCH₂— |
| B-450 | CH | N | 4 | 4 | Me | H | singlebond | singlebond |
| B-451 | CH | N | 4 | 4 | H | Me | —O— | —O— |
| B-452 | CH | N | 4 | 4 | H | Me | —O— | —S— |
| B-453 | CH | N | 4 | 4 | H | Me | —O— | —OCH₂— |
| B-454 | CH | N | 4 | 4 | H | Me | —O— | singlebond |
| B-455 | CH | N | 4 | 4 | H | Me | —S— | —O— |
| B-456 | CH | N | 4 | 4 | H | Me | —CH₂O— | —O— |
| B-457 | CH | N | 4 | 4 | H | Me | singlebond | —O— |
| B-458 | CH | N | 4 | 4 | H | Me | —S— | —S— |
| B-459 | CH | N | 4 | 4 | H | Me | —CH₂O— | —OCH₂— |
| B-460 | CH | N | 4 | 4 | H | Me | singlebond | singlebond |
| B-461 | CH | N | 4 | 4 | Ph | H | —O— | —O— |
| B-462 | CH | N | 4 | 4 | Ph | H | —O— | —S— |
| B-463 | CH | N | 4 | 4 | Ph | H | —O— | —OCH₂— |
| B-464 | CH | N | 4 | 4 | Ph | H | —O— | singlebond |
| B-465 | CH | N | 4 | 4 | Ph | H | —S— | —O— |
| B-466 | CH | N | 4 | 4 | Ph | H | —CH₂O— | —O— |
| B-467 | CH | N | 4 | 4 | Ph | H | singlebond | —O— |
| B-468 | CH | N | 4 | 4 | Ph | H | —S— | —S— |
| B-469 | CH | N | 4 | 4 | Ph | H | —CH₂O— | —OCH₂— |
| B-470 | CH | N | 4 | 4 | Ph | H | singlebond | singlebond |
| B-471 | CH | N | 4 | 4 | H | Ph | —O— | —O— |
| B-472 | CH | N | 4 | 4 | H | Ph | —O— | —S— |
| B-473 | CH | N | 4 | 4 | H | Ph | —O— | —OCH₂— |
| B-474 | CH | N | 4 | 4 | H | Ph | —O— | singlebond |
| B-475 | CH | N | 4 | 4 | H | Ph | —S— | —O— |
| B-476 | CH | N | 4 | 4 | H | Ph | —CH₂O— | —O— |
| B-477 | CH | N | 4 | 4 | H | Ph | singlebond | —O— |
| B-478 | CH | N | 4 | 4 | H | Ph | —S— | —S— |
| B-479 | CH | N | 4 | 4 | H | Ph | —CH₂O— | —OCH₂— |
| B-480 | CH | N | 4 | 4 | H | Ph | singlebond | singlebond |
| B-481 | CH | CH | 2 | 5 | H | H | —O— | —O— |
| B-482 | CH | CH | 3 | 5 | H | H | —O— | —O— |
| B-483 | CH | CH | 5 | 2 | H | H | —O— | —O— |
| B-484 | CH | CH | 5 | 3 | H | H | —O— | —O— |

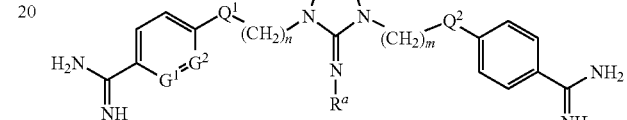

TABLE 11

| Compound No. | G¹ | G² | n | m | $R^a$ | Q¹ | Q² |
|---|---|---|---|---|---|---|---|
| C-1 | CH | CH | 3 | 3 | H | —O— | —O— |
| C-2 | CH | CH | 3 | 3 | H | —O— | —S— |
| C-3 | CH | CH | 3 | 3 | H | —O— | —OCH₂— |
| C-4 | CH | CH | 3 | 3 | H | —O— | singlebond |
| C-5 | CH | CH | 3 | 3 | H | —S— | —O— |
| C-6 | CH | CH | 3 | 3 | H | —CH₂O— | —O— |
| C-7 | CH | CH | 3 | 3 | H | singlebond | —O— |
| C-8 | CH | CH | 3 | 3 | H | —S— | —S— |
| C-9 | CH | CH | 3 | 3 | H | —CH₂O— | —OCH₂— |
| C-10 | CH | CH | 3 | 3 | H | singlebond | singlebond |
| C-11 | CH | CH | 3 | 3 | Me | —O— | —O— |
| C-12 | CH | CH | 3 | 3 | Me | —O— | —S— |
| C-13 | CH | CH | 3 | 3 | Me | —O— | —OCH₂— |
| C-14 | CH | CH | 3 | 3 | Me | —O— | singlebond |
| C-15 | CH | CH | 3 | 3 | Me | —S— | —O— |
| C-16 | CH | CH | 3 | 3 | Me | —CH₂O— | —O— |
| C-17 | CH | CH | 3 | 3 | Me | singlebond | —O— |
| C-18 | CH | CH | 3 | 3 | Me | —S— | —S— |
| C-19 | CH | CH | 3 | 3 | Me | —CH₂O— | —OCH₂— |
| C-20 | CH | CH | 3 | 3 | Me | singlebond | singlebond |
| C-21 | CH | CH | 3 | 3 | Ph | —O— | —O— |
| C-22 | CH | CH | 3 | 3 | Ph | —O— | —S— |
| C-23 | CH | CH | 3 | 3 | Ph | —O— | —OCH₂— |
| C-24 | CH | CH | 3 | 3 | Ph | —O— | singlebond |
| C-25 | CH | CH | 3 | 3 | Ph | —S— | —O— |
| C-26 | CH | CH | 3 | 3 | Ph | —CH₂O— | —O— |
| C-27 | CH | CH | 3 | 3 | Ph | singlebond | —O— |
| C-28 | CH | CH | 3 | 3 | Ph | —S— | —S— |
| C-29 | CH | CH | 3 | 3 | Ph | —CH₂O— | —OCH₂— |
| C-30 | CH | CH | 3 | 3 | Ph | singlebond | singlebond |
| C-31 | CH | CH | 3 | 4 | H | —O— | —O— |
| C-32 | CH | CH | 3 | 4 | H | —O— | —S— |
| C-33 | CH | CH | 3 | 4 | H | —O— | —OCH₂— |
| C-34 | CH | CH | 3 | 4 | H | —O— | singlebond |
| C-35 | CH | CH | 3 | 4 | H | —S— | —O— |
| C-36 | CH | CH | 3 | 4 | H | —CH₂O— | —O— |
| C-37 | CH | CH | 3 | 4 | H | singlebond | —O— |
| C-38 | CH | CH | 3 | 4 | H | —S— | —S— |
| C-39 | CH | CH | 3 | 4 | H | —CH₂O— | —OCH₂— |
| C-40 | CH | CH | 3 | 4 | H | singlebond | singlebond |
| C-41 | CH | CH | 3 | 4 | Me | —O— | —O— |
| C-42 | CH | CH | 3 | 4 | Me | —O— | —S— |
| C-43 | CH | CH | 3 | 4 | Me | —O— | —OCH₂— |
| C-44 | CH | CH | 3 | 4 | Me | —O— | singlebond |

TABLE 11-continued

| Compound No. | G¹ | G² | n | m | $R^a$ | Q¹ | Q² |
|---|---|---|---|---|---|---|---|
| C-45 | CH | CH | 3 | 4 | Me | —S— | —O— |
| C-46 | CH | CH | 3 | 4 | Me | —CH₂O— | —O— |
| C-47 | CH | CH | 3 | 4 | Me | singlebond | —O— |
| C-48 | CH | CH | 3 | 4 | Me | —S— | —S— |
| C-49 | CH | CH | 3 | 4 | Me | —CH₂O— | —OCH₂— |
| C-50 | CH | CH | 3 | 4 | Me | singlebond | singlebond |
| C-51 | CH | CH | 3 | 4 | Ph | —O— | —O— |
| C-52 | CH | CH | 3 | 4 | Ph | —O— | —S— |
| C-53 | CH | CH | 3 | 4 | Ph | —O— | —OCH₂— |
| C-54 | CH | CH | 3 | 4 | Ph | —O— | singlebond |
| C-55 | CH | CH | 3 | 4 | Ph | —S— | —O— |
| C-56 | CH | CH | 3 | 4 | Ph | —CH₂O— | —O— |
| C-57 | CH | CH | 3 | 4 | Ph | singlebond | —O— |
| C-58 | CH | CH | 3 | 4 | Ph | —S— | —S— |
| C-59 | CH | CH | 3 | 4 | Ph | —CH₂O— | —OCH₂— |
| C-60 | CH | CH | 3 | 4 | Ph | singlebond | singlebond |
| C-61 | CH | CH | 4 | 3 | H | —O— | —O— |
| C-62 | CH | CH | 4 | 3 | H | —O— | —S— |
| C-63 | CH | CH | 4 | 3 | H | —O— | —OCH₂— |
| C-64 | CH | CH | 4 | 3 | H | —O— | singlebond |
| C-65 | CH | CH | 4 | 3 | H | —S— | —O— |
| C-66 | CH | CH | 4 | 3 | H | —CH₂O— | —O— |
| C-67 | CH | CH | 4 | 3 | H | singlebond | —O— |
| C-68 | CH | CH | 4 | 3 | H | —S— | —S— |
| C-69 | CH | CH | 4 | 3 | H | —CH₂O— | —OCH₂— |
| C-70 | CH | CH | 4 | 3 | H | singlebond | singlebond |
| C-71 | CH | CH | 4 | 3 | Me | —O— | —O— |
| C-72 | CH | CH | 4 | 3 | Me | —O— | —S— |
| C-73 | CH | CH | 4 | 3 | Me | —O— | —OCH₂— |
| C-74 | CH | CH | 4 | 3 | Me | —O— | singlebond |
| C-75 | CH | CH | 4 | 3 | Me | —S— | —O— |
| C-76 | CH | CH | 4 | 3 | Me | —CH₂O— | —O— |
| C-77 | CH | CH | 4 | 3 | Me | singlebond | —O— |
| C-78 | CH | CH | 4 | 3 | Me | —S— | —S— |
| C-79 | CH | CH | 4 | 3 | Me | —CH₂O— | —OCH₂— |
| C-80 | CH | CH | 4 | 3 | Me | singlebond | singlebond |
| C-81 | CH | CH | 4 | 3 | Ph | —O— | —O— |
| C-82 | CH | CH | 4 | 3 | Ph | —O— | —S— |
| C-83 | CH | CH | 4 | 3 | Ph | —O— | —OCH₂— |
| C-84 | CH | CH | 4 | 3 | Ph | —O— | singlebond |
| C-85 | CH | CH | 4 | 3 | Ph | —S— | —O— |
| C-86 | CH | CH | 4 | 3 | Ph | —CH₂O— | —O— |
| C-87 | CH | CH | 4 | 3 | Ph | singlebond | —O— |
| C-88 | CH | CH | 4 | 3 | Ph | —S— | —S— |
| C-89 | CH | CH | 4 | 3 | Ph | —CH₂O— | —OCH₂— |
| C-90 | CH | CH | 4 | 3 | Ph | singlebond | singlebond |
| C-91 | CH | CH | 4 | 4 | H | —O— | —O— |
| C-92 | CH | CH | 4 | 4 | H | —O— | —S— |
| C-93 | CH | CH | 4 | 4 | H | —O— | —OCH₂— |
| C-94 | CH | CH | 4 | 4 | H | —O— | singlebond |
| C-95 | CH | CH | 4 | 4 | H | —S— | —O— |
| C-96 | CH | CH | 4 | 4 | H | —CH₂O— | —O— |
| C-97 | CH | CH | 4 | 4 | H | singlebond | —O— |
| C-98 | CH | CH | 4 | 4 | H | —S— | —S— |
| C-99 | CH | CH | 4 | 4 | H | —CH₂O— | —OCH₂— |
| C-100 | CH | CH | 4 | 4 | H | singlebond | singlebond |
| C-101 | CH | CH | 4 | 4 | Me | —O— | —O— |
| C-102 | CH | CH | 4 | 4 | Me | —O— | —S— |
| C-103 | CH | CH | 4 | 4 | Me | —O— | —OCH₂— |
| C-104 | CH | CH | 4 | 4 | Me | —O— | singlebond |
| C-105 | CH | CH | 4 | 4 | Me | —S— | —O— |
| C-106 | CH | CH | 4 | 4 | Me | —CH₂O— | —O— |
| C-107 | CH | CH | 4 | 4 | Me | singlebond | —O— |
| C-108 | CH | CH | 4 | 4 | Me | —S— | —S— |
| C-109 | CH | CH | 4 | 4 | Me | —CH₂O— | —OCH₂— |
| C-110 | CH | CH | 4 | 4 | Me | singlebond | singlebond |

TABLE 12

| Compound No. | G¹ | G² | n | m | $R^a$ | Q¹ | Q² |
|---|---|---|---|---|---|---|---|
| C-111 | CH | CH | 4 | 4 | Ph | —O— | —O— |
| C-112 | CH | CH | 4 | 4 | Ph | —O— | —S— |
| C-113 | CH | CH | 4 | 4 | Ph | —O— | —OCH₂— |
| C-114 | CH | CH | 4 | 4 | Ph | —O— | singlebond |
| C-115 | CH | CH | 4 | 4 | Ph | —S— | —O— |
| C-116 | CH | CH | 4 | 4 | Ph | —CH₂O— | —O— |
| C-117 | CH | CH | 4 | 4 | Ph | singlebond | —O— |
| C-118 | CH | CH | 4 | 4 | Ph | —S— | —S— |
| C-119 | CH | CH | 4 | 4 | Ph | —CH₂O— | —OCH₂— |
| C-120 | CH | CH | 4 | 4 | Ph | singlebond | singlebond |
| C-121 | N | CH | 3 | 3 | H | —O— | —O— |
| C-122 | N | CH | 3 | 3 | H | —O— | —S— |
| C-123 | N | CH | 3 | 3 | H | —O— | —OCH₂— |
| C-124 | N | CH | 3 | 3 | H | —O— | singlebond |
| C-125 | N | CH | 3 | 3 | H | —S— | —O— |
| C-126 | N | CH | 3 | 3 | H | —CH₂O— | —O— |
| C-127 | N | CH | 3 | 3 | H | singlebond | —O— |
| C-128 | N | CH | 3 | 3 | H | —S— | —S— |
| C-129 | N | CH | 3 | 3 | H | —CH₂O— | —OCH₂— |
| C-130 | N | CH | 3 | 3 | H | singlebond | singlebond |
| C-131 | N | CH | 3 | 3 | Me | —O— | —O— |
| C-132 | N | CH | 3 | 3 | Me | —O— | —S— |
| C-133 | N | CH | 3 | 3 | Me | —O— | —OCH₂— |
| C-134 | N | CH | 3 | 3 | Me | —O— | singlebond |
| C-135 | N | CH | 3 | 3 | Me | —S— | —O— |
| C-136 | N | CH | 3 | 3 | Me | —CH₂O— | —O— |
| C-137 | N | CH | 3 | 3 | Me | singlebond | —O— |
| C-138 | N | CH | 3 | 3 | Me | —S— | —S— |
| C-139 | N | CH | 3 | 3 | Me | —CH₂O— | —OCH₂— |
| C-140 | N | CH | 3 | 3 | Me | singlebond | singlebond |
| C-141 | N | CH | 3 | 3 | Ph | —O— | —O— |
| C-142 | N | CH | 3 | 3 | Ph | —O— | —S— |
| C-143 | N | CH | 3 | 3 | Ph | —O— | —OCH₂— |
| C-144 | N | CH | 3 | 3 | Ph | —O— | singlebond |
| C-145 | N | CH | 3 | 3 | Ph | —S— | —O— |
| C-146 | N | CH | 3 | 3 | Ph | —CH₂O— | —O— |
| C-147 | N | CH | 3 | 3 | Ph | singlebond | —O— |
| C-148 | N | CH | 3 | 3 | Ph | —S— | —S— |
| C-149 | N | CH | 3 | 3 | Ph | —CH₂O— | —OCH₂— |
| C-150 | N | CH | 3 | 3 | Ph | singlebond | singlebond |
| C-151 | N | CH | 3 | 4 | H | —O— | —O— |
| C-152 | N | CH | 3 | 4 | H | —O— | —S— |
| C-153 | N | CH | 3 | 4 | H | —O— | —OCH₂— |
| C-154 | N | CH | 3 | 4 | H | —O— | singlebond |
| C-155 | N | CH | 3 | 4 | H | —S— | —O— |
| C-156 | N | CH | 3 | 4 | H | —CH₂O— | —O— |
| C-157 | N | CH | 3 | 4 | H | singlebond | —O— |
| C-158 | N | CH | 3 | 4 | H | —S— | —S— |
| C-159 | N | CH | 3 | 4 | H | —CH₂O— | —OCH₂— |
| C-160 | N | CH | 3 | 4 | H | singlebond | singlebond |
| C-161 | N | CH | 3 | 4 | Me | —O— | —O— |
| C-162 | N | CH | 3 | 4 | Me | —O— | —S— |
| C-163 | N | CH | 3 | 4 | Me | —O— | —OCH₂— |
| C-164 | N | CH | 3 | 4 | Me | —O— | singlebond |
| C-165 | N | CH | 3 | 4 | Me | —S— | —O— |
| C-166 | N | CH | 3 | 4 | Me | —CH₂O— | —O— |
| C-167 | N | CH | 3 | 4 | Me | singlebond | —O— |
| C-168 | N | CH | 3 | 4 | Me | —S— | —S— |
| C-169 | N | CH | 3 | 4 | Me | —CH₂O— | —OCH₂— |
| C-170 | N | CH | 3 | 4 | Me | singlebond | singlebond |
| C-171 | N | CH | 3 | 4 | Ph | —O— | —O— |
| C-172 | N | CH | 3 | 4 | Ph | —O— | —S— |
| C-173 | N | CH | 3 | 4 | Ph | —O— | —OCH₂— |
| C-174 | N | CH | 3 | 4 | Ph | —O— | singlebond |
| C-175 | N | CH | 3 | 4 | Ph | —S— | —O— |
| C-176 | N | CH | 3 | 4 | Ph | —CH₂O— | —O— |
| C-177 | N | CH | 3 | 4 | Ph | singlebond | —O— |
| C-178 | N | CH | 3 | 4 | Ph | —S— | —S— |
| C-179 | N | CH | 3 | 4 | Ph | —CH₂O— | —OCH₂— |
| C-180 | N | CH | 3 | 4 | Ph | singlebond | singlebond |
| C-181 | N | CH | 4 | 3 | H | —O— | —O— |
| C-182 | N | CH | 4 | 3 | H | —O— | —S— |
| C-183 | N | CH | 4 | 3 | H | —O— | —OCH₂— |
| C-184 | N | CH | 4 | 3 | H | —O— | singlebond |
| C-185 | N | CH | 4 | 3 | H | —S— | —O— |
| C-186 | N | CH | 4 | 3 | H | —CH₂O— | —O— |
| C-187 | N | CH | 4 | 3 | H | singlebond | —O— |
| C-188 | N | CH | 4 | 3 | H | —S— | —S— |
| C-189 | N | CH | 4 | 3 | H | —CH₂O— | —OCH₂— |

TABLE 12-continued

| Compound No. | G¹ | G² | n | m | Rᵃ | Q¹ | Q² |
|---|---|---|---|---|---|---|---|
| C-190 | N | CH | 4 | 3 | H | singlebond | singlebond |
| C-191 | N | CH | 4 | 3 | Me | —O— | —O— |
| C-192 | N | CH | 4 | 3 | Me | —O— | —S— |
| C-193 | N | CH | 4 | 3 | Me | —O— | —OCH₂— |
| C-194 | N | CH | 4 | 3 | Me | —O— | singlebond |
| C-195 | N | CH | 4 | 3 | Me | —S— | —O— |
| C-196 | N | CH | 4 | 3 | Me | —CH₂O— | —O— |
| C-197 | N | CH | 4 | 3 | Me | singlebond | —O— |
| C-198 | N | CH | 4 | 3 | Me | —S— | —S— |
| C-199 | N | CH | 4 | 3 | Me | —CH₂O— | —OCH₂— |
| C-200 | N | CH | 4 | 3 | Me | singlebond | singlebond |
| C-201 | N | CH | 4 | 3 | Ph | —O— | —O— |
| C-202 | N | CH | 4 | 3 | Ph | —O— | —S— |
| C-203 | N | CH | 4 | 3 | Ph | —O— | —OCH₂— |
| C-204 | N | CH | 4 | 3 | Ph | —O— | singlebond |
| C-205 | N | CH | 4 | 3 | Ph | —S— | —O— |
| C-206 | N | CH | 4 | 3 | Ph | —CH₂O— | —O— |
| C-207 | N | CH | 4 | 3 | Ph | singlebond | —O— |
| C-208 | N | CH | 4 | 3 | Ph | —S— | —S— |
| C-209 | N | CH | 4 | 3 | Ph | —CH₂O— | —OCH₂— |
| C-210 | N | CH | 4 | 3 | Ph | singlebond | singlebond |
| C-211 | N | CH | 4 | 4 | H | —O— | —O— |
| C-212 | N | CH | 4 | 4 | H | —O— | —S— |
| C-213 | N | CH | 4 | 4 | H | —O— | —OCH₂— |
| C-214 | N | CH | 4 | 4 | H | —O— | singlebond |
| C-215 | N | CH | 4 | 4 | H | —S— | —O— |
| C-216 | N | CH | 4 | 4 | H | —CH₂O— | —O— |
| C-217 | N | CH | 4 | 4 | H | singlebond | —O— |
| C-218 | N | CH | 4 | 4 | H | —S— | —S— |
| C-219 | N | CH | 4 | 4 | H | —CH₂O— | —OCH₂— |
| C-220 | N | CH | 4 | 4 | H | singlebond | singlebond |

TABLE 13

| Compound No. | G¹ | G² | n | m | Rᵃ | Q¹ | Q² |
|---|---|---|---|---|---|---|---|
| C-221 | N | CH | 4 | 4 | Me | —O— | —O— |
| C-222 | N | CH | 4 | 4 | Me | —O— | —S— |
| C-223 | N | CH | 4 | 4 | Me | —O— | —OCH₂— |
| C-224 | N | CH | 4 | 4 | Me | —O— | singlebond |
| C-225 | N | CH | 4 | 4 | Me | —S— | —O— |
| C-226 | N | CH | 4 | 4 | Me | —CH₂O— | —O— |
| C-227 | N | CH | 4 | 4 | Me | singlebond | —O— |
| C-228 | N | CH | 4 | 4 | Me | —S— | —S— |
| C-229 | N | CH | 4 | 4 | Me | —CH₂O— | —OCH₂— |
| C-230 | N | CH | 4 | 4 | Me | singlebond | singlebond |
| C-231 | N | CH | 4 | 4 | Ph | —O— | —O— |
| C-232 | N | CH | 4 | 4 | Ph | —O— | —S— |
| C-233 | N | CH | 4 | 4 | Ph | —O— | —OCH₂— |
| C-234 | N | CH | 4 | 4 | Ph | —O— | singlebond |
| C-235 | N | CH | 4 | 4 | Ph | —S— | —O— |
| C-236 | N | CH | 4 | 4 | Ph | —CH₂O— | —O— |
| C-237 | N | CH | 4 | 4 | Ph | singlebond | —O— |
| C-238 | N | CH | 4 | 4 | Ph | —S— | —S— |
| C-239 | N | CH | 4 | 4 | Ph | —CH₂O— | —OCH₂— |
| C-240 | N | CH | 4 | 4 | Ph | singlebond | singlebond |
| C-241 | CH | N | 3 | 3 | H | —O— | —O— |
| C-242 | CH | N | 3 | 3 | H | —O— | —S— |
| C-243 | CH | N | 3 | 3 | H | —O— | —OCH₂— |
| C-244 | CH | N | 3 | 3 | H | —O— | singlebond |
| C-245 | CH | N | 3 | 3 | H | —S— | —O— |
| C-246 | CH | N | 3 | 3 | H | —CH₂O— | —O— |
| C-247 | CH | N | 3 | 3 | H | singlebond | —O— |
| C-248 | CH | N | 3 | 3 | H | —S— | —S— |
| C-249 | CH | N | 3 | 3 | H | —CH₂O— | —OCH₂— |
| C-250 | CH | N | 3 | 3 | H | singlebond | singlebond |
| C-251 | CH | N | 3 | 3 | Me | —O— | —O— |
| C-252 | CH | N | 3 | 3 | Me | —O— | —S— |
| C-253 | CH | N | 3 | 3 | Me | —O— | —OCH₂— |
| C-254 | CH | N | 3 | 3 | Me | —O— | singlebond |
| C-255 | CH | N | 3 | 3 | Me | —S— | —O— |
| C-256 | CH | N | 3 | 3 | Me | —CH₂O— | —O— |
| C-257 | CH | N | 3 | 3 | Me | singlebond | —O— |
| C-258 | CH | N | 3 | 3 | Me | —S— | —S— |
| C-259 | CH | N | 3 | 3 | Me | —CH₂O— | —OCH₂— |
| C-260 | CH | N | 3 | 3 | Me | singlebond | singlebond |
| C-261 | CH | N | 3 | 3 | Ph | —O— | —O— |
| C-262 | CH | N | 3 | 3 | Ph | —O— | —S— |
| C-263 | CH | N | 3 | 3 | Ph | —O— | —OCH₂— |
| C-264 | CH | N | 3 | 3 | Ph | —O— | singlebond |
| C-265 | CH | N | 3 | 3 | Ph | —S— | —O— |
| C-266 | CH | N | 3 | 3 | Ph | —CH₂O— | —O— |
| C-267 | CH | N | 3 | 3 | Ph | singlebond | —O— |
| C-268 | CH | N | 3 | 3 | Ph | —S— | —O— |
| C-269 | CH | N | 3 | 3 | Ph | —CH₂O— | —OCH₂— |
| C-270 | CH | N | 3 | 3 | Ph | singlebond | singlebond |
| C-271 | CH | N | 3 | 4 | H | —O— | —O— |
| C-272 | CH | N | 3 | 4 | H | —O— | —S— |
| C-273 | CH | N | 3 | 4 | H | —O— | —OCH₂— |
| C-274 | CH | N | 3 | 4 | H | —O— | singlebond |
| C-275 | CH | N | 3 | 4 | H | —S— | —O— |
| C-276 | CH | N | 3 | 4 | H | —CH₂O— | —O— |
| C-277 | CH | N | 3 | 4 | H | singlebond | —O— |
| C-278 | CH | N | 3 | 4 | H | —S— | —S— |
| C-279 | CH | N | 3 | 4 | H | —CH₂O— | —OCH₂— |
| C-280 | CH | N | 3 | 4 | H | singlebond | singlebond |
| C-281 | CH | N | 3 | 4 | Me | —O— | —O— |
| C-282 | CH | N | 3 | 4 | Me | —O— | —S— |
| C-283 | CH | N | 3 | 4 | Me | —O— | —OCH₂— |
| C-284 | CH | N | 3 | 4 | Me | —O— | singlebond |
| C-285 | CH | N | 3 | 4 | Me | —S— | —O— |
| C-286 | CH | N | 3 | 4 | Me | —CH₂O— | —O— |
| C-287 | CH | N | 3 | 4 | Me | singlebond | —O— |
| C-288 | CH | N | 3 | 4 | Me | —S— | —S— |
| C-289 | CH | N | 3 | 4 | Me | —CH₂O— | —OCH₂— |
| C-290 | CH | N | 3 | 4 | Me | singlebond | singlebond |
| C-291 | CH | N | 3 | 4 | Ph | —O— | —O— |
| C-292 | CH | N | 3 | 4 | Ph | —O— | —S— |
| C-293 | CH | N | 3 | 4 | Ph | —O— | —OCH₂— |
| C-294 | CH | N | 3 | 4 | Ph | —O— | singlebond |
| C-295 | CH | N | 3 | 4 | Ph | —S— | —O— |
| C-296 | CH | N | 3 | 4 | Ph | —CH₂O— | —O— |
| C-297 | CH | N | 3 | 4 | Ph | singlebond | —O— |
| C-298 | CH | N | 3 | 4 | Ph | —S— | —S— |
| C-299 | CH | N | 3 | 4 | Ph | —CH₂O— | —OCH₂— |
| C-300 | CH | N | 3 | 4 | Ph | singlebond | singlebond |
| C-301 | CH | N | 4 | 3 | H | —O— | —O— |
| C-302 | CH | N | 4 | 3 | H | —O— | —S— |
| C-303 | CH | N | 4 | 3 | H | —O— | —OCH₂— |
| C-304 | CH | N | 4 | 3 | H | —O— | singlebond |
| C-305 | CH | N | 4 | 3 | H | —S— | —O— |
| C-306 | CH | N | 4 | 3 | H | —CH₂O— | —O— |
| C-307 | CH | N | 4 | 3 | H | singlebond | —O— |
| C-308 | CH | N | 4 | 3 | H | —S— | —S— |
| C-309 | CH | N | 4 | 3 | H | —CH₂O— | —OCH₂— |
| C-310 | CH | N | 4 | 3 | H | singlebond | singlebond |
| C-311 | CH | N | 4 | 3 | Me | —O— | —O— |
| C-312 | CH | N | 4 | 3 | Me | —O— | —S— |
| C-313 | CH | N | 4 | 3 | Me | —O— | —OCH₂— |
| C-314 | CH | N | 4 | 3 | Me | —O— | singlebond |
| C-315 | CH | N | 4 | 3 | Me | —S— | —O— |
| C-316 | CH | N | 4 | 3 | Me | —CH₂O— | —O— |
| C-317 | CH | N | 4 | 3 | Me | singlebond | —O— |
| C-318 | CH | N | 4 | 3 | Me | —S— | —S— |
| C-319 | CH | N | 4 | 3 | Me | —CH₂O— | —OCH₂— |
| C-320 | CH | N | 4 | 3 | Me | singlebond | singlebond |
| C-321 | CH | N | 4 | 3 | Ph | —O— | —O— |
| C-322 | CH | N | 4 | 3 | Ph | —O— | —S— |
| C-323 | CH | N | 4 | 3 | Ph | —O— | —OCH₂— |
| C-324 | CH | N | 4 | 3 | Ph | —O— | singlebond |
| C-325 | CH | N | 4 | 3 | Ph | —S— | —O— |
| C-326 | CH | N | 4 | 3 | Ph | —CH₂O— | —O— |
| C-327 | CH | N | 4 | 3 | Ph | singlebond | —O— |
| C-328 | CH | N | 4 | 3 | Ph | —S— | —S— |
| C-329 | CH | N | 4 | 3 | Ph | —CH₂O— | —OCH₂— |
| C-330 | CH | N | 4 | 3 | Ph | singlebond | singlebond |

TABLE 14

| Compound No. | $G^1$ | $G^2$ | n | m | $R^a$ | $Q^1$ | $Q^2$ |
|---|---|---|---|---|---|---|---|
| C-331 | CH | N | 4 | 4 | H | —O— | —O— |
| C-332 | CH | N | 4 | 4 | H | —O— | —S— |
| C-333 | CH | N | 4 | 4 | H | —O— | —OCH$_2$— |
| C-334 | CH | N | 4 | 4 | H | —O— | singlebond |
| C-335 | CH | N | 4 | 4 | H | —S— | —O— |
| C-336 | CH | N | 4 | 4 | H | —CH$_2$O— | —O— |
| C-337 | CH | N | 4 | 4 | H | singlebond | —O— |
| C-338 | CH | N | 4 | 4 | H | —S— | —S— |
| C-339 | CH | N | 4 | 4 | H | —CH$_2$O— | —OCH$_2$— |
| C-340 | CH | N | 4 | 4 | H | singlebond | singlebond |
| C-341 | CH | N | 4 | 4 | Me | —O— | —O— |
| C-342 | CH | N | 4 | 4 | Me | —O— | —S— |
| C-343 | CH | N | 4 | 4 | Me | —O— | —OCH$_2$— |
| C-344 | CH | N | 4 | 4 | Me | —O— | singlebond |
| C-345 | CH | N | 4 | 4 | Me | —S— | —O— |
| C-346 | CH | N | 4 | 4 | Me | —CH$_2$O— | —O— |
| C-347 | CH | N | 4 | 4 | Me | singlebond | —O— |
| C-348 | CH | N | 4 | 4 | Me | —S— | —S— |
| C-349 | CH | N | 4 | 4 | Me | —CH$_2$O— | —OCH$_2$— |
| C-350 | CH | N | 4 | 4 | Me | singlebond | singlebond |
| C-351 | CH | N | 4 | 4 | Ph | —O— | —O— |
| C-352 | CH | N | 4 | 4 | Ph | —O— | —S— |
| C-353 | CH | N | 4 | 4 | Ph | —O— | —OCH$_2$— |
| C-354 | CH | N | 4 | 4 | Ph | —O— | singlebond |
| C-355 | CH | N | 4 | 4 | Ph | —S— | —O— |
| C-356 | CH | N | 4 | 4 | Ph | —CH$_2$O— | —O— |
| C-357 | CH | N | 4 | 4 | Ph | singlebond | —O— |
| C-358 | CH | N | 4 | 4 | Ph | —S— | —S— |
| C-359 | CH | N | 4 | 4 | Ph | —CH$_2$O— | —OCH$_2$— |
| C-360 | CH | N | 4 | 4 | Ph | singlebond | singlebond |
| C-361 | CH | CH | 2 | 5 | H | —O— | —O— |
| C-362 | CH | CH | 3 | 5 | H | —O— | —O— |
| C-363 | CH | CH | 5 | 2 | H | —O— | —O— |
| C-364 | CH | CH | 5 | 2 | H | —O— | —O— |

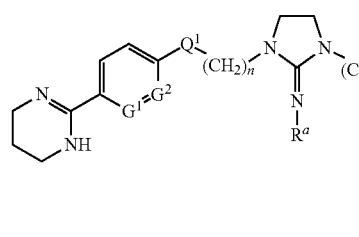

TABLE 15

| Compound No. | $G^1$ | $G^2$ | n | m | $R^a$ | $Q^1$ | $Q^2$ |
|---|---|---|---|---|---|---|---|
| D-1 | CH | CH | 3 | 3 | H | —O— | —O— |
| D-2 | CH | CH | 3 | 3 | H | —O— | —S— |
| D-3 | CH | CH | 3 | 3 | H | —O— | —OCH$_2$— |
| D-4 | CH | CH | 3 | 3 | H | —O— | singlebond |
| D-5 | CH | CH | 3 | 3 | H | —S— | —O— |
| D-6 | CH | CH | 3 | 3 | H | —CH$_2$O— | —O— |
| D-7 | CH | CH | 3 | 3 | H | singlebond | —O— |
| D-8 | CH | CH | 3 | 3 | H | —S— | —S— |
| D-9 | CH | CH | 3 | 3 | H | —CH$_2$O— | —OCH$_2$— |
| D-10 | CH | CH | 3 | 3 | H | singlebond | singlebond |
| D-11 | CH | CH | 3 | 3 | Me | —O— | —O— |
| D-12 | CH | CH | 3 | 3 | Me | —O— | —S— |
| D-13 | CH | CH | 3 | 3 | Me | —O— | —OCH$_2$— |
| D-14 | CH | CH | 3 | 3 | Me | —O— | singlebond |
| D-15 | CH | CH | 3 | 3 | Me | —S— | —O— |
| D-16 | CH | CH | 3 | 3 | Me | —CH$_2$O— | —O— |
| D-17 | CH | CH | 3 | 3 | Me | singlebond | —O— |
| D-18 | CH | CH | 3 | 3 | Me | —S— | —S— |
| D-19 | CH | CH | 3 | 3 | Me | —CH$_2$O— | —OCH$_2$— |
| D-20 | CH | CH | 3 | 3 | Me | singlebond | singlebond |
| D-21 | CH | CH | 3 | 3 | Ph | —O— | —O— |
| D-22 | CH | CH | 3 | 3 | Ph | —O— | —S— |
| D-23 | CH | CH | 3 | 3 | Ph | —O— | —OCH$_2$— |
| D-24 | CH | CH | 3 | 3 | Ph | —O— | singlebond |
| D-25 | CH | CH | 3 | 3 | Ph | —S— | —O— |
| D-26 | CH | CH | 3 | 3 | Ph | —CH$_2$O— | —O— |
| D-27 | CH | CH | 3 | 3 | Ph | singlebond | —O— |
| D-28 | CH | CH | 3 | 3 | Ph | —S— | —S— |
| D-29 | CH | CH | 3 | 3 | Ph | —CH$_2$O— | —OCH$_2$— |
| D-30 | CH | CH | 3 | 3 | Ph | singlebond | singlebond |
| D-31 | CH | CH | 3 | 4 | H | —O— | —O— |
| D-32 | CH | CH | 3 | 4 | H | —O— | —S— |
| D-33 | CH | CH | 3 | 4 | H | —O— | —OCH$_2$— |
| D-34 | CH | CH | 3 | 4 | H | —O— | singlebond |
| D-35 | CH | CH | 3 | 4 | H | —S— | —O— |
| D-36 | CH | CH | 3 | 4 | H | —CH$_2$O— | —O— |
| D-37 | CH | CH | 3 | 4 | H | singlebond | —O— |
| D-38 | CH | CH | 3 | 4 | H | —S— | —S— |
| D-39 | CH | CH | 3 | 4 | H | —CH$_2$O— | —OCH$_2$— |
| D-40 | CH | CH | 3 | 4 | H | singlebond | singlebond |
| D-41 | CH | CH | 3 | 4 | Me | —O— | —O— |
| D-42 | CH | CH | 3 | 4 | Me | —O— | —S— |
| D-43 | CH | CH | 3 | 4 | Me | —O— | —OCH$_2$— |
| D-44 | CH | CH | 3 | 4 | Me | —O— | singlebond |
| D-45 | CH | CH | 3 | 4 | Me | —S— | —O— |
| D-46 | CH | CH | 3 | 4 | Me | —CH$_2$O— | —O— |
| D-47 | CH | CH | 3 | 4 | Me | singlebond | —O— |
| D-48 | CH | CH | 3 | 4 | Me | —S— | —S— |
| D-49 | CH | CH | 3 | 4 | Me | —CH$_2$O— | —OCH$_2$— |
| D-50 | CH | CH | 3 | 4 | Me | singlebond | singlebond |
| D-51 | CH | CH | 3 | 4 | Ph | —O— | —O— |
| D-52 | CH | CH | 3 | 4 | Ph | —O— | —S— |
| D-53 | CH | CH | 3 | 4 | Ph | —O— | —OCH$_2$— |
| D-54 | CH | CH | 3 | 4 | Ph | —O— | singlebond |
| D-55 | CH | CH | 3 | 4 | Ph | —S— | —O— |
| D-56 | CH | CH | 3 | 4 | Ph | —CH$_2$O— | —O— |
| D-57 | CH | CH | 3 | 4 | Ph | singlebond | —O— |
| D-58 | CH | CH | 3 | 4 | Ph | —S— | —S— |
| D-59 | CH | CH | 3 | 4 | Ph | —CH$_2$O— | —OCH$_2$— |
| D-60 | CH | CH | 3 | 4 | Ph | singlebond | singlebond |
| D-61 | CH | CH | 4 | 3 | H | —O— | —O— |
| D-62 | CH | CH | 4 | 3 | H | —O— | —S— |
| D-63 | CH | CH | 4 | 3 | H | —O— | —OCH$_2$— |
| D-64 | CH | CH | 4 | 3 | H | —O— | singlebond |
| D-65 | CH | CH | 4 | 3 | H | —S— | —O— |
| D-66 | CH | CH | 4 | 3 | H | —CH$_2$O— | —O— |
| D-67 | CH | CH | 4 | 3 | H | singlebond | —O— |
| D-68 | CH | CH | 4 | 3 | H | —S— | —S— |
| D-69 | CH | CH | 4 | 3 | H | —CH$_2$O— | —OCH$_2$— |
| D-70 | CH | CH | 4 | 3 | H | singlebond | singlebond |
| D-71 | CH | CH | 4 | 3 | Me | —O— | —O— |
| D-72 | CH | CH | 4 | 3 | Me | —O— | —S— |
| D-73 | CH | CH | 4 | 3 | Me | —O— | —OCH$_2$— |
| D-74 | CH | CH | 4 | 3 | Me | —O— | singlebond |
| D-75 | CH | CH | 4 | 3 | Me | —S— | —O— |
| D-76 | CH | CH | 4 | 3 | Me | —CH$_2$O— | —O— |
| D-77 | CH | CH | 4 | 3 | Me | singlebond | —O— |
| D-78 | CH | CH | 4 | 3 | Me | —S— | —S— |
| D-79 | CH | CH | 4 | 3 | Me | —CH$_2$O— | —OCH$_2$— |
| D-80 | CH | CH | 4 | 3 | Me | singlebond | singlebond |
| D-81 | CH | CH | 4 | 3 | Ph | —O— | —O— |
| D-82 | CH | CH | 4 | 3 | Ph | —O— | —S— |
| D-83 | CH | CH | 4 | 3 | Ph | —O— | —OCH$_2$— |
| D-84 | CH | CH | 4 | 3 | Ph | —O— | singlebond |
| D-85 | CH | CH | 4 | 3 | Ph | —S— | —O— |
| D-86 | CH | CH | 4 | 3 | Ph | —CH$_2$O— | —O— |
| D-87 | CH | CH | 4 | 3 | Ph | singlebond | —O— |
| D-88 | CH | CH | 4 | 3 | Ph | —S— | —S— |
| D-89 | CH | CH | 4 | 3 | Ph | —CH$_2$O— | —OCH$_2$— |
| D-90 | CH | CH | 4 | 3 | Ph | singlebond | singlebond |
| D-91 | CH | CH | 4 | 4 | H | —O— | —O— |
| D-92 | CH | CH | 4 | 4 | H | —O— | —S— |
| D-93 | CH | CH | 4 | 4 | H | —O— | —OCH$_2$— |
| D-94 | CH | CH | 4 | 4 | H | —O— | singlebond |
| D-95 | CH | CH | 4 | 4 | H | —S— | —O— |
| D-96 | CH | CH | 4 | 4 | H | —CH$_2$O— | —O— |
| D-97 | CH | CH | 4 | 4 | H | singlebond | —O— |
| D-98 | CH | CH | 4 | 4 | H | —S— | —S— |
| D-99 | CH | CH | 4 | 4 | H | —CH$_2$O— | —OCH$_2$— |
| D-100 | CH | CH | 4 | 4 | H | singlebond | singlebond |

TABLE 15-continued

| Compound No. | G¹ | G² | n | m | R$^a$ | Q¹ | Q² |
|---|---|---|---|---|---|---|---|
| D-101 | CH | CH | 4 | 4 | Me | —O— | —O— |
| D-102 | CH | CH | 4 | 4 | Me | —O— | —S— |
| D-103 | CH | CH | 4 | 4 | Me | —O— | —OCH$_2$— |
| D-104 | CH | CH | 4 | 4 | Me | —O— | singlebond |
| D-105 | CH | CH | 4 | 4 | Me | —S— | —O— |
| D-106 | CH | CH | 4 | 4 | Me | —CH$_2$O— | —O— |
| D-107 | CH | CH | 4 | 4 | Me | singlebond | —O— |
| D-108 | CH | CH | 4 | 4 | Me | —S— | —S— |
| D-109 | CH | CH | 4 | 4 | Me | —CH$_2$O— | —OCH$_2$— |
| D-110 | CH | CH | 4 | 4 | Me | singlebond | singlebond |

TABLE 16

| Compound No. | G¹ | G² | n | m | R$^a$ | Q¹ | Q² |
|---|---|---|---|---|---|---|---|
| D-111 | CH | CH | 4 | 4 | Ph | —O— | —O— |
| D-112 | CH | CH | 4 | 4 | Ph | —O— | —S— |
| D-113 | CH | CH | 4 | 4 | Ph | —O— | —OCH$_2$— |
| D-114 | CH | CH | 4 | 4 | Ph | —O— | singlebond |
| D-115 | CH | CH | 4 | 4 | Ph | —S— | —O— |
| D-116 | CH | CH | 4 | 4 | Ph | —CH$_2$O— | —O— |
| D-117 | CH | CH | 4 | 4 | Ph | singlebond | —O— |
| D-118 | CH | CH | 4 | 4 | Ph | —S— | —S— |
| D-119 | CH | CH | 4 | 4 | Ph | —CH$_2$O— | —OCH$_2$— |
| D-120 | CH | CH | 4 | 4 | Ph | singlebond | singlebond |
| D-121 | N | CH | 3 | 3 | H | —O— | —O— |
| D-122 | N | CH | 3 | 3 | H | —O— | —S— |
| D-123 | N | CH | 3 | 3 | H | —O— | —OCH$_2$— |
| D-124 | N | CH | 3 | 3 | H | —O— | singlebond |
| D-125 | N | CH | 3 | 3 | H | —S— | —O— |
| D-126 | N | CH | 3 | 3 | H | —CH$_2$O— | —O— |
| D-127 | N | CH | 3 | 3 | H | singlebond | —O— |
| D-128 | N | CH | 3 | 3 | H | —S— | —S— |
| D-129 | N | CH | 3 | 3 | H | —CH$_2$O— | —OCH$_2$— |
| D-130 | N | CH | 3 | 3 | H | singlebond | singlebond |
| D-131 | N | CH | 3 | 3 | Me | —O— | —O— |
| D-132 | N | CH | 3 | 3 | Me | —O— | —S— |
| D-133 | N | CH | 3 | 3 | Me | —O— | —OCH$_2$— |
| D-134 | N | CH | 3 | 3 | Me | —O— | singlebond |
| D-135 | N | CH | 3 | 3 | Me | —S— | —O— |
| D-136 | N | CH | 3 | 3 | Me | —CH$_2$O— | —O— |
| D-137 | N | CH | 3 | 3 | Me | singlebond | —O— |
| D-138 | N | CH | 3 | 3 | Me | —S— | —S— |
| D-139 | N | CH | 3 | 3 | Me | —CH$_2$O— | —OCH$_2$— |
| D-140 | N | CH | 3 | 3 | Me | singlebond | singlebond |
| D-141 | N | CH | 3 | 3 | Ph | —O— | —O— |
| D-142 | N | CH | 3 | 3 | Ph | —O— | —S— |
| D-143 | N | CH | 3 | 3 | Ph | —O— | —OCH$_2$— |
| D-144 | N | CH | 3 | 3 | Ph | —O— | singlebond |
| D-145 | N | CH | 3 | 3 | Ph | —S— | —O— |
| D-146 | N | CH | 3 | 3 | Ph | —CH$_2$O— | —O— |
| D-147 | N | CH | 3 | 3 | Ph | singlebond | —O— |
| D-148 | N | CH | 3 | 3 | Ph | —S— | —S— |
| D-149 | N | CH | 3 | 3 | Ph | —CH$_2$O— | —OCH$_2$— |
| D-150 | N | CH | 3 | 3 | Ph | singlebond | singlebond |
| D-151 | N | CH | 3 | 4 | H | —O— | —O— |
| D-152 | N | CH | 3 | 4 | H | —O— | —S— |
| D-153 | N | CH | 3 | 4 | H | —O— | —OCH$_2$— |
| D-154 | N | CH | 3 | 4 | H | —O— | singlebond |
| D-155 | N | CH | 3 | 4 | H | —S— | —O— |
| D-156 | N | CH | 3 | 4 | H | —CH$_2$O— | —O— |
| D-157 | N | CH | 3 | 4 | H | singlebond | —O— |
| D-158 | N | CH | 3 | 4 | H | —S— | —S— |
| D-159 | N | CH | 3 | 4 | H | —CH$_2$O— | —OCH$_2$— |
| D-160 | N | CH | 3 | 4 | H | singlebond | singlebond |
| D-161 | N | CH | 3 | 4 | Me | —O— | —O— |
| D-162 | N | CH | 3 | 4 | Me | —O— | —S— |
| D-163 | N | CH | 3 | 4 | Me | —O— | —OCH$_2$— |
| D-164 | N | CH | 3 | 4 | Me | —O— | singlebond |
| D-165 | N | CH | 3 | 4 | Me | —S— | —O— |
| D-166 | N | CH | 3 | 4 | Me | —CH$_2$O— | —O— |
| D-167 | N | CH | 3 | 4 | Me | singlebond | —O— |
| D-168 | N | CH | 3 | 4 | Me | —S— | —S— |

TABLE 16-continued

| Compound No. | G¹ | G² | n | m | R$^a$ | Q¹ | Q² |
|---|---|---|---|---|---|---|---|
| D-169 | N | CH | 3 | 4 | Me | —CH$_2$O— | —OCH$_2$— |
| D-170 | N | CH | 3 | 4 | Me | singlebond | singlebond |
| D-171 | N | CH | 3 | 4 | Ph | —O— | —O— |
| D-172 | N | CH | 3 | 4 | Ph | —O— | —S— |
| D-173 | N | CH | 3 | 4 | Ph | —O— | —OCH$_2$— |
| D-174 | N | CH | 3 | 4 | Ph | —O— | singlebond |
| D-175 | N | CH | 3 | 4 | Ph | —S— | —O— |
| D-176 | N | CH | 3 | 4 | Ph | —CH$_2$O— | —O— |
| D-177 | N | CH | 3 | 4 | Ph | singlebond | —O— |
| D-178 | N | CH | 3 | 4 | Ph | —S— | —S— |
| D-179 | N | CH | 3 | 4 | Ph | —CH$_2$O— | —OCH$_2$— |
| D-180 | N | CH | 3 | 4 | Ph | singlebond | singlebond |
| D-181 | N | CH | 4 | 3 | H | —O— | —O— |
| D-182 | N | CH | 4 | 3 | H | —O— | —S— |
| D-183 | N | CH | 4 | 3 | H | —O— | —OCH$_2$— |
| D-184 | N | CH | 4 | 3 | H | —O— | singlebond |
| D-185 | N | CH | 4 | 3 | H | —S— | —O— |
| D-186 | N | CH | 4 | 3 | H | —CH$_2$O— | —O— |
| D-187 | N | CH | 4 | 3 | H | singlebond | —O— |
| D-188 | N | CH | 4 | 3 | H | —S— | —S— |
| D-189 | N | CH | 4 | 3 | H | —CH$_2$O— | —OCH$_2$— |
| D-190 | N | CH | 4 | 3 | H | singlebond | singlebond |
| D-191 | N | CH | 4 | 3 | Me | —O— | —O— |
| D-192 | N | CH | 4 | 3 | Me | —O— | —S— |
| D-193 | N | CH | 4 | 3 | Me | —O— | —OCH$_2$— |
| D-194 | N | CH | 4 | 3 | Me | —O— | singlebond |
| D-195 | N | CH | 4 | 3 | Me | —S— | —O— |
| D-196 | N | CH | 4 | 3 | Me | —CH$_2$O— | —O— |
| D-197 | N | CH | 4 | 3 | Me | singlebond | —O— |
| D-198 | N | CH | 4 | 3 | Me | —S— | —S— |
| D-199 | N | CH | 4 | 3 | Me | —CH$_2$O— | —OCH$_2$— |
| D-200 | N | CH | 4 | 3 | Me | singlebond | singlebond |
| D-201 | N | CH | 4 | 3 | Ph | —O— | —O— |
| D-202 | N | CH | 4 | 3 | Ph | —O— | —S— |
| D-203 | N | CH | 4 | 3 | Ph | —O— | —OCH$_2$— |
| D-204 | N | CH | 4 | 3 | Ph | —O— | singlebond |
| D-205 | N | CH | 4 | 3 | Ph | —S— | —O— |
| D-206 | N | CH | 4 | 3 | Ph | —CH$_2$O— | —O— |
| D-207 | N | CH | 4 | 3 | Ph | singlebond | —O— |
| D-208 | N | CH | 4 | 3 | Ph | —S— | —S— |
| D-209 | N | CH | 4 | 3 | Ph | —CH$_2$O— | —OCH$_2$— |
| D-210 | N | CH | 4 | 3 | Ph | singlebond | singlebond |
| D-211 | N | CH | 4 | 4 | H | —O— | —O— |
| D-212 | N | CH | 4 | 4 | H | —O— | —S— |
| D-213 | N | CH | 4 | 4 | H | —O— | —OCH$_2$— |
| D-214 | N | CH | 4 | 4 | H | —O— | singlebond |
| D-215 | N | CH | 4 | 4 | H | —S— | —O— |
| D-216 | N | CH | 4 | 4 | H | —CH$_2$O— | —O— |
| D-217 | N | CH | 4 | 4 | H | singlebond | —O— |
| D-218 | N | CH | 4 | 4 | H | —S— | —S— |
| D-219 | N | CH | 4 | 4 | H | —CH$_2$O— | —OCH$_2$— |
| D-220 | N | CH | 4 | 4 | H | singlebond | singlebond |

TABLE 17

| Compound No. | G¹ | G² | n | m | R$^a$ | Q¹ | Q² |
|---|---|---|---|---|---|---|---|
| D-221 | N | CH | 4 | 4 | Me | —O— | —O— |
| D-222 | N | CH | 4 | 4 | Me | —O— | —S— |
| D-223 | N | CH | 4 | 4 | Me | —O— | —OCH$_2$— |
| D-224 | N | CH | 4 | 4 | Me | —O— | singlebond |
| D-225 | N | CH | 4 | 4 | Me | —S— | —O— |
| D-226 | N | CH | 4 | 4 | Me | —CH$_2$O— | —O— |
| D-227 | N | CH | 4 | 4 | Me | singlebond | —O— |
| D-228 | N | CH | 4 | 4 | Me | —S— | —S— |
| D-229 | N | CH | 4 | 4 | Me | —CH$_2$O— | —OCH$_2$— |
| D-230 | N | CH | 4 | 4 | Me | singlebond | singlebond |
| D-231 | N | CH | 4 | 4 | Ph | —O— | —O— |
| D-232 | N | CH | 4 | 4 | Ph | —O— | —S— |
| D-233 | N | CH | 4 | 4 | Ph | —O— | —OCH$_2$— |
| D-234 | N | CH | 4 | 4 | Ph | —O— | singlebond |
| D-235 | N | CH | 4 | 4 | Ph | —S— | —O— |
| D-236 | N | CH | 4 | 4 | Ph | —CH$_2$O— | —O— |

TABLE 17-continued

| Compound No. | G¹ | G² | n | m | $R^a$ | Q¹ | Q² |
|---|---|---|---|---|---|---|---|
| D-237 | N | CH | 4 | 4 | Ph | singlebond | —O— |
| D-238 | N | CH | 4 | 4 | Ph | —S— | —S— |
| D-239 | N | CH | 4 | 4 | Ph | —CH$_2$O— | —OCH$_2$— |
| D-240 | N | CH | 4 | 4 | Ph | singlebond | singlebond |
| D-241 | CH | N | 3 | 3 | H | —O— | —O— |
| D-242 | CH | N | 3 | 3 | H | —O— | —S— |
| D-243 | CH | N | 3 | 3 | H | —O— | —OCH$_2$— |
| D-244 | CH | N | 3 | 3 | H | —O— | singlebond |
| D-245 | CH | N | 3 | 3 | H | —S— | —O— |
| D-246 | CH | N | 3 | 3 | H | —CH$_2$O— | —O— |
| D-247 | CH | N | 3 | 3 | H | singlebond | —O— |
| D-248 | CH | N | 3 | 3 | H | —S— | —S— |
| D-249 | CH | N | 3 | 3 | H | —CH$_2$O— | —OCH$_2$— |
| D-250 | CH | N | 3 | 3 | H | singlebond | singlebond |
| D-251 | CH | N | 3 | 3 | Me | —O— | —O— |
| D-252 | CH | N | 3 | 3 | Me | —O— | —S— |
| D-253 | CH | N | 3 | 3 | Me | —O— | —OCH$_2$— |
| D-254 | CH | N | 3 | 3 | Me | —O— | singlebond |
| D-255 | CH | N | 3 | 3 | Me | —S— | —O— |
| D-256 | CH | N | 3 | 3 | Me | —CH$_2$O— | —O— |
| D-257 | CH | N | 3 | 3 | Me | singlebond | —O— |
| D-258 | CH | N | 3 | 3 | Me | —S— | —S— |
| D-259 | CH | N | 3 | 3 | Me | —CH$_2$O— | —OCH$_2$— |
| D-260 | CH | N | 3 | 3 | Me | singlebond | singlebond |
| D-261 | CH | N | 3 | 3 | Ph | —O— | —O— |
| D-262 | CH | N | 3 | 3 | Ph | —O— | —S— |
| D-263 | CH | N | 3 | 3 | Ph | —O— | —OCH$_2$— |
| D-264 | CH | N | 3 | 3 | Ph | —O— | singlebond |
| D-265 | CH | N | 3 | 3 | Ph | —S— | —O— |
| D-266 | CH | N | 3 | 3 | Ph | —CH$_2$O— | —O— |
| D-267 | CH | N | 3 | 3 | Ph | singlebond | —O— |
| D-268 | CH | N | 3 | 3 | Ph | —S— | —S— |
| D-269 | CH | N | 3 | 3 | Ph | —CH$_2$O— | —OCH$_2$— |
| D-270 | CH | N | 3 | 3 | Ph | singlebond | singlebond |
| D-271 | CH | N | 3 | 4 | H | —O— | —O— |
| D-272 | CH | N | 3 | 4 | H | —O— | —S— |
| D-273 | CH | N | 3 | 4 | H | —O— | —OCH$_2$— |
| D-274 | CH | N | 3 | 4 | H | —O— | singlebond |
| D-275 | CH | N | 3 | 4 | H | —S— | —O— |
| D-276 | CH | N | 3 | 4 | H | —CH$_2$O— | —O— |
| D-277 | CH | N | 3 | 4 | H | singlebond | —O— |
| D-278 | CH | N | 3 | 4 | H | —S— | —S— |
| D-279 | CH | N | 3 | 4 | H | —CH$_2$O— | —OCH$_2$— |
| D-280 | CH | N | 3 | 4 | H | singlebond | singlebond |
| D-281 | CH | N | 3 | 4 | Me | —O— | —O— |
| D-282 | CH | N | 3 | 4 | Me | —O— | —S— |
| D-283 | CH | N | 3 | 4 | Me | —O— | —OCH$_2$— |
| D-284 | CH | N | 3 | 4 | Me | —O— | singlebond |
| D-285 | CH | N | 3 | 4 | Me | —S— | —O— |
| D-286 | CH | N | 3 | 4 | Me | —CH$_2$O— | —O— |
| D-287 | CH | N | 3 | 4 | Me | singlebond | —O— |
| D-288 | CH | N | 3 | 4 | Me | —S— | —S— |
| D-289 | CH | N | 3 | 4 | Me | —CH$_2$O— | —OCH$_2$— |
| D-290 | CH | N | 3 | 4 | Me | singlebond | singlebond |
| D-291 | CH | N | 3 | 4 | Ph | —O— | —O— |
| D-292 | CH | N | 3 | 4 | Ph | —O— | —S— |
| D-293 | CH | N | 3 | 4 | Ph | —O— | —OCH$_2$— |
| D-294 | CH | N | 3 | 4 | Ph | —O— | singlebond |
| D-295 | CH | N | 3 | 4 | Ph | —S— | —O— |
| D-296 | CH | N | 3 | 4 | Ph | —CH$_2$O— | —O— |
| D-297 | CH | N | 3 | 4 | Ph | singlebond | —O— |
| D-298 | CH | N | 3 | 4 | Ph | —S— | —S— |
| D-299 | CH | N | 3 | 4 | Ph | —CH$_2$O— | —OCH$_2$— |
| D-300 | CH | N | 3 | 4 | Ph | singlebond | singlebond |
| D-301 | CH | N | 4 | 3 | H | —O— | —O— |
| D-302 | CH | N | 4 | 3 | H | —O— | —S— |
| D-303 | CH | N | 4 | 3 | H | —O— | —OCH$_2$— |
| D-304 | CH | N | 4 | 3 | H | —O— | singlebond |
| D-305 | CH | N | 4 | 3 | H | —S— | —O— |
| D-306 | CH | N | 4 | 3 | H | —CH$_2$O— | —O— |
| D-307 | CH | N | 4 | 3 | H | singlebond | —O— |
| D-308 | CH | N | 4 | 3 | H | —S— | —S— |
| D-309 | CH | N | 4 | 3 | H | —CH$_2$O— | —OCH$_2$— |
| D-310 | CH | N | 4 | 3 | H | singlebond | singlebond |
| D-311 | CH | N | 4 | 3 | Me | —O— | —O— |
| D-312 | CH | N | 4 | 3 | Me | —O— | —S— |
| D-313 | CH | N | 4 | 3 | Me | —O— | —OCH$_2$— |
| D-314 | CH | N | 4 | 3 | Me | —O— | singlebond |
| D-315 | CH | N | 4 | 3 | Me | —S— | —O— |
| D-316 | CH | N | 4 | 3 | Me | —CH$_2$O— | —O— |
| D-317 | CH | N | 4 | 3 | Me | singlebond | —O— |
| D-318 | CH | N | 4 | 3 | Me | —S— | —S— |
| D-319 | CH | N | 4 | 3 | Me | —CH$_2$O— | —OCH$_2$— |
| D-320 | CH | N | 4 | 3 | Me | singlebond | singlebond |
| D-321 | CH | N | 4 | 3 | Ph | —O— | —O— |
| D-322 | CH | N | 4 | 3 | Ph | —O— | —S— |
| D-323 | CH | N | 4 | 3 | Ph | —O— | —OCH$_2$— |
| D-324 | CH | N | 4 | 3 | Ph | —O— | singlebond |
| D-325 | CH | N | 4 | 3 | Ph | —S— | —O— |
| D-326 | CH | N | 4 | 3 | Ph | —CH$_2$O— | —O— |
| D-327 | CH | N | 4 | 3 | Ph | singlebond | —O— |
| D-328 | CH | N | 4 | 3 | Ph | —S— | —S— |
| D-329 | CH | N | 4 | 3 | Ph | —CH$_2$O— | —OCH$_2$— |
| D-330 | CH | N | 4 | 3 | Ph | singlebond | singlebond |

TABLE 18

| Compound No. | G¹ | G² | n | m | $R^a$ | Q¹ | Q² |
|---|---|---|---|---|---|---|---|
| D-331 | CH | N | 4 | 4 | H | —O— | —O— |
| D-332 | CH | N | 4 | 4 | H | —O— | —S— |
| D-333 | CH | N | 4 | 4 | H | —O— | —OCH$_2$— |
| D-334 | CH | N | 4 | 4 | H | —O— | singlebond |
| D-335 | CH | N | 4 | 4 | H | —S— | —O— |
| D-336 | CH | N | 4 | 4 | H | —CH$_2$O— | —O— |
| D-337 | CH | N | 4 | 4 | H | singlebond | —O— |
| D-338 | CH | N | 4 | 4 | H | —S— | —S— |
| D-339 | CH | N | 4 | 4 | H | —CH$_2$O— | —OCH$_2$— |
| D-340 | CH | N | 4 | 4 | H | singlebond | singlebond |
| D-341 | CH | N | 4 | 4 | Me | —O— | —O— |
| D-342 | CH | N | 4 | 4 | Me | —O— | —S— |
| D-343 | CH | N | 4 | 4 | Me | —O— | —OCH$_2$— |
| D-344 | CH | N | 4 | 4 | Me | —O— | singlebond |
| D-345 | CH | N | 4 | 4 | Me | —S— | —O— |
| D-346 | CH | N | 4 | 4 | Me | —CH$_2$O— | —O— |
| D-347 | CH | N | 4 | 4 | Me | singlebond | —O— |
| D-348 | CH | N | 4 | 4 | Me | —S— | —S— |
| D-349 | CH | N | 4 | 4 | Me | —CH$_2$O— | —OCH$_2$— |
| D-350 | CH | N | 4 | 4 | Me | singlebond | singlebond |
| D-351 | CH | N | 4 | 4 | Ph | —O— | —O— |
| D-352 | CH | N | 4 | 4 | Ph | —O— | —S— |
| D-353 | CH | N | 4 | 4 | Ph | —O— | —OCH$_2$— |
| D-354 | CH | N | 4 | 4 | Ph | —O— | singlebond |
| D-355 | CH | N | 4 | 4 | Ph | —S— | —O— |
| D-356 | CH | N | 4 | 4 | Ph | —CH$_2$O— | —O— |
| D-357 | CH | N | 4 | 4 | Ph | singlebond | —O— |
| D-358 | CH | N | 4 | 4 | Ph | —S— | —S— |
| D-359 | CH | N | 4 | 4 | Ph | —CH$_2$O— | —OCH$_2$— |
| D-360 | CH | N | 4 | 4 | Ph | singlebond | singlebond |
| D-361 | CH | CH | 2 | 5 | H | —O— | —O— |
| D-362 | CH | CH | 3 | 5 | H | —O— | —O— |
| D-363 | CH | CH | 5 | 2 | H | —O— | —O— |
| D-364 | CH | CH | 5 | 3 | H | —O— | —O— |

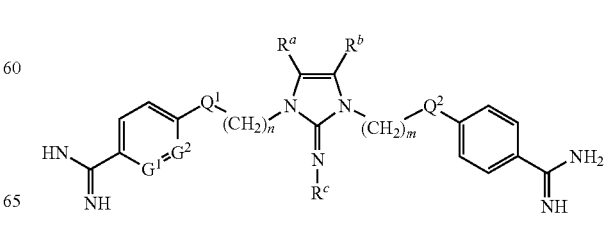

TABLE 19

| Compound No. | G$^1$ | G$^2$ | n | m | R$^a$ | R$^b$ | R$^c$ | Q$^1$ | Q$^2$ |
|---|---|---|---|---|---|---|---|---|---|
| E-1 | CH | CH | 3 | 3 | Me | H | H | —O— | —O— |
| E-2 | CH | CH | 3 | 3 | Me | H | H | —O— | —S— |
| E-3 | CH | CH | 3 | 3 | Me | H | H | —O— | —OCH$_2$— |
| E-4 | CH | CH | 3 | 3 | Me | H | H | —O— | singlebond |
| E-5 | CH | CH | 3 | 3 | Me | H | H | —S— | —O— |
| E-6 | CH | CH | 3 | 3 | Me | H | H | —CH$_2$O— | —O— |
| E-7 | CH | CH | 3 | 3 | Me | H | H | singlebond | —O— |
| E-8 | CH | CH | 3 | 3 | Me | H | H | —S— | —S— |
| E-9 | CH | CH | 3 | 3 | Me | H | H | —CH$_2$O— | —OCH$_2$— |
| E-10 | CH | CH | 3 | 3 | Me | H | H | singlebond | singlebond |
| E-11 | CH | CH | 3 | 3 | Me | Me | H | —O— | —O— |
| E-12 | CH | CH | 3 | 3 | Me | Me | H | —O— | —S— |
| E-13 | CH | CH | 3 | 3 | Me | Me | H | —O— | —OCH$_2$— |
| E-14 | CH | CH | 3 | 3 | Me | Me | H | —O— | singlebond |
| E-15 | CH | CH | 3 | 3 | Me | Me | H | —S— | —O— |
| E-16 | CH | CH | 3 | 3 | Me | Me | H | —CH$_2$O— | —O— |
| E-17 | CH | CH | 3 | 3 | Me | Me | H | singlebond | —O— |
| E-18 | CH | CH | 3 | 3 | Me | Me | H | —S— | —S— |
| E-19 | CH | CH | 3 | 3 | Me | Me | H | —CH$_2$O— | —OCH$_2$— |
| E-20 | CH | CH | 3 | 3 | Me | Me | H | singlebond | singlebond |
| E-21 | CH | CH | 3 | 3 | H | H | Me | —O— | —O— |
| E-22 | CH | CH | 3 | 3 | H | H | Me | —O— | —S— |
| E-23 | CH | CH | 3 | 3 | H | H | Me | —O— | —OCH$_2$— |
| E-24 | CH | CH | 3 | 3 | H | H | Me | —O— | singlebond |
| E-25 | CH | CH | 3 | 3 | H | H | Me | —S— | —O— |
| E-26 | CH | CH | 3 | 3 | H | H | Me | —CH$_2$O— | —O— |
| E-27 | CH | CH | 3 | 3 | H | H | Me | singlebond | —O— |
| E-28 | CH | CH | 3 | 3 | H | H | Me | —S— | —S— |
| E-29 | CH | CH | 3 | 3 | H | H | Me | —CH$_2$O— | —OCH$_2$— |
| E-30 | CH | CH | 3 | 3 | H | H | Me | singlebond | singlebond |
| E-31 | CH | CH | 3 | 3 | Ph | H | H | —O— | —O— |
| E-32 | CH | CH | 3 | 3 | Ph | H | H | —O— | —S— |
| E-33 | CH | CH | 3 | 3 | Ph | H | H | —O— | —OCH$_2$— |
| E-34 | CH | CH | 3 | 3 | Ph | H | H | —O— | singlebond |
| E-35 | CH | CH | 3 | 3 | Ph | H | H | —S— | —O— |
| E-36 | CH | CH | 3 | 3 | Ph | H | H | —CH$_2$O— | —O— |
| E-37 | CH | CH | 3 | 3 | Ph | H | H | singlebond | —O— |
| E-38 | CH | CH | 3 | 3 | Ph | H | H | —S— | —S— |
| E-39 | CH | CH | 3 | 3 | Ph | H | H | —CH$_2$O— | —OCH$_2$— |
| E-40 | CH | CH | 3 | 3 | Ph | H | H | singlebond | singlebond |
| E-41 | CH | CH | 3 | 4 | Me | H | H | —O— | —O— |
| E-42 | CH | CH | 3 | 4 | Me | H | H | —O— | —S— |
| E-43 | CH | CH | 3 | 4 | Me | H | H | —O— | —OCH$_2$— |
| E-44 | CH | CH | 3 | 4 | Me | H | H | —O— | singlebond |
| E-45 | CH | CH | 3 | 4 | Me | H | H | —S— | —O— |
| E-46 | CH | CH | 3 | 4 | Me | H | H | —CH$_2$O— | —O— |
| E-47 | CH | CH | 3 | 4 | Me | H | H | singlebond | —O— |
| E-48 | CH | CH | 3 | 4 | Me | H | H | —S— | —S— |
| E-49 | CH | CH | 3 | 4 | Me | H | H | —CH$_2$O— | —OCH$_2$— |
| E-50 | CH | CH | 3 | 4 | Me | H | H | singlebond | singlebond |
| E-51 | CH | CH | 3 | 4 | Me | Me | H | —O— | —O— |
| E-52 | CH | CH | 3 | 4 | Me | Me | H | —O— | —S— |
| E-53 | CH | CH | 3 | 4 | Me | Me | H | —O— | —OCH$_2$— |
| E-54 | CH | CH | 3 | 4 | Me | Me | H | —O— | singlebond |
| E-55 | CH | CH | 3 | 4 | Me | Me | H | —S— | —O— |
| E-56 | CH | CH | 3 | 4 | Me | Me | H | —CH$_2$O— | —O— |
| E-57 | CH | CH | 3 | 4 | Me | Me | H | singlebond | —O— |
| E-58 | CH | CH | 3 | 4 | Me | Me | H | —S— | —S— |
| E-59 | CH | CH | 3 | 4 | Me | Me | H | —CH$_2$O— | —OCH$_2$— |
| E-60 | CH | CH | 3 | 4 | Me | Me | H | singlebond | singlebond |
| E-61 | CH | CH | 3 | 4 | H | H | Me | —O— | —O— |
| E-62 | CH | CH | 3 | 4 | H | H | Me | —O— | —S— |
| E-63 | CH | CH | 3 | 4 | H | H | Me | —O— | —OCH$_2$— |
| E-64 | CH | CH | 3 | 4 | H | H | Me | —O— | singlebond |
| E-65 | CH | CH | 3 | 4 | H | H | Me | —S— | —O— |
| E-66 | CH | CH | 3 | 4 | H | H | Me | —CH$_2$O— | —O— |
| E-67 | CH | CH | 3 | 4 | H | H | Me | singlebond | —O— |
| E-68 | CH | CH | 3 | 4 | H | H | Me | —S— | —S— |
| E-69 | CH | CH | 3 | 4 | H | H | Me | —CH$_2$O— | —OCH$_2$— |
| E-70 | CH | CH | 3 | 4 | H | H | Me | singlebond | singlebond |
| E-71 | CH | CH | 3 | 4 | Ph | H | H | —O— | —O— |
| E-72 | CH | CH | 3 | 4 | Ph | H | H | —O— | —S— |
| E-73 | CH | CH | 3 | 4 | Ph | H | H | —O— | —OCH$_2$— |
| E-74 | CH | CH | 3 | 4 | Ph | H | H | —O— | singlebond |
| E-75 | CH | CH | 3 | 4 | Ph | H | H | —S— | —O— |
| E-76 | CH | CH | 3 | 4 | Ph | H | H | —CH$_2$O— | —O— |
| E-77 | CH | CH | 3 | 4 | Ph | H | H | singlebond | —O— |
| E-78 | CH | CH | 3 | 4 | Ph | H | H | —S— | —S— |
| E-79 | CH | CH | 3 | 4 | Ph | H | H | —CH$_2$O— | —OCH$_2$— |
| E-80 | CH | CH | 3 | 4 | Ph | H | H | singlebond | singlebond |
| E-81 | CH | CH | 4 | 3 | Me | H | H | —O— | —O— |
| E-82 | CH | CH | 4 | 3 | Me | H | H | —O— | —S— |
| E-83 | CH | CH | 4 | 3 | Me | H | H | —O— | —OCH$_2$— |
| E-84 | CH | CH | 4 | 3 | Me | H | H | —O— | singlebond |
| E-85 | CH | CH | 4 | 3 | Me | H | H | —S— | —O— |
| E-86 | CH | CH | 4 | 3 | Me | H | H | —CH$_2$O— | —O— |
| E-87 | CH | CH | 4 | 3 | Me | H | H | singlebond | —O— |
| E-88 | CH | CH | 4 | 3 | Me | H | H | —S— | —S— |
| E-89 | CH | CH | 4 | 3 | Me | H | H | —CH$_2$O— | —OCH$_2$— |
| E-90 | CH | CH | 4 | 3 | Me | H | H | singlebond | singlebond |
| E-91 | CH | CH | 4 | 3 | Me | Me | H | —O— | —O— |
| E-92 | CH | CH | 4 | 3 | Me | Me | H | —O— | —S— |
| E-93 | CH | CH | 4 | 3 | Me | Me | H | —O— | —OCH$_2$— |
| E-94 | CH | CH | 4 | 3 | Me | Me | H | —O— | singlebond |
| E-95 | CH | CH | 4 | 3 | Me | Me | H | —S— | —O— |
| E-96 | CH | CH | 4 | 3 | Me | Me | H | —CH$_2$O— | —O— |
| E-97 | CH | CH | 4 | 3 | Me | Me | H | singlebond | —O— |
| E-98 | CH | CH | 4 | 3 | Me | Me | H | —S— | —S— |
| E-99 | CH | CH | 4 | 3 | Me | Me | H | —CH$_2$O— | —OCH$_2$— |
| E-100 | CH | CH | 4 | 3 | Me | Me | H | singlebond | singlebond |
| E-101 | CH | CH | 4 | 3 | H | H | Me | —O— | —O— |
| E-102 | CH | CH | 4 | 3 | H | H | Me | —O— | —S— |
| E-103 | CH | CH | 4 | 3 | H | H | Me | —O— | —OCH$_2$— |
| E-104 | CH | CH | 4 | 3 | H | H | Me | —O— | singlebond |
| E-105 | CH | CH | 4 | 3 | H | H | Me | —S— | —O— |
| E-106 | CH | CH | 4 | 3 | H | H | Me | —CH$_2$O— | —O— |
| E-107 | CH | CH | 4 | 3 | H | H | Me | singlebond | —O— |
| E-108 | CH | CH | 4 | 3 | H | H | Me | —S— | —S— |
| E-109 | CH | CH | 4 | 3 | H | H | Me | —CH$_2$O— | —OCH$_2$— |
| E-110 | CH | CH | 4 | 3 | H | H | Me | singlebond | singlebond |

TABLE 20

| Compound No. | G$^1$ | G$^2$ | n | m | R$^a$ | R$^b$ | R$^c$ | Q$^1$ | Q$^2$ |
|---|---|---|---|---|---|---|---|---|---|
| E-111 | CH | CH | 4 | 3 | Ph | H | H | —O— | —O— |
| E-112 | CH | CH | 4 | 3 | Ph | H | H | —O— | —S— |
| E-113 | CH | CH | 4 | 3 | Ph | H | H | —O— | —OCH$_2$— |
| E-114 | CH | CH | 4 | 3 | Ph | H | H | —O— | singlebond |
| E-115 | CH | CH | 4 | 3 | Ph | H | H | —S— | —O— |
| E-116 | CH | CH | 4 | 3 | Ph | H | H | —CH$_2$O— | —O— |
| E-117 | CH | CH | 4 | 3 | Ph | H | H | singlebond | —O— |
| E-118 | CH | CH | 4 | 3 | Ph | H | H | —S— | —S— |
| E-119 | CH | CH | 4 | 3 | Ph | H | H | —CH$_2$O— | —OCH$_2$— |
| E-120 | CH | CH | 4 | 3 | Ph | H | H | singlebond | singlebond |
| E-121 | CH | CH | 4 | 4 | Me | H | H | —O— | —O— |
| E-122 | CH | CH | 4 | 4 | Me | H | H | —O— | —S— |
| E-123 | CH | CH | 4 | 4 | Me | H | H | —O— | —OCH$_2$— |
| E-124 | CH | CH | 4 | 4 | Me | H | H | —O— | singlebond |
| E-125 | CH | CH | 4 | 4 | Me | H | H | —S— | —O— |
| E-126 | CH | CH | 4 | 4 | Me | H | H | —CH$_2$O— | —O— |
| E-127 | CH | CH | 4 | 4 | Me | H | H | singlebond | —O— |
| E-128 | CH | CH | 4 | 4 | Me | H | H | —S— | —S— |
| E-129 | CH | CH | 4 | 4 | Me | H | H | —CH$_2$O— | —OCH$_2$— |
| E-130 | CH | CH | 4 | 4 | Me | H | H | singlebond | singlebond |
| E-131 | CH | CH | 4 | 4 | Me | Me | H | —O— | —O— |
| E-132 | CH | CH | 4 | 4 | Me | Me | H | —O— | —S— |
| E-133 | CH | CH | 4 | 4 | Me | Me | H | —O— | —OCH$_2$— |
| E-134 | CH | CH | 4 | 4 | Me | Me | H | —O— | singlebond |
| E-135 | CH | CH | 4 | 4 | Me | Me | H | —S— | —O— |
| E-136 | CH | CH | 4 | 4 | Me | Me | H | —CH$_2$O— | —O— |
| E-137 | CH | CH | 4 | 4 | Me | Me | H | singlebond | —O— |
| E-138 | CH | CH | 4 | 4 | Me | Me | H | —S— | —S— |
| E-139 | CH | CH | 4 | 4 | Me | Me | H | —CH$_2$O— | —OCH$_2$— |
| E-140 | CH | CH | 4 | 4 | Me | Me | H | singlebond | singlebond |
| E-141 | CH | CH | 4 | 4 | H | H | Me | —O— | —O— |
| E-142 | CH | CH | 4 | 4 | H | H | Me | —O— | —S— |

TABLE 20-continued

| Compound No. | G¹ | G² | n | m | $R^a$ | $R^b$ | $R^c$ | Q¹ | Q² |
|---|---|---|---|---|---|---|---|---|---|
| E-143 | CH | CH | 4 | 4 | H | H | Me | —O— | —O— |
| E-144 | CH | CH | 4 | 4 | H | H | Me | —O— | singlebond |
| E-145 | CH | CH | 4 | 4 | H | H | Me | —S— | —O— |
| E-146 | CH | CH | 4 | 4 | H | H | Me | —CH₂O— | —O— |
| E-147 | CH | CH | 4 | 4 | H | H | Me | singlebond | —O— |
| E-148 | CH | CH | 4 | 4 | H | H | Me | —S— | —S— |
| E-149 | CH | CH | 4 | 4 | H | H | Me | —CH₂O— | —OCH₂— |
| E-150 | CH | CH | 4 | 4 | H | H | Me | singlebond | singlebond |
| E-151 | CH | CH | 4 | 4 | Ph | H | H | —O— | —O— |
| E-152 | CH | CH | 4 | 4 | Ph | H | H | —O— | —S— |
| E-153 | CH | CH | 4 | 4 | Ph | H | H | —O— | —OCH₂— |
| E-154 | CH | CH | 4 | 4 | Ph | H | H | —O— | singlebond |
| E-155 | CH | CH | 4 | 4 | Ph | H | H | —S— | —O— |
| E-156 | CH | CH | 4 | 4 | Ph | H | H | —CH₂O— | —O— |
| E-157 | CH | CH | 4 | 4 | Ph | H | H | singlebond | —O— |
| E-158 | CH | CH | 4 | 4 | Ph | H | H | —S— | —S— |
| E-159 | CH | CH | 4 | 4 | Ph | H | H | —CH₂O— | —OCH₂— |
| E-160 | CH | CH | 4 | 4 | Ph | H | H | singlebond | singlebond |
| E-161 | N | CH | 3 | 3 | Me | H | H | —O— | —O— |
| E-162 | N | CH | 3 | 3 | Me | H | H | —O— | —S— |
| E-163 | N | CH | 3 | 3 | Me | H | H | —O— | —OCH₂— |
| E-164 | N | CH | 3 | 3 | Me | H | H | —O— | singlebond |
| E-165 | N | CH | 3 | 3 | Me | H | H | —S— | —O— |
| E-166 | N | CH | 3 | 3 | Me | H | H | —CH₂O— | —O— |
| E-167 | N | CH | 3 | 3 | Me | H | H | singlebond | —O— |
| E-168 | N | CH | 3 | 3 | Me | H | H | —S— | —S— |
| E-169 | N | CH | 3 | 3 | Me | H | H | —CH₂O— | —OCH₂— |
| E-170 | N | CH | 3 | 3 | Me | H | H | singlebond | singlebond |
| E-171 | N | CH | 3 | 3 | Me | Me | H | —O— | —O— |
| E-172 | N | CH | 3 | 3 | Me | Me | H | —O— | —S— |
| E-173 | N | CH | 3 | 3 | Me | Me | H | —O— | —OCH₂— |
| E-174 | N | CH | 3 | 3 | Me | Me | H | —O— | singlebond |
| E-175 | N | CH | 3 | 3 | Me | Me | H | —S— | —O— |
| E-176 | N | CH | 3 | 3 | Me | Me | H | —CH₂O— | —O— |
| E-177 | N | CH | 3 | 3 | Me | Me | H | singlebond | —O— |
| E-178 | N | CH | 3 | 3 | Me | Me | H | —S— | —S— |
| E-179 | N | CH | 3 | 3 | Me | Me | H | —CH₂O— | —OCH₂— |
| E-180 | N | CH | 3 | 3 | Me | Me | H | singlebond | singlebond |
| E-181 | N | CH | 3 | 3 | H | H | Me | —O— | —O— |
| E-182 | N | CH | 3 | 3 | H | H | Me | —O— | —S— |
| E-183 | N | CH | 3 | 3 | H | H | Me | —O— | —OCH₂— |
| E-184 | N | CH | 3 | 3 | H | H | Me | —O— | singlebond |
| E-185 | N | CH | 3 | 3 | H | H | Me | —S— | —O— |
| E-186 | N | CH | 3 | 3 | H | H | Me | —CH₂O— | —O— |
| E-187 | N | CH | 3 | 3 | H | H | Me | singlebond | —O— |
| E-188 | N | CH | 3 | 3 | H | H | Me | —S— | —S— |
| E-189 | N | CH | 3 | 3 | H | H | Me | —CH₂O— | —OCH₂— |
| E-190 | N | CH | 3 | 3 | H | H | Me | singlebond | singlebond |
| E-191 | N | CH | 3 | 3 | Ph | H | H | —O— | —O— |
| E-192 | N | CH | 3 | 3 | Ph | H | H | —O— | —S— |
| E-193 | N | CH | 3 | 3 | Ph | H | H | —O— | —OCH₂— |
| E-194 | N | CH | 3 | 3 | Ph | H | H | —O— | singlebond |
| E-195 | N | CH | 3 | 3 | Ph | H | H | —S— | —O— |
| E-196 | N | CH | 3 | 3 | Ph | H | H | —CH₂O— | —O— |
| E-197 | N | CH | 3 | 3 | Ph | H | H | singlebond | —O— |
| E-198 | N | CH | 3 | 3 | Ph | H | H | —S— | —S— |
| E-199 | N | CH | 3 | 3 | Ph | H | H | —CH₂O— | —OCH₂— |
| E-200 | N | CH | 3 | 3 | Ph | H | H | singlebond | singlebond |
| E-201 | N | CH | 3 | 4 | Me | H | H | —O— | —O— |
| E-202 | N | CH | 3 | 4 | Me | H | H | —O— | —S— |
| E-203 | N | CH | 3 | 4 | Me | H | H | —O— | —OCH₂— |
| E-204 | N | CH | 3 | 4 | Me | H | H | —O— | singlebond |
| E-205 | N | CH | 3 | 4 | Me | H | H | —S— | —O— |
| E-206 | N | CH | 3 | 4 | Me | H | H | —CH₂O— | —O— |
| E-207 | N | CH | 3 | 4 | Me | H | H | singlebond | —O— |
| E-208 | N | CH | 3 | 4 | Me | H | H | —S— | —S— |
| E-209 | N | CH | 3 | 4 | Me | H | H | —CH₂O— | —OCH₂— |
| E-210 | N | CH | 3 | 4 | Me | H | H | singlebond | singlebond |
| E-211 | N | CH | 3 | 4 | Me | Me | H | —O— | —O— |
| E-212 | N | CH | 3 | 4 | Me | Me | H | —O— | —S— |
| E-213 | N | CH | 3 | 4 | Me | Me | H | —O— | —OCH₂— |
| E-214 | N | CH | 3 | 4 | Me | Me | H | —O— | singlebond |
| E-215 | N | CH | 3 | 4 | Me | Me | H | —S— | —O— |
| E-216 | N | CH | 3 | 4 | Me | Me | H | —CH₂O— | —O— |
| E-217 | N | CH | 3 | 4 | Me | Me | H | singlebond | —O— |
| E-218 | N | CH | 3 | 4 | Me | Me | H | —S— | —S— |
| E-219 | N | CH | 3 | 4 | Me | Me | H | —CH₂O— | —OCH₂— |
| E-220 | N | CH | 3 | 4 | Me | Me | H | singlebond | singlebond |

TABLE 21

| Compound No. | G¹ | G² | n | m | $R^a$ | $R^b$ | $R^c$ | Q¹ | Q² |
|---|---|---|---|---|---|---|---|---|---|
| E-221 | N | CH | 3 | 4 | H | H | Me | —O— | —O— |
| E-222 | N | CH | 3 | 4 | H | H | Me | —O— | —S— |
| E-223 | N | CH | 3 | 4 | H | H | Me | —O— | —OCH₂— |
| E-224 | N | CH | 3 | 4 | H | H | Me | —O— | singlebond |
| E-225 | N | CH | 3 | 4 | H | H | Me | —S— | —O— |
| E-226 | N | CH | 3 | 4 | H | H | Me | —CH₂O— | —O— |
| E-227 | N | CH | 3 | 4 | H | H | Me | singlebond | —O— |
| E-228 | N | CH | 3 | 4 | H | H | Me | —S— | —S— |
| E-229 | N | CH | 3 | 4 | H | H | Me | —CH₂O— | —OCH₂— |
| E-230 | N | CH | 3 | 4 | H | H | Me | singlebond | singlebond |
| E-231 | N | CH | 3 | 4 | Ph | H | H | —O— | —O— |
| E-232 | N | CH | 3 | 4 | Ph | H | H | —O— | —S— |
| E-233 | N | CH | 3 | 4 | Ph | H | H | —O— | —OCH₂— |
| E-234 | N | CH | 3 | 4 | Ph | H | H | —O— | singlebond |
| E-235 | N | CH | 3 | 4 | Ph | H | H | —S— | —O— |
| E-236 | N | CH | 3 | 4 | Ph | H | H | —CH₂O— | —O— |
| E-237 | N | CH | 3 | 4 | Ph | H | H | singlebond | —O— |
| E-238 | N | CH | 3 | 4 | Ph | H | H | —S— | —S— |
| E-239 | N | CH | 3 | 4 | Ph | H | H | —CH₂O— | —OCH₂— |
| E-240 | N | CH | 3 | 4 | Ph | H | H | singlebond | singlebond |
| E-241 | N | CH | 4 | 3 | Me | H | H | —O— | —O— |
| E-242 | N | CH | 4 | 3 | Me | H | H | —O— | —S— |
| E-243 | N | CH | 4 | 3 | Me | H | H | —O— | —OCH₂— |
| E-244 | N | CH | 4 | 3 | Me | H | H | —O— | singlebond |
| E-245 | N | CH | 4 | 3 | Me | H | H | —S— | —O— |
| E-246 | N | CH | 4 | 3 | Me | H | H | —CH₂O— | —O— |
| E-247 | N | CH | 4 | 3 | Me | H | H | singlebond | —O— |
| E-248 | N | CH | 4 | 3 | Me | H | H | —S— | —S— |
| E-249 | N | CH | 4 | 3 | Me | H | H | —CH₂O— | —OCH₂— |
| E-250 | N | CH | 4 | 3 | Me | H | H | singlebond | singlebond |
| E-251 | N | CH | 4 | 3 | Me | Me | H | —O— | —O— |
| E-252 | N | CH | 4 | 3 | Me | Me | H | —O— | —S— |
| E-253 | N | CH | 4 | 3 | Me | Me | H | —O— | —OCH₂— |
| E-254 | N | CH | 4 | 3 | Me | Me | H | —O— | singlebond |
| E-255 | N | CH | 4 | 3 | Me | Me | H | —S— | —O— |
| E-256 | N | CH | 4 | 3 | Me | Me | H | —CH₂O— | —O— |
| E-257 | N | CH | 4 | 3 | Me | Me | H | singlebond | —O— |
| E-258 | N | CH | 4 | 3 | Me | Me | H | —S— | —S— |
| E-259 | N | CH | 4 | 3 | Me | Me | H | —CH₂O— | —OCH₂— |
| E-260 | N | CH | 4 | 3 | Me | Me | H | singlebond | singlebond |
| E-261 | N | CH | 4 | 3 | H | H | Me | —O— | —O— |
| E-262 | N | CH | 4 | 3 | H | H | Me | —O— | —S— |
| E-263 | N | CH | 4 | 3 | H | H | Me | —O— | —OCH₂— |
| E-264 | N | CH | 4 | 3 | H | H | Me | —O— | singlebond |
| E-265 | N | CH | 4 | 3 | H | H | Me | —S— | —O— |
| E-266 | N | CH | 4 | 3 | H | H | Me | —CH₂O— | —O— |
| E-267 | N | CH | 4 | 3 | H | H | Me | singlebond | —O— |
| E-268 | N | CH | 4 | 3 | H | H | Me | —S— | —S— |
| E-269 | N | CH | 4 | 3 | H | H | Me | —CH₂O— | —OCH₂— |
| E-270 | N | CH | 4 | 3 | H | H | Me | singlebond | singlebond |
| E-271 | N | CH | 4 | 3 | Ph | H | H | —O— | —O— |
| E-272 | N | CH | 4 | 3 | Ph | H | H | —O— | —S— |
| E-273 | N | CH | 4 | 3 | Ph | H | H | —O— | —OCH₂— |
| E-274 | N | CH | 4 | 3 | Ph | H | H | —O— | singlebond |
| E-275 | N | CH | 4 | 3 | Ph | H | H | —S— | —O— |
| E-276 | N | CH | 4 | 3 | Ph | H | H | —CH₂O— | —O— |
| E-277 | N | CH | 4 | 3 | Ph | H | H | singlebond | —O— |
| E-278 | N | CH | 4 | 3 | Ph | H | H | —S— | —S— |
| E-279 | N | CH | 4 | 3 | Ph | H | H | —CH₂O— | —OCH₂— |
| E-280 | N | CH | 4 | 3 | Ph | H | H | singlebond | —O— |
| E-281 | N | CH | 4 | 4 | Me | H | H | —O— | —O— |
| E-282 | N | CH | 4 | 4 | Me | H | H | —O— | —S— |
| E-283 | N | CH | 4 | 4 | Me | H | H | —O— | —OCH₂— |
| E-284 | N | CH | 4 | 4 | Me | H | H | —O— | singlebond |

TABLE 21-continued

| Compound No. | G¹ | G² | n | m | R$^a$ | R$^b$ | R$^c$ | Q¹ | Q² |
|---|---|---|---|---|---|---|---|---|---|
| E-285 | N | CH | 4 | 4 | Me | H | H | —S— | —O— |
| E-286 | N | CH | 4 | 4 | Me | H | H | —CH₂O— | —O— |
| E-287 | N | CH | 4 | 4 | Me | H | H | singlebond | —O— |
| E-288 | N | CH | 4 | 4 | Me | H | H | —S— | —S— |
| E-289 | N | CH | 4 | 4 | Me | H | H | —CH₂O— | —OCH₂— |
| E-290 | N | CH | 4 | 4 | Me | H | H | singlebond | singlebond |
| E-291 | N | CH | 4 | 4 | Me | Me | H | —O— | —O— |
| E-292 | N | CH | 4 | 4 | Me | Me | H | —O— | —S— |
| E-293 | N | CH | 4 | 4 | Me | Me | H | —O— | —OCH₂— |
| E-294 | N | CH | 4 | 4 | Me | Me | H | —O— | singlebond |
| E-295 | N | CH | 4 | 4 | Me | Me | H | —S— | —O— |
| E-296 | N | CH | 4 | 4 | Me | Me | H | —CH₂O— | —O— |
| E-297 | N | CH | 4 | 4 | Me | Me | H | singlebond | —O— |
| E-298 | N | CH | 4 | 4 | Me | Me | H | —S— | —S— |
| E-299 | N | CH | 4 | 4 | Me | Me | H | —CH₂O— | —OCH₂— |
| E-300 | N | CH | 4 | 4 | Me | Me | H | singlebond | singlebond |
| E-301 | N | CH | 4 | 4 | H | H | Me | —O— | —O— |
| E-302 | N | CH | 4 | 4 | H | H | Me | —O— | —S— |
| E-303 | N | CH | 4 | 4 | H | H | Me | —O— | —OCH₂— |
| E-304 | N | CH | 4 | 4 | H | H | Me | —O— | singlebond |
| E-305 | N | CH | 4 | 4 | H | H | Me | —S— | —O— |
| E-306 | N | CH | 4 | 4 | H | H | Me | —CH₂O— | —O— |
| E-307 | N | CH | 4 | 4 | H | H | Me | singlebond | —O— |
| E-308 | N | CH | 4 | 4 | H | H | Me | —S— | —S— |
| E-309 | N | CH | 4 | 4 | H | H | Me | —CH₂O— | —OCH₂— |
| E-310 | N | CH | 4 | 4 | H | H | Me | singlebond | singlebond |
| E-311 | N | CH | 4 | 4 | Ph | H | H | —O— | —O— |
| E-312 | N | CH | 4 | 4 | Ph | H | H | —O— | —S— |
| E-313 | N | CH | 4 | 4 | Ph | H | H | —O— | —OCH₂— |
| E-314 | N | CH | 4 | 4 | Ph | H | H | —O— | singlebond |
| E-315 | N | CH | 4 | 4 | Ph | H | H | —S— | —O— |
| E-316 | N | CH | 4 | 4 | Ph | H | H | —CH₂O— | —O— |
| E-317 | N | CH | 4 | 4 | Ph | H | H | singlebond | —O— |
| E-318 | N | CH | 4 | 4 | Ph | H | H | —S— | —S— |
| E-319 | N | CH | 4 | 4 | Ph | H | H | —CH₂O— | —OCH₂— |
| E-320 | N | CH | 4 | 4 | Ph | H | H | singlebond | singlebond |
| E-321 | CH | N | 3 | 3 | Me | H | H | —O— | —O— |
| E-322 | CH | N | 3 | 3 | Me | H | H | —O— | —S— |
| E-323 | CH | N | 3 | 3 | Me | H | H | —O— | —OCH₂— |
| E-324 | CH | N | 3 | 3 | Me | H | H | —O— | singlebond |
| E-325 | CH | N | 3 | 3 | Me | H | H | —S— | —O— |
| E-326 | CH | N | 3 | 3 | Me | H | H | —CH₂O— | —O— |
| E-327 | CH | N | 3 | 3 | Me | H | H | singlebond | —O— |
| E-328 | CH | N | 3 | 3 | Me | H | H | —S— | —S— |
| E-329 | CH | N | 3 | 3 | Me | H | H | —CH₂O— | —OCH₂— |
| E-330 | CH | N | 3 | 3 | Me | H | H | singlebond | singlebond |

TABLE 22

| Compound No. | G¹ | G² | n | m | R$^a$ | R$^b$ | R$^c$ | Q¹ | Q² |
|---|---|---|---|---|---|---|---|---|---|
| E-331 | CH | N | 3 | 3 | Me | Me | H | —O— | —O— |
| E-332 | CH | N | 3 | 3 | Me | Me | H | —O— | —S— |
| E-333 | CH | N | 3 | 3 | Me | Me | H | —O— | —OCH₂— |
| E-334 | CH | N | 3 | 3 | Me | Me | H | —O— | singlebond |
| E-335 | CH | N | 3 | 3 | Me | Me | H | —S— | —O— |
| E-336 | CH | N | 3 | 3 | Me | Me | H | —CH₂O— | —O— |
| E-337 | CH | N | 3 | 3 | Me | Me | H | singlebond | —O— |
| E-338 | CH | N | 3 | 3 | Me | Me | H | —S— | —S— |
| E-339 | CH | N | 3 | 3 | Me | Me | H | —CH₂O— | —OCH₂— |
| E-340 | CH | N | 3 | 3 | Me | Me | H | singlebond | singlebond |
| E-341 | CH | N | 3 | 3 | H | H | Me | —O— | —O— |
| E-342 | CH | N | 3 | 3 | H | H | Me | —O— | —S— |
| E-343 | CH | N | 3 | 3 | H | H | Me | —O— | —OCH₂— |
| E-344 | CH | N | 3 | 3 | H | H | Me | —O— | singlebond |
| E-345 | CH | N | 3 | 3 | H | H | Me | —S— | —O— |
| E-346 | CH | N | 3 | 3 | H | H | Me | —CH₂O— | —O— |
| E-347 | CH | N | 3 | 3 | H | H | Me | singlebond | —O— |
| E-348 | CH | N | 3 | 3 | H | H | Me | —S— | —S— |
| E-349 | CH | N | 3 | 3 | H | H | Me | —CH₂O— | —OCH₂— |
| E-350 | CH | N | 3 | 3 | H | H | Me | singlebond | singlebond |

TABLE 22-continued

| Compound No. | G¹ | G² | n | m | R$^a$ | R$^b$ | R$^c$ | Q¹ | Q² |
|---|---|---|---|---|---|---|---|---|---|
| E-351 | CH | N | 3 | 3 | Ph | H | H | —O— | —O— |
| E-352 | CH | N | 3 | 3 | Ph | H | H | —O— | —S— |
| E-353 | CH | N | 3 | 3 | Ph | H | H | —O— | —OCH₂— |
| E-354 | CH | N | 3 | 3 | Ph | H | H | —O— | singlebond |
| E-355 | CH | N | 3 | 3 | Ph | H | H | —S— | —O— |
| E-356 | CH | N | 3 | 3 | Ph | H | H | —CH₂O— | —O— |
| E-357 | CH | N | 3 | 3 | Ph | H | H | singlebond | —O— |
| E-358 | CH | N | 3 | 3 | Ph | H | H | —S— | —S— |
| E-359 | CH | N | 3 | 3 | Ph | H | H | —CH₂O— | —OCH₂— |
| E-360 | CH | N | 3 | 3 | Ph | H | H | singlebond | singlebond |
| E-361 | CH | N | 3 | 4 | Me | H | H | —O— | —O— |
| E-362 | CH | N | 3 | 4 | Me | H | H | —O— | —S— |
| E-363 | CH | N | 3 | 4 | Me | H | H | —O— | —OCH₂— |
| E-364 | CH | N | 3 | 4 | Me | H | H | —O— | singlebond |
| E-365 | CH | N | 3 | 4 | Me | H | H | —S— | —O— |
| E-366 | CH | N | 3 | 4 | Me | H | H | —CH₂O— | —O— |
| E-367 | CH | N | 3 | 4 | Me | H | H | singlebond | —O— |
| E-368 | CH | N | 3 | 4 | Me | H | H | —S— | —S— |
| E-369 | CH | N | 3 | 4 | Me | H | H | —CH₂O— | —OCH₂— |
| E-370 | CH | N | 3 | 4 | Me | H | H | singlebond | singlebond |
| E-371 | CH | N | 3 | 4 | Me | Me | H | —O— | —O— |
| E-372 | CH | N | 3 | 4 | Me | Me | H | —O— | —S— |
| E-373 | CH | N | 3 | 4 | Me | Me | H | —O— | —OCH₂— |
| E-374 | CH | N | 3 | 4 | Me | Me | H | —O— | singlebond |
| E-375 | CH | N | 3 | 4 | Me | Me | H | —S— | —O— |
| E-376 | CH | N | 3 | 4 | Me | Me | H | —CH₂O— | —O— |
| E-377 | CH | N | 3 | 4 | Me | Me | H | singlebond | —O— |
| E-378 | CH | N | 3 | 4 | Me | Me | H | —S— | —S— |
| E-379 | CH | N | 3 | 4 | Me | Me | H | —CH₂O— | —OCH₂— |
| E-380 | CH | N | 3 | 4 | Me | Me | H | singlebond | singlebond |
| E-381 | CH | N | 3 | 4 | H | H | Me | —O— | —O— |
| E-382 | CH | N | 3 | 4 | H | H | Me | —O— | —S— |
| E-383 | CH | N | 3 | 4 | H | H | Me | —O— | —OCH₂— |
| E-384 | CH | N | 3 | 4 | H | H | Me | —O— | singlebond |
| E-385 | CH | N | 3 | 4 | H | H | Me | —S— | —O— |
| E-386 | CH | N | 3 | 4 | H | H | Me | —CH₂O— | —O— |
| E-387 | CH | N | 3 | 4 | H | H | Me | singlebond | —O— |
| E-388 | CH | N | 3 | 4 | H | H | Me | —S— | —S— |
| E-389 | CH | N | 3 | 4 | H | H | Me | —CH₂O— | —OCH₂— |
| E-390 | CH | N | 3 | 4 | H | H | Me | singlebond | singlebond |
| E-391 | CH | N | 3 | 4 | Ph | H | H | —O— | —O— |
| E-392 | CH | N | 3 | 4 | Ph | H | H | —O— | —S— |
| E-393 | CH | N | 3 | 4 | Ph | H | H | —O— | —OCH₂— |
| E-394 | CH | N | 3 | 4 | Ph | H | H | —O— | singlebond |
| E-395 | CH | N | 3 | 4 | Ph | H | H | —S— | —O— |
| E-396 | CH | N | 3 | 4 | Ph | H | H | —CH₂O— | —O— |
| E-397 | CH | N | 3 | 4 | Ph | H | H | singlebond | —O— |
| E-398 | CH | N | 3 | 4 | Ph | H | H | —S— | —S— |
| E-399 | CH | N | 3 | 4 | Ph | H | H | —CH₂O— | —OCH₂— |
| E-400 | CH | N | 3 | 4 | Ph | H | H | singlebond | singlebond |
| E-401 | CH | N | 4 | 3 | Me | H | H | —O— | —O— |
| E-402 | CH | N | 4 | 3 | Me | H | H | —O— | —S— |
| E-403 | CH | N | 4 | 3 | Me | H | H | —O— | —OCH₂— |
| E-404 | CH | N | 4 | 3 | Me | H | H | —O— | singlebond |
| E-405 | CH | N | 4 | 3 | Me | H | H | —S— | —O— |
| E-406 | CH | N | 4 | 3 | Me | H | H | —CH₂O— | —O— |
| E-407 | CH | N | 4 | 3 | Me | H | H | singlebond | —O— |
| E-408 | CH | N | 4 | 3 | Me | H | H | —S— | —S— |
| E-409 | CH | N | 4 | 3 | Me | H | H | —CH₂O— | —OCH₂— |
| E-410 | CH | N | 4 | 3 | Me | H | H | singlebond | singlebond |
| E-411 | CH | N | 4 | 3 | Me | Me | H | —O— | —O— |
| E-412 | CH | N | 4 | 3 | Me | Me | H | —O— | —S— |
| E-413 | CH | N | 4 | 3 | Me | Me | H | —O— | —OCH₂— |
| E-414 | CH | N | 4 | 3 | Me | Me | H | —O— | singlebond |
| E-415 | CH | N | 4 | 3 | Me | Me | H | —S— | —O— |
| E-416 | CH | N | 4 | 3 | Me | Me | H | —CH₂O— | —O— |
| E-417 | CH | N | 4 | 3 | Me | Me | H | singlebond | —O— |
| E-418 | CH | N | 4 | 3 | Me | Me | H | —S— | —S— |
| E-419 | CH | N | 4 | 3 | Me | Me | H | —CH₂O— | —OCH₂— |
| E-420 | CH | N | 4 | 3 | Me | Me | H | singlebond | singlebond |
| E-421 | CH | N | 4 | 3 | H | H | Me | —O— | —O— |
| E-422 | CH | N | 4 | 3 | H | H | Me | —O— | —S— |
| E-423 | CH | N | 4 | 3 | H | H | Me | —O— | —OCH₂— |
| E-424 | CH | N | 4 | 3 | H | H | Me | —O— | singlebond |
| E-425 | CH | N | 4 | 3 | H | H | Me | —S— | —O— |
| E-426 | CH | N | 4 | 3 | H | H | Me | —CH₂O— | —O— |

TABLE 22-continued

| Compound No. | G¹ | G² | n | m | $R^a$ | $R^b$ | $R^c$ | Q¹ | Q² |
|---|---|---|---|---|---|---|---|---|---|
| E-427 | CH | N | 4 | 3 | H | H | Me | singlebond | —O— |
| E-428 | CH | N | 4 | 3 | H | H | Me | —S— | —S— |
| E-429 | CH | N | 4 | 3 | H | H | Me | —CH$_2$O— | —OCH$_2$— |
| E-430 | CH | N | 4 | 3 | H | H | Me | singlebond | singlebond |
| E-431 | CH | N | 4 | 3 | Ph | H | H | —O— | —O— |
| E-432 | CH | N | 4 | 3 | Ph | H | H | —O— | —S— |
| E-433 | CH | N | 4 | 3 | Ph | H | H | —O— | —OCH$_2$— |
| E-434 | CH | N | 4 | 3 | Ph | H | H | —O— | singlebond |
| E-435 | CH | N | 4 | 3 | Ph | H | H | —S— | —O— |
| E-436 | CH | N | 4 | 3 | Ph | H | H | —CH$_2$O— | —O— |
| E-437 | CH | N | 4 | 3 | Ph | H | H | singlebond | —O— |
| E-438 | CH | N | 4 | 3 | Ph | H | H | —S— | —S— |
| E-439 | CH | N | 4 | 3 | Ph | H | H | —CH$_2$O— | —OCH$_2$— |
| E-440 | CH | N | 4 | 3 | Ph | H | H | singlebond | singlebond |

TABLE 23

| Compound No. | G¹ | G² | n | m | $R^a$ | $R^b$ | $R^c$ | Q¹ | Q² |
|---|---|---|---|---|---|---|---|---|---|
| E-441 | CH | N | 4 | 4 | Me | H | H | —O— | —O— |
| E-442 | CH | N | 4 | 4 | Me | H | H | —O— | —S— |
| E-443 | CH | N | 4 | 4 | Me | H | H | —O— | —OCH$_2$— |
| E-444 | CH | N | 4 | 4 | Me | H | H | —O— | singlebond |
| E-445 | CH | N | 4 | 4 | Me | H | H | —S— | —O— |
| E-446 | CH | N | 4 | 4 | Me | H | H | —CH$_2$O— | —O— |
| E-447 | CH | N | 4 | 4 | Me | H | H | singlebond | —O— |
| E-448 | CH | N | 4 | 4 | Me | H | H | —S— | —S— |
| E-449 | CH | N | 4 | 4 | Me | H | H | —CH$_2$O— | —OCH$_2$— |
| E-450 | CH | N | 4 | 4 | Me | H | H | singlebond | singlebond |
| E-451 | CH | N | 4 | 4 | Me | Me | H | —O— | —O— |
| E-452 | CH | N | 4 | 4 | Me | Me | H | —O— | —S— |
| E-453 | CH | N | 4 | 4 | Me | Me | H | —O— | —OCH$_2$— |
| E-454 | CH | N | 4 | 4 | Me | Me | H | —O— | ssinglebondd |
| E-455 | CH | N | 4 | 4 | Me | Me | H | —S— | —O— |
| E-456 | CH | N | 4 | 4 | Me | Me | H | —CH$_2$O— | —O— |
| E-457 | CH | N | 4 | 4 | Me | Me | H | singlebond | —O— |
| E-458 | CH | N | 4 | 4 | Me | Me | H | —S— | —S— |
| E-459 | CH | N | 4 | 4 | Me | Me | H | —CH$_2$O— | —OCH$_2$— |
| E-460 | CH | N | 4 | 4 | Me | Me | H | singlebond | singlebond |
| E-461 | CH | N | 4 | 4 | H | H | Me | —O— | —O— |
| E-462 | CH | N | 4 | 4 | H | H | Me | —O— | —S— |
| E-463 | CH | N | 4 | 4 | H | H | Me | —O— | —OCH$_2$— |
| E-464 | CH | N | 4 | 4 | H | H | Me | —O— | singlebond |
| E-465 | CH | N | 4 | 4 | H | H | Me | —S— | —O— |
| E-466 | CH | N | 4 | 4 | H | H | Me | —CH$_2$O— | —O— |
| E-467 | CH | N | 4 | 4 | H | H | Me | singlebond | —O— |
| E-468 | CH | N | 4 | 4 | H | H | Me | —S— | —S— |
| E-469 | CH | N | 4 | 4 | H | H | Me | —CH$_2$O— | —OCH$_2$— |
| E-470 | CH | N | 4 | 4 | H | H | Me | singlebond | singlebond |
| E-471 | CH | N | 4 | 4 | Ph | H | H | —O— | —O— |
| E-472 | CH | N | 4 | 4 | Ph | H | H | —O— | —S— |
| E-473 | CH | N | 4 | 4 | Ph | H | H | —O— | —OCH$_2$— |
| E-474 | CH | N | 4 | 4 | Ph | H | H | —O— | singlebond |
| E-475 | CH | N | 4 | 4 | Ph | H | H | —S— | —O— |
| E-476 | CH | N | 4 | 4 | Ph | H | H | —CH$_2$O— | —O— |
| E-477 | CH | N | 4 | 4 | Ph | H | H | singlebond | —O— |
| E-478 | CH | N | 4 | 4 | Ph | H | H | —S— | —S— |
| E-479 | CH | N | 4 | 4 | Ph | H | H | —CH$_2$O— | —OCH$_2$— |
| E-480 | CH | N | 4 | 4 | Ph | H | H | singlebond | singlebond |
| E-481 | CH | CH | 2 | 5 | H | H | H | —O— | —O— |
| E-482 | CH | CH | 3 | 5 | H | H | H | —O— | —O— |
| E-483 | CH | CH | 5 | 2 | H | H | H | —O— | —O— |
| E-484 | CH | CH | 5 | 3 | H | H | H | —O— | —O— |

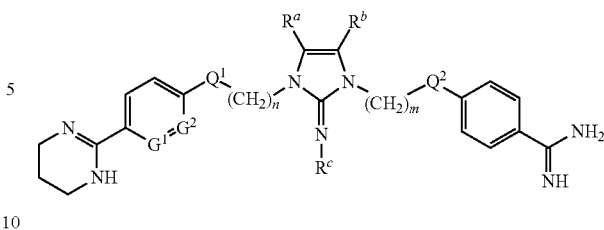

TABLE 24

| Compound No. | G¹ | G² | n | m | $R^a$ | $R^b$ | $R^c$ | Q¹ | Q² |
|---|---|---|---|---|---|---|---|---|---|
| F-1 | CH | CH | 3 | 3 | Me | H | H | —O— | —O— |
| F-2 | CH | CH | 3 | 3 | Me | H | H | —O— | —S— |
| F-3 | CH | CH | 3 | 3 | Me | H | H | —O— | —OCH$_2$— |
| F-4 | CH | CH | 3 | 3 | Me | H | H | —O— | singlebond |
| F-5 | CH | CH | 3 | 3 | Me | H | H | —S— | —O— |
| F-6 | CH | CH | 3 | 3 | Me | H | H | —CH$_2$O— | —O— |
| F-7 | CH | CH | 3 | 3 | Me | H | H | singlebond | —O— |
| F-8 | CH | CH | 3 | 3 | Me | H | H | —S— | —S— |
| F-9 | CH | CH | 3 | 3 | Me | H | H | —CH$_2$O— | —OCH$_2$— |
| F-10 | CH | CH | 3 | 3 | Me | H | H | singlebond | singlebond |
| F-11 | CH | CH | 3 | 3 | Me | Me | H | —O— | —O— |
| F-12 | CH | CH | 3 | 3 | Me | Me | H | —O— | —S— |
| F-13 | CH | CH | 3 | 3 | Me | Me | H | —O— | —OCH$_2$— |
| F-14 | CH | CH | 3 | 3 | Me | Me | H | —O— | singlebond |
| F-15 | CH | CH | 3 | 3 | Me | Me | H | —S— | —O— |
| F-16 | CH | CH | 3 | 3 | Me | Me | H | —CH$_2$O— | —O— |
| F-17 | CH | CH | 3 | 3 | Me | Me | H | singlebond | —O— |
| F-18 | CH | CH | 3 | 3 | Me | Me | H | —S— | —S— |
| F-19 | CH | CH | 3 | 3 | Me | Me | H | —CH$_2$O— | —OCH$_2$— |
| F-20 | CH | CH | 3 | 3 | Me | Me | H | singlebond | singlebond |
| F-21 | CH | CH | 3 | 3 | H | H | Me | —O— | —O— |
| F-22 | CH | CH | 3 | 3 | H | H | Me | —O— | —S— |
| F-23 | CH | CH | 3 | 3 | H | H | Me | —O— | —OCH$_2$— |
| F-24 | CH | CH | 3 | 3 | H | H | Me | —O— | singlebond |
| F-25 | CH | CH | 3 | 3 | H | H | Me | —S— | —O— |
| F-26 | CH | CH | 3 | 3 | H | H | Me | —CH$_2$O— | —O— |
| F-27 | CH | CH | 3 | 3 | H | H | Me | singlebond | —O— |
| F-28 | CH | CH | 3 | 3 | H | H | Me | —S— | —S— |
| F-29 | CH | CH | 3 | 3 | H | H | Me | —CH$_2$O— | —OCH$_2$— |
| F-30 | CH | CH | 3 | 3 | H | H | Me | singlebond | singlebond |
| F-31 | CH | CH | 3 | 3 | Ph | H | H | —O— | —O— |
| F-32 | CH | CH | 3 | 3 | Ph | H | H | —O— | —S— |
| F-33 | CH | CH | 3 | 3 | Ph | H | H | —O— | —OCH$_2$— |
| F-34 | CH | CH | 3 | 3 | Ph | H | H | —O— | singlebond |
| F-35 | CH | CH | 3 | 3 | Ph | H | H | —S— | —O— |
| F-36 | CH | CH | 3 | 3 | Ph | H | H | —CH$_2$O— | —O— |
| F-37 | CH | CH | 3 | 3 | Ph | H | H | singlebond | —O— |
| F-38 | CH | CH | 3 | 3 | Ph | H | H | —S— | —S— |
| F-39 | CH | CH | 3 | 3 | Ph | H | H | —CH$_2$O— | —OCH$_2$— |
| F-40 | CH | CH | 3 | 3 | Ph | H | H | singlebond | singlebond |
| F-41 | CH | CH | 3 | 4 | Me | H | H | —O— | —O— |
| F-42 | CH | CH | 3 | 4 | Me | H | H | —O— | —S— |
| F-43 | CH | CH | 3 | 4 | Me | H | H | —O— | —OCH$_2$— |
| F-44 | CH | CH | 3 | 4 | Me | H | H | —O— | singlebond |
| F-45 | CH | CH | 3 | 4 | Me | H | H | —S— | —O— |
| F-46 | CH | CH | 3 | 4 | Me | H | H | —CH$_2$O— | —O— |
| F-47 | CH | CH | 3 | 4 | Me | H | H | singlebond | —O— |
| F-48 | CH | CH | 3 | 4 | Me | H | H | —S— | —S— |
| F-49 | CH | CH | 3 | 4 | Me | H | H | —CH$_2$O— | —OCH$_2$— |
| F-50 | CH | CH | 3 | 4 | Me | H | H | singlebond | singlebond |
| F-51 | CH | CH | 3 | 4 | Me | Me | H | —O— | —O— |
| F-52 | CH | CH | 3 | 4 | Me | Me | H | —O— | —S— |
| F-53 | CH | CH | 3 | 4 | Me | Me | H | —O— | —OCH$_2$— |
| F-54 | CH | CH | 3 | 4 | Me | Me | H | —O— | singlebond |
| F-55 | CH | CH | 3 | 4 | Me | Me | H | —S— | —O— |
| F-56 | CH | CH | 3 | 4 | Me | Me | H | —CH$_2$O— | —O— |
| F-57 | CH | CH | 3 | 4 | Me | Me | H | singlebond | —O— |
| F-58 | CH | CH | 3 | 4 | Me | Me | H | —S— | —S— |
| F-59 | CH | CH | 3 | 4 | Me | Me | H | —CH$_2$O— | —OCH$_2$— |
| F-60 | CH | CH | 3 | 4 | Me | Me | H | singlebond | singlebond |
| F-61 | CH | CH | 3 | 4 | H | H | Me | —O— | —O— |
| F-62 | CH | CH | 3 | 4 | H | H | Me | —O— | —S— |

TABLE 24-continued

| Compound No. | G¹ | G² | n | m | $R^a$ | $R^b$ | $R^c$ | Q¹ | Q² |
|---|---|---|---|---|---|---|---|---|---|
| F-63 | CH | CH | 3 | 4 | H | H | Me | —O— | —OCH₂— |
| F-64 | CH | CH | 3 | 4 | H | H | Me | —O— | singlebond |
| F-65 | CH | CH | 3 | 4 | H | H | Me | —S— | —O— |
| F-66 | CH | CH | 3 | 4 | H | H | Me | —CH₂O— | —O— |
| F-67 | CH | CH | 3 | 4 | H | H | Me | singlebond | —O— |
| F-68 | CH | CH | 3 | 4 | H | H | Me | —S— | —S— |
| F-69 | CH | CH | 3 | 4 | H | H | Me | —CH₂O— | —OCH₂— |
| F-70 | CH | CH | 3 | 4 | H | H | Me | singlebond | singlebond |
| F-71 | CH | CH | 3 | 4 | Ph | H | H | —O— | —O— |
| F-72 | CH | CH | 3 | 4 | Ph | H | H | —O— | —S— |
| F-73 | CH | CH | 3 | 4 | Ph | H | H | —O— | —OCH₂— |
| F-74 | CH | CH | 3 | 4 | Ph | H | H | —O— | singlebond |
| F-75 | CH | CH | 3 | 4 | Ph | H | H | —S— | —O— |
| F-76 | CH | CH | 3 | 4 | Ph | H | H | —CH₂O— | —O— |
| F-77 | CH | CH | 3 | 4 | Ph | H | H | singlebond | —O— |
| F-78 | CH | CH | 3 | 4 | Ph | H | H | —S— | —S— |
| F-79 | CH | CH | 3 | 4 | Ph | H | H | —CH₂O— | —OCH₂— |
| F-80 | CH | CH | 3 | 4 | Ph | H | H | singlebond | singlebond |
| F-81 | CH | CH | 4 | 3 | Me | H | H | —O— | —O— |
| F-82 | CH | CH | 4 | 3 | Me | H | H | —O— | —S— |
| F-83 | CH | CH | 4 | 3 | Me | H | H | —O— | —OCH₂— |
| F-84 | CH | CH | 4 | 3 | Me | H | H | —O— | singlebond |
| F-85 | CH | CH | 4 | 3 | Me | H | H | —S— | —O— |
| F-86 | CH | CH | 4 | 3 | Me | H | H | —CH₂O— | —O— |
| F-87 | CH | CH | 4 | 3 | Me | H | H | singlebond | —O— |
| F-88 | CH | CH | 4 | 3 | Me | H | H | —S— | —S— |
| F-89 | CH | CH | 4 | 3 | Me | H | H | —CH₂O— | —OCH₂— |
| F-90 | CH | CH | 4 | 3 | Me | H | H | singlebond | singlebond |
| F-91 | CH | CH | 4 | 3 | Me | Me | H | —O— | —O— |
| F-92 | CH | CH | 4 | 3 | Me | Me | H | —O— | —S— |
| F-93 | CH | CH | 4 | 3 | Me | Me | H | —O— | —OCH₂— |
| F-94 | CH | CH | 4 | 3 | Me | Me | H | —O— | singlebond |
| F-95 | CH | CH | 4 | 3 | Me | Me | H | —S— | —O— |
| F-96 | CH | CH | 4 | 3 | Me | Me | H | —CH₂O— | —O— |
| F-97 | CH | CH | 4 | 3 | Me | Me | H | singlebond | —O— |
| F-98 | CH | CH | 4 | 3 | Me | Me | H | —S— | —S— |
| F-99 | CH | CH | 4 | 3 | Me | Me | H | —CH₂O— | —OCH₂— |
| F-100 | CH | CH | 4 | 3 | Me | Me | H | singlebond | singlebond |
| F-101 | CH | CH | 4 | 3 | H | H | Me | —O— | —O— |
| F-102 | CH | CH | 4 | 3 | H | H | Me | —O— | —S— |
| F-103 | CH | CH | 4 | 3 | H | H | Me | —O— | —OCH₂— |
| F-104 | CH | CH | 4 | 3 | H | H | Me | —O— | singlebond |
| F-105 | CH | CH | 4 | 3 | H | H | Me | —S— | —O— |
| F-106 | CH | CH | 4 | 3 | H | H | Me | —CH₂O— | —O— |
| F-107 | CH | CH | 4 | 3 | H | H | Me | singlebond | —O— |
| F-108 | CH | CH | 4 | 3 | H | H | Me | —S— | —S— |
| F-109 | CH | CH | 4 | 3 | H | H | Me | —CH₂O— | —OCH₂— |
| F-110 | CH | CH | 4 | 3 | H | H | Me | singlebond | singlebond |

TABLE 25

| Compound No. | G¹ | G² | n | m | $R^a$ | $R^b$ | $R^c$ | Q¹ | Q² |
|---|---|---|---|---|---|---|---|---|---|
| F-111 | CH | CH | 4 | 3 | Ph | H | H | —O— | —O— |
| F-112 | CH | CH | 4 | 3 | Ph | H | H | —O— | —S— |
| F-113 | CH | CH | 4 | 3 | Ph | H | H | —O— | —OCH₂— |
| F-114 | CH | CH | 4 | 3 | Ph | H | H | —O— | singlebond |
| F-115 | CH | CH | 4 | 3 | Ph | H | H | —S— | —O— |
| F-116 | CH | CH | 4 | 3 | Ph | H | H | —CH₂O— | —O— |
| F-117 | CH | CH | 4 | 3 | Ph | H | H | singlebond | —O— |
| F-118 | CH | CH | 4 | 3 | Ph | H | H | —S— | —S— |
| F-119 | CH | CH | 4 | 3 | Ph | H | H | —CH₂O— | —OCH₂— |
| F-120 | CH | CH | 4 | 3 | Ph | H | H | singlebond | singlebond |
| F-121 | CH | CH | 4 | 4 | Me | H | H | —O— | —O— |
| F-122 | CH | CH | 4 | 4 | Me | H | H | —O— | —S— |
| F-123 | CH | CH | 4 | 4 | Me | H | H | —O— | —OCH₂— |
| F-124 | CH | CH | 4 | 4 | Me | H | H | —O— | singlebond |
| F-125 | CH | CH | 4 | 4 | Me | H | H | —S— | —O— |
| F-126 | CH | CH | 4 | 4 | Me | H | H | —CH₂O— | —O— |
| F-127 | CH | CH | 4 | 4 | Me | H | H | singlebond | —O— |
| F-128 | CH | CH | 4 | 4 | Me | H | H | —S— | —S— |
| F-129 | CH | CH | 4 | 4 | Me | H | H | —CH₂O— | —OCH₂— |
| F-130 | CH | CH | 4 | 4 | Me | H | H | singlebond | singlebond |
| F-131 | CH | CH | 4 | 4 | Me | Me | H | —O— | —O— |
| F-132 | CH | CH | 4 | 4 | Me | Me | H | —O— | —S— |
| F-133 | CH | CH | 4 | 4 | Me | Me | H | —O— | —OCH₂— |
| F-134 | CH | CH | 4 | 4 | Me | Me | H | —O— | singlebond |
| F-135 | CH | CH | 4 | 4 | Me | Me | H | —S— | —O— |
| F-136 | CH | CH | 4 | 4 | Me | Me | H | —CH₂O— | —O— |
| F-137 | CH | CH | 4 | 4 | Me | Me | H | singlebond | —O— |
| F-138 | CH | CH | 4 | 4 | Me | Me | H | —S— | —S— |
| F-139 | CH | CH | 4 | 4 | Me | Me | H | —CH₂O— | —OCH₂— |
| F-140 | CH | CH | 4 | 4 | Me | Me | H | singlebond | singlebond |
| F-141 | CH | CH | 4 | 4 | H | H | Me | —O— | —O— |
| F-142 | CH | CH | 4 | 4 | H | H | Me | —O— | —S— |
| F-143 | CH | CH | 4 | 4 | H | H | Me | —O— | —OCH₂— |
| F-144 | CH | CH | 4 | 4 | H | H | Me | —O— | singlebond |
| F-145 | CH | CH | 4 | 4 | H | H | Me | —S— | —O— |
| F-146 | CH | CH | 4 | 4 | H | H | Me | —CH₂O— | —O— |
| F-147 | CH | CH | 4 | 4 | H | H | Me | singlebond | —O— |
| F-148 | CH | CH | 4 | 4 | H | H | Me | —S— | —S— |
| F-149 | CH | CH | 4 | 4 | H | H | Me | —CH₂O— | —OCH₂— |
| F-150 | CH | CH | 4 | 4 | H | H | Me | singlebond | singlebond |
| F-151 | CH | CH | 4 | 4 | Ph | H | H | —O— | —O— |
| F-152 | CH | CH | 4 | 4 | Ph | H | H | —O— | —S— |
| F-153 | CH | CH | 4 | 4 | Ph | H | H | —O— | —OCH₂— |
| F-154 | CH | CH | 4 | 4 | Ph | H | H | —O— | singlebond |
| F-155 | CH | CH | 4 | 4 | Ph | H | H | —S— | —O— |
| F-156 | CH | CH | 4 | 4 | Ph | H | H | —CH₂O— | —O— |
| F-157 | CH | CH | 4 | 4 | Ph | H | H | singlebond | —O— |
| F-158 | CH | CH | 4 | 4 | Ph | H | H | —S— | —S— |
| F-159 | CH | CH | 4 | 4 | Ph | H | H | —CH₂O— | —OCH₂— |
| F-160 | CH | CH | 4 | 4 | Ph | H | H | singlebond | singlebond |
| F-161 | N | CH | 3 | 3 | Me | H | H | —O— | —O— |
| F-162 | N | CH | 3 | 3 | Me | H | H | —O— | —S— |
| F-163 | N | CH | 3 | 3 | Me | H | H | —O— | —OCH₂— |
| F-164 | N | CH | 3 | 3 | Me | H | H | —O— | singlebond |
| F-165 | N | CH | 3 | 3 | Me | H | H | —S— | —O— |
| F-166 | N | CH | 3 | 3 | Me | H | H | —CH₂O— | —O— |
| F-167 | N | CH | 3 | 3 | Me | H | H | singlebond | —O— |
| F-168 | N | CH | 3 | 3 | Me | H | H | —S— | —S— |
| F-169 | N | CH | 3 | 3 | Me | H | H | —CH₂O— | —OCH₂— |
| F-170 | N | CH | 3 | 3 | Me | H | H | singlebond | singlebond |
| F-171 | N | CH | 3 | 3 | Me | Me | H | —O— | —O— |
| F-172 | N | CH | 3 | 3 | Me | Me | H | —O— | —S— |
| F-173 | N | CH | 3 | 3 | Me | Me | H | —O— | —OCH₂— |
| F-174 | N | CH | 3 | 3 | Me | Me | H | —O— | singlebond |
| F-175 | N | CH | 3 | 3 | Me | Me | H | —S— | —O— |
| F-176 | N | CH | 3 | 3 | Me | Me | H | —CH₂O— | —O— |
| F-177 | N | CH | 3 | 3 | Me | Me | H | singlebond | —O— |
| F-178 | N | CH | 3 | 3 | Me | Me | H | —S— | —S— |
| F-179 | N | CH | 3 | 3 | Me | Me | H | —CH₂O— | —OCH₂— |
| F-180 | N | CH | 3 | 3 | Me | Me | H | singlebond | singlebond |
| F-181 | N | CH | 3 | 3 | H | H | Me | —O— | —O— |
| F-182 | N | CH | 3 | 3 | H | H | Me | —O— | —S— |
| F-183 | N | CH | 3 | 3 | H | H | Me | —O— | —OCH₂— |
| F-184 | N | CH | 3 | 3 | H | H | Me | —O— | singlebond |
| F-185 | N | CH | 3 | 3 | H | H | Me | —S— | —O— |
| F-186 | N | CH | 3 | 3 | H | H | Me | —CH₂O— | —O— |
| F-187 | N | CH | 3 | 3 | H | H | Me | singlebond | —O— |
| F-188 | N | CH | 3 | 3 | H | H | Me | —S— | —S— |
| F-189 | N | CH | 3 | 3 | H | H | Me | —CH₂O— | —OCH₂— |
| F-190 | N | CH | 3 | 3 | H | H | Me | singlebond | singlebond |
| F-191 | N | CH | 3 | 3 | Ph | H | H | —O— | —O— |
| F-192 | N | CH | 3 | 3 | Ph | H | H | —O— | —S— |
| F-193 | N | CH | 3 | 3 | Ph | H | H | —O— | —OCH₂— |
| F-194 | N | CH | 3 | 3 | Ph | H | H | —O— | singlebond |
| F-195 | N | CH | 3 | 3 | Ph | H | H | —S— | —O— |
| F-196 | N | CH | 3 | 3 | Ph | H | H | —CH₂O— | —O— |
| F-197 | N | CH | 3 | 3 | Ph | H | H | singlebond | —O— |
| F-198 | N | CH | 3 | 3 | Ph | H | H | —S— | —S— |
| F-199 | N | CH | 3 | 3 | Ph | H | H | —CH₂O— | —OCH₂— |
| F-200 | N | CH | 3 | 3 | Ph | H | H | singlebond | singlebond |
| F-201 | N | CH | 3 | 4 | Me | H | H | —O— | —O— |
| F-202 | N | CH | 3 | 4 | Me | H | H | —O— | —S— |
| F-203 | N | CH | 3 | 4 | Me | H | H | —O— | —OCH₂— |
| F-204 | N | CH | 3 | 4 | Me | H | H | —O— | singlebond |

TABLE 25-continued

| Compound No. | $G^1$ | $G^2$ | n | m | $R^a$ | $R^b$ | $R^c$ | $Q^1$ | $Q^2$ |
|---|---|---|---|---|---|---|---|---|---|
| F-205 | N | CH | 3 | 4 | Me | H | H | —S— | —O— |
| F-206 | N | CH | 3 | 4 | Me | H | H | —CH$_2$O— | —O— |
| F-207 | N | CH | 3 | 4 | Me | H | H | singlebond | —O— |
| F-208 | N | CH | 3 | 4 | Me | H | H | —S— | —S— |
| F-209 | N | CH | 3 | 4 | Me | H | H | —CH$_2$O— | —OCH$_2$— |
| F-210 | N | CH | 3 | 4 | Me | H | H | singlebond | singlebond |
| F-211 | N | CH | 3 | 4 | Me | Me | H | —O— | —O— |
| F-212 | N | CH | 3 | 4 | Me | Me | H | —O— | —S— |
| F-213 | N | CH | 3 | 4 | Me | Me | H | —O— | —OCH$_2$— |
| F-214 | N | CH | 3 | 4 | Me | Me | H | —O— | singlebond |
| F-215 | N | CH | 3 | 4 | Me | Me | H | —S— | —O— |
| F-216 | N | CH | 3 | 4 | Me | Me | H | —CH$_2$O— | —O— |
| F-217 | N | CH | 3 | 4 | Me | Me | H | singlebond | —O— |
| F-218 | N | CH | 3 | 4 | Me | Me | H | —S— | —S— |
| F-219 | N | CH | 3 | 4 | Me | Me | H | —CH$_2$O— | —OCH$_2$— |
| F-220 | N | CH | 3 | 4 | Me | Me | H | singlebond | singlebond |

TABLE 26

| Compound No. | $G^1$ | $G^2$ | n | m | $R^a$ | $R^b$ | $R^c$ | $Q^1$ | $Q^2$ |
|---|---|---|---|---|---|---|---|---|---|
| F-221 | N | CH | 3 | 4 | H | H | Me | —O— | —O— |
| F-222 | N | CH | 3 | 4 | H | H | Me | —O— | —S— |
| F-223 | N | CH | 3 | 4 | H | H | Me | —O— | —OCH$_2$— |
| F-224 | N | CH | 3 | 4 | H | H | Me | —O— | singlebond |
| F-225 | N | CH | 3 | 4 | H | H | Me | —S— | —O— |
| F-226 | N | CH | 3 | 4 | H | H | Me | —CH$_2$O— | —O— |
| F-227 | N | CH | 3 | 4 | H | H | Me | singlebond | —O— |
| F-228 | N | CH | 3 | 4 | H | H | Me | —S— | —S— |
| F-229 | N | CH | 3 | 4 | H | H | Me | —CH$_2$O— | —OCH$_2$— |
| F-230 | N | CH | 3 | 4 | H | H | Me | singlebond | singlebond |
| F-231 | N | CH | 3 | 4 | Ph | H | H | —O— | —O— |
| F-232 | N | CH | 3 | 4 | Ph | H | H | —O— | —S— |
| F-233 | N | CH | 3 | 4 | Ph | H | H | —O— | —OCH$_2$— |
| F-234 | N | CH | 3 | 4 | Ph | H | H | —O— | singlebond |
| F-235 | N | CH | 3 | 4 | Ph | H | H | —S— | —O— |
| F-236 | N | CH | 3 | 4 | Ph | H | H | —CH$_2$O— | —O— |
| F-237 | N | CH | 3 | 4 | Ph | H | H | singlebond | —O— |
| F-238 | N | CH | 3 | 4 | Ph | H | H | —S— | —S— |
| F-239 | N | CH | 3 | 4 | Ph | H | H | —CH$_2$O— | —OCH$_2$— |
| F-240 | N | CH | 3 | 4 | Ph | H | H | singlebond | singlebond |
| F-241 | N | CH | 4 | 3 | Me | H | H | —O— | —O— |
| F-242 | N | CH | 4 | 3 | Me | H | H | —O— | —S— |
| F-243 | N | CH | 4 | 3 | Me | H | H | —O— | —OCH$_2$— |
| F-244 | N | CH | 4 | 3 | Me | H | H | —O— | singlebond |
| F-245 | N | CH | 4 | 3 | Me | H | H | —S— | —O— |
| F-246 | N | CH | 4 | 3 | Me | H | H | —CH$_2$O— | —O— |
| F-247 | N | CH | 4 | 3 | Me | H | H | singlebond | —O— |
| F-248 | N | CH | 4 | 3 | Me | H | H | —S— | —S— |
| F-249 | N | CH | 4 | 3 | Me | H | H | —CH$_2$O— | —OCH$_2$— |
| F-250 | N | CH | 4 | 3 | Me | H | H | singlebond | singlebond |
| F-251 | N | CH | 4 | 3 | Me | Me | H | —O— | —O— |
| F-252 | N | CH | 4 | 3 | Me | Me | H | —O— | —S— |
| F-253 | N | CH | 4 | 3 | Me | Me | H | —O— | —OCH$_2$— |
| F-254 | N | CH | 4 | 3 | Me | Me | H | —O— | singlebond |
| F-255 | N | CH | 4 | 3 | Me | Me | H | —S— | —O— |
| F-256 | N | CH | 4 | 3 | Me | Me | H | —CH$_2$O— | —O— |
| F-257 | N | CH | 4 | 3 | Me | Me | H | singlebond | —O— |
| F-258 | N | CH | 4 | 3 | Me | Me | H | —S— | —S— |
| F-259 | N | CH | 4 | 3 | Me | Me | H | —CH$_2$O— | —OCH$_2$— |
| F-260 | N | CH | 4 | 3 | Me | Me | H | singlebond | singlebond |
| F-261 | N | CH | 4 | 3 | H | H | Me | —O— | —O— |
| F-262 | N | CH | 4 | 3 | H | H | Me | —O— | —S— |
| F-263 | N | CH | 4 | 3 | H | H | Me | —O— | —OCH$_2$— |
| F-264 | N | CH | 4 | 3 | H | H | Me | —O— | singlebond |
| F-265 | N | CH | 4 | 3 | H | H | Me | —S— | —O— |
| F-266 | N | CH | 4 | 3 | H | H | Me | —CH$_2$O— | —O— |
| F-267 | N | CH | 4 | 3 | H | H | Me | singlebond | —O— |
| F-268 | N | CH | 4 | 3 | H | H | Me | —S— | —S— |
| F-269 | N | CH | 4 | 3 | H | H | Me | —CH$_2$O— | —OCH$_2$— |
| F-270 | N | CH | 4 | 3 | H | H | Me | singlebond | singlebond |

TABLE 26-continued

| Compound No. | $G^1$ | $G^2$ | n | m | $R^a$ | $R^b$ | $R^c$ | $Q^1$ | $Q^2$ |
|---|---|---|---|---|---|---|---|---|---|
| F-271 | N | CH | 4 | 3 | Ph | H | H | —O— | —O— |
| F-272 | N | CH | 4 | 3 | Ph | H | H | —O— | —S— |
| F-273 | N | CH | 4 | 3 | Ph | H | H | —O— | —OCH$_2$— |
| F-274 | N | CH | 4 | 3 | Ph | H | H | —O— | singlebond |
| F-275 | N | CH | 4 | 3 | Ph | H | H | —S— | —O— |
| F-276 | N | CH | 4 | 3 | Ph | H | H | —CH$_2$O— | —O— |
| F-277 | N | CH | 4 | 3 | Ph | H | H | singlebond | —O— |
| F-278 | N | CH | 4 | 3 | Ph | H | H | —S— | —S— |
| F-279 | N | CH | 4 | 3 | Ph | H | H | —CH$_2$O— | —OCH$_2$— |
| F-280 | N | CH | 4 | 3 | Ph | H | H | singlebond | singlebond |
| F-281 | N | CH | 4 | 4 | Me | H | H | —O— | —O— |
| F-282 | N | CH | 4 | 4 | Me | H | H | —O— | —S— |
| F-283 | N | CH | 4 | 4 | Me | H | H | —O— | —OCH$_2$— |
| F-284 | N | CH | 4 | 4 | Me | H | H | —O— | singlebond |
| F-285 | N | CH | 4 | 4 | Me | H | H | —S— | —O— |
| F-286 | N | CH | 4 | 4 | Me | H | H | —CH$_2$O— | —O— |
| F-287 | N | CH | 4 | 4 | Me | H | H | singlebond | —O— |
| F-288 | N | CH | 4 | 4 | Me | H | H | —S— | —S— |
| F-289 | N | CH | 4 | 4 | Me | H | H | —CH$_2$O— | —OCH$_2$— |
| F-290 | N | CH | 4 | 4 | Me | H | H | singlebond | singlebond |
| F-291 | N | CH | 4 | 4 | Me | Me | H | —O— | —O— |
| F-292 | N | CH | 4 | 4 | Me | Me | H | —O— | —S— |
| F-293 | N | CH | 4 | 4 | Me | Me | H | —O— | —OCH$_2$— |
| F-294 | N | CH | 4 | 4 | Me | Me | H | —O— | singlebond |
| F-295 | N | CH | 4 | 4 | Me | Me | H | —S— | —O— |
| F-296 | N | CH | 4 | 4 | Me | Me | H | —CH$_2$O— | —O— |
| F-297 | N | CH | 4 | 4 | Me | Me | H | singlebond | —O— |
| F-298 | N | CH | 4 | 4 | Me | Me | H | —S— | —S— |
| F-299 | N | CH | 4 | 4 | Me | Me | H | —CH$_2$O— | —OCH$_2$— |
| F-300 | N | CH | 4 | 4 | Me | Me | H | singlebond | singlebond |
| F-301 | N | CH | 4 | 4 | H | H | Me | —O— | —O— |
| F-302 | N | CH | 4 | 4 | H | H | Me | —O— | —S— |
| F-303 | N | CH | 4 | 4 | H | H | Me | —O— | —OCH$_2$— |
| F-304 | N | CH | 4 | 4 | H | H | Me | —O— | singlebond |
| F-305 | N | CH | 4 | 4 | H | H | Me | —S— | —O— |
| F-306 | N | CH | 4 | 4 | H | H | Me | —CH$_2$O— | —O— |
| F-307 | N | CH | 4 | 4 | H | H | Me | singlebond | —O— |
| F-308 | N | CH | 4 | 4 | H | H | Me | —S— | —S— |
| F-309 | N | CH | 4 | 4 | H | H | Me | —CH$_2$O— | —OCH$_2$— |
| F-310 | N | CH | 4 | 4 | H | H | Me | singlebond | singlebond |
| F-311 | N | CH | 4 | 4 | Ph | H | H | —O— | —O— |
| F-312 | N | CH | 4 | 4 | Ph | H | H | —O— | —S— |
| F-313 | N | CH | 4 | 4 | Ph | H | H | —O— | —OCH$_2$— |
| F-314 | N | CH | 4 | 4 | Ph | H | H | —O— | singlebond |
| F-315 | N | CH | 4 | 4 | Ph | H | H | —S— | —O— |
| F-316 | N | CH | 4 | 4 | Ph | H | H | —CH$_2$O— | —O— |
| F-317 | N | CH | 4 | 4 | Ph | H | H | singlebond | —O— |
| F-318 | N | CH | 4 | 4 | Ph | H | H | —S— | —S— |
| F-319 | N | CH | 4 | 4 | Ph | H | H | —CH$_2$O— | —OCH$_2$— |
| F-320 | N | CH | 4 | 4 | Ph | H | H | singlebond | singlebond |
| F-321 | CH | N | 3 | 3 | Me | H | H | —O— | —O— |
| F-322 | CH | N | 3 | 3 | Me | H | H | —O— | —S— |
| F-323 | CH | N | 3 | 3 | Me | H | H | —O— | —OCH$_2$— |
| F-324 | CH | N | 3 | 3 | Me | H | H | —O— | singlebond |
| F-325 | CH | N | 3 | 3 | Me | H | H | —S— | —O— |
| F-326 | CH | N | 3 | 3 | Me | H | H | —CH$_2$O— | —O— |
| F-327 | CH | N | 3 | 3 | Me | H | H | singlebond | —O— |
| F-328 | CH | N | 3 | 3 | Me | H | H | —S— | —S— |
| F-329 | CH | N | 3 | 3 | Me | H | H | —CH$_2$O— | —OCH$_2$— |
| F-330 | CH | N | 3 | 3 | Me | H | H | singlebond | singlebond |

TABLE 27

| Compound No. | $G^1$ | $G^2$ | n | m | $R^a$ | $R^b$ | $R^c$ | $Q^1$ | $Q^2$ |
|---|---|---|---|---|---|---|---|---|---|
| F-331 | CH | N | 3 | 3 | Me | Me | H | —O— | —O— |
| F-332 | CH | N | 3 | 3 | Me | Me | H | —O— | —S— |
| F-333 | CH | N | 3 | 3 | Me | Me | H | —O— | —OCH$_2$— |
| F-334 | CH | N | 3 | 3 | Me | Me | H | —O— | singlebond |
| F-335 | CH | N | 3 | 3 | Me | Me | H | —S— | —O— |
| F-336 | CH | N | 3 | 3 | Me | Me | H | —CH$_2$O— | —O— |

TABLE 27-continued

| Compound No. | $G^1$ | $G^2$ | n | m | $R^a$ | $R^b$ | $R^c$ | $Q^1$ | $Q^2$ |
|---|---|---|---|---|---|---|---|---|---|
| F-337 | CH | N | 3 | 3 | Me | Me | H | singlebond | —O— |
| F-338 | CH | N | 3 | 3 | Me | Me | H | —S— | —S— |
| F-339 | CH | N | 3 | 3 | Me | Me | H | —CH$_2$O— | —OCH$_2$— |
| F-340 | CH | N | 3 | 3 | Me | Me | H | singlebond | singlebond |
| F-341 | CH | N | 3 | 3 | H | H | Me | —O— | —O— |
| F-342 | CH | N | 3 | 3 | H | H | Me | —O— | —S— |
| F-343 | CH | N | 3 | 3 | H | H | Me | —O— | —OCH$_2$— |
| F-344 | CH | N | 3 | 3 | H | H | Me | —O— | singlebond |
| F-345 | CH | N | 3 | 3 | H | H | Me | —S— | —O— |
| F-346 | CH | N | 3 | 3 | H | H | Me | —CH$_2$O— | —O— |
| F-347 | CH | N | 3 | 3 | H | H | Me | singlebond | —O— |
| F-348 | CH | N | 3 | 3 | H | H | Me | —S— | —S— |
| F-349 | CH | N | 3 | 3 | H | H | Me | —CH$_2$O— | —OCH$_2$— |
| F-350 | CH | N | 3 | 3 | H | H | Me | singlebond | singlebond |
| F-351 | CH | N | 3 | 3 | Ph | H | H | —O— | —O— |
| F-352 | CH | N | 3 | 3 | Ph | H | H | —O— | —S— |
| F-353 | CH | N | 3 | 3 | Ph | H | H | —O— | —OCH$_2$— |
| F-354 | CH | N | 3 | 3 | Ph | H | H | —O— | singlebond |
| F-355 | CH | N | 3 | 3 | Ph | H | H | —S— | —O— |
| F-356 | CH | N | 3 | 3 | Ph | H | H | —CH$_2$O— | —O— |
| F-357 | CH | N | 3 | 3 | Ph | H | H | singlebond | —O— |
| F-358 | CH | N | 3 | 3 | Ph | H | H | —S— | —S— |
| F-359 | CH | N | 3 | 3 | Ph | H | H | —CH$_2$O— | —OCH$_2$— |
| F-360 | CH | N | 3 | 3 | Ph | H | H | singlebond | singlebond |
| F-361 | CH | N | 3 | 4 | Me | H | H | —O— | —O— |
| F-362 | CH | N | 3 | 4 | Me | H | H | —O— | —S— |
| F-363 | CH | N | 3 | 4 | Me | H | H | —O— | —OCH$_2$— |
| F-364 | CH | N | 3 | 4 | Me | H | H | —O— | singlebond |
| F-365 | CH | N | 3 | 4 | Me | H | H | —S— | —O— |
| F-366 | CH | N | 3 | 4 | Me | H | H | —CH$_2$O— | —O— |
| F-367 | CH | N | 3 | 4 | Me | H | H | singlebond | —O— |
| F-368 | CH | N | 3 | 4 | Me | H | H | —S— | —S— |
| F-369 | CH | N | 3 | 4 | Me | H | H | —CH$_2$O— | —OCH$_2$— |
| F-370 | CH | N | 3 | 4 | Me | H | H | singlebond | singlebond |
| F-371 | CH | N | 3 | 4 | Me | Me | H | —O— | —O— |
| F-372 | CH | N | 3 | 4 | Me | Me | H | —O— | —S— |
| F-373 | CH | N | 3 | 4 | Me | Me | H | —O— | —OCH$_2$— |
| F-374 | CH | N | 3 | 4 | Me | Me | H | —O— | singlebond |
| F-375 | CH | N | 3 | 4 | Me | Me | H | —S— | —O— |
| F-376 | CH | N | 3 | 4 | Me | Me | H | —CH$_2$O— | —O— |
| F-377 | CH | N | 3 | 4 | Me | Me | H | singlebond | —O— |
| F-378 | CH | N | 3 | 4 | Me | Me | H | —S— | —S— |
| F-379 | CH | N | 3 | 4 | Me | Me | H | —CH$_2$O— | —OCH$_2$— |
| F-380 | CH | N | 3 | 4 | Me | Me | H | singlebond | singlebond |
| F-381 | CH | N | 3 | 4 | H | H | Me | —O— | —O— |
| F-382 | CH | N | 3 | 4 | H | H | Me | —O— | —S— |
| F-383 | CH | N | 3 | 4 | H | H | Me | —O— | —OCH$_2$— |
| F-384 | CH | N | 3 | 4 | H | H | Me | —O— | singlebond |
| F-385 | CH | N | 3 | 4 | H | H | Me | —S— | —O— |
| F-386 | CH | N | 3 | 4 | H | H | Me | —CH$_2$O— | —O— |
| F-387 | CH | N | 3 | 4 | H | H | Me | singlebond | —O— |
| F-388 | CH | N | 3 | 4 | H | H | Me | —S— | —S— |
| F-389 | CH | N | 3 | 4 | H | H | Me | —CH$_2$O— | —OCH$_2$— |
| F-390 | CH | N | 3 | 4 | H | H | Me | singlebond | singlebond |
| F-391 | CH | N | 3 | 4 | Ph | H | H | —O— | —O— |
| F-392 | CH | N | 3 | 4 | Ph | H | H | —O— | —S— |
| F-393 | CH | N | 3 | 4 | Ph | H | H | —O— | —OCH$_2$— |
| F-394 | CH | N | 3 | 4 | Ph | H | H | —O— | singlebond |
| F-395 | CH | N | 3 | 4 | Ph | H | H | —S— | —O— |
| F-396 | CH | N | 3 | 4 | Ph | H | H | —CH$_2$O— | —O— |
| F-397 | CH | N | 3 | 4 | Ph | H | H | singlebond | —O— |
| F-398 | CH | N | 3 | 4 | Ph | H | H | —S— | —S— |
| F-399 | CH | N | 3 | 4 | Ph | H | H | —CH$_2$O— | —OCH$_2$— |
| F-400 | CH | N | 3 | 4 | Ph | H | H | singlebond | singlebond |
| F-401 | CH | N | 4 | 3 | Me | H | H | —O— | —O— |
| F-402 | CH | N | 4 | 3 | Me | H | H | —O— | —S— |
| F-403 | CH | N | 4 | 3 | Me | H | H | —O— | —OCH$_2$— |
| F-404 | CH | N | 4 | 3 | Me | H | H | —O— | singlebond |
| F-405 | CH | N | 4 | 3 | Me | H | H | —S— | —O— |
| F-406 | CH | N | 4 | 3 | Me | H | H | —CH$_2$O— | —O— |
| F-407 | CH | N | 4 | 3 | Me | H | H | singlebond | —O— |
| F-408 | CH | N | 4 | 3 | Me | H | H | —S— | —S— |
| F-409 | CH | N | 4 | 3 | Me | H | H | —CH$_2$O— | —OCH$_2$— |
| F-410 | CH | N | 4 | 3 | Me | H | H | singlebond | singlebond |
| F-411 | CH | N | 4 | 3 | Me | Me | H | —O— | —O— |
| F-412 | CH | N | 4 | 3 | Me | Me | H | —O— | —S— |
| F-413 | CH | N | 4 | 3 | Me | Me | H | —O— | —OCH$_2$— |
| F-414 | CH | N | 4 | 3 | Me | Me | H | —O— | singlebond |
| F-415 | CH | N | 4 | 3 | Me | Me | H | —S— | —O— |
| F-416 | CH | N | 4 | 3 | Me | Me | H | —CH$_2$O— | —O— |
| F-417 | CH | N | 4 | 3 | Me | Me | H | singlebond | —O— |
| F-418 | CH | N | 4 | 3 | Me | Me | H | —S— | —S— |
| F-419 | CH | N | 4 | 3 | Me | Me | H | —CH$_2$O— | —OCH$_2$— |
| F-420 | CH | N | 4 | 3 | Me | Me | H | singlebond | singlebond |
| F-421 | CH | N | 4 | 3 | H | H | Me | —O— | —O— |
| F-422 | CH | N | 4 | 3 | H | H | Me | —O— | —S— |
| F-423 | CH | N | 4 | 3 | H | H | Me | —O— | —OCH$_2$— |
| F-424 | CH | N | 4 | 3 | H | H | Me | —O— | singlebond |
| F-425 | CH | N | 4 | 3 | H | H | Me | —S— | —O— |
| F-426 | CH | N | 4 | 3 | H | H | Me | —CH$_2$O— | —O— |
| F-427 | CH | N | 4 | 3 | H | H | Me | singlebond | —O— |
| F-428 | CH | N | 4 | 3 | H | H | Me | —S— | —S— |
| F-429 | CH | N | 4 | 3 | H | H | Me | —CH$_2$O— | —OCH$_2$— |
| F-430 | CH | N | 4 | 3 | H | H | Me | singlebond | singlebond |
| F-431 | CH | N | 4 | 3 | Ph | H | H | —O— | —O— |
| F-432 | CH | N | 4 | 3 | Ph | H | H | —O— | —S— |
| F-433 | CH | N | 4 | 3 | Ph | H | H | —O— | —OCH$_2$— |
| F-434 | CH | N | 4 | 3 | Ph | H | H | —O— | singlebond |
| F-435 | CH | N | 4 | 3 | Ph | H | H | —S— | —O— |
| F-436 | CH | N | 4 | 3 | Ph | H | H | —CH$_2$O— | —O— |
| F-437 | CH | N | 4 | 3 | Ph | H | H | singlebond | —O— |
| F-438 | CH | N | 4 | 3 | Ph | H | H | —S— | —S— |
| F-439 | CH | N | 4 | 3 | Ph | H | H | —CH$_2$O— | —OCH$_2$— |
| F-440 | CH | N | 4 | 3 | Ph | H | H | singlebond | singlebond |

TABLE 28

| Compound No. | $G^1$ | $G^2$ | n | m | $R^a$ | $R^b$ | $R^c$ | $Q^1$ | $Q^2$ |
|---|---|---|---|---|---|---|---|---|---|
| F-441 | CH | N | 4 | 4 | Me | H | H | —O— | —O— |
| F-442 | CH | N | 4 | 4 | Me | H | H | —O— | —S— |
| F-443 | CH | N | 4 | 4 | Me | H | H | —O— | —OCH$_2$— |
| F-444 | CH | N | 4 | 4 | Me | H | H | —O— | singlebond |
| F-445 | CH | N | 4 | 4 | Me | H | H | —S— | —O— |
| F-446 | CH | N | 4 | 4 | Me | H | H | —CH$_2$O— | —O— |
| F-447 | CH | N | 4 | 4 | Me | H | H | singlebond | —O— |
| F-448 | CH | N | 4 | 4 | Me | H | H | —S— | —S— |
| F-449 | CH | N | 4 | 4 | Me | H | H | —CH$_2$O— | —OCH$_2$— |
| F-450 | CH | N | 4 | 4 | Me | H | H | singlebond | singlebond |
| F-451 | CH | N | 4 | 4 | Me | Me | H | —O— | —O— |
| F-452 | CH | N | 4 | 4 | Me | Me | H | —O— | —S— |
| F-453 | CH | N | 4 | 4 | Me | Me | H | —O— | —OCH$_2$— |
| F-454 | CH | N | 4 | 4 | Me | Me | H | —O— | singlebond |
| F-455 | CH | N | 4 | 4 | Me | Me | H | —S— | —O— |
| F-456 | CH | N | 4 | 4 | Me | Me | H | —CH$_2$O— | —O— |
| F-457 | CH | N | 4 | 4 | Me | Me | H | singlebond | —O— |
| F-458 | CH | N | 4 | 4 | Me | Me | H | —S— | —S— |
| F-459 | CH | N | 4 | 4 | Me | Me | H | —CH$_2$O— | —OCH$_2$— |
| F-460 | CH | N | 4 | 4 | Me | Me | H | singlebond | singlebond |
| F-461 | CH | N | 4 | 4 | H | H | Me | —O— | —O— |
| F-462 | CH | N | 4 | 4 | H | H | Me | —O— | —S— |
| F-463 | CH | N | 4 | 4 | H | H | Me | —O— | —OCH$_2$— |
| F-464 | CH | N | 4 | 4 | H | H | Me | —O— | singlebond |
| F-465 | CH | N | 4 | 4 | H | H | Me | —S— | —O— |
| F-466 | CH | N | 4 | 4 | H | H | Me | —CH$_2$O— | —O— |
| F-467 | CH | N | 4 | 4 | H | H | Me | singlebond | —O— |
| F-468 | CH | N | 4 | 4 | H | H | Me | —S— | —S— |
| F-469 | CH | N | 4 | 4 | H | H | Me | —CH$_2$O— | —OCH$_2$— |
| F-470 | CH | N | 4 | 4 | H | H | Me | singlebond | singlebond |
| F-471 | CH | N | 4 | 4 | Ph | H | H | —O— | —O— |
| F-472 | CH | N | 4 | 4 | Ph | H | H | —O— | —S— |
| F-473 | CH | N | 4 | 4 | Ph | H | H | —O— | —OCH$_2$— |
| F-474 | CH | N | 4 | 4 | Ph | H | H | —O— | singlebond |
| F-475 | CH | N | 4 | 4 | Ph | H | H | —S— | —O— |
| F-476 | CH | N | 4 | 4 | Ph | H | H | —CH$_2$O— | —O— |
| F-477 | CH | N | 4 | 4 | Ph | H | H | singlebond | —O— |
| F-478 | CH | N | 4 | 4 | Ph | H | H | —S— | —S— |

TABLE 28-continued

| Compound No. | G¹ | G² | n | m | $R^a$ | $R^b$ | $R^c$ | Q¹ | Q² |
|---|---|---|---|---|---|---|---|---|---|
| F-479 | CH | N | 4 | 4 | Ph | H | H | —CH₂O— | —OCH₂— |
| F-480 | CH | N | 4 | 4 | Ph | H | H | singlebond | singlebond |
| F-481 | CH | CH | 2 | 5 | H | H | H | —O— | —O— |
| F-482 | CH | CH | 3 | 5 | H | H | H | —O— | —O— |
| F-483 | CH | CH | 5 | 2 | H | H | H | —O— | —O— |
| F-484 | CH | CH | 5 | 3 | H | H | H | —O— | —O— |

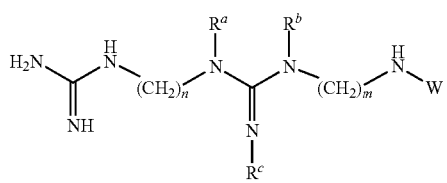

TABLE 29

| Compound No. | $R^a$ | $R^b$ | $R^c$ | n | m | W |
|---|---|---|---|---|---|---|
| G-1 | Me | H | H | 6 | 6 |  |
| G-2 | Me | H | H | 6 | 7 | |
| G-3 | Me | H | H | 6 | 8 | |
| G-4 | Me | H | H | 6 | 9 | |
| G-5 | Me | H | H | 7 | 6 | |
| G-6 | Me | H | H | 7 | 7 | |
| G-7 | Me | H | H | 7 | 8 | |
| G-8 | Me | H | H | 7 | 9 | |
| G-9 | Me | H | H | 8 | 6 | |
| G-10 | Me | H | H | 8 | 7 | |
| G-11 | Me | H | H | 8 | 8 | |
| G-12 | Me | H | H | 8 | 9 | |
| G-13 | Me | H | H | 9 | 6 | |
| G-14 | Me | H | H | 9 | 7 | |
| G-15 | Me | H | H | 9 | 8 | |
| G-16 | Me | H | H | 9 | 9 | |
| G-17 | H | H | Me | 6 | 6 | |
| G-18 | H | H | Me | 6 | 7 | |
| G-19 | H | H | Me | 6 | 8 | |
| G-20 | H | H | Me | 6 | 9 | |
| G-21 | H | H | Me | 7 | 6 | |
| G-22 | H | H | Me | 7 | 7 | |
| G-23 | H | H | Me | 7 | 8 | |
| G-24 | H | H | Me | 7 | 9 | |
| G-25 | H | H | Me | 8 | 6 | |
| G-26 | H | H | Me | 8 | 7 | |
| G-27 | H | H | Me | 8 | 8 | |
| G-28 | H | H | Me | 8 | 9 | |
| G-29 | H | H | Me | 9 | 6 | |
| G-30 | H | H | Me | 9 | 7 | |
| G-31 | H | H | Me | 9 | 8 | |
| G-32 | H | H | Me | 9 | 9 | |
| G-33 | Me | Me | H | 6 | 6 | |
| G-34 | Me | Me | H | 6 | 7 | |
| G-35 | Me | Me | H | 6 | 8 | |
| G-36 | Me | Me | H | 6 | 9 | |
| G-37 | Me | Me | H | 7 | 6 | |
| G-38 | Me | Me | H | 7 | 7 | |
| G-39 | Me | Me | H | 7 | 8 | |
| G-40 | Me | Me | H | 7 | 9 | |
| G-41 | Me | Me | H | 8 | 6 | |
| G-42 | Me | Me | H | 8 | 7 | |
| G-43 | Me | Me | H | 8 | 8 | |
| G-44 | Me | Me | H | 8 | 9 | |
| G-45 | Me | Me | H | 9 | 6 | |
| G-46 | Me | Me | H | 9 | 7 | |
| G-47 | Me | Me | H | 9 | 8 | |
| G-48 | Me | Me | H | 9 | 9 | |
| G-49 | H | Me | Me | 6 | 6 | |
| G-50 | H | Me | Me | 6 | 7 | |
| G-51 | H | Me | Me | 6 | 8 | |
| G-52 | H | Me | Me | 6 | 9 | |
| G-53 | H | Me | Me | 7 | 6 | |
| G-54 | H | Me | Me | 7 | 7 | |
| G-55 | H | Me | Me | 7 | 8 | |
| G-56 | H | Me | Me | 7 | 9 | |
| G-57 | H | Me | Me | 8 | 6 | |
| G-58 | H | Me | Me | 8 | 7 | |
| G-59 | H | Me | Me | 8 | 8 | |
| G-60 | H | Me | Me | 8 | 9 | |
| G-61 | H | Me | Me | 9 | 6 | |
| G-62 | H | Me | Me | 9 | 7 | |
| G-63 | H | Me | Me | 9 | 8 | |
| G-64 | H | Me | Me | 9 | 9 | |
| G-65 | Me | Me | Me | 6 | 6 | |
| G-66 | Me | Me | Me | 6 | 7 | |
| G-67 | Me | Me | Me | 6 | 8 | |
| G-68 | Me | Me | Me | 6 | 9 | |
| G-69 | Me | Me | Me | 7 | 6 | |
| G-70 | Me | Me | Me | 7 | 7 | |
| G-71 | Me | Me | Me | 7 | 8 | |
| G-72 | Me | Me | Me | 7 | 9 | |
| G-73 | Me | Me | Me | 8 | 6 | |
| G-74 | Me | Me | Me | 8 | 7 | |
| G-75 | Me | Me | Me | 8 | 8 | |
| G-76 | Me | Me | Me | 8 | 9 | |
| G-77 | Me | Me | Me | 9 | 6 | |
| G-78 | Me | Me | Me | 9 | 7 | |
| G-79 | Me | Me | Me | 9 | 8 | |
| G-80 | Me | Me | Me | 9 | 9 | |
| G-81 | Me | H | H | 6 | 6 |  |
| G-82 | Me | H | H | 6 | 7 | |
| G-83 | Me | H | H | 6 | 8 | |
| G-84 | Me | H | H | 6 | 9 | |
| G-85 | Me | H | H | 7 | 6 | |
| G-86 | Me | H | H | 7 | 7 | |
| G-87 | Me | H | H | 7 | 8 | |
| G-88 | Me | H | H | 7 | 9 | |
| G-89 | Me | H | H | 8 | 6 | |
| G-90 | Me | H | H | 8 | 7 | |
| G-91 | Me | H | H | 8 | 8 | |
| G-92 | Me | H | H | 8 | 9 | |
| G-93 | Me | H | H | 9 | 6 | |
| G-94 | Me | H | H | 9 | 7 | |
| G-95 | Me | H | H | 9 | 8 | |
| G-96 | Me | H | H | 9 | 9 | |
| G-97 | H | H | Me | 6 | 6 | |
| G-98 | H | H | Me | 6 | 7 | |
| G-99 | H | H | Me | 6 | 8 | |
| G-100 | H | H | Me | 6 | 9 | |
| G-101 | H | H | Me | 7 | 6 | |
| G-102 | H | H | Me | 7 | 7 | |
| G-103 | H | H | Me | 7 | 8 | |
| G-104 | H | H | Me | 7 | 9 | |
| G-105 | H | H | Me | 8 | 6 | |
| G-106 | H | H | Me | 8 | 7 | |
| G-107 | H | H | Me | 8 | 8 | |
| G-108 | H | H | Me | 8 | 9 | |
| G-109 | H | H | Me | 9 | 6 | |
| G-110 | H | H | Me | 9 | 7 | |

TABLE 30

| Compound No. | $R^a$ | $R^b$ | $R^c$ | n | m | W |
|---|---|---|---|---|---|---|
| G-111 | H | H | Me | 9 | 8 | |
| G-112 | H | H | Me | 9 | 9 | |
| G-113 | Me | Me | H | 6 | 6 | |
| G-114 | Me | Me | H | 6 | 7 | |
| G-115 | Me | Me | H | 6 | 8 | |

TABLE 30-continued

| Compound No. | $R^a$ | $R^b$ | $R^c$ | n | m | W |
|---|---|---|---|---|---|---|
| G-116 | Me | Me | H | 6 | 9 | |
| G-117 | Me | Me | H | 7 | 6 | |
| G-118 | Me | Me | H | 7 | 7 | |
| G-119 | Me | Me | H | 7 | 8 | |
| G-120 | Me | Me | H | 7 | 9 | |
| G-121 | Me | Me | H | 8 | 6 | |
| G-122 | Me | Me | H | 8 | 7 | |
| G-123 | Me | Me | H | 8 | 8 | |
| G-124 | Me | Me | H | 8 | 9 | |
| G-125 | Me | Me | H | 9 | 6 | |
| G-126 | Me | Me | H | 9 | 7 | |
| G-127 | Me | Me | H | 9 | 8 | |
| G-128 | Me | Me | H | 9 | 9 | |
| G-129 | H | Me | Me | 6 | 6 | |
| G-130 | H | Me | Me | 6 | 7 | |
| G-131 | H | Me | Me | 6 | 8 | |
| G-132 | H | Me | Me | 6 | 9 | |
| G-133 | H | Me | Me | 7 | 6 | |
| G-134 | H | Me | Me | 7 | 7 | |
| G-135 | H | Me | Me | 7 | 8 | |
| G-136 | H | Me | Me | 7 | 9 | |
| G-137 | H | Me | Me | 8 | 6 | |
| G-138 | H | Me | Me | 8 | 7 | |
| G-139 | H | Me | Me | 8 | 8 | |
| G-140 | H | Me | Me | 8 | 9 | |
| G-141 | H | Me | Me | 9 | 6 | |
| G-142 | H | Me | Me | 9 | 7 | |
| G-143 | H | Me | Me | 9 | 8 | |
| G-144 | H | Me | Me | 9 | 9 | |
| G-145 | Me | Me | Me | 6 | 6 | |
| G-146 | Me | Me | Me | 6 | 7 | |
| G-147 | Me | Me | Me | 6 | 8 | |
| G-148 | Me | Me | Me | 6 | 9 | |
| G-149 | Me | Me | Me | 7 | 6 | |
| G-150 | Me | Me | Me | 7 | 7 | |
| G-151 | Me | Me | Me | 7 | 8 | |
| G-152 | Me | Me | Me | 7 | 9 | |
| G-153 | Me | Me | Me | 8 | 6 | |
| G-154 | Me | Me | Me | 8 | 7 | |
| G-155 | Me | Me | Me | 8 | 8 | |
| G-156 | Me | Me | Me | 8 | 9 | |
| G-157 | Me | Me | Me | 9 | 6 | |
| G-158 | Me | Me | Me | 9 | 7 | |
| G-159 | Me | Me | Me | 9 | 8 | |
| G-160 | Me | Me | Me | 9 | 9 | |
| G-161 | Me | H | H | 6 | 6 | 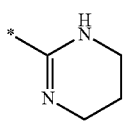 |
| G-162 | Me | H | H | 6 | 7 | |
| G-163 | Me | H | H | 6 | 8 | |
| G-164 | Me | H | H | 6 | 9 | |
| G-165 | Me | H | H | 7 | 6 | |
| G-166 | Me | H | H | 7 | 7 | |
| G-167 | Me | H | H | 7 | 8 | |
| G-168 | Me | H | H | 7 | 9 | |
| G-169 | Me | H | H | 8 | 6 | |
| G-170 | Me | H | H | 8 | 7 | |
| G-171 | Me | H | H | 8 | 8 | |
| G-172 | Me | H | H | 8 | 9 | |
| G-173 | Me | H | H | 9 | 6 | |
| G-174 | Me | H | H | 9 | 7 | |
| G-175 | Me | H | H | 9 | 8 | |
| G-176 | Me | H | H | 9 | 9 | |
| G-177 | H | H | Me | 6 | 6 | |
| G-178 | H | H | Me | 6 | 7 | |
| G-179 | H | H | Me | 6 | 8 | |
| G-180 | H | H | Me | 6 | 9 | |
| G-181 | H | H | Me | 7 | 6 | |
| G-182 | H | H | Me | 7 | 7 | |
| G-183 | H | H | Me | 7 | 8 | |
| G-184 | H | H | Me | 7 | 9 | |
| G-185 | H | H | Me | 8 | 6 | |
| G-186 | H | H | Me | 8 | 7 | |
| G-187 | H | H | Me | 8 | 8 | |
| G-188 | H | H | Me | 8 | 9 | |
| G-189 | H | H | Me | 9 | 6 | |
| G-190 | H | H | Me | 9 | 7 | |
| G-191 | H | H | Me | 9 | 8 | |
| G-192 | H | H | Me | 9 | 9 | |
| G-193 | Me | Me | H | 6 | 6 | |
| G-194 | Me | Me | H | 6 | 7 | |
| G-195 | Me | Me | H | 6 | 8 | |
| G-196 | Me | Me | H | 6 | 9 | |
| G-197 | Me | Me | H | 7 | 6 | |
| G-198 | Me | Me | H | 7 | 7 | |
| G-199 | Me | Me | H | 7 | 8 | |
| G-200 | Me | Me | H | 7 | 9 | |
| G-201 | Me | Me | H | 8 | 6 | |
| G-202 | Me | Me | H | 8 | 7 | |
| G-203 | Me | Me | H | 8 | 8 | |
| G-204 | Me | Me | H | 8 | 9 | |
| G-205 | Me | Me | H | 9 | 6 | |
| G-206 | Me | Me | H | 9 | 7 | |
| G-207 | Me | Me | H | 9 | 8 | |
| G-208 | Me | Me | H | 9 | 9 | |
| G-209 | H | Me | Me | 6 | 6 | |
| G-210 | H | Me | Me | 6 | 7 | |
| G-211 | H | Me | Me | 6 | 8 | |
| G-212 | H | Me | Me | 6 | 9 | |
| G-213 | H | Me | Me | 7 | 6 | |
| G-214 | H | Me | Me | 7 | 7 | |
| G-215 | H | Me | Me | 7 | 8 | |
| G-216 | H | Me | Me | 7 | 9 | |
| G-217 | H | Me | Me | 8 | 6 | |
| G-218 | H | Me | Me | 8 | 7 | |
| G-219 | H | Me | Me | 8 | 8 | |
| G-220 | H | Me | Me | 8 | 9 | |

TABLE 31

| Compound No. | $R^a$ | $R^b$ | $R^c$ | n | m | W |
|---|---|---|---|---|---|---|
| G-221 | H | Me | Me | 9 | 6 | 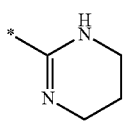 |
| G-222 | H | Me | Me | 9 | 7 | |
| G-223 | H | Me | Me | 9 | 8 | |
| G-224 | H | Me | Me | 9 | 9 | |
| G-225 | Me | Me | Me | 6 | 6 | |
| G-226 | Me | Me | Me | 6 | 7 | |
| G-227 | Me | Me | Me | 6 | 8 | |
| G-228 | Me | Me | Me | 6 | 9 | |
| G-229 | Me | Me | Me | 7 | 6 | |
| G-230 | Me | Me | Me | 7 | 7 | |
| G-231 | Me | Me | Me | 7 | 8 | |
| G-232 | Me | Me | Me | 7 | 9 | |
| G-233 | Me | Me | Me | 8 | 6 | |
| G-234 | Me | Me | Me | 8 | 7 | |
| G-235 | Me | Me | Me | 8 | 8 | |
| G-236 | Me | Me | Me | 8 | 9 | |
| G-237 | Me | Me | Me | 9 | 6 | |
| G-238 | Me | Me | Me | 9 | 7 | |
| G-239 | Me | Me | Me | 9 | 8 | |
| G-240 | Me | Me | Me | 9 | 9 | |

TABLE 32

| Compound No. | $R^a$ | n | m | W |
|---|---|---|---|---|
| H-1 | H | 6 | 6 | |
| H-2 | H | 6 | 7 | |
| H-3 | H | 6 | 8 | |
| H-4 | H | 6 | 9 | |
| H-5 | H | 7 | 6 | |
| H-6 | H | 7 | 7 | |
| H-7 | H | 7 | 8 | |
| H-8 | H | 7 | 9 | |
| H-9 | H | 8 | 6 | |
| H-10 | H | 8 | 7 | |
| H-11 | H | 8 | 8 | |
| H-12 | H | 8 | 9 | |
| H-13 | H | 9 | 6 | |
| H-14 | H | 9 | 7 | |
| H-15 | H | 9 | 8 | |
| H-16 | H | 9 | 9 | |
| H-17 | Me | 6 | 6 | |
| H-18 | Me | 6 | 7 | |
| H-19 | Me | 6 | 8 | |
| H-20 | Me | 6 | 9 | |
| H-21 | Me | 7 | 6 | |
| H-22 | Me | 7 | 7 | |
| H-23 | Me | 7 | 8 | |
| H-24 | Me | 7 | 9 | |
| H-25 | Me | 8 | 6 | |
| H-26 | Me | 8 | 7 | |
| H-27 | Me | 8 | 8 | |
| H-28 | Me | 8 | 9 | |
| H-29 | Me | 9 | 6 | |
| H-30 | Me | 9 | 7 | |
| H-31 | Me | 9 | 8 | |
| H-32 | Me | 9 | 9 | |
| H-33 | H | 6 | 6 | |
| H-34 | H | 6 | 7 | |
| H-35 | H | 6 | 8 | |
| H-36 | H | 6 | 9 | |
| H-37 | H | 7 | 6 | |
| H-38 | H | 7 | 7 | |
| H-39 | H | 7 | 8 | |
| H-40 | H | 7 | 9 | |
| H-41 | H | 8 | 6 | |
| H-42 | H | 8 | 7 | |
| H-43 | H | 8 | 8 | |
| H-44 | H | 8 | 9 | |
| H-45 | H | 9 | 6 | |
| H-46 | H | 9 | 7 | |
| H-47 | H | 9 | 8 | |
| H-48 | H | 9 | 9 | |
| H-49 | Me | 6 | 6 | |
| H-50 | Me | 6 | 7 | |
| H-51 | Me | 6 | 8 | |
| H-52 | Me | 6 | 9 | |
| H-53 | Me | 7 | 6 | |
| H-54 | Me | 7 | 7 | |
| H-55 | Me | 7 | 8 | |
| H-56 | Me | 7 | 9 | |
| H-57 | Me | 8 | 6 | |
| H-58 | Me | 8 | 7 | |
| H-59 | Me | 8 | 8 | |
| H-60 | Me | 8 | 9 | |
| H-61 | Me | 9 | 6 | |
| H-62 | Me | 9 | 7 | |
| H-63 | Me | 9 | 8 | |
| H-64 | Me | 9 | 9 | |
| H-65 | H | 6 | 6 | |
| H-66 | H | 6 | 7 | |
| H-67 | H | 6 | 8 | |
| H-68 | H | 6 | 9 | |
| H-69 | H | 7 | 6 | |
| H-70 | H | 7 | 7 | |
| H-71 | H | 7 | 8 | |
| H-72 | H | 7 | 9 | |
| H-73 | H | 8 | 6 | |
| H-74 | H | 8 | 7 | |
| H-75 | H | 8 | 8 | |
| H-76 | H | 8 | 9 | |
| H-77 | H | 9 | 6 | |
| H-78 | H | 9 | 7 | |
| H-79 | H | 9 | 8 | |
| H-80 | H | 9 | 9 | |
| H-81 | Me | 6 | 6 | |
| H-82 | Me | 6 | 7 | |
| H-83 | Me | 6 | 8 | |
| H-84 | Me | 6 | 9 | |
| H-85 | Me | 7 | 6 | |
| H-86 | Me | 7 | 7 | |
| H-87 | Me | 7 | 8 | |
| H-88 | Me | 7 | 9 | |
| H-89 | Me | 8 | 6 | |
| H-90 | Me | 8 | 7 | |
| H-91 | Me | 8 | 8 | |
| H-92 | Me | 8 | 9 | |
| H-93 | Me | 9 | 6 | |
| H-94 | Me | 9 | 7 | |
| H-95 | Me | 9 | 8 | |
| H-96 | Me | 9 | 9 | |

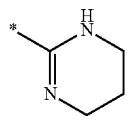

TABLE 33

| Compound No. | $R^a$ | $R^b$ | $R^c$ | n | m | W |
|---|---|---|---|---|---|---|
| I-1 | Me | H | H | 6 | 6 | |
| I-2 | Me | H | H | 6 | 7 | |
| I-3 | Me | H | H | 6 | 8 | |
| I-4 | Me | H | H | 6 | 9 | |
| I-5 | Me | H | H | 7 | 6 | |
| I-6 | Me | H | H | 7 | 7 | |
| I-7 | Me | H | H | 7 | 8 | |
| I-8 | Me | H | H | 7 | 9 | |
| I-9 | Me | H | H | 8 | 6 | |
| I-10 | Me | H | H | 8 | 7 | |
| I-11 | Me | H | H | 8 | 8 | |
| I-12 | Me | H | H | 8 | 9 | |
| I-13 | Me | H | H | 9 | 6 | |
| I-14 | Me | H | H | 9 | 7 | |
| I-15 | Me | H | H | 9 | 8 | |
| I-16 | Me | H | H | 9 | 9 | |
| I-17 | H | H | Me | 6 | 6 | |
| I-18 | H | H | Me | 6 | 7 | |
| I-19 | H | H | Me | 6 | 8 | |
| I-20 | H | H | Me | 6 | 9 | |
| I-21 | H | H | Me | 7 | 6 | |
| I-22 | H | H | Me | 7 | 7 | |
| I-23 | H | H | Me | 7 | 8 | |
| I-24 | H | H | Me | 7 | 9 | |
| I-25 | H | H | Me | 8 | 6 | |
| I-26 | H | H | Me | 8 | 7 | |
| I-27 | H | H | Me | 8 | 8 | |
| I-28 | H | H | Me | 8 | 9 | |
| I-29 | H | H | Me | 9 | 6 | |
| I-30 | H | H | Me | 9 | 7 | |
| I-31 | H | H | Me | 9 | 8 | |
| I-32 | H | H | Me | 9 | 9 | |

TABLE 33-continued

| Compound No. | $R^a$ | $R^b$ | $R^c$ | n | m | W |
|---|---|---|---|---|---|---|
| I-33 | Me | Me | H | 6 | 6 | |
| I-34 | Me | Me | H | 6 | 7 | |
| I-35 | Me | Me | H | 6 | 8 | |
| I-36 | Me | Me | H | 6 | 9 | |
| I-37 | Me | Me | H | 7 | 6 | |
| I-38 | Me | Me | H | 7 | 7 | |
| I-39 | Me | Me | H | 7 | 8 | |
| I-40 | Me | Me | H | 7 | 9 | |
| I-41 | Me | Me | H | 8 | 6 | |
| I-42 | Me | Me | H | 8 | 7 | |
| I-43 | Me | Me | H | 8 | 8 | |
| I-44 | Me | Me | H | 8 | 9 | |
| I-45 | Me | Me | H | 9 | 6 | |
| I-46 | Me | Me | H | 9 | 7 | |
| I-47 | Me | Me | H | 9 | 8 | |
| I-48 | Me | Me | H | 9 | 9 | |
| I-49 | H | Me | Me | 6 | 6 | |
| I-50 | H | Me | Me | 6 | 7 | |
| I-51 | H | Me | Me | 6 | 8 | |
| I-52 | H | Me | Me | 6 | 9 | |
| I-53 | H | Me | Me | 7 | 6 | |
| I-54 | H | Me | Me | 7 | 7 | |
| I-55 | H | Me | Me | 7 | 8 | |
| I-56 | H | Me | Me | 7 | 9 | |
| I-57 | H | Me | Me | 8 | 6 | |
| I-58 | H | Me | Me | 8 | 7 | |
| I-59 | H | Me | Me | 8 | 8 | |
| I-60 | H | Me | Me | 8 | 9 | |
| I-61 | H | Me | Me | 9 | 6 | |
| I-62 | H | Me | Me | 9 | 7 | |
| I-63 | H | Me | Me | 9 | 8 | |
| I-64 | H | Me | Me | 9 | 9 | |
| I-65 | Me | Me | Me | 6 | 6 | |
| I-66 | Me | Me | Me | 6 | 7 | |
| I-67 | Me | Me | Me | 6 | 8 | |
| I-68 | Me | Me | Me | 6 | 9 | |
| I-69 | Me | Me | Me | 7 | 6 | |
| I-70 | Me | Me | Me | 7 | 7 | |
| I-71 | Me | Me | Me | 7 | 8 | |
| I-72 | Me | Me | Me | 7 | 9 | |
| I-73 | Me | Me | Me | 8 | 6 | |
| I-74 | Me | Me | Me | 8 | 7 | |
| I-75 | Me | Me | Me | 8 | 8 | |
| I-76 | Me | Me | Me | 8 | 9 | |
| I-77 | Me | Me | Me | 9 | 6 | |
| I-78 | Me | Me | Me | 9 | 7 | |
| I-79 | Me | Me | Me | 9 | 8 | |
| I-80 | Me | Me | Me | 9 | 9 | |
| I-81 | Me | H | H | 6 | 6 | |
| I-82 | Me | H | H | 6 | 7 | |
| I-83 | Me | H | H | 6 | 8 | |
| I-84 | Me | H | H | 6 | 9 | |
| I-85 | Me | H | H | 7 | 6 | |
| I-86 | Me | H | H | 7 | 7 | |
| I-87 | Me | H | H | 7 | 8 | |
| I-88 | Me | H | H | 7 | 9 | |
| I-89 | Me | H | H | 8 | 6 | |
| I-90 | Me | H | H | 8 | 7 | |
| I-91 | Me | H | H | 8 | 8 | |
| I-92 | Me | H | H | 8 | 9 | |
| I-93 | Me | H | H | 9 | 6 | |
| I-94 | Me | H | H | 9 | 7 | |
| I-95 | Me | H | H | 9 | 8 | |
| I-96 | Me | H | H | 9 | 9 | |
| I-97 | H | H | Me | 6 | 6 | |
| I-98 | H | H | Me | 6 | 7 | |
| I-99 | H | H | Me | 6 | 8 | |
| I-100 | H | H | Me | 6 | 9 | |
| I-101 | H | H | Me | 7 | 6 | |
| I-102 | H | H | Me | 7 | 7 | |
| I-103 | H | H | Me | 7 | 8 | |
| I-104 | H | H | Me | 7 | 9 | |
| I-105 | H | H | Me | 8 | 6 | |
| I-106 | H | H | Me | 8 | 7 | |
| I-107 | H | H | Me | 8 | 8 | |
| I-108 | H | H | Me | 8 | 9 | |
| I-109 | H | H | Me | 9 | 6 | |
| I-110 | H | H | Me | 9 | 7 | |

TABLE 34

| Compound No. | $R^a$ | $R^b$ | $R^c$ | n | m | W |
|---|---|---|---|---|---|---|
| I-111 | H | H | Me | 9 | 8 | |
| I-112 | H | H | Me | 9 | 9 | |
| I-113 | Me | Me | H | 6 | 6 | |
| I-114 | Me | Me | H | 6 | 7 | |
| I-115 | Me | Me | H | 6 | 8 | |
| I-116 | Me | Me | H | 6 | 9 | |
| I-117 | Me | Me | H | 7 | 6 | |
| I-118 | Me | Me | H | 7 | 7 | |
| I-119 | Me | Me | H | 7 | 8 | |
| I-120 | Me | Me | H | 7 | 9 | |
| I-121 | Me | Me | H | 8 | 6 | |
| I-122 | Me | Me | H | 8 | 7 | |
| I-123 | Me | Me | H | 8 | 8 | |
| I-124 | Me | Me | H | 8 | 9 | |
| I-125 | Me | Me | H | 9 | 6 | |
| I-126 | Me | Me | H | 9 | 7 | |
| I-127 | Me | Me | H | 9 | 8 | |
| I-128 | Me | Me | H | 9 | 9 | |
| I-129 | H | Me | Me | 6 | 6 | |
| I-130 | H | Me | Me | 6 | 7 | |
| I-131 | H | Me | Me | 6 | 8 | |
| I-132 | H | Me | Me | 6 | 9 | |
| I-133 | H | Me | Me | 7 | 6 | |
| I-134 | H | Me | Me | 7 | 7 | |
| I-135 | H | Me | Me | 7 | 8 | |
| I-136 | H | Me | Me | 7 | 9 | |
| I-137 | H | Me | Me | 8 | 6 | |
| I-138 | H | Me | Me | 8 | 7 | |
| I-139 | H | Me | Me | 8 | 8 | |
| I-140 | H | Me | Me | 8 | 9 | |
| I-141 | H | Me | Me | 9 | 6 | |
| I-142 | H | Me | Me | 9 | 7 | |
| I-143 | H | Me | Me | 9 | 8 | |
| I-144 | H | Me | Me | 9 | 9 | |
| I-145 | Me | Me | Me | 6 | 6 | |
| I-146 | Me | Me | Me | 6 | 7 | |
| I-147 | Me | Me | Me | 6 | 8 | |
| I-148 | Me | Me | Me | 6 | 9 | |
| I-149 | Me | Me | Me | 7 | 6 | |
| I-150 | Me | Me | Me | 7 | 7 | |
| I-151 | Me | Me | Me | 7 | 8 | |
| I-152 | Me | Me | Me | 7 | 9 | |
| I-153 | Me | Me | Me | 8 | 6 | |
| I-154 | Me | Me | Me | 8 | 7 | |
| I-155 | Me | Me | Me | 8 | 8 | |
| I-156 | Me | Me | Me | 8 | 9 | |
| I-157 | Me | Me | Me | 9 | 6 | |
| I-158 | Me | Me | Me | 9 | 7 | |
| I-159 | Me | Me | Me | 9 | 8 | |
| I-160 | Me | Me | Me | 9 | 9 | |
| I-161 | Me | H | H | 6 | 6 | |
| I-162 | Me | H | H | 6 | 7 | |
| I-163 | Me | H | H | 6 | 8 | |
| I-164 | Me | H | H | 6 | 9 | |
| I-165 | Me | H | H | 7 | 6 | |
| I-166 | Me | H | H | 7 | 7 | |
| I-167 | Me | H | H | 7 | 8 | |
| I-168 | Me | H | H | 7 | 9 | |
| I-169 | Me | H | H | 8 | 6 | |
| I-170 | Me | H | H | 8 | 7 | |
| I-171 | Me | H | H | 8 | 8 | |
| I-172 | Me | H | H | 8 | 9 | |
| I-173 | Me | H | H | 9 | 6 | |
| I-174 | Me | H | H | 9 | 7 | |
| I-175 | Me | H | H | 9 | 8 | |

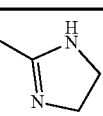

TABLE 34-continued

| Compound No. | $R^a$ | $R^b$ | $R^c$ | n | m | W |
|---|---|---|---|---|---|---|
| I-176 | Me | H | H | 9 | 9 | |
| I-177 | H | H | Me | 6 | 6 | |
| I-178 | H | H | Me | 6 | 7 | |
| I-179 | H | H | Me | 6 | 8 | |
| I-180 | H | H | Me | 6 | 9 | |
| I-181 | H | H | Me | 7 | 6 | |
| I-182 | H | H | Me | 7 | 7 | |
| I-183 | H | H | Me | 7 | 8 | |
| I-184 | H | H | Me | 7 | 9 | |
| I-185 | H | H | Me | 8 | 6 | |
| I-186 | H | H | Me | 8 | 7 | |
| I-187 | H | H | Me | 8 | 8 | |
| I-188 | H | H | Me | 8 | 9 | |
| I-189 | H | H | Me | 9 | 6 | |
| I-190 | H | H | Me | 9 | 7 | |
| I-191 | H | H | Me | 9 | 8 | |
| I-192 | H | H | Me | 9 | 9 | |
| I-193 | Me | Me | H | 6 | 6 | |
| I-194 | Me | Me | H | 6 | 7 | |
| I-195 | Me | Me | H | 6 | 8 | |
| I-196 | Me | Me | H | 6 | 9 | |
| I-197 | Me | Me | H | 7 | 6 | |
| I-198 | Me | Me | H | 7 | 7 | |
| I-199 | Me | Me | H | 7 | 8 | |
| I-200 | Me | Me | H | 7 | 9 | |
| I-201 | Me | Me | H | 8 | 6 | |
| I-202 | Me | Me | H | 8 | 7 | |
| I-203 | Me | Me | H | 8 | 8 | |
| I-204 | Me | Me | H | 8 | 9 | |
| I-205 | Me | Me | H | 9 | 6 | |
| I-206 | Me | Me | H | 9 | 7 | |
| I-207 | Me | Me | H | 9 | 8 | |
| I-208 | Me | Me | H | 9 | 9 | |
| I-209 | H | Me | Me | 6 | 6 | |
| I-210 | H | Me | Me | 6 | 7 | |
| I-211 | H | Me | Me | 6 | 8 | |
| I-212 | H | Me | Me | 6 | 9 | |
| I-213 | H | Me | Me | 7 | 6 | |
| I-214 | H | Me | Me | 7 | 7 | |
| I-215 | H | Me | Me | 7 | 8 | |
| I-216 | H | Me | Me | 7 | 9 | |
| I-217 | H | Me | Me | 8 | 6 | |
| I-218 | H | Me | Me | 8 | 7 | |
| I-219 | H | Me | Me | 8 | 8 | |
| I-220 | H | Me | Me | 8 | 9 | |

TABLE 35

| Compound No. | $R^a$ | $R^b$ | $R^c$ | n | m | W |
|---|---|---|---|---|---|---|
| I-221 | H | Me | Me | 9 | 6 | * ![pyrimidine] |
| I-222 | H | Me | Me | 9 | 7 | |
| I-223 | H | Me | Me | 9 | 8 | |
| I-224 | H | Me | Me | 9 | 9 | |
| I-225 | Me | Me | Me | 6 | 6 | |
| I-226 | Me | Me | Me | 6 | 7 | |
| I-227 | Me | Me | Me | 6 | 8 | |
| I-228 | Me | Me | Me | 6 | 9 | |
| I-229 | Me | Me | Me | 7 | 6 | |
| I-230 | Me | Me | Me | 7 | 7 | |
| I-231 | Me | Me | Me | 7 | 8 | |
| I-232 | Me | Me | Me | 7 | 9 | |
| I-233 | Me | Me | Me | 8 | 6 | |
| I-234 | Me | Me | Me | 8 | 7 | |
| I-235 | Me | Me | Me | 8 | 8 | |
| I-236 | Me | Me | Me | 8 | 9 | |
| I-237 | Me | Me | Me | 9 | 6 | |
| I-238 | Me | Me | Me | 9 | 7 | |
| I-239 | Me | Me | Me | 9 | 8 | |
| I-240 | Me | Me | Me | 9 | 9 | |

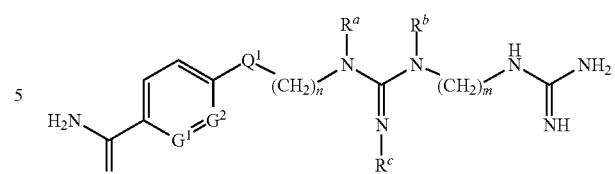

TABLE 36

| Compound No. | $G^1$ | $G^2$ | $Q^1$ | $R^a$ | $R^b$ | $R^c$ | n | m |
|---|---|---|---|---|---|---|---|---|
| J-1 | CH | CH | —O— | Me | H | H | 1 | 7 |
| J-2 | CH | CH | —O— | Me | H | H | 1 | 8 |
| J-3 | CH | CH | —O— | Me | H | H | 1 | 9 |
| J-4 | CH | CH | —O— | Me | H | H | 2 | 7 |
| J-5 | CH | CH | —O— | Me | H | H | 2 | 8 |
| J-6 | CH | CH | —O— | Me | H | H | 2 | 9 |
| J-7 | CH | CH | —O— | Me | H | H | 3 | 7 |
| J-8 | CH | CH | —O— | Me | H | H | 3 | 8 |
| J-9 | CH | CH | —O— | Me | H | H | 3 | 9 |
| J-10 | CH | CH | —O— | Me | H | H | 4 | 7 |
| J-11 | CH | CH | —O— | Me | H | H | 4 | 8 |
| J-12 | CH | CH | —O— | Me | H | H | 4 | 9 |
| J-13 | CH | CH | —O— | Me | H | H | 5 | 7 |
| J-14 | CH | CH | —O— | Me | H | H | 5 | 8 |
| J-15 | CH | CH | —O— | Me | H | H | 5 | 9 |
| J-16 | CH | CH | —O— | H | H | Me | 1 | 7 |
| J-17 | CH | CH | —O— | H | H | Me | 1 | 8 |
| J-18 | CH | CH | —O— | H | H | Me | 1 | 9 |
| J-19 | CH | CH | —O— | H | H | Me | 2 | 7 |
| J-20 | CH | CH | —O— | H | H | Me | 2 | 8 |
| J-21 | CH | CH | —O— | H | H | Me | 2 | 9 |
| J-22 | CH | CH | —O— | H | H | Me | 3 | 7 |
| J-23 | CH | CH | —O— | H | H | Me | 3 | 8 |
| J-24 | CH | CH | —O— | H | H | Me | 3 | 9 |
| J-25 | CH | CH | —O— | H | H | Me | 4 | 7 |
| J-26 | CH | CH | —O— | H | H | Me | 4 | 8 |
| J-27 | CH | CH | —O— | H | H | Me | 4 | 9 |
| J-28 | CH | CH | —O— | H | H | Me | 5 | 7 |
| J-29 | CH | CH | —O— | H | H | Me | 5 | 8 |
| J-30 | CH | CH | —O— | H | H | Me | 5 | 9 |
| J-31 | CH | CH | —O— | Me | Me | H | 1 | 7 |
| J-32 | CH | CH | —O— | Me | Me | H | 1 | 8 |
| J-33 | CH | CH | —O— | Me | Me | H | 1 | 9 |
| J-34 | CH | CH | —O— | Me | Me | H | 2 | 7 |
| J-35 | CH | CH | —O— | Me | Me | H | 2 | 8 |
| J-36 | CH | CH | —O— | Me | Me | H | 2 | 9 |
| J-37 | CH | CH | —O— | Me | Me | H | 3 | 7 |
| J-38 | CH | CH | —O— | Me | Me | H | 3 | 8 |
| J-39 | CH | CH | —O— | Me | Me | H | 3 | 9 |
| J-40 | CH | CH | —O— | Me | Me | H | 4 | 7 |
| J-41 | CH | CH | —O— | Me | Me | H | 4 | 8 |
| J-42 | CH | CH | —O— | Me | Me | H | 4 | 9 |
| J-43 | CH | CH | —O— | Me | Me | H | 5 | 7 |
| J-44 | CH | CH | —O— | Me | Me | H | 5 | 8 |
| J-45 | CH | CH | —O— | Me | Me | H | 5 | 9 |
| J-46 | CH | CH | —O— | H | Me | Me | 1 | 7 |
| J-47 | CH | CH | —O— | H | Me | Me | 1 | 8 |
| J-48 | CH | CH | —O— | H | Me | Me | 1 | 9 |
| J-49 | CH | CH | —O— | H | Me | Me | 2 | 7 |
| J-50 | CH | CH | —O— | H | Me | Me | 2 | 8 |
| J-51 | CH | CH | —O— | H | Me | Me | 2 | 9 |
| J-52 | CH | CH | —O— | H | Me | Me | 3 | 7 |
| J-53 | CH | CH | —O— | H | Me | Me | 3 | 8 |
| J-54 | CH | CH | —O— | H | Me | Me | 3 | 9 |
| J-55 | CH | CH | —O— | H | Me | Me | 4 | 7 |
| J-56 | CH | CH | —O— | H | Me | Me | 4 | 8 |
| J-57 | CH | CH | —O— | H | Me | Me | 4 | 9 |
| J-58 | CH | CH | —O— | H | Me | Me | 5 | 7 |
| J-59 | CH | CH | —O— | H | Me | Me | 5 | 8 |
| J-60 | CH | CH | —O— | H | Me | Me | 5 | 9 |
| J-61 | CH | CH | —CH$_2$O— | Me | H | H | 1 | 7 |
| J-62 | CH | CH | —CH$_2$O— | Me | H | H | 1 | 8 |
| J-63 | CH | CH | —CH$_2$O— | Me | H | H | 1 | 9 |
| J-64 | CH | CH | —CH$_2$O— | Me | H | H | 2 | 7 |

TABLE 36-continued

| Compound No. | G¹ | G² | Q¹ | $R^a$ | $R^b$ | $R^c$ | n | m |
|---|---|---|---|---|---|---|---|---|
| J-65 | CH | CH | —CH₂O— | Me | H | H | 2 | 8 |
| J-66 | CH | CH | —CH₂O— | Me | H | H | 2 | 9 |
| J-67 | CH | CH | —CH₂O— | Me | H | H | 3 | 7 |
| J-68 | CH | CH | —CH₂O— | Me | H | H | 3 | 8 |
| J-69 | CH | CH | —CH₂O— | Me | H | H | 3 | 9 |
| J-70 | CH | CH | —CH₂O— | Me | H | H | 4 | 7 |
| J-71 | CH | CH | —CH₂O— | Me | H | H | 4 | 8 |
| J-72 | CH | CH | —CH₂O— | Me | H | H | 4 | 9 |
| J-73 | CH | CH | —CH₂O— | Me | H | H | 5 | 7 |
| J-74 | CH | CH | —CH₂O— | Me | H | H | 5 | 8 |
| J-75 | CH | CH | —CH₂O— | Me | H | H | 5 | 9 |
| J-76 | CH | CH | —CH₂O— | H | H | Me | 1 | 7 |
| J-77 | CH | CH | —CH₂O— | H | H | Me | 1 | 8 |
| J-78 | CH | CH | —CH₂O— | H | H | Me | 1 | 9 |
| J-79 | CH | CH | —CH₂O— | H | H | Me | 2 | 7 |
| J-80 | CH | CH | —CH₂O— | H | H | Me | 2 | 8 |
| J-81 | CH | CH | —CH₂O— | H | H | Me | 2 | 9 |
| J-82 | CH | CH | —CH₂O— | H | H | Me | 3 | 7 |
| J-83 | CH | CH | —CH₂O— | H | H | Me | 3 | 8 |
| J-84 | CH | CH | —CH₂O— | H | H | Me | 3 | 9 |
| J-85 | CH | CH | —CH₂O— | H | H | Me | 4 | 7 |
| J-86 | CH | CH | —CH₂O— | H | H | Me | 4 | 8 |
| J-87 | CH | CH | —CH₂O— | H | H | Me | 4 | 9 |
| J-88 | CH | CH | —CH₂O— | H | H | Me | 5 | 7 |
| J-89 | CH | CH | —CH₂O— | H | H | Me | 5 | 8 |
| J-90 | CH | CH | —CH₂O— | H | H | Me | 5 | 9 |
| J-91 | CH | CH | —CH₂O— | Me | Me | H | 1 | 7 |
| J-92 | CH | CH | —CH₂O— | Me | Me | H | 1 | 8 |
| J-93 | CH | CH | —CH₂O— | Me | Me | H | 1 | 9 |
| J-94 | CH | CH | —CH₂O— | Me | Me | H | 2 | 7 |
| J-95 | CH | CH | —CH₂O— | Me | Me | H | 2 | 8 |
| J-96 | CH | CH | —CH₂O— | Me | Me | H | 2 | 9 |
| J-97 | CH | CH | —CH₂O— | Me | Me | H | 3 | 7 |
| J-98 | CH | CH | —CH₂O— | Me | Me | H | 3 | 8 |
| J-99 | CH | CH | —CH₂O— | Me | Me | H | 3 | 9 |
| J-100 | CH | CH | —CH₂O— | Me | Me | H | 4 | 7 |
| J-101 | CH | CH | —CH₂O— | Me | Me | H | 4 | 8 |
| J-102 | CH | CH | —CH₂O— | Me | Me | H | 4 | 9 |
| J-103 | CH | CH | —CH₂O— | Me | Me | H | 5 | 7 |
| J-104 | CH | CH | —CH₂O— | Me | Me | H | 5 | 8 |
| J-105 | CH | CH | —CH₂O— | Me | Me | H | 5 | 9 |
| J-106 | CH | CH | —CH₂O— | H | Me | Me | 1 | 7 |
| J-107 | CH | CH | —CH₂O— | H | Me | Me | 1 | 8 |
| J-108 | CH | CH | —CH₂O— | H | Me | Me | 1 | 9 |
| J-109 | CH | CH | —CH₂O— | H | Me | Me | 2 | 7 |
| J-110 | CH | CH | —CH₂O— | H | Me | Me | 2 | 8 |

TABLE 37

| Compound No. | G¹ | G² | Q¹ | $R^a$ | $R^b$ | $R^c$ | n | m |
|---|---|---|---|---|---|---|---|---|
| J-111 | CH | CH | —CH₂O— | H | Me | Me | 2 | 9 |
| J-112 | CH | CH | —CH₂O— | H | Me | Me | 3 | 7 |
| J-113 | CH | CH | —CH₂O— | H | Me | Me | 3 | 8 |
| J-114 | CH | CH | —CH₂O— | H | Me | Me | 3 | 9 |
| J-115 | CH | CH | —CH₂O— | H | Me | Me | 4 | 7 |
| J-116 | CH | CH | —CH₂O— | H | Me | Me | 4 | 8 |
| J-117 | CH | CH | —CH₂O— | H | Me | Me | 4 | 9 |
| J-118 | CH | CH | —CH₂O— | H | Me | Me | 5 | 7 |
| J-119 | CH | CH | —CH₂O— | H | Me | Me | 5 | 8 |
| J-120 | CH | CH | —CH₂O— | H | Me | Me | 5 | 9 |
| J-121 | CH | CH | singlebond | Me | H | H | 1 | 7 |
| J-122 | CH | CH | singlebond | Me | H | H | 1 | 8 |
| J-123 | CH | CH | singlebond | Me | H | H | 1 | 9 |
| J-124 | CH | CH | singlebond | Me | H | H | 2 | 7 |
| J-125 | CH | CH | singlebond | Me | H | H | 2 | 8 |
| J-126 | CH | CH | singlebond | Me | H | H | 2 | 9 |
| J-127 | CH | CH | singlebond | Me | H | H | 3 | 7 |
| J-128 | CH | CH | singlebond | Me | H | H | 3 | 8 |
| J-129 | CH | CH | singlebond | Me | H | H | 3 | 9 |
| J-130 | CH | CH | singlebond | Me | H | H | 4 | 7 |
| J-131 | CH | CH | singlebond | Me | H | H | 4 | 8 |
| J-132 | CH | CH | singlebond | Me | H | H | 4 | 9 |

TABLE 37-continued

| Compound No. | G¹ | G² | Q¹ | $R^a$ | $R^b$ | $R^c$ | n | m |
|---|---|---|---|---|---|---|---|---|
| J-133 | CH | CH | singlebond | Me | H | H | 5 | 7 |
| J-134 | CH | CH | singlebond | Me | H | H | 5 | 8 |
| J-135 | CH | CH | singlebond | Me | H | H | 5 | 9 |
| J-136 | CH | CH | singlebond | H | H | Me | 1 | 7 |
| J-137 | CH | CH | singlebond | H | H | Me | 1 | 8 |
| J-138 | CH | CH | singlebond | H | H | Me | 1 | 9 |
| J-139 | CH | CH | singlebond | H | H | Me | 2 | 7 |
| J-140 | CH | CH | singlebond | H | H | Me | 2 | 8 |
| J-141 | CH | CH | singlebond | H | H | Me | 2 | 9 |
| J-142 | CH | CH | singlebond | H | H | Me | 3 | 7 |
| J-143 | CH | CH | singlebond | H | H | Me | 3 | 8 |
| J-144 | CH | CH | singlebond | H | H | Me | 3 | 9 |
| J-145 | CH | CH | singlebond | H | H | Me | 4 | 7 |
| J-146 | CH | CH | singlebond | H | H | Me | 4 | 8 |
| J-147 | CH | CH | singlebond | H | H | Me | 4 | 9 |
| J-148 | CH | CH | singlebond | H | H | Me | 5 | 7 |
| J-149 | CH | CH | singlebond | H | H | Me | 5 | 8 |
| J-150 | CH | CH | singlebond | H | H | Me | 5 | 9 |
| J-151 | CH | CH | singlebond | Me | Me | H | 1 | 7 |
| J-152 | CH | CH | singlebond | Me | Me | H | 1 | 8 |
| J-153 | CH | CH | singlebond | Me | Me | H | 1 | 9 |
| J-154 | CH | CH | singlebond | Me | Me | H | 2 | 7 |
| J-155 | CH | CH | singlebond | Me | Me | H | 2 | 8 |
| J-156 | CH | CH | singlebond | Me | Me | H | 2 | 9 |
| J-157 | CH | CH | singlebond | Me | Me | H | 3 | 7 |
| J-158 | CH | CH | singlebond | Me | Me | H | 3 | 8 |
| J-159 | CH | CH | singlebond | Me | Me | H | 3 | 9 |
| J-160 | CH | CH | singlebond | Me | Me | H | 4 | 7 |
| J-161 | CH | CH | singlebond | Me | Me | H | 4 | 8 |
| J-162 | CH | CH | singlebond | Me | Me | H | 4 | 9 |
| J-163 | CH | CH | singlebond | Me | Me | H | 5 | 7 |
| J-164 | CH | CH | singlebond | Me | Me | H | 5 | 8 |
| J-165 | CH | CH | singlebond | Me | Me | H | 5 | 9 |
| J-166 | CH | CH | singlebond | H | Me | Me | 1 | 7 |
| J-167 | CH | CH | singlebond | H | Me | Me | 1 | 8 |
| J-168 | CH | CH | singlebond | H | Me | Me | 1 | 9 |
| J-169 | CH | CH | singlebond | H | Me | Me | 2 | 7 |
| J-170 | CH | CH | singlebond | H | Me | Me | 2 | 8 |
| J-171 | CH | CH | singlebond | H | Me | Me | 2 | 9 |
| J-172 | CH | CH | singlebond | H | Me | Me | 3 | 7 |
| J-173 | CH | CH | singlebond | H | Me | Me | 3 | 8 |
| J-174 | CH | CH | singlebond | H | Me | Me | 3 | 9 |
| J-175 | CH | CH | singlebond | H | Me | Me | 4 | 7 |
| J-176 | CH | CH | singlebond | H | Me | Me | 4 | 8 |
| J-177 | CH | CH | singlebond | H | Me | Me | 4 | 9 |
| J-178 | CH | CH | singlebond | H | Me | Me | 5 | 7 |
| J-179 | CH | CH | singlebond | H | Me | Me | 5 | 8 |
| J-180 | CH | CH | singlebond | H | Me | Me | 5 | 9 |
| J-181 | N | CH | —O— | Me | H | H | 1 | 7 |
| J-182 | N | CH | —O— | Me | H | H | 1 | 8 |
| J-183 | N | CH | —O— | Me | H | H | 1 | 9 |
| J-184 | N | CH | —O— | Me | H | H | 2 | 7 |
| J-185 | N | CH | —O— | Me | H | H | 2 | 8 |
| J-186 | N | CH | —O— | Me | H | H | 2 | 9 |
| J-187 | N | CH | —O— | Me | H | H | 3 | 7 |
| J-188 | N | CH | —O— | Me | H | H | 3 | 8 |
| J-189 | N | CH | —O— | Me | H | H | 3 | 9 |
| J-190 | N | CH | —O— | Me | H | H | 4 | 7 |
| J-191 | N | CH | —O— | Me | H | H | 4 | 8 |
| J-192 | N | CH | —O— | Me | H | H | 4 | 9 |
| J-193 | N | CH | —O— | Me | H | H | 5 | 7 |
| J-194 | N | CH | —O— | Me | H | H | 5 | 8 |
| J-195 | N | CH | —O— | Me | H | H | 5 | 9 |
| J-196 | N | CH | —O— | H | H | Me | 1 | 7 |
| J-197 | N | CH | —O— | H | H | Me | 1 | 8 |
| J-198 | N | CH | —O— | H | H | Me | 1 | 9 |
| J-199 | N | CH | —O— | H | H | Me | 2 | 7 |
| J-200 | N | CH | —O— | H | H | Me | 2 | 8 |
| J-201 | N | CH | —O— | H | H | Me | 2 | 9 |
| J-202 | N | CH | —O— | H | H | Me | 3 | 7 |
| J-203 | N | CH | —O— | H | H | Me | 3 | 8 |
| J-204 | N | CH | —O— | H | H | Me | 3 | 9 |
| J-205 | N | CH | —O— | H | H | Me | 4 | 7 |
| J-206 | N | CH | —O— | H | H | Me | 4 | 8 |
| J-207 | N | CH | —O— | H | H | Me | 4 | 9 |
| J-208 | N | CH | —O— | H | H | Me | 5 | 7 |
| J-209 | N | CH | —O— | H | H | Me | 5 | 8 |

TABLE 37-continued

| Compound No. | G¹ | G² | Q¹ | $R^a$ | $R^b$ | $R^c$ | n | m |
|---|---|---|---|---|---|---|---|---|
| J-210 | N | CH | —O— | H | H | Me | 5 | 9 |
| J-211 | N | CH | —O— | Me | Me | H | 1 | 7 |
| J-212 | N | CH | —O— | Me | Me | H | 1 | 8 |
| J-213 | N | CH | —O— | Me | Me | H | 1 | 9 |
| J-214 | N | CH | —O— | Me | Me | H | 2 | 7 |
| J-215 | N | CH | —O— | Me | Me | H | 2 | 8 |
| J-216 | N | CH | —O— | Me | Me | H | 2 | 9 |
| J-217 | N | CH | —O— | Me | Me | H | 3 | 7 |
| J-218 | N | CH | —O— | Me | Me | H | 3 | 8 |
| J-219 | N | CH | —O— | Me | Me | H | 3 | 9 |
| J-220 | N | CH | —O— | Me | Me | H | 4 | 7 |

TABLE 38

| Compound No. | G¹ | G² | Q¹ | $R^a$ | $R^b$ | $R^c$ | n | m |
|---|---|---|---|---|---|---|---|---|
| J-221 | N | CH | —O— | Me | Me | H | 4 | 8 |
| J-222 | N | CH | —O— | Me | Me | H | 4 | 9 |
| J-223 | N | CH | —O— | Me | Me | H | 5 | 7 |
| J-224 | N | CH | —O— | Me | Me | H | 5 | 8 |
| J-225 | N | CH | —O— | Me | Me | H | 5 | 9 |
| J-226 | N | CH | —O— | H | Me | Me | 1 | 7 |
| J-227 | N | CH | —O— | H | Me | Me | 1 | 8 |
| J-228 | N | CH | —O— | H | Me | Me | 1 | 9 |
| J-229 | N | CH | —O— | H | Me | Me | 2 | 7 |
| J-230 | N | CH | —O— | H | Me | Me | 2 | 8 |
| J-231 | N | CH | —O— | H | Me | Me | 2 | 9 |
| J-232 | N | CH | —O— | H | Me | Me | 3 | 7 |
| J-233 | N | CH | —O— | H | Me | Me | 3 | 8 |
| J-234 | N | CH | —O— | H | Me | Me | 3 | 9 |
| J-235 | N | CH | —O— | H | Me | Me | 4 | 7 |
| J-236 | N | CH | —O— | H | Me | Me | 4 | 8 |
| J-237 | N | CH | —O— | H | Me | Me | 4 | 9 |
| J-238 | N | CH | —O— | H | Me | Me | 5 | 7 |
| J-239 | N | CH | —O— | H | Me | Me | 5 | 8 |
| J-240 | N | CH | —O— | H | Me | Me | 5 | 9 |
| J-241 | N | CH | —CH₂O— | Me | H | H | 1 | 7 |
| J-242 | N | CH | —CH₂O— | Me | H | H | 1 | 8 |
| J-243 | N | CH | —CH₂O— | Me | H | H | 1 | 9 |
| J-244 | N | CH | —CH₂O— | Me | H | H | 2 | 7 |
| J-245 | N | CH | —CH₂O— | Me | H | H | 2 | 8 |
| J-246 | N | CH | —CH₂O— | Me | H | H | 2 | 9 |
| J-247 | N | CH | —CH₂O— | Me | H | H | 3 | 7 |
| J-248 | N | CH | —CH₂O— | Me | H | H | 3 | 8 |
| J-249 | N | CH | —CH₂O— | Me | H | H | 3 | 9 |
| J-250 | N | CH | —CH₂O— | Me | H | H | 4 | 7 |
| J-251 | N | CH | —CH₂O— | Me | H | H | 4 | 8 |
| J-252 | N | CH | —CH₂O— | Me | H | H | 4 | 9 |
| J-253 | N | CH | —CH₂O— | Me | H | H | 5 | 7 |
| J-254 | N | CH | —CH₂O— | Me | H | H | 5 | 8 |
| J-255 | N | CH | —CH₂O— | Me | H | H | 5 | 9 |
| J-256 | N | CH | —CH₂O— | H | H | Me | 1 | 7 |
| J-257 | N | CH | —CH₂O— | H | H | Me | 1 | 8 |
| J-258 | N | CH | —CH₂O— | H | H | Me | 1 | 9 |
| J-259 | N | CH | —CH₂O— | H | H | Me | 2 | 7 |
| J-260 | N | CH | —CH₂O— | H | H | Me | 2 | 8 |
| J-261 | N | CH | —CH₂O— | H | H | Me | 2 | 9 |
| J-262 | N | CH | —CH₂O— | H | H | Me | 3 | 7 |
| J-263 | N | CH | —CH₂O— | H | H | Me | 3 | 8 |
| J-264 | N | CH | —CH₂O— | H | H | Me | 3 | 9 |
| J-265 | N | CH | —CH₂O— | H | H | Me | 4 | 7 |
| J-266 | N | CH | —CH₂O— | H | H | Me | 4 | 8 |
| J-267 | N | CH | —CH₂O— | H | H | Me | 4 | 9 |
| J-268 | N | CH | —CH₂O— | H | H | Me | 5 | 7 |
| J-269 | N | CH | —CH₂O— | H | H | Me | 5 | 8 |
| J-270 | N | CH | —CH₂O— | H | H | Me | 5 | 9 |
| J-271 | N | CH | —CH₂O— | Me | Me | H | 1 | 7 |
| J-272 | N | CH | —CH₂O— | Me | Me | H | 1 | 8 |
| J-273 | N | CH | —CH₂O— | Me | Me | H | 1 | 9 |
| J-274 | N | CH | —CH₂O— | Me | Me | H | 2 | 7 |
| J-275 | N | CH | —CH₂O— | Me | Me | H | 2 | 8 |
| J-276 | N | CH | —CH₂O— | Me | Me | H | 2 | 9 |
| J-277 | N | CH | —CH₂O— | Me | Me | H | 3 | 7 |

TABLE 38-continued

| Compound No. | G¹ | G² | Q¹ | $R^a$ | $R^b$ | $R^c$ | n | m |
|---|---|---|---|---|---|---|---|---|
| J-278 | N | CH | —CH₂O— | Me | Me | H | 3 | 8 |
| J-279 | N | CH | —CH₂O— | Me | Me | H | 3 | 9 |
| J-280 | N | CH | —CH₂O— | Me | Me | H | 4 | 7 |
| J-281 | N | CH | —CH₂O— | Me | Me | H | 4 | 8 |
| J-282 | N | CH | —CH₂O— | Me | Me | H | 4 | 9 |
| J-283 | N | CH | —CH₂O— | Me | Me | H | 5 | 7 |
| J-284 | N | CH | —CH₂O— | Me | Me | H | 5 | 8 |
| J-285 | N | CH | —CH₂O— | Me | Me | H | 5 | 9 |
| J-286 | N | CH | —CH₂O— | H | Me | Me | 1 | 7 |
| J-287 | N | CH | —CH₂O— | H | Me | Me | 1 | 8 |
| J-288 | N | CH | —CH₂O— | H | Me | Me | 1 | 9 |
| J-289 | N | CH | —CH₂O— | H | Me | Me | 2 | 7 |
| J-290 | N | CH | —CH₂O— | H | Me | Me | 2 | 8 |
| J-291 | N | CH | —CH₂O— | H | Me | Me | 2 | 9 |
| J-292 | N | CH | —CH₂O— | H | Me | Me | 3 | 7 |
| J-293 | N | CH | —CH₂O— | H | Me | Me | 3 | 8 |
| J-294 | N | CH | —CH₂O— | H | Me | Me | 3 | 9 |
| J-295 | N | CH | —CH₂O— | H | Me | Me | 4 | 7 |
| J-296 | N | CH | —CH₂O— | H | Me | Me | 4 | 8 |
| J-297 | N | CH | —CH₂O— | H | Me | Me | 4 | 9 |
| J-298 | N | CH | —CH₂O— | H | Me | Me | 5 | 7 |
| J-299 | N | CH | —CH₂O— | H | Me | Me | 5 | 8 |
| J-300 | N | CH | —CH₂O— | H | Me | Me | 5 | 9 |
| J-301 | N | CH | singlebond | Me | H | H | 1 | 7 |
| J-302 | N | CH | singlebond | Me | H | H | 1 | 8 |
| J-303 | N | CH | singlebond | Me | H | H | 1 | 9 |
| J-304 | N | CH | singlebond | Me | H | H | 2 | 7 |
| J-305 | N | CH | singlebond | Me | H | H | 2 | 8 |
| J-306 | N | CH | singlebond | Me | H | H | 2 | 9 |
| J-307 | N | CH | singlebond | Me | H | H | 3 | 7 |
| J-308 | N | CH | singlebond | Me | H | H | 3 | 8 |
| J-309 | N | CH | singlebond | Me | H | H | 3 | 9 |
| J-310 | N | CH | singlebond | Me | H | H | 4 | 7 |
| J-311 | N | CH | singlebond | Me | H | H | 4 | 8 |
| J-312 | N | CH | singlebond | Me | H | H | 4 | 9 |
| J-313 | N | CH | singlebond | Me | H | H | 5 | 7 |
| J-314 | N | CH | singlebond | Me | H | H | 5 | 8 |
| J-315 | N | CH | singlebond | Me | H | H | 5 | 9 |
| J-316 | N | CH | singlebond | H | H | Me | 1 | 7 |
| J-317 | N | CH | singlebond | H | H | Me | 1 | 8 |
| J-318 | N | CH | singlebond | H | H | Me | 1 | 9 |
| J-319 | N | CH | singlebond | H | H | Me | 2 | 7 |
| J-320 | N | CH | singlebond | H | H | Me | 2 | 8 |
| J-321 | N | CH | singlebond | H | H | Me | 2 | 9 |
| J-322 | N | CH | singlebond | H | H | Me | 3 | 7 |
| J-323 | N | CH | singlebond | H | H | Me | 3 | 8 |
| J-324 | N | CH | singlebond | H | H | Me | 3 | 9 |
| J-325 | N | CH | singlebond | H | H | Me | 4 | 7 |
| J-326 | N | CH | singlebond | H | H | Me | 4 | 8 |
| J-327 | N | CH | singlebond | H | H | Me | 4 | 9 |
| J-328 | N | CH | singlebond | H | H | Me | 5 | 7 |
| J-329 | N | CH | singlebond | H | H | Me | 5 | 8 |
| J-330 | N | CH | singlebond | H | H | Me | 5 | 9 |

TABLE 39

| Compound No. | G¹ | G² | Q¹ | $R^a$ | $R^b$ | $R^c$ | n | m |
|---|---|---|---|---|---|---|---|---|
| J-331 | N | CH | singlebond | Me | Me | H | 1 | 7 |
| J-332 | N | CH | singlebond | Me | Me | H | 1 | 8 |
| J-333 | N | CH | singlebond | Me | Me | H | 1 | 9 |
| J-334 | N | CH | singlebond | Me | Me | H | 2 | 7 |
| J-335 | N | CH | singlebond | Me | Me | H | 2 | 8 |
| J-336 | N | CH | singlebond | Me | Me | H | 2 | 9 |
| J-337 | N | CH | singlebond | Me | Me | H | 3 | 7 |
| J-338 | N | CH | singlebond | Me | Me | H | 3 | 8 |
| J-339 | N | CH | singlebond | Me | Me | H | 3 | 9 |
| J-340 | N | CH | singlebond | Me | Me | H | 4 | 7 |
| J-341 | N | CH | singlebond | Me | Me | H | 4 | 8 |
| J-342 | N | CH | singlebond | Me | Me | H | 4 | 9 |
| J-343 | N | CH | singlebond | Me | Me | H | 5 | 7 |
| J-344 | N | CH | singlebond | Me | Me | H | 5 | 8 |
| J-345 | N | CH | singlebond | Me | Me | H | 5 | 9 |

TABLE 39-continued

| Compound No. | G¹ | G² | Q¹ | $R^a$ | $R^b$ | $R^c$ | n | m |
|---|---|---|---|---|---|---|---|---|
| J-346 | N | CH | singlebond | H | Me | Me | 1 | 7 |
| J-347 | N | CH | singlebond | H | Me | Me | 1 | 8 |
| J-348 | N | CH | singlebond | H | Me | Me | 1 | 9 |
| J-349 | N | CH | singlebond | H | Me | Me | 2 | 7 |
| J-350 | N | CH | singlebond | H | Me | Me | 2 | 8 |
| J-351 | N | CH | singlebond | H | Me | Me | 2 | 9 |
| J-352 | N | CH | singlebond | H | Me | Me | 3 | 7 |
| J-353 | N | CH | singlebond | H | Me | Me | 3 | 8 |
| J-354 | N | CH | singlebond | H | Me | Me | 3 | 9 |
| J-355 | N | CH | singlebond | H | Me | Me | 4 | 7 |
| J-356 | N | CH | singlebond | H | Me | Me | 4 | 8 |
| J-357 | N | CH | singlebond | H | Me | Me | 4 | 9 |
| J-358 | N | CH | singlebond | H | Me | Me | 5 | 7 |
| J-359 | N | CH | singlebond | H | Me | Me | 5 | 8 |
| J-360 | N | CH | singlebond | H | Me | Me | 5 | 9 |
| J-361 | CH | N | —O— | Me | H | H | 1 | 7 |
| J-362 | CH | N | —O— | Me | H | H | 1 | 8 |
| J-363 | CH | N | —O— | Me | H | H | 1 | 9 |
| J-364 | CH | N | —O— | Me | H | H | 2 | 7 |
| J-365 | CH | N | —O— | Me | H | H | 2 | 8 |
| J-366 | CH | N | —O— | Me | H | H | 2 | 9 |
| J-367 | CH | N | —O— | Me | H | H | 3 | 7 |
| J-368 | CH | N | —O— | Me | H | H | 3 | 8 |
| J-369 | CH | N | —O— | Me | H | H | 3 | 9 |
| J-370 | CH | N | —O— | Me | H | H | 4 | 7 |
| J-371 | CH | N | —O— | Me | H | H | 4 | 8 |
| J-372 | CH | N | —O— | Me | H | H | 4 | 9 |
| J-373 | CH | N | —O— | Me | H | H | 5 | 7 |
| J-374 | CH | N | —O— | Me | H | H | 5 | 8 |
| J-375 | CH | N | —O— | Me | H | H | 5 | 9 |
| J-376 | CH | N | —O— | H | H | Me | 1 | 7 |
| J-377 | CH | N | —O— | H | H | Me | 1 | 8 |
| J-378 | CH | N | —O— | H | H | Me | 1 | 9 |
| J-379 | CH | N | —O— | H | H | Me | 2 | 7 |
| J-380 | CH | N | —O— | H | H | Me | 2 | 8 |
| J-381 | CH | N | —O— | H | H | Me | 2 | 9 |
| J-382 | CH | N | —O— | H | H | Me | 3 | 7 |
| J-383 | CH | N | —O— | H | H | Me | 3 | 8 |
| J-384 | CH | N | —O— | H | H | Me | 3 | 9 |
| J-385 | CH | N | —O— | H | H | Me | 4 | 7 |
| J-386 | CH | N | —O— | H | H | Me | 4 | 8 |
| J-387 | CH | N | —O— | H | H | Me | 4 | 9 |
| J-388 | CH | N | —O— | H | H | Me | 5 | 7 |
| J-389 | CH | N | —O— | H | H | Me | 5 | 8 |
| J-390 | CH | N | —O— | H | H | Me | 5 | 9 |
| J-391 | CH | N | —O— | Me | Me | H | 1 | 7 |
| J-392 | CH | N | —O— | Me | Me | H | 1 | 8 |
| J-393 | CH | N | —O— | Me | Me | H | 1 | 9 |
| J-394 | CH | N | —O— | Me | Me | H | 2 | 7 |
| J-395 | CH | N | —O— | Me | Me | H | 2 | 8 |
| J-396 | CH | N | —O— | Me | Me | H | 2 | 9 |
| J-397 | CH | N | —O— | Me | Me | H | 3 | 7 |
| J-398 | CH | N | —O— | Me | Me | H | 3 | 8 |
| J-399 | CH | N | —O— | Me | Me | H | 3 | 9 |
| J-400 | CH | N | —O— | Me | Me | H | 4 | 7 |
| J-401 | CH | N | —O— | Me | Me | H | 4 | 8 |
| J-402 | CH | N | —O— | Me | Me | H | 4 | 9 |
| J-403 | CH | N | —O— | Me | Me | H | 5 | 7 |
| J-404 | CH | N | —O— | Me | Me | H | 5 | 8 |
| J-405 | CH | N | —O— | Me | Me | H | 5 | 9 |
| J-406 | CH | N | —O— | H | Me | Me | 1 | 7 |
| J-407 | CH | N | —O— | H | Me | Me | 1 | 8 |
| J-408 | CH | N | —O— | H | Me | Me | 1 | 9 |
| J-409 | CH | N | —O— | H | Me | Me | 2 | 7 |
| J-410 | CH | N | —O— | H | Me | Me | 2 | 8 |
| J-411 | CH | N | —O— | H | Me | Me | 2 | 9 |
| J-412 | CH | N | —O— | H | Me | Me | 3 | 7 |
| J-413 | CH | N | —O— | H | Me | Me | 3 | 8 |
| J-414 | CH | N | —O— | H | Me | Me | 3 | 9 |
| J-415 | CH | N | —O— | H | Me | Me | 4 | 7 |
| J-416 | CH | N | —O— | H | Me | Me | 4 | 8 |
| J-417 | CH | N | —O— | H | Me | Me | 4 | 9 |
| J-418 | CH | N | —O— | H | Me | Me | 5 | 7 |
| J-419 | CH | N | —O— | H | Me | Me | 5 | 8 |
| J-420 | CH | N | —O— | H | Me | Me | 5 | 9 |
| J-421 | CH | N | —CH₂O— | Me | H | H | 1 | 7 |
| J-422 | CH | N | —CH₂O— | Me | H | H | 1 | 8 |
| J-423 | CH | N | —CH₂O— | Me | H | H | 1 | 9 |
| J-424 | CH | N | —CH₂O— | Me | H | H | 2 | 7 |
| J-425 | CH | N | —CH₂O— | Me | H | H | 2 | 8 |
| J-426 | CH | N | —CH₂O— | Me | H | H | 2 | 9 |
| J-427 | CH | N | —CH₂O— | Me | H | H | 3 | 7 |
| J-428 | CH | N | —CH₂O— | Me | H | H | 3 | 8 |
| J-429 | CH | N | —CH₂O— | Me | H | H | 3 | 9 |
| J-430 | CH | N | —CH₂O— | Me | H | H | 4 | 7 |
| J-431 | CH | N | —CH₂O— | Me | H | H | 4 | 8 |
| J-432 | CH | N | —CH₂O— | Me | H | H | 4 | 9 |
| J-433 | CH | N | —CH₂O— | Me | H | H | 5 | 7 |
| J-434 | CH | N | —CH₂O— | Me | H | H | 5 | 8 |
| J-435 | CH | N | —CH₂O— | Me | H | H | 5 | 9 |
| J-436 | CH | N | —CH₂O— | H | H | Me | 1 | 7 |
| J-437 | CH | N | —CH₂O— | H | H | Me | 1 | 8 |
| J-438 | CH | N | —CH₂O— | H | H | Me | 1 | 9 |
| J-439 | CH | N | —CH₂O— | H | H | Me | 2 | 7 |
| J-440 | CH | N | —CH₂O— | H | H | Me | 2 | 8 |

TABLE 40

| Compound No. | G¹ | G² | Q¹ | $R^a$ | $R^b$ | $R^c$ | n | m |
|---|---|---|---|---|---|---|---|---|
| J-441 | CH | N | —CH₂O— | H | H | Me | 2 | 9 |
| J-442 | CH | N | —CH₂O— | H | H | Me | 3 | 7 |
| J-443 | CH | N | —CH₂O— | H | H | Me | 3 | 8 |
| J-444 | CH | N | —CH₂O— | H | H | Me | 3 | 9 |
| J-445 | CH | N | —CH₂O— | H | H | Me | 4 | 7 |
| J-446 | CH | N | —CH₂O— | H | H | Me | 4 | 8 |
| J-447 | CH | N | —CH₂O— | H | H | Me | 4 | 9 |
| J-448 | CH | N | —CH₂O— | H | H | Me | 5 | 7 |
| J-449 | CH | N | —CH₂O— | H | H | Me | 5 | 8 |
| J-450 | CH | N | —CH₂O— | H | H | Me | 5 | 9 |
| J-451 | CH | N | —CH₂O— | Me | Me | H | 1 | 7 |
| J-452 | CH | N | —CH₂O— | Me | Me | H | 1 | 8 |
| J-453 | CH | N | —CH₂O— | Me | Me | H | 1 | 9 |
| J-454 | CH | N | —CH₂O— | Me | Me | H | 2 | 7 |
| J-455 | CH | N | —CH₂O— | Me | Me | H | 2 | 8 |
| J-456 | CH | N | —CH₂O— | Me | Me | H | 2 | 9 |
| J-457 | CH | N | —CH₂O— | Me | Me | H | 3 | 7 |
| J-458 | CH | N | —CH₂O— | Me | Me | H | 3 | 8 |
| J-459 | CH | N | —CH₂O— | Me | Me | H | 3 | 9 |
| J-460 | CH | N | —CH₂O— | Me | Me | H | 4 | 7 |
| J-461 | CH | N | —CH₂O— | Me | Me | H | 4 | 8 |
| J-462 | CH | N | —CH₂O— | Me | Me | H | 4 | 9 |
| J-463 | CH | N | —CH₂O— | Me | Me | H | 5 | 7 |
| J-464 | CH | N | —CH₂O— | Me | Me | H | 5 | 8 |
| J-465 | CH | N | —CH₂O— | Me | Me | H | 5 | 9 |
| J-466 | CH | N | —CH₂O— | H | Me | Me | 1 | 7 |
| J-467 | CH | N | —CH₂O— | H | Me | Me | 1 | 8 |
| J-468 | CH | N | —CH₂O— | H | Me | Me | 1 | 9 |
| J-469 | CH | N | —CH₂O— | H | Me | Me | 2 | 7 |
| J-470 | CH | N | —CH₂O— | H | Me | Me | 2 | 8 |
| J-471 | CH | N | —CH₂O— | H | Me | Me | 2 | 9 |
| J-472 | CH | N | —CH₂O— | H | Me | Me | 3 | 7 |
| J-473 | CH | N | —CH₂O— | H | Me | Me | 3 | 8 |
| J-474 | CH | N | —CH₂O— | H | Me | Me | 3 | 9 |
| J-475 | CH | N | —CH₂O— | H | Me | Me | 4 | 7 |
| J-476 | CH | N | —CH₂O— | H | Me | Me | 4 | 8 |
| J-477 | CH | N | —CH₂O— | H | Me | Me | 4 | 9 |
| J-478 | CH | N | —CH₂O— | H | Me | Me | 5 | 7 |
| J-479 | CH | N | —CH₂O— | H | Me | Me | 5 | 8 |
| J-480 | CH | N | —CH₂O— | H | Me | Me | 5 | 9 |
| J-481 | CH | N | singlebond | Me | H | H | 1 | 7 |
| J-482 | CH | N | singlebond | Me | H | H | 1 | 8 |
| J-483 | CH | N | singlebond | Me | H | H | 1 | 9 |
| J-484 | CH | N | singlebond | Me | H | H | 2 | 7 |
| J-485 | CH | N | singlebond | Me | H | H | 2 | 8 |
| J-486 | CH | N | singlebond | Me | H | H | 2 | 9 |
| J-487 | CH | N | singlebond | Me | H | H | 3 | 7 |
| J-488 | CH | N | singlebond | Me | H | H | 3 | 8 |
| J-489 | CH | N | singlebond | Me | H | H | 3 | 9 |
| J-490 | CH | N | singlebond | Me | H | H | 4 | 7 |

TABLE 40-continued

| Compound No. | G¹ | G² | Q¹ | R$^a$ | R$^b$ | R$^c$ | n | m |
|---|---|---|---|---|---|---|---|---|
| J-491 | CH | N | singlebond | Me | H | H | 4 | 8 |
| J-492 | CH | N | singlebond | Me | H | H | 4 | 9 |
| J-493 | CH | N | singlebond | Me | H | H | 5 | 7 |
| J-494 | CH | N | singlebond | Me | H | H | 5 | 8 |
| J-495 | CH | N | singlebond | Me | H | H | 5 | 9 |
| J-496 | CH | N | singlebond | H | H | Me | 1 | 7 |
| J-497 | CH | N | singlebond | H | H | Me | 1 | 8 |
| J-498 | CH | N | singlebond | H | H | Me | 1 | 9 |
| J-499 | CH | N | singlebond | H | H | Me | 2 | 7 |
| J-500 | CH | N | singlebond | H | H | Me | 2 | 8 |
| J-501 | CH | N | singlebond | H | H | Me | 2 | 9 |
| J-502 | CH | N | singlebond | H | H | Me | 3 | 7 |
| J-503 | CH | N | singlebond | H | H | Me | 3 | 8 |
| J-504 | CH | N | singlebond | H | H | Me | 3 | 9 |
| J-505 | CH | N | singlebond | H | H | Me | 4 | 7 |
| J-506 | CH | N | singlebond | H | H | Me | 4 | 8 |
| J-507 | CH | N | singlebond | H | H | Me | 4 | 9 |
| J-508 | CH | N | singlebond | H | H | Me | 5 | 7 |
| J-509 | CH | N | singlebond | H | H | Me | 5 | 8 |
| J-510 | CH | N | singlebond | H | H | Me | 5 | 9 |
| J-511 | CH | N | singlebond | Me | Me | H | 1 | 7 |
| J-512 | CH | N | singlebond | Me | Me | H | 1 | 8 |
| J-513 | CH | N | singlebond | Me | Me | H | 1 | 9 |
| J-514 | CH | N | singlebond | Me | Me | H | 2 | 7 |
| J-515 | CH | N | singlebond | Me | Me | H | 2 | 8 |
| J-516 | CH | N | singlebond | Me | Me | H | 2 | 9 |
| J-517 | CH | N | singlebond | Me | Me | H | 3 | 7 |
| J-518 | CH | N | singlebond | Me | Me | H | 3 | 8 |
| J-519 | CH | N | singlebond | Me | Me | H | 3 | 9 |
| J-520 | CH | N | singlebond | Me | Me | H | 4 | 7 |
| J-521 | CH | N | singlebond | Me | Me | H | 4 | 8 |
| J-522 | CH | N | singlebond | Me | Me | H | 4 | 9 |
| J-523 | CH | N | singlebond | Me | Me | H | 5 | 7 |
| J-524 | CH | N | singlebond | Me | Me | H | 5 | 8 |
| J-525 | CH | N | singlebond | Me | Me | H | 5 | 9 |
| J-526 | CH | N | singlebond | H | Me | Me | 1 | 7 |
| J-527 | CH | N | singlebond | H | Me | Me | 1 | 8 |
| J-528 | CH | N | singlebond | H | Me | Me | 1 | 9 |
| J-529 | CH | N | singlebond | H | Me | Me | 2 | 7 |
| J-530 | CH | N | singlebond | H | Me | Me | 2 | 8 |
| J-531 | CH | N | singlebond | H | Me | Me | 2 | 9 |
| J-532 | CH | N | singlebond | H | Me | Me | 3 | 7 |
| J-533 | CH | N | singlebond | H | Me | Me | 3 | 8 |
| J-534 | CH | N | singlebond | H | Me | Me | 3 | 9 |
| J-535 | CH | N | singlebond | H | Me | Me | 4 | 7 |
| J-536 | CH | N | singlebond | H | Me | Me | 4 | 8 |
| J-537 | CH | N | singlebond | H | Me | Me | 4 | 9 |
| J-538 | CH | N | singlebond | H | Me | Me | 5 | 7 |
| J-539 | CH | N | singlebond | H | Me | Me | 5 | 8 |
| J-540 | CH | N | singlebond | H | Me | Me | 5 | 9 |

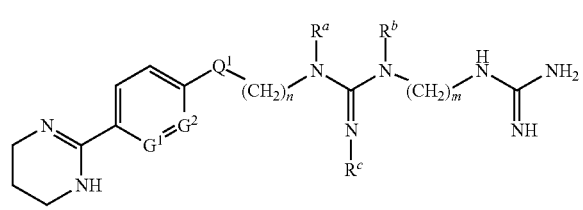

TABLE 41

| Compound No. | G¹ | G² | Q¹ | R$^a$ | R$^b$ | R$^c$ | n | m |
|---|---|---|---|---|---|---|---|---|
| K-1 | CH | CH | —O— | Me | H | H | 1 | 7 |
| K-2 | CH | CH | —O— | Me | H | H | 1 | 8 |
| K-3 | CH | CH | —O— | Me | H | H | 1 | 9 |
| K-4 | CH | CH | —O— | Me | H | H | 2 | 7 |
| K-5 | CH | CH | —O— | Me | H | H | 2 | 8 |
| K-6 | CH | CH | —O— | Me | H | H | 2 | 9 |
| K-7 | CH | CH | —O— | Me | H | H | 3 | 7 |
| K-8 | CH | CH | —O— | Me | H | H | 3 | 8 |
| K-9 | CH | CH | —O— | Me | H | H | 3 | 9 |
| K-10 | CH | CH | —O— | Me | H | H | 4 | 7 |
| K-11 | CH | CH | —O— | Me | H | H | 4 | 8 |
| K-12 | CH | CH | —O— | Me | H | H | 4 | 9 |
| K-13 | CH | CH | —O— | Me | H | H | 5 | 7 |
| K-14 | CH | CH | —O— | Me | H | H | 5 | 8 |
| K-15 | CH | CH | —O— | Me | H | H | 5 | 9 |
| K-16 | CH | CH | —O— | H | H | Me | 1 | 7 |
| K-17 | CH | CH | —O— | H | H | Me | 1 | 8 |
| K-18 | CH | CH | —O— | H | H | Me | 1 | 9 |
| K-19 | CH | CH | —O— | H | H | Me | 2 | 7 |
| K-20 | CH | CH | —O— | H | H | Me | 2 | 8 |
| K-21 | CH | CH | —O— | H | H | Me | 2 | 9 |
| K-22 | CH | CH | —O— | H | H | Me | 3 | 7 |
| K-23 | CH | CH | —O— | H | H | Me | 3 | 8 |
| K-24 | CH | CH | —O— | H | H | Me | 3 | 9 |
| K-25 | CH | CH | —O— | H | H | Me | 4 | 7 |
| K-26 | CH | CH | —O— | H | H | Me | 4 | 8 |
| K-27 | CH | CH | —O— | H | H | Me | 4 | 9 |
| K-28 | CH | CH | —O— | H | H | Me | 5 | 7 |
| K-29 | CH | CH | —O— | H | H | Me | 5 | 8 |
| K-30 | CH | CH | —O— | H | H | Me | 5 | 9 |
| K-31 | CH | CH | —O— | Me | Me | H | 1 | 7 |
| K-32 | CH | CH | —O— | Me | Me | H | 1 | 8 |
| K-33 | CH | CH | —O— | Me | Me | H | 1 | 9 |
| K-34 | CH | CH | —O— | Me | Me | H | 2 | 7 |
| K-35 | CH | CH | —O— | Me | Me | H | 2 | 8 |
| K-36 | CH | CH | —O— | Me | Me | H | 2 | 9 |
| K-37 | CH | CH | —O— | Me | Me | H | 3 | 7 |
| K-38 | CH | CH | —O— | Me | Me | H | 3 | 8 |
| K-39 | CH | CH | —O— | Me | Me | H | 3 | 9 |
| K-40 | CH | CH | —O— | Me | Me | H | 4 | 7 |
| K-41 | CH | CH | —O— | Me | Me | H | 4 | 8 |
| K-42 | CH | CH | —O— | Me | Me | H | 4 | 9 |
| K-43 | CH | CH | —O— | Me | Me | H | 5 | 7 |
| K-44 | CH | CH | —O— | Me | Me | H | 5 | 8 |
| K-45 | CH | CH | —O— | Me | Me | H | 5 | 9 |
| K-46 | CH | CH | —O— | H | Me | Me | 1 | 7 |
| K-47 | CH | CH | —O— | H | Me | Me | 1 | 8 |
| K-48 | CH | CH | —O— | H | Me | Me | 1 | 9 |
| K-49 | CH | CH | —O— | H | Me | Me | 2 | 7 |
| K-50 | CH | CH | —O— | H | Me | Me | 2 | 8 |
| K-51 | CH | CH | —O— | H | Me | Me | 2 | 9 |
| K-52 | CH | CH | —O— | H | Me | Me | 3 | 7 |
| K-53 | CH | CH | —O— | H | Me | Me | 3 | 8 |
| K-54 | CH | CH | —O— | H | Me | Me | 3 | 9 |
| K-55 | CH | CH | —O— | H | Me | Me | 4 | 7 |
| K-56 | CH | CH | —O— | H | Me | Me | 4 | 8 |
| K-57 | CH | CH | —O— | H | Me | Me | 4 | 9 |
| K-58 | CH | CH | —O— | H | Me | Me | 5 | 7 |
| K-59 | CH | CH | —O— | H | Me | Me | 5 | 8 |
| K-60 | CH | CH | —O— | H | Me | Me | 5 | 9 |
| K-61 | CH | CH | —CH$_2$O— | Me | H | H | 1 | 7 |
| K-62 | CH | CH | —CH$_2$O— | Me | H | H | 1 | 8 |
| K-63 | CH | CH | —CH$_2$O— | Me | H | H | 1 | 9 |
| K-64 | CH | CH | —CH$_2$O— | Me | H | H | 2 | 7 |
| K-65 | CH | CH | —CH$_2$O— | Me | H | H | 2 | 8 |
| K-66 | CH | CH | —CH$_2$O— | Me | H | H | 2 | 9 |
| K-67 | CH | CH | —CH$_2$O— | Me | H | H | 3 | 7 |
| K-68 | CH | CH | —CH$_2$O— | Me | H | H | 3 | 8 |
| K-69 | CH | CH | —CH$_2$O— | Me | H | H | 3 | 9 |
| K-70 | CH | CH | —CH$_2$O— | Me | H | H | 4 | 7 |
| K-71 | CH | CH | —CH$_2$O— | Me | H | H | 4 | 8 |
| K-72 | CH | CH | —CH$_2$O— | Me | H | H | 4 | 9 |
| K-73 | CH | CH | —CH$_2$O— | Me | H | H | 5 | 7 |
| K-74 | CH | CH | —CH$_2$O— | Me | H | H | 5 | 8 |
| K-75 | CH | CH | —CH$_2$O— | Me | H | H | 5 | 9 |
| K-76 | CH | CH | —CH$_2$O— | H | H | Me | 1 | 7 |
| K-77 | CH | CH | —CH$_2$O— | H | H | Me | 1 | 8 |
| K-78 | CH | CH | —CH$_2$O— | H | H | Me | 1 | 9 |
| K-79 | CH | CH | —CH$_2$O— | H | H | Me | 2 | 7 |
| K-80 | CH | CH | —CH$_2$O— | H | H | Me | 2 | 8 |
| K-81 | CH | CH | —CH$_2$O— | H | H | Me | 2 | 9 |
| K-82 | CH | CH | —CH$_2$O— | H | H | Me | 3 | 7 |

TABLE 41-continued

| Compound No. | G¹ | G² | Q¹ | $R^a$ | $R^b$ | $R^c$ | n | m |
|---|---|---|---|---|---|---|---|---|
| K-83 | CH | CH | —CH₂O— | H | H | Me | 3 | 8 |
| K-84 | CH | CH | —CH₂O— | H | H | Me | 3 | 9 |
| K-85 | CH | CH | —CH₂O— | H | H | Me | 4 | 7 |
| K-86 | CH | CH | —CH₂O— | H | H | Me | 4 | 8 |
| K-87 | CH | CH | —CH₂O— | H | H | Me | 4 | 9 |
| K-88 | CH | CH | —CH₂O— | H | H | Me | 5 | 7 |
| K-89 | CH | CH | —CH₂O— | H | H | Me | 5 | 8 |
| K-90 | CH | CH | —CH₂O— | H | H | Me | 5 | 9 |
| K-91 | CH | CH | —CH₂O— | Me | Me | H | 1 | 7 |
| K-92 | CH | CH | —CH₂O— | Me | Me | H | 1 | 8 |
| K-93 | CH | CH | —CH₂O— | Me | Me | H | 1 | 9 |
| K-94 | CH | CH | —CH₂O— | Me | Me | H | 2 | 7 |
| K-95 | CH | CH | —CH₂O— | Me | Me | H | 2 | 8 |
| K-96 | CH | CH | —CH₂O— | Me | Me | H | 2 | 9 |
| K-97 | CH | CH | —CH₂O— | Me | Me | H | 3 | 7 |
| K-98 | CH | CH | —CH₂O— | Me | Me | H | 3 | 8 |
| K-99 | CH | CH | —CH₂O— | Me | Me | H | 3 | 9 |
| K-100 | CH | CH | —CH₂O— | Me | Me | H | 4 | 7 |
| K-101 | CH | CH | —CH₂O— | Me | Me | H | 4 | 8 |
| K-102 | CH | CH | —CH₂O— | Me | Me | H | 4 | 9 |
| K-103 | CH | CH | —CH₂O— | Me | Me | H | 5 | 7 |
| K-104 | CH | CH | —CH₂O— | Me | Me | H | 5 | 8 |
| K-105 | CH | CH | —CH₂O— | Me | Me | H | 5 | 9 |
| K-106 | CH | CH | —CH₂O— | H | Me | Me | 1 | 7 |
| K-107 | CH | CH | —CH₂O— | H | Me | Me | 1 | 8 |
| K-108 | CH | CH | —CH₂O— | H | Me | Me | 1 | 9 |
| K-109 | CH | CH | —CH₂O— | H | Me | Me | 2 | 7 |
| K-110 | CH | CH | —CH₂O— | H | Me | Me | 2 | 8 |

TABLE 42

| Compound No. | G¹ | G² | Q¹ | $R^a$ | $R^b$ | $R^c$ | n | m |
|---|---|---|---|---|---|---|---|---|
| K-111 | CH | CH | —CH₂O— | H | Me | Me | 2 | 9 |
| K-112 | CH | CH | —CH₂O— | H | Me | Me | 3 | 7 |
| K-113 | CH | CH | —CH₂O— | H | Me | Me | 3 | 8 |
| K-114 | CH | CH | —CH₂O— | H | Me | Me | 3 | 9 |
| K-115 | CH | CH | —CH₂O— | H | Me | Me | 4 | 7 |
| K-116 | CH | CH | —CH₂O— | H | Me | Me | 4 | 8 |
| K-117 | CH | CH | —CH₂O— | H | Me | Me | 4 | 9 |
| K-118 | CH | CH | —CH₂O— | H | Me | Me | 5 | 7 |
| K-119 | CH | CH | —CH₂O— | H | Me | Me | 5 | 8 |
| K-120 | CH | CH | —CH₂O— | H | Me | Me | 5 | 9 |
| K-121 | CH | CH | singlebond | Me | H | H | 1 | 7 |
| K-122 | CH | CH | singlebond | Me | H | H | 1 | 8 |
| K-123 | CH | CH | singlebond | Me | H | H | 1 | 9 |
| K-124 | CH | CH | singlebond | Me | H | H | 2 | 7 |
| K-125 | CH | CH | singlebond | Me | H | H | 2 | 8 |
| K-126 | CH | CH | singlebond | Me | H | H | 2 | 9 |
| K-127 | CH | CH | singlebond | Me | H | H | 3 | 7 |
| K-128 | CH | CH | singlebond | Me | H | H | 3 | 8 |
| K-129 | CH | CH | singlebond | Me | H | H | 3 | 9 |
| K-130 | CH | CH | singlebond | Me | H | H | 4 | 7 |
| K-131 | CH | CH | singlebond | Me | H | H | 4 | 8 |
| K-132 | CH | CH | singlebond | Me | H | H | 4 | 9 |
| K-133 | CH | CH | singlebond | Me | H | H | 5 | 7 |
| K-134 | CH | CH | singlebond | Me | H | H | 5 | 8 |
| K-135 | CH | CH | singlebond | Me | H | H | 5 | 9 |
| K-136 | CH | CH | singlebond | H | H | Me | 1 | 7 |
| K-137 | CH | CH | singlebond | H | H | Me | 1 | 8 |
| K-138 | CH | CH | singlebond | H | H | Me | 1 | 9 |
| K-139 | CH | CH | singlebond | H | H | Me | 2 | 7 |
| K-140 | CH | CH | singlebond | H | H | Me | 2 | 8 |
| K-141 | CH | CH | singlebond | H | H | Me | 2 | 9 |
| K-142 | CH | CH | singlebond | H | H | Me | 3 | 7 |
| K-143 | CH | CH | singlebond | H | H | Me | 3 | 8 |
| K-144 | CH | CH | singlebond | H | H | Me | 3 | 9 |
| K-145 | CH | CH | singlebond | H | H | Me | 4 | 7 |
| K-146 | CH | CH | singlebond | H | H | Me | 4 | 8 |
| K-147 | CH | CH | singlebond | H | H | Me | 4 | 9 |
| K-148 | CH | CH | singlebond | H | H | Me | 5 | 7 |
| K-149 | CH | CH | singlebond | H | H | Me | 5 | 8 |
| K-150 | CH | CH | singlebond | H | H | Me | 5 | 9 |

TABLE 42-continued

| Compound No. | G¹ | G² | Q¹ | $R^a$ | $R^b$ | $R^c$ | n | m |
|---|---|---|---|---|---|---|---|---|
| K-151 | CH | CH | singlebond | Me | Me | H | 1 | 7 |
| K-152 | CH | CH | singlebond | Me | Me | H | 1 | 8 |
| K-153 | CH | CH | singlebond | Me | Me | H | 1 | 9 |
| K-154 | CH | CH | singlebond | Me | Me | H | 2 | 7 |
| K-155 | CH | CH | singlebond | Me | Me | H | 2 | 8 |
| K-156 | CH | CH | singlebond | Me | Me | H | 2 | 9 |
| K-157 | CH | CH | singlebond | Me | Me | H | 3 | 7 |
| K-158 | CH | CH | singlebond | Me | Me | H | 3 | 8 |
| K-159 | CH | CH | singlebond | Me | Me | H | 3 | 9 |
| K-160 | CH | CH | singlebond | Me | Me | H | 4 | 7 |
| K-161 | CH | CH | singlebond | Me | Me | H | 4 | 8 |
| K-162 | CH | CH | singlebond | Me | Me | H | 4 | 9 |
| K-163 | CH | CH | singlebond | Me | Me | H | 5 | 7 |
| K-164 | CH | CH | singlebond | Me | Me | H | 5 | 8 |
| K-165 | CH | CH | singlebond | Me | Me | H | 5 | 9 |
| K-166 | CH | CH | singlebond | H | Me | Me | 1 | 7 |
| K-167 | CH | CH | singlebond | H | Me | Me | 1 | 8 |
| K-168 | CH | CH | singlebond | H | Me | Me | 1 | 9 |
| K-169 | CH | CH | singlebond | H | Me | Me | 2 | 7 |
| K-170 | CH | CH | singlebond | H | Me | Me | 2 | 8 |
| K-171 | CH | CH | singlebond | H | Me | Me | 2 | 9 |
| K-172 | CH | CH | singlebond | H | Me | Me | 3 | 7 |
| K-173 | CH | CH | singlebond | H | Me | Me | 3 | 8 |
| K-174 | CH | CH | singlebond | H | Me | Me | 3 | 9 |
| K-175 | CH | CH | singlebond | H | Me | Me | 4 | 7 |
| K-176 | CH | CH | singlebond | H | Me | Me | 4 | 8 |
| K-177 | CH | CH | singlebond | H | Me | Me | 4 | 9 |
| K-178 | CH | CH | singlebond | H | Me | Me | 5 | 7 |
| K-179 | CH | CH | singlebond | H | Me | Me | 5 | 8 |
| K-180 | CH | CH | singlebond | H | Me | Me | 5 | 9 |
| K-181 | N | CH | —O— | Me | H | H | 1 | 7 |
| K-182 | N | CH | —O— | Me | H | H | 1 | 8 |
| K-183 | N | CH | —O— | Me | H | H | 1 | 9 |
| K-184 | N | CH | —O— | Me | H | H | 2 | 7 |
| K-185 | N | CH | —O— | Me | H | H | 2 | 8 |
| K-186 | N | CH | —O— | Me | H | H | 2 | 9 |
| K-187 | N | CH | —O— | Me | H | H | 3 | 7 |
| K-188 | N | CH | —O— | Me | H | H | 3 | 8 |
| K-189 | N | CH | —O— | Me | H | H | 3 | 9 |
| K-190 | N | CH | —O— | Me | H | H | 4 | 7 |
| K-191 | N | CH | —O— | Me | H | H | 4 | 8 |
| K-192 | N | CH | —O— | Me | H | H | 4 | 9 |
| K-193 | N | CH | —O— | Me | H | H | 5 | 7 |
| K-194 | N | CH | —O— | Me | H | H | 5 | 8 |
| K-195 | N | CH | —O— | Me | H | H | 5 | 9 |
| K-196 | N | CH | —O— | H | H | Me | 1 | 7 |
| K-197 | N | CH | —O— | H | H | Me | 1 | 8 |
| K-198 | N | CH | —O— | H | H | Me | 1 | 9 |
| K-199 | N | CH | —O— | H | H | Me | 2 | 7 |
| K-200 | N | CH | —O— | H | H | Me | 2 | 8 |
| K-201 | N | CH | —O— | H | H | Me | 2 | 9 |
| K-202 | N | CH | —O— | H | H | Me | 3 | 7 |
| K-203 | N | CH | —O— | H | H | Me | 3 | 8 |
| K-204 | N | CH | —O— | H | H | Me | 3 | 9 |
| K-205 | N | CH | —O— | H | H | Me | 4 | 7 |
| K-206 | N | CH | —O— | H | H | Me | 4 | 8 |
| K-207 | N | CH | —O— | H | H | Me | 4 | 9 |
| K-208 | N | CH | —O— | H | H | Me | 5 | 7 |
| K-209 | N | CH | —O— | H | H | Me | 5 | 8 |
| K-210 | N | CH | —O— | H | H | Me | 5 | 9 |
| K-211 | N | CH | —O— | Me | Me | H | 1 | 7 |
| K-212 | N | CH | —O— | Me | Me | H | 1 | 8 |
| K-213 | N | CH | —O— | Me | Me | H | 1 | 9 |
| K-214 | N | CH | —O— | Me | Me | H | 2 | 7 |
| K-215 | N | CH | —O— | Me | Me | H | 2 | 8 |
| K-216 | N | CH | —O— | Me | Me | H | 2 | 9 |
| K-217 | N | CH | —O— | Me | Me | H | 3 | 7 |
| K-218 | N | CH | —O— | Me | Me | H | 3 | 8 |
| K-219 | N | CH | —O— | Me | Me | H | 3 | 9 |
| K-220 | N | CH | —O— | Me | Me | H | 4 | 7 |

TABLE 43

| Compound No. | $G^1$ | $G^2$ | $Q^1$ | $R^a$ | $R^b$ | $R^c$ | n | m |
|---|---|---|---|---|---|---|---|---|
| K-221 | N | CH | —O— | Me | Me | H | 4 | 8 |
| K-222 | N | CH | —O— | Me | Me | H | 4 | 9 |
| K-223 | N | CH | —O— | Me | Me | H | 5 | 7 |
| K-224 | N | CH | —O— | Me | Me | H | 5 | 8 |
| K-225 | N | CH | —O— | Me | Me | H | 5 | 9 |
| K-226 | N | CH | —O— | H | Me | Me | 1 | 7 |
| K-227 | N | CH | —O— | H | Me | Me | 1 | 8 |
| K-228 | N | CH | —O— | H | Me | Me | 1 | 9 |
| K-229 | N | CH | —O— | H | Me | Me | 2 | 7 |
| K-230 | N | CH | —O— | H | Me | Me | 2 | 8 |
| K-231 | N | CH | —O— | H | Me | Me | 2 | 9 |
| K-232 | N | CH | —O— | H | Me | Me | 3 | 7 |
| K-233 | N | CH | —O— | H | Me | Me | 3 | 8 |
| K-234 | N | CH | —O— | H | Me | Me | 3 | 9 |
| K-235 | N | CH | —O— | H | Me | Me | 4 | 7 |
| K-236 | N | CH | —O— | H | Me | Me | 4 | 8 |
| K-237 | N | CH | —O— | H | Me | Me | 4 | 9 |
| K-238 | N | CH | —O— | H | Me | Me | 5 | 7 |
| K-239 | N | CH | —O— | H | Me | Me | 5 | 8 |
| K-240 | N | CH | —O— | H | Me | Me | 5 | 9 |
| K-241 | N | CH | —CH$_2$O— | Me | H | H | 1 | 7 |
| K-242 | N | CH | —CH$_2$O— | Me | H | H | 1 | 8 |
| K-243 | N | CH | —CH$_2$O— | Me | H | H | 1 | 9 |
| K-244 | N | CH | —CH$_2$O— | Me | H | H | 2 | 7 |
| K-245 | N | CH | —CH$_2$O— | Me | H | H | 2 | 8 |
| K-246 | N | CH | —CH$_2$O— | Me | H | H | 2 | 9 |
| K-247 | N | CH | —CH$_2$O— | Me | H | H | 3 | 7 |
| K-248 | N | CH | —CH$_2$O— | Me | H | H | 3 | 8 |
| K-249 | N | CH | —CH$_2$O— | Me | H | H | 3 | 9 |
| K-250 | N | CH | —CH$_2$O— | Me | H | H | 4 | 7 |
| K-251 | N | CH | —CH$_2$O— | Me | H | H | 4 | 8 |
| K-252 | N | CH | —CH$_2$O— | Me | H | H | 4 | 9 |
| K-253 | N | CH | —CH$_2$O— | Me | H | H | 5 | 7 |
| K-254 | N | CH | —CH$_2$O— | Me | H | H | 5 | 8 |
| K-255 | N | CH | —CH$_2$O— | Me | H | H | 5 | 9 |
| K-256 | N | CH | —CH$_2$O— | H | H | Me | 1 | 7 |
| K-257 | N | CH | —CH$_2$O— | H | H | Me | 1 | 8 |
| K-258 | N | CH | —CH$_2$O— | H | H | Me | 1 | 9 |
| K-259 | N | CH | —CH$_2$O— | H | H | Me | 2 | 7 |
| K-260 | N | CH | —CH$_2$O— | H | H | Me | 2 | 8 |
| K-261 | N | CH | —CH$_2$O— | H | H | Me | 2 | 9 |
| K-262 | N | CH | —CH$_2$O— | H | H | Me | 3 | 7 |
| K-263 | N | CH | —CH$_2$O— | H | H | Me | 3 | 8 |
| K-264 | N | CH | —CH$_2$O— | H | H | Me | 3 | 9 |
| K-265 | N | CH | —CH$_2$O— | H | H | Me | 4 | 7 |
| K-266 | N | CH | —CH$_2$O— | H | H | Me | 4 | 8 |
| K-267 | N | CH | —CH$_2$O— | H | H | Me | 4 | 9 |
| K-268 | N | CH | —CH$_2$O— | H | H | Me | 5 | 7 |
| K-269 | N | CH | —CH$_2$O— | H | H | Me | 5 | 8 |
| K-270 | N | CH | —CH$_2$O— | H | H | Me | 5 | 9 |
| K-271 | N | CH | —CH$_2$O— | Me | Me | H | 1 | 7 |
| K-272 | N | CH | —CH$_2$O— | Me | Me | H | 1 | 8 |
| K-273 | N | CH | —CH$_2$O— | Me | Me | H | 1 | 9 |
| K-274 | N | CH | —CH$_2$O— | Me | Me | H | 2 | 7 |
| K-275 | N | CH | —CH$_2$O— | Me | Me | H | 2 | 8 |
| K-276 | N | CH | —CH$_2$O— | Me | Me | H | 2 | 9 |
| K-277 | N | CH | —CH$_2$O— | Me | Me | H | 3 | 7 |
| K-278 | N | CH | —CH$_2$O— | Me | Me | H | 3 | 8 |
| K-279 | N | CH | —CH$_2$O— | Me | Me | H | 3 | 9 |
| K-280 | N | CH | —CH$_2$O— | Me | Me | H | 4 | 7 |
| K-281 | N | CH | —CH$_2$O— | Me | Me | H | 4 | 8 |
| K-282 | N | CH | —CH$_2$O— | Me | Me | H | 4 | 9 |
| K-283 | N | CH | —CH$_2$O— | Me | Me | H | 5 | 7 |
| K-284 | N | CH | —CH$_2$O— | Me | Me | H | 5 | 8 |
| K-285 | N | CH | —CH$_2$O— | Me | Me | H | 5 | 9 |
| K-286 | N | CH | —CH$_2$O— | H | Me | Me | 1 | 7 |
| K-287 | N | CH | —CH$_2$O— | H | Me | Me | 1 | 8 |
| K-288 | N | CH | —CH$_2$O— | H | Me | Me | 1 | 9 |
| K-289 | N | CH | —CH$_2$O— | H | Me | Me | 2 | 7 |
| K-290 | N | CH | —CH$_2$O— | H | Me | Me | 2 | 8 |
| K-291 | N | CH | —CH$_2$O— | H | Me | Me | 2 | 9 |
| K-292 | N | CH | —CH$_2$O— | H | Me | Me | 3 | 7 |
| K-293 | N | CH | —CH$_2$O— | H | Me | Me | 3 | 8 |
| K-294 | N | CH | —CH$_2$O— | H | Me | Me | 3 | 9 |
| K-295 | N | CH | —CH$_2$O— | H | Me | Me | 4 | 7 |
| K-296 | N | CH | —CH$_2$O— | H | Me | Me | 4 | 8 |
| K-297 | N | CH | —CH$_2$O— | H | Me | Me | 4 | 9 |
| K-298 | N | CH | —CH$_2$O— | H | Me | Me | 5 | 7 |
| K-299 | N | CH | —CH$_2$O— | H | Me | Me | 5 | 8 |
| K-300 | N | CH | —CH$_2$O— | H | Me | Me | 5 | 9 |
| K-301 | N | CH | singlebond | Me | H | H | 1 | 7 |
| K-302 | N | CH | singlebond | Me | H | H | 1 | 8 |
| K-303 | N | CH | singlebond | Me | H | H | 1 | 9 |
| K-304 | N | CH | singlebond | Me | H | H | 2 | 7 |
| K-305 | N | CH | singlebond | Me | H | H | 2 | 8 |
| K-306 | N | CH | singlebond | Me | H | H | 2 | 9 |
| K-307 | N | CH | singlebond | Me | H | H | 3 | 7 |
| K-308 | N | CH | singlebond | Me | H | H | 3 | 8 |
| K-309 | N | CH | singlebond | Me | H | H | 3 | 9 |
| K-310 | N | CH | singlebond | Me | H | H | 4 | 7 |
| K-311 | N | CH | singlebond | Me | H | H | 4 | 8 |
| K-312 | N | CH | singlebond | Me | H | H | 4 | 9 |
| K-313 | N | CH | singlebond | Me | H | H | 5 | 7 |
| K-314 | N | CH | singlebond | Me | H | H | 5 | 8 |
| K-315 | N | CH | singlebond | Me | H | H | 5 | 9 |
| K-316 | N | CH | singlebond | H | H | Me | 1 | 7 |
| K-317 | N | CH | singlebond | H | H | Me | 1 | 8 |
| K-318 | N | CH | singlebond | H | H | Me | 1 | 9 |
| K-319 | N | CH | singlebond | H | H | Me | 2 | 7 |
| K-320 | N | CH | singlebond | H | H | Me | 2 | 8 |
| K-321 | N | CH | singlebond | H | H | Me | 2 | 9 |
| K-322 | N | CH | singlebond | H | H | Me | 3 | 7 |
| K-323 | N | CH | singlebond | H | H | Me | 3 | 8 |
| K-324 | N | CH | singlebond | H | H | Me | 3 | 9 |
| K-325 | N | CH | singlebond | H | H | Me | 4 | 7 |
| K-326 | N | CH | singlebond | H | H | Me | 4 | 8 |
| K-327 | N | CH | singlebond | H | H | Me | 4 | 9 |
| K-328 | N | CH | singlebond | H | H | Me | 5 | 7 |
| K-329 | N | CH | singlebond | H | H | Me | 5 | 8 |
| K-330 | N | CH | singlebond | H | H | Me | 5 | 9 |

TABLE 44

| Compound No. | $G^1$ | $G^2$ | $Q^1$ | $R^a$ | $R^b$ | $R^c$ | n | m |
|---|---|---|---|---|---|---|---|---|
| K-331 | N | CH | singlebond | Me | Me | H | 1 | 7 |
| K-332 | N | CH | singlebond | Me | Me | H | 1 | 8 |
| K-333 | N | CH | singlebond | Me | Me | H | 1 | 9 |
| K-334 | N | CH | singlebond | Me | Me | H | 2 | 7 |
| K-335 | N | CH | singlebond | Me | Me | H | 2 | 8 |
| K-336 | N | CH | singlebond | Me | Me | H | 2 | 9 |
| K-337 | N | CH | singlebond | Me | Me | H | 3 | 7 |
| K-338 | N | CH | singlebond | Me | Me | H | 3 | 8 |
| K-339 | N | CH | singlebond | Me | Me | H | 3 | 9 |
| K-340 | N | CH | singlebond | Me | Me | H | 4 | 7 |
| K-341 | N | CH | singlebond | Me | Me | H | 4 | 8 |
| K-342 | N | CH | singlebond | Me | Me | H | 4 | 9 |
| K-343 | N | CH | singlebond | Me | Me | H | 5 | 7 |
| K-344 | N | CH | singlebond | Me | Me | H | 5 | 8 |
| K-345 | N | CH | singlebond | Me | Me | H | 5 | 9 |
| K-346 | N | CH | singlebond | H | Me | Me | 1 | 7 |
| K-347 | N | CH | singlebond | H | Me | Me | 1 | 8 |
| K-348 | N | CH | singlebond | H | Me | Me | 1 | 9 |
| K-349 | N | CH | singlebond | H | Me | Me | 2 | 7 |
| K-350 | N | CH | singlebond | H | Me | Me | 2 | 8 |
| K-351 | N | CH | singlebond | H | Me | Me | 2 | 9 |
| K-352 | N | CH | singlebond | H | Me | Me | 3 | 7 |
| K-353 | N | CH | singlebond | H | Me | Me | 3 | 8 |
| K-354 | N | CH | singlebond | H | Me | Me | 3 | 9 |
| K-355 | N | CH | singlebond | H | Me | Me | 4 | 7 |
| K-356 | N | CH | singlebond | H | Me | Me | 4 | 8 |
| K-357 | N | CH | singlebond | H | Me | Me | 4 | 9 |
| K-358 | N | CH | singlebond | H | Me | Me | 5 | 7 |
| K-359 | N | CH | singlebond | H | Me | Me | 5 | 8 |
| K-360 | N | CH | singlebond | H | Me | Me | 5 | 9 |
| K-361 | CH | N | —O— | Me | H | H | 1 | 7 |
| K-362 | CH | N | —O— | Me | H | H | 1 | 8 |
| K-363 | CH | N | —O— | Me | H | H | 1 | 9 |
| K-364 | CH | N | —O— | Me | H | H | 2 | 7 |
| K-365 | CH | N | —O— | Me | H | H | 2 | 8 |

TABLE 44-continued

| Compound No. | G¹ | G² | Q¹ | $R^a$ | $R^b$ | $R^c$ | n | m |
|---|---|---|---|---|---|---|---|---|
| K-366 | CH | N | —O— | Me | H | H | 2 | 9 |
| K-367 | CH | N | —O— | Me | H | H | 3 | 7 |
| K-368 | CH | N | —O— | Me | H | H | 3 | 8 |
| K-369 | CH | N | —O— | Me | H | H | 3 | 9 |
| K-370 | CH | N | —O— | Me | H | H | 4 | 7 |
| K-371 | CH | N | —O— | Me | H | H | 4 | 8 |
| K-372 | CH | N | —O— | Me | H | H | 4 | 9 |
| K-373 | CH | N | —O— | Me | H | H | 5 | 7 |
| K-374 | CH | N | —O— | Me | H | H | 5 | 8 |
| K-375 | CH | N | —O— | Me | H | H | 5 | 9 |
| K-376 | CH | N | —O— | H | H | Me | 1 | 7 |
| K-377 | CH | N | —O— | H | H | Me | 1 | 8 |
| K-378 | CH | N | —O— | H | H | Me | 1 | 9 |
| K-379 | CH | N | —O— | H | H | Me | 2 | 7 |
| K-380 | CH | N | —O— | H | H | Me | 2 | 8 |
| K-381 | CH | N | —O— | H | H | Me | 2 | 9 |
| K-382 | CH | N | —O— | H | H | Me | 3 | 7 |
| K-383 | CH | N | —O— | H | H | Me | 3 | 8 |
| K-384 | CH | N | —O— | H | H | Me | 3 | 9 |
| K-385 | CH | N | —O— | H | H | Me | 4 | 7 |
| K-386 | CH | N | —O— | H | H | Me | 4 | 8 |
| K-387 | CH | N | —O— | H | H | Me | 4 | 9 |
| K-388 | CH | N | —O— | H | H | Me | 5 | 7 |
| K-389 | CH | N | —O— | H | H | Me | 5 | 8 |
| K-390 | CH | N | —O— | H | H | Me | 5 | 9 |
| K-391 | CH | N | —O— | Me | Me | H | 1 | 7 |
| K-392 | CH | N | —O— | Me | Me | H | 1 | 8 |
| K-393 | CH | N | —O— | Me | Me | H | 1 | 9 |
| K-394 | CH | N | —O— | Me | Me | H | 2 | 7 |
| K-395 | CH | N | —O— | Me | Me | H | 2 | 8 |
| K-396 | CH | N | —O— | Me | Me | H | 2 | 9 |
| K-397 | CH | N | —O— | Me | Me | H | 3 | 7 |
| K-398 | CH | N | —O— | Me | Me | H | 3 | 8 |
| K-399 | CH | N | —O— | Me | Me | H | 3 | 9 |
| K-400 | CH | N | —O— | Me | Me | H | 4 | 7 |
| K-401 | CH | N | —O— | Me | Me | H | 4 | 8 |
| K-402 | CH | N | —O— | Me | Me | H | 4 | 9 |
| K-403 | CH | N | —O— | Me | Me | H | 5 | 7 |
| K-404 | CH | N | —O— | Me | Me | H | 5 | 8 |
| K-405 | CH | N | —O— | Me | Me | H | 5 | 9 |
| K-406 | CH | N | —O— | H | Me | Me | 1 | 7 |
| K-407 | CH | N | —O— | H | Me | Me | 1 | 8 |
| K-408 | CH | N | —O— | H | Me | Me | 1 | 9 |
| K-409 | CH | N | —O— | H | Me | Me | 2 | 7 |
| K-410 | CH | N | —O— | H | Me | Me | 2 | 8 |
| K-411 | CH | N | —O— | H | Me | Me | 2 | 9 |
| K-412 | CH | N | —O— | H | Me | Me | 3 | 7 |
| K-413 | CH | N | —O— | H | Me | Me | 3 | 8 |
| K-414 | CH | N | —O— | H | Me | Me | 3 | 9 |
| K-415 | CH | N | —O— | H | Me | Me | 4 | 7 |
| K-416 | CH | N | —O— | H | Me | Me | 4 | 8 |
| K-417 | CH | N | —O— | H | Me | Me | 4 | 9 |
| K-418 | CH | N | —O— | H | Me | Me | 5 | 7 |
| K-419 | CH | N | —O— | H | Me | Me | 5 | 8 |
| K-420 | CH | N | —O— | H | Me | Me | 5 | 9 |
| K-421 | CH | N | —CH₂O— | Me | H | H | 1 | 7 |
| K-422 | CH | N | —CH₂O— | Me | H | H | 1 | 8 |
| K-423 | CH | N | —CH₂O— | Me | H | H | 1 | 9 |
| K-424 | CH | N | —CH₂O— | Me | H | H | 2 | 7 |
| K-425 | CH | N | —CH₂O— | Me | H | H | 2 | 8 |
| K-426 | CH | N | —CH₂O— | Me | H | H | 2 | 9 |
| K-427 | CH | N | —CH₂O— | Me | H | H | 3 | 7 |
| K-428 | CH | N | —CH₂O— | Me | H | H | 3 | 8 |
| K-429 | CH | N | —CH₂O— | Me | H | H | 3 | 9 |
| K-430 | CH | N | —CH₂O— | Me | H | H | 4 | 7 |
| K-431 | CH | N | —CH₂O— | Me | H | H | 4 | 8 |
| K-432 | CH | N | —CH₂O— | Me | H | H | 4 | 9 |
| K-433 | CH | N | —CH₂O— | Me | H | H | 5 | 7 |
| K-434 | CH | N | —CH₂O— | Me | H | H | 5 | 8 |
| K-435 | CH | N | —CH₂O— | Me | H | H | 5 | 9 |
| K-436 | CH | N | —CH₂O— | H | H | Me | 1 | 7 |
| K-437 | CH | N | —CH₂O— | H | H | Me | 1 | 8 |
| K-438 | CH | N | —CH₂O— | H | H | Me | 1 | 9 |
| K-439 | CH | N | —CH₂O— | H | H | Me | 2 | 7 |
| K-440 | CH | N | —CH₂O— | H | H | Me | 2 | 8 |

TABLE 45

| Compound No. | G¹ | G² | Q¹ | $R^a$ | $R^b$ | $R^c$ | n | m |
|---|---|---|---|---|---|---|---|---|
| K-441 | CH | N | —CH₂O— | H | H | Me | 2 | 9 |
| K-442 | CH | N | —CH₂O— | H | H | Me | 3 | 7 |
| K-443 | CH | N | —CH₂O— | H | H | Me | 3 | 8 |
| K-444 | CH | N | —CH₂O— | H | H | Me | 3 | 9 |
| K-445 | CH | N | —CH₂O— | H | H | Me | 4 | 7 |
| K-446 | CH | N | —CH₂O— | H | H | Me | 4 | 8 |
| K-447 | CH | N | —CH₂O— | H | H | Me | 4 | 9 |
| K-448 | CH | N | —CH₂O— | H | H | Me | 5 | 7 |
| K-449 | CH | N | —CH₂O— | H | H | Me | 5 | 8 |
| K-450 | CH | N | —CH₂O— | H | H | Me | 5 | 9 |
| K-451 | CH | N | —CH₂O— | Me | Me | H | 1 | 7 |
| K-452 | CH | N | —CH₂O— | Me | Me | H | 1 | 8 |
| K-453 | CH | N | —CH₂O— | Me | Me | H | 1 | 9 |
| K-454 | CH | N | —CH₂O— | Me | Me | H | 2 | 7 |
| K-455 | CH | N | —CH₂O— | Me | Me | H | 2 | 8 |
| K-456 | CH | N | —CH₂O— | Me | Me | H | 2 | 9 |
| K-457 | CH | N | —CH₂O— | Me | Me | H | 3 | 7 |
| K-458 | CH | N | —CH₂O— | Me | Me | H | 3 | 8 |
| K-459 | CH | N | —CH₂O— | Me | Me | H | 3 | 9 |
| K-460 | CH | N | —CH₂O— | Me | Me | H | 4 | 7 |
| K-461 | CH | N | —CH₂O— | Me | Me | H | 4 | 8 |
| K-462 | CH | N | —CH₂O— | Me | Me | H | 4 | 9 |
| K-463 | CH | N | —CH₂O— | Me | Me | H | 5 | 7 |
| K-464 | CH | N | —CH₂O— | Me | Me | H | 5 | 8 |
| K-465 | CH | N | —CH₂O— | Me | Me | H | 5 | 9 |
| K-466 | CH | N | —CH₂O— | H | Me | Me | 1 | 7 |
| K-467 | CH | N | —CH₂O— | H | Me | Me | 1 | 8 |
| K-468 | CH | N | —CH₂O— | H | Me | Me | 1 | 9 |
| K-469 | CH | N | —CH₂O— | H | Me | Me | 2 | 7 |
| K-470 | CH | N | —CH₂O— | H | Me | Me | 2 | 8 |
| K-471 | CH | N | —CH₂O— | H | Me | Me | 2 | 9 |
| K-472 | CH | N | —CH₂O— | H | Me | Me | 3 | 7 |
| K-473 | CH | N | —CH₂O— | H | Me | Me | 3 | 8 |
| K-474 | CH | N | —CH₂O— | H | Me | Me | 3 | 9 |
| K-475 | CH | N | —CH₂O— | H | Me | Me | 4 | 7 |
| K-476 | CH | N | —CH₂O— | H | Me | Me | 4 | 8 |
| K-477 | CH | N | —CH₂O— | H | Me | Me | 4 | 9 |
| K-478 | CH | N | —CH₂O— | H | Me | Me | 5 | 7 |
| K-479 | CH | N | —CH₂O— | H | Me | Me | 5 | 8 |
| K-480 | CH | N | —CH₂O— | H | Me | Me | 5 | 9 |
| K-481 | CH | N | singlebond | Me | H | H | 1 | 7 |
| K-482 | CH | N | singlebond | Me | H | H | 1 | 8 |
| K-483 | CH | N | singlebond | Me | H | H | 1 | 9 |
| K-484 | CH | N | singlebond | Me | H | H | 2 | 7 |
| K-485 | CH | N | singlebond | Me | H | H | 2 | 8 |
| K-486 | CH | N | singlebond | Me | H | H | 2 | 9 |
| K-487 | CH | N | singlebond | Me | H | H | 3 | 7 |
| K-488 | CH | N | singlebond | Me | H | H | 3 | 8 |
| K-489 | CH | N | singlebond | Me | H | H | 3 | 9 |
| K-490 | CH | N | singlebond | Me | H | H | 4 | 7 |
| K-491 | CH | N | singlebond | Me | H | H | 4 | 8 |
| K-492 | CH | N | singlebond | Me | H | H | 4 | 9 |
| K-493 | CH | N | singlebond | Me | H | H | 5 | 7 |
| K-494 | CH | N | singlebond | Me | H | H | 5 | 8 |
| K-495 | CH | N | singlebond | Me | H | H | 5 | 9 |
| K-496 | CH | N | singlebond | H | H | Me | 1 | 7 |
| K-497 | CH | N | singlebond | H | H | Me | 1 | 8 |
| K-498 | CH | N | singlebond | H | H | Me | 1 | 9 |
| K-499 | CH | N | singlebond | H | H | Me | 2 | 7 |
| K-500 | CH | N | singlebond | H | H | Me | 2 | 8 |
| K-501 | CH | N | singlebond | H | H | Me | 2 | 9 |
| K-502 | CH | N | singlebond | H | H | Me | 3 | 7 |
| K-503 | CH | N | singlebond | H | H | Me | 3 | 8 |
| K-504 | CH | N | singlebond | H | H | Me | 3 | 9 |
| K-505 | CH | N | singlebond | H | H | Me | 4 | 7 |
| K-506 | CH | N | singlebond | H | H | Me | 4 | 8 |
| K-507 | CH | N | singlebond | H | H | Me | 4 | 9 |
| K-508 | CH | N | singlebond | H | H | Me | 5 | 7 |
| K-509 | CH | N | singlebond | H | H | Me | 5 | 8 |
| K-510 | CH | N | singlebond | H | H | Me | 5 | 9 |
| K-511 | CH | N | singlebond | Me | Me | H | 1 | 7 |
| K-512 | CH | N | singlebond | Me | Me | H | 1 | 8 |
| K-513 | CH | N | singlebond | Me | Me | H | 1 | 9 |
| K-514 | CH | N | singlebond | Me | Me | H | 2 | 7 |
| K-515 | CH | N | singlebond | Me | Me | H | 2 | 8 |
| K-516 | CH | N | singlebond | Me | Me | H | 2 | 9 |
| K-517 | CH | N | singlebond | Me | Me | H | 3 | 7 |

TABLE 45-continued

| Compound No. | G¹ | G² | Q¹ | Rᵃ | Rᵇ | Rᶜ | n | m |
|---|---|---|---|---|---|---|---|---|
| K-518 | CH | N | singlebond | Me | Me | H | 3 | 8 |
| K-519 | CH | N | singlebond | Me | Me | H | 3 | 9 |
| K-520 | CH | N | singlebond | Me | Me | H | 4 | 7 |
| K-521 | CH | N | singlebond | Me | Me | H | 4 | 8 |
| K-522 | CH | N | singlebond | Me | Me | H | 4 | 9 |
| K-523 | CH | N | singlebond | Me | Me | H | 5 | 7 |
| K-524 | CH | N | singlebond | Me | Me | H | 5 | 8 |
| K-525 | CH | N | singlebond | Me | Me | H | 5 | 9 |
| K-526 | CH | N | singlebond | H | Me | Me | 1 | 7 |
| K-527 | CH | N | singlebond | H | Me | Me | 1 | 8 |
| K-528 | CH | N | singlebond | H | Me | Me | 1 | 9 |
| K-529 | CH | N | singlebond | H | Me | Me | 2 | 7 |
| K-530 | CH | N | singlebond | H | Me | Me | 2 | 8 |
| K-531 | CH | N | singlebond | H | Me | Me | 2 | 9 |
| K-532 | CH | N | singlebond | H | Me | Me | 3 | 7 |
| K-533 | CH | N | singlebond | H | Me | Me | 3 | 8 |
| K-534 | CH | N | singlebond | H | Me | Me | 3 | 9 |
| K-535 | CH | N | singlebond | H | Me | Me | 4 | 7 |
| K-536 | CH | N | singlebond | H | Me | Me | 4 | 8 |
| K-537 | CH | N | singlebond | H | Me | Me | 4 | 9 |
| K-538 | CH | N | singlebond | H | Me | Me | 5 | 7 |
| K-539 | CH | N | singlebond | H | Me | Me | 5 | 8 |
| K-540 | CH | N | singlebond | H | Me | Me | 5 | 9 |

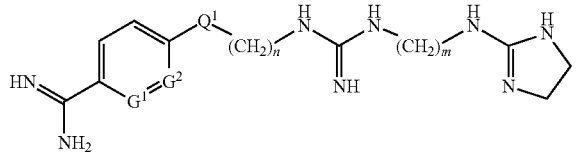

TABLE 46

| Compound No. | G¹ | G² | Q¹ | n | m |
|---|---|---|---|---|---|
| L-1 | CH | CH | —O— | 1 | 7 |
| L-2 | CH | CH | —O— | 1 | 8 |
| L-3 | CH | CH | —O— | 1 | 9 |
| L-4 | CH | CH | —O— | 2 | 7 |
| L-5 | CH | CH | —O— | 2 | 8 |
| L-6 | CH | CH | —O— | 2 | 9 |
| L-7 | CH | CH | —O— | 3 | 7 |
| L-8 | CH | CH | —O— | 3 | 8 |
| L-9 | CH | CH | —O— | 3 | 9 |
| L-10 | CH | CH | —O— | 4 | 7 |
| L-11 | CH | CH | —O— | 4 | 8 |
| L-12 | CH | CH | —O— | 4 | 9 |
| L-13 | CH | CH | —O— | 5 | 7 |
| L-14 | CH | CH | —O— | 5 | 8 |
| L-15 | CH | CH | —O— | 5 | 9 |
| L-16 | CH | CH | —CH₂O— | 1 | 7 |
| L-17 | CH | CH | —CH₂O— | 1 | 8 |
| L-18 | CH | CH | —CH₂O— | 1 | 9 |
| L-19 | CH | CH | —CH₂O— | 2 | 7 |
| L-20 | CH | CH | —CH₂O— | 2 | 8 |
| L-21 | CH | CH | —CH₂O— | 2 | 9 |
| L-22 | CH | CH | —CH₂O— | 3 | 7 |
| L-23 | CH | CH | —CH₂O— | 3 | 8 |
| L-24 | CH | CH | —CH₂O— | 3 | 9 |
| L-25 | CH | CH | —CH₂O— | 4 | 7 |
| L-26 | CH | CH | —CH₂O— | 4 | 8 |
| L-27 | CH | CH | —CH₂O— | 4 | 9 |
| L-28 | CH | CH | —CH₂O— | 5 | 7 |
| L-29 | CH | CH | —CH₂O— | 5 | 8 |
| L-30 | CH | CH | —CH₂O— | 5 | 9 |
| L-31 | CH | CH | singlebond | 1 | 7 |
| L-32 | CH | CH | singlebond | 1 | 8 |
| L-33 | CH | CH | singlebond | 1 | 9 |
| L-34 | CH | CH | singlebond | 2 | 7 |

TABLE 46-continued

| Compound No. | G¹ | G² | Q¹ | n | m |
|---|---|---|---|---|---|
| L-35 | CH | CH | singlebond | 2 | 8 |
| L-36 | CH | CH | singlebond | 2 | 9 |
| L-37 | CH | CH | singlebond | 3 | 7 |
| L-38 | CH | CH | singlebond | 3 | 8 |
| L-39 | CH | CH | singlebond | 3 | 9 |
| L-40 | CH | CH | singlebond | 4 | 7 |
| L-41 | CH | CH | singlebond | 4 | 8 |
| L-42 | CH | CH | singlebond | 4 | 9 |
| L-43 | CH | CH | singlebond | 5 | 7 |
| L-44 | CH | CH | singlebond | 5 | 8 |
| L-45 | CH | CH | singlebond | 5 | 9 |
| L-46 | N | CH | —O— | 1 | 7 |
| L-47 | N | CH | —O— | 1 | 8 |
| L-48 | N | CH | —O— | 1 | 9 |
| L-49 | N | CH | —O— | 2 | 7 |
| L-50 | N | CH | —O— | 2 | 8 |
| L-51 | N | CH | —O— | 2 | 9 |
| L-52 | N | CH | —O— | 3 | 7 |
| L-53 | N | CH | —O— | 3 | 8 |
| L-54 | N | CH | —O— | 3 | 9 |
| L-55 | N | CH | —O— | 4 | 7 |
| L-56 | N | CH | —O— | 4 | 8 |
| L-57 | N | CH | —O— | 4 | 9 |
| L-58 | N | CH | —O— | 5 | 7 |
| L-59 | N | CH | —O— | 5 | 8 |
| L-60 | N | CH | —O— | 5 | 9 |
| L-61 | N | CH | —CH₂O— | 1 | 7 |
| L-62 | N | CH | —CH₂O— | 1 | 8 |
| L-63 | N | CH | —CH₂O— | 1 | 9 |
| L-64 | N | CH | —CH₂O— | 2 | 7 |
| L-65 | N | CH | —CH₂O— | 2 | 8 |
| L-66 | N | CH | —CH₂O— | 2 | 9 |
| L-67 | N | CH | —CH₂O— | 3 | 7 |
| L-68 | N | CH | —CH₂O— | 3 | 8 |
| L-69 | N | CH | —CH₂O— | 3 | 9 |
| L-70 | N | CH | —CH₂O— | 4 | 7 |
| L-71 | N | CH | —CH₂O— | 4 | 8 |
| L-72 | N | CH | —CH₂O— | 4 | 9 |
| L-73 | N | CH | —CH₂O— | 5 | 7 |
| L-74 | N | CH | —CH₂O— | 5 | 8 |
| L-75 | N | CH | —CH₂O— | 5 | 9 |
| L-76 | N | CH | singlebond | 1 | 7 |
| L-77 | N | CH | singlebond | 1 | 8 |
| L-78 | N | CH | singlebond | 1 | 9 |
| L-79 | N | CH | singlebond | 2 | 7 |
| L-80 | N | CH | singlebond | 2 | 8 |
| L-81 | N | CH | singlebond | 2 | 9 |
| L-82 | N | CH | singlebond | 3 | 7 |
| L-83 | N | CH | singlebond | 3 | 8 |
| L-84 | N | CH | singlebond | 3 | 9 |
| L-85 | N | CH | singlebond | 4 | 7 |
| L-86 | N | CH | singlebond | 4 | 8 |
| L-87 | N | CH | singlebond | 4 | 9 |
| L-88 | N | CH | singlebond | 5 | 7 |
| L-89 | N | CH | singlebond | 5 | 8 |
| L-90 | N | CH | singlebond | 5 | 9 |
| L-91 | CH | N | —O— | 1 | 7 |
| L-92 | CH | N | —O— | 1 | 8 |
| L-93 | CH | N | —O— | 1 | 9 |
| L-94 | CH | N | —O— | 2 | 7 |
| L-95 | CH | N | —O— | 2 | 8 |
| L-96 | CH | N | —O— | 2 | 9 |
| L-97 | CH | N | —O— | 3 | 7 |
| L-98 | CH | N | —O— | 3 | 8 |
| L-99 | CH | N | —O— | 3 | 9 |
| L-100 | CH | N | —O— | 4 | 7 |
| L-101 | CH | N | —O— | 4 | 8 |
| L-102 | CH | N | —O— | 4 | 9 |
| L-103 | CH | N | —O— | 5 | 7 |
| L-104 | CH | N | —O— | 5 | 8 |
| L-105 | CH | N | —O— | 5 | 9 |
| L-106 | CH | N | —CH₂O— | 1 | 7 |
| L-107 | CH | N | —CH₂O— | 1 | 8 |
| L-108 | CH | N | —CH₂O— | 1 | 9 |
| L-109 | CH | N | —CH₂O— | 2 | 7 |
| L-110 | CH | N | —CH₂O— | 2 | 8 |

TABLE 47

| Compound No. | G¹ | G² | Q¹ | n | m |
|---|---|---|---|---|---|
| L-111 | CH | N | —CH₂O— | 2 | 9 |
| L-112 | CH | N | —CH₂O— | 3 | 7 |
| L-113 | CH | N | —CH₂O— | 3 | 8 |
| L-114 | CH | N | —CH₂O— | 3 | 9 |
| L-115 | CH | N | —CH₂O— | 4 | 7 |
| L-116 | CH | N | —CH₂O— | 4 | 8 |
| L-117 | CH | N | —CH₂O— | 4 | 9 |
| L-118 | CH | N | —CH₂O— | 5 | 7 |
| L-119 | CH | N | —CH₂O— | 5 | 8 |
| L-120 | CH | N | —CH₂O— | 5 | 9 |
| L-121 | CH | N | singlebond | 1 | 7 |
| L-122 | CH | N | singlebond | 1 | 8 |
| L-123 | CH | N | singlebond | 1 | 9 |
| L-124 | CH | N | singlebond | 2 | 7 |
| L-125 | CH | N | singlebond | 2 | 8 |
| L-126 | CH | N | singlebond | 2 | 9 |
| L-127 | CH | N | singlebond | 3 | 7 |
| L-128 | CH | N | singlebond | 3 | 8 |
| L-129 | CH | N | singlebond | 3 | 9 |
| L-130 | CH | N | singlebond | 4 | 7 |
| L-131 | CH | N | singlebond | 4 | 8 |
| L-132 | CH | N | singlebond | 4 | 9 |
| L-133 | CH | N | singlebond | 5 | 7 |
| L-134 | CH | N | singlebond | 5 | 8 |
| L-135 | CH | N | singlebond | 5 | 9 |

TABLE 48

| Compound No. | G¹ | G² | Q¹ | n | m |
|---|---|---|---|---|---|
| M-1 | CH | CH | —O— | 1 | 7 |
| M-2 | CH | CH | —O— | 1 | 8 |
| M-3 | CH | CH | —O— | 1 | 9 |
| M-4 | CH | CH | —O— | 2 | 7 |
| M-5 | CH | CH | —O— | 2 | 8 |
| M-6 | CH | CH | —O— | 2 | 9 |
| M-7 | CH | CH | —O— | 3 | 7 |
| M-8 | CH | CH | —O— | 3 | 8 |
| M-9 | CH | CH | —O— | 3 | 9 |
| M-10 | CH | CH | —O— | 4 | 7 |
| M-11 | CH | CH | —O— | 4 | 8 |
| M-12 | CH | CH | —O— | 4 | 9 |
| M-13 | CH | CH | —O— | 5 | 7 |
| M-14 | CH | CH | —O— | 5 | 8 |
| M-15 | CH | CH | —O— | 5 | 9 |
| M-16 | CH | CH | —CH₂O— | 1 | 7 |
| M-17 | CH | CH | —CH₂O— | 1 | 8 |
| M-18 | CH | CH | —CH₂O— | 1 | 9 |
| M-19 | CH | CH | —CH₂O— | 2 | 7 |
| M-20 | CH | CH | —CH₂O— | 2 | 8 |
| M-21 | CH | CH | —CH₂O— | 2 | 9 |
| M-22 | CH | CH | —CH₂O— | 3 | 7 |
| M-23 | CH | CH | —CH₂O— | 3 | 8 |
| M-24 | CH | CH | —CH₂O— | 3 | 9 |
| M-25 | CH | CH | —CH₂O— | 4 | 7 |
| M-26 | CH | CH | —CH₂O— | 4 | 8 |
| M-27 | CH | CH | —CH₂O— | 4 | 9 |
| M-28 | CH | CH | —CH₂O— | 5 | 7 |
| M-29 | CH | CH | —CH₂O— | 5 | 8 |
| M-30 | CH | CH | —CH₂O— | 5 | 9 |
| M-31 | CH | CH | singlebond | 1 | 7 |
| M-32 | CH | CH | singlebond | 1 | 8 |
| M-33 | CH | CH | singlebond | 1 | 9 |
| M-34 | CH | CH | singlebond | 2 | 7 |
| M-35 | CH | CH | singlebond | 2 | 8 |
| M-36 | CH | CH | singlebond | 2 | 9 |
| M-37 | CH | CH | singlebond | 3 | 7 |
| M-38 | CH | CH | singlebond | 3 | 8 |
| M-39 | CH | CH | singlebond | 3 | 9 |
| M-40 | CH | CH | singlebond | 4 | 7 |
| M-41 | CH | CH | singlebond | 4 | 8 |
| M-42 | CH | CH | singlebond | 4 | 9 |
| M-43 | CH | CH | singlebond | 5 | 7 |
| M-44 | CH | CH | singlebond | 5 | 8 |
| M-45 | CH | CH | singlebond | 5 | 9 |
| M-46 | N | CH | —O— | 1 | 7 |
| M-47 | N | CH | —O— | 1 | 8 |
| M-48 | N | CH | —O— | 1 | 9 |
| M-49 | N | CH | —O— | 2 | 7 |
| M-50 | N | CH | —O— | 2 | 8 |
| M-51 | N | CH | —O— | 2 | 9 |
| M-52 | N | CH | —O— | 3 | 7 |
| M-53 | N | CH | —O— | 3 | 8 |
| M-54 | N | CH | —O— | 3 | 9 |
| M-55 | N | CH | —O— | 4 | 7 |
| M-56 | N | CH | —O— | 4 | 8 |
| M-57 | N | CH | —O— | 4 | 9 |
| M-58 | N | CH | —O— | 5 | 7 |
| M-59 | N | CH | —O— | 5 | 8 |
| M-60 | N | CH | —O— | 5 | 9 |
| M-61 | N | CH | —CH₂O— | 1 | 7 |
| M-62 | N | CH | —CH₂O— | 1 | 8 |
| M-63 | N | CH | —CH₂O— | 1 | 9 |
| M-64 | N | CH | —CH₂O— | 2 | 7 |
| M-65 | N | CH | —CH₂O— | 2 | 8 |
| M-66 | N | CH | —CH₂O— | 2 | 9 |
| M-67 | N | CH | —CH₂O— | 3 | 7 |
| M-68 | N | CH | —CH₂O— | 3 | 8 |
| M-69 | N | CH | —CH₂O— | 3 | 9 |
| M-70 | N | CH | —CH₂O— | 4 | 7 |
| M-71 | N | CH | —CH₂O— | 4 | 8 |
| M-72 | N | CH | —CH₂O— | 4 | 9 |
| M-73 | N | CH | —CH₂O— | 5 | 7 |
| M-74 | N | CH | —CH₂O— | 5 | 8 |
| M-75 | N | CH | —CH₂O— | 5 | 9 |
| M-76 | N | CH | singlebond | 1 | 7 |
| M-77 | N | CH | singlebond | 1 | 8 |
| M-78 | N | CH | singlebond | 1 | 9 |
| M-79 | N | CH | singlebond | 2 | 7 |
| M-80 | N | CH | singlebond | 2 | 8 |
| M-81 | N | CH | singlebond | 2 | 9 |
| M-82 | N | CH | singlebond | 3 | 7 |
| M-83 | N | CH | singlebond | 3 | 8 |
| M-84 | N | CH | singlebond | 3 | 9 |
| M-85 | N | CH | singlebond | 4 | 7 |
| M-86 | N | CH | singlebond | 4 | 8 |
| M-87 | N | CH | singlebond | 4 | 9 |
| M-88 | N | CH | singlebond | 5 | 7 |
| M-89 | N | CH | singlebond | 5 | 8 |
| M-90 | N | CH | singlebond | 5 | 9 |
| M-91 | CH | N | —O— | 1 | 7 |
| M-92 | CH | N | —O— | 1 | 8 |
| M-93 | CH | N | —O— | 1 | 9 |
| M-94 | CH | N | —O— | 2 | 7 |
| M-95 | CH | N | —O— | 2 | 8 |
| M-96 | CH | N | —O— | 2 | 9 |
| M-97 | CH | N | —O— | 3 | 7 |
| M-98 | CH | N | —O— | 3 | 8 |
| M-99 | CH | N | —O— | 3 | 9 |
| M-100 | CH | N | —O— | 4 | 7 |
| M-101 | CH | N | —O— | 4 | 8 |
| M-102 | CH | N | —O— | 4 | 9 |
| M-103 | CH | N | —O— | 5 | 7 |
| M-104 | CH | N | —O— | 5 | 8 |
| M-105 | CH | N | —O— | 5 | 9 |
| M-106 | CH | N | —CH₂O— | 1 | 7 |
| M-107 | CH | N | —CH₂O— | 1 | 8 |
| M-108 | CH | N | —CH₂O— | 1 | 9 |

TABLE 48-continued

| Compound No. | G¹ | G² | Q¹ | n | m |
|---|---|---|---|---|---|
| M-109 | CH | N | —CH₂O— | 2 | 7 |
| M-110 | CH | N | —CH₂O— | 2 | 8 |

TABLE 49

| Compound No. | G¹ | G² | Q¹ | n | m |
|---|---|---|---|---|---|
| M-111 | CH | N | —CH₂O— | 2 | 9 |
| M-112 | CH | N | —CH₂O— | 3 | 7 |
| M-113 | CH | N | —CH₂O— | 3 | 8 |
| M-114 | CH | N | —CH₂O— | 3 | 9 |
| M-115 | CH | N | —CH₂O— | 4 | 7 |
| M-116 | CH | N | —CH₂O— | 4 | 8 |
| M-117 | CH | N | —CH₂O— | 4 | 9 |
| M-118 | CH | N | —CH₂O— | 5 | 7 |
| M-119 | CH | N | —CH₂O— | 5 | 8 |
| M-120 | CH | N | —CH₂O— | 5 | 9 |
| M-121 | CH | N | singlebond | 1 | 7 |
| M-122 | CH | N | singlebond | 1 | 8 |
| M-123 | CH | N | singlebond | 1 | 9 |
| M-124 | CH | N | singlebond | 2 | 7 |
| M-125 | CH | N | singlebond | 2 | 8 |
| M-126 | CH | N | singlebond | 2 | 9 |
| M-127 | CH | N | singlebond | 3 | 7 |
| M-128 | CH | N | singlebond | 3 | 8 |
| M-129 | CH | N | singlebond | 3 | 9 |
| M-130 | CH | N | singlebond | 4 | 7 |
| M-131 | CH | N | singlebond | 4 | 8 |
| M-132 | CH | N | singlebond | 4 | 9 |
| M-133 | CH | N | singlebond | 5 | 7 |
| M-134 | CH | N | singlebond | 5 | 8 |
| M-135 | CH | N | singlebond | 5 | 9 |

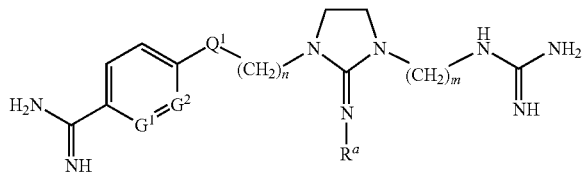

TABLE 50

| Compound No. | G¹ | G² | Q¹ | Rᵃ | n | m |
|---|---|---|---|---|---|---|
| N-1 | CH | CH | —O— | H | 1 | 7 |
| N-2 | CH | CH | —O— | H | 1 | 8 |
| N-3 | CH | CH | —O— | H | 1 | 9 |
| N-4 | CH | CH | —O— | H | 2 | 7 |
| N-5 | CH | CH | —O— | H | 2 | 8 |
| N-6 | CH | CH | —O— | H | 2 | 9 |
| N-7 | CH | CH | —O— | H | 3 | 7 |
| N-8 | CH | CH | —O— | H | 3 | 8 |
| N-9 | CH | CH | —O— | H | 3 | 9 |
| N-10 | CH | CH | —O— | H | 4 | 7 |
| N-11 | CH | CH | —O— | H | 4 | 8 |
| N-12 | CH | CH | —O— | H | 4 | 9 |
| N-13 | CH | CH | —O— | H | 5 | 7 |
| N-14 | CH | CH | —O— | H | 5 | 8 |
| N-15 | CH | CH | —O— | H | 5 | 9 |
| N-16 | CH | CH | —O— | Me | 1 | 7 |
| N-17 | CH | CH | —O— | Me | 1 | 8 |
| N-18 | CH | CH | —O— | Me | 1 | 9 |
| N-19 | CH | CH | —O— | Me | 2 | 7 |
| N-20 | CH | CH | —O— | Me | 2 | 8 |
| N-21 | CH | CH | —O— | Me | 2 | 9 |

TABLE 50-continued

| Compound No. | G¹ | G² | Q¹ | Rᵃ | n | m |
|---|---|---|---|---|---|---|
| N-22 | CH | CH | —O— | Me | 3 | 7 |
| N-23 | CH | CH | —O— | Me | 3 | 8 |
| N-24 | CH | CH | —O— | Me | 3 | 9 |
| N-25 | CH | CH | —O— | Me | 4 | 7 |
| N-26 | CH | CH | —O— | Me | 4 | 8 |
| N-27 | CH | CH | —O— | Me | 4 | 9 |
| N-28 | CH | CH | —O— | Me | 5 | 7 |
| N-29 | CH | CH | —O— | Me | 5 | 8 |
| N-30 | CH | CH | —O— | Me | 5 | 9 |
| N-31 | CH | CH | —CH₂O— | H | 1 | 7 |
| N-32 | CH | CH | —CH₂O— | H | 1 | 8 |
| N-33 | CH | CH | —CH₂O— | H | 1 | 9 |
| N-34 | CH | CH | —CH₂O— | H | 2 | 7 |
| N-35 | CH | CH | —CH₂O— | H | 2 | 8 |
| N-36 | CH | CH | —CH₂O— | H | 2 | 9 |
| N-37 | CH | CH | —CH₂O— | H | 3 | 7 |
| N-38 | CH | CH | —CH₂O— | H | 3 | 8 |
| N-39 | CH | CH | —CH₂O— | H | 3 | 9 |
| N-40 | CH | CH | —CH₂O— | H | 4 | 7 |
| N-41 | CH | CH | —CH₂O— | H | 4 | 8 |
| N-42 | CH | CH | —CH₂O— | H | 4 | 9 |
| N-43 | CH | CH | —CH₂O— | H | 5 | 7 |
| N-44 | CH | CH | —CH₂O— | H | 5 | 8 |
| N-45 | CH | CH | —CH₂O— | H | 5 | 9 |
| N-46 | CH | CH | —CH₂O— | Me | 1 | 7 |
| N-47 | CH | CH | —CH₂O— | Me | 1 | 8 |
| N-48 | CH | CH | —CH₂O— | Me | 1 | 9 |
| N-49 | CH | CH | —CH₂O— | Me | 2 | 7 |
| N-50 | CH | CH | —CH₂O— | Me | 2 | 8 |
| N-51 | CH | CH | —CH₂O— | Me | 2 | 9 |
| N-52 | CH | CH | —CH₂O— | Me | 3 | 7 |
| N-53 | CH | CH | —CH₂O— | Me | 3 | 8 |
| N-54 | CH | CH | —CH₂O— | Me | 3 | 9 |
| N-55 | CH | CH | —CH₂O— | Me | 4 | 7 |
| N-56 | CH | CH | —CH₂O— | Me | 4 | 8 |
| N-57 | CH | CH | —CH₂O— | Me | 4 | 9 |
| N-58 | CH | CH | —CH₂O— | Me | 5 | 7 |
| N-59 | CH | CH | —CH₂O— | Me | 5 | 8 |
| N-60 | CH | CH | —CH₂O— | Me | 5 | 9 |
| N-61 | CH | CH | singlebond | H | 1 | 7 |
| N-62 | CH | CH | singlebond | H | 1 | 8 |
| N-63 | CH | CH | singlebond | H | 1 | 9 |
| N-64 | CH | CH | singlebond | H | 2 | 7 |
| N-65 | CH | CH | singlebond | H | 2 | 8 |
| N-66 | CH | CH | singlebond | H | 2 | 9 |
| N-67 | CH | CH | singlebond | H | 3 | 7 |
| N-68 | CH | CH | singlebond | H | 3 | 8 |
| N-69 | CH | CH | singlebond | H | 3 | 9 |
| N-70 | CH | CH | singlebond | H | 4 | 7 |
| N-71 | CH | CH | singlebond | H | 4 | 8 |
| N-72 | CH | CH | singlebond | H | 4 | 9 |
| N-73 | CH | CH | singlebond | H | 5 | 7 |
| N-74 | CH | CH | singlebond | H | 5 | 8 |
| N-75 | CH | CH | singlebond | H | 5 | 9 |
| N-76 | CH | CH | singlebond | Me | 1 | 7 |
| N-77 | CH | CH | singlebond | Me | 1 | 8 |
| N-78 | CH | CH | singlebond | Me | 1 | 9 |
| N-79 | CH | CH | singlebond | Me | 2 | 7 |
| N-80 | CH | CH | singlebond | Me | 2 | 8 |
| N-81 | CH | CH | singlebond | Me | 2 | 9 |
| N-82 | CH | CH | singlebond | Me | 3 | 7 |
| N-83 | CH | CH | singlebond | Me | 3 | 8 |
| N-84 | CH | CH | singlebond | Me | 3 | 9 |
| N-85 | CH | CH | singlebond | Me | 4 | 7 |
| N-86 | CH | CH | singlebond | Me | 4 | 8 |
| N-87 | CH | CH | singlebond | Me | 4 | 9 |
| N-88 | CH | CH | singlebond | Me | 5 | 7 |
| N-89 | CH | CH | singlebond | Me | 5 | 8 |
| N-90 | CH | CH | singlebond | Me | 5 | 9 |
| N-91 | N | CH | —O— | H | 1 | 7 |
| N-92 | N | CH | —O— | H | 1 | 8 |
| N-93 | N | CH | —O— | H | 1 | 9 |
| N-94 | N | CH | —O— | H | 2 | 7 |
| N-95 | N | CH | —O— | H | 2 | 8 |
| N-96 | N | CH | —O— | H | 2 | 9 |
| N-97 | N | CH | —O— | H | 3 | 7 |
| N-98 | N | CH | —O— | H | 3 | 8 |

TABLE 50-continued

| Compound No. | G¹ | G² | Q¹ | $R^a$ | n | m |
|---|---|---|---|---|---|---|
| N-99 | N | CH | —O— | H | 3 | 9 |
| N-100 | N | CH | —O— | H | 4 | 7 |
| N-101 | N | CH | —O— | H | 4 | 8 |
| N-102 | N | CH | —O— | H | 4 | 9 |
| N-103 | N | CH | —O— | H | 5 | 7 |
| N-104 | N | CH | —O— | H | 5 | 8 |
| N-105 | N | CH | —O— | H | 5 | 9 |
| N-106 | N | CH | —O— | Me | 1 | 7 |
| N-107 | N | CH | —O— | Me | 1 | 8 |
| N-108 | N | CH | —O— | Me | 1 | 9 |
| N-109 | N | CH | —O— | Me | 2 | 7 |
| N-110 | N | CH | —O— | Me | 2 | 8 |

TABLE 51

| Compound No. | G¹ | G² | Q¹ | $R^a$ | n | m |
|---|---|---|---|---|---|---|
| N-111 | N | CH | —O— | Me | 2 | 9 |
| N-112 | N | CH | —O— | Me | 3 | 7 |
| N-113 | N | CH | —O— | Me | 3 | 8 |
| N-114 | N | CH | —O— | Me | 3 | 9 |
| N-115 | N | CH | —O— | Me | 4 | 7 |
| N-116 | N | CH | —O— | Me | 4 | 8 |
| N-117 | N | CH | —O— | Me | 4 | 9 |
| N-118 | N | CH | —O— | Me | 5 | 7 |
| N-119 | N | CH | —O— | Me | 5 | 8 |
| N-120 | N | CH | —O— | Me | 5 | 9 |
| N-121 | N | CH | —CH₂O— | H | 1 | 7 |
| N-122 | N | CH | —CH₂O— | H | 1 | 8 |
| N-123 | N | CH | —CH₂O— | H | 1 | 9 |
| N-124 | N | CH | —CH₂O— | H | 2 | 7 |
| N-125 | N | CH | —CH₂O— | H | 2 | 8 |
| N-126 | N | CH | —CH₂O— | H | 2 | 9 |
| N-127 | N | CH | —CH₂O— | H | 3 | 7 |
| N-128 | N | CH | —CH₂O— | H | 3 | 8 |
| N-129 | N | CH | —CH₂O— | H | 3 | 9 |
| N-130 | N | CH | —CH₂O— | H | 4 | 7 |
| N-131 | N | CH | —CH₂O— | H | 4 | 8 |
| N-132 | N | CH | —CH₂O— | H | 4 | 9 |
| N-133 | N | CH | —CH₂O— | H | 5 | 7 |
| N-134 | N | CH | —CH₂O— | H | 5 | 8 |
| N-135 | N | CH | —CH₂O— | H | 5 | 9 |
| N-136 | N | CH | —CH₂O— | Me | 1 | 7 |
| N-137 | N | CH | —CH₂O— | Me | 1 | 8 |
| N-138 | N | CH | —CH₂O— | Me | 1 | 9 |
| N-139 | N | CH | —CH₂O— | Me | 2 | 7 |
| N-140 | N | CH | —CH₂O— | Me | 2 | 8 |
| N-141 | N | CH | —CH₂O— | Me | 2 | 9 |
| N-142 | N | CH | —CH₂O— | Me | 3 | 7 |
| N-143 | N | CH | —CH₂O— | Me | 3 | 8 |
| N-144 | N | CH | —CH₂O— | Me | 3 | 9 |
| N-145 | N | CH | —CH₂O— | Me | 4 | 7 |
| N-146 | N | CH | —CH₂O— | Me | 4 | 8 |
| N-147 | N | CH | —CH₂O— | Me | 4 | 9 |
| N-148 | N | CH | —CH₂O— | Me | 5 | 7 |
| N-149 | N | CH | —CH₂O— | Me | 5 | 8 |
| N-150 | N | CH | —CH₂O— | Me | 5 | 9 |
| N-151 | N | CH | singlebond | H | 1 | 7 |
| N-152 | N | CH | singlebond | H | 1 | 8 |
| N-153 | N | CH | singlebond | H | 1 | 9 |
| N-154 | N | CH | singlebond | H | 2 | 7 |
| N-155 | N | CH | singlebond | H | 2 | 8 |
| N-156 | N | CH | singlebond | H | 2 | 9 |
| N-157 | N | CH | singlebond | H | 3 | 7 |
| N-158 | N | CH | singlebond | H | 3 | 8 |
| N-159 | N | CH | singlebond | H | 3 | 9 |
| N-160 | N | CH | singlebond | H | 4 | 7 |
| N-161 | N | CH | singlebond | H | 4 | 8 |
| N-162 | N | CH | singlebond | H | 4 | 9 |
| N-163 | N | CH | singlebond | H | 5 | 7 |
| N-164 | N | CH | singlebond | H | 5 | 8 |
| N-165 | N | CH | singlebond | H | 5 | 9 |
| N-166 | N | CH | singlebond | Me | 1 | 7 |
| N-167 | N | CH | singlebond | Me | 1 | 8 |
| N-168 | N | CH | singlebond | Me | 1 | 9 |
| N-169 | N | CH | singlebond | Me | 2 | 7 |
| N-170 | N | CH | singlebond | Me | 2 | 8 |
| N-171 | N | CH | singlebond | Me | 2 | 9 |
| N-172 | N | CH | singlebond | Me | 3 | 7 |
| N-173 | N | CH | singlebond | Me | 3 | 8 |
| N-174 | N | CH | singlebond | Me | 3 | 9 |
| N-175 | N | CH | singlebond | Me | 4 | 7 |
| N-176 | N | CH | singlebond | Me | 4 | 8 |
| N-177 | N | CH | singlebond | Me | 4 | 9 |
| N-178 | N | CH | singlebond | Me | 5 | 7 |
| N-179 | N | CH | singlebond | Me | 5 | 8 |
| N-180 | N | CH | singlebond | Me | 5 | 9 |
| N-181 | CH | N | —O— | H | 1 | 7 |
| N-182 | CH | N | —O— | H | 1 | 8 |
| N-183 | CH | N | —O— | H | 1 | 9 |
| N-184 | CH | N | —O— | H | 2 | 7 |
| N-185 | CH | N | —O— | H | 2 | 8 |
| N-186 | CH | N | —O— | H | 2 | 9 |
| N-187 | CH | N | —O— | H | 3 | 7 |
| N-188 | CH | N | —O— | H | 3 | 8 |
| N-189 | CH | N | —O— | H | 3 | 9 |
| N-190 | CH | N | —O— | H | 4 | 7 |
| N-191 | CH | N | —O— | H | 4 | 8 |
| N-192 | CH | N | —O— | H | 4 | 9 |
| N-193 | CH | N | —O— | H | 5 | 7 |
| N-194 | CH | N | —O— | H | 5 | 8 |
| N-195 | CH | N | —O— | H | 5 | 9 |
| N-196 | CH | N | —O— | Me | 1 | 7 |
| N-197 | CH | N | —O— | Me | 1 | 8 |
| N-198 | CH | N | —O— | Me | 1 | 9 |
| N-199 | CH | N | —O— | Me | 2 | 7 |
| N-200 | CH | N | —O— | Me | 2 | 8 |
| N-201 | CH | N | —O— | Me | 2 | 9 |
| N-202 | CH | N | —O— | Me | 3 | 7 |
| N-203 | CH | N | —O— | Me | 3 | 8 |
| N-204 | CH | N | —O— | Me | 3 | 9 |
| N-205 | CH | N | —O— | Me | 4 | 7 |
| N-206 | CH | N | —O— | Me | 4 | 8 |
| N-207 | CH | N | —O— | Me | 4 | 9 |
| N-208 | CH | N | —O— | Me | 5 | 7 |
| N-209 | CH | N | —O— | Me | 5 | 8 |
| N-210 | CH | N | —O— | Me | 5 | 9 |
| N-211 | CH | N | —CH₂O— | H | 1 | 7 |
| N-212 | CH | N | —CH₂O— | H | 1 | 8 |
| N-213 | CH | N | —CH₂O— | H | 1 | 9 |
| N-214 | CH | N | —CH₂O— | H | 2 | 7 |
| N-215 | CH | N | —CH₂O— | H | 2 | 8 |
| N-216 | CH | N | —CH₂O— | H | 2 | 9 |
| N-217 | CH | N | —CH₂O— | H | 3 | 7 |
| N-218 | CH | N | —CH₂O— | H | 3 | 8 |
| N-219 | CH | N | —CH₂O— | H | 3 | 9 |
| N-220 | CH | N | —CH₂O— | H | 4 | 7 |

TABLE 52

| Compound No. | G¹ | G² | Q¹ | $R^a$ | n | m |
|---|---|---|---|---|---|---|
| N-221 | CH | N | —CH₂O— | H | 4 | 8 |
| N-222 | CH | N | —CH₂O— | H | 4 | 9 |
| N-223 | CH | N | —CH₂O— | H | 5 | 7 |
| N-224 | CH | N | —CH₂O— | H | 5 | 8 |
| N-225 | CH | N | —CH₂O— | H | 5 | 9 |
| N-226 | CH | N | —CH₂O— | Me | 1 | 7 |
| N-227 | CH | N | —CH₂O— | Me | 1 | 8 |
| N-228 | CH | N | —CH₂O— | Me | 1 | 9 |
| N-229 | CH | N | —CH₂O— | Me | 2 | 7 |
| N-230 | CH | N | —CH₂O— | Me | 2 | 8 |
| N-231 | CH | N | —CH₂O— | Me | 2 | 9 |
| N-232 | CH | N | —CH₂O— | Me | 3 | 7 |
| N-233 | CH | N | —CH₂O— | Me | 3 | 8 |
| N-234 | CH | N | —CH₂O— | Me | 3 | 9 |

TABLE 52-continued

| Compound No. | G¹ | G² | Q¹ | Rᵃ | n | m |
|---|---|---|---|---|---|---|
| N-235 | CH | N | —CH₂O— | Me | 4 | 7 |
| N-236 | CH | N | —CH₂O— | Me | 4 | 8 |
| N-237 | CH | N | —CH₂O— | Me | 4 | 9 |
| N-238 | CH | N | —CH₂O— | Me | 5 | 7 |
| N-239 | CH | N | —CH₂O— | Me | 5 | 8 |
| N-240 | CH | N | —CH₂O— | Me | 5 | 9 |
| N-241 | CH | N | singlebond | H | 1 | 7 |
| N-242 | CH | N | singlebond | H | 1 | 8 |
| N-243 | CH | N | singlebond | H | 1 | 9 |
| N-244 | CH | N | singlebond | H | 2 | 7 |
| N-245 | CH | N | singlebond | H | 2 | 8 |
| N-246 | CH | N | singlebond | H | 2 | 9 |
| N-247 | CH | N | singlebond | H | 3 | 7 |
| N-248 | CH | N | singlebond | H | 3 | 8 |
| N-249 | CH | N | singlebond | H | 3 | 9 |
| N-250 | CH | N | singlebond | H | 4 | 7 |
| N-251 | CH | N | singlebond | H | 4 | 8 |
| N-252 | CH | N | singlebond | H | 4 | 9 |
| N-253 | CH | N | singlebond | H | 5 | 7 |
| N-254 | CH | N | singlebond | H | 5 | 8 |
| N-255 | CH | N | singlebond | H | 5 | 9 |
| N-256 | CH | N | singlebond | Me | 1 | 7 |
| N-257 | CH | N | singlebond | Me | 1 | 8 |
| N-258 | CH | N | singlebond | Me | 1 | 9 |
| N-259 | CH | N | singlebond | Me | 2 | 7 |
| N-260 | CH | N | singlebond | Me | 2 | 8 |
| N-261 | CH | N | singlebond | Me | 2 | 9 |
| N-262 | CH | N | singlebond | Me | 3 | 7 |
| N-263 | CH | N | singlebond | Me | 3 | 8 |
| N-264 | CH | N | singlebond | Me | 3 | 9 |
| N-265 | CH | N | singlebond | Me | 4 | 7 |
| N-266 | CH | N | singlebond | Me | 4 | 8 |
| N-267 | CH | N | singlebond | Me | 4 | 9 |
| N-268 | CH | N | singlebond | Me | 5 | 7 |
| N-269 | CH | N | singlebond | Me | 5 | 8 |
| N-270 | CH | N | singlebond | Me | 5 | 9 |

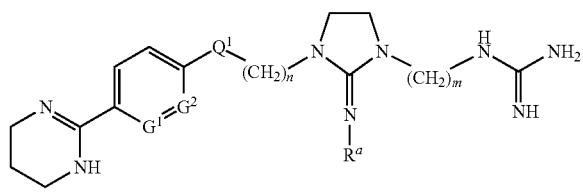

TABLE 53

| Compound No. | G¹ | G² | Q¹ | Rᵃ | n | m |
|---|---|---|---|---|---|---|
| O-1 | CH | CH | —O— | H | 1 | 7 |
| O-2 | CH | CH | —O— | H | 1 | 8 |
| O-3 | CH | CH | —O— | H | 1 | 9 |
| O-4 | CH | CH | —O— | H | 2 | 7 |
| O-5 | CH | CH | —O— | H | 2 | 8 |
| O-6 | CH | CH | —O— | H | 2 | 9 |
| O-7 | CH | CH | —O— | H | 3 | 7 |
| O-8 | CH | CH | —O— | H | 3 | 8 |
| O-9 | CH | CH | —O— | H | 3 | 9 |
| O-10 | CH | CH | —O— | H | 4 | 7 |
| O-11 | CH | CH | —O— | H | 4 | 8 |
| O-12 | CH | CH | —O— | H | 4 | 9 |
| O-13 | CH | CH | —O— | H | 5 | 7 |
| O-14 | CH | CH | —O— | H | 5 | 8 |
| O-15 | CH | CH | —O— | H | 5 | 9 |
| O-16 | CH | CH | —O— | Me | 1 | 7 |
| O-17 | CH | CH | —O— | Me | 1 | 8 |
| O-18 | CH | CH | —O— | Me | 1 | 9 |
| O-19 | CH | CH | —O— | Me | 2 | 7 |
| O-20 | CH | CH | —O— | Me | 2 | 8 |

TABLE 53-continued

| Compound No. | G¹ | G² | Q¹ | Rᵃ | n | m |
|---|---|---|---|---|---|---|
| O-21 | CH | CH | —O— | Me | 2 | 9 |
| O-22 | CH | CH | —O— | Me | 3 | 7 |
| O-23 | CH | CH | —O— | Me | 3 | 8 |
| O-24 | CH | CH | —O— | Me | 3 | 9 |
| O-25 | CH | CH | —O— | Me | 4 | 7 |
| O-26 | CH | CH | —O— | Me | 4 | 8 |
| O-27 | CH | CH | —O— | Me | 4 | 9 |
| O-28 | CH | CH | —O— | Me | 5 | 7 |
| O-29 | CH | CH | —O— | Me | 5 | 8 |
| O-30 | CH | CH | —O— | Me | 5 | 9 |
| O-31 | CH | CH | —CH₂O— | H | 1 | 7 |
| O-32 | CH | CH | —CH₂O— | H | 1 | 8 |
| O-33 | CH | CH | —CH₂O— | H | 1 | 9 |
| O-34 | CH | CH | —CH₂O— | H | 2 | 7 |
| O-35 | CH | CH | —CH₂O— | H | 2 | 8 |
| O-36 | CH | CH | —CH₂O— | H | 2 | 9 |
| O-37 | CH | CH | —CH₂O— | H | 3 | 7 |
| O-38 | CH | CH | —CH₂O— | H | 3 | 8 |
| O-39 | CH | CH | —CH₂O— | H | 3 | 9 |
| O-40 | CH | CH | —CH₂O— | H | 4 | 7 |
| O-41 | CH | CH | —CH₂O— | H | 4 | 8 |
| O-42 | CH | CH | —CH₂O— | H | 4 | 9 |
| O-43 | CH | CH | —CH₂O— | H | 5 | 7 |
| O-44 | CH | CH | —CH₂O— | H | 5 | 8 |
| O-45 | CH | CH | —CH₂O— | H | 5 | 9 |
| O-46 | CH | CH | —CH₂O— | Me | 1 | 7 |
| O-47 | CH | CH | —CH₂O— | Me | 1 | 8 |
| O-48 | CH | CH | —CH₂O— | Me | 1 | 9 |
| O-49 | CH | CH | —CH₂O— | Me | 2 | 7 |
| O-50 | CH | CH | —CH₂O— | Me | 2 | 8 |
| O-51 | CH | CH | —CH₂O— | Me | 2 | 9 |
| O-52 | CH | CH | —CH₂O— | Me | 3 | 7 |
| O-53 | CH | CH | —CH₂O— | Me | 3 | 8 |
| O-54 | CH | CH | —CH₂O— | Me | 3 | 9 |
| O-55 | CH | CH | —CH₂O— | Me | 4 | 7 |
| O-56 | CH | CH | —CH₂O— | Me | 4 | 8 |
| O-57 | CH | CH | —CH₂O— | Me | 4 | 9 |
| O-58 | CH | CH | —CH₂O— | Me | 5 | 7 |
| O-59 | CH | CH | —CH₂O— | Me | 5 | 8 |
| O-60 | CH | CH | —CH₂O— | Me | 5 | 9 |
| O-61 | CH | CH | singlebond | H | 1 | 7 |
| O-62 | CH | CH | singlebond | H | 1 | 8 |
| O-63 | CH | CH | singlebond | H | 1 | 9 |
| O-64 | CH | CH | singlebond | H | 2 | 7 |
| O-65 | CH | CH | singlebond | H | 2 | 8 |
| O-66 | CH | CH | singlebond | H | 2 | 9 |
| O-67 | CH | CH | singlebond | H | 3 | 7 |
| O-68 | CH | CH | singlebond | H | 3 | 8 |
| O-69 | CH | CH | singlebond | H | 3 | 9 |
| O-70 | CH | CH | singlebond | H | 4 | 7 |
| O-71 | CH | CH | singlebond | H | 4 | 8 |
| O-72 | CH | CH | singlebond | H | 4 | 9 |
| O-73 | CH | CH | singlebond | H | 5 | 7 |
| O-74 | CH | CH | singlebond | H | 5 | 8 |
| O-75 | CH | CH | singlebond | H | 5 | 9 |
| O-76 | CH | CH | singlebond | Me | 1 | 7 |
| O-77 | CH | CH | singlebond | Me | 1 | 8 |
| O-78 | CH | CH | singlebond | Me | 1 | 9 |
| O-79 | CH | CH | singlebond | Me | 2 | 7 |
| O-80 | CH | CH | singlebond | Me | 2 | 8 |
| O-81 | CH | CH | singlebond | Me | 2 | 9 |
| O-82 | CH | CH | singlebond | Me | 3 | 7 |
| O-83 | CH | CH | singlebond | Me | 3 | 8 |
| O-84 | CH | CH | singlebond | Me | 3 | 9 |
| O-85 | CH | CH | singlebond | Me | 4 | 7 |
| O-86 | CH | CH | singlebond | Me | 4 | 8 |
| O-87 | CH | CH | singlebond | Me | 4 | 9 |
| O-88 | CH | CH | singlebond | Me | 5 | 7 |
| O-89 | CH | CH | singlebond | Me | 5 | 8 |
| O-90 | CH | CH | singlebond | Me | 5 | 9 |
| O-91 | N | CH | —O— | H | 1 | 7 |
| O-92 | N | CH | —O— | H | 1 | 8 |
| O-93 | N | CH | —O— | H | 1 | 9 |
| O-94 | N | CH | —O— | H | 2 | 7 |
| O-95 | N | CH | —O— | H | 2 | 8 |
| O-96 | N | CH | —O— | H | 2 | 9 |
| O-97 | N | CH | —O— | H | 3 | 7 |

TABLE 53-continued

| Compound No. | G¹ | G² | Q¹ | Rᵃ | n | m |
|---|---|---|---|---|---|---|
| O-98 | N | CH | —O— | H | 3 | 8 |
| O-99 | N | CH | —O— | H | 3 | 9 |
| O-100 | N | CH | —O— | H | 4 | 7 |
| O-101 | N | CH | —O— | H | 4 | 8 |
| O-102 | N | CH | —O— | H | 4 | 9 |
| O-103 | N | CH | —O— | H | 5 | 7 |
| O-104 | N | CH | —O— | H | 5 | 8 |
| O-105 | N | CH | —O— | H | 5 | 9 |
| O-106 | N | CH | —O— | Me | 1 | 7 |
| O-107 | N | CH | —O— | Me | 1 | 8 |
| O-108 | N | CH | —O— | Me | 1 | 9 |
| O-109 | N | CH | —O— | Me | 2 | 7 |
| O-110 | N | CH | —O— | Me | 2 | 8 |

TABLE 54

| Compound No. | G¹ | G² | Q¹ | Rᵃ | n | m |
|---|---|---|---|---|---|---|
| O-111 | N | CH | —O— | Me | 2 | 9 |
| O-112 | N | CH | —O— | Me | 3 | 7 |
| O-113 | N | CH | —O— | Me | 3 | 8 |
| O-114 | N | CH | —O— | Me | 3 | 9 |
| O-115 | N | CH | —O— | Me | 4 | 7 |
| O-116 | N | CH | —O— | Me | 4 | 8 |
| O-117 | N | CH | —O— | Me | 4 | 9 |
| O-118 | N | CH | —O— | Me | 5 | 7 |
| O-119 | N | CH | —O— | Me | 5 | 8 |
| O-120 | N | CH | —O— | Me | 5 | 9 |
| O-121 | N | CH | —CH₂O— | H | 1 | 7 |
| O-122 | N | CH | —CH₂O— | H | 1 | 8 |
| O-123 | N | CH | —CH₂O— | H | 1 | 9 |
| O-124 | N | CH | —CH₂O— | H | 2 | 7 |
| O-125 | N | CH | —CH₂O— | H | 2 | 8 |
| O-126 | N | CH | —CH₂O— | H | 2 | 9 |
| O-127 | N | CH | —CH₂O— | H | 3 | 7 |
| O-128 | N | CH | —CH₂O— | H | 3 | 8 |
| O-129 | N | CH | —CH₂O— | H | 3 | 9 |
| O-130 | N | CH | —CH₂O— | H | 4 | 7 |
| O-131 | N | CH | —CH₂O— | H | 4 | 8 |
| O-132 | N | CH | —CH₂O— | H | 4 | 9 |
| O-133 | N | CH | —CH₂O— | H | 5 | 7 |
| O-134 | N | CH | —CH₂O— | H | 5 | 8 |
| O-135 | N | CH | —CH₂O— | H | 5 | 9 |
| O-136 | N | CH | —CH₂O— | Me | 1 | 7 |
| O-137 | N | CH | —CH₂O— | Me | 1 | 8 |
| O-138 | N | CH | —CH₂O— | Me | 1 | 9 |
| O-139 | N | CH | —CH₂O— | Me | 2 | 7 |
| O-140 | N | CH | —CH₂O— | Me | 2 | 8 |
| O-141 | N | CH | —CH₂O— | Me | 2 | 9 |
| O-142 | N | CH | —CH₂O— | Me | 3 | 7 |
| O-143 | N | CH | —CH₂O— | Me | 3 | 8 |
| O-144 | N | CH | —CH₂O— | Me | 3 | 9 |
| O-145 | N | CH | —CH₂O— | Me | 4 | 7 |
| O-146 | N | CH | —CH₂O— | Me | 4 | 8 |
| O-147 | N | CH | —CH₂O— | Me | 4 | 9 |
| O-148 | N | CH | —CH₂O— | Me | 5 | 7 |
| O-149 | N | CH | —CH₂O— | Me | 5 | 8 |
| O-150 | N | CH | —CH₂O— | Me | 5 | 9 |
| O-151 | N | CH | singlebond | H | 1 | 7 |
| O-152 | N | CH | singlebond | H | 1 | 8 |
| O-153 | N | CH | singlebond | H | 1 | 9 |
| O-154 | N | CH | singlebond | H | 2 | 7 |
| O-155 | N | CH | singlebond | H | 2 | 8 |
| O-156 | N | CH | singlebond | H | 2 | 9 |
| O-157 | N | CH | singlebond | H | 3 | 7 |
| O-158 | N | CH | singlebond | H | 3 | 8 |
| O-159 | N | CH | singlebond | H | 3 | 9 |
| O-160 | N | CH | singlebond | H | 4 | 7 |
| O-161 | N | CH | singlebond | H | 4 | 8 |
| O-162 | N | CH | singlebond | H | 4 | 9 |
| O-163 | N | CH | singlebond | H | 5 | 7 |
| O-164 | N | CH | singlebond | H | 5 | 8 |
| O-165 | N | CH | singlebond | H | 5 | 9 |

TABLE 54-continued

| Compound No. | G¹ | G² | Q¹ | Rᵃ | n | m |
|---|---|---|---|---|---|---|
| O-166 | N | CH | singlebond | Me | 1 | 7 |
| O-167 | N | CH | singlebond | Me | 1 | 8 |
| O-168 | N | CH | singlebond | Me | 1 | 9 |
| O-169 | N | CH | singlebond | Me | 2 | 7 |
| O-170 | N | CH | singlebond | Me | 2 | 8 |
| O-171 | N | CH | singlebond | Me | 2 | 9 |
| O-172 | N | CH | singlebond | Me | 3 | 7 |
| O-173 | N | CH | singlebond | Me | 3 | 8 |
| O-174 | N | CH | singlebond | Me | 3 | 9 |
| O-175 | N | CH | singlebond | Me | 4 | 7 |
| O-176 | N | CH | singlebond | Me | 4 | 8 |
| O-177 | N | CH | singlebond | Me | 4 | 9 |
| O-178 | N | CH | singlebond | Me | 5 | 7 |
| O-179 | N | CH | singlebond | Me | 5 | 8 |
| O-180 | N | CH | singlebond | Me | 5 | 9 |
| O-181 | CH | N | —O— | H | 1 | 7 |
| O-182 | CH | N | —O— | H | 1 | 8 |
| O-183 | CH | N | —O— | H | 1 | 9 |
| O-184 | CH | N | —O— | H | 2 | 7 |
| O-185 | CH | N | —O— | H | 2 | 8 |
| O-186 | CH | N | —O— | H | 2 | 9 |
| O-187 | CH | N | —O— | H | 3 | 7 |
| O-188 | CH | N | —O— | H | 3 | 8 |
| O-189 | CH | N | —O— | H | 3 | 9 |
| O-190 | CH | N | —O— | H | 4 | 7 |
| O-191 | CH | N | —O— | H | 4 | 8 |
| O-192 | CH | N | —O— | H | 4 | 9 |
| O-193 | CH | N | —O— | H | 5 | 7 |
| O-194 | CH | N | —O— | H | 5 | 8 |
| O-195 | CH | N | —O— | H | 5 | 9 |
| O-196 | CH | N | —O— | Me | 1 | 7 |
| O-197 | CH | N | —O— | Me | 1 | 8 |
| O-198 | CH | N | —O— | Me | 1 | 9 |
| O-199 | CH | N | —O— | Me | 2 | 7 |
| O-200 | CH | N | —O— | Me | 2 | 8 |
| O-201 | CH | N | —O— | Me | 2 | 9 |
| O-202 | CH | N | —O— | Me | 3 | 7 |
| O-203 | CH | N | —O— | Me | 3 | 8 |
| O-204 | CH | N | —O— | Me | 3 | 9 |
| O-205 | CH | N | —O— | Me | 4 | 7 |
| O-206 | CH | N | —O— | Me | 4 | 8 |
| O-207 | CH | N | —O— | Me | 4 | 9 |
| O-208 | CH | N | —O— | Me | 5 | 7 |
| O-209 | CH | N | —O— | Me | 5 | 8 |
| O-210 | CH | N | —O— | Me | 5 | 9 |
| O-211 | CH | N | —CH₂O— | H | 1 | 7 |
| O-212 | CH | N | —CH₂O— | H | 1 | 8 |
| O-213 | CH | N | —CH₂O— | H | 1 | 9 |
| O-214 | CH | N | —CH₂O— | H | 2 | 7 |
| O-215 | CH | N | —CH₂O— | H | 2 | 8 |
| O-216 | CH | N | —CH₂O— | H | 2 | 9 |
| O-217 | CH | N | —CH₂O— | H | 3 | 7 |
| O-218 | CH | N | —CH₂O— | H | 3 | 8 |
| O-219 | CH | N | —CH₂O— | H | 3 | 9 |
| O-220 | CH | N | —CH₂O— | H | 4 | 7 |

TABLE 55

| Compound No. | G¹ | G² | Q¹ | Rᵃ | n | m |
|---|---|---|---|---|---|---|
| O-221 | CH | N | —CH₂O— | H | 4 | 8 |
| O-222 | CH | N | —CH₂O— | H | 4 | 9 |
| O-223 | CH | N | —CH₂O— | H | 5 | 7 |
| O-224 | CH | N | —CH₂O— | H | 5 | 8 |
| O-225 | CH | N | —CH₂O— | H | 5 | 9 |
| O-226 | CH | N | —CH₂O— | Me | 1 | 7 |
| O-227 | CH | N | —CH₂O— | Me | 1 | 8 |
| O-228 | CH | N | —CH₂O— | Me | 1 | 9 |
| O-229 | CH | N | —CH₂O— | Me | 2 | 7 |
| O-230 | CH | N | —CH₂O— | Me | 2 | 8 |
| O-231 | CH | N | —CH₂O— | Me | 2 | 9 |
| O-232 | CH | N | —CH₂O— | Me | 3 | 7 |
| O-233 | CH | N | —CH₂O— | Me | 3 | 8 |

TABLE 55-continued

| Compound No. | G¹ | G² | Q¹ | R$^a$ | n | m |
| --- | --- | --- | --- | --- | --- | --- |
| O-234 | CH | N | —CH$_2$O— | Me | 3 | 9 |
| O-235 | CH | N | —CH$_2$O— | Me | 4 | 7 |
| O-236 | CH | N | —CH$_2$O— | Me | 4 | 8 |
| O-237 | CH | N | —CH$_2$O— | Me | 4 | 9 |
| O-238 | CH | N | —CH$_2$O— | Me | 5 | 7 |
| O-239 | CH | N | —CH$_2$O— | Me | 5 | 8 |
| O-240 | CH | N | —CH$_2$O— | Me | 5 | 9 |
| O-241 | CH | N | singlebond | H | 1 | 7 |
| O-242 | CH | N | singlebond | H | 1 | 8 |
| O-243 | CH | N | singlebond | H | 1 | 9 |
| O-244 | CH | N | singlebond | H | 2 | 7 |
| O-245 | CH | N | singlebond | H | 2 | 8 |
| O-246 | CH | N | singlebond | H | 2 | 9 |
| O-247 | CH | N | singlebond | H | 3 | 7 |
| O-248 | CH | N | singlebond | H | 3 | 8 |
| O-249 | CH | N | singlebond | H | 3 | 9 |
| O-250 | CH | N | singlebond | H | 4 | 7 |
| O-251 | CH | N | singlebond | H | 4 | 8 |
| O-252 | CH | N | singlebond | H | 4 | 9 |
| O-253 | CH | N | singlebond | H | 5 | 7 |
| O-254 | CH | N | singlebond | H | 5 | 8 |
| O-255 | CH | N | singlebond | H | 5 | 9 |
| O-256 | CH | N | singlebond | Me | 1 | 7 |
| O-257 | CH | N | singlebond | Me | 1 | 8 |
| O-258 | CH | N | singlebond | Me | 1 | 9 |
| O-259 | CH | N | singlebond | Me | 2 | 7 |
| O-260 | CH | N | singlebond | Me | 2 | 8 |
| O-261 | CH | N | singlebond | Me | 2 | 9 |
| O-262 | CH | N | singlebond | Me | 3 | 7 |
| O-263 | CH | N | singlebond | Me | 3 | 8 |
| O-264 | CH | N | singlebond | Me | 3 | 9 |
| O-265 | CH | N | singlebond | Me | 4 | 7 |
| O-266 | CH | N | singlebond | Me | 4 | 8 |
| O-267 | CH | N | singlebond | Me | 4 | 9 |
| O-268 | CH | N | singlebond | Me | 5 | 7 |
| O-269 | CH | N | singlebond | Me | 5 | 8 |
| O-270 | CH | N | singlebond | Me | 5 | 9 |

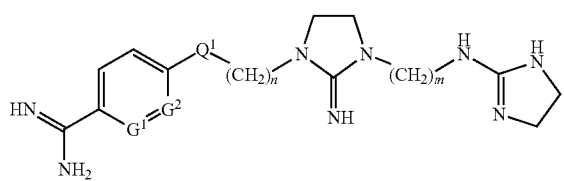

TABLE 56

| Compound No. | G¹ | G² | Q¹ | n | m |
| --- | --- | --- | --- | --- | --- |
| P-1 | CH | CH | —O— | 1 | 7 |
| P-2 | CH | CH | —O— | 1 | 8 |
| P-3 | CH | CH | —O— | 1 | 9 |
| P-4 | CH | CH | —O— | 2 | 7 |
| P-5 | CH | CH | —O— | 2 | 8 |
| P-6 | CH | CH | —O— | 2 | 9 |
| P-7 | CH | CH | —O— | 3 | 7 |
| P-8 | CH | CH | —O— | 3 | 8 |
| P-9 | CH | CH | —O— | 3 | 9 |
| P-10 | CH | CH | —O— | 4 | 7 |
| P-11 | CH | CH | —O— | 4 | 8 |
| P-12 | CH | CH | —O— | 4 | 9 |
| P-13 | CH | CH | —O— | 5 | 7 |
| P-14 | CH | CH | —O— | 5 | 8 |
| P-15 | CH | CH | —O— | 5 | 9 |
| P-16 | CH | CH | —CH$_2$O— | 1 | 7 |
| P-17 | CH | CH | —CH$_2$O— | 1 | 8 |
| P-18 | CH | CH | —CH$_2$O— | 1 | 9 |
| P-19 | CH | CH | —CH$_2$O— | 2 | 7 |
| P-20 | CH | CH | —CH$_2$O— | 2 | 8 |
| P-21 | CH | CH | —CH$_2$O— | 2 | 9 |
| P-22 | CH | CH | —CH$_2$O— | 3 | 7 |
| P-23 | CH | CH | —CH$_2$O— | 3 | 8 |
| P-24 | CH | CH | —CH$_2$O— | 3 | 9 |
| P-25 | CH | CH | —CH$_2$O— | 4 | 7 |
| P-26 | CH | CH | —CH$_2$O— | 4 | 8 |
| P-27 | CH | CH | —CH$_2$O— | 4 | 9 |
| P-28 | CH | CH | —CH$_2$O— | 5 | 7 |
| P-29 | CH | CH | —CH$_2$O— | 5 | 8 |
| P-30 | CH | CH | —CH$_2$O— | 5 | 9 |
| P-31 | CH | CH | singlebond | 1 | 7 |
| P-32 | CH | CH | singlebond | 1 | 8 |
| P-33 | CH | CH | singlebond | 1 | 9 |
| P-34 | CH | CH | singlebond | 2 | 7 |
| P-35 | CH | CH | singlebond | 2 | 8 |
| P-36 | CH | CH | singlebond | 2 | 9 |
| P-37 | CH | CH | singlebond | 3 | 7 |
| P-38 | CH | CH | singlebond | 3 | 8 |
| P-39 | CH | CH | singlebond | 3 | 9 |
| P-40 | CH | CH | singlebond | 4 | 7 |
| P-41 | CH | CH | singlebond | 4 | 8 |
| P-42 | CH | CH | singlebond | 4 | 9 |
| P-43 | CH | CH | singlebond | 5 | 7 |
| P-44 | CH | CH | singlebond | 5 | 8 |
| P-45 | CH | CH | singlebond | 5 | 9 |
| P-46 | N | CH | —O— | 1 | 7 |
| P-47 | N | CH | —O— | 1 | 8 |
| P-48 | N | CH | —O— | 1 | 9 |
| P-49 | N | CH | —O— | 2 | 7 |
| P-50 | N | CH | —O— | 2 | 8 |
| P-51 | N | CH | —O— | 2 | 9 |
| P-52 | N | CH | —O— | 3 | 7 |
| P-53 | N | CH | —O— | 3 | 8 |
| P-54 | N | CH | —O— | 3 | 9 |
| P-55 | N | CH | —O— | 4 | 7 |
| P-56 | N | CH | —O— | 4 | 8 |
| P-57 | N | CH | —O— | 4 | 9 |
| P-58 | N | CH | —O— | 5 | 7 |
| P-59 | N | CH | —O— | 5 | 8 |
| P-60 | N | CH | —O— | 5 | 9 |
| P-61 | N | CH | —CH$_2$O— | 1 | 7 |
| P-62 | N | CH | —CH$_2$O— | 1 | 8 |
| P-63 | N | CH | —CH$_2$O— | 1 | 9 |
| P-64 | N | CH | —CH$_2$O— | 2 | 7 |
| P-65 | N | CH | —CH$_2$O— | 2 | 8 |
| P-66 | N | CH | —CH$_2$O— | 2 | 9 |
| P-67 | N | CH | —CH$_2$O— | 3 | 7 |
| P-68 | N | CH | —CH$_2$O— | 3 | 8 |
| P-69 | N | CH | —CH$_2$O— | 3 | 9 |
| P-70 | N | CH | —CH$_2$O— | 4 | 7 |
| P-71 | N | CH | —CH$_2$O— | 4 | 8 |
| P-72 | N | CH | —CH$_2$O— | 4 | 9 |
| P-73 | N | CH | —CH$_2$O— | 5 | 7 |
| P-74 | N | CH | —CH$_2$O— | 5 | 8 |
| P-75 | N | CH | —CH$_2$O— | 5 | 9 |
| P-76 | N | CH | singlebond | 1 | 7 |
| P-77 | N | CH | singlebond | 1 | 8 |
| P-78 | N | CH | singlebond | 1 | 9 |
| P-79 | N | CH | singlebond | 2 | 7 |
| P-80 | N | CH | singlebond | 2 | 8 |
| P-81 | N | CH | singlebond | 2 | 9 |
| P-82 | N | CH | singlebond | 3 | 7 |
| P-83 | N | CH | singlebond | 3 | 8 |
| P-84 | N | CH | singlebond | 3 | 9 |
| P-85 | N | CH | singlebond | 4 | 7 |
| P-86 | N | CH | singlebond | 4 | 8 |
| P-87 | N | CH | singlebond | 4 | 9 |
| P-88 | N | CH | singlebond | 5 | 7 |
| P-89 | N | CH | singlebond | 5 | 8 |
| P-90 | N | CH | singlebond | 5 | 9 |
| P-91 | CH | N | —O— | 1 | 7 |
| P-92 | CH | N | —O— | 1 | 8 |
| P-93 | CH | N | —O— | 1 | 9 |
| P-94 | CH | N | —O— | 2 | 7 |
| P-95 | CH | N | —O— | 2 | 8 |
| P-96 | CH | N | —O— | 2 | 9 |

TABLE 56-continued

| Compound No. | G¹ | G² | Q¹ | n | m |
|---|---|---|---|---|---|
| P-97 | CH | N | —O— | 3 | 7 |
| P-98 | CH | N | —O— | 3 | 8 |
| P-99 | CH | N | —O— | 3 | 9 |
| P-100 | CH | N | —O— | 4 | 7 |
| P-101 | CH | N | —O— | 4 | 8 |
| P-102 | CH | N | —O— | 4 | 9 |
| P-103 | CH | N | —O— | 5 | 7 |
| P-104 | CH | N | —O— | 5 | 8 |
| P-105 | CH | N | —O— | 5 | 9 |
| P-106 | CH | N | —CH₂O— | 1 | 7 |
| P-107 | CH | N | —CH₂O— | 1 | 8 |
| P-108 | CH | N | —CH₂O— | 1 | 9 |
| P-109 | CH | N | —CH₂O— | 2 | 7 |
| P-110 | CH | N | —CH₂O— | 2 | 8 |

TABLE 57

| Compound No. | G¹ | G² | Q¹ | n | m |
|---|---|---|---|---|---|
| P-111 | CH | N | —CH₂O— | 2 | 9 |
| P-112 | CH | N | —CH₂O— | 3 | 7 |
| P-113 | CH | N | —CH₂O— | 3 | 8 |
| P-114 | CH | N | —CH₂O— | 3 | 9 |
| P-115 | CH | N | —CH₂O— | 4 | 7 |
| P-116 | CH | N | —CH₂O— | 4 | 8 |
| P-117 | CH | N | —CH₂O— | 4 | 9 |
| P-118 | CH | N | —CH₂O— | 5 | 7 |
| P-119 | CH | N | —CH₂O— | 5 | 8 |
| P-120 | CH | N | —CH₂O— | 5 | 9 |
| P-121 | CH | N | singlebond | 1 | 7 |
| P-122 | CH | N | singlebond | 1 | 8 |
| P-123 | CH | N | singlebond | 1 | 9 |
| P-124 | CH | N | singlebond | 2 | 7 |
| P-125 | CH | N | singlebond | 2 | 8 |
| P-126 | CH | N | singlebond | 2 | 9 |
| P-127 | CH | N | singlebond | 3 | 7 |
| P-128 | CH | N | singlebond | 3 | 8 |
| P-129 | CH | N | singlebond | 3 | 9 |
| P-130 | CH | N | singlebond | 4 | 7 |
| P-131 | CH | N | singlebond | 4 | 8 |
| P-132 | CH | N | singlebond | 4 | 9 |
| P-133 | CH | N | singlebond | 5 | 7 |
| P-134 | CH | N | singlebond | 5 | 8 |
| P-135 | CH | N | singlebond | 5 | 9 |

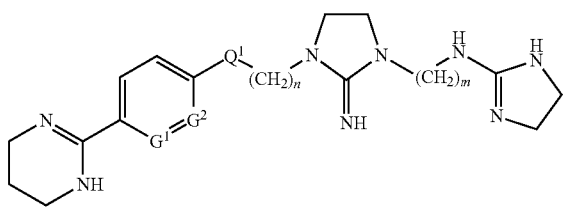

TABLE 58

| Compound No. | G¹ | G² | Q¹ | n | m |
|---|---|---|---|---|---|
| Q-1 | CH | CH | —O— | 1 | 7 |
| Q-2 | CH | CH | —O— | 1 | 8 |
| Q-3 | CH | CH | —O— | 1 | 9 |
| Q-4 | CH | CH | —O— | 2 | 7 |
| Q-5 | CH | CH | —O— | 2 | 8 |
| Q-6 | CH | CH | —O— | 2 | 9 |
| Q-7 | CH | CH | —O— | 3 | 7 |
| Q-8 | CH | CH | —O— | 3 | 8 |

TABLE 58-continued

| Compound No. | G¹ | G² | Q¹ | n | m |
|---|---|---|---|---|---|
| Q-9 | CH | CH | —O— | 3 | 9 |
| Q-10 | CH | CH | —O— | 4 | 7 |
| Q-11 | CH | CH | —O— | 4 | 8 |
| Q-12 | CH | CH | —O— | 4 | 9 |
| Q-13 | CH | CH | —O— | 5 | 7 |
| Q-14 | CH | CH | —O— | 5 | 8 |
| Q-15 | CH | CH | —O— | 5 | 9 |
| Q-16 | CH | CH | —CH₂O— | 1 | 7 |
| Q-17 | CH | CH | —CH₂O— | 1 | 8 |
| Q-18 | CH | CH | —CH₂O— | 1 | 9 |
| Q-19 | CH | CH | —CH₂O— | 2 | 7 |
| Q-20 | CH | CH | —CH₂O— | 2 | 8 |
| Q-21 | CH | CH | —CH₂O— | 2 | 9 |
| Q-22 | CH | CH | —CH₂O— | 3 | 7 |
| Q-23 | CH | CH | —CH₂O— | 3 | 8 |
| Q-24 | CH | CH | —CH₂O— | 3 | 9 |
| Q-25 | CH | CH | —CH₂O— | 4 | 7 |
| Q-26 | CH | CH | —CH₂O— | 4 | 8 |
| Q-27 | CH | CH | —CH₂O— | 4 | 9 |
| Q-28 | CH | CH | —CH₂O— | 5 | 7 |
| Q-29 | CH | CH | —CH₂O— | 5 | 8 |
| Q-30 | CH | CH | —CH₂O— | 5 | 9 |
| Q-31 | CH | CH | singlebond | 1 | 7 |
| Q-32 | CH | CH | singlebond | 1 | 8 |
| Q-33 | CH | CH | singlebond | 1 | 9 |
| Q-34 | CH | CH | singlebond | 2 | 7 |
| Q-35 | CH | CH | singlebond | 2 | 8 |
| Q-36 | CH | CH | singlebond | 2 | 9 |
| Q-37 | CH | CH | singlebond | 3 | 7 |
| Q-38 | CH | CH | singlebond | 3 | 8 |
| Q-39 | CH | CH | singlebond | 3 | 9 |
| Q-40 | CH | CH | singlebond | 4 | 7 |
| Q-41 | CH | CH | singlebond | 4 | 8 |
| Q-42 | CH | CH | singlebond | 4 | 9 |
| Q-43 | CH | CH | singlebond | 5 | 7 |
| Q-44 | CH | CH | singlebond | 5 | 8 |
| Q-45 | CH | CH | singlebond | 5 | 9 |
| Q-46 | N | CH | —O— | 1 | 7 |
| Q-47 | N | CH | —O— | 1 | 8 |
| Q-48 | N | CH | —O— | 1 | 9 |
| Q-49 | N | CH | —O— | 2 | 7 |
| Q-50 | N | CH | —O— | 2 | 8 |
| Q-51 | N | CH | —O— | 2 | 9 |
| Q-52 | N | CH | —O— | 3 | 7 |
| Q-53 | N | CH | —O— | 3 | 8 |
| Q-54 | N | CH | —O— | 3 | 9 |
| Q-55 | N | CH | —O— | 4 | 7 |
| Q-56 | N | CH | —O— | 4 | 8 |
| Q-57 | N | CH | —O— | 4 | 9 |
| Q-58 | N | CH | —O— | 5 | 7 |
| Q-59 | N | CH | —O— | 5 | 8 |
| Q-60 | N | CH | —O— | 5 | 9 |
| Q-61 | N | CH | —CH₂O— | 1 | 7 |
| Q-62 | N | CH | —CH₂O— | 1 | 8 |
| Q-63 | N | CH | —CH₂O— | 1 | 9 |
| Q-64 | N | CH | —CH₂O— | 2 | 7 |
| Q-65 | N | CH | —CH₂O— | 2 | 8 |
| Q-66 | N | CH | —CH₂O— | 2 | 9 |
| Q-67 | N | CH | —CH₂O— | 3 | 7 |
| Q-68 | N | CH | —CH₂O— | 3 | 8 |
| Q-69 | N | CH | —CH₂O— | 3 | 9 |
| Q-70 | N | CH | —CH₂O— | 4 | 7 |
| Q-71 | N | CH | —CH₂O— | 4 | 8 |
| Q-72 | N | CH | —CH₂O— | 4 | 9 |
| Q-73 | N | CH | —CH₂O— | 5 | 7 |
| Q-74 | N | CH | —CH₂O— | 5 | 8 |
| Q-75 | N | CH | —CH₂O— | 5 | 9 |
| Q-76 | N | CH | singlebond | 1 | 7 |
| Q-77 | N | CH | singlebond | 1 | 8 |
| Q-78 | N | CH | singlebond | 1 | 9 |
| Q-79 | N | CH | singlebond | 2 | 7 |
| Q-80 | N | CH | singlebond | 2 | 8 |
| Q-81 | N | CH | singlebond | 2 | 9 |
| Q-82 | N | CH | singlebond | 3 | 7 |
| Q-83 | N | CH | singlebond | 3 | 8 |
| Q-84 | N | CH | singlebond | 3 | 9 |
| Q-85 | N | CH | singlebond | 4 | 7 |

TABLE 58-continued

| Compound No. | G¹ | G² | Q¹ | n | m |
|---|---|---|---|---|---|
| Q-86 | N | CH | singlebond | 4 | 8 |
| Q-87 | N | CH | singlebond | 4 | 9 |
| Q-88 | N | CH | singlebond | 5 | 7 |
| Q-89 | N | CH | singlebond | 5 | 8 |
| Q-90 | N | CH | singlebond | 5 | 9 |
| Q-91 | CH | N | —O— | 1 | 7 |
| Q-92 | CH | N | —O— | 1 | 8 |
| Q-93 | CH | N | —O— | 1 | 9 |
| Q-94 | CH | N | —O— | 2 | 7 |
| Q-95 | CH | N | —O— | 2 | 8 |
| Q-96 | CH | N | —O— | 2 | 9 |
| Q-97 | CH | N | —O— | 3 | 7 |
| Q-98 | CH | N | —O— | 3 | 8 |
| Q-99 | CH | N | —O— | 3 | 9 |
| Q-100 | CH | N | —O— | 4 | 7 |
| Q-101 | CH | N | —O— | 4 | 8 |
| Q-102 | CH | N | —O— | 4 | 9 |
| Q-103 | CH | N | —O— | 5 | 7 |
| Q-104 | CH | N | —O— | 5 | 8 |
| Q-105 | CH | N | —O— | 5 | 9 |
| Q-106 | CH | N | —CH₂O— | 1 | 7 |
| Q-107 | CH | N | —CH₂O— | 1 | 8 |
| Q-108 | CH | N | —CH₂O— | 1 | 9 |
| Q-109 | CH | N | —CH₂O— | 2 | 7 |
| Q-110 | CH | N | —CH₂O— | 2 | 8 |

TABLE 59

| Compound No. | G¹ | G² | Q¹ | n | m |
|---|---|---|---|---|---|
| Q-111 | CH | N | —CH₂O— | 2 | 9 |
| Q-112 | CH | N | —CH₂O— | 3 | 7 |
| Q-113 | CH | N | —CH₂O— | 3 | 8 |
| Q-114 | CH | N | —CH₂O— | 3 | 9 |
| Q-115 | CH | N | —CH₂O— | 4 | 7 |
| Q-116 | CH | N | —CH₂O— | 4 | 8 |
| Q-117 | CH | N | —CH₂O— | 4 | 9 |
| Q-118 | CH | N | —CH₂O— | 5 | 7 |
| Q-119 | CH | N | —CH₂O— | 5 | 8 |
| Q-120 | CH | N | —CH₂O— | 5 | 9 |
| Q-121 | CH | N | singlebond | 1 | 7 |
| Q-122 | CH | N | singlebond | 1 | 8 |
| Q-123 | CH | N | singlebond | 1 | 9 |
| Q-124 | CH | N | singlebond | 2 | 7 |
| Q-125 | CH | N | singlebond | 2 | 8 |
| Q-126 | CH | N | singlebond | 2 | 9 |
| Q-127 | CH | N | singlebond | 3 | 7 |
| Q-128 | CH | N | singlebond | 3 | 8 |
| Q-129 | CH | N | singlebond | 3 | 9 |
| Q-130 | CH | N | singlebond | 4 | 7 |
| Q-131 | CH | N | singlebond | 4 | 8 |
| Q-132 | CH | N | singlebond | 4 | 9 |
| Q-133 | CH | N | singlebond | 5 | 7 |
| Q-134 | CH | N | singlebond | 5 | 8 |
| Q-135 | CH | N | singlebond | 5 | 9 |

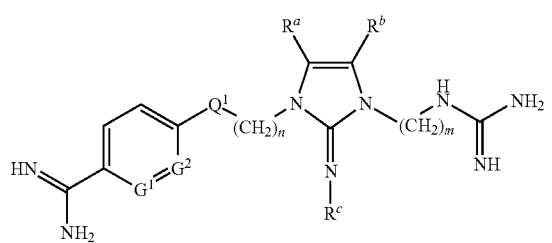

TABLE 60

| Compound No. | G¹ | G² | Q¹ | Rᵃ | Rᵇ | Rᶜ | n | m |
|---|---|---|---|---|---|---|---|---|
| R-1 | CH | CH | —O— | Me | H | H | 1 | 7 |
| R-2 | CH | CH | —O— | Me | H | H | 1 | 8 |
| R-3 | CH | CH | —O— | Me | H | H | 1 | 9 |
| R-4 | CH | CH | —O— | Me | H | H | 2 | 7 |
| R-5 | CH | CH | —O— | Me | H | H | 2 | 8 |
| R-6 | CH | CH | —O— | Me | H | H | 2 | 9 |
| R-7 | CH | CH | —O— | Me | H | H | 3 | 7 |
| R-8 | CH | CH | —O— | Me | H | H | 3 | 8 |
| R-9 | CH | CH | —O— | Me | H | H | 3 | 9 |
| R-10 | CH | CH | —O— | Me | H | H | 4 | 7 |
| R-11 | CH | CH | —O— | Me | H | H | 4 | 8 |
| R-12 | CH | CH | —O— | Me | H | H | 4 | 9 |
| R-13 | CH | CH | —O— | Me | H | H | 5 | 7 |
| R-14 | CH | CH | —O— | Me | H | H | 5 | 8 |
| R-15 | CH | CH | —O— | Me | H | H | 5 | 9 |
| R-16 | CH | CH | —O— | H | H | Me | 1 | 7 |
| R-17 | CH | CH | —O— | H | H | Me | 1 | 8 |
| R-18 | CH | CH | —O— | H | H | Me | 1 | 9 |
| R-19 | CH | CH | —O— | H | H | Me | 2 | 7 |
| R-20 | CH | CH | —O— | H | H | Me | 2 | 8 |
| R-21 | CH | CH | —O— | H | H | Me | 2 | 9 |
| R-22 | CH | CH | —O— | H | H | Me | 3 | 7 |
| R-23 | CH | CH | —O— | H | H | Me | 3 | 8 |
| R-24 | CH | CH | —O— | H | H | Me | 3 | 9 |
| R-25 | CH | CH | —O— | H | H | Me | 4 | 7 |
| R-26 | CH | CH | —O— | H | H | Me | 4 | 8 |
| R-27 | CH | CH | —O— | H | H | Me | 4 | 9 |
| R-28 | CH | CH | —O— | H | H | Me | 5 | 7 |
| R-29 | CH | CH | —O— | H | H | Me | 5 | 8 |
| R-30 | CH | CH | —O— | H | H | Me | 5 | 9 |
| R-31 | CH | CH | —O— | Me | Me | H | 1 | 7 |
| R-32 | CH | CH | —O— | Me | Me | H | 1 | 8 |
| R-33 | CH | CH | —O— | Me | Me | H | 1 | 9 |
| R-34 | CH | CH | —O— | Me | Me | H | 2 | 7 |
| R-35 | CH | CH | —O— | Me | Me | H | 2 | 8 |
| R-36 | CH | CH | —O— | Me | Me | H | 2 | 9 |
| R-37 | CH | CH | —O— | Me | Me | H | 3 | 7 |
| R-38 | CH | CH | —O— | Me | Me | H | 3 | 8 |
| R-39 | CH | CH | —O— | Me | Me | H | 3 | 9 |
| R-40 | CH | CH | —O— | Me | Me | H | 4 | 7 |
| R-41 | CH | CH | —O— | Me | Me | H | 4 | 8 |
| R-42 | CH | CH | —O— | Me | Me | H | 4 | 9 |
| R-43 | CH | CH | —O— | Me | Me | H | 5 | 7 |
| R-44 | CH | CH | —O— | Me | Me | H | 5 | 8 |
| R-45 | CH | CH | —O— | Me | Me | H | 5 | 9 |
| R-46 | CH | CH | —O— | H | Me | Me | 1 | 7 |
| R-47 | CH | CH | —O— | H | Me | Me | 1 | 8 |
| R-48 | CH | CH | —O— | H | Me | Me | 1 | 9 |
| R-49 | CH | CH | —O— | H | Me | Me | 2 | 7 |
| R-50 | CH | CH | —O— | H | Me | Me | 2 | 8 |
| R-51 | CH | CH | —O— | H | Me | Me | 2 | 9 |
| R-52 | CH | CH | —O— | H | Me | Me | 3 | 7 |
| R-53 | CH | CH | —O— | H | Me | Me | 3 | 8 |
| R-54 | CH | CH | —O— | H | Me | Me | 3 | 9 |
| R-55 | CH | CH | —O— | H | Me | Me | 4 | 7 |
| R-56 | CH | CH | —O— | H | Me | Me | 4 | 8 |
| R-57 | CH | CH | —O— | H | Me | Me | 4 | 9 |
| R-58 | CH | CH | —O— | H | Me | Me | 5 | 7 |
| R-59 | CH | CH | —O— | H | Me | Me | 5 | 8 |
| R-60 | CH | CH | —O— | H | Me | Me | 5 | 9 |
| R-61 | CH | CH | —CH₂O— | Me | H | H | 1 | 7 |
| R-62 | CH | CH | —CH₂O— | Me | H | H | 1 | 8 |
| R-63 | CH | CH | —CH₂O— | Me | H | H | 1 | 9 |
| R-64 | CH | CH | —CH₂O— | Me | H | H | 2 | 7 |
| R-65 | CH | CH | —CH₂O— | Me | H | H | 2 | 8 |
| R-66 | CH | CH | —CH₂O— | Me | H | H | 2 | 9 |
| R-67 | CH | CH | —CH₂O— | Me | H | H | 3 | 7 |
| R-68 | CH | CH | —CH₂O— | Me | H | H | 3 | 8 |
| R-69 | CH | CH | —CH₂O— | Me | H | H | 3 | 9 |
| R-70 | CH | CH | —CH₂O— | Me | H | H | 4 | 7 |
| R-71 | CH | CH | —CH₂O— | Me | H | H | 4 | 8 |
| R-72 | CH | CH | —CH₂O— | Me | H | H | 4 | 9 |
| R-73 | CH | CH | —CH₂O— | Me | H | H | 5 | 7 |
| R-74 | CH | CH | —CH₂O— | Me | H | H | 5 | 8 |
| R-75 | CH | CH | —CH₂O— | Me | H | H | 5 | 9 |
| R-76 | CH | CH | —CH₂O— | H | H | Me | 1 | 7 |
| R-77 | CH | CH | —CH₂O— | H | H | Me | 1 | 8 |

TABLE 60-continued

| Compound No. | G¹ | G² | Q¹ | $R^a$ | $R^b$ | $R^c$ | n | m |
|---|---|---|---|---|---|---|---|---|
| R-78 | CH | CH | —CH₂O— | H | H | Me | 1 | 9 |
| R-79 | CH | CH | —CH₂O— | H | H | Me | 2 | 7 |
| R-80 | CH | CH | —CH₂O— | H | H | Me | 2 | 8 |
| R-81 | CH | CH | —CH₂O— | H | H | Me | 2 | 9 |
| R-82 | CH | CH | —CH₂O— | H | H | Me | 3 | 7 |
| R-83 | CH | CH | —CH₂O— | H | H | Me | 3 | 8 |
| R-84 | CH | CH | —CH₂O— | H | H | Me | 3 | 9 |
| R-85 | CH | CH | —CH₂O— | H | H | Me | 4 | 7 |
| R-86 | CH | CH | —CH₂O— | H | H | Me | 4 | 8 |
| R-87 | CH | CH | —CH₂O— | H | H | Me | 4 | 9 |
| R-88 | CH | CH | —CH₂O— | H | H | Me | 5 | 7 |
| R-89 | CH | CH | —CH₂O— | H | H | Me | 5 | 8 |
| R-90 | CH | CH | —CH₂O— | H | H | Me | 5 | 9 |
| R-91 | CH | CH | —CH₂O— | Me | Me | H | 1 | 7 |
| R-92 | CH | CH | —CH₂O— | Me | Me | H | 1 | 8 |
| R-93 | CH | CH | —CH₂O— | Me | Me | H | 1 | 9 |
| R-94 | CH | CH | —CH₂O— | Me | Me | H | 2 | 7 |
| R-95 | CH | CH | —CH₂O— | Me | Me | H | 2 | 8 |
| R-96 | CH | CH | —CH₂O— | Me | Me | H | 2 | 9 |
| R-97 | CH | CH | —CH₂O— | Me | Me | H | 3 | 7 |
| R-98 | CH | CH | —CH₂O— | Me | Me | H | 3 | 8 |
| R-99 | CH | CH | —CH₂O— | Me | Me | H | 3 | 9 |
| R-100 | CH | CH | —CH₂O— | Me | Me | H | 4 | 7 |
| R-101 | CH | CH | —CH₂O— | Me | Me | H | 4 | 8 |
| R-102 | CH | CH | —CH₂O— | Me | Me | H | 4 | 9 |
| R-103 | CH | CH | —CH₂O— | Me | Me | H | 5 | 7 |
| R-104 | CH | CH | —CH₂O— | Me | Me | H | 5 | 8 |
| R-105 | CH | CH | —CH₂O— | Me | Me | H | 5 | 9 |
| R-106 | CH | CH | —CH₂O— | H | Me | Me | 1 | 7 |
| R-107 | CH | CH | —CH₂O— | H | Me | Me | 1 | 8 |
| R-108 | CH | CH | —CH₂O— | H | Me | Me | 1 | 9 |
| R-109 | CH | CH | —CH₂O— | H | Me | Me | 2 | 7 |
| R-110 | CH | CH | —CH₂O— | H | Me | Me | 2 | 8 |

TABLE 61

| Compound No. | G¹ | G² | Q¹ | $R^a$ | $R^b$ | $R^c$ | n | m |
|---|---|---|---|---|---|---|---|---|
| R-111 | CH | CH | —CH₂O— | H | Me | Me | 2 | 9 |
| R-112 | CH | CH | —CH₂O— | H | Me | Me | 3 | 7 |
| R-113 | CH | CH | —CH₂O— | H | Me | Me | 3 | 8 |
| R-114 | CH | CH | —CH₂O— | H | Me | Me | 3 | 9 |
| R-115 | CH | CH | —CH₂O— | H | Me | Me | 4 | 7 |
| R-116 | CH | CH | —CH₂O— | H | Me | Me | 4 | 8 |
| R-117 | CH | CH | —CH₂O— | H | Me | Me | 4 | 9 |
| R-118 | CH | CH | —CH₂O— | H | Me | Me | 5 | 7 |
| R-119 | CH | CH | —CH₂O— | H | Me | Me | 5 | 8 |
| R-120 | CH | CH | —CH₂O— | H | Me | Me | 5 | 9 |
| R-121 | CH | CH | singlebond | Me | H | H | 1 | 7 |
| R-122 | CH | CH | singlebond | Me | H | H | 1 | 8 |
| R-123 | CH | CH | singlebond | Me | H | H | 1 | 9 |
| R-124 | CH | CH | singlebond | Me | H | H | 2 | 7 |
| R-125 | CH | CH | singlebond | Me | H | H | 2 | 8 |
| R-126 | CH | CH | singlebond | Me | H | H | 2 | 9 |
| R-127 | CH | CH | singlebond | Me | H | H | 3 | 7 |
| R-128 | CH | CH | singlebond | Me | H | H | 3 | 8 |
| R-129 | CH | CH | singlebond | Me | H | H | 3 | 9 |
| R-130 | CH | CH | singlebond | Me | H | H | 4 | 7 |
| R-131 | CH | CH | singlebond | Me | H | H | 4 | 8 |
| R-132 | CH | CH | singlebond | Me | H | H | 4 | 9 |
| R-133 | CH | CH | singlebond | Me | H | H | 5 | 7 |
| R-134 | CH | CH | singlebond | Me | H | H | 5 | 8 |
| R-135 | CH | CH | singlebond | Me | H | H | 5 | 9 |
| R-136 | CH | CH | singlebond | H | H | Me | 1 | 7 |
| R-137 | CH | CH | singlebond | H | H | Me | 1 | 8 |
| R-138 | CH | CH | singlebond | H | H | Me | 1 | 9 |
| R-139 | CH | CH | singlebond | H | H | Me | 2 | 7 |
| R-140 | CH | CH | singlebond | H | H | Me | 2 | 8 |
| R-141 | CH | CH | singlebond | H | H | Me | 2 | 9 |
| R-142 | CH | CH | singlebond | H | H | Me | 3 | 7 |
| R-143 | CH | CH | singlebond | H | H | Me | 3 | 8 |
| R-144 | CH | CH | singlebond | H | H | Me | 3 | 9 |
| R-145 | CH | CH | singlebond | H | H | Me | 4 | 7 |

TABLE 61-continued

| Compound No. | G¹ | G² | Q¹ | $R^a$ | $R^b$ | $R^c$ | n | m |
|---|---|---|---|---|---|---|---|---|
| R-146 | CH | CH | singlebond | H | H | Me | 4 | 8 |
| R-147 | CH | CH | singlebond | H | H | Me | 4 | 9 |
| R-148 | CH | CH | singlebond | H | H | Me | 5 | 7 |
| R-149 | CH | CH | singlebond | H | H | Me | 5 | 8 |
| R-150 | CH | CH | singlebond | H | H | Me | 5 | 9 |
| R-151 | CH | CH | singlebond | Me | Me | H | 1 | 7 |
| R-152 | CH | CH | singlebond | Me | Me | H | 1 | 8 |
| R-153 | CH | CH | singlebond | Me | Me | H | 1 | 9 |
| R-154 | CH | CH | singlebond | Me | Me | H | 2 | 7 |
| R-155 | CH | CH | singlebond | Me | Me | H | 2 | 8 |
| R-156 | CH | CH | singlebond | Me | Me | H | 2 | 9 |
| R-157 | CH | CH | singlebond | Me | Me | H | 3 | 7 |
| R-158 | CH | CH | singlebond | Me | Me | H | 3 | 8 |
| R-159 | CH | CH | singlebond | Me | Me | H | 3 | 9 |
| R-160 | CH | CH | singlebond | Me | Me | H | 4 | 7 |
| R-161 | CH | CH | singlebond | Me | Me | H | 4 | 8 |
| R-162 | CH | CH | singlebond | Me | Me | H | 4 | 9 |
| R-163 | CH | CH | singlebond | Me | Me | H | 5 | 7 |
| R-164 | CH | CH | singlebond | Me | Me | H | 5 | 8 |
| R-165 | CH | CH | singlebond | Me | Me | H | 5 | 9 |
| R-166 | CH | CH | singlebond | H | Me | Me | 1 | 7 |
| R-167 | CH | CH | singlebond | H | Me | Me | 1 | 8 |
| R-168 | CH | CH | singlebond | H | Me | Me | 1 | 9 |
| R-169 | CH | CH | singlebond | H | Me | Me | 2 | 7 |
| R-170 | CH | CH | singlebond | H | Me | Me | 2 | 8 |
| R-171 | CH | CH | singlebond | H | Me | Me | 2 | 9 |
| R-172 | CH | CH | singlebond | H | Me | Me | 3 | 7 |
| R-173 | CH | CH | singlebond | H | Me | Me | 3 | 8 |
| R-174 | CH | CH | singlebond | H | Me | Me | 3 | 9 |
| R-175 | CH | CH | singlebond | H | Me | Me | 4 | 7 |
| R-176 | CH | CH | singlebond | H | Me | Me | 4 | 8 |
| R-177 | CH | CH | singlebond | H | Me | Me | 4 | 9 |
| R-178 | CH | CH | singlebond | H | Me | Me | 5 | 7 |
| R-179 | CH | CH | singlebond | H | Me | Me | 5 | 8 |
| R-180 | CH | CH | singlebond | H | Me | Me | 5 | 9 |
| R-181 | N | CH | —O— | Me | H | H | 1 | 7 |
| R-182 | N | CH | —O— | Me | H | H | 1 | 8 |
| R-183 | N | CH | —O— | Me | H | H | 1 | 9 |
| R-184 | N | CH | —O— | Me | H | H | 2 | 7 |
| R-185 | N | CH | —O— | Me | H | H | 2 | 8 |
| R-186 | N | CH | —O— | Me | H | H | 2 | 9 |
| R-187 | N | CH | —O— | Me | H | H | 3 | 7 |
| R-188 | N | CH | —O— | Me | H | H | 3 | 8 |
| R-189 | N | CH | —O— | Me | H | H | 3 | 9 |
| R-190 | N | CH | —O— | Me | H | H | 4 | 7 |
| R-191 | N | CH | —O— | Me | H | H | 4 | 8 |
| R-192 | N | CH | —O— | Me | H | H | 4 | 9 |
| R-193 | N | CH | —O— | Me | H | H | 5 | 7 |
| R-194 | N | CH | —O— | Me | H | H | 5 | 8 |
| R-195 | N | CH | —O— | Me | H | H | 5 | 9 |
| R-196 | N | CH | —O— | H | H | Me | 1 | 7 |
| R-197 | N | CH | —O— | H | H | Me | 1 | 8 |
| R-198 | N | CH | —O— | H | H | Me | 1 | 9 |
| R-199 | N | CH | —O— | H | H | Me | 2 | 7 |
| R-200 | N | CH | —O— | H | H | Me | 2 | 8 |
| R-201 | N | CH | —O— | H | H | Me | 2 | 9 |
| R-202 | N | CH | —O— | H | H | Me | 3 | 7 |
| R-203 | N | CH | —O— | H | H | Me | 3 | 8 |
| R-204 | N | CH | —O— | H | H | Me | 3 | 9 |
| R-205 | N | CH | —O— | H | H | Me | 4 | 7 |
| R-206 | N | CH | —O— | H | H | Me | 4 | 8 |
| R-207 | N | CH | —O— | H | H | Me | 4 | 9 |
| R-208 | N | CH | —O— | H | H | Me | 5 | 7 |
| R-209 | N | CH | —O— | H | H | Me | 5 | 8 |
| R-210 | N | CH | —O— | H | H | Me | 5 | 9 |
| R-211 | N | CH | —O— | Me | Me | H | 1 | 7 |
| R-212 | N | CH | —O— | Me | Me | H | 1 | 8 |
| R-213 | N | CH | —O— | Me | Me | H | 1 | 9 |
| R-214 | N | CH | —O— | Me | Me | H | 2 | 7 |
| R-215 | N | CH | —O— | Me | Me | H | 2 | 8 |
| R-216 | N | CH | —O— | Me | Me | H | 2 | 9 |
| R-217 | N | CH | —O— | Me | Me | H | 3 | 7 |
| R-218 | N | CH | —O— | Me | Me | H | 3 | 8 |
| R-219 | N | CH | —O— | Me | Me | H | 3 | 9 |
| R-220 | N | CH | —O— | Me | Me | H | 4 | 7 |

TABLE 62

| Compound No. | $G^1$ | $G^2$ | $Q^1$ | $R^a$ | $R^b$ | $R^c$ | n | m |
|---|---|---|---|---|---|---|---|---|
| R-221 | N | CH | —O— | Me | Me | H | 4 | 8 |
| R-222 | N | CH | —O— | Me | Me | H | 4 | 9 |
| R-223 | N | CH | —O— | Me | Me | H | 5 | 7 |
| R-224 | N | CH | —O— | Me | Me | H | 5 | 8 |
| R-225 | N | CH | —O— | Me | Me | H | 5 | 9 |
| R-226 | N | CH | —O— | H | Me | Me | 1 | 7 |
| R-227 | N | CH | —O— | H | Me | Me | 1 | 8 |
| R-228 | N | CH | —O— | H | Me | Me | 1 | 9 |
| R-229 | N | CH | —O— | H | Me | Me | 2 | 7 |
| R-230 | N | CH | —O— | H | Me | Me | 2 | 8 |
| R-231 | N | CH | —O— | H | Me | Me | 2 | 9 |
| R-232 | N | CH | —O— | H | Me | Me | 3 | 7 |
| R-233 | N | CH | —O— | H | Me | Me | 3 | 8 |
| R-234 | N | CH | —O— | H | Me | Me | 3 | 9 |
| R-235 | N | CH | —O— | H | Me | Me | 4 | 7 |
| R-236 | N | CH | —O— | H | Me | Me | 4 | 8 |
| R-237 | N | CH | —O— | H | Me | Me | 4 | 9 |
| R-238 | N | CH | —O— | H | Me | Me | 5 | 7 |
| R-239 | N | CH | —O— | H | Me | Me | 5 | 8 |
| R-240 | N | CH | —O— | H | Me | Me | 5 | 9 |
| R-241 | N | CH | —CH$_2$O— | Me | H | H | 1 | 7 |
| R-242 | N | CH | —CH$_2$O— | Me | H | H | 1 | 8 |
| R-243 | N | CH | —CH$_2$O— | Me | H | H | 1 | 9 |
| R-244 | N | CH | —CH$_2$O— | Me | H | H | 2 | 7 |
| R-245 | N | CH | —CH$_2$O— | Me | H | H | 2 | 8 |
| R-246 | N | CH | —CH$_2$O— | Me | H | H | 2 | 9 |
| R-247 | N | CH | —CH$_2$O— | Me | H | H | 3 | 7 |
| R-248 | N | CH | —CH$_2$O— | Me | H | H | 3 | 8 |
| R-249 | N | CH | —CH$_2$O— | Me | H | H | 3 | 9 |
| R-250 | N | CH | —CH$_2$O— | Me | H | H | 4 | 7 |
| R-251 | N | CH | —CH$_2$O— | Me | H | H | 4 | 8 |
| R-252 | N | CH | —CH$_2$O— | Me | H | H | 4 | 9 |
| R-253 | N | CH | —CH$_2$O— | Me | H | H | 5 | 7 |
| R-254 | N | CH | —CH$_2$O— | Me | H | H | 5 | 8 |
| R-255 | N | CH | —CH$_2$O— | Me | H | H | 5 | 9 |
| R-256 | N | CH | —CH$_2$O— | H | H | Me | 1 | 7 |
| R-257 | N | CH | —CH$_2$O— | H | H | Me | 1 | 8 |
| R-258 | N | CH | —CH$_2$O— | H | H | Me | 1 | 9 |
| R-259 | N | CH | —CH$_2$O— | H | H | Me | 2 | 7 |
| R-260 | N | CH | —CH$_2$O— | H | H | Me | 2 | 8 |
| R-261 | N | CH | —CH$_2$O— | H | H | Me | 2 | 9 |
| R-262 | N | CH | —CH$_2$O— | H | H | Me | 3 | 7 |
| R-263 | N | CH | —CH$_2$O— | H | H | Me | 3 | 8 |
| R-264 | N | CH | —CH$_2$O— | H | H | Me | 3 | 9 |
| R-265 | N | CH | —CH$_2$O— | H | H | Me | 4 | 7 |
| R-266 | N | CH | —CH$_2$O— | H | H | Me | 4 | 8 |
| R-267 | N | CH | —CH$_2$O— | H | H | Me | 4 | 9 |
| R-268 | N | CH | —CH$_2$O— | H | H | Me | 5 | 7 |
| R-269 | N | CH | —CH$_2$O— | H | H | Me | 5 | 8 |
| R-270 | N | CH | —CH$_2$O— | H | H | Me | 5 | 9 |
| R-271 | N | CH | —CH$_2$O— | Me | Me | H | 1 | 7 |
| R-272 | N | CH | —CH$_2$O— | Me | Me | H | 1 | 8 |
| R-273 | N | CH | —CH$_2$O— | Me | Me | H | 1 | 9 |
| R-274 | N | CH | —CH$_2$O— | Me | Me | H | 2 | 7 |
| R-275 | N | CH | —CH$_2$O— | Me | Me | H | 2 | 8 |
| R-276 | N | CH | —CH$_2$O— | Me | Me | H | 2 | 9 |
| R-277 | N | CH | —CH$_2$O— | Me | Me | H | 3 | 7 |
| R-278 | N | CH | —CH$_2$O— | Me | Me | H | 3 | 8 |
| R-279 | N | CH | —CH$_2$O— | Me | Me | H | 3 | 9 |
| R-280 | N | CH | —CH$_2$O— | Me | Me | H | 4 | 7 |
| R-281 | N | CH | —CH$_2$O— | Me | Me | H | 4 | 8 |
| R-282 | N | CH | —CH$_2$O— | Me | Me | H | 4 | 9 |
| R-283 | N | CH | —CH$_2$O— | Me | Me | H | 5 | 7 |
| R-284 | N | CH | —CH$_2$O— | Me | Me | H | 5 | 8 |
| R-285 | N | CH | —CH$_2$O— | Me | Me | H | 5 | 9 |
| R-286 | N | CH | —CH$_2$O— | H | Me | Me | 1 | 7 |
| R-287 | N | CH | —CH$_2$O— | H | Me | Me | 1 | 8 |
| R-288 | N | CH | —CH$_2$O— | H | Me | Me | 1 | 9 |
| R-289 | N | CH | —CH$_2$O— | H | Me | Me | 2 | 7 |
| R-290 | N | CH | —CH$_2$O— | H | Me | Me | 2 | 8 |
| R-291 | N | CH | —CH$_2$O— | H | Me | Me | 2 | 9 |
| R-292 | N | CH | —CH$_2$O— | H | Me | Me | 3 | 7 |
| R-293 | N | CH | —CH$_2$O— | H | Me | Me | 3 | 8 |
| R-294 | N | CH | —CH$_2$O— | H | Me | Me | 3 | 9 |
| R-295 | N | CH | —CH$_2$O— | H | Me | Me | 4 | 7 |
| R-296 | N | CH | —CH$_2$O— | H | Me | Me | 4 | 8 |
| R-297 | N | CH | —CH$_2$O— | H | Me | Me | 4 | 9 |

TABLE 62-continued

| Compound No. | $G^1$ | $G^2$ | $Q^1$ | $R^a$ | $R^b$ | $R^c$ | n | m |
|---|---|---|---|---|---|---|---|---|
| R-298 | N | CH | —CH$_2$O— | H | Me | Me | 5 | 7 |
| R-299 | N | CH | —CH$_2$O— | H | Me | Me | 5 | 8 |
| R-300 | N | CH | —CH$_2$O— | H | Me | Me | 5 | 9 |
| R-301 | N | CH | singlebond | Me | H | H | 1 | 7 |
| R-302 | N | CH | singlebond | Me | H | H | 1 | 8 |
| R-303 | N | CH | singlebond | Me | H | H | 1 | 9 |
| R-304 | N | CH | singlebond | Me | H | H | 2 | 7 |
| R-305 | N | CH | singlebond | Me | H | H | 2 | 8 |
| R-306 | N | CH | singlebond | Me | H | H | 2 | 9 |
| R-307 | N | CH | singlebond | Me | H | H | 3 | 7 |
| R-308 | N | CH | singlebond | Me | H | H | 3 | 8 |
| R-309 | N | CH | singlebond | Me | H | H | 3 | 9 |
| R-310 | N | CH | singlebond | Me | H | H | 4 | 7 |
| R-311 | N | CH | singlebond | Me | H | H | 4 | 8 |
| R-312 | N | CH | singlebond | Me | H | H | 4 | 9 |
| R-313 | N | CH | singlebond | Me | H | H | 5 | 7 |
| R-314 | N | CH | singlebond | Me | H | H | 5 | 8 |
| R-315 | N | CH | singlebond | Me | H | H | 5 | 9 |
| R-316 | N | CH | singlebond | H | H | Me | 1 | 7 |
| R-317 | N | CH | singlebond | H | H | Me | 1 | 8 |
| R-318 | N | CH | singlebond | H | H | Me | 1 | 9 |
| R-319 | N | CH | singlebond | H | H | Me | 2 | 7 |
| R-320 | N | CH | singlebond | H | H | Me | 2 | 8 |
| R-321 | N | CH | singlebond | H | H | Me | 2 | 9 |
| R-322 | N | CH | singlebond | H | H | Me | 3 | 7 |
| R-323 | N | CH | singlebond | H | H | Me | 3 | 8 |
| R-324 | N | CH | singlebond | H | H | Me | 3 | 9 |
| R-325 | N | CH | singlebond | H | H | Me | 4 | 7 |
| R-326 | N | CH | singlebond | H | H | Me | 4 | 8 |
| R-327 | N | CH | singlebond | H | H | Me | 4 | 9 |
| R-323 | N | CH | singlebond | H | H | Me | 5 | 7 |
| R-329 | N | CH | singlebond | H | H | Me | 5 | 8 |
| R-330 | N | CH | singlebond | H | H | Me | 5 | 9 |

TABLE 63

| Compound No. | $G^1$ | $G^2$ | $Q^1$ | $R^a$ | $R^b$ | $R^c$ | n | m |
|---|---|---|---|---|---|---|---|---|
| R-331 | N | CH | singlebond | Me | Me | H | 1 | 7 |
| R-332 | N | CH | singlebond | Me | Me | H | 1 | 8 |
| R-333 | N | CH | singlebond | Me | Me | H | 1 | 9 |
| R-334 | N | CH | singlebond | Me | Me | H | 2 | 7 |
| R-335 | N | CH | singlebond | Me | Me | H | 2 | 8 |
| R-336 | N | CH | singlebond | Me | Me | H | 2 | 9 |
| R-337 | N | CH | singlebond | Me | Me | H | 3 | 7 |
| R-338 | N | CH | singlebond | Me | Me | H | 3 | 8 |
| R-339 | N | CH | singlebond | Me | Me | H | 3 | 9 |
| R-340 | N | CH | singlebond | Me | Me | H | 4 | 7 |
| R-341 | N | CH | singlebond | Me | Me | H | 4 | 8 |
| R-342 | N | CH | singlebond | Me | Me | H | 4 | 9 |
| R-343 | N | CH | singlebond | Me | Me | H | 5 | 7 |
| R-344 | N | CH | singlebond | Me | Me | H | 5 | 8 |
| R-345 | N | CH | singlebond | Me | Me | H | 5 | 9 |
| R-346 | N | CH | singlebond | H | Me | Me | 1 | 7 |
| R-347 | N | CH | singlebond | H | Me | Me | 1 | 8 |
| R-348 | N | CH | singlebond | H | Me | Me | 1 | 9 |
| R-349 | N | CH | singlebond | H | Me | Me | 2 | 7 |
| R-350 | N | CH | singlebond | H | Me | Me | 2 | 8 |
| R-351 | N | CH | singlebond | H | Me | Me | 2 | 9 |
| R-352 | N | CH | singlebond | H | Me | Me | 3 | 7 |
| R-353 | N | CH | singlebond | H | Me | Me | 3 | 8 |
| R-354 | N | CH | singlebond | H | Me | Me | 3 | 9 |
| R-355 | N | CH | singlebond | H | Me | Me | 4 | 7 |
| R-356 | N | CH | singlebond | H | Me | Me | 4 | 8 |
| R-357 | N | CH | singlebond | H | Me | Me | 4 | 9 |
| R-358 | N | CH | singlebond | H | Me | Me | 5 | 7 |
| R-359 | N | CH | singlebond | H | Me | Me | 5 | 8 |
| R-360 | N | CH | singlebond | H | Me | Me | 5 | 9 |
| R-361 | CH | N | —O— | Me | H | H | 1 | 7 |
| R-362 | CH | N | —O— | Me | H | H | 1 | 8 |
| R-363 | CH | N | —O— | Me | H | H | 1 | 9 |
| R-364 | CH | N | —O— | Me | H | H | 2 | 7 |
| R-365 | CH | N | —O— | Me | H | H | 2 | 8 |

TABLE 63-continued

| Compound No. | G¹ | G² | Q¹ | $R^a$ | $R^b$ | $R^c$ | n | m |
|---|---|---|---|---|---|---|---|---|
| R-366 | CH | N | —O— | Me | H | H | 2 | 9 |
| R-367 | CH | N | —O— | Me | H | H | 3 | 7 |
| R-368 | CH | N | —O— | Me | H | H | 3 | 8 |
| R-369 | CH | N | —O— | Me | H | H | 3 | 9 |
| R-370 | CH | N | —O— | Me | H | H | 4 | 7 |
| R-371 | CH | N | —O— | Me | H | H | 4 | 8 |
| R-372 | CH | N | —O— | Me | H | H | 4 | 9 |
| R-373 | CH | N | —O— | Me | H | H | 5 | 7 |
| R-374 | CH | N | —O— | Me | H | H | 5 | 8 |
| R-375 | CH | N | —O— | Me | H | H | 5 | 9 |
| R-376 | CH | N | —O— | H | H | Me | 1 | 7 |
| R-377 | CH | N | —O— | H | H | Me | 1 | 8 |
| R-378 | CH | N | —O— | H | H | Me | 1 | 9 |
| R-379 | CH | N | —O— | H | H | Me | 2 | 7 |
| R-380 | CH | N | —O— | H | H | Me | 2 | 8 |
| R-381 | CH | N | —O— | H | H | Me | 2 | 9 |
| R-382 | CH | N | —O— | H | H | Me | 3 | 7 |
| R-383 | CH | N | —O— | H | H | Me | 3 | 8 |
| R-384 | CH | N | —O— | H | H | Me | 3 | 9 |
| R-385 | CH | N | —O— | H | H | Me | 4 | 7 |
| R-386 | CH | N | —O— | H | H | Me | 4 | 8 |
| R-387 | CH | N | —O— | H | H | Me | 4 | 9 |
| R-388 | CH | N | —O— | H | H | Me | 5 | 7 |
| R-389 | CH | N | —O— | H | H | Me | 5 | 8 |
| R-390 | CH | N | —O— | H | H | Me | 5 | 9 |
| R-391 | CH | N | —O— | Me | Me | H | 1 | 7 |
| R-392 | CH | N | —O— | Me | Me | H | 1 | 8 |
| R-393 | CH | N | —O— | Me | Me | H | 1 | 9 |
| R-394 | CH | N | —O— | Me | Me | H | 2 | 7 |
| R-395 | CH | N | —O— | Me | Me | H | 2 | 8 |
| R-396 | CH | N | —O— | Me | Me | H | 2 | 9 |
| R-397 | CH | N | —O— | Me | Me | H | 3 | 7 |
| R-398 | CH | N | —O— | Me | Me | H | 3 | 8 |
| R-399 | CH | N | —O— | Me | Me | H | 3 | 9 |
| R-400 | CH | N | —O— | Me | Me | H | 4 | 7 |
| R-401 | CH | N | —O— | Me | Me | H | 4 | 8 |
| R-402 | CH | N | —O— | Me | Me | H | 4 | 9 |
| R-403 | CH | N | —O— | Me | Me | H | 5 | 7 |
| R-404 | CH | N | —O— | Me | Me | H | 5 | 8 |
| R-405 | CH | N | —O— | Me | Me | H | 5 | 9 |
| R-406 | CH | N | —O— | H | Me | Me | 1 | 7 |
| R-407 | CH | N | —O— | H | Me | Me | 1 | 8 |
| R-408 | CH | N | —O— | H | Me | Me | 1 | 9 |
| R-409 | CH | N | —O— | H | Me | Me | 2 | 7 |
| R-410 | CH | N | —O— | H | Me | Me | 2 | 8 |
| R-411 | CH | N | —O— | H | Me | Me | 2 | 9 |
| R-412 | CH | N | —O— | H | Me | Me | 3 | 7 |
| R-413 | CH | N | —O— | H | Me | Me | 3 | 8 |
| R-414 | CH | N | —O— | H | Me | Me | 3 | 9 |
| R-415 | CH | N | —O— | H | Me | Me | 4 | 7 |
| R-416 | CH | N | —O— | H | Me | Me | 4 | 8 |
| R-417 | CH | N | —O— | H | Me | Me | 4 | 9 |
| R-418 | CH | N | —O— | H | Me | Me | 5 | 7 |
| R-419 | CH | N | —O— | H | Me | Me | 5 | 8 |
| R-420 | CH | N | —O— | H | Me | Me | 5 | 9 |
| R-421 | CH | N | —CH₂O— | Me | H | H | 1 | 7 |
| R-422 | CH | N | —CH₂O— | Me | H | H | 1 | 8 |
| R-423 | CH | N | —CH₂O— | Me | H | H | 1 | 9 |
| R-424 | CH | N | —CH₂O— | Me | H | H | 2 | 7 |
| R-425 | CH | N | —CH₂O— | Me | H | H | 2 | 8 |
| R-426 | CH | N | —CH₂O— | Me | H | H | 2 | 9 |
| R-427 | CH | N | —CH₂O— | Me | H | H | 3 | 7 |
| R-428 | CH | N | —CH₂O— | Me | H | H | 3 | 8 |
| R-429 | CH | N | —CH₂O— | Me | H | H | 3 | 9 |
| R-430 | CH | N | —CH₂O— | Me | H | H | 4 | 7 |
| R-431 | CH | N | —CH₂O— | Me | H | H | 4 | 8 |
| R-432 | CH | N | —CH₂O— | Me | H | H | 4 | 9 |
| R-433 | CH | N | —CH₂O— | Me | H | H | 5 | 7 |
| R-434 | CH | N | —CH₂O— | Me | H | H | 5 | 8 |
| R-435 | CH | N | —CH₂O— | Me | H | H | 5 | 9 |
| R-436 | CH | N | —CH₂O— | H | H | Me | 1 | 7 |
| R-437 | CH | N | —CH₂O— | H | H | Me | 1 | 8 |
| R-438 | CH | N | —CH₂O— | H | H | Me | 1 | 9 |
| R-439 | CH | N | —CH₂O— | H | H | Me | 2 | 7 |
| R-440 | CH | N | —CH₂O— | H | H | Me | 2 | 8 |

TABLE 64

| Compound No. | G¹ | G² | Q¹ | $R^a$ | $R^b$ | $R^c$ | n | m |
|---|---|---|---|---|---|---|---|---|
| R-441 | CH | N | —CH₂O— | H | H | Me | 2 | 9 |
| R-442 | CH | N | —CH₂O— | H | H | Me | 3 | 7 |
| R-443 | CH | N | —CH₂O— | H | H | Me | 3 | 8 |
| R-444 | CH | N | —CH₂O— | H | H | Me | 3 | 9 |
| R-445 | CH | N | —CH₂O— | H | H | Me | 4 | 7 |
| R-446 | CH | N | —CH₂O— | H | H | Me | 4 | 8 |
| R-447 | CH | N | —CH₂O— | H | H | Me | 4 | 9 |
| R-448 | CH | N | —CH₂O— | H | H | Me | 5 | 7 |
| R-449 | CH | N | —CH₂O— | H | H | Me | 5 | 8 |
| R-450 | CH | N | —CH₂O— | H | H | Me | 5 | 9 |
| R-451 | CH | N | —CH₂O— | Me | Me | H | 1 | 7 |
| R-452 | CH | N | —CH₂O— | Me | Me | H | 1 | 8 |
| R-453 | CH | N | —CH₂O— | Me | Me | H | 1 | 9 |
| R-454 | CH | N | —CH₂O— | Me | Me | H | 2 | 7 |
| R-455 | CH | N | —CH₂O— | Me | Me | H | 2 | 8 |
| R-456 | CH | N | —CH₂O— | Me | Me | H | 2 | 9 |
| R-457 | CH | N | —CH₂O— | Me | Me | H | 3 | 7 |
| R-458 | CH | N | —CH₂O— | Me | Me | H | 3 | 8 |
| R-459 | CH | N | —CH₂O— | Me | Me | H | 3 | 9 |
| R-460 | CH | N | —CH₂O— | Me | Me | H | 4 | 7 |
| R-461 | CH | N | —CH₂O— | Me | Me | H | 4 | 8 |
| R-462 | CH | N | —CH₂O— | Me | Me | H | 4 | 9 |
| R-463 | CH | N | —CH₂O— | Me | Me | H | 5 | 7 |
| R-464 | CH | N | —CH₂O— | Me | Me | H | 5 | 8 |
| R-465 | CH | N | —CH₂O— | Me | Me | H | 5 | 9 |
| R-466 | CH | N | —CH₂O— | H | Me | Me | 1 | 7 |
| R-467 | CH | N | —CH₂O— | H | Me | Me | 1 | 8 |
| R-468 | CH | N | —CH₂O— | H | Me | Me | 1 | 9 |
| R-469 | CH | N | —CH₂O— | H | Me | Me | 2 | 7 |
| R-470 | CH | N | —CH₂O— | H | Me | Me | 2 | 8 |
| R-471 | CH | N | —CH₂O— | H | Me | Me | 2 | 9 |
| R-472 | CH | N | —CH₂O— | H | Me | Me | 3 | 7 |
| R-473 | CH | N | —CH₂O— | H | Me | Me | 3 | 8 |
| R-474 | CH | N | —CH₂O— | H | Me | Me | 3 | 9 |
| R-475 | CH | N | —CH₂O— | H | Me | Me | 4 | 7 |
| R-476 | CH | N | —CH₂O— | H | Me | Me | 4 | 8 |
| R-477 | CH | N | —CH₂O— | H | Me | Me | 4 | 9 |
| R-478 | CH | N | —CH₂O— | H | Me | Me | 5 | 7 |
| R-479 | CH | N | —CH₂O— | H | Me | Me | 5 | 8 |
| R-480 | CH | N | —CH₂O— | H | Me | Me | 5 | 9 |
| R-481 | CH | N | singlebond | Me | H | H | 1 | 7 |
| R-482 | CH | N | singlebond | Me | H | H | 1 | 8 |
| R-483 | CH | N | singlebond | Me | H | H | 1 | 9 |
| R-484 | CH | N | singlebond | Me | H | H | 2 | 7 |
| R-485 | CH | N | singlebond | Me | H | H | 2 | 8 |
| R-486 | CH | N | singlebond | Me | H | H | 2 | 9 |
| R-487 | CH | N | singlebond | Me | H | H | 3 | 7 |
| R-488 | CH | N | singlebond | Me | H | H | 3 | 8 |
| R-489 | CH | N | singlebond | Me | H | H | 3 | 9 |
| R-490 | CH | N | singlebond | Me | H | H | 4 | 7 |
| R-491 | CH | N | singlebond | Me | H | H | 4 | 8 |
| R-492 | CH | N | singlebond | Me | H | H | 4 | 9 |
| R-493 | CH | N | singlebond | Me | H | H | 5 | 7 |
| R-494 | CH | N | singlebond | Me | H | H | 5 | 8 |
| R-495 | CH | N | singlebond | Me | H | H | 5 | 9 |
| R-496 | CH | N | singlebond | H | H | Me | 1 | 7 |
| R-497 | CH | N | singlebond | H | H | Me | 1 | 8 |
| R-498 | CH | N | singlebond | H | H | Me | 1 | 9 |
| R-499 | CH | N | singlebond | H | H | Me | 2 | 7 |
| R-500 | CH | N | singlebond | H | H | Me | 2 | 8 |
| R-501 | CH | N | singlebond | H | H | Me | 2 | 9 |
| R-502 | CH | N | singlebond | H | H | Me | 3 | 7 |
| R-503 | CH | N | singlebond | H | H | Me | 3 | 8 |
| R-504 | CH | N | singlebond | H | H | Me | 3 | 9 |
| R-505 | CH | N | singlebond | H | H | Me | 4 | 7 |
| R-506 | CH | N | singlebond | H | H | Me | 4 | 8 |
| R-507 | CH | N | singlebond | H | H | Me | 4 | 9 |
| R-508 | CH | N | singlebond | H | H | Me | 5 | 7 |
| R-509 | CH | N | singlebond | H | H | Me | 5 | 8 |
| R-510 | CH | N | singlebond | H | H | Me | 5 | 9 |
| R-511 | CH | N | singlebond | Me | Me | H | 1 | 7 |
| R-512 | CH | N | singlebond | Me | Me | H | 1 | 8 |
| R-513 | CH | N | singlebond | Me | Me | H | 1 | 9 |
| R-514 | CH | N | singlebond | Me | Me | H | 2 | 7 |
| R-515 | CH | N | singlebond | Me | Me | H | 2 | 8 |
| R-516 | CH | N | singlebond | Me | Me | H | 2 | 9 |
| R-517 | CH | N | singlebond | Me | Me | H | 3 | 7 |

TABLE 64-continued

| Compound No. | G¹ | G² | Q¹ | $R^a$ | $R^b$ | $R^c$ | n | m |
|---|---|---|---|---|---|---|---|---|
| R-518 | CH | N | singlebond | Me | Me | H | 3 | 8 |
| R-519 | CH | N | singlebond | Me | Me | H | 3 | 9 |
| R-520 | CH | N | singlebond | Me | Me | H | 4 | 7 |
| R-521 | CH | N | singlebond | Me | Me | H | 4 | 8 |
| R-522 | CH | N | singlebond | Me | Me | H | 4 | 9 |
| R-523 | CH | N | singlebond | Me | Me | H | 5 | 7 |
| R-524 | CH | N | singlebond | Me | Me | H | 5 | 8 |
| R-525 | CH | N | singlebond | Me | Me | H | 5 | 9 |
| R-526 | CH | N | singlebond | H | Me | Me | 1 | 7 |
| R-527 | CH | N | singlebond | H | Me | Me | 1 | 8 |
| R-528 | CH | N | singlebond | H | Me | Me | 1 | 9 |
| R-529 | CH | N | singlebond | H | Me | Me | 2 | 7 |
| R-530 | CH | N | singlebond | H | Me | Me | 2 | 8 |
| R-531 | CH | N | singlebond | H | Me | Me | 2 | 9 |
| R-532 | CH | N | singlebond | H | Me | Me | 3 | 7 |
| R-533 | CH | N | singlebond | H | Me | Me | 3 | 8 |
| R-534 | CH | N | singlebond | H | Me | Me | 3 | 9 |
| R-535 | CH | N | singlebond | H | Me | Me | 4 | 7 |
| R-536 | CH | N | singlebond | H | Me | Me | 4 | 8 |
| R-537 | CH | N | singlebond | H | Me | Me | 4 | 9 |
| R-538 | CH | N | singlebond | H | Me | Me | 5 | 7 |
| R-539 | CH | N | singlebond | H | Me | Me | 5 | 8 |
| R-540 | CH | N | singlebond | H | Me | Me | 5 | 9 |

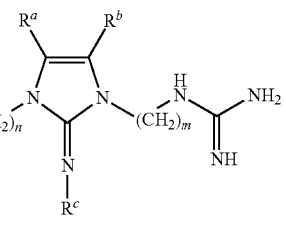

TABLE 65

| Compound No. | G¹ | G² | Q¹ | $R^a$ | $R^b$ | $R^c$ | n | m |
|---|---|---|---|---|---|---|---|---|
| S-1 | CH | CH | —O— | Me | H | H | 1 | 7 |
| S-2 | CH | CH | —O— | Me | H | H | 1 | 8 |
| S-3 | CH | CH | —O— | Me | H | H | 1 | 9 |
| S-4 | CH | CH | —O— | Me | H | H | 2 | 7 |
| S-5 | CH | CH | —O— | Me | H | H | 2 | 8 |
| S-6 | CH | CH | —O— | Me | H | H | 2 | 9 |
| S-7 | CH | CH | —O— | Me | H | H | 3 | 7 |
| S-8 | CH | CH | —O— | Me | H | H | 3 | 8 |
| S-9 | CH | CH | —O— | Me | H | H | 3 | 9 |
| S-10 | CH | CH | —O— | Me | H | H | 4 | 7 |
| S-11 | CH | CH | —O— | Me | H | H | 4 | 8 |
| S-12 | CH | CH | —O— | Me | H | H | 4 | 9 |
| S-13 | CH | CH | —O— | Me | H | H | 5 | 7 |
| S-14 | CH | CH | —O— | Me | H | H | 5 | 8 |
| S-15 | CH | CH | —O— | Me | H | H | 5 | 9 |
| S-16 | CH | CH | —O— | H | H | Me | 1 | 7 |
| S-17 | CH | CH | —O— | H | H | Me | 1 | 8 |
| S-18 | CH | CH | —O— | H | H | Me | 1 | 9 |
| S-19 | CH | CH | —O— | H | H | Me | 2 | 7 |
| S-20 | CH | CH | —O— | H | H | Me | 2 | 8 |
| S-21 | CH | CH | —O— | H | H | Me | 2 | 9 |
| S-22 | CH | CH | —O— | H | H | Me | 3 | 7 |
| S-23 | CH | CH | —O— | H | H | Me | 3 | 8 |
| S-24 | CH | CH | —O— | H | H | Me | 3 | 9 |
| S-25 | CH | CH | —O— | H | H | Me | 4 | 7 |
| S-26 | CH | CH | —O— | H | H | Me | 4 | 8 |
| S-27 | CH | CH | —O— | H | H | Me | 4 | 9 |
| S-28 | CH | CH | —O— | H | H | Me | 5 | 7 |
| S-29 | CH | CH | —O— | H | H | Me | 5 | 8 |
| S-30 | CH | CH | —O— | H | H | Me | 5 | 9 |

TABLE 65-continued

| Compound No. | G¹ | G² | Q¹ | $R^a$ | $R^b$ | $R^c$ | n | m |
|---|---|---|---|---|---|---|---|---|
| S-31 | CH | CH | —O— | Me | Me | H | 1 | 7 |
| S-32 | CH | CH | —O— | Me | Me | H | 1 | 8 |
| S-33 | CH | CH | —O— | Me | Me | H | 1 | 9 |
| S-34 | CH | CH | —O— | Me | Me | H | 2 | 7 |
| S-35 | CH | CH | —O— | Me | Me | H | 2 | 8 |
| S-36 | CH | CH | —O— | Me | Me | H | 2 | 9 |
| S-37 | CH | CH | —O— | Me | Me | H | 3 | 7 |
| S-38 | CH | CH | —O— | Me | Me | H | 3 | 8 |
| S-39 | CH | CH | —O— | Me | Me | H | 3 | 9 |
| S-40 | CH | CH | —O— | Me | Me | H | 4 | 7 |
| S-41 | CH | CH | —O— | Me | Me | H | 4 | 8 |
| S-42 | CH | CH | —O— | Me | Me | H | 4 | 9 |
| S-43 | CH | CH | —O— | Me | Me | H | 5 | 7 |
| S-44 | CH | CH | —O— | Me | Me | H | 5 | 8 |
| S-45 | CH | CH | —O— | Me | Me | H | 5 | 9 |
| S-46 | CH | CH | —O— | H | Me | Me | 1 | 7 |
| S-47 | CH | CH | —O— | H | Me | Me | 1 | 8 |
| S-48 | CH | CH | —O— | H | Me | Me | 1 | 9 |
| S-49 | CH | CH | —O— | H | Me | Me | 2 | 7 |
| S-50 | CH | CH | —O— | H | Me | Me | 2 | 8 |
| S-51 | CH | CH | —O— | H | Me | Me | 2 | 9 |
| S-52 | CH | CH | —O— | H | Me | Me | 3 | 7 |
| S-53 | CH | CH | —O— | H | Me | Me | 3 | 8 |
| S-54 | CH | CH | —O— | H | Me | Me | 3 | 9 |
| S-55 | CH | CH | —O— | H | Me | Me | 4 | 7 |
| S-56 | CH | CH | —O— | H | Me | Me | 4 | 8 |
| S-57 | CH | CH | —O— | H | Me | Me | 4 | 9 |
| S-58 | CH | CH | —O— | H | Me | Me | 5 | 7 |
| S-59 | CH | CH | —O— | H | Me | Me | 5 | 8 |
| S-60 | CH | CH | —O— | H | Me | Me | 5 | 9 |
| S-61 | CH | CH | —CH₂O— | Me | H | H | 1 | 7 |
| S-62 | CH | CH | —CH₂O— | Me | H | H | 1 | 8 |
| S-63 | CH | CH | —CH₂O— | Me | H | H | 1 | 9 |
| S-64 | CH | CH | —CH₂O— | Me | H | H | 2 | 7 |
| S-65 | CH | CH | —CH₂O— | Me | H | H | 2 | 8 |
| S-66 | CH | CH | —CH₂O— | Me | H | H | 2 | 9 |
| S-67 | CH | CH | —CH₂O— | Me | H | H | 3 | 7 |
| S-68 | CH | CH | —CH₂O— | Me | H | H | 3 | 8 |
| S-69 | CH | CH | —CH₂O— | Me | H | H | 3 | 9 |
| S-70 | CH | CH | —CH₂O— | Me | H | H | 4 | 7 |
| S-71 | CH | CH | —CH₂O— | Me | H | H | 4 | 8 |
| S-72 | CH | CH | —CH₂O— | Me | H | H | 4 | 9 |
| S-73 | CH | CH | —CH₂O— | Me | H | H | 5 | 7 |
| S-74 | CH | CH | —CH₂O— | Me | H | H | 5 | 8 |
| S-75 | CH | CH | —CH₂O— | Me | H | H | 5 | 9 |
| S-76 | CH | CH | —CH₂O— | H | H | Me | 1 | 7 |
| S-77 | CH | CH | —CH₂O— | H | H | Me | 1 | 8 |
| S-78 | CH | CH | —CH₂O— | H | H | Me | 1 | 9 |
| S-79 | CH | CH | —CH₂O— | H | H | Me | 2 | 7 |
| S-80 | CH | CH | —CH₂O— | H | H | Me | 2 | 8 |
| S-81 | CH | CH | —CH₂O— | H | H | Me | 2 | 9 |
| S-82 | CH | CH | —CH₂O— | H | H | Me | 3 | 7 |
| S-83 | CH | CH | —CH₂O— | H | H | Me | 3 | 8 |
| S-84 | CH | CH | —CH₂O— | H | H | Me | 3 | 9 |
| S-85 | CH | CH | —CH₂O— | H | H | Me | 4 | 7 |
| S-86 | CH | CH | —CH₂O— | H | H | Me | 4 | 8 |
| S-87 | CH | CH | —CH₂O— | H | H | Me | 4 | 9 |
| S-88 | CH | CH | —CH₂O— | H | H | Me | 5 | 7 |
| S-89 | CH | CH | —CH₂O— | H | H | Me | 5 | 8 |
| S-90 | CH | CH | —CH₂O— | H | H | Me | 5 | 9 |
| S-91 | CH | CH | —CH₂O— | Me | Me | H | 1 | 7 |
| S-92 | CH | CH | —CH₂O— | Me | Me | H | 1 | 8 |
| S-93 | CH | CH | —CH₂O— | Me | Me | H | 1 | 9 |
| S-94 | CH | CH | —CH₂O— | Me | Me | H | 2 | 7 |
| S-95 | CH | CH | —CH₂O— | Me | Me | H | 2 | 8 |
| S-96 | CH | CH | —CH₂O— | Me | Me | H | 2 | 9 |
| S-97 | CH | CH | —CH₂O— | Me | Me | H | 3 | 7 |
| S-98 | CH | CH | —CH₂O— | Me | Me | H | 3 | 8 |
| S-99 | CH | CH | —CH₂O— | Me | Me | H | 3 | 9 |
| S-100 | CH | CH | —CH₂O— | Me | Me | H | 4 | 7 |
| S-101 | CH | CH | —CH₂O— | Me | Me | H | 4 | 8 |
| S-102 | CH | CH | —CH₂O— | Me | Me | H | 4 | 9 |
| S-103 | CH | CH | —CH₂O— | Me | Me | H | 5 | 7 |
| S-104 | CH | CH | —CH₂O— | Me | Me | H | 5 | 8 |
| S-105 | CH | CH | —CH₂O— | Me | Me | H | 5 | 9 |
| S-106 | CH | CH | —CH₂O— | H | Me | Me | 1 | 7 |
| S-107 | CH | CH | —CH₂O— | H | Me | Me | 1 | 8 |

TABLE 65-continued

| Compound No. | $G^1$ | $G^2$ | $Q^1$ | $R^a$ | $R^b$ | $R^c$ | n | m |
|---|---|---|---|---|---|---|---|---|
| S-108 | CH | CH | —CH$_2$O— | H | Me | Me | 1 | 9 |
| S-109 | CH | CH | —CH$_2$O— | H | Me | Me | 2 | 7 |
| S-110 | CH | CH | —CH$_2$O— | H | Me | Me | 2 | 8 |

TABLE 66

| Compound No. | $G^1$ | $G^2$ | $Q^1$ | $R^a$ | $R^b$ | $R^c$ | n | m |
|---|---|---|---|---|---|---|---|---|
| S-111 | CH | CH | —CH$_2$O— | H | Me | Me | 2 | 9 |
| S-112 | CH | CH | —CH$_2$O— | H | Me | Me | 3 | 7 |
| S-113 | CH | CH | —CH$_2$O— | H | Me | Me | 3 | 8 |
| S-114 | CH | CH | —CH$_2$O— | H | Me | Me | 3 | 9 |
| S-115 | CH | CH | —CH$_2$O— | H | Me | Me | 4 | 7 |
| S-116 | CH | CH | —CH$_2$O— | H | Me | Me | 4 | 8 |
| S-117 | CH | CH | —CH$_2$O— | H | Me | Me | 4 | 9 |
| S-118 | CH | CH | —CH$_2$O— | H | Me | Me | 5 | 7 |
| S-119 | CH | CH | —CH$_2$O— | H | Me | Me | 5 | 8 |
| S-120 | CH | CH | —CH$_2$O— | H | Me | Me | 5 | 9 |
| S-121 | CH | CH | singlebond | Me | H | H | 1 | 7 |
| S-122 | CH | CH | singlebond | Me | H | H | 1 | 8 |
| S-123 | CH | CH | singlebond | Me | H | H | 1 | 9 |
| S-124 | CH | CH | singlebond | Me | H | H | 2 | 7 |
| S-125 | CH | CH | singlebond | Me | H | H | 2 | 8 |
| S-126 | CH | CH | singlebond | Me | H | H | 2 | 9 |
| S-127 | CH | CH | singlebond | Me | H | H | 3 | 7 |
| S-128 | CH | CH | singlebond | Me | H | H | 3 | 8 |
| S-129 | CH | CH | singlebond | Me | H | H | 3 | 9 |
| S-130 | CH | CH | singlebond | Me | H | H | 4 | 7 |
| S-131 | CH | CH | singlebond | Me | H | H | 4 | 8 |
| S-132 | CH | CH | singlebond | Me | H | H | 4 | 9 |
| S-133 | CH | CH | singlebond | Me | H | H | 5 | 7 |
| S-134 | CH | CH | singlebond | Me | H | H | 5 | 8 |
| S-135 | CH | CH | singlebond | Me | H | H | 5 | 9 |
| S-136 | CH | CH | singlebond | H | H | Me | 1 | 7 |
| S-137 | CH | CH | singlebond | H | H | Me | 1 | 8 |
| S-138 | CH | CH | singlebond | H | H | Me | 1 | 9 |
| S-139 | CH | CH | singlebond | H | H | Me | 2 | 7 |
| S-140 | CH | CH | singlebond | H | H | Me | 2 | 8 |
| S-141 | CH | CH | singlebond | H | H | Me | 2 | 9 |
| S-142 | CH | CH | singlebond | H | H | Me | 3 | 7 |
| S-143 | CH | CH | singlebond | H | H | Me | 3 | 8 |
| S-144 | CH | CH | singlebond | H | H | Me | 3 | 9 |
| S-145 | CH | CH | singlebond | H | H | Me | 4 | 7 |
| S-146 | CH | CH | singlebond | H | H | Me | 4 | 8 |
| S-147 | CH | CH | singlebond | H | H | Me | 4 | 9 |
| S-148 | CH | CH | singlebond | H | H | Me | 5 | 7 |
| S-149 | CH | CH | singlebond | H | H | Me | 5 | 8 |
| S-150 | CH | CH | singlebond | H | H | Me | 5 | 9 |
| S-151 | CH | CH | singlebond | Me | Me | H | 1 | 7 |
| S-152 | CH | CH | singlebond | Me | Me | H | 1 | 8 |
| S-153 | CH | CH | singlebond | Me | Me | H | 1 | 9 |
| S-154 | CH | CH | singlebond | Me | Me | H | 2 | 7 |
| S-155 | CH | CH | singlebond | Me | Me | H | 2 | 8 |
| S-156 | CH | CH | singlebond | Me | Me | H | 2 | 9 |
| S-157 | CH | CH | singlebond | Me | Me | H | 3 | 7 |
| S-158 | CH | CH | singlebond | Me | Me | H | 3 | 8 |
| S-159 | CH | CH | singlebond | Me | Me | H | 3 | 9 |
| S-160 | CH | CH | singlebond | Me | Me | H | 4 | 7 |
| S-161 | CH | CH | singlebond | Me | Me | H | 4 | 8 |
| S-162 | CH | CH | singlebond | Me | Me | H | 4 | 9 |
| S-163 | CH | CH | singlebond | Me | Me | H | 5 | 7 |
| S-164 | CH | CH | singlebond | Me | Me | H | 5 | 8 |
| S-165 | CH | CH | singlebond | Me | Me | H | 5 | 9 |
| S-166 | CH | CH | singlebond | H | Me | Me | 1 | 7 |
| S-167 | CH | CH | singlebond | H | Me | Me | 1 | 8 |
| S-168 | CH | CH | singlebond | H | Me | Me | 1 | 9 |
| S-169 | CH | CH | singlebond | H | Me | Me | 2 | 7 |
| S-170 | CH | CH | singlebond | H | Me | Me | 2 | 8 |
| S-171 | CH | CH | singlebond | H | Me | Me | 2 | 9 |
| S-172 | CH | CH | singlebond | H | Me | Me | 3 | 7 |
| S-173 | CH | CH | singlebond | H | Me | Me | 3 | 8 |
| S-174 | CH | CH | singlebond | H | Me | Me | 3 | 9 |
| S-175 | CH | CH | singlebond | H | Me | Me | 4 | 7 |
| S-176 | CH | CH | singlebond | H | Me | Me | 4 | 8 |
| S-177 | CH | CH | singlebond | H | Me | Me | 4 | 9 |
| S-178 | CH | CH | singlebond | H | Me | Me | 5 | 7 |
| S-179 | CH | CH | singlebond | H | Me | Me | 5 | 8 |
| S-180 | CH | CH | singlebond | H | Me | Me | 5 | 9 |
| S-181 | N | CH | —O— | Me | H | H | 1 | 7 |
| S-182 | N | CH | —O— | Me | H | H | 1 | 8 |
| S-183 | N | CH | —O— | Me | H | H | 1 | 9 |
| S-184 | N | CH | —O— | Me | H | H | 2 | 7 |
| S-185 | N | CH | —O— | Me | H | H | 2 | 8 |
| S-186 | N | CH | —O— | Me | H | H | 2 | 9 |
| S-187 | N | CH | —O— | Me | H | H | 3 | 7 |
| S-188 | N | CH | —O— | Me | H | H | 3 | 8 |
| S-189 | N | CH | —O— | Me | H | H | 3 | 9 |
| S-190 | N | CH | —O— | Me | H | H | 4 | 7 |
| S-191 | N | CH | —O— | Me | H | H | 4 | 8 |
| S-192 | N | CH | —O— | Me | H | H | 4 | 9 |
| S-193 | N | CH | —O— | Me | H | H | 5 | 7 |
| S-194 | N | CH | —O— | Me | H | H | 5 | 8 |
| S-195 | N | CH | —O— | Me | H | H | 5 | 9 |
| S-196 | N | CH | —O— | H | H | Me | 1 | 7 |
| S-197 | N | CH | —O— | H | H | Me | 1 | 8 |
| S-198 | N | CH | —O— | H | H | Me | 1 | 9 |
| S-199 | N | CH | —O— | H | H | Me | 2 | 7 |
| S-200 | N | CH | —O— | H | H | Me | 2 | 8 |
| S-201 | N | CH | —O— | H | H | Me | 2 | 9 |
| S-202 | N | CH | —O— | H | H | Me | 3 | 7 |
| S-203 | N | CH | —O— | H | H | Me | 3 | 8 |
| S-204 | N | CH | —O— | H | H | Me | 3 | 9 |
| S-205 | N | CH | —O— | H | H | Me | 4 | 7 |
| S-206 | N | CH | —O— | H | H | Me | 4 | 8 |
| S-207 | N | CH | —O— | H | H | Me | 4 | 9 |
| S-208 | N | CH | —O— | H | H | Me | 5 | 7 |
| S-209 | N | CH | —O— | H | H | Me | 5 | 8 |
| S-210 | N | CH | —O— | H | H | Me | 5 | 9 |
| S-211 | N | CH | —O— | Me | Me | H | 1 | 7 |
| S-212 | N | CH | —O— | Me | Me | H | 1 | 8 |
| S-213 | N | CH | —O— | Me | Me | H | 1 | 9 |
| S-214 | N | CH | —O— | Me | Me | H | 2 | 7 |
| S-215 | N | CH | —O— | Me | Me | H | 2 | 8 |
| S-216 | N | CH | —O— | Me | Me | H | 2 | 9 |
| S-217 | N | CH | —O— | Me | Me | H | 3 | 7 |
| S-218 | N | CH | —O— | Me | Me | H | 3 | 8 |
| S-219 | N | CH | —O— | Me | Me | H | 3 | 9 |
| S-220 | N | CH | —O— | Me | Me | H | 4 | 7 |

TABLE 67

| Compound No. | $G^1$ | $G^2$ | $Q^1$ | $R^a$ | $R^b$ | $R^c$ | n | m |
|---|---|---|---|---|---|---|---|---|
| S-221 | N | CH | —O— | Me | Me | H | 4 | 8 |
| S-222 | N | CH | —O— | Me | Me | H | 4 | 9 |
| S-223 | N | CH | —O— | Me | Me | H | 5 | 7 |
| S-224 | N | CH | —O— | Me | Me | H | 5 | 8 |
| S-225 | N | CH | —O— | Me | Me | H | 5 | 9 |
| S-226 | N | CH | —O— | H | Me | Me | 1 | 7 |
| S-227 | N | CH | —O— | H | Me | Me | 1 | 8 |
| S-228 | N | CH | —O— | H | Me | Me | 1 | 9 |
| S-229 | N | CH | —O— | H | Me | Me | 2 | 7 |
| S-230 | N | CH | —O— | H | Me | Me | 2 | 8 |
| S-231 | N | CH | —O— | H | Me | Me | 2 | 9 |
| S-232 | N | CH | —O— | H | Me | Me | 3 | 7 |
| S-233 | N | CH | —O— | H | Me | Me | 3 | 8 |
| S-234 | N | CH | —O— | H | Me | Me | 3 | 9 |
| S-235 | N | CH | —O— | H | Me | Me | 4 | 7 |
| S-236 | N | CH | —O— | H | Me | Me | 4 | 8 |
| S-237 | N | CH | —O— | H | Me | Me | 4 | 9 |
| S-238 | N | CH | —O— | H | Me | Me | 5 | 7 |
| S-239 | N | CH | —O— | H | Me | Me | 5 | 8 |
| S-240 | N | CH | —O— | H | Me | Me | 5 | 9 |
| S-241 | N | CH | —CH$_2$O— | Me | H | H | 1 | 7 |
| S-242 | N | CH | —CH$_2$O— | Me | H | H | 1 | 8 |
| S-243 | N | CH | —CH$_2$O— | Me | H | H | 1 | 9 |

TABLE 67-continued

| Compound No. | G¹ | G² | Q¹ | $R^a$ | $R^b$ | $R^c$ | n | m |
|---|---|---|---|---|---|---|---|---|
| S-244 | N | CH | —CH₂O— | Me | H | H | 2 | 7 |
| S-245 | N | CH | —CH₂O— | Me | H | H | 2 | 8 |
| S-246 | N | CH | —CH₂O— | Me | H | H | 2 | 9 |
| S-247 | N | CH | —CH₂O— | Me | H | H | 3 | 7 |
| S-248 | N | CH | —CH₂O— | Me | H | H | 3 | 8 |
| S-249 | N | CH | —CH₂O— | Me | H | H | 3 | 9 |
| S-250 | N | CH | —CH₂O— | Me | H | H | 4 | 7 |
| S-251 | N | CH | —CH₂O— | Me | H | H | 4 | 8 |
| S-252 | N | CH | —CH₂O— | Me | H | H | 4 | 9 |
| S-253 | N | CH | —CH₂O— | Me | H | H | 5 | 7 |
| S-254 | N | CH | —CH₂O— | Me | H | H | 5 | 8 |
| S-255 | N | CH | —CH₂O— | Me | H | H | 5 | 9 |
| S-256 | N | CH | —CH₂O— | H | H | Me | 1 | 7 |
| S-257 | N | CH | —CH₂O— | H | H | Me | 1 | 8 |
| S-258 | N | CH | —CH₂O— | H | H | Me | 1 | 9 |
| S-259 | N | CH | —CH₂O— | H | H | Me | 2 | 7 |
| S-260 | N | CH | —CH₂O— | H | H | Me | 2 | 8 |
| S-261 | N | CH | —CH₂O— | H | H | Me | 2 | 9 |
| S-262 | N | CH | —CH₂O— | H | H | Me | 3 | 7 |
| S-263 | N | CH | —CH₂O— | H | H | Me | 3 | 8 |
| S-264 | N | CH | —CH₂O— | H | H | Me | 3 | 9 |
| S-265 | N | CH | —CH₂O— | H | H | Me | 4 | 7 |
| S-266 | N | CH | —CH₂O— | H | H | Me | 4 | 8 |
| S-267 | N | CH | —CH₂O— | H | H | Me | 4 | 9 |
| S-268 | N | CH | —CH₂O— | H | H | Me | 5 | 7 |
| S-269 | N | CH | —CH₂O— | H | H | Me | 5 | 8 |
| S-270 | N | CH | —CH₂O— | H | H | Me | 5 | 9 |
| S-271 | N | CH | —CH₂O— | Me | Me | H | 1 | 7 |
| S-272 | N | CH | —CH₂O— | Me | Me | H | 1 | 8 |
| S-273 | N | CH | —CH₂O— | Me | Me | H | 1 | 9 |
| S-274 | N | CH | —CH₂O— | Me | Me | H | 2 | 7 |
| S-275 | N | CH | —CH₂O— | Me | Me | H | 2 | 8 |
| S-276 | N | CH | —CH₂O— | Me | Me | H | 2 | 9 |
| S-277 | N | CH | —CH₂O— | Me | Me | H | 3 | 7 |
| S-278 | N | CH | —CH₂O— | Me | Me | H | 3 | 8 |
| S-279 | N | CH | —CH₂O— | Me | Me | H | 3 | 9 |
| S-280 | N | CH | —CH₂O— | Me | Me | H | 4 | 7 |
| S-281 | N | CH | —CH₂O— | Me | Me | H | 4 | 8 |
| S-282 | N | CH | —CH₂O— | Me | Me | H | 4 | 9 |
| S-283 | N | CH | —CH₂O— | Me | Me | H | 5 | 7 |
| S-284 | N | CH | —CH₂O— | Me | Me | H | 5 | 8 |
| S-285 | N | CH | —CH₂O— | Me | Me | H | 5 | 9 |
| S-286 | N | CH | —CH₂O— | H | Me | Me | 1 | 7 |
| S-287 | N | CH | —CH₂O— | H | Me | Me | 1 | 8 |
| S-288 | N | CH | —CH₂O— | H | Me | Me | 1 | 9 |
| S-289 | N | CH | —CH₂O— | H | Me | Me | 2 | 7 |
| S-290 | N | CH | —CH₂O— | H | Me | Me | 2 | 8 |
| S-291 | N | CH | —CH₂O— | H | Me | Me | 2 | 9 |
| S-292 | N | CH | —CH₂O— | H | Me | Me | 3 | 7 |
| S-293 | N | CH | —CH₂O— | H | Me | Me | 3 | 8 |
| S-294 | N | CH | —CH₂O— | H | Me | Me | 3 | 9 |
| S-295 | N | CH | —CH₂O— | H | Me | Me | 4 | 7 |
| S-296 | N | CH | —CH₂O— | H | Me | Me | 4 | 8 |
| S-297 | N | CH | —CH₂O— | H | Me | Me | 4 | 9 |
| S-298 | N | CH | —CH₂O— | H | Me | Me | 5 | 7 |
| S-299 | N | CH | —CH₂O— | H | Me | Me | 5 | 8 |
| S-300 | N | CH | —CH₂O— | H | Me | Me | 5 | 9 |
| S-301 | N | CH | singlebond | Me | H | H | 1 | 7 |
| S-302 | N | CH | singlebond | Me | H | H | 1 | 8 |
| S-303 | N | CH | singlebond | Me | H | H | 1 | 9 |
| S-304 | N | CH | singlebond | Me | H | H | 2 | 7 |
| S-305 | N | CH | singlebond | Me | H | H | 2 | 8 |
| S-306 | N | CH | singlebond | Me | H | H | 2 | 9 |
| S-307 | N | CH | singlebond | Me | H | H | 3 | 7 |
| S-308 | N | CH | singlebond | Me | H | H | 3 | 8 |
| S-309 | N | CH | singlebond | Me | H | H | 3 | 9 |
| S-310 | N | CH | singlebond | Me | H | H | 4 | 7 |
| S-311 | N | CH | singlebond | Me | H | H | 4 | 8 |
| S-312 | N | CH | singlebond | Me | H | H | 4 | 9 |
| S-313 | N | CH | singlebond | Me | H | H | 5 | 7 |
| S-314 | N | CH | singlebond | Me | H | H | 5 | 8 |
| S-315 | N | CH | singlebond | Me | H | H | 5 | 9 |
| S-316 | N | CH | singlebond | H | H | Me | 1 | 7 |
| S-317 | N | CH | singlebond | H | H | Me | 1 | 8 |
| S-318 | N | CH | singlebond | H | H | Me | 1 | 9 |
| S-319 | N | CH | singlebond | H | H | Me | 2 | 7 |
| S-320 | N | CH | singlebond | H | H | Me | 2 | 8 |
| S-321 | N | CH | singlebond | H | H | Me | 2 | 9 |
| S-322 | N | CH | singlebond | H | H | Me | 3 | 7 |
| S-323 | N | CH | singlebond | H | H | Me | 3 | 8 |
| S-324 | N | CH | singlebond | H | H | Me | 3 | 9 |
| S-325 | N | CH | singlebond | H | H | Me | 4 | 7 |
| S-326 | N | CH | singlebond | H | H | Me | 4 | 8 |
| S-327 | N | CH | singlebond | H | H | Me | 4 | 9 |
| S-328 | N | CH | singlebond | H | H | Me | 5 | 7 |
| S-329 | N | CH | singlebond | H | H | Me | 5 | 8 |
| S-330 | N | CH | singlebond | H | H | Me | 5 | 9 |

TABLE 68

| Compound No. | G¹ | G² | Q¹ | $R^a$ | $R^b$ | $R^c$ | n | m |
|---|---|---|---|---|---|---|---|---|
| S-331 | N | CH | singlebond | Me | Me | H | 1 | 7 |
| S-332 | N | CH | singlebond | Me | Me | H | 1 | 8 |
| S-333 | N | CH | singlebond | Me | Me | H | 1 | 9 |
| S-334 | N | CH | singlebond | Me | Me | H | 2 | 7 |
| S-335 | N | CH | singlebond | Me | Me | H | 2 | 8 |
| S-336 | N | CH | singlebond | Me | Me | H | 2 | 9 |
| S-337 | N | CH | singlebond | Me | Me | H | 3 | 7 |
| S-338 | N | CH | singlebond | Me | Me | H | 3 | 8 |
| S-339 | N | CH | singlebond | Me | Me | H | 3 | 9 |
| S-340 | N | CH | singlebond | Me | Me | H | 4 | 7 |
| S-341 | N | CH | singlebond | Me | Me | H | 4 | 8 |
| S-342 | N | CH | singlebond | Me | Me | H | 4 | 9 |
| S-343 | N | CH | singlebond | Me | Me | H | 5 | 7 |
| S-344 | N | CH | singlebond | Me | Me | H | 5 | 8 |
| S-345 | N | CH | singlebond | Me | Me | H | 5 | 9 |
| S-346 | N | CH | singlebond | H | Me | Me | 1 | 7 |
| S-347 | N | CH | singlebond | H | Me | Me | 1 | 8 |
| S-348 | N | CH | singlebond | H | Me | Me | 1 | 9 |
| S-349 | N | CH | singlebond | H | Me | Me | 2 | 7 |
| S-350 | N | CH | singlebond | H | Me | Me | 2 | 8 |
| S-351 | N | CH | singlebond | H | Me | Me | 2 | 9 |
| S-352 | N | CH | singlebond | H | Me | Me | 3 | 7 |
| S-353 | N | CH | singlebond | H | Me | Me | 3 | 8 |
| S-354 | N | CH | singlebond | H | Me | Me | 3 | 9 |
| S-355 | N | CH | singlebond | H | Me | Me | 4 | 7 |
| S-356 | N | CH | singlebond | H | Me | Me | 4 | 8 |
| S-357 | N | CH | singlebond | H | Me | Me | 4 | 9 |
| S-358 | N | CH | singlebond | H | Me | Me | 5 | 7 |
| S-359 | N | CH | singlebond | H | Me | Me | 5 | 8 |
| S-360 | N | CH | singlebond | H | Me | Me | 5 | 9 |
| S-361 | CH | N | —O— | Me | H | H | 1 | 7 |
| S-362 | CH | N | —O— | Me | H | H | 1 | 8 |
| S-363 | CH | N | —O— | Me | H | H | 1 | 9 |
| S-364 | CH | N | —O— | Me | H | H | 2 | 7 |
| S-365 | CH | N | —O— | Me | H | H | 2 | 8 |
| S-366 | CH | N | —O— | Me | H | H | 2 | 9 |
| S-367 | CH | N | —O— | Me | H | H | 3 | 7 |
| S-368 | CH | N | —O— | Me | H | H | 3 | 8 |
| S-369 | CH | N | —O— | Me | H | H | 3 | 9 |
| S-370 | CH | N | —O— | Me | H | H | 4 | 7 |
| S-371 | CH | N | —O— | Me | H | H | 4 | 8 |
| S-372 | CH | N | —O— | Me | H | H | 4 | 9 |
| S-373 | CH | N | —O— | Me | H | H | 5 | 7 |
| S-374 | CH | N | —O— | Me | H | H | 5 | 8 |
| S-375 | CH | N | —O— | Me | H | H | 5 | 9 |
| S-376 | CH | N | —O— | H | H | Me | 1 | 7 |
| S-377 | CH | N | —O— | H | H | Me | 1 | 8 |
| S-378 | CH | N | —O— | H | H | Me | 1 | 9 |
| S-379 | CH | N | —O— | H | H | Me | 2 | 7 |
| S-380 | CH | N | —O— | H | H | Me | 2 | 8 |
| S-381 | CH | N | —O— | H | H | Me | 2 | 9 |
| S-382 | CH | N | —O— | H | H | Me | 3 | 7 |
| S-383 | CH | N | —O— | H | H | Me | 3 | 8 |
| S-384 | CH | N | —O— | H | H | Me | 3 | 9 |
| S-385 | CH | N | —O— | H | H | Me | 4 | 7 |
| S-386 | CH | N | —O— | H | H | Me | 4 | 8 |
| S-387 | CH | N | —O— | H | H | Me | 4 | 9 |
| S-388 | CH | N | —O— | H | H | Me | 5 | 7 |

TABLE 68-continued

| Compound No. | G¹ | G² | Q¹ | $R^a$ | $R^b$ | $R^c$ | n | m |
|---|---|---|---|---|---|---|---|---|
| S-389 | CH | N | —O— | H | H | Me | 5 | 8 |
| S-390 | CH | N | —O— | H | H | Me | 5 | 9 |
| S-391 | CH | N | —O— | Me | Me | H | 1 | 7 |
| S-392 | CH | N | —O— | Me | Me | H | 1 | 8 |
| S-393 | CH | N | —O— | Me | Me | H | 1 | 9 |
| S-394 | CH | N | —O— | Me | Me | H | 2 | 7 |
| S-395 | CH | N | —O— | Me | Me | H | 2 | 8 |
| S-396 | CH | N | —O— | Me | Me | H | 2 | 9 |
| S-397 | CH | N | —O— | Me | Me | H | 3 | 7 |
| S-398 | CH | N | —O— | Me | Me | H | 3 | 8 |
| S-399 | CH | N | —O— | Me | Me | H | 3 | 9 |
| S-400 | CH | N | —O— | Me | Me | H | 4 | 7 |
| S-401 | CH | N | —O— | Me | Me | H | 4 | 8 |
| S-402 | CH | N | —O— | Me | Me | H | 4 | 9 |
| S-403 | CH | N | —O— | Me | Me | H | 5 | 7 |
| S-404 | CH | N | —O— | Me | Me | H | 5 | 8 |
| S-405 | CH | N | —O— | Me | Me | H | 5 | 9 |
| S-406 | CH | N | —O— | H | Me | Me | 1 | 7 |
| S-407 | CH | N | —O— | H | Me | Me | 1 | 8 |
| S-408 | CH | N | —O— | H | Me | Me | 1 | 9 |
| S-409 | CH | N | —O— | H | Me | Me | 2 | 7 |
| S-410 | CH | N | —O— | H | Me | Me | 2 | 8 |
| S-411 | CH | N | —O— | H | Me | Me | 2 | 9 |
| S-412 | CH | N | —O— | H | Me | Me | 3 | 7 |
| S-413 | CH | N | —O— | H | Me | Me | 3 | 8 |
| S-414 | CH | N | —O— | H | Me | Me | 3 | 9 |
| S-415 | CH | N | —O— | H | Me | Me | 4 | 7 |
| S-416 | CH | N | —O— | H | Me | Me | 4 | 8 |
| S-417 | CH | N | —O— | H | Me | Me | 4 | 9 |
| S-418 | CH | N | —O— | H | Me | Me | 5 | 7 |
| S-419 | CH | N | —O— | H | Me | Me | 5 | 8 |
| S-420 | CH | N | —O— | H | Me | Me | 5 | 9 |
| S-421 | CH | N | —CH₂O— | Me | H | H | 1 | 7 |
| S-422 | CH | N | —CH₂O— | Me | H | H | 1 | 8 |
| S-423 | CH | N | —CH₂O— | Me | H | H | 1 | 9 |
| S-424 | CH | N | —CH₂O— | Me | H | H | 2 | 7 |
| S-425 | CH | N | —CH₂O— | Me | H | H | 2 | 8 |
| S-426 | CH | N | —CH₂O— | Me | H | H | 2 | 9 |
| S-427 | CH | N | —CH₂O— | Me | H | H | 3 | 7 |
| S-428 | CH | N | —CH₂O— | Me | H | H | 3 | 8 |
| S-429 | CH | N | —CH₂O— | Me | H | H | 3 | 9 |
| S-430 | CH | N | —CH₂O— | Me | H | H | 4 | 7 |
| S-431 | CH | N | —CH₂O— | Me | H | H | 4 | 8 |
| S-432 | CH | N | —CH₂O— | Me | H | H | 4 | 9 |
| S-433 | CH | N | —CH₂O— | Me | H | H | 5 | 7 |
| S-434 | CH | N | —CH₂O— | Me | H | H | 5 | 8 |
| S-435 | CH | N | —CH₂O— | Me | H | H | 5 | 9 |
| S-436 | CH | N | —CH₂O— | H | H | Me | 1 | 7 |
| S-437 | CH | N | —CH₂O— | H | H | Me | 1 | 8 |
| S-438 | CH | N | —CH₂O— | H | H | Me | 1 | 9 |
| S-439 | CH | N | —CH₂O— | H | H | Me | 2 | 7 |
| S-440 | CH | N | —CH₂O— | H | H | Me | 2 | 8 |

TABLE 69

| Compound No. | G¹ | G² | Q¹ | $R^a$ | $R^b$ | $R^c$ | n | m |
|---|---|---|---|---|---|---|---|---|
| S-441 | CH | N | —CH₂O— | H | H | Me | 2 | 9 |
| S-442 | CH | N | —CH₂O— | H | H | Me | 3 | 7 |
| S-443 | CH | N | —CH₂O— | H | H | Me | 3 | 8 |
| S-444 | CH | N | —CH₂O— | H | H | Me | 3 | 9 |
| S-445 | CH | N | —CH₂O— | H | H | Me | 4 | 7 |
| S-446 | CH | N | —CH₂O— | H | H | Me | 4 | 8 |
| S-447 | CH | N | —CH₂O— | H | H | Me | 4 | 9 |
| S-448 | CH | N | —CH₂O— | H | H | Me | 5 | 7 |
| S-449 | CH | N | —CH₂O— | H | H | Me | 5 | 8 |
| S-450 | CH | N | —CH₂O— | H | H | Me | 5 | 9 |
| S-451 | CH | N | —CH₂O— | Me | Me | H | 1 | 7 |
| S-452 | CH | N | —CH₂O— | Me | Me | H | 1 | 8 |
| S-453 | CH | N | —CH₂O— | Me | Me | H | 1 | 9 |
| S-454 | CH | N | —CH₂O— | Me | Me | H | 2 | 7 |
| S-455 | CH | N | —CH₂O— | Me | Me | H | 2 | 8 |
| S-456 | CH | N | —CH₂O— | Me | Me | H | 2 | 9 |
| S-457 | CH | N | —CH₂O— | Me | Me | H | 3 | 7 |
| S-458 | CH | N | —CH₂O— | Me | Me | H | 3 | 8 |
| S-459 | CH | N | —CH₂O— | Me | Me | H | 3 | 9 |
| S-460 | CH | N | —CH₂O— | Me | Me | H | 4 | 7 |
| S-461 | CH | N | —CH₂O— | Me | Me | H | 4 | 8 |
| S-462 | CH | N | —CH₂O— | Me | Me | H | 4 | 9 |
| S-463 | CH | N | —CH₂O— | Me | Me | H | 5 | 7 |
| S-464 | CH | N | —CH₂O— | Me | Me | H | 5 | 8 |
| S-465 | CH | N | —CH₂O— | Me | Me | H | 5 | 9 |
| S-466 | CH | N | —CH₂O— | H | Me | Me | 1 | 7 |
| S-467 | CH | N | —CH₂O— | H | Me | Me | 1 | 8 |
| S-468 | CH | N | —CH₂O— | H | Me | Me | 1 | 9 |
| S-469 | CH | N | —CH₂O— | H | Me | Me | 2 | 7 |
| S-470 | CH | N | —CH₂O— | H | Me | Me | 2 | 8 |
| S-471 | CH | N | —CH₂O— | H | Me | Me | 2 | 9 |
| S-472 | CH | N | —CH₂O— | H | Me | Me | 3 | 7 |
| S-473 | CH | N | —CH₂O— | H | Me | Me | 3 | 8 |
| S-474 | CH | N | —CH₂O— | H | Me | Me | 3 | 9 |
| S-475 | CH | N | —CH₂O— | H | Me | Me | 4 | 7 |
| S-476 | CH | N | —CH₂O— | H | Me | Me | 4 | 8 |
| S-477 | CH | N | —CH₂O— | H | Me | Me | 4 | 9 |
| S-478 | CH | N | —CH₂O— | H | Me | Me | 5 | 7 |
| S-479 | CH | N | —CH₂O— | H | Me | Me | 5 | 8 |
| S-480 | CH | N | —CH₂O— | H | Me | Me | 5 | 9 |
| S-481 | CH | N | singlebond | Me | H | H | 1 | 7 |
| S-482 | CH | N | singlebond | Me | H | H | 1 | 8 |
| S-483 | CH | N | singlebond | Me | H | H | 1 | 9 |
| S-484 | CH | N | singlebond | Me | H | H | 2 | 7 |
| S-485 | CH | N | singlebond | Me | H | H | 2 | 8 |
| S-486 | CH | N | singlebond | Me | H | H | 2 | 9 |
| S-487 | CH | N | singlebond | Me | H | H | 3 | 7 |
| S-488 | CH | N | singlebond | Me | H | H | 3 | 8 |
| S-489 | CH | N | singlebond | Me | H | H | 3 | 9 |
| S-490 | CH | N | singlebond | Me | H | H | 4 | 7 |
| S-491 | CH | N | singlebond | Me | H | H | 4 | 8 |
| S-492 | CH | N | singlebond | Me | H | H | 4 | 9 |
| S-493 | CH | N | singlebond | Me | H | H | 5 | 7 |
| S-494 | CH | N | singlebond | Me | H | H | 5 | 8 |
| S-495 | CH | N | singlebond | Me | H | H | 5 | 9 |
| S-496 | CH | N | singlebond | H | H | Me | 1 | 7 |
| S-497 | CH | N | singlebond | H | H | Me | 1 | 8 |
| S-498 | CH | N | singlebond | H | H | Me | 1 | 9 |
| S-499 | CH | N | singlebond | H | H | Me | 2 | 7 |
| S-500 | CH | N | singlebond | H | H | Me | 2 | 8 |
| S-501 | CH | N | singlebond | H | H | Me | 2 | 9 |
| S-502 | CH | N | singlebond | H | H | Me | 3 | 7 |
| S-503 | CH | N | singlebond | H | H | Me | 3 | 8 |
| S-504 | CH | N | singlebond | H | H | Me | 3 | 9 |
| S-505 | CH | N | singlebond | H | H | Me | 4 | 7 |
| S-506 | CH | N | singlebond | H | H | Me | 4 | 8 |
| S-507 | CH | N | singlebond | H | H | Me | 4 | 9 |
| S-508 | CH | N | singlebond | H | H | Me | 5 | 7 |
| S-509 | CH | N | singlebond | H | H | Me | 5 | 8 |
| S-510 | CH | N | singlebond | H | H | Me | 5 | 9 |
| S-511 | CH | N | singlebond | Me | Me | H | 1 | 7 |
| S-512 | CH | N | singlebond | Me | Me | H | 1 | 8 |
| S-513 | CH | N | singlebond | Me | Me | H | 1 | 9 |
| S-514 | CH | N | singlebond | Me | Me | H | 2 | 7 |
| S-515 | CH | N | singlebond | Me | Me | H | 2 | 8 |
| S-516 | CH | N | singlebond | Me | Me | H | 2 | 9 |
| S-517 | CH | N | singlebond | Me | Me | H | 3 | 7 |
| S-518 | CH | N | singlebond | Me | Me | H | 3 | 8 |
| S-519 | CH | N | singlebond | Me | Me | H | 3 | 9 |
| S-520 | CH | N | singlebond | Me | Me | H | 4 | 7 |
| S-521 | CH | N | singlebond | Me | Me | H | 4 | 8 |
| S-522 | CH | N | singlebond | Me | Me | H | 4 | 9 |
| S-523 | CH | N | singlebond | Me | Me | H | 5 | 7 |
| S-524 | CH | N | singlebond | Me | Me | H | 5 | 8 |
| S-525 | CH | N | singlebond | Me | Me | H | 5 | 9 |
| S-526 | CH | N | singlebond | H | Me | Me | 1 | 7 |
| S-527 | CH | N | singlebond | H | Me | Me | 1 | 8 |
| S-528 | CH | N | singlebond | H | Me | Me | 1 | 9 |
| S-529 | CH | N | singlebond | H | Me | Me | 2 | 7 |
| S-530 | CH | N | singlebond | H | Me | Me | 2 | 8 |
| S-531 | CH | N | singlebond | H | Me | Me | 2 | 9 |
| S-532 | CH | N | singlebond | H | Me | Me | 3 | 7 |
| S-533 | CH | N | singlebond | H | Me | Me | 3 | 8 |

TABLE 69-continued

| Compound No. | G¹ | G² | Q¹ | $R^a$ | $R^b$ | $R^c$ | n | m |
|---|---|---|---|---|---|---|---|---|
| S-534 | CH | N | singlebond | H | Me | Me | 3 | 9 |
| S-535 | CH | N | singlebond | H | Me | Me | 4 | 7 |
| S-536 | CH | N | singlebond | H | Me | Me | 4 | 8 |
| S-537 | CH | N | singlebond | H | Me | Me | 4 | 9 |
| S-538 | CH | N | singlebond | H | Me | Me | 5 | 7 |
| S-539 | CH | N | singlebond | H | Me | Me | 5 | 8 |
| S-540 | CH | N | singlebond | H | Me | Me | 5 | 9 |

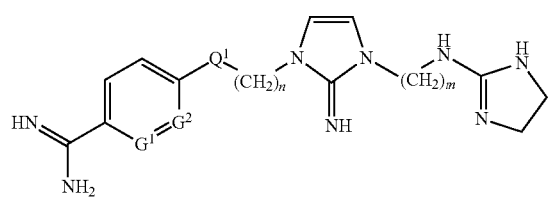

TABLE 70

| Compound No. | G¹ | G² | Q¹ | n | m |
|---|---|---|---|---|---|
| T-1 | CH | CH | —O— | 1 | 7 |
| T-2 | CH | CH | —O— | 1 | 8 |
| T-3 | CH | CH | —O— | 1 | 9 |
| T-4 | CH | CH | —O— | 2 | 7 |
| T-5 | CH | CH | —O— | 2 | 8 |
| T-6 | CH | CH | —O— | 2 | 9 |
| T-7 | CH | CH | —O— | 3 | 7 |
| T-8 | CH | CH | —O— | 3 | 8 |
| T-9 | CH | CH | —O— | 3 | 9 |
| T-10 | CH | CH | —O— | 4 | 7 |
| T-11 | CH | CH | —O— | 4 | 8 |
| T-12 | CH | CH | —O— | 4 | 9 |
| T-13 | CH | CH | —O— | 5 | 7 |
| T-14 | CH | CH | —O— | 5 | 8 |
| T-15 | CH | CH | —O— | 5 | 9 |
| T-16 | CH | CH | —CH₂O— | 1 | 7 |
| T-17 | CH | CH | —CH₂O— | 1 | 8 |
| T-18 | CH | CH | —CH₂O— | 1 | 9 |
| T-19 | CH | CH | —CH₂O— | 2 | 7 |
| T-20 | CH | CH | —CH₂O— | 2 | 8 |
| T-21 | CH | CH | —CH₂O— | 2 | 9 |
| T-22 | CH | CH | —CH₂O— | 3 | 7 |
| T-23 | CH | CH | —CH₂O— | 3 | 8 |
| T-24 | CH | CH | —CH₂O— | 3 | 9 |
| T-25 | CH | CH | —CH₂O— | 4 | 7 |
| T-26 | CH | CH | —CH₂O— | 4 | 8 |
| T-27 | CH | CH | —CH₂O— | 4 | 9 |
| T-28 | CH | CH | —CH₂O— | 5 | 7 |
| T-29 | CH | CH | —CH₂O— | 5 | 8 |
| T-30 | CH | CH | —CH₂O— | 5 | 9 |
| T-31 | CH | CH | singlebond | 1 | 7 |
| T-32 | CH | CH | singlebond | 1 | 8 |
| T-33 | CH | CH | singlebond | 1 | 9 |
| T-34 | CH | CH | singlebond | 2 | 7 |
| T-35 | CH | CH | singlebond | 2 | 8 |
| T-36 | CH | CH | singlebond | 2 | 9 |
| T-37 | CH | CH | singlebond | 3 | 7 |
| T-38 | CH | CH | singlebond | 3 | 8 |
| T-39 | CH | CH | singlebond | 3 | 9 |
| T-40 | CH | CH | singlebond | 4 | 7 |
| T-41 | CH | CH | singlebond | 4 | 8 |
| T-42 | CH | CH | singlebond | 4 | 9 |
| T-43 | CH | CH | singlebond | 5 | 7 |
| T-44 | CH | CH | singlebond | 5 | 8 |
| T-45 | CH | CH | singlebond | 5 | 9 |
| T-46 | N | CH | —O— | 1 | 7 |
| T-47 | N | CH | —O— | 1 | 8 |
| T-48 | N | CH | —O— | 1 | 9 |
| T-49 | N | CH | —O— | 2 | 7 |
| T-50 | N | CH | —O— | 2 | 8 |
| T-51 | N | CH | —O— | 2 | 9 |
| T-52 | N | CH | —O— | 3 | 7 |
| T-53 | N | CH | —O— | 3 | 8 |
| T-54 | N | CH | —O— | 3 | 9 |
| T-55 | N | CH | —O— | 4 | 7 |
| T-56 | N | CH | —O— | 4 | 8 |
| T-57 | N | CH | —O— | 4 | 9 |
| T-58 | N | CH | —O— | 5 | 7 |
| T-59 | N | CH | —O— | 5 | 8 |
| T-60 | N | CH | —O— | 5 | 9 |
| T-61 | N | CH | —CH₂O— | 1 | 7 |
| T-62 | N | CH | —CH₂O— | 1 | 8 |
| T-63 | N | CH | —CH₂O— | 1 | 9 |
| T-64 | N | CH | —CH₂O— | 2 | 7 |
| T-65 | N | CH | —CH₂O— | 2 | 8 |
| T-66 | N | CH | —CH₂O— | 2 | 9 |
| T-67 | N | CH | —CH₂O— | 3 | 7 |
| T-68 | N | CH | —CH₂O— | 3 | 8 |
| T-69 | N | CH | —CH₂O— | 3 | 9 |
| T-70 | N | CH | —CH₂O— | 4 | 7 |
| T-71 | N | CH | —CH₂O— | 4 | 8 |
| T-72 | N | CH | —CH₂O— | 4 | 9 |
| T-73 | N | CH | —CH₂O— | 5 | 7 |
| T-74 | N | CH | —CH₂O— | 5 | 8 |
| T-75 | N | CH | —CH₂O— | 5 | 9 |
| T-76 | N | CH | singlebond | 1 | 7 |
| T-77 | N | CH | singlebond | 1 | 8 |
| T-78 | N | CH | singlebond | 1 | 9 |
| T-79 | N | CH | singlebond | 2 | 7 |
| T-80 | N | CH | singlebond | 2 | 8 |
| T-81 | N | CH | singlebond | 2 | 9 |
| T-82 | N | CH | singlebond | 3 | 7 |
| T-83 | N | CH | singlebond | 3 | 8 |
| T-84 | N | CH | singlebond | 3 | 9 |
| T-85 | N | CH | singlebond | 4 | 7 |
| T-86 | N | CH | singlebond | 4 | 8 |
| T-87 | N | CH | singlebond | 4 | 9 |
| T-88 | N | CH | singlebond | 5 | 7 |
| T-89 | N | CH | singlebond | 5 | 8 |
| T-90 | N | CH | singlebond | 5 | 9 |
| T-91 | CH | N | —O— | 1 | 7 |
| T-92 | CH | N | —O— | 1 | 8 |
| T-93 | CH | N | —O— | 1 | 9 |
| T-94 | CH | N | —O— | 2 | 7 |
| T-95 | CH | N | —O— | 2 | 8 |
| T-96 | CH | N | —O— | 2 | 9 |
| T-97 | CH | N | —O— | 3 | 7 |
| T-98 | CH | N | —O— | 3 | 8 |
| T-99 | CH | N | —O— | 3 | 9 |
| T-100 | CH | N | —O— | 4 | 7 |
| T-101 | CH | N | —O— | 4 | 8 |
| T-102 | CH | N | —O— | 4 | 9 |
| T-103 | CH | N | —O— | 5 | 7 |
| T-104 | CH | N | —O— | 5 | 8 |
| T-105 | CH | N | —O— | 5 | 9 |
| T-106 | CH | N | —CH₂O— | 1 | 7 |
| T-107 | CH | N | —CH₂O— | 1 | 8 |
| T-108 | CH | N | —CH₂O— | 1 | 9 |
| T-109 | CH | N | —CH₂O— | 2 | 7 |
| T-110 | CH | N | —CH₂O— | 2 | 8 |

TABLE 71

| Compound No. | G¹ | G² | Q¹ | n | m |
|---|---|---|---|---|---|
| T-111 | CH | N | —CH₂O— | 2 | 9 |
| T-112 | CH | N | —CH₂O— | 3 | 7 |
| T-113 | CH | N | —CH₂O— | 3 | 8 |
| T-114 | CH | N | —CH₂O— | 3 | 9 |
| T-115 | CH | N | —CH₂O— | 4 | 7 |
| T-116 | CH | N | —CH₂O— | 4 | 8 |

TABLE 71-continued

| Compound No. | G¹ | G² | Q¹ | n | m |
|---|---|---|---|---|---|
| T-117 | CH | N | —CH$_2$O— | 4 | 9 |
| T-118 | CH | N | —CH$_2$O— | 5 | 7 |
| T-119 | CH | N | —CH$_2$O— | 5 | 8 |
| T-120 | CH | N | —CH$_2$O— | 5 | 9 |
| T-121 | CH | N | singlebond | 1 | 7 |
| T-122 | CH | N | singlebond | 1 | 8 |
| T-123 | CH | N | singlebond | 1 | 9 |
| T-124 | CH | N | singlebond | 2 | 7 |
| T-125 | CH | N | singlebond | 2 | 8 |
| T-126 | CH | N | singlebond | 2 | 9 |
| T-127 | CH | N | singlebond | 3 | 7 |
| T-128 | CH | N | singlebond | 3 | 8 |
| T-129 | CH | N | singlebond | 3 | 9 |
| T-130 | CH | N | singlebond | 4 | 7 |
| T-131 | CH | N | singlebond | 4 | 8 |
| T-132 | CH | N | singlebond | 4 | 9 |
| T-133 | CH | N | singlebond | 5 | 7 |
| T-134 | CH | N | singlebond | 5 | 8 |
| T-135 | CH | N | singlebond | 5 | 9 |

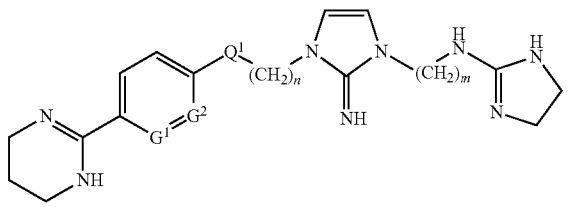

TABLE 72

| Compound No. | G¹ | G² | Q¹ | n | m |
|---|---|---|---|---|---|
| U-1 | CH | CH | —O— | 1 | 7 |
| U-2 | CH | CH | —O— | 1 | 8 |
| U-3 | CH | CH | —O— | 1 | 9 |
| U-4 | CH | CH | —O— | 2 | 7 |
| U-5 | CH | CH | —O— | 2 | 8 |
| U-6 | CH | CH | —O— | 2 | 9 |
| U-7 | CH | CH | —O— | 3 | 7 |
| U-8 | CH | CH | —O— | 3 | 8 |
| U-9 | CH | CH | —O— | 3 | 9 |
| U-10 | CH | CH | —O— | 4 | 7 |
| U-11 | CH | CH | —O— | 4 | 8 |
| U-12 | CH | CH | —O— | 4 | 9 |
| U-13 | CH | CH | —O— | 5 | 7 |
| U-14 | CH | CH | —O— | 5 | 8 |
| U-15 | CH | CH | —O— | 5 | 9 |
| U-16 | CH | CH | —CH$_2$O— | 1 | 7 |
| U-17 | CH | CH | —CH$_2$O— | 1 | 8 |
| U-18 | CH | CH | —CH$_2$O— | 1 | 9 |
| U-19 | CH | CH | —CH$_2$O— | 2 | 7 |
| U-20 | CH | CH | —CH$_2$O— | 2 | 8 |
| U-21 | CH | CH | —CH$_2$O— | 2 | 9 |
| U-22 | CH | CH | —CH$_2$O— | 3 | 7 |
| U-23 | CH | CH | —CH$_2$O— | 3 | 8 |
| U-24 | CH | CH | —CH$_2$O— | 3 | 9 |
| U-25 | CH | CH | —CH$_2$O— | 4 | 7 |
| U-26 | CH | CH | —CH$_2$O— | 4 | 8 |
| U-27 | CH | CH | —CH$_2$O— | 4 | 9 |
| U-28 | CH | CH | —CH$_2$O— | 5 | 7 |
| U-29 | CH | CH | —CH$_2$O— | 5 | 8 |
| U-30 | CH | CH | —CH$_2$O— | 5 | 9 |
| U-31 | CH | CH | singlebond | 1 | 7 |
| U-32 | CH | CH | singlebond | 1 | 8 |
| U-33 | CH | CH | singlebond | 1 | 9 |
| U-34 | CH | CH | singlebond | 2 | 7 |
| U-35 | CH | CH | singlebond | 2 | 8 |
| U-36 | CH | CH | singlebond | 2 | 9 |

TABLE 72-continued

| Compound No. | G¹ | G² | Q¹ | n | m |
|---|---|---|---|---|---|
| U-37 | CH | CH | singlebond | 3 | 7 |
| U-38 | CH | CH | singlebond | 3 | 8 |
| U-39 | CH | CH | singlebond | 3 | 9 |
| U-40 | CH | CH | singlebond | 4 | 7 |
| U-41 | CH | CH | singlebond | 4 | 8 |
| U-42 | CH | CH | singlebond | 4 | 9 |
| U-43 | CH | CH | singlebond | 5 | 7 |
| U-44 | CH | CH | singlebond | 5 | 8 |
| U-45 | CH | CH | singlebond | 5 | 9 |
| U-46 | N | CH | —O— | 1 | 7 |
| U-47 | N | CH | —O— | 1 | 8 |
| U-48 | N | CH | —O— | 1 | 9 |
| U-49 | N | CH | —O— | 2 | 7 |
| U-50 | N | CH | —O— | 2 | 8 |
| U-51 | N | CH | —O— | 2 | 9 |
| U-52 | N | CH | —O— | 3 | 7 |
| U-53 | N | CH | —O— | 3 | 8 |
| U-54 | N | CH | —O— | 3 | 9 |
| U-55 | N | CH | —O— | 4 | 7 |
| U-56 | N | CH | —O— | 4 | 8 |
| U-57 | N | CH | —O— | 4 | 9 |
| U-58 | N | CH | —O— | 5 | 7 |
| U-59 | N | CH | —O— | 5 | 8 |
| U-60 | N | CH | —O— | 5 | 9 |
| U-61 | N | CH | —CH$_2$O— | 1 | 7 |
| U-62 | N | CH | —CH$_2$O— | 1 | 8 |
| U-63 | N | CH | —CH$_2$O— | 1 | 9 |
| U-64 | N | CH | —CH$_2$O— | 2 | 7 |
| U-65 | N | CH | —CH$_2$O— | 2 | 8 |
| U-66 | N | CH | —CH$_2$O— | 2 | 9 |
| U-67 | N | CH | —CH$_2$O— | 3 | 7 |
| U-68 | N | CH | —CH$_2$O— | 3 | 8 |
| U-69 | N | CH | —CH$_2$O— | 3 | 9 |
| U-70 | N | CH | —CH$_2$O— | 4 | 7 |
| U-71 | N | CH | —CH$_2$O— | 4 | 8 |
| U-72 | N | CH | —CH$_2$O— | 4 | 9 |
| U-73 | N | CH | —CH$_2$O— | 5 | 7 |
| U-74 | N | CH | —CH$_2$O— | 5 | 8 |
| U-75 | N | CH | —CH$_2$O— | 5 | 9 |
| U-76 | N | CH | singlebond | 1 | 7 |
| U-77 | N | CH | singlebond | 1 | 8 |
| U-78 | N | CH | singlebond | 1 | 9 |
| U-79 | N | CH | singlebond | 2 | 7 |
| U-80 | N | CH | singlebond | 2 | 8 |
| U-81 | N | CH | singlebond | 2 | 9 |
| U-82 | N | CH | singlebond | 3 | 7 |
| U-83 | N | CH | singlebond | 3 | 8 |
| U-84 | N | CH | singlebond | 3 | 9 |
| U-85 | N | CH | singlebond | 4 | 7 |
| U-86 | N | CH | singlebond | 4 | 8 |
| U-87 | N | CH | singlebond | 4 | 9 |
| U-88 | N | CH | singlebond | 5 | 7 |
| U-89 | N | CH | singlebond | 5 | 8 |
| U-90 | N | CH | singlebond | 5 | 9 |
| U-91 | CH | N | —O— | 1 | 7 |
| U-92 | CH | N | —O— | 1 | 8 |
| U-93 | CH | N | —O— | 1 | 9 |
| U-94 | CH | N | —O— | 2 | 7 |
| U-95 | CH | N | —O— | 2 | 8 |
| U-96 | CH | N | —O— | 2 | 9 |
| U-97 | CH | N | —O— | 3 | 7 |
| U-98 | CH | N | —O— | 3 | 8 |
| U-99 | CH | N | —O— | 3 | 9 |
| U-100 | CH | N | —O— | 4 | 7 |
| U-101 | CH | N | —O— | 4 | 8 |
| U-102 | CH | N | —O— | 4 | 9 |
| U-103 | CH | N | —O— | 5 | 7 |
| U-104 | CH | N | —O— | 5 | 8 |
| U-105 | CH | N | —O— | 5 | 9 |
| U-106 | CH | N | —CH$_2$O— | 1 | 7 |
| U-107 | CH | N | —CH$_2$O— | 1 | 8 |
| U-108 | CH | N | —CH$_2$O— | 1 | 9 |
| U-109 | CH | N | —CH$_2$O— | 2 | 7 |
| U-110 | CH | N | —CH$_2$O— | 2 | 8 |

TABLE 73

| Compound No. | $G^1$ | $G^2$ | $Q^1$ | n | m |
|---|---|---|---|---|---|
| U-111 | CH | N | —CH$_2$O— | 2 | 9 |
| U-112 | CH | N | —CH$_2$O— | 3 | 7 |
| U-113 | CH | N | —CH$_2$O— | 3 | 8 |
| U-114 | CH | N | —CH$_2$O— | 3 | 9 |
| U-115 | CH | N | —CH$_2$O— | 4 | 7 |
| U-116 | CH | N | —CH$_2$O— | 4 | 8 |
| U-117 | CH | N | —CH$_2$O— | 4 | 9 |
| U-118 | CH | N | —CH$_2$O— | 5 | 7 |
| U-119 | CH | N | —CH$_2$O— | 5 | 8 |
| U-120 | CH | N | —CH$_2$O— | 5 | 9 |
| U-121 | CH | N | singlebond | 1 | 7 |
| U-122 | CH | N | singlebond | 1 | 8 |
| U-123 | CH | N | singlebond | 1 | 9 |
| U-124 | CH | N | singlebond | 2 | 7 |
| U-125 | CH | N | singlebond | 2 | 8 |
| U-126 | CH | N | singlebond | 2 | 9 |
| U-127 | CH | N | singlebond | 3 | 7 |
| U-128 | CH | N | singlebond | 3 | 8 |
| U-129 | CH | N | singlebond | 3 | 9 |
| U-130 | CH | N | singlebond | 4 | 7 |
| U-131 | CH | N | singlebond | 4 | 8 |
| U-132 | CH | N | singlebond | 4 | 9 |
| U-133 | CH | N | singlebond | 5 | 7 |
| U-134 | CH | N | singlebond | 5 | 8 |
| U-135 | CH | N | singlebond | 5 | 9 |

The compound [I] according to the present invention includes hydrates, various solvates and crystal polymorphs. Furthermore, the compound [I] according to the present invention includes stereoisomers and tautomers based on an asymmetric carbon atom, a double bond, or the like, and mixtures thereof.

Salts of the compound [I] according to the present invention are not particularly limited, provided that the salts are agriculturally and horticulturally acceptable salts. Examples thereof include: salts of inorganic acid such as hydrochloric acid or sulfuric acid; salts of organic acid such as acetic acid or lactic acid; salts of alkali metal such as lithium, sodium, or potassium; salts of alkaline earth metal such as calcium or magnesium; salts of transition metal such as iron or copper; salts of organic base such as ammonia, triethylamine, tributylamine, pyridine, or hydrazine. Salts of the compound [I] may be obtained by a known method from the compound [I].

Next, production examples of the amidine compound represented by formula [I] and salts thereof will be described. The production examples shown below are intended to illustrate the present invention and are not intended to limit the scope of the present invention.

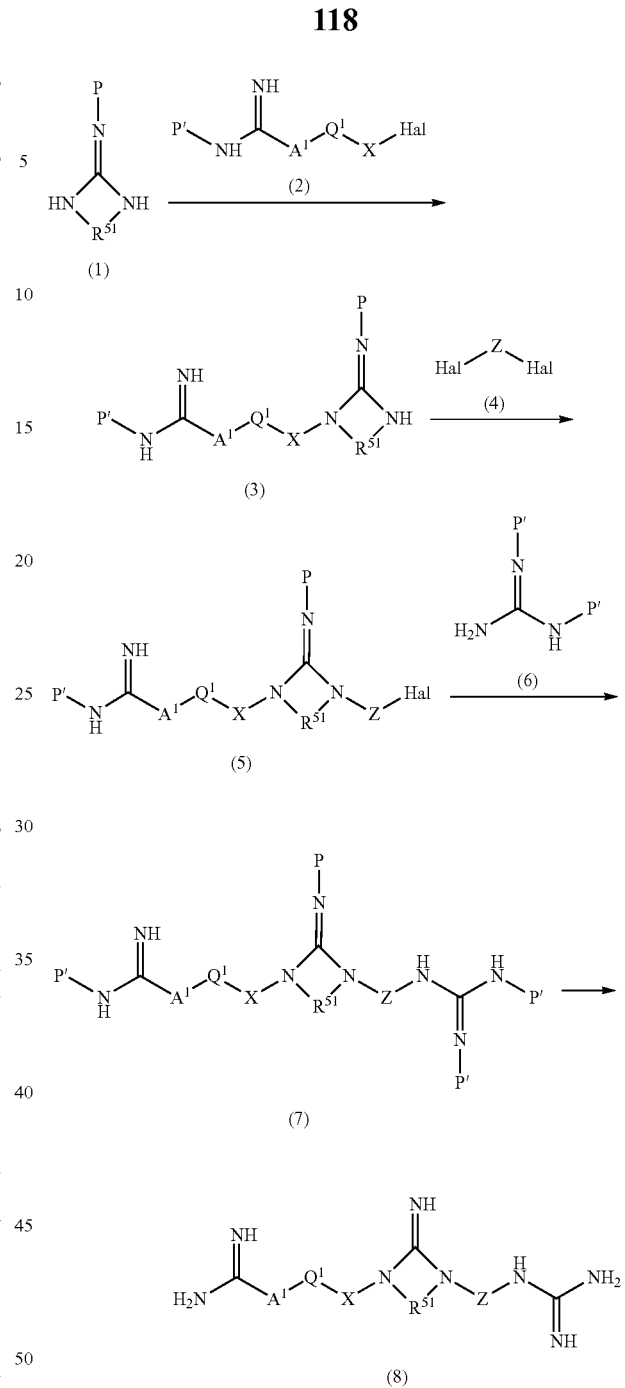

In the formulae, $A^1$, $Q^1$, X, Z, and $R^{51}$ are described above. Hal represents a halogen atom and P and P' represent protective groups.

PRODUCTION EXAMPLE 1

Cyclic guanidine compound (1) and a compound (2) are reacted to obtain a compound (3). The compound (3) and a halogen compound (4) are reacted to obtain a compound (5). A guanidine derivative (6) and the compound (5) are reacted to obtain a compound (7). A protecting group P and a protective group P' of the compound (7) are deprotected to obtain a guanidine compound (8) according to the present invention.

PRODUCTION EXAMPLE 2

An alcohol compound (9) and a guanidine derivative (10) are reacted by Mitsunobu reaction to obtain a compound (11). The compound (11) and the guanidine derivative (6) are reacted to obtain a compound (12). A protecting group P and a protective group P' of the compound (12) are deprotected to obtain a guanidine compound (13) according to the present invention.

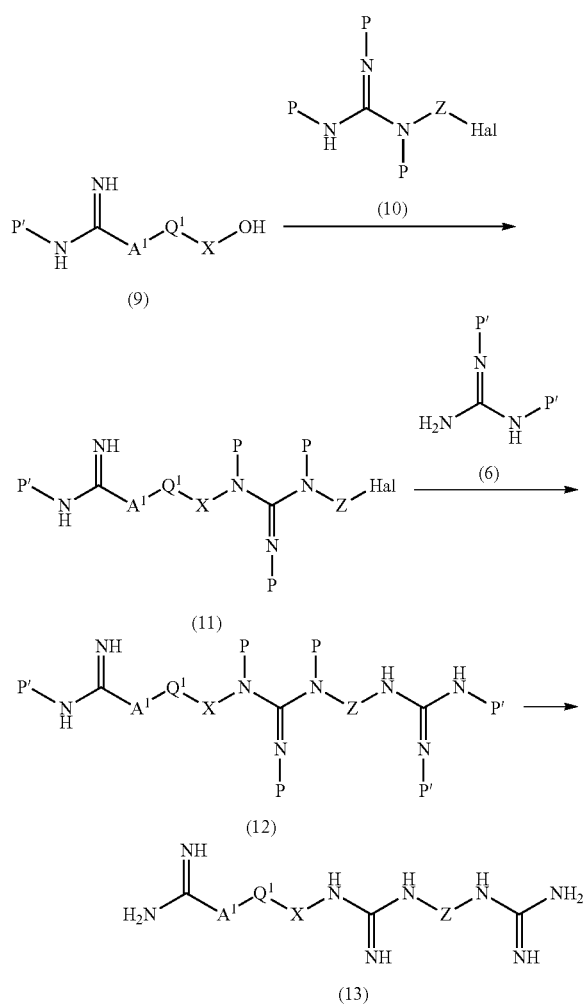

In the formulae, $A^1$, $Q^1$, X, and Z are described above. Hal represents a halogen atom and P and P' represent protective groups.

After a completion of the synthesis reaction, post-treatments which are ordinary conducted in organic synthetic chemistry, and, as needed, conventionally known separation and puririfaction procedures make it possible to efficiently isolate a target product.

Structure of the target product can be identified and confirmed by measurement of $^1$H-NMR spectrum, IR spectrum, or mass spectrum, or elemental analysis.

The fungicide or plant disease control agent according to the present invention contains at least one selected from the group consisting of the compound [I] and the salt thereof as an active component thereof. The amount of the active ingredient contained in the fungicide or plant disease control agent according to the present invention, relative to the whole formulation, is preferably 0.01 to 90% by weight, and more preferably 0.05 to 85% by weight.

The fungicide or plant disease-controlling agent according to the present invention may be used in an agrochemically acceptable form, that is, in a form of an agrochemical formulation, such as water-dispersible powder, granule, powder, emulsion, water-soluble powder, suspension, or water-dispersible granule.

Examples of an additive and a carrier used in solid formulation include: vegetable powder such as soybean flour or wheat flour; mineral fine powder such as diatomite, apatite, plaster, talc, bentonite, pyrophylite, or clay; and an organic or inorganic compound such as sodium benzoate, urea, or sulfate of soda.

Examples of a solvent used in liquid formulation include: kerosene, xylene, petroleum-based aromatic hydrocarbons, cyclohexane, cyclohexanone, dimethyl formamide, dimethyl sulfoxide, alcohol, acetone, trichloroethylene, methylisobutylketone, mineral oil, vegetable oil, and water.

In addition, a surfactant may be added to the formulation, as necessary, in order to realize a uniform and stable form.

The surfactant which may be added is not particularly limited. Examples of the surfactant include: non-ionic surfactants such as polyoxyethylene-added alkylphenylether, polyoxyethylene-added alkylether, polyoxyethylene-added higher fatty acid ester, polyoxyethylene-added sorbitan higher fatty acid ester, polyoxyethylene-added tristyrylphenylether; sulfuric ester salts of polyoxyethylene-added alkylphenylethers, alkylbenzene sulfonates, sulfuric ester salts of higher alcohol, alkylnaphthalene sulfonates, polycarboxylates, lignin sulfonates, formaldehyde condensates of alkylnaphthalene sulfonates, and isobutylene-anhydrous maleic acid copolymers.

The thus obtained water-dispersible powder, emulsion, flowable agent, water-soluble powder, or water-dispersible granules are diluted with water to a predetermined concentration and used as a solution, a suspension, or an emulsion to be sprayed onto plants. Also, the powder and the granules are used to be sprayed directly onto plants.

The fungicide or plant disease control agent according to the present invention can be used to control a variety of diseases that occur upon the cultivation of agricultural and horticultural crops, including flowers, lawns, and grass, by seed treatment, foliage application, soil application or submerged application.

Although the application amount of the fungicide or plant disease-controlling agent according to the present invention is influenced by weather conditions, formulation form, application time, application method, application place, target disease to be controlled, or target crops, an amount of an active ingredient thereof per 1 hectare is preferably 1 to 1,000 g, and more preferably 10 to 100 g.

In the case where a water-dispersible powder, emulsion, suspension, water-soluble powder, or water-dispersible granule is applied after being diluted with water, the application concentration is preferably 1 to 1,000 ppm, and more preferably 10 to 250 ppm.

The fungicide or plant disease-controlling agent according to the present invention may be used to control against plant diseases caused by a wide range of types of fungus belonging to filamentous fungi such as phycomycetes (Oomycetes), ascomycetes (sac) fungi (Ascomycetes), imperfect fungi (Deuteromycetes), basidiomycetes (Basidiomycetes), or zygomycetes (Zygomycetes).

Examples of plant diseases and pathogens to be controlled include the followings.

Sugar beet: brown spot disease (*Cercospora beticola*), black root disease (*Aphanomyces cochlioides*), root rot disease (*Thanatephorus cucumeris*), leaf rot disease (*Thanatephorus cucumeris*), and the like.

Peanut: brown spot disease (*Mycosphaerella arachidis*), leaf mold (*Ascochyta* sp.), rust disease (*Puccinia arachidis*), damping-off disease (*Pythium debaryanum*), rust spot disease (*Alternaria alternate*), stem rot disease (*Sclerotium rolfsii*), black rust disease (*Mycosphaerella berkeleyi*), and the like.

Cucumber: powdery mildew (*Sphaerotheca fuliginea*), downy mildew (*Pseudoperonospora cubensis*), gummy stem blight (*Mycosphaerella melonis*), wilt disease (*Fusarium oxysporum*), sclerotinia rot (*Sclerotinia sclerotiorum*), gray mold (*Botrytis cinerea*), anthracnose (*Colletotrichum orbiculare*), scab (*Cladosporium cucumerinum*), brown spot disease (*Corynespora cassiicola*), damping-off disease (*Pythium debaryanam, Rhizoctonia solani Kuhn*), Phomopsis root rot disease (*Phomopsis* sp.), Bacterial spot (*Pseudomonas syringae pv.Lecrymans*), and the like.

Tomato: gray mold disease (*Botrytis cinerea*), leaf mold disease (*Cladosporium fulvum*), late blight disease (*Phytophthora infestans*), verticillium wilt disease (*Verticillium albo-atrum*), powdery mildew disease (*Oidium neolycopersici*), early blight disease (*Alternaria solani*), leaf mold disease (*Pseudocercospora fuligena*), and the like.

Eggplant: gray mold disease (*Botrytis cinerea*), black rot disease (*Corynespora melongenae*), powdery mildew disease (*Erysiphe cichoracearum*), leaf mold disease (*Mycovellosiella nattrassii*), sclerotinia rot disease (*Sclerotinia sclerotiorum*), and the like.

Strawberry: gray mold disease (*Botrytis cinerea*), powdery mildew disease (*Sphaerotheca humuli*), anthracnose disease (*Colletotrichum acutatum, Colletotrichum fragariae*), phytophthora rot disease (*Phytophthora cactorum*), soft rot disease (*Rhizopus stolonifer*), fsarium wilt disease (*Fusarium oxysporum*), and the like.

Onion: neck rot disease (*Botrytis allii*), gray mold disease (*Botrytis cinerea*), leaf blight disease (*Botrytis squamosal*), downy mildew disease (*Peronospora destructor*), Phytophthora porri disease (*Phytophthora porri*), and the like.

Cabbage: clubroot disease (*Plasmodiophora brassicae*), soft rot disease (*Erwinia carotovora*), black rot disease (*Xanthomonas campesrtis pv. Campestris*), bacterial black spot disease (*Pseudomonas syringae pv. maculicala, Pseudomonas syringae pv. Alisalensis*), downy mildew disease (*Peronospora parasitica*), sclerotinia rot disease (*Sclerotinia sclerotiorum*), black spot disease (*Alternaria brassicicola*), gray mold disease (*Botrytis cinerea*), and the like.

Common bean: sclerotinia rot disease (*Sclerotinia sclerotiorum*), gray mold disease (*Botrytis cinerea*), anthracnose (*Colletotrichum lindemuthianum*), angular spot disease (*Phaeoisariopsis griseola*), and the like.

Apple: powdery mildew disease (*Podosphaera leucotricha*), scab disease (*Venturia inaequalis*), Monilinia disease (*Monilinia mali*), black spot disease (*Mycosphaerella pomi*), valsa canker disease (*Valsa mali*), alternaria blotch disease (*Alternaria mali*), rust disease (*Gymnosporangium yamadae*), ring rot disease (*Botryosphaeria berengeriana*), anthracnose disease (*Glomerella cingulata, Colletotrichum acutatum*), leaf srot disease (*Diplocarpon mali*), fly speck disease (*Zygophiala jamaicensis*), Sooty blotch (*Gloeodes pomigena*), violet root rot disease (*Helicobasidium mompa*), gray mold disease (*Botrytis cinerea*), and the like.

Japanese apricot: scab disease (*Cladosporium carpophilum*), gray mold disease (*Botrytis cinerea*), brown rot disease (*Monilinia mumecola*), and the like.

Persimmon: powdery mildew disease (*Phyllactinia kakicola*), anthracnose disease (*Gloeosporium kaki*), angular leaf spot (*Cercospora kaki*), and the like.

Peach: brown rot disease (*Monilinia fructicola*), scab disease (*Cladosporium carpophilum*), phomopsis rot disease (*Phomopsis* sp.), bacterial shot hole disease (*Xanthomonas campestris pv. Pruni*), and the like.

Almond: brown rot disease (*Monilinia laxa*), spot blotch disease (*Stigmina carpophila*), scab disease (*Cladosporium carpophilum*), red leaf spot disease (*Polystigma rubrum*), alternaria blotch disease (*Alternaria alternata*), anthracnose (*Colletotrichum gloeospoides*), and the like.

Yellow peach: brown rot disease (*Monilinia fructicola*), anthracnose disease (*Colletotrichum acutatum*), black spot disease (*Alternaria* sp.), Monilinia Kusanoi disease (*Monilinia kusanoi*), and the like.

Grape: gray mold disease (*Botrytis cinerea*), powdery mildew disease (*Uncinula necator*), ripe rot disease (*Glomerella cingulata, Colletotrichum acutatum*), downy mildew disease (*Plasmopara viticola*), anthracnose disease (*Elsinoe ampelina*), brown spot disease (*Pseudocercospora vitis*), black rot disease (*Guignardia bidwellii*), white rot disease (*Coniella castaneicola*), and the like.

Pear: scab disease (*Venturia nashicola*), rust disease (*Gymnosporangium asiaticum*), black spot disease (*Alternaria kikuchiana*), ring rot disease (*Botryosphaeria berengeriana*), powdery mildew disease (*Phyllactinia mali*), cytospora canker disease (*Phomopsis fukushii*), brown spot blotch disease (*Stemphylium vesicarium*), anthracnose disease (*Glomerella cingulate*), and the like.

Tea: ring spot disease (*Pestalotia theae*), anthracnose disease (*Colletotrichum theae-sinensis*), and the like.

Citrus fruits: scab disease (*Elsinoe fawcetti*), blue mold disease (*Penicillium italicum*), common green mold disease (*Penicillium digitatum*), gray mold disease (*Botrytis cinerea*), melanose disease (*Diaporthe citri*), canker disease (*Xanthomonas campestris pv.Citri*), powdery mildew disease (*Oidium* sp.), and the like.

Wheat: powdery mildew (*Erysiphe graminis f.sp. Tritici*), red mold disease (*Gibberella zeae*), red rust disease (*Puccinia recondite*), brown snow mold disease (Pythium iwayamai), pink snow mold disease (*Monographella nivalis*), eye spot disease (*Pseudocercosporella herpotrichoides*), leaf scorch disease (*Septoria tritici*), glume blotch disease (*Leptosphaeria nodorum*), typhulasnow blight disease (*Typhula incarnate*), sclerotinia snow blight disease (Myriosclerotinia borealis), damping-off disease (*Gaeumanomyces graminis*), ergot disease (*Claviceps purpurea*), stinking smut disease (*Tilletia caries*), loose smut disease (*Ustilago nuda*), and the like.

Barley: leaf spot disease (*Pyrenophora graminea*), net blotch disease (*Pyrenophora teres*), leaf blotch disease (*Rhynchosporium secalis*), loose smut disease (*Ustilago tritici, U.nuda*), and the like.

Rice: blast disease (*Pyricularia oryzae*), sheath blight disease (*Rhizoctonia solani*), bakanae disease (*Gibberella fujikuroi*), brown spot disease (*Cochliobolus miyabeanus*), damping-off disease (*Pythium graminicolum*), bacterial leaf blight (*Xanthomonas oryzae*), bacterial seedling blight disease (*Burkholderia plantarii*), brown stripe disease (*Acidovorax avenae*), bacterial grain rot disease (*Burkholderia glumae*), Cercospora leaf spot disease (*Cercospora oryzae*), false smut disease (*Ustilaginoidea virens*), rice brown spot disease (*Alternaria alternata, Curvularia intermedia*), kernel discoloration of rice (*Alternaria padwickii*), pink coloring of rice grains (*Epicoccam purpurascenns*), and the like.

Tobacco: sclerotinia rot disease (*Sclerotinia sclerotiorum*), powdery mildew disease (*Erysiphe cichoracearum*), phytophthora rot disease (*Phytophthora nicotianae*), and the like.

Tulip: gray mold disease (*Botrytis cinerea*), and the like.

Sunflower: downy mildew disease (*Plasmopara halstedii*), sclerotinia rot disease (*Sclerotinia sclerotiorum*), and the like.

Bent grass: Sclerotinia snow blight (*Sclerotinia borealis*), Large patch (*Rhizoctonia solani*), Dollar spot (*Sclerotinia*

*homoeocarpa*), blast disease (*Pyricularia* sp.), Pythium red blight disease (*Pythium aphanidermatum*), anthracnose disease (*Colletotrichum graminicola*), and the like.

Orchard grass: powdery mildew disease (*Erysiphe graminis*), and the like.

Soybean: purple stain disease (*Cercospora kikuchii*), downy mildew disease (*Peronospora manshurica*), phytophthora rot disease (*Phytophthora sojae*), rust disease (*Phakopsora pachyrhizi*), sclerotinia rot disease (*Sclerotinia sclerotiorum*), anthracnose disease (*Colletotrichum truncatum*), gray mold disease (*Botrytis cinerea*), and the like.

Potato: hytophthora rot disease (*Phytophthora infestans*), early blight disease (*Aleternaria solani*), scurf disease (*Thanatephorus cucumeris*), and the like.

Banana: Panama disease (*Fusarium oxysporum*), Sigatoka disease (*Mycosphaerella fijiensis, Mycosphaerella musicola*), and the like.

Rape seed: sclerotinia rot disease (*Sclerotinia sclerotiorum*), root rot disease (*Phoma lingam*), black leaf spot disease (*Alternaria brassicae*), and the like.

Coffee: rust disease (*Hemileia vastatrix*), anthracnose (*Colletotrichum coffeanum*), leaf spot disease (*Cercospora coffeicola*), and the like.

Sugarcane: brown rust disease (*Puccinia melanocephala*), and the like.

Corn: zonate spot disease (*Gloecercospora sorghi*), rust disease (*Puccinia sorghi*), southern rust disease (*Puccinia polysora*), smut disease (*Ustilago maydis*), brown spot disease (*Cochliobolus heterostrophus*), northern leaf blight (*Setophaeria turcica*), and the like.

Cotton: seedling blight disease (*Pythium* sp), rust disease (*Phakopsora gossypii*), sour rot disease (*Mycosphaerella areola*), anthracnose (*Glomerella gossypii*), and the like.

The fungicide or plant disease-controlling agent according to the present invention is an agent with low phytotoxicity, low toxicity to fish or warm-blooded animals, and is safe to use.

The fungicide or plant disease-controlling agent according to the present invention may be mixed or used with other fungicides, insecticides, acaricides, nematocides, soil pesticides, anthelmintics, plant growth regulators, synergists, or the like.

Examples thereof are shown below.

Fungicide:
(1) Nucleic acid biosynthesis inhibitors:
(a) RNA polymerase I inhibitors: benalaxyl, benalaxyl-M, furalaxyl, metalaxyl, metalaxyl-M; oxadixyl; clozylacon, ofurace;
(b) Adenosine deaminase inhibitors: bupirimate, dimethirimol, ethirimol;
(c) DNA/RNA synthesis inhibitors: hymexazol, octhilinone;
(d) DNA topoisomerase II inhibitors: oxolinic acid;
(2) Mitotic inhibitors and cell division inhibitors:
(a) β-tubulin polymerization inhibitors: benomyl, carbendazim, chlorfenazole, fuberidazole, thiabendazole; thiophanate, thiophanate-methyl; diethofencarb; zoxamide; ethaboxam;
(b) Cell division inhibitors: pencycuron;
(c) Spectrin-like protein delocalization inhibitors: fluopicolide;
(3) Respiration inhibitors:
(a) Complex I NADH oxidation-reduction enzyme inhibitors: diflumetorimu; tolfenpyrad;
(b) Complex II succinate dehydrogenase inhibitors: benodanil, flutolanil, mepronil; isofetamide; fluopyram; fenfuram, furmecyclox; carboxin, oxycarboxin; thifluz-amide; benzovindiflupyr, bixafen, fluxapyroxad, furametpyr, isopyrazam, penflufen, penthiopyrad, sedaxane; boscalid;
(c) Complex III ubiquinol oxidase Qo inhibitors: azoxystrobin, coumoxystrobin, coumethoxystrobin, enoxastrobin, flufenoxystrobin, picoxystrobin, pyraoxystrobin; pyraclostrobin, pyrametostrobin, triclopyricarb; kresoxim-methyl, trifloxystrobin; dimoxystrobin, fenaminstrobin, metominostrobin, orysastrobin; famoxadone; fluoxastrobin; fenamidone; pyribencarb;
(d) Complex III ubiquinol reductase Qi inhibitors: cyazofamid; amisulbrom;
(e) Oxidative phosphorylation uncoupling agenst: binapacryl, meptyldinocap, dinocap; fluazinam; ferimzone;
(f) Oxidative phosphorylation inhibitors (ATP synthase inhibitors): fentin acetate, fentin chloride, fentin hydroxide
(g) ATP production inhibitors: silthiofam:
(h) Complex III: Qx (unknown) inhibitor of cytochrome bc1 (ubiquinone reductase): ametoctradin;
(4) Amino acid and protein synthesis inhibitors
(a) Methionine biosynthesis inhibitors: andoprim, cyprodinil, mepanipyrim, pyrimethanil;
(b) Protein synthesis inhibitors: blasticidin-S; kasugamycin, kasugamycin hydrochloride; streptomycin; oxytetracycline;
(5) Signal transduction inhibitors:
(a) Signal transduction inhibitors: quinoxyfen, proquinazid;
(b) Inhibitors of MAP/histidine kinase in osmotic signal transduction: fenpiclonil, fludioxonil; chlozolinate, iprodione, procymidone, vinclozolin;
(6) Lipids and cell membrane synthesis inhibitors:
(a) Inhibitors of phospholipid biosynthesis or methyltransferase: edifenphos, iprobenfos, pyrazophos; isoprothiolane;
(b) Lipid peroxidation agent: biphenyl, chloroneb, dicloran, quintozene, tecnazene, tolclofos-methyl; etridiazole;
(c) Agents that act on cell membrane: iodocarb, propamocarb, propamocarb hydrochloride, propamocarb fosetylate, prothiocarb;
(d) Microorganisms that disrupt cell membrane of pathogens: *Bacillus subtilis* bacteria, *Bacillus subtilis* QST713 strain, *Bacillus subtilis* FZB24 strain, *Bacillus subtilis* MBI600 strain, *Bacillus subtilis* strain D747 strain;
(e) Agents that disrupt cell membrane: extract of *Melaleuca alternifolia* (tea tree).
(7) Inhibitors of sterol biosynthesis in cell membrane:
(a) Inhibitors of demethylation at the C14 position in sterol biosynthesis: triforine; pyrifenox, pyrisoxazole; fenarimol, flurprimidol, nuarimol; imazalil, imazalil sulfate, oxpoconazole, pefurazoate, prochloraz, triflumizole, viniconazole;
azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, fluconazole, fluconazole-cis, hexaconazole, imibenconazole, ipconazole, metconazole, myclobutanil, penconazole, propiconazole, fluquinconazole, simeconazole, tebuconazole, tetraconazole, triadimefon, triadimenol, triticonazole; prothioconazole, voriconazole;
(b) Inhibitors of Δ14 reductase and Δ8→Δ7-isomerase in sterol biosynthesis: aldimorph, dodemorph, dodemorph acetate, fenpropimorph, tridemorph; fenpropidin, piperalin; spiroxamine;
(c) Inhibitors of 3-keto reductase in C4 demethylation in sterol biosynthesis: fenhexamid; fenpyrazamine;

(d) Inhibitors of squalene epoxidase in sterol biosynthesis: pyributicarb; naftifin, terbinafine;
(8) Cell wall synthesis inhibitors
(a) Trehalase inhibitor: validamycin;
(b) Chitin synthesis inhibitors: polyoxin, polyoxorim;
(c) Cellulose synthase inhibitors: dimethomorph, flumorph, pyrimorph; benthiavalicarb, iprovalicarb, tolprocarb, valifenalate; mandipropamid;
(9) Melanin biosynthesis inhibitors
(a) Melanin biosynthesis reductase inhibitors: fthalide; pyroquilon, tricyclazole;
(b) Melanin biosynthesis anhydrase inhibitors: carpropamid; diclocymet; fenoxanil;
(10) Host plant resistance inducer:
(a) Agents that act on salicylic acid synthesis pathway: acibenzolar-S-methyl;
(b) Others: probenazole; tiadinil; isotianil; laminarin; Giant Knotweed Extract;
(11) Agents, action of which is unclear: cymoxanil, fosetyl aluminum, phosphoric acid (phosphate), tecloftalam, triazoxide, flusulfamide, diclomezine, methasulfocarb, cyflufenamid, metrafenone, piriofenon, dodine, dodine free base, flutianil;
(12) Agents having multi-functional points: copper (copper salt), Bordeaux mixture, copper hydroxide, copper naphthalate, copper oxide, copper oxychloride, copper sulfate, sulfur, sulfur products, calcium polysulfide; ferbam, mancozeb, maneb, mancopper, metiram, polycarbamate, propineb, thiram, zineb, ziram; captan, captafol, folpet; chlorothalonil; dichlofluanid, tolylfluanid; guazatine, iminoctadine triacetate, iminoctadine trialbesilate; anilazine; dithianon; chinomethionate; fluoroimide;
(13) Other agents: DBEDC, fluoro folpet, guazatine acetate, bis (8-quinolinolato) copper (II), propamidine, chloropicrin, cyprofuram, *agrobacterium*, bethoxazin, diphenylamine, methyl isothiocyanate (MITC), mildiomycin, capsaicin, cufraneb, cyprosulfamide, dazomet, debacarb, dichlorophene, difenzoquat, difenzoquat methyl sulfonate, flumetover, fosetyl calcium, fosetyl sodium, irumamycin, natamycin, nitrothal-isopropyl, oxamocarb, sodium propanosine, pyrrolnitrin, tebufloquin, tolnifanide, zarilamid, algophase, amicarthiazol, oxathiapiprolin, metiram zinc, benthiazole, trichlamide, uniconazole, mildiomycin, oxyfenthiin, picarbutrazox;
Insecticides, Acaricides, Nematocides, Soil Pesticides:
(1) Acetylcholinesterase inhibitors:
(a) Carbamates: alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, oxamyl, pirimicarb, propoxur, thiodicarb, thiofanox, triazamate, trimethacarb, XMC, xylylcarb, fenothiocarb, MIPC, MPMC, MTMC, aldoxycarb, allyxycarb, aminocarb, bufencarb, chloethocarb, metam sodium, promecarb;
(b) Organophosphate-based: acephate, azamethiphos, azinphos-ethyl, azinphos-methyl, cadusafos, chloroethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isocarbophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimphos, temephos, terbufos, tetrachlorvinphos, thiometon, triazophos, trichlorfon, vamidothion; bromophos-ethyl, BRP, carbophenothion, cyanofenphos, CYAP, demeton-S-methylsulfone, dialifos, dichlofenthion, dioxabenzofos, etrimfos, fensulfothion, flupyrazofos, fonofos, formothion, phosmethylan, isazophos, iodofenphos, methacrifos, pirimiphos-ethyl, phosphocarb, propaphos, prothoate, sulprophos;
(2) GABAergic chloride ion channel antagonists: chlordene, endosulfan, ethiprole, fipronil, pyrafluoprole, pyriprole; camphlechlor, heptachlor, dienochlor;
(3) Sodium channel modulators: acrinathrin, d-cis-trans allethrin, d-trans allethrin, bifenthrin, bioallethrin, bioallethrin S-cyclopentyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomers], deltamethrin, empenthrin [(EZ)-(1R)-isomer], esfenvalerate, ethofenprox, fenpropathrin, fenvalerate, flucythrinate, flumethrin, tau-fluvalinate, halfenprox, imiprothrin, kadethrin, permethrin, phenothrin [(1R)-trans isomer], pralethrin, pyrethrum, resmethrin, silafluofen, tefluthrin, tetramethrin, tetramethrin [(1R)-isomer], tralomethrin, transfluthrin; allethrin, pyrethrin, pyrethrin I, pyrethrin II, profluthrin, dimefluthrin, bioethanomethrin, biopermethrin, transpermethrin, fenfluthrin, fenpirithrin, flubrocythrinate, flufenprox, metofluthrin, protrifenbute, pyresmethrin, terallethrin;
(4) Nicotinic acetylcholine receptor agonist: acetamiprid, clothianidin, dinotefuran, imidacloprid, nitenpyram, nithiazine, thiacloprid, thiamethoxam, sulfoxaflor, nicotine, flupyradifurone;
(5) Nicotinic acetylcholine receptor allosteric modulators: spinetoram, spinosad;
(6) Chloride channel activators: abamectin, emamectin benzoate, lepimectin, milbemectin; ivermectin, selamectin, doramectin, eprinomectin, moxidectin, milbemycin, milbemycin oxime;
(7) Juvenile hormone-like substances: hydroprene, kinoprene, methoprene, fenoxycarb, pyriproxyfen; diofenolan, epofenonane, triprene;
(8) Other non-specific inhibitors: methyl bromide, chloropicrin, sulfuryl fluoride, borax, tartar emetic;
(9) Homoptera selective feeding inhibitors: flonicamid, pymetrozine, pyrifluquinazon;
(10) Mite growth inhibitors: clofentezine, diflovidazin, hexythiazox, etoxazole;
(11) Insect's midgut inner membrane disrupting agent derived from microorganisms: *Bacillus thuringiensis* subspecies Isuraerenshi, *Bacillus sphaericus*, *Bacillus thuringiensis* subsp. Aizawai, *Bacillus thuringiensis* subspecies *Kurstaki*, *Bacillus thuringiensis* subspecies Tenebrionis, Bt crop protein: Cry1Ab, Cry1Ac, Cry1Fa, Cry1A.105, Cry2Ab, Vip3A, mCry3A, Cry3Ab, Cry3Bb, Cry34Ab1/Cry35Ab1;
(12) Mitochondrial ATP biosynthetic enzyme inhibitors: diafenthiuron, azocyclotin, cyhexatin, fenbutatin oxide, propargite, tetradifon;
(13) Oxidative phosphorylation uncouplers: chlorfenapyr, sulfluramid, DNOC; binapacryl, dinobuton, dinocap;
(14) Nicotinic acetylcholine receptor channel blockers: bensultap, cartap hydrochloride; nereistoxin; thiosultap sodium, thiocyclam;
(15) Chitin synthesis inhibitors: bistrifluron, chlorfluazuron, diflubenzuron, flucycloxuron, flufenoxuron, hexaflumuron, lufenuron, novaluron, noviflumuron, teflubenzuron, triflumuron, buprofezin, fluazuron;
(16) Diptera molting disrupting agents: cyromazine;
(17) Molting hormone receptor agonists: chromafenozide, halofenozide, methoxyfenozide, tebufenozide;

(18) Octopamine receptor agonists: amitraz, demiditraz, chlordimeform;
(19) Mitochondrial electron transport system complex III inhibitors: acequinocyl, fluacrypyrim, hydramethylnon;
(20) Mitochondrial electron transport system complex I inhibitors: fenazaquin, fenpyroximate, pyrimidifen, pyridaben, tebufenpyrad, tolfenpyrad, rotenone;
(21) Voltage-dependent sodium channel blockers: indoxacarb, metaflumizone;
(22) Acetyl CoA carboxylase inhibitors: spirodiclofen, spiromesifen, spirotetramat;
(23) Mitochondrial electron transport system complex IV inhibitors: aluminum phosphide, calcium phosphide, phosphine, zinc phosphide, cyanide;
(24) Mitochondrial electron transport system complex II inhibitors: cyenopyrafen, cyflumetofen, pyflubumide;
(25) Ryanodine receptor modulators: chlorantraniliprole, cyantraniliprole, flubendiamide, cyclaniliprole, tetraniliprole;
(26) Mixed function oxidase inhibitor compounds: piperonyl butoxide;
(27) Latrophilin receptor agonists: depsipeptide, cyclic depsipeptide, 24-membered cyclic depsipeptide, emodepside;
(28) Other agents (mechanism of which has not been known): azadirachtin, benzoximate, bifenazate, bromopropylate, chinomethionate, cryolite, dicofol, pyridalyl; benclothiaz, sulfur, amidoflumet, 1,3-dichloropropene, DCIP, phenisobromolate, benzomate, metaldehyde, chlorobenzilate, clothiazoben, dicyclanil, fenoxacrim, fentrifanil, flubenzimin, fluphenazine, gossyplure, japonilure, metoxadiazone, oil, potassium oleate, tetrasul, triarathene; afidopyropen, flometoquin, flufiprole, fluensulfone, meperfluthrin, tetramethylfluthrin, tralopyril, dimefluthrin, methylneodecanamide; fluralaner, afoxolaner, fluxametamide, 5-[5-(3,5-dichlorophenyl)-5-trifluoromethyl-4,5-dihydroisoxazole-3-yl]-2-(1H-1,2,4-triazol-1-yl) benzonitrile (CAS: 943137-49-3), broflanilide, other meta-diamides.

The following examples illustrate the present invention more specifically. The present invention is not intended to be limited to the following examples, may be practiced with appropriate modifications within the scope adaptable to the gist of the present invention, and all of which are encompassed in the technical scope of the present application.

EXAMPLE 1

Synthesis of tert-butyl N-[4-[3-[3-[3-[4-(N-tert-butoxycarbonylcarbamimidoyl)phenoxy]propyl]-2-imino-imidazolidin-1-yl]propoxy]benzenecarboximidoyl]carbamate

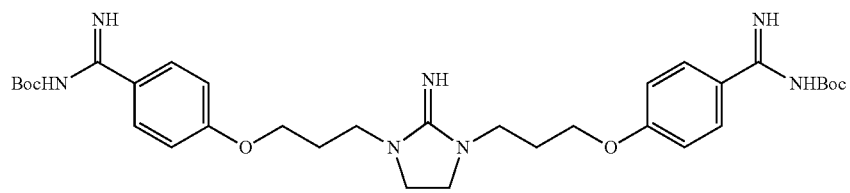 [SMILES: CC(C)(C)OC(=O)NC(=N)c1ccc(OCCCN2CCN(CCCOc3ccc(C(=N)NC(=O)OC(C)(C)C)cc3)C2=N)cc1]

Tert-butyl((4-(3-bromopropoxy)phenyl)(imino)methyl)carbamate (697 mg) was dissolved in N, N-dimethylformamide (7 mL). Potassium carbonate (1.15 g) and 2-amino-imidazoline hydrobromide (500 mg) were added to the resultant at room temperature. The resultant mixture was stirred at 40° C. for 6 hours. The resultant mixture was cooled to room temperature, and then water was added thereto to conduct extraction with ethyl acetate. The organic layer was dried over anhydrous sodium sulfate, and filtered. The filtrate was concentrated under reduced pressure. The resulting residue was purified by silica gel column chromatography to obtain the title compound (compound No. 1: 99.4 mg, in a yield of 3.7%).

$^1$HNMR (CDCl$_3$): 1.55 (s, 18H), 2.00-2.11 (m, 4H), 3.27 (s, 4H), 3.36 (t, 4H), 4.06 (t, 4H), 6.88 (d, 4H), 7.81 (d, 4H).

EXAMPLE 2

Synthesis of hydrochloride salt of 4-[3-[3-[3-(4-carbamimidoylphenoxy)propyl]-2-imino-imidazolidin-1-yl]propoxy]benzamidine

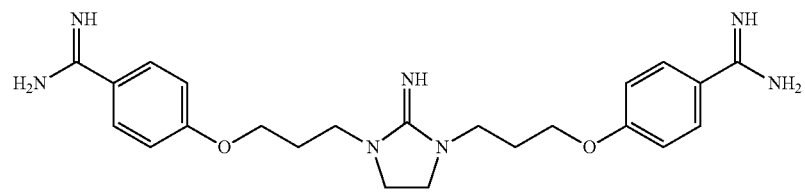 [SMILES: N=C(N)c1ccc(OCCCN2CCN(CCCOc3ccc(C(=N)N)cc3)C2=N)cc1]

The tert-butyl N-[4-[3-[3-[3-[4-(N-tert-butoxycarbonyl-carbamimidoyl)phenoxy]propyl]-2-imino-imidazolidin-1-yl]propoxy]benzenecarboximidoyl]carbamate (99 mg) obtained in Example 1 was dissolved in dichloromethane (1 mL). Trifluoroacetic acid (1 mL) was added to the resultant at room temperature and the mixture was stirred at the same temperature overnight. The resultant mixture was concentrated under reduced pressure, and the residue was dissolved in methanol (1 mL). Hydrogen chloride (4M in dioxane solution, 1 mL) was added to the resultant at room temperature. The resultant mixture was stirred at room temperature for 1 hour. Then, the resultant was concentrated under reduced pressure to obtain the title compound (compound No. 2: 77 mg).

$^1$HNMR (CD$_3$OD): 1.29-1.41 (m, 4H), 2.08-2.18 (m, 4H), 3.55 (t, 4H), 4.18 (t, 4H), 7.16 (d, 4H), 7.80 (d, 4H).

EXAMPLE 3

Synthesis of tert-butyl-N-[[6-[3-[6-[[N,N'-bis(tert-butoxycarbonyl)carbamimidoyl]amino]hexyl]-2-imino-imidazolidin-1-yl]hexylamino]-(tert-butoxycarbonylamino)methylene]carbamate

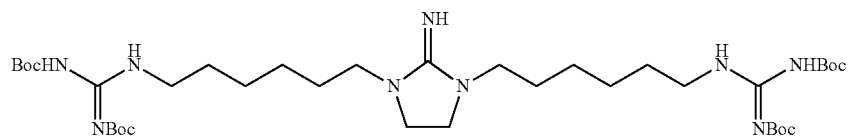

The title compound (compound No. 3) was obtained in the same manner as in Example 1.

$^1$HNMR (CDCl$_3$): 1.32-1.41 (m, 10H), 1.48-1.52 (m, 36H), 1.52-1.64 (m, 10H), 3.21 (s, 4H), 3.87-3.96 (m, 4H).

EXAMPLE 4

Synthesis of hydrochloride salt of 1-[6-[3-(6-guanidinohexyl)-2-imino-imidazolidin-1-yl]hexyl]guanidine

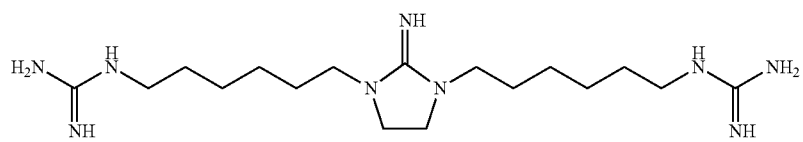 [SMILES: N=C(N)NCCCCCCN1CCN(CCCCCCNC(=N)N)C1=N]

The title compound (compound No. 4) was obtained in the same manner as in Example 2.

$^1$HNMR (CD$_3$OD): 1.34-1.52 (m, 10H), 1.54-1.71 (m, 10H), 3.14-3.23 (m, 4H), 3.66-3.69 (m, 4H).

EXAMPLE 5

Synthesis of tert-butyl N-[4-[4-[3-[4-[4-(N-tert-butoxycarbonylcarbamimidoyl)phenoxy]butyl]-2-imino-imidazolidin-1-yl]butoxy]benzenecarboximidoyl]carbamate

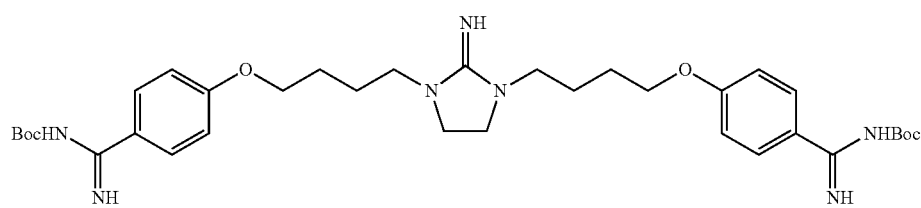 [SMILES: CC(C)(C)OC(=O)NC(=N)c1ccc(OCCCCN2CCN(CCCCOc3ccc(C(=N)NC(=O)OC(C)(C)C)cc3)C2=N)cc1]

The title compound (compound No. 5) was obtained in the same manner as in Example 1.
$^1$HNMR (CDCl$_3$): 1.55 (s, 18H), 1.57-1.78 (m, 12H), 1.79-1.91 (m, 4H), 4.02 (t, 4H), 6.89 (d, 4H), 7.82 (d, 4H).

EXAMPLE 6

Synthesis of hydrochloride salt of 4-[4-[3-[4-(4-carbamimidoylphenoxy)butyl]-2-imino-imidazolidin-1-yl]butoxy]benzamidine

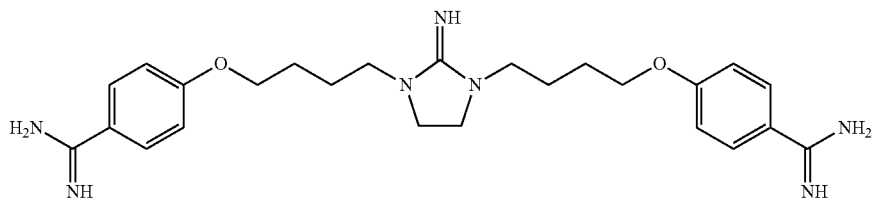 [SMILES: N=C(N)c1ccc(OCCCCN2CCN(CCCCOc3ccc(C(=N)N)cc3)C2=N)cc1]

The title compound (compound No. 6) was obtained in the same manner as in Example 2.
$^1$HNMR (CD$_3$OD): 1.75-1.96 (m, 8H), 3.37-3.46 (m, 4H), 3.67-3.70 (m, 4H), 4.10-4.18 (m, 4H), 7.13 (d, 4H), 7.79 (d, 4H).

EXAMPLE 7

Synthesis of tert-butyl N-[[7-[3-[7-[[N,N'-bis(tert-butoxycarbonyl)carbamimidoyl]amino]heptyl]-2-imino-imidazolidin-1-yl]heptylamino]-(tert-butoxycarbonylamino)methylene]carbamate

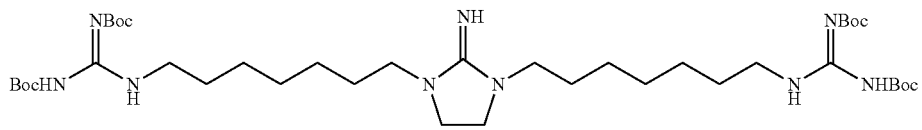

The title compound (compound No. 7) was obtained in the same manner as in Example 1.
$^1$HNMR (CDCl$_3$): 1.27-1.38 (m, 14H), 1.47-1.59 (m, 42H), 3.16-3.00 (m, 4H), 3.20 (s, 4H), 3.88 (dd, 4H).

EXAMPLE 8

Synthesis of hydrochloride salt of 1-[7-[3-(7-guanidinoheptyl)-2-imino-imidazolidin-1-yl]heptyl]guanidine

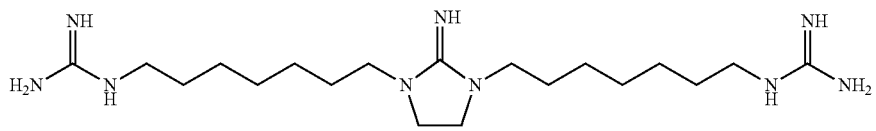 [SMILES: N=C(N)NCCCCCCCN1CCN(CCCCCCCNC(=N)N)C1=N]

The title compound (compound No. 8) was obtained in the same manner as in Example 2.
$^1$HNMR (CD$_3$OD): 1.36-1.47 (m, 12H), 1.54-1.69 (m, 8H), 3.10-3.22 (m, 4H), 3.30-3.44 (m, 4H), 3.58-3.72 (m, 4H).

EXAMPLE 9

(Step 1) Synthesis of tert-butyl N-(4-bromobutyl)-N-[N-(4-bromobutyl)-N,N'-bis (tert-butoxycarbonyl)carbamimidoyl]carbamate

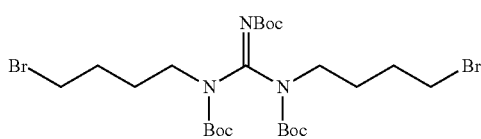

Tert-butyl N-[bis(tert-butoxycarbonylamino)methylene]carbamate (1 g) was dissolved in tetrahydrofuran (7 mL). Triphenylphosphine (1.83 g), 4-bromobutane-1-ol (1.07 g), and diethyl azodicarboxylate (2.2M in toluene solution, 3.2 mL) were added to the resultant under ice-cooling. The mixture was stirred at room temperature overnight. Water was added to the reaction mixture, and the mixture was subjected to extraction with ethyl acetate. The resultant organic layer was dried over anhydrous sodium sulfate, and filtered. The filtrate was concentrated under reduced pressure, and the resulting residue was purified by silica gel column chromatography to obtain the title compound (935 mg, in a yield of 53.4%).

$^1$HNMR (CDCl$_3$): 1.48 (s, 27H), 1.74-1.95 (m, 8H), 3.42 (t, 4H), 3.56 (dd, 4H).

(Step 2) Synthesis of tert-butyl N-[N,N'-bis(tert-butoxycarbonyl)-N-[4-[4-(N-tert-butoxycarbonylcarbamimidoyl)phenoxy]butyl]carbamimidoyl]-N-[4-[4-(N-tert-butoxy carbonylcarbamimidoyl)phenoxy]butyl]carbamate

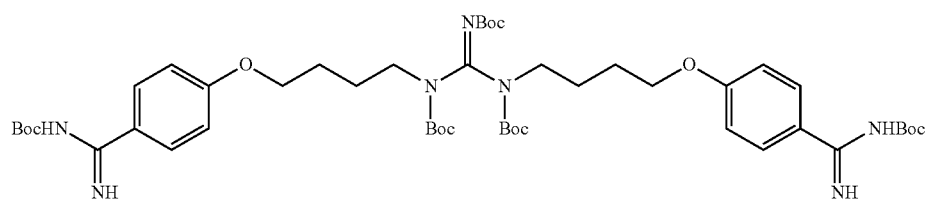

The tert-butyl N-(4-bromobutyl)-N-[N-(4-bromobutyl)-N,N'-bis(tert-butoxy carbonyl)carbamimidoyl]carbamate (400 mg) obtained in the step 1 was dissolved in acetonitrile (5 mL). Potassium carbonate (263 mg) and tert-butyl N-(4-hydroxybenzene carboximidoyl)carbamate (330 mg) were added to the resultant. The reaction mixture was stirred overnight while heating the reaction mixture under reflux. The reaction mixture was cooled to room temperature, water was added to the reaction mixture, and the resultant was subjected to extraction with ethyl acetate. The resultant organic layer was dried over anhydrous sodium sulfate, and filtered. The filtrate was concentrated under reduced pressure, and the resulting residue was purified by silica gel column chromatography to obtain the title compound (compound No. 9: 292 mg, in a yield of 48.8%).

$^1$HNMR (CDCl$_3$): 1.45-1.60 (m, 45H), 1.74-1.92 (m, 8H), 3.61 (dd, 4H), 3.94 (t, 4H), 6.78 (d, 4H), 7.75 (d, 4H).

EXAMPLE 10

Synthesis of hydrochloride salt of 4-[4-[[N-[4-(4-carbamimidoylphenoxy)butyl]carbamimidoyl]amino]butoxy]benzamidine

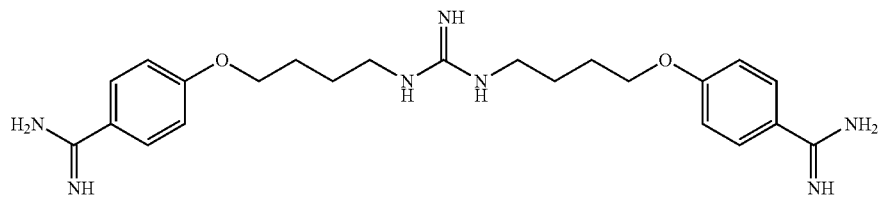 [SMILES: N=C(NCCCCOc1ccc(C(=N)N)cc1)NCCCCOc1ccc(C(=N)N)cc1]

The title compound (compound No. 10) was obtained in the same manner as in Example 2.

$^1$HNMR (CD$_3$OD): 1.75-1.95 (m, 8H), 3.34-3.45 (m, 4H), 4.14 (t, 4H), 7.14 (d, 4H), 7.78 (d, 4H).

EXAMPLE 11

(Step 1) Synthesis of tert-butyl N-(7-bromoheptyl)-N-[N-(7-bromoheptyl)-N,N'-bis (tert-butoxycarbonyl)carbamimidoyl]carbamate

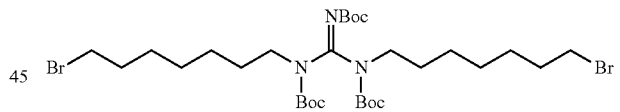

The title compound was obtained in the same manner as in Step 1 of Example 9.

$^1$HNMR (CDCl$_3$): 1.25-1.40 (m, 8H), 1.44-1.56 (m, 31H), 1.60-1.71 (m, 4H), 1.85 (tt, 4H), 3.39 (t, 4H), 3.52 (dd, 4H).

(Step 2) Synthesis of tert-butyl N-[7-[[N,N'-bis(tert-butoxycarbonyl)carbamimidoyl]amino]heptyl]-N-[N-[7-[[N,N'-bis(tert-butoxycarbonyl)carbamimidoyl]amino]heptyl]-N, N'-bis(tert-butoxycarbonyl) carbamimidoyl]carbamate

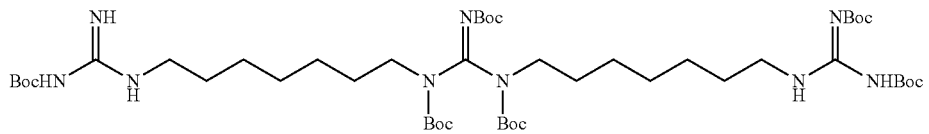

The tert-butyl N-(7-bromoheptyl)-N-[N-(7-bromoheptyl)-N,N'-bis(tert-butoxy carbonyl)carbamimidoyl]carbamate (400 mg) obtained in the step 1 was dissolved in N,N-dimethylformamide (5 mL). Potassium carbonate (232 mg) and tert-butyl N-[amino(tert-butoxycarbonylamino)methylene]carbamate (363 mg) were added to the resultant at room temperature. The resultant was stirred at 50° C. overnight, and then the reaction mixture was cooled to room temperature. Water was added to the reaction mixture, and the mixture was subjected to extraction with ethyl acetate. The resultant organic layer was dried over anhydrous sodium sulfate, and filtered. The filtrate was concentrated under reduced pressure, and the resulting residue was purified by silica gel column chromatography to obtain the title compound (compound No. 11: 404 mg, in a yield of 67.3%).

$^1$HNMR (CDCl$_3$): 1.24-1.40 (m, 12H), 1.47-1.60 (m, 63H), 1.54-1.76 (m, 8H), 3.47 (dd, 4H), 3.87 (t, 4H).

EXAMPLE 12

Synthesis of hydrochloride salt of 1,3-bis(7-guanidinoheptyl)guanidine

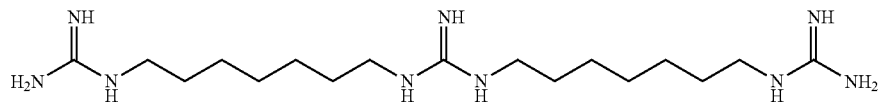 [SMILES: N=C(N)NCCCCCCCNC(=N)NCCCCCCCNC(=N)N]

The title compound (compound No. 12) was obtained in the same manner as in Example 2.

$^1$HNMR (CD$_3$OD): 1.37-1.45 (m, 12H), 1.55-1.66 (m, 8H), 3.14-3.24 (m, 8H).

EXAMPLE 13

Synthesis of tert-butyl N-[N,N'-bis(tert-butoxycarbonyl)-N-[7-[4-(N-tert-butoxycarbonyl carbamimidoyl)phenoxy]heptyl]carbamimidoyl]-N-[7-[4-(N-tert-butoxycarbonylcarbamimidoyl)phenoxy]heptyl]carbamate

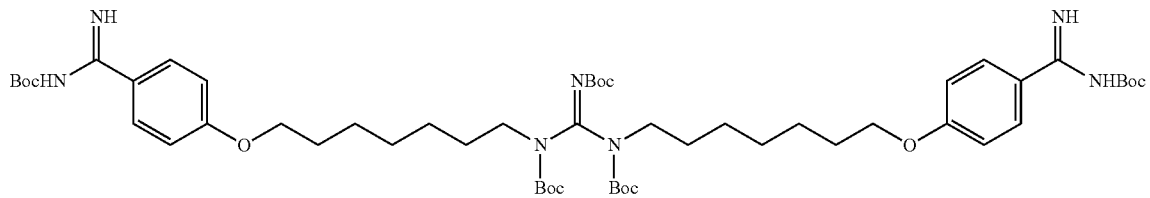

The title compound (compound No. 13) was obtained in the same manner as in Example 9.
$^1$HNMR (CDCl$_3$): 1.20-1.42 (m, 8H), 1.42-1.55 (m, 49H), 1.57-1.65 (m, 4H), 1.77 (tt, 4H), 3.49 (dd, 4H), 3.95 (t, 4H), 6.85 (d, 4H), 7.78 (d, 4H).

EXAMPLE 14

Synthesis of hydrochloride salt of 4-[7-[[N-[7-(4-carbamimidoylphenoxy)heptyl]carbamimidoyl]amino]heptoxy]benzamidine

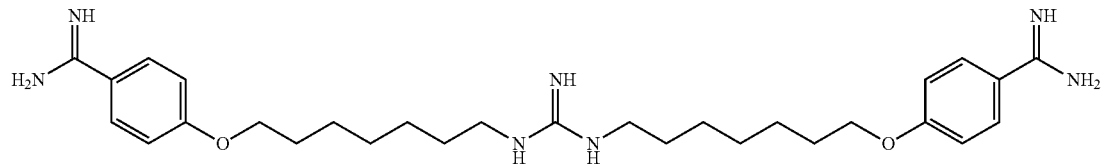 [SMILES: N=C(NCCCCCCCOc1ccc(C(=N)N)cc1)NCCCCCCCOc1ccc(C(=N)N)cc1]

The title compound (compound No. 14) was obtained in the same manner as in Example 2.
$^1$HNMR (CD$_3$OD): 1.39-1.50 (m, 8H), 1.52-1.63 (m, 4H), 1.59-1.64 (m, 4H), 1.83 (tt, 4H), 3.19 (t, 4H), 4.09 (t, 4H), 7.11 (d, 4H), 7.78 (d, 4H).

EXAMPLE 15

(Step 1) Synthesis of tert-butyl N-[N,N'-bis(tert-butoxycarbonyl)carbamimidoyl]-N-[4-[4-(N-tert-butoxycarbonylcarbamimidoyl)phenoxy]butyl]carbamate

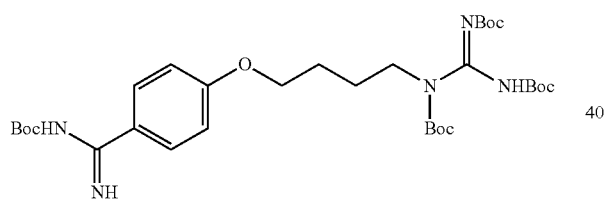

The title compound was obtained in the same manner as in the step 2 of Example 11 using tert-butyl ((4-(4-bromobutoxy)phenyl)(imino)methyl)carbamate and tert-butyl N-[bis(tert-butoxycarbonylamino)methylene]carbamate.
$^1$HNMR (CDCl$_3$): 1.42-1.56 (m, 36H), 1.80-1.86 (m, 4H), 3.87 (dd, 2H), 4.01 (dd, 2H), 6.91 (d, 2H), 7.82 (d, 2H).

(Step 2) Synthesis of tert-butyl N-[N,N'-bis(tert-butoxycarbonyl)-N-[4-[4-(N-tert-butoxy carbonylcarbamimidoyl)phenoxy]butyl]carbamimidoyl]-N-(7-bromoheptyl)carbamate

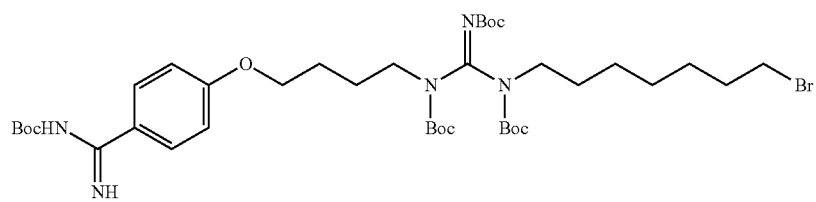

The title compound was obtained in the same manner as in the step 1 of Example 9 using the tert-butyl N-[N,N'-bis(tert-butoxycarbonyl)carbamimidoyl]-N-[4-[4-(N-tert-butoxycarbonylcarbamimidoyl)phenoxy]butyl]carbamate obtained in the step 1.

$^1$HNMR (CDCl$_3$): 1.21-1.34 (m, 4H), 1.42-1.49 (m, 38H), 1.61-1.70 (m, 2H), 1.78-1.89 (m, 6H), 3.38 (t, 2H), 3.51 (dd, 2H), 3.58 (dd, 2H), 4.00 (t, 2H), 6.89 (d, 2H), 7.82 (d, 2H).

(Step 3) Synthesis of tert-butyl N-[N,N'-bis(tert-butoxycarbonyl)-N-[4-[4-(N-tert-butoxy carbonylcarbamimidoyl)phenoxy]butyl]carbamimidoyl]-N-[7-[[N,N'-bis(tert-butoxy carbonyl)carbamimidoyl]amino]heptyl]carbamate

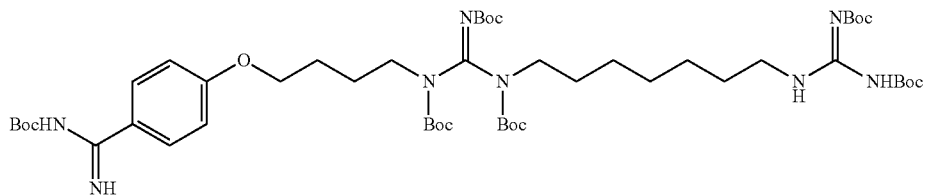

The title compound (compound No. 15) was obtained in the same manner as in the step 2 of Example 11 using the tert-butyl N-[N,N'-bis(tert-butoxycarbonyl)-N-[4-[4-(N-tert-butoxycarbonylcarbamimidoyl)phenoxy]butyl]carbamimidoyl]-N-(7-bromoheptyl)carbamate obtained in the step 2.

$^1$HNMR (CDCl$_3$): 1.12-1.36 (m, 8H), 1.42-1.52 (m, 54H), 1.76-1.90 (m, 6H), 3.43-3.50 (m, 2H), 3.56-3.63 (m, 2H), 3.82 (dd, 2H), 4.00 (t, 2H), 6.88 (d, 2H), 7.88 (d, 2H).

EXAMPLE 16

Synthesis of hydrochloride salt of 4-[4-[[N-(7-guanidinoheptyl)carbamimidoyl]amino]butoxy]benzamidine

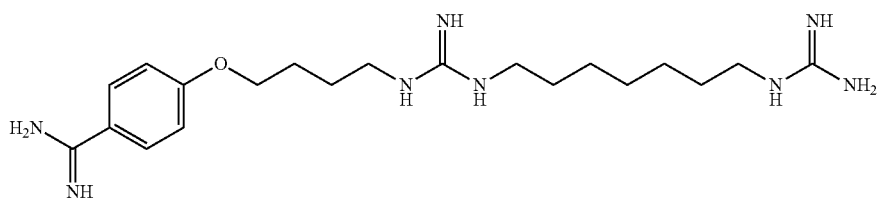 [SMILES: N=C(N)NCCCCCCCNC(=N)NCCCCOc1ccc(C(=N)N)cc1]

The title compound (compound No. 16) was obtained in the same manner as in Example 2.

$^1$HNMR (CD$_3$OD): 1.36-1.44 (m, 8H), 1.54-1.67 (m, 4H), 1.76-1.93 (m, 4H), 3.10-3.24 (m, 4H), 4.14 (t, 2H), 7.14 (d, 2H), 7.79 (d, 2H).

EXAMPLE 17

Synthesis of hydrochloride salt of 6,6'-((((iminomethylene)bis(azanediyl))bis (propane-3,1-diyl))bis (oxy))dinicotinimidamide

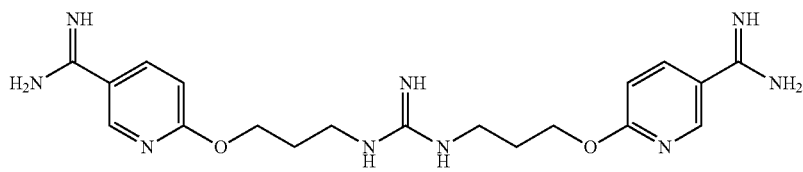

Ttert-butyl ((6-(3-hydroxypropoxy)pyridin-3-yl)(imino)methyl)carbamate (0.53 g) was dissolved in tetrahydrofuran (8 mL). Tert-butyl N-[bis(tert-butoxycarbonylamino) methylene]carbamate (0.36 g) was added to the resultant at room temperature. Triphenylphosphine (0.66 g) and diethyl azodicarboxylate (1.2 mL, 2.2 M in toluene solution) were added to the resultant at room temperature. The mixture was stirred for 24 hours, and then the solvent was distilled off from the reaction mixture. The residue was purified by silica gel column chromatograph. The obtained crude product was dissolved in dichloromethane (3 mL), and then trifluoroacetic acid (1.5 mL) was added to the solution. After the mixture was stirred at room temperature for 72 hours, the solvent was distilled off from the reaction mixture. The crude product was dissolved in methanol (3 mL), and then hydrogen chloride (3 mL, 4M in 1,4-dioxane solution) was added to the solution. The mixture was stirred at room temperature for 18 hours, and then the solvent was distilled off from the reaction mixture to obtain the title compound (compound No. 17: 0.23 g).

$^1$HNMR (CDCl$_3$): 2.16 (m, 4H), 3.48 (m, 4H), 4.58 (m, 4H), 7.32 (d, 2H), 8.37 (d, 2H), 8.79 (s, 2H).

EXAMPLE 18

Synthesis of tert-butyl N-[4-[3-[3-[3-[4-(N-tert-butoxycarbonylcarbamimidoyl)phenoxy]propyl]-2-(2,2,2-trifluoroacetyl)imino-imidazol-1-yl]propoxy]benzenecarboximidoyl]carbamate

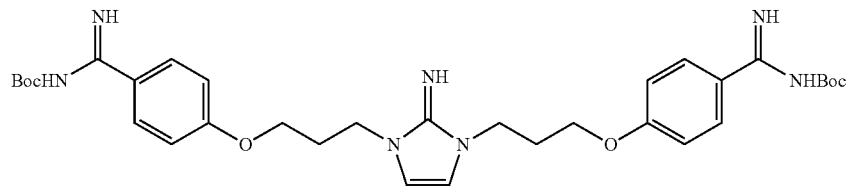

N-(1,3-dihydroimidazole-2-ylidene)-2,2,2-trifluoroacetamide (250 mg) was dissolved in acetonitrile (5 mL) and benzene (2 mL). Potassium carbonate (580 mg) and tert-butyl N-[4-(3-bromopropoxy)benzenecarboximidoyl]carbamate (1.09 g) were added to the solution at room temperature. The reaction mixture was heated to 50° C., and then stirred at the same temperature overnight. The reaction mixture was cooled to room temperature, water was added thereto, and then the mixture was subjected to extraction with ethyl acetate. The resultant organic layer was dried over anhydrous sodium sulfate, and filtered. The filtrate was concentrated under reduced pressure, and the resulting residue was purified by silica gel column chromatography to obtain the title compound (compound No. 18: 465 mg, in a yield of 45.6%) and a compound A (183 mg, in a yield of 28.8%).

Compound No. 18:

$^1$HNMR (CDCl$_3$): 1.55 (s, 18H), 2.25 (tt, 4H), 3.95 (t, 4H), 4.11 (t, 4H), 6.67 (d, 2H), 6.84 (d, 4H), 7.81 (d, 4H).

Compound A:

Tert-butyl N-[4-[3-[2-(2,2,2-trifluoroacetyl)imino-1H-imidazol-3-yl]propoxy]benzene carboximidoyl] carbamate

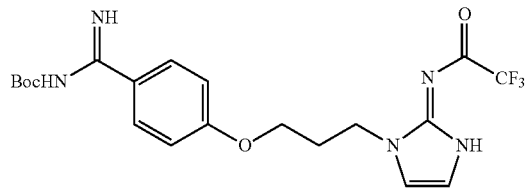

$^1$HNMR (CDCl$_3$): 1.55 (s, 9H), 2.30 (tt, 2H), 4.02 (t, 2H), 4.23 (t, 2H), 6.64 (d, 1H), 6.77 (d, 1H), 6.89 (d, 2H), 7.83 (d, 2H).

EXAMPLE 19

Synthesis of tert-butyl N-[4-[3-[3-[3-[4-(N-tert-butoxycarbonylcarbamimidoyl)phenoxy]propyl]-2-imino-imidazol-1-yl]propoxy]benzenecarboximidoyl]carbamate

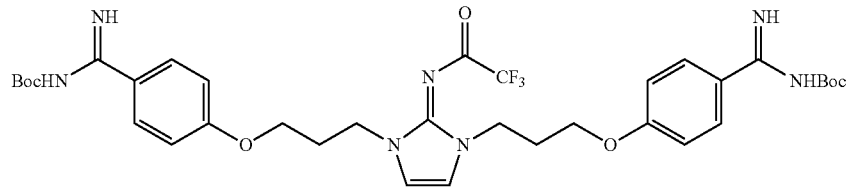 [SMILES: CC(C)(C)OC(=O)NC(=N)c1ccc(OCCCn2ccn(CCCOc3ccc(C(=N)NC(=O)OC(C)(C)C)cc3)c2=NC(=O)C(F)(F)F)cc1]

The tert-butyl N-[4-[3-[3-[3-[4-(N-tert-butoxycarbonylcarbamimidoyl)phenoxy]propyl]-2-(2,2,2-trifluoroacetyl)imino-imidazol-1-yl]propoxy]benzenecarboximidoyl]carbamate (465 mg) obtained in Example 18 was dissolved in methanol (5 mL). Potassium carbonate (97 mg) was added to the solution at room temperature. Then, the mixture was stirred at 60° C. overnight. The reaction mixture was cooled to room temperature, and then the resultant was concentrated under reduced pressure. Water was added to the resulting residue, and the mixture was subjected to extraction with ethyl acetate. The resultant organic layer was dried over anhydrous sodium sulfate, and filtered. The filtrate was concentrated under reduced pressure, and the resulting residue was purified by silica gel column chromatography to obtain the title compound (compound No. 19: 139 mg, in a yield of 34.3%).

$^1$H NMR (CDCl$_3$): 1.55 (s, 18H), 2.16 (tt, 4H), 3.77 (t, 4H), 3.99 (t, 4H), 6.01 (s, 2H), 6.88 (d, 4H), 7.81 (d, 4H).

EXAMPLE 20

Synthesis of hydrochloride salt of 4-[3-[3-[3-(4-carbamimidoylphenoxy)propyl]-2-imino-imidazol-1-yl]propoxy]benzamidine

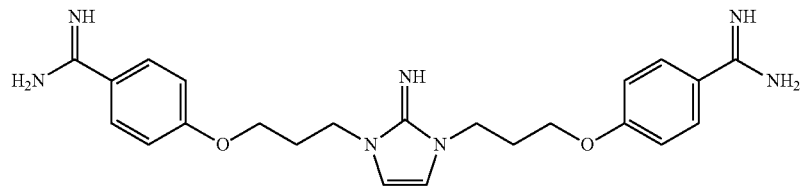 [SMILES: N=C(N)c1ccc(OCCCn2ccn(CCCOc3ccc(C(=N)N)cc3)c2=N)cc1]

The title compound (compound No. 20) was obtained in the same manner as in Example 2.
Melting point (mp): 284-286° C.

EXAMPLE 21

Synthesis of tert-butyl N-[N,N'-bis(tert-butoxycarbonyl)-N-[5-[4-(N-tert-butoxycarbonyl carbamimidoyl)phenyl]pent-4-ynyl]carbamimidoyl]-N-[5-[4-(N-tert-butoxycarbonyl carbamimidoyl)phenyl]pent-4-ynyl]carbamate

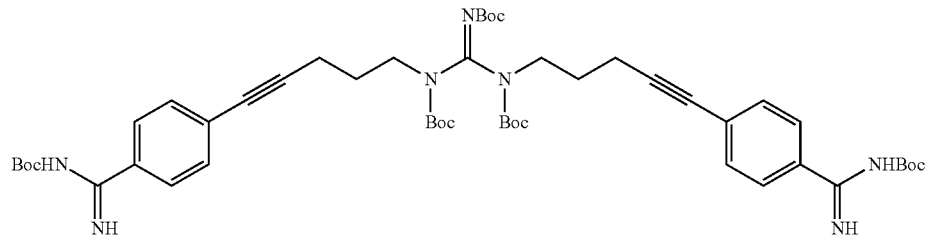

Tert-butyl N-[bis(tert-butoxycarbonylamino)methylene]carbamate (360 mg) was dissolved in tetrahydrofuran (4 mL). Tert-butyl N-[4-(5-bromopent-1-ynyl) benzenecarboximidoyl]carbamate (194 mg), triphenylphosphine (312 mg), and diisopropyl azodicarboxylate (2.2M in toluene solution) (541 µL) were added to the solution under ice-cooling. The reaction mixture was warmed to room temperature and then stirred at the same temperature overnight. The reaction mixture was concentrated under reduced pressure, and the resulting residue was purified by silica gel column chromatography to obtain the title compound (compound No. 21: 268 mg, in a yield of 53.4%).

$^1$HNMR (CDCl$_3$): 1.47-1.59 (m, 45H), 1.98 (tt, 4H), 2.47 (t, 4H), 3.69 (dd, 4H), 7.38 (d, 4H), 7.71 (d, 4H).

EXAMPLE 22

Synthesis of hydrochloride salt of 4-[5-[[N-[5-(4-carbamimidoylphenyl)pent-4-ynyl]carbamimidoyl]amino]pent-1-ynyl]benzamidine

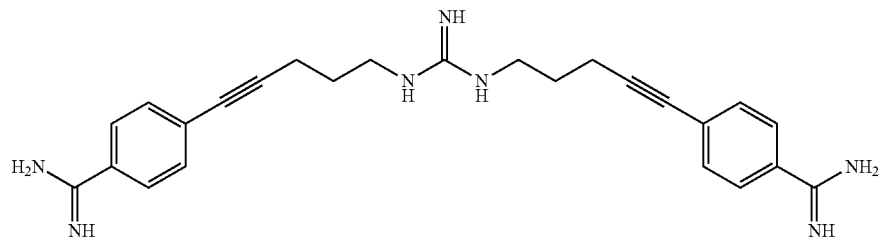 [SMILES: N=C(NCCCC#Cc1ccc(C(=N)N)cc1)NCCCC#Cc1ccc(C(=N)N)cc1]

The title compound (compound No. 22) was obtained in the same manner as in Example 2.

¹HNMR (CD₃OD): 1.91 (tt, 4H), 2.59 (t, 4H), 3.38 (t, 4H), 7.62 (d, 4H), 7.76 (d, 4H).

EXAMPLE 23

(Step 1) synthesis of tert-butyl N-[4-[3-[3-(7-bromoheptyl)-2-(2,2,2-trifluoroacetyl)imino-imidazol-1-yl]propoxy]benzenecarboximidoyl]carbamate

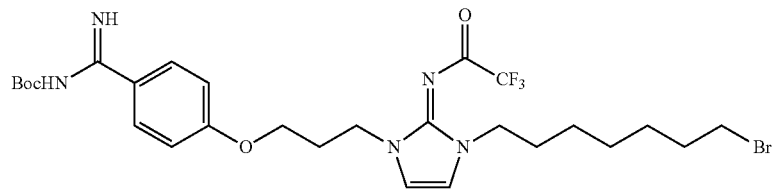 [SMILES: CC(C)(C)OC(=O)NC(=N)c1ccc(OCCCn2ccn(CCCCCCCBr)/c2=N\C(=O)C(F)(F)F)cc1]

The tert-butyl N-[4-[3-[2-(2,2,2-trifluoroacetyl)imino-1H-imidazol-3-yl]propoxy]benzenecarboximidoyl]carbamate (compound A: 297 mg) obtained in Example 18 was dissolved in acetonitrile (6 mL). Potassium carbonate (99 mg) and 1,7-dibromoheptane (709 mg) were added to the solution at room temperature. The mixture was stirred at 60° C. overnight, and the reaction mixture was cooled to room temperature. Then, the reaction mixture was concentrated under reduced pressure, water was added to the resulting residue, and then the mixture was subjected to extraction with ethyl acetate. The resultant organic layer was dried over anhydrous sodium sulfate, and filtered. The filtrate was concentrated under reduced pressure, and the resulting residue was purified by silica gel column chromatography to obtain the title compound (172 mg, in a yield of 40.8%).

¹HNMR (CDCl₃): 1.28-1.36 (m, 6H), 1.55 (s, 9H), 1.64-1.79 (m, 2H), 1.80-1.90 (m, 2H), 2.25 (tt, 2H), 3.40 (t, 2H), 3.84 (dd, 2H), 3.98 (t, 2H), 4.12 (t, 2H), 6.70 (s, 2H), 6.89 (d, 2H), 7.82 (d, 2H).

(Step 2) Synthesis of tert-butyl N-[4-[3-[3-[7-[[N,N'-bis(tert-butoxycarbonyl) carbamimidoyl]amino]heptyl]-2-(2,2,2-trifluoroacetyl)imino-imidazol-1-yl]propoxy]benzenecarboximidoyl]carbamate

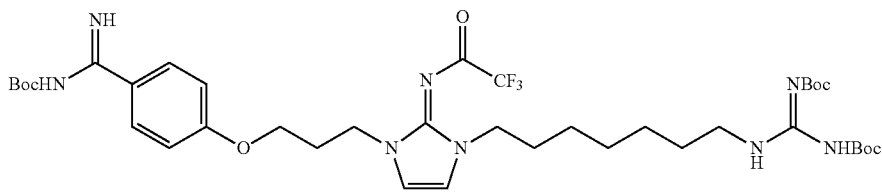

The title compound (compound No. 23) was obtained in the same manner as in step 2 of Example 11.

¹HNMR (CDCl₃): 1.23-1.36 (m, 6H), 1.44-1.60 (m, 29H), 1.63-1.76 (m, 2H), 2.25 (tt, 2H), 3.82-3.92 (m, 4H), 3.98 (t, 2H), 4.12 (t, 2H), 6.70 (s, 2H), 6.89 (d, 2H), 7.85 (d, 2H).

EXAMPLE 24

Synthesis of tert-butyl N-[4-[3-[3-[7-[[N,N'-bis(tert-butoxycarbonyl)carbamimidoyl]amino]heptyl]-2-imino-imidazol-1-yl]propoxy]benzenecarboximidoyl]carbamate

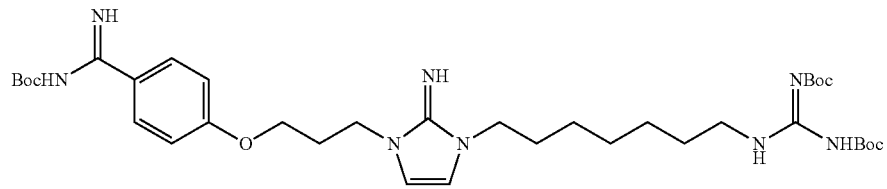

The title compound (compound No. 24) was obtained in the same manner as in Example 19.

¹HNMR (CDCl₃): 1.26-1.36 (m, 6H), 1.47-1.64 (m, 29H), 1.66-1.75 (m, 2H), 2.26 (tt, 2H), 3.11 (t, 2H), 3.85 (t, 2H), 3.98 (t, 2H), 4.11 (t, 2H), 6.71-6.74 (m, 2H), 6.89 (d, 2H), 7.83 (d, 2H).

EXAMPLE 25

Synthesis of hydrochloride salt of 4-[3-[3-(7-guanidinoheptyl)-2-imino-imidazol-1-yl]propoxy]benzamidine

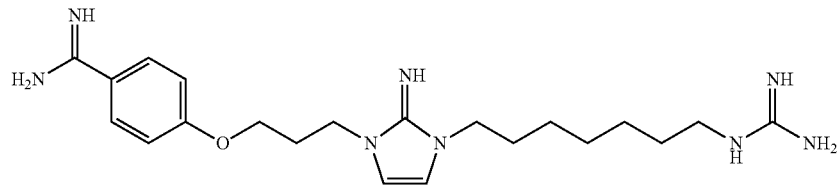 [SMILES: N=C(N)NCCCCCCCn1ccn(CCCOc2ccc(C(=N)N)cc2)c1=N]

The title compound (compound No. 25) was obtained in the same manner as in Example 2

¹HNMR (CD₃OD): 1.33-1.42 (m, 6H), 1.52-1.64 (m, 2H), 1.72-1.79 (m, 2H), 2.25-2.33 (m, 2H), 3.16 (t, 2H), 3.86 (t, 2H), 4.12-4.22 (m, 4H), 6.97 (s, 2H), 7.14 (d, 2H), 7.81 (d, 2H).

EXAMPLE 26

Synthesis of tert-Butyl N-[4-[4-[3-[4-[4-(N-tert-butoxycarbonylcarbamimidoyl)phenoxy]butyl]-2-imino-benzimidazol-1-yl]butoxy]benzenecarboximidoyl]carbamate 1,3-dihydro-benzimidazol-2-imine (200 mg) was dissolved in acetonitrile (15 mL). Potassium carbonate (414 mg), tetrabutylammonium bromide (73 mg) and tert-butyl N-[4-(4-bromobutoxy)benzenecarboximidoyl]carbamate (1.11 g) were added to the solution under ice-cooling. Then, the mixture was stirred at room temperature overnight. Then, the reaction mixture was heated to 60° C., and stirred at the same temperature for 5 hours. N, N-dimethylformamide (5 mL) was added to the reaction mixture, and then the mixture was heated to 80° C. and stirred at the same temperature overnight. The reaction mixture was cooled to room temperature and was concentrated under reduced pressure. Water was added to the resulting residue, and the mixture was subjected to extraction with ethyl acetate. The resultant organic layer was dried over anhydrous sodium sulfate, and filtered. The filtrate was concentrated under reduced pressure, and the resulting residue was purified by silica gel column chromatography to obtain the title compound (compound No. 26: 121 mg, in a yield of 11.3%).

¹HNMR (CDCl₃): 1.55 (s, 18H), 1.82-2.00 (m, 8H), 3.84-3.94 (m, 4H), 4.02 (t, 4H), 6.83-6.85 (m, 6H), 6.99 (dd, 2H), 7.79 (d, 4H).

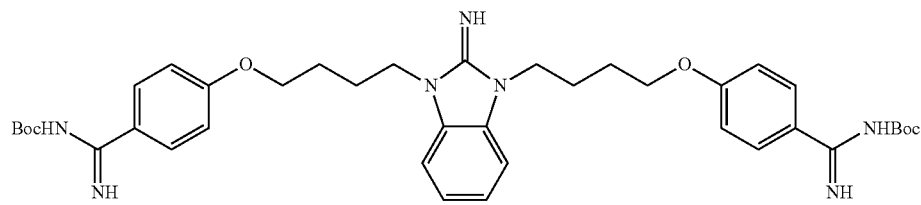 [SMILES: CC(C)(C)OC(=O)NC(=N)c1ccc(OCCCCn2c(=N)n(CCCCOc3ccc(C(=N)NC(=O)OC(C)(C)C)cc3)c3ccccc32)cc1]

EXAMPLE 27

Synthesis of hydrochloride salt of 4-[4-[3-[4-(4-carbamimidoylphenoxy)butyl]-2-imino-benzimidazol-1-yl]butoxy]benzamidine

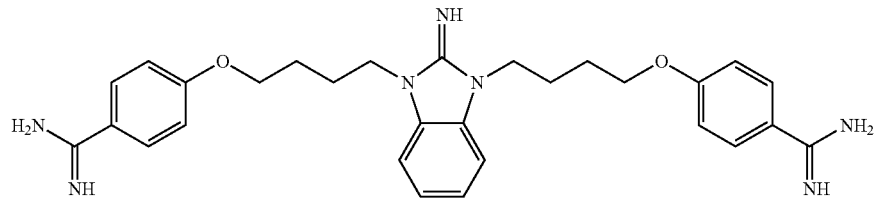 [SMILES: N=C(N)c1ccc(OCCCCn2c(=N)n(CCCCOc3ccc(C(=N)N)cc3)c3ccccc32)cc1]

The title compound (compound No. 27) was obtained in the same manner as in Example 2.

$^1$HNMR (CD$_3$OD): 1.87-2.12 (m, 8H), 4.16 (t, 4H), 4.30 (t, 4H), 7.11 (d, 4H), 7.40 (dd, 2H), 7.57 (dd, 2H), 7.77 (d, 4H).

EXAMPLE 28

(Step 1) Synthesis of tert-butyl N-[N,N'-bis(tert-butoxycarbonyl)-N-[3-[4-(N-tert-butoxycarbonylcarbamimidoyl)phenoxy]propyl]carbamimidoyl]-N-(7-bromoheptyl) carbamate

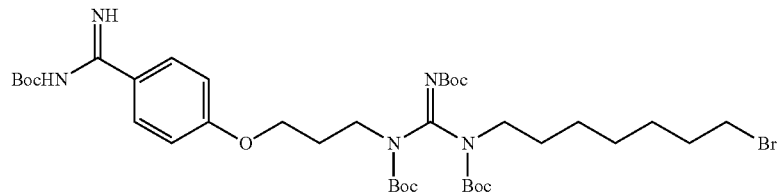

Tert-butyl N-(7-bromoheptyl)-N-[N-tert-butoxycarbonyl-N'-isopropoxycarbonyl-carbamimidoyl]carbamate (480 mg) was dissolved in tetrahydrofuran (7 mL). Triphenylphosphine (304 mg), tert-butyl N-[4-(3-hydroxypropoxy)benzenecarboximidoyl]carbamate (342 mg), and diethyl azodicarboxylate (2.2 M in toluene solution) (527 µL) were added to the solution under ice-cooling. The mixture was stirred at room temperature overnight, and the reaction mixture was concentrated under reduced pressure. The resulting residue was purified by silica gel column chromatography to obtain the title compound (365 mg, in a yield of 50.2%).

$^1$HNMR (CDCl$_3$): 1.24-1.36 (m, 4H), 1.46-1.55 (m, 38H), 1.59-1.68 (m, 2H), 1.83 (tt, 2H), 2.16 (tt, 2H), 3.38 (t, 2H), 3.49 (dd, 2H), 3.73 (dd, 2H), 4.07 (t, 2H), 6.90 (d, 2H), 7.82 (d, 2H).

(Step 2) Synthesis of tert-butyl N-[N,N'-bis(tert-butoxycarbonyl)-N-[3-[4-(N-tert-butoxy carbonyl-carbamimidoyl)phenoxy]propyl]carbamimidoyl]-N-[7-[[N,N'-bis(tert-butoxy carbonyl)carbamimidoyl]amino]heptyl]carbamate

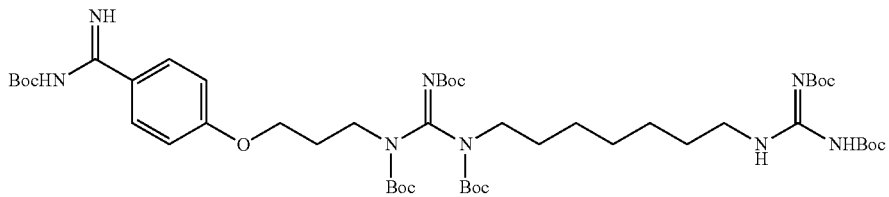

The title compound (compound No. 28) was obtained in the same manner as in the step 2 of Example 11.

$^1$HNMR (CDCl$_3$): 1.10-1.22 (m, 6H), 1.47-1.62 (m, 58H), 2.10-2.22 (m, 2H), 3.63-3.53 (m, 2H), 3.74 (t, 2H), 3.81 (t, 2H), 4.07 (d, 2H), 6.90 (d, 2H), 7.93 (d, 2H).

EXAMPLE 29

Synthesis of hydrochloride salt of 4-[3-[[N-(7-guanidinoheptyl)carbamimidoyl]amino]propoxy]benzamidine

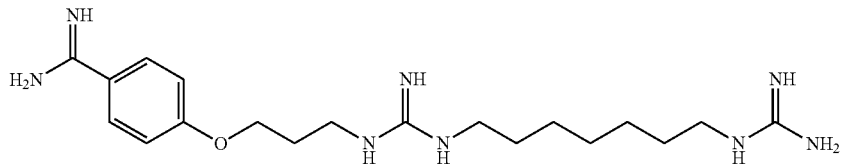 [SMILES: N=C(N)NCCCCCCCNC(=N)NCCCOc1ccc(C(=N)N)cc1]

The title compound (compound No. 29) was obtained in the same manner as in Example 2.

$^1$HNMR (CD$_3$OD): 1.35-1.46 (m, 6H), 1.54-1.66 (m, 4H), 2.08-2.15 (m, 2H), 3.16-3.24 (m, 4H), 3.41-3.46 (m, 2H), 4.19 (t, 2H), 7.16 (d, 2H), 7.80 (d, 2H).

EXAMPLE 30

Synthesis of acetic acid salt of 4-[4-[[N-(7-guanidinoheptyl)carbamimidoyl]amino]butoxy]benzamidine

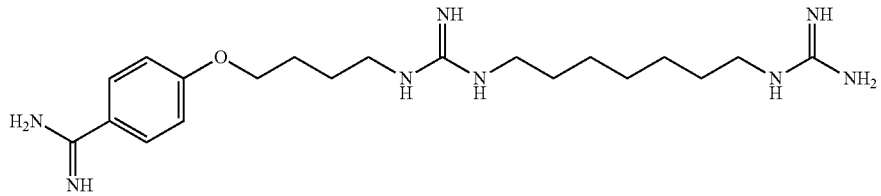 [SMILES: N=C(N)NCCCCCCCNC(=N)NCCCCOc1ccc(C(=N)N)cc1]

The hydrochloride salt of 4-[4-[[N-(7-guanidinoheptyl)carbamimidoyl]amino]butoxy]benzamidine (390 mg) obtained in Example 16 was dissolved in dichloromethane (2.5 mL) and methanol (1.5 mL). A 10% aqueous solution of sodium hydroxide (3 mL) was added to the solution at room temperature. The mixture was further stirred for 1 hour at room temperature. Water was added to the reaction mixture, and the mixture was subjected to extraction with a mixture solvent composed of dichloromethane and methanol (2:1). The resultant organic layer was dried over anhydrous sodium sulfate, and filtered. The filtrate was concentrated under reduced pressure, and the resulting residue was dissolved in methanol (4 mL). An acetic acid (222 μL) was added to the resultant at room temperature, and then the mixture was stirred for 1 hour. The reaction mixture was concentrated under reduced pressure to obtain the title compound (compound No. 30: 108 mg).

$^1$HNMR (CD$_3$OD): 1.35-1.44 (m, 4H), 1.45-1.52 (m, 2H), 1.56-1.64 (m, 2H), 1.74-1.85 (m, 4H), 1.87-1.94 (m, 2H), 1.95 (s, 9H), 3.18 (t, 2H), 3.27 (t, 2H), 3.55 (t, 2H), 4.14 (t, 2H), 7.12 (d, 2H), 7.80 (d, 2H).

EXAMPLE 31

(Step 1) Synthesis of tert-butyl N-[N,N'-bis(tert-butoxycarbonyl)-N-[4-[[5-(N-tert-butoxycarbonylcarbamimidoyl)-2-pyridyl]oxy]butyl]carbamimidoyl]-N-(7-bromoheptyl) carbamate

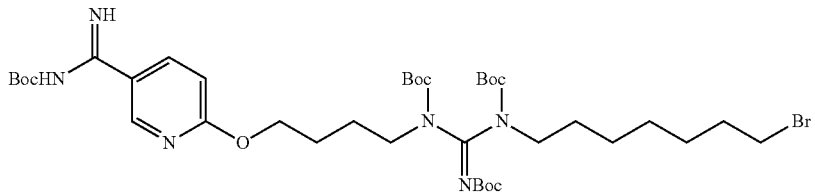

The title compound was obtained in the same manner as in the step 1 of Example 28.

¹HNMR (CDCl₃): 1.24-1.30 (m, 4H), 1.42-1.63 (m, 42H), 1.81-1.85 (m, 4H), 3.39 (t, 2H), 3.48 (t, 2H), 3.56 (m, 2H), 4.35 (t, 2H), 6.73 (t, 1H), 8.13 (d, 1H), 8.87 (d, 1H).

(Step 2) Synthesis of tert-butyl N-[N,N'-bis(tert-butoxycarbonyl)-N-[4-[[5-(N-tert-butoxycarbonyl-carbamimidoyl)-2-pyridyl]oxy]butyl]carbamimidoyl]-N-[7-[[N,N'-bis(tert-butoxycarbonyl)carbamimidoyl]amino]heptyl]carbamate

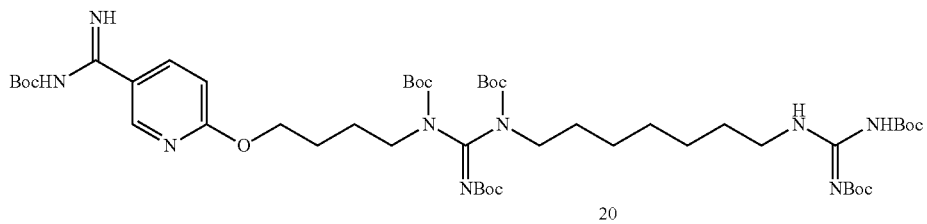

The title compound (compound No. 31) was obtained in the same manner as in the step 2 of Example 28.

¹HNMR (CDCl₃): 1.22-1.28 (m, 6H), 1.46-1.60 (m, 58H), 1.75-1.82 (m, 4H), 3.39 (m, 2H), 3.59 (m, 2H), 3.82 (t, 2H), 4.13 (t, 2H), 6.72 (d, 1H), 8.19 (d, 1H), 8.68 (s, 1H).

EXAMPLE 32

Synthesis of 6-(4-(3-(7-guanidinoheptyl)guanidino)butoxy)nicotinimidamide

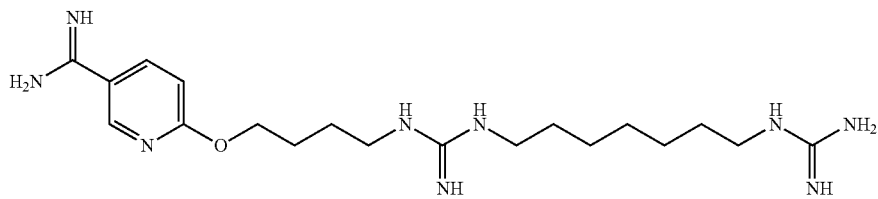 [SMILES: N=C(N)NCCCCCCCNC(=N)NCCCCOc1ccc(C(=N)N)cn1]

The title compound (compound No. 32) was obtained in the same manner as in Example 2.

¹HNMR (CDCl₃): 1.18-1.28 (m, 6H), 1.46-1.58 (m, 4H), 1.74 (m, 2H), 1.87 (m, 2H), 3.13-3.19 (m, 4H), 3.28 (m, 2H), 4.44 (m, 2H), 7.01 (br, 1H), 8.09 (br, 1H), 8.64 (s, 1H).

EXAMPLE 33

(Step 1) Synthesis of tert-butyl N-[N,N'-bis(tert-butoxycarbonyl)-N-[3-[5-(N-tert-butoxy carbonyl-carbamimidoyl)benzofuran-2-yl]propyl]carbamimidoyl]-N-(7-bromoheptyl) carbamate

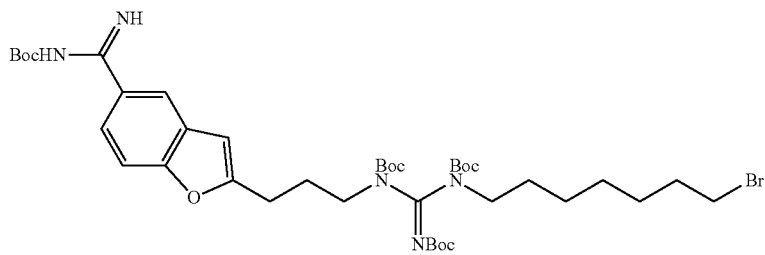

The title compound was obtained in the same manner as in the step 1 of Example 28.

$^1$HNMR (CDCl$_3$): 1.25-1.56 (m, 44H), 1.84 (m, 2H), 2.12 (br, 2H), 2.82 (m, 2H), 3.38 (t, 2H), 3.49 (m, 2H), 3.62 (m, 2H), 6.45 (s, 1H), 7.40 (d, 1H), 7.72 (d, 1H), 8.05 (s, 1H).

(Step 2) Synthesis of tert-butyl N-[N,N'-bis(tert-butoxycarbonyl)-N-[3-[5-(N-tert-butoxy carbonyl-carbamimidoyl)benzofuran-2-yl]propyl]carbamimidoyl]-N-[7-[[N,N'-bis(tert-butoxycarbonyl) carbamimidoyl]amino]heptyl]carbamate

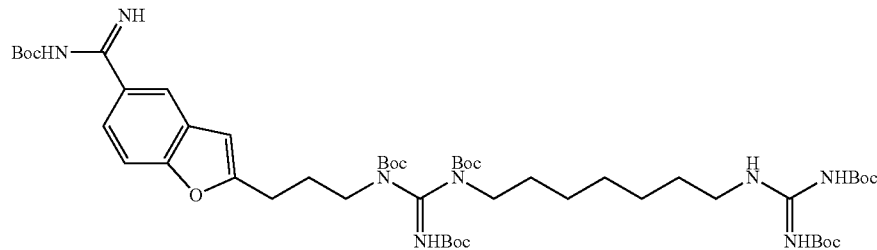

The title compound (compound No. 33) was obtained in the same manner as in the step 2 of Example 28.

$^1$HNMR (CDCl$_3$): 1.20-1.28 (m, 6H), 1.45-1.57 (m, 58H), 2.12 (m, 2H), 2.81 (t, 2H), 3.47 (t, 2H), 3.62 (t, 2H), 3.82 (t, 2H), 6.46 (s, 1H), 7.40 (d, 1H), 7.78 (d, 1H), 8.11 (s, 1H).

EXAMPLE 34

Synthesis of 2-(3-(3-(7-guanidinoheptyl)guanidino)propyl)benzofuran-5-carboximidamide

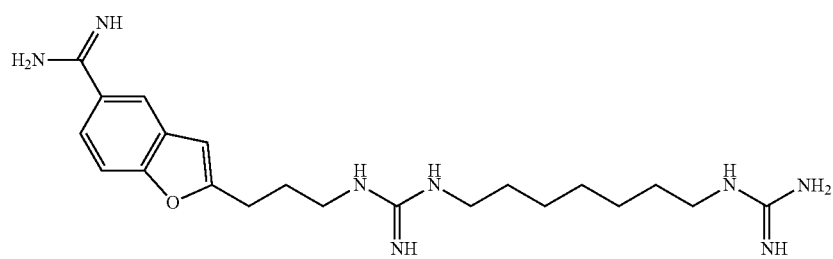 [SMILES: N=C(N)NCCCCCCCNC(=N)NCCCc1cc2cc(C(=N)N)ccc2o1]

The title compound (compound No. 34) was obtained in the same manner as in Example 2.

$^1$HNMR (CDCl$_3$): 1.30-1.42 (m, 6H), 1.55-1.62 (m, 4H), 2.05 (m, 2H), 2.93 (t, 2H), 3.30 (m, 2H), 3.10-3.18 (m, 4H), 6.73 (s, 1H), 7.64-7.66 (m, 2H), 8.02 (s, 1H).

EXAMPLE 35

Synthesis of tert-butyl N-[4-[4-[3-[4-[4-(N-tert-butoxycarbonylcarbamimidoyl)phenoxy]butyl]-2-(2,2,2-trifluoroacetyl)imino-imidazol-1-yl]butoxy]benzenecarboximidoyl]carbamate

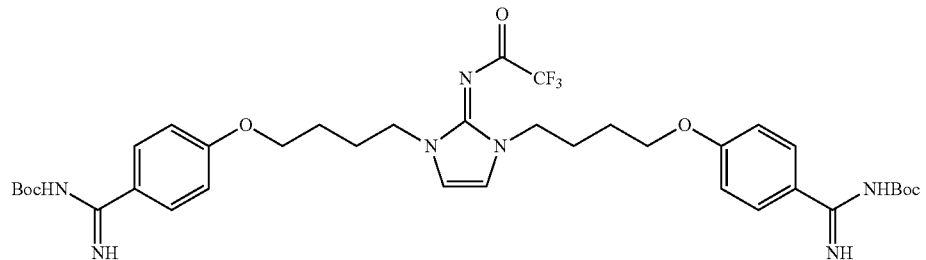 [SMILES: CC(C)(C)OC(=O)NC(=N)c1ccc(OCCCCn2ccn(CCCCOc3ccc(C(=N)NC(=O)OC(C)(C)C)cc3)c2=NC(=O)C(F)(F)F)cc1]

The title compound (compound No. 35) was obtained in the same manner as in Example 18.

$^1$HNMR (CDCl$_3$): 1.55 (s, 18H), 1.79 (tt, 4H), 1.97 (tt, 4H), 3.96 (t, 4H), 4.00 (t, 4H), 6.78 (s, 2H), 6.89 (d, 4H), 7.81 (d, 4H).

EXAMPLE 36

Synthesis of hydrochloride salt of 4-[4-[3-[4-(4-carbamimidoylphenoxy)butyl]-2-imino-imidazol-1-yl]butoxy]benzamidine

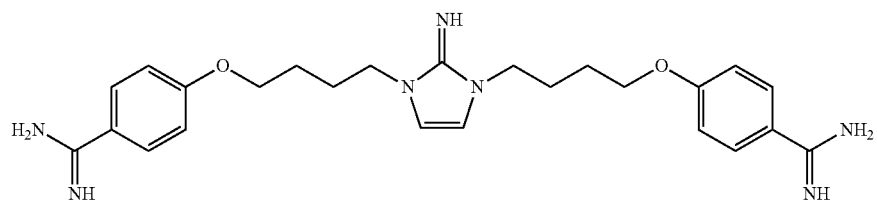

The tert-butyl N-[4-[4-[3-[4-[4-(N-tert-butoxycarbonylcarbamimidoyl)phenoxy]butyl]-2-(2,2,2-trifluoroacetyl)imino-imidazol-1-yl]butoxy]benzenecarboximidoyl]carbamate (666 mg) obtained in Example 35 was dissolved in methanol (4 mL). Hydrogen chloride (4M in dioxane solution) (10 mL) was added to the solution at room temperature. The reaction mixture was stirred at 50° C. overnight. The reaction mixture was cooled to room temperature, and then concentrated under reduced pressure to obtain the title compound (compound No. 36: 536 mg).

Melting point (mp): 178-180° C.

EXAMPLE 37

(Step 1) Synthesis of N-[1,3-bis(4-bromobutyl)imidazolidin-2-ylidene]nitramide

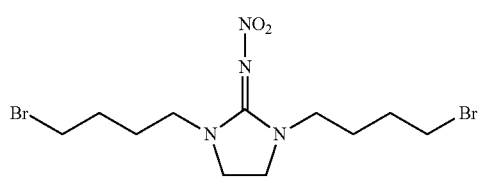 [SMILES: O=[N+]([O-])N=C1N(CCCCBr)CCN1CCCCBr]

N-imidazolidin-2-ylidene-nitramide (1.5 g) was dissolved in acetonitrile (15 mL). Potassium carbonate (4.77 mg) and 1,4-dibromobutane (9.96 g) were added to the solution at room temperature. The reaction mixture was stirred at 80° C. overnight. The reaction mixture was cooled to room temperature, and then was concentrated under reduced pressure. Water was added to the resulting residue, and then the mixture was subjected to extraction with ethyl acetate. The resultant organic layer was dried over anhydrous sodium sulfate, and filtered. The filtrate was concentrated under reduced pressure and the resulting residue was purified by silica gel column chromatography to obtain the title compound (83 mg, in a yield of 1.8%).

$^1$HNMR (CDCl$_3$): 1.74-1.83 (m, 4H), 1.85-1.94 (m, 4H), 3.33 (t, 4H), 3.44 (t, 4H), 3.75 (s, 4H).

(Step 2) Synthesis of tert-butyl N-[4-[4-[3-[4-[4-(N-tert-butoxycarbonylcarbamimidoyl) phenoxy]butyl]-2-nitroimino-imidazolidin-1-yl]butoxy]benzenecarboximidoyl]carbamate

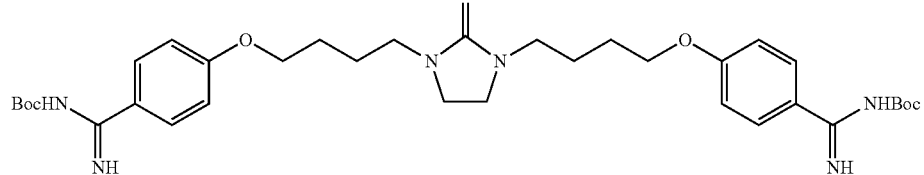

N-[1,3-bis(4-bromobutyl)imidazolidin-2-ylidene]nitramide (84 mg) obtained in the step 1 was dissolved in acetonitrile (3 mg). Potassium carbonate (115 mg) and tert-butyl N-(4-hydroxybenzenecarboximidoyl)carbamate (149 mg) were added to the solution at room temperature. The reaction mixture was stirred at 80° C. overnight. The reaction mixture was cooled to room temperature and then was concentrated under reduced pressure. Water was added to the resulting residue, and the mixture was subjected to extraction with ethyl acetate. The resultant organic layer was dried over anhydrous sodium sulfate, and filtered. The filtrate was concentrated under reduced pressure and the resulting residue was purified by silica gel column chromatography to obtain the title compound (compound No. 37: 38 mg, in a yield of 25.7%).

$^1$HNMR (CDCl$_3$): 1.55-1.59 (m, 22H), 1.17-1.85 (m, 8H), 3.37 (t, 4H), 4.00-4.04 (m, 4H), 6.89 (d, 4H), 7.81 (d, 4H).

EXAMPLE 38

Synthesis of hydrochloride salt of 4-[4-[3-[4-(4-carbamimidoylphenoxy)butyl]-2-nitroimino-imidazolidin-1-yl]butoxy]benzamidine

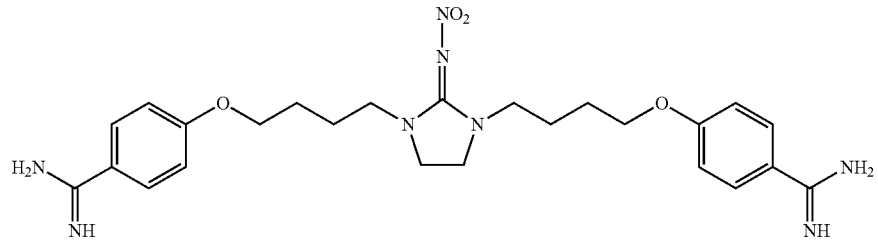 [SMILES: N=C(N)c1ccc(OCCCCN2CCN(CCCCOc3ccc(C(=N)N)cc3)C2=N[N+](=O)[O-])cc1]

The title compound (compound No. 38) was obtained in the same manner as in Example 2.

$^1$HNMR (CD$_3$OD): 1.31 (t, 4H), 1.82-1.88 (m, 8H), 3.20 (dd, 4H), 4.11-4.16 (m, 4H), 7.13 (d, 4H), 7.86 (d, 4H).

EXAMPLE 39

Synthesis of tert-butyl N-[4-[3-[3-[4-[4-(N-tert-butoxycarbonylcarbamimidoyl)phenoxy]butyl]-2-(2,2,2-trifluoroacetyl)imino-imidazol-1-yl]propoxy]benzenecarboximidoyl]carbamate

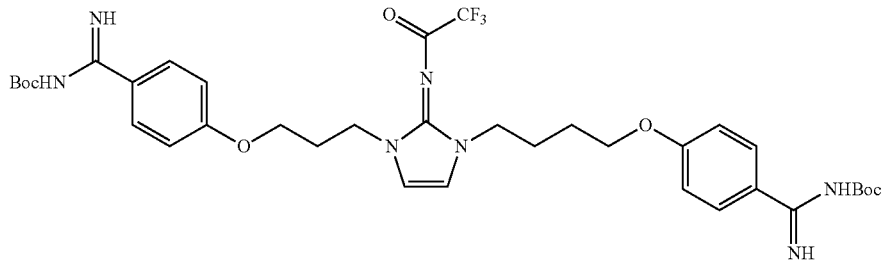 [SMILES: CC(C)(C)OC(=O)NC(=N)c1ccc(OCCCCn2ccn(CCCOc3ccc(C(=N)NC(=O)OC(C)(C)C)cc3)c2=NC(=O)C(F)(F)F)cc1]

The title compound (compound No. 39) was obtained in the same manner as in Example 18.

$^1$HNMR (CDCl$_3$): 1.55 (s, 18H), 1.76-1.84 (m, 2H), 1.96 (tt, 2H), 2.25 (tt, 2H), 3.94-4.04 (m, 6H), 4.12 (t, 2H), 6.72 (dd, 2H), 6.88 (dd, 4H), 7.81 (d, 4H).

EXAMPLE 40

Synthesis of hydrochloride salt of 4-[4-[3-[3-(4-carbamimidoylphenoxy)propyl]-2-imino-imidazol-1-yl]butoxy]benzamidine

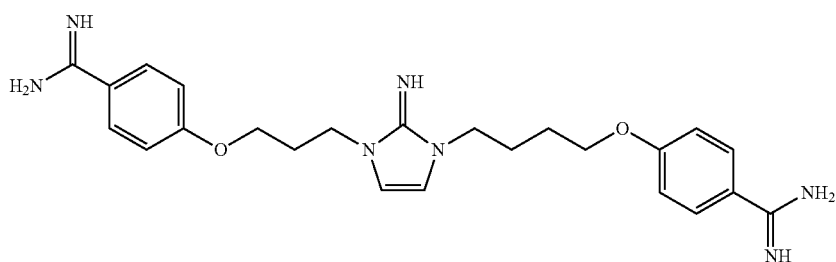 [SMILES: N=C(N)c1ccc(OCCCCn2ccn(CCCOc3ccc(C(=N)N)cc3)c2=N)cc1]

The title compound (compound No. 40) was obtained in the same manner as in Examples 19 and 20.

$^1$HNMR (CD$_3$OD): 1.82-2.00 (m, 4H), 2.29 (tt, 2H), 3.97 (t, 2H), 4.11-4.22 (m, 6H), 6.96 (dd, 2H), 7.14 (dd, 4H), 7.79 (d, 2H), 7.81 (d, 2H).

EXAMPLE 41

Synthesis of tert-butyl N-[N,N'-bis(tert-butoxycarbonyl)-N-[3-[4-(N-tert-butoxy carbonylcarbamimidoyl)phenoxy]propyl]carbamimidoyl]-N-[3-[4-(N-tert-butoxycarbonyl carbamimidoyl)phenoxy]propyl]carbamate

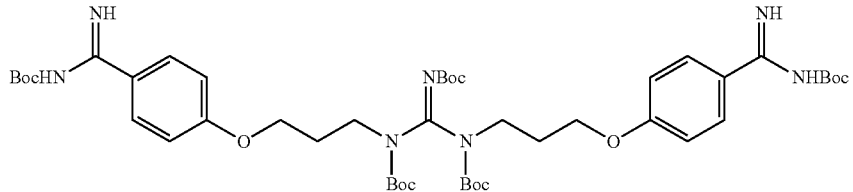

The title compound (compound No. 41) was obtained in the same manner as in Example 9.

¹HNMR (CDCl₃): 1.44-1.59 (m, 45H), 2.13 (dt, 4H), 3.69 (t, 4H), 3.99 (t, 4H), 6.81 (d, 4H), 7.74 (d, 4H).

EXAMPLE 42

Synthesis of hydrochloride salt of 4-[3-[[N-[3-(4-carbamimidoylphenoxy)propyl]carbamimidoyl]amino]propoxy]benzamidine

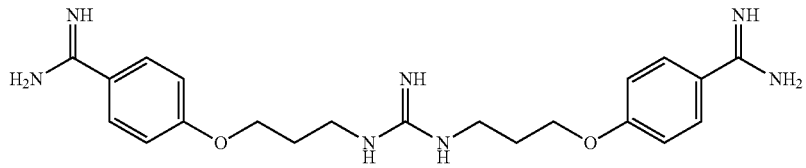 [SMILES: N=C(NCCCOc1ccc(C(=N)N)cc1)NCCCOc1ccc(C(=N)N)cc1]

The title compound (compound No. 42) was obtained in the same manner as in Example 2.

¹HNMR (CD₃OD): 2.12 (tt, 4H), 3.41-3.51 (m, 4H), 4.19 (t, 4H), 7.16 (d, 4H), 7.79 (d, 4H).

EXAMPLE 43

(Step 1) Synthesis of 6-(3-((tert-butyldimethylsilyl)oxy)propoxy)pyridazine-3-carbonitrile

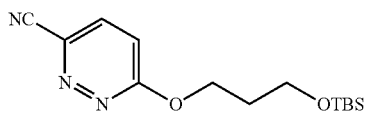 [SMILES: CC(C)(C)[Si](C)(C)OCCCOc1ccc(C#N)nn1]

3-((tert-butyldimethylsilyl)oxy)propan-1-ol (2.5 g) was dissolved in tetrahydrofuran (30 mL). At 0° C., sodium hydride (0.58 g) was added to the solution, and then 6-chloro-pyridazine-3-carbonitrile (1.7 g) was added thereto. The mixture was stirred for 18 hours at room temperature, and then saturated aqueous ammonium chloride solution was added thereto. The resultant was subjected to extraction with ethyl acetate, and the resultant organic layer was concentrated. The resulting residue was purified by silica gel column chromatography to obtain the title compound (2.2 g).

¹HNMR (CDCl₃): 0.037 (s, 6H), 0.87 (s, 9H), 2.04 (m, 2H), 3.79 (t, 2H), 4.71 (t, 2H), 7.04 (d, 1H), 7.65 (d, 1H).

Step 2

Synthesis of tert-butyl ((6-(3-hydroxypropoxy)pyridazin-3-yl)(imino)methyl)carbamate

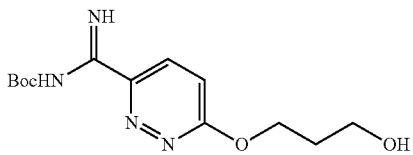 [SMILES: CC(C)(C)OC(=O)NC(=N)c1ccc(OCCCO)nn1]

The 6-(3-((tert-butyldimethylsilyl)oxy)propoxy)pyridazine-3-carbonitrile (0.59 g) obtained in the step 1 was dissolved in tetrahydrofuran (6 mL). Lithium bis(trimethylsilyl)amide (2 mL, 1.3M in tetrahydrofuran solution) was added to the solution at room temperature. The mixture was stirred for 2 hours at room temperature, and then hydrogen chloride (3 mL, in 4M 1,4-dioxane solution) was added thereto. The resultant was stirred for 2 hours at room temperature, and then the solvent was distilled off therefrom. The obtained crude product was dissolved in N, N-dimethylformamide (4 mL). Triethylamine (1.0 g) and di-tert-butyl dicarbonate (0.65 g) were added to the solution. The mixture was stirred for 3 hours, and then saturated aqueous ammonium chloride solution was added thereto. The mixture was subjected to extraction with ethyl acetate, and the resultant organic layer was concentrated. The obtained crystal was washed with hexane to obtain the title compound (0.40 g).

¹HNMR (CDCl₃): 1.55 (s, 9H), 2.11 (m, 2H), 3.80 (t, 2H), 4.74 (t, 2H), 7.03 (d, 1H), 8.41 (d, 1H).

(Step 3) Synthesis of tert-butyl N-[-N,N'-bis(tert-butoxycarbonyl)-N-[3-[6-(N-tert-butoxycarbonylcarbamimidoyl)pyridazin-3-yl]oxypropyl]carbamimidoyl]-N-(7-bromo heptyl)carbamate

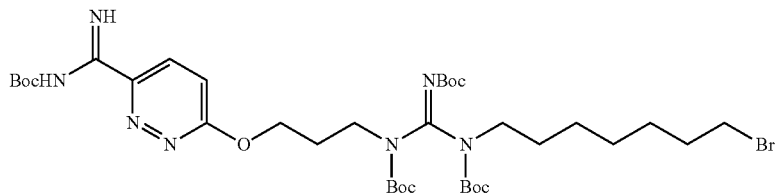

The title compound was obtained in the same manner as in the step 1 of Example 28.

¹HNMR (CDCl₃): 1.25-1.55 (m, 42H), 1.62 (m, 2H), 1.81 (m, 2H), 2.20 (m, 2H), 3.38 (t, 2H), 3.42 (m, 2H), 3.70 (m, 2H), 4.60 (t, 2H), 7.01 (d, 1H), 8.39 (d, 1H).

(Step 4) Synthesis of tert-butyl N-[N,N'-bis(tert-butoxycarbonyl)-N-[3-[6-(N-tert-butoxycarbonylcarbamimidoyl)pyridazin-3-yl]oxypropyl]carbamimidoyl]-N-[7-[[N,N'-bis (tert-butoxycarbonyl) carbamimidoyl]amino]heptyl]carbamate

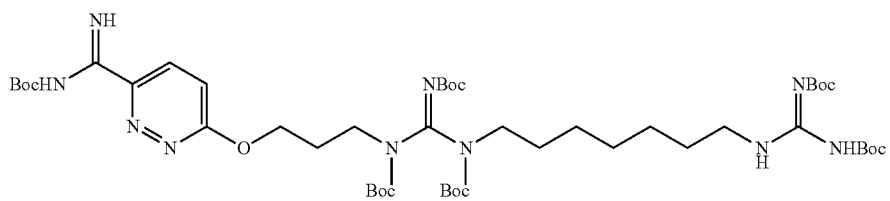

The title compound (compound No. 43) was obtained in the same manner as in the step 2 of Example 11.

¹HNMR (CDCl₃): 1.44-1.65 (m, 64H), 2.22 (m, 2H), 3.48 (m, 2H), 3.71 (t, 2H), 3.85 (m, 2H), 4.61 (t, 2H), 7.01 (d, 1H), 8.38 (d, 1H).

EXAMPLE 44

Synthesis of hydrochloride salt 6-(3-(3-(7-guanidinoheptyl)guanidino)propoxy) pyridazine-3-carboxamidine

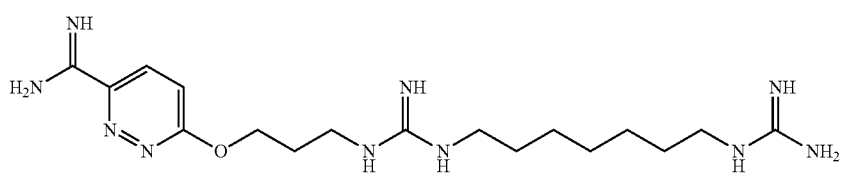 [SMILES: N=C(N)NCCCCCCCNC(=N)NCCCOc1ccc(C(=N)N)nn1]

The title compound (compound No. 44) was obtained in the same manner as in Example 2.

Melting point (mp) 242-249° C.

EXAMPLE 45

(Step 1) synthesis of 6-(4-bromobutoxy)nicotinonitrile

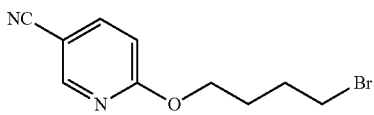 [SMILES: N#Cc1ccc(OCCCCBr)nc1]

6-(4-hydroxybutoxy)nicotinonitrile (2.47 g) was dissolved in tetrahydrofuran (30 mL). Carbon tetrabromide (5.6 g) and triphenylphosphine (4.4 g) were added to the solution at 0° C. The mixture was stirred for 23 hours at room temperature, and then saturated aqueous sodium hydrogen carbonate solution was added thereto. The resultant was subjected to extraction with ethyl acetate, the solvent was distilled off therefrom, and then the resultant residue was purified by silica gel column chromatography to obtain the title compound (2.8 g).

$^1$HNMR (CDCl$_3$): 1.93-2.04 (m, 4H), 3.45 (d, 2H), 4.38 (t, 2H), 6.78 (d, 1H), 7.76 (dd, 1H), 8.45 (d, 1H).

(Step 2) Synthesis of tert-butyl ((6-(4-bromobutoxy)pyridin-3-yl)(imino)methyl) carbamate

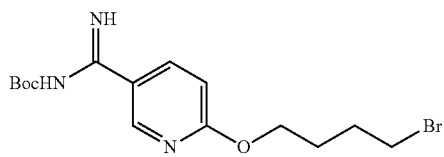 [SMILES: CC(C)(C)OC(=O)NC(=N)c1ccc(OCCCCBr)nc1]

6-(4-bromobutoxy)nicotinonitrile (2.8 g) obtained in the step 1 was dissolved in tetrahydrofuran (30 mL). Lithium bis(trimethylsilyl)amide (10 mL, in 1.3M tetrahydrofuran solution) was added to the solution at 0° C. The resultant was stirred for 4 hours at room temperature, and then cooled to 0° C., followed by adding methanol (10 mL) and hydrogen chloride (10 mL, in 4M 1,4-dioxane solution) thereto. The resultant was stirred for 30 minutes at 0° C., and then the solvent was distilled off therefrom. The resultant crude product was dissolved in N, N-dimethylformamide (30 mL), and triethylamine (5.6 g) and di-tert-butyl dicarbonate (3.6 g) were added thereto. The resultant was stirred for 1.5 hours and then purified by silica gel column chromatography to obtain the title compound (4.0 g).

$^1$HNMR (CDCl$_3$): 1.55 (s, 9H), 1.90-2.04 (m, 4H), 3.46 (d, 2H), 4.36 (t, 2H), 6.73 (d, 1H), 8.10 (d, 1H), 8.57 (s, 1H).

(Step 3) Synthesis of di-tert-butyl (((((2-((2,2,2-trifluoroacetyl)imino)-1H-imidazole-1,3(2H)-diyl)bis(butane-4,1-diyl))bis(oxy))bis(pyridine-6,3-diyl))bis(iminomethylene)) dicarbamate

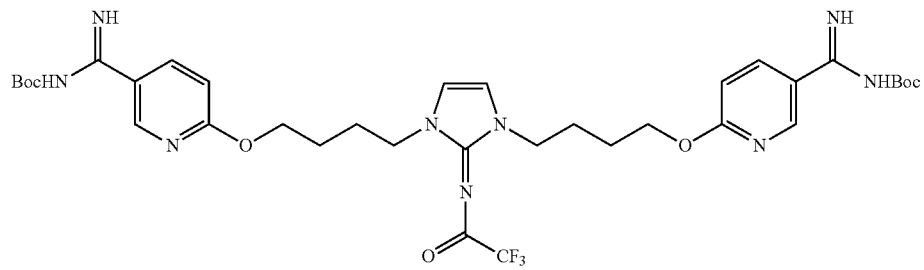 [SMILES: CC(C)(C)OC(=O)NC(=N)c1ccc(OCCCCn2ccn(CCCCOc3ccc(C(=N)NC(=O)OC(C)(C)C)cn3)c2=NC(=O)C(F)(F)F)nc1]

The tert-butyl ((6-(4-bromobutoxy)pyridin-3-yl)(imino)methyl) carbamate (0.74 g) obtained in the step 2 was dissolved in N, N-dimethylformamide (3 mL). N-(1,3-dihydro-2H-imidazol-2-ylidene)-2,2,2-trifluoroacetamide (0.14 g), sodium iodide (0.36 g), and potassium carbonate (0.28 g) were added to the solution. The resultant was stirred for 9 hours at 60° C., and then water was added thereto. The resultant was subjected to extraction with ethyl acetate, and the resultant organic layer was concentrated under reduced pressure. The residue was purified by silica gel column chromatography to obtain the title compound (compound No. 45: 0.41 g).

$^1$HNMR (CDCl$_3$): 1.51 (s, 18H), 1.75 (m, 4H), 1.87 (m, 4H), 3.89 (m, 4H), 4.31 (m, 4H), 6.65 (d, 2H), 6.75 (s, 2H), 8.07 (d, 2H), 8.55 (s, 2H).

EXAMPLE 46

Synthesis of trifluoroacetic acid salt of N-(1,3-bis (4-((5-carbamimidoylpyridin-2-yl) oxy)butyl)-1,3-dihydro-2H-imidazol-2-ylidene)-2,2,2-trifluoroacetamide

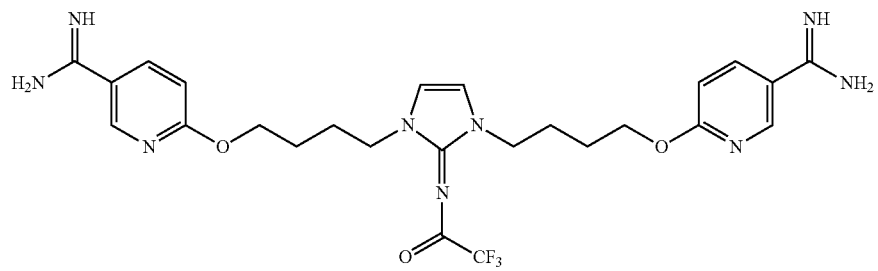 [SMILES: N=C(N)c1ccc(OCCCCn2ccn(CCCCOc3ccc(C(=N)N)cn3)c2=NC(=O)C(F)(F)F)nc1]

The di-tert-butyl (((((2-((2,2,2-trifluoroacetyl)imino)-1H-imidazole-1,3(2H)-diyl) bis(butane-4,1-diyl))bis(oxy))bis(pyridine-6,3-diyl))bis(iminomethylene)) dicarbamate (0.41 g) obtained in the step 3 of Example 45 was dissolved in dichloromethane (3 mL). Trifluoroacetic acid (1.5 mL) was added to the solution at room temperature, and then the mixture was stirred for 17 hours at room temperature. The solvent in the reaction mixture was distilled off therefrom to obtain the title compound (compound No. 46: 0.20 g).

$^1$HNMR (CDCl$_3$): 1.77 (m, 4H), 1.91 (m, 4H), 3.93 (t, 4H), 4.41 (t, 4H), 6.93 (d, 2H), 7.25 (s, 2H), 8.00 (d, 2H), 8.59 (s, 2H).

EXAMPLE 47

(Step 1) Synthesis of tert-butyl N-[5-(hydroxymethyl)thiophene-3-carboximidoyl]carbamate

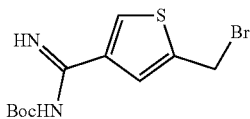 [SMILES: CC(C)(C)OC(=O)NC(=N)c1csc(CBr)c1]

5-[[tert-butyl(dimethyl)silyl]oxymethyl]thiophene-3-carbonitrile (2 g) was dissolved in tetrahydrofuran (20 mL). Lithium bis(trimethylsilyl)amide (1.3M in tetrahydrofuran solution) (9.1 mL) was added to the solution at room temperature. The mixture was stirred for 1 hour at the same temperature, and then hydrogen chloride (4M in dioxane solution) (20 mL) and methanol (20 mL) were added thereto under ice-cooling. The reaction mixture was stirred for 2 hours at room temperature. The reaction mixture was concentrated under reduced pressure, and the resulting residue was dissolved in N, N-dimethylformamide (20 mL). Triethylamine (4.79 g) and di-tert-butyl dicarbonate (5.16 g) were added to the solution under ice-cooling. The mixture was stirred for 4 hours at room temperature. Water was added to the reaction mixture, and the mixture was subjected to extraction with ethyl acetate. The resultant organic layer was dried over anhydrous sodium sulfate, and filtered. The filtrate was concentrated under reduced pressure and the resulting residue was purified by silica gel column chromatography to obtain the title compound (392 mg, in a yield of 19.4%).

$^1$HNMR (CDCl$_3$): 1.54 (s, 9H), 4.81 (s, 2H), 7.38 (s, 1H), 7.92 (s, 1H).

(Step 2) Synthesis of tert-butyl N-[5-(bromomethyl)thiophene-3-carboximidoyl]carbamate

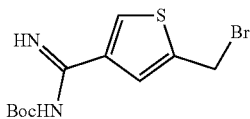 [SMILES: CC(C)(C)OC(=O)NC(=N)c1csc(CBr)c1]

The tert-butyl N-[5-(hydroxymethyl)thiophene-3-carboximidoyl]carbamate (134 mg) obtained in the step 1 was dissolved in tetrahydrofuran (3 mL). Triphenylphosphine (150 mg) and carbon tetrabromide (190 mg) were added to the solution under ice-cooling. The reaction mixture was stirred for 4 hours at room temperature. The reaction mixture was concentrated under reduced pressure and the resulting residue was purified by silica gel column chromatography to obtain the title compound (81 mg, in a yield of 16.7%).

$^1$HNMR (CDCl$_3$): 1.54 (s, 9H), 4.67 (s, 2H), 7.51 (d, 1H), 7.97 (d, 1H).

(Step 3) Synthesis of tert-butyl N-[5-(2-hydroxyethoxymethyl)thiophene-3-carboximidoyl]carbamate

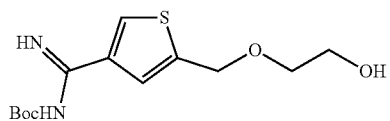 [SMILES: CC(C)(C)OC(=O)NC(=N)c1csc(COCCO)c1]

The tert-butyl N-[5-(bromomethyl)thiophene-3-carboximidoyl]carbamate (81 mg) obtained in the step 2 was dissolved in ethylene glycol (2 mL) and N, N-dimethylformamide (2 mL), and potassium carbonate (70 mg) was added thereto at room temperature. The reaction mixture was concentrated under reduced pressure, and the resulting residue was purified by silica gel column chromatography to obtain the title compound (31 mg, in a yield of 40.8%).

$^1$HNMR (CDCl$_3$): 1.55 (s, 9H), 3.60 (t, 2H), 3.76 (t, 2H), 4.69 (s, 2H), 7.41 (s, 1H), 7.93 (s, 1H).

(Step 4) Synthesis of tert-butyl N-[N,N'-bis(tert-butoxycarbonyl)-N-[2-[[4-(N-tert-butoxycarbonyl-carbamimidoyl)-2-thienyl]methoxy]ethyl]carbamimidoyl]-N-(7-bromo heptyl)carbamate

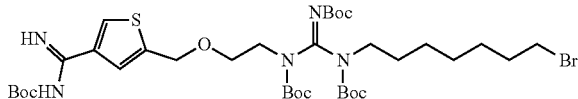

The title compound was obtained in the same manner as in the step 1 of Example 28.

¹HNMR (CDCl₃): 1.12-1.25 (m, 4H), 1.33-1.40 (m, 2H), 1.43-1.60 (m, 38H), 1.75-1.86 (m, 4H), 3.38 (t, 2H), 3.72 (t, 2H), 3.87 (t, 2H), 4.63 (s, 2H), 7.49 (s, 1H), 8.07 (s, 1H).

(Step 5) Synthesis of tert-butyl N-[N,N'-bis(tert-butoxycarbonyl)-N-[2-[[4-(N-tert-butoxycarbonyl-carbamimidoyl)-2-thienyl]methoxy]ethyl]carbamimidoyl]-N-[7-[[N,N'-bis (tert-butoxycarbonyl)carbamimidoyl]-tert-butoxycarbonyl-amino]heptyl]carbamate

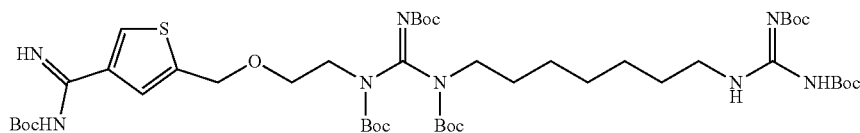

The title compound (compound No. 47) was obtained in the same manner as in the step 2 of Example 28.

¹HNMR (CDCl₃): 1.01-1.16 (m, 6H), 1.43-1.62 (m, 58H), 3.34-3.42 (m, 2H), 3.71-3.75 (m, 2H), 3.76-3.83 (m, 2H), 3.84-3.91 (m, 2H), 4.62 (s, 2H), 7.54 (s, 1H), 8.16 (s, 1H).

EXAMPLE 48

Synthesis of hydrochloride salt of 5-[2-[[N-(7-guanidinoheptyl)carbamimidoyl]amino]ethoxymethyl]thiophene-3-carboxamidine

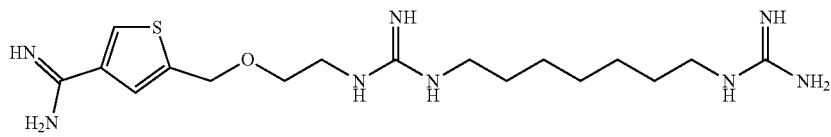 [SMILES: N=C(N)NCCCCCCCNC(=N)NCCOCc1cc(C(=N)N)cs1]

The title compound (compound No. 48) was obtained in the same manner as in Example 2.

¹HNMR (CD₃OD): 1.36-1.45 (m, 6H), 1.53-1.67 (m, 4H), 3.11-3.23 (m, 6H), 3.41-3.50 (m, 2H), 3.65-3.72 (m, 2H), 7.52 (d, 1H), 8.37 (d, 1H).

EXAMPLE 49

(Step 1) Synthesis of ethyl 2-(5-hydroxypent-1-ynyl)thiazole-4-carboxylate

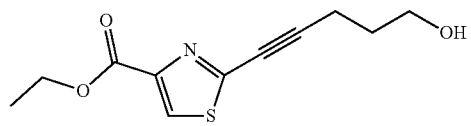 [SMILES: CCOC(=O)c1csc(C#CCCCO)n1]

Ethyl 2-bromothiazole-4-carboxylate (2.32 g) was dissolved in diisopropylamine. Pent-4-yn-1-ol (1.07 g), bis(triphenylphosphine)palladium (II) dichloride (344 mg), and copper iodide (56 mg) were added to the solution at room temperature. The mixture was stirred at 70° C. for 6 hours. The reaction mixture was cooled to room temperature, and then filtered with Celite (trademark). Water was added to the filtrate, and the mixture was subjected to extraction with ethyl acetate. The resultant organic layer was dried over anhydrous sodium sulfate and then filtered. The filtrate was concentrated under reduced pressure and the resulting residue was purified by silica gel column chromatography to obtain a mixture containing the title compound and an unknown structure product (992 mg).

¹HNMR (CDCl₃): 1.41 (t, 3H), 1.88 (dt, 2H), 2.61 (t, 2H), 3.80 (dd, 2H), 4.44 (dd, 2H), 8.11 (s, 1H)

(Step 2) Synthesis of ethyl 2-[5-[tert-butyl(dimethyl)silyl]oxypent-1-ynyl]thiazole-4-carboxylate

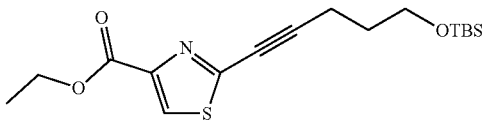 [SMILES: CCOC(=O)c1csc(C#CCCCO[Si](C)(C)C(C)(C)C)n1]

The mixture (992 mg) containing ethyl 2-(5-hydroxypent-1-ynyl)thiazole-4-carboxylate obtained in the step 1 was dissolved in dichloromethane (10 mL). Triethylamine (1.05 g), tert-butyldimethylsilyl chloride (750 mg), N,N-dimethyl-4-aminopyridine (50 mg) were added to the solution under ice-cooling. The mixture was stirred for 2 hours at room temperature. Water was added to the reaction mixture, and the mixture was subjected to extraction with ethyl acetate. The resultant organic layer was dried over anhydrous sodium sulfate, and filtered. The filtrate was concentrated under reduced pressure and the resulting residue was purified by silica gel column chromatography to obtain the title compound (817 mg, in a yield of 55.9%).

¹HNMR (CDCl₃): 0.07 (s, 6H), 0.90 (s, 9H), 1.41 (t, 3H), 1.83 (dt, 2H), 2.56 (t, 2H), 3.73 (t, 2H), 4.42 (dd, 2H), 8.10 (s, 1H).

(Step 3) Synthesis of 2-[5-[tert-butyl(dimethyl)silyl]oxypent-1-ynyl]thiazole-4-carboximidic acid

The ethyl 2-[5-[tert-butyl(dimethyl)silyl]oxypent-1-ynyl]thiazole-4-carboxylate (1 g) obtained in the step 2 was dissolved in methanol (6 mL) in a sealed tube, and ammonia (7M in methanol solution) (4 mL) was added thereto at room temperature. The reaction container was sealed and heated to 80° C. The reaction mixture was stirred at the same temperature overnight. The reaction mixture was cooled to room temperature, and then concentrated under reduced pressure. The resulting residue was purified by silica gel column chromatography to obtain the title compound (862 mg, in a yield of 91.8%).
¹HNMR (CDCl₃): 0.07 (s, 6H), 0.91 (s, 9H), 1.85 (dt, 2H), 2.59 (t, 2H), 3.74 (t, 2H), 8.09 (s, 1H).

(Step 4) Synthesis of tert-butyl N-[2-(5-hydroxypent-1-ynyl)thiazole-4-carboximidoyl]carbamate

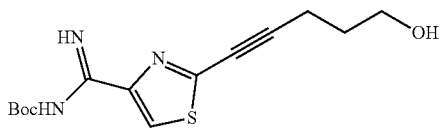 [SMILES: CC(C)(C)OC(=O)NC(=N)c1csc(C#CCCCO)n1]

The 2-[5-[tert-butyl(dimethyl)silyl]oxypent-1-ynyl]thiazole-4-carboximidic acid (264 mg) obtained in the step 3 was dissolved in dichloromethane (4 mL). Trimethyloxonium tetrafluoroborate (Me₃OBF₄) (144 mg) was added to the solution under ice-cooling. The reaction mixture was stirred at room temperature overnight. The reaction mixture was concentrated under reduced pressure and the resulting residue was dissolved in methanol (2 mL). Ammonia (7M in methanol solution) (4 mL) was added to the resultant under ice-cooling. The mixture was stirred at room temperature overnight. The reaction mixture was concentrated under reduced pressure, the resulting residue was dissolved in N, N-dimethylformamide (3 mL), and then trifluoroacetic acid (329 mg) and di-tert-butyl dicarbonate (266 mg) were added thereto under ice-cooling. The resultant was stirred for 5 hours at room temperature. Water was added to the reaction mixture, and the mixture was subjected to extraction with ethyl acetate. The resultant organic layer was dried over anhydrous sodium sulfate, and filtered. The filtrate was concentrated under reduced pressure and the resulting residue was purified by silica gel column chromatography to obtain the title compound (35.4 mg, in a yield of 10.2%).
¹HNMR (CDCl₃): 1.55 (s, 9H), 1.91 (dt, 2H), 2.64 (t, 2H), 3.82 (dd, 2H), 8.29 (s, 1H).

(Step 5) Synthesis of tert-butyl N—[N,N'-bis(tert-butoxycarbonyl)-N-[5-[4-(N-tert-butoxy carbonyl-carbamimidoyl)thiazol-2-yl]pent-4-ynyl]carbamimidoyl]-N-(7-bromoheptyl) carbamate

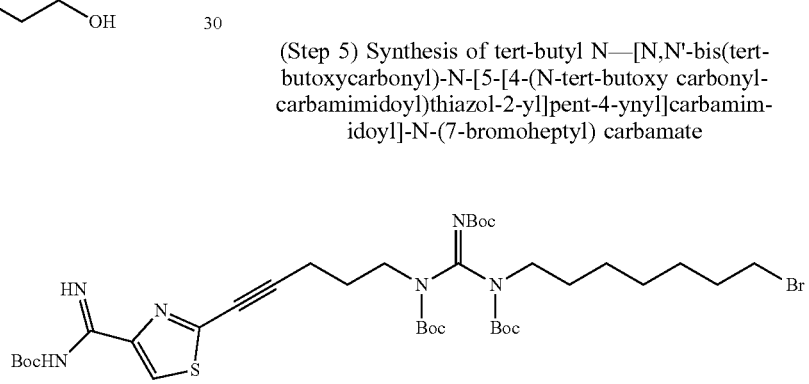

The title compound was obtained in the same manner as in the step 1 of Example 28.
¹HNMR (CDCl₃): 1.24-1.38 (m, 4H), 1.45-1.56 (m, 36H), 1.62-1.72 (m, 4H), 1.83 (dt, 2H), 1.98-2.05 (m, 2H), 2.56 (t, 2H), 3.39 (t, 2H), 3.51 (dd, 2H), 3.67 (dd, 2H), 8.28 (s, 1H).

(Step 6) Synthesis of tert-butyl N—[N,N'-bis(tert-butoxycarbonyl)-N-[5-[4-(N-tert-butoxy carbonyl-carbamimidoyl)thiazol-2-yl]pent-4-ynyl]carbamimidoyl]-N-[7-[[N,N'-bis(tert-butoxycarbonyl)carbamimidoyl]-tert-butoxycarbonyl-amino]heptyl]carbamate

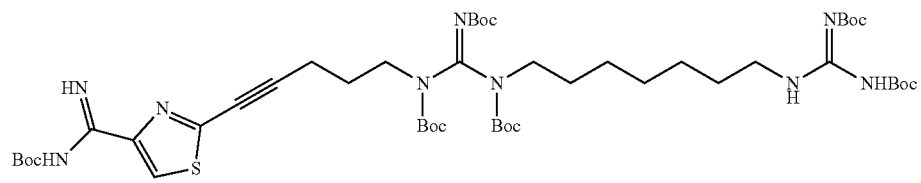

The title compound (compound No. 49) was obtained in the same manner as in the step 2 of Example 28.

$^1$HNMR (CDCl$_3$): 1.23-1.33 (m, 6H), 1.45-1.56 (m, 54H), 1.60-1.72 (m, 6H), 2.56 (t, 2H), 3.49 (dd, 2H), 3.66 (dd, 2H), 3.87 (dd, 2H), 8.28 (s, 1H).

EXAMPLE 50

Synthesis of hydrochloride salt of 2-[5-[[N-(7-guanidinoheptyl)carbamimidoyl]amino]pent-1-ynyl]thiazole-4-carboxamidine

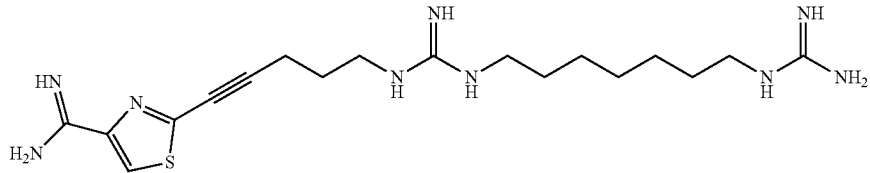 [SMILES: N=C(N)NCCCCCCCNC(=N)NCCCC#Cc1nc(C(=N)N)cs1]

The title compound (compound No. 50) was obtained in the same manner as in Example 2.

$^1$HNMR (CD$_3$OD): 1.36-1.46 (m, 6H), 1.54-1.68 (m, 4H), 1.93 (dt, 2H), 2.66 (t, 2H), 3.12-3.24 (m, 6H), 8.66 (s, 1H).

EXAMPLE 51

(Step 1) Synthesis of tert-butyl N-[4-[4-[2-(2,2,2-trifluoroacetyl)imino-1H-imidazol-3-yl]butoxy]benzenecarboximidoyl]carbamate

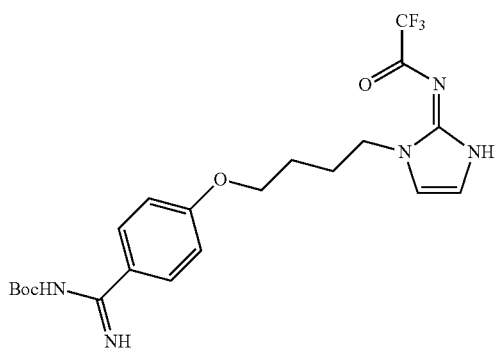 [SMILES: CC(C)(C)OC(=O)NC(=N)c1ccc(OCCCCn2cc[nH]/c2=N/C(=O)C(F)(F)F)cc1]

Tert-butyl N-[4-(4-bromobutoxy)benzenecarboximidoyl]carbamate (3.00 g) was dissolved in acetonitrile (50 mL) and benzene (25 mL). N-(1,3-dihydroimidazol-2-ylidene)-2,2,2-trifluoro-acetamide (4.34 g), potassium carbonate (1.68 g) and sodium iodide (1.33 g) were sequentially added to the solution, and the mixture was stirred at 50° C. overnight. Then, the reaction mixture was cooled to room temperature, water was added thereto, and the resultant was subjected to extraction with chloroform. The resultant organic layer was dried over anhydrous magnesium sulfate, and then filtered. The filtrate was concentrated under reduced pressure, and then the resulting residue was purified by silica gel column chromatography to obtain the title compound (0.93 g, in a yield of 25%).

$^1$H NMR (CDCl$_3$): 1.55 (s, 9H), 1.76-1.87 (m, 2H), 2.01 (tt, 2H), 4.03-4.14 (m, 4H), 6.70 (d, 1H), 6.81 (d, 1H), 6.90 (d, 2H), 7.83 (d, 2H).

(Step 2) Synthesis of tert-butyl N-[4-[4-[3-[7-[[N,N'-bis(tert-butoxycarbonyl) carbamimidoyl]amino]heptyl]-2-(2,2,2-trifluoroacetyl)imino-imidazol-1-yl]butoxy]benzenecarboximidoyl]carbamate

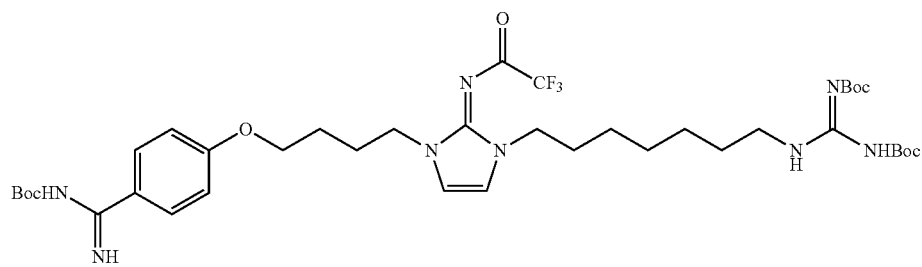

The tert-butyl N-[4-[4-[2-(2,2,2-trifluoroacetyl)imino-1H-imidazol-3-yl]butoxy]benzenecarboximidoyl]carbamate (491.3 mg) obtained in the step 1 and tert-butyl N-[(7-bromoheptylamino)-(tert-butoxycarbonylamino)methylene]carbamate (0.68 g) were dissolved in acetonitrile (10 mL) and benzene (5 mL). Potassium carbonate (0.18 g) was added to the solution, and the mixture was stirred at 50° C. for 2 days. Then, the reaction mixture was cooled to room temperature, and filtered with Celite (trademark). The filtrate was concentrated under reduced pressure, and the resulting residue was purified by silica gel column chromatography to obtain the title compound (compound No. 51: 278 mg, in a yield of 32%).

$^1$H NMR (CDCl$_3$): 1.23-1.39 (m, 6H), 1.45-1.63 (m, 29H), 1.68-1.86 (m, 4H), 1.97 (tt, 2H), 3.81-3.91 (m, 4H), 3.95 (t, 2H), 4.02 (t, 2H), 6.74 (d, 1H), 6.77 (d, 1H), 6.88 (d, 2H), 7.83 (d, 2H).

EXAMPLE 52

Synthesis of hydrochloride salt of 4-[4-[3-(7-guanidinoheptyl)-2-imino-imidazol-1-yl]butoxy]benzamidine

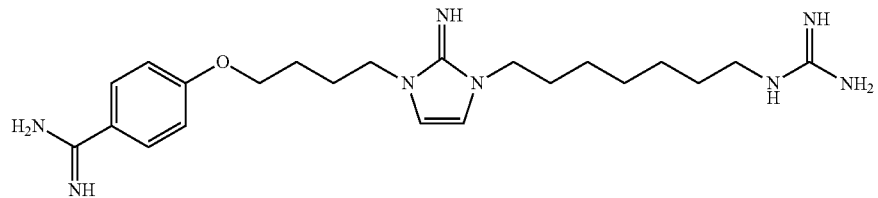 [SMILES: N=C(N)NCCCCCCCn1ccn(CCCCOc2ccc(C(=N)N)cc2)c1=N]

The tert-butyl N-[4-[4-[3-[7-[[N,N'-bis(tert-butoxycarbonyl)carbamimidoyl]amino]heptyl]-2-(2,2,2-trifluoroacetyl)imino-imidazol-1-yl]butoxy]benzene carboximidoyl]carbamate (278 mg) obtained in Example 51 was dissolved in methanol (10 mL). Hydrogen chloride in a 1,4-dioxane solution (4M, 10 mL) was added to the resultant at room temperature, and the mixture was stirred at 50° C. overnight. The reaction mixture was cooled to room temperature and was concentrated under reduced pressure to obtain the title compound (compound No. 52: 230 mg, quantitative).

$^1$H NMR (CD$_3$OD): 1.33-1.46 (m, 6H), 1.59 (tt, 2H), 1.76 (tt, 2H), 1.82-2.02 (m, 4H), 3.17 (t, 2H), 3.88 (t, 2H), 3.98 (t, 2H), 4.15 (t, 2H), 6.98 (d, 1H), 7.01 (d, 1H), 7.14 (d, 2H), 7.80 (d, 2H).

EXAMPLE 53

(Step 1) Synthesis of N-[1,3-bis[3-hydroxypropyl]-1,3-dihydro-2H-imidazol-2-ylidene]-2,2,2-trifluoroacetamide

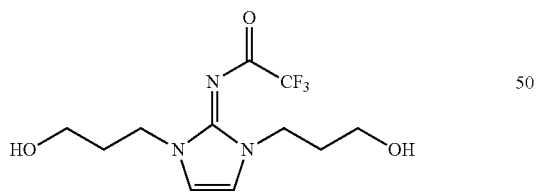

N-[1,3-dihydro-2H-imidazol-2-ylidene]-2,2,2-trifluoroacetamide (0.31 g) was dissolved in acetonitrile (10 mL). Potassium carbonate (0.75 g) and 3-bromo-1-propanol (0.75 g) were added to the solution at room temperature. The reaction mixture was heated to 60° C., and stirred at the same temperature overnight, followed by pouring the resultant into water to conduct extraction with ethyl acetate. The resultant organic layer was washed with saturated saline solution, and then dried over anhydrous sodium sulfate. The organic layer was concentrated and the resulting residue was purified by silica gel column chromatography to obtain the title compound (0.32 g).

$^1$H NMR (CD$_3$OD): 1.93 (tt, 4H), 3.53 (t, 4H), 3.98 (t, 4H), 7.21 (s, 2H).

(Step 2) Synthesis of tert-butyl N-[3-bromo-4-[3-[3-[3-[2-bromo-4-(N-tert-butoxy carbonylcarbamimidoyl)phenoxy]propyl]-2-(2,2,2-trifluoroacetyl)imino-imidazol-1-yl]propoxy]benzenecarboximidoyl]carbamate

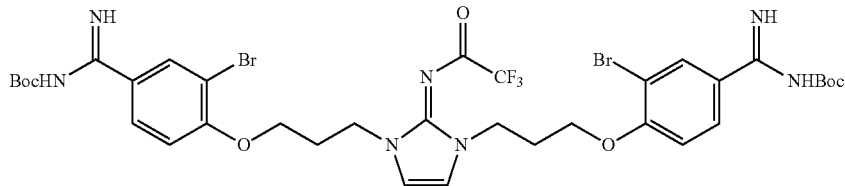 [SMILES: CC(C)(C)OC(=O)NC(=N)c1ccc(OCCCn2ccn(CCCOc3ccc(C(=N)NC(=O)OC(C)(C)C)cc3Br)c2=NC(=O)C(F)(F)F)c(Br)c1]

N-[1,3-bis[3-hydroxypropyl]-1,3-dihydro-2H-imidazol-2-ylidene]-2,2,2-trifluoro acetamide (0.32 g) obtained in the step 1 was dissolved in toluene (30 mL). At room temperature, tetrahydrofuran (10 mL) was added to the solution, and tert-butyl N-(3-bromo-4-hydroxy-benzenecarboximidoyl)carbamate (0.76 g) was added thereto. At room temperature, tributylphosphine (0.90 g) and 1,1'-(azodicarbonyl)dipiperidine (1.10 g) were added to the mixture. The mixture was stirred overnight, and then the resultant was poured into water to conduct extraction with ethyl acetate. The resultant organic layer was washed with saturated saline solution, dried over anhydrous sodium sulfate, and then filtered. The filtrate was concentrated under reduced pressure and the resulting residue was purified by silica gel column chromatography to obtain the title compound (compound No. 53: 0.40 g).

$^1$H NMR (CD$_3$OD): 1.51 (s, 18H), 2.29 (tt, 4H), 4.10 (t, 4H), 4.15 (t, 4H), 7.04 (d, 2H), 7.79 (dd, 2H), 8.07 (d, 2H).

EXAMPLE 54

Synthesis of hydrochloride salt of 3-bromo-4-[3-[3-[3-(2-bromo-4-carbamimidoyl-phenoxy)propyl]-2-imino-imidazol-1-yl]propoxy]benzamidine

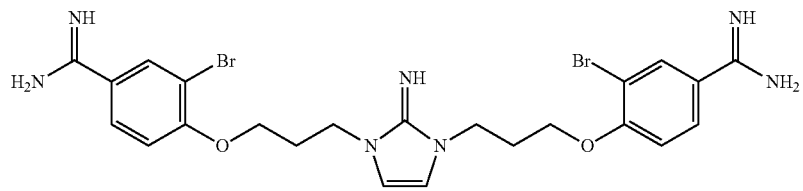 [SMILES: N=C(N)c1ccc(OCCCn2ccn(CCCOc3ccc(C(=N)N)cc3Br)c2=N)c(Br)c1]

The title compound (compound No. 54) was obtained in the same manner as in Example 52.
Melting point: 193-197° C.

EXAMPLE 55

Synthesis of N-[1,3-bis[3-[4-[N'-hydroxycarbamimidoyl]phenoxy]propyl]-1,3-dihydro-2H-imidazol-2-ylidene]-2,2,2-trifluoroacetamide

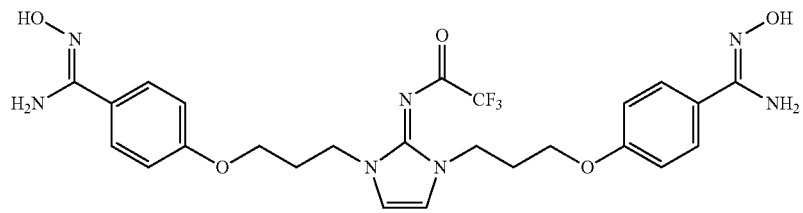 [SMILES: N/C(=N\O)c1ccc(OCCCn2ccn(CCCOc3ccc(/C(N)=N/O)cc3)c2=NC(=O)C(F)(F)F)cc1]

N-[1,3-bis[3-[4-cyanophenoxy]propyl]-1,3-dihydro-2H-imidazol-2-ylidene]-2,2,2-trifluoroacetamide (0.60 g) was dissolved in N,N-dimethyl sulfoxide (6 mL). A 50% hydroxylamine solution (0.13 g) was added to the solution at room temperature. The reaction mixture was heated to 50° C. and stirred at the same temperature overnight. A 2N aqueous sodium hydroxide solution was poured into the reaction mixture, and the mixture was subjected to extraction with tetrahydrofuran. The resultant organic layer was dried over anhydrous sodium sulfate and then filtered. The filtrate was concentrated under reduced pressure, and the concentrated residue was washed sequentially with water, ethyl acetate, and hexane to obtain the title compound (compound No. 55: 0.39 g).

Melting point: 187-201° C.

EXAMPLE 56

(Step 1) Synthesis of tert-butyl N-[4-[3-[3-[4-(N-tert-butoxycarbonylcarbamimidoyl) phenoxy]propylcarbamothioylamino]propoxy]benzenecarboximidoyl]carbamate

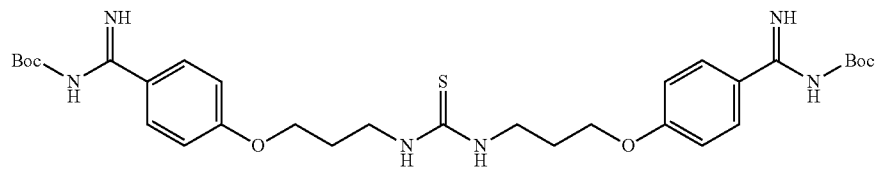 [SMILES: CC(C)(C)OC(=O)NC(=N)c1ccc(OCCCNC(=S)NCCCOc2ccc(C(=N)NC(=O)OC(C)(C)C)cc2)cc1]

Tert-butyl N-[4-(3-aminopropoxy)benzenecarboximidoyl]carbamate (445 mg) was dissolved in dichloromethane (5 mL). Triethylamine (273 mg) and tert-butyl N-[4-(3-isothiocyanatopropoxy)benzenecarboximidoyl]carbamate (389 g) were added to the solution at room temperature. The mixture was stirred at the same temperature for 3 hours, water was added to the reaction mixture, and then the resultant was subjected to extraction with chloroform. The resultant organic layer was dried over anhydrous sodium sulfate, and filtered. The filtrate was concentrated under reduced pressure and the resulting residue was purified by silica gel column chromatography to obtain the title compound (767 mg, in a yield of 91.7%).

$^1$H NMR (CDCl$_3$): 1.55 (s, 18H), 2.03-2.10 (m, 4H), 3.57-3.73 (m, 4H), 4.04 (t, 4H), 6.79 (d, 4H), 7.70 (t, 4H).

(Step 2) Synthesis of tert-butyl N-[4-[3-[(Z)-[[3-[4-(N-tert-butoxycarbonylcarbamimidoyl) phenoxy] propylamino]-methylsulfanyl-methylene]amino] propoxy]benzenecarboximidoyl]carbamate

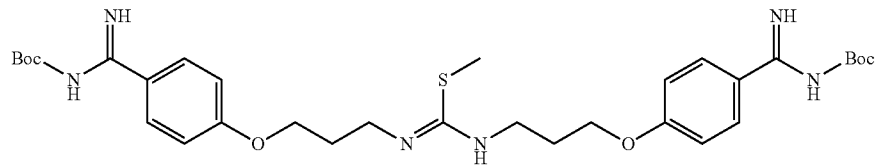 [SMILES: CS/C(=N\CCCOc1ccc(C(=N)NC(=O)OC(C)(C)C)cc1)NCCCOc1ccc(C(=N)NC(=O)OC(C)(C)C)cc1]

The tert-butyl N-[4-[3-[3-[4-(N-tert-butoxycarbonylcarbamimidoyl)phenoxy]propylcarbamothioylamino]propoxy] benzenecarboximidoyl]carbamate (767 mg) obtained in the step 1 was dissolved in acetone (10 mL). Potassium carbonate (253 mg) and methyl iodide (259 mg) were added to the solution under ice-cooling. The reaction mixture was warmed to room temperature and stirred at the same temperature for 4 hours. Water was added to the reaction mixture, and the mixture was subjected to extraction with ethyl acetate. The resultant organic layer was dried over anhydrous sodium sulfate, filtered, and then concentrated under reduced pressure. The resulting residue was purified by silica gel column chromatography to obtain the title compound (566 mg, in a yield of 72%).

$^1$H NMR (CDCl$_3$): 1.55 (s, 18H), 2.00-2.09 (m, 4H), 2.33 (s, 3H), 3.39-3.51 (m, 4H), 4.07 (dd, 4H), 6.86 (d, 4H), 7.77 (d, 4H).

(Step 3) Synthesis of tert-butyl N-[N,N'-bis[3-[4-(N-tert-butoxycarbonylcarbamimidoyl) phenoxy]propyl]carbamimidoyl]-N-methyl-carbamate

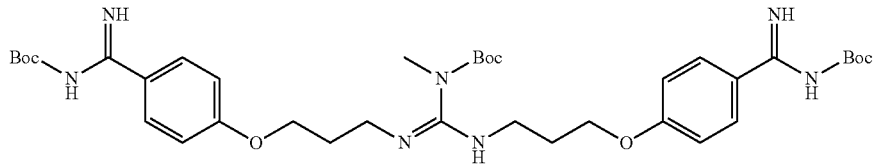 [SMILES: CN(C(=O)OC(C)(C)C)/C(=N\CCCOc1ccc(C(=N)NC(=O)OC(C)(C)C)cc1)NCCCOc1ccc(C(=N)NC(=O)OC(C)(C)C)cc1]

The tert-butyl N-[4-[3-[(Z)-[[3-[4-(N-tert-butoxycarbonylcarbamimidoyl) phenoxy]propylamino]-methylsulfanylmethylene]amino]propoxy]benzenecarboximidoyl]carbamate (250 mg) obtained in the step 2 was dissolved in tetrahydrofuran (4 mL). Triethylamine (118 mg), silver trifluoromethanesulfonate (120 mg), and methylamine (2M in tetrahydrofuran solution 253 mL) were added to the resultant under ice-cooling. The reaction mixture was warmed to room temperature and stirred at the same temperature overnight. The reaction mixture was filtered, and then concentrated under reduced pressure.

The resulting residue was dissolved in N, N-dimethylformamide (4 mL), and triethylamine (197 mg) and di-tert-butyl dicarbonate (255 mg) were added thereto under ice-cooling. The reaction mixture was warmed to room temperature and stirred at the same temperature overnight. Water was added to the reaction mixture, and the mixture was subjected to extraction with ethyl acetate. The resultant organic layer was dried over anhydrous sodium sulfate, filtered, and then concentrated under reduced pressure. The resulting residue was purified by silica gel column chromatography to obtain the title compound (compound No. 56: 12 mg, in a yield of 3.7%).

$^1$H NMR (CDCl$_3$): 1.37-1.69 (m, 36H), 2.00-2.07 (m, 4H), 2.76 (s, 3H), 3.27-3.36 (m, 4H), 3.99-4.08 (m, 4H), 6.79-6.87 (m, 4H), 7.33-7.41 (m, 2H), 7.72 (d, 2H).

EXAMPLE 57

Synthesis of hydrochloride salt of 4-[3-[[N-[3-(4-carbamimidoylphenoxy)propyl]-N'-methyl-carbamimidoyl]amino]propoxy]benzamidine The title compound (compound No. 57) was obtained in the same manner as in Example 2.

Melting point: 219-220° C.

EXAMPLE 58

(Step 1) Synthesis of tert-butyl N-[N,N'-bis(tert-butoxycarbonyl)carbamimidoyl]-N-[5-[[N,N'-bis(tert-butoxycarbonyl)carbamimidoyl]amino]pentyl]carbamate

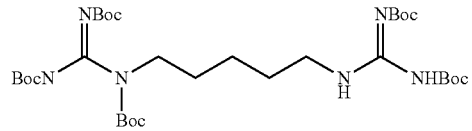

Tert-butyl N-[[tert-butoxycarbonylamino]-[5-hydroxypentylamino]methylene]carbamate (2.61 g) was dissolved in toluene (50 mL). 1,2,3-tris(tert-butoxycarbonyl)guanidine (4.11 g) was added to the solution at room temperature. Triphenylphosphine (3.02 g) and bis(2-methoxyethyl)azodicarboxylate (2.74 g) were added to the mixture at room temperature. The resultant was stirred overnight and then poured into water to conduct extraction with ethyl acetate. The resultant organic layer was washed with saturated saline solution, dried over anhydrous sodium sulfate, and then concentrated, followed by purifying the resulting residue by silica gel column chromatography to obtain the title compound (2.59 g).

$^1$H NMR (CDCl$_3$): 1.30-1.74 (m, 51H), 3.40 (q, 2H), 3.77 (t, 2H).

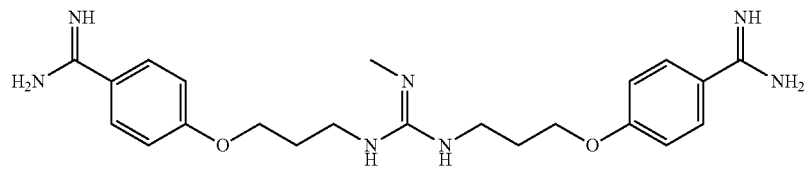 [SMILES: CN=C(NCCCOc1ccc(C(=N)N)cc1)NCCCOc1ccc(C(=N)N)cc1]

(Step 2) Synthesis of tert-butyl N-[N,N'-bis(tert-butoxycarbonyl)-N-[4-[4-(N-tert-butoxycarbonylcarbamimidoyl)phenoxy]butyl]carbamimidoyl]-N-[5-[[N,N'-bis(tert-butoxycarbonyl)carbamimidoyl]amino]pentyl]carbamate

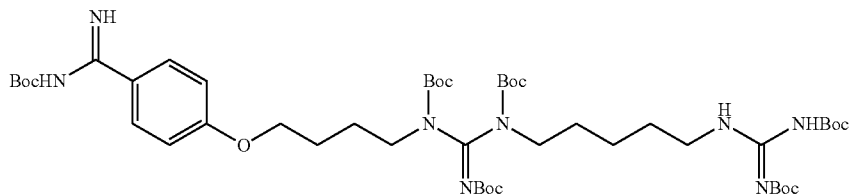

Tert-butyl ((4-(4-hydroxybutoxy)phenyl)(imino)methyl)carbamate (0.25 g) was dissolved in tetrahydrofuran (10 mL). Tert-butyl N—[N,N'-bis(tert-butoxycarbonyl) carbamimidoyl]-N-[5-[[N,N'-bis(tert-butoxycarbonyl)carbamimidoyl]amino]pentyl]carbamate (0.58 g) was added to the solution at room temperature. Triphenylphosphine (0.36 g) and bis(2-methoxyethyl)azodicarboxylate (0.35 g) were added to the mixture at room temperature. The resultant was stirred overnight and then concentrated, followed by purifying the resulting residue by silica gel column chromatography to obtain the title compound (0.33 g).

$^1$HNMR (CDCl$_3$): 1.21-1.70 (m, 60H), 1.75-1.89 (m, 4H), 3.34 (q, 2H), 3.50 (t, 2H), 3.57 (t, 2H), 4.01 (t, 2H), 6.89 (d, 2H), 7.85 (d, 2H).

EXAMPLE 59

Synthesis of hydrochloride salt of 4-[3-[[(5-guanidinopentyl)carbamimidoyl]amino]butoxy]benzamidine

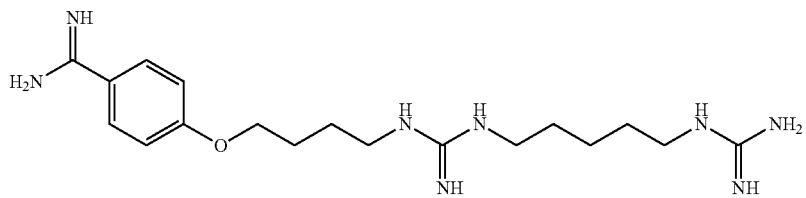 [SMILES: N=C(N)NCCCCCNC(=N)NCCCCOc1ccc(C(=N)N)cc1]

The title compound (compound No. 59) was obtained in the same manner as in Example 2.

$^1$H NMR (CD$_3$OD): 1.41-1.53 (m, 2H), 1.58-1.71 (m, 4H), 1.75-1.97 (m, 4H), 3.16-3.25 (m, 4H), 3.26-3.37 (m, 2H), 4.15 (t, 2H), 7.14 (d, 2H), 7.79 (d, 2H).

EXAMPLE 60

(Step 1) Synthesis of tert-butyl N-[N,N'-bis(tert-butoxycarbonyl)carbamimidoyl]-N-[4-[[5-(N-tert-butoxycarbonylcarbamimidoyl)-2-pyridyl]oxy]butyl]carbamate

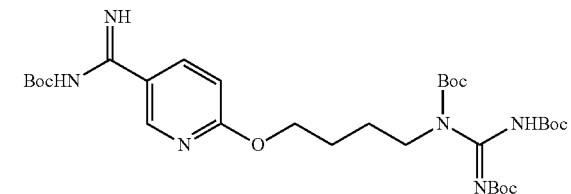

Tert-butyl N-[6-(4-bromobutoxy)pyridine-3-carboximidoyl]carbamate (0.50 g) and 1,2,3-tris(tert-butoxycarbonyl) guanidine (0.97 g) were dissolved in N,N-dimethylformamide (13 mL). Potassium carbonate (0.20 g) was added to the solution, and the resultant was stirred at room temperature overnight. Then, the reaction mixture was cooled to room temperature, water was added thereto, and then the resultant was subjected to extraction with chloroform. The resultant organic layer was dried over anhydrous magnesium sulfate and filtered. The filtrate was concentrated under reduced pressure and the resulting residue was purified by silica gel column chromatography to obtain the title compound (0.16 g, in a yield of 18%).

$^1$H NMR (CDCl$_3$): 1.45-1.57 (m, 36H), 1.73-1.88 (m, 4H), 3.79-3.93 (m, 2H), 4.29-4.40 (m, 2H), 6.71 (d, 1H), 8.12 (dd, 1H), 8.59 (d, 1H).

(Step 2) Synthesis of tert-butyl N—[N,N'-bis(tert-butoxycarbonyl)-N-[4-[[5-(N-tert-butoxy carbonyl-carbamimidoyl)-2-pyridyl]oxy]butyl]carbamimidoyl]-N-[8-[[N,N'-bis(tert-butoxy carbonyl)carbamimidoyl]amino]octyl]carbamate

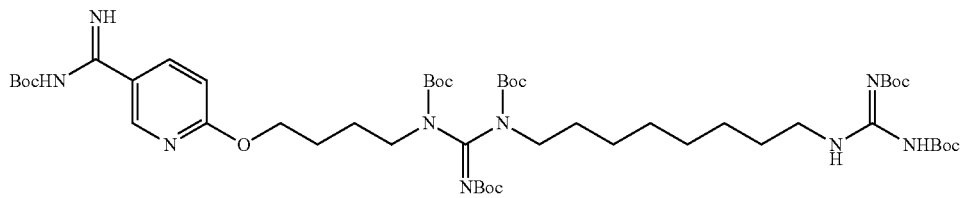

The tert-butyl N-[N,N'-bis(tert-butoxycarbonyl)carbamimidoyl]-N-[4-[[5-(N-tert-butoxycarbonylcarbamimidoyl)-2-pyridyl]oxy]butyl]carbamate (0.16 g) obtained in the step 1 and tert-butyl N-[(8-bromooctylamino)-(tert-butoxycarbonylamino)methylene]carbamate (0.17 g) were dissolved in N,N-dimethylformamide (5 mL). Potassium carbonate (0.07 g) was added to the solution and the mixture was stirred at 50° C. overnight. Then, the reaction mixture was cooled to room temperature, water was added thereto, and the resultant was subjected to extraction with chloroform. The resultant organic layer was dried over anhydrous magnesium sulfate and filtered. The filtrate was concentrated under reduced pressure and the resulting residue was purified by silica gel column chromatography to obtain the title compound (compound No. 60: 81 mg, in a yield of 32%).
$^1$H NMR (CDCl$_3$): 1.08-1.37 (m, 10H), 1.39-1.65 (m, 56H), 1.73-1.88 (m, 4H), 3.48 (t, 2H), 3.60 (t, 2H), 3.82 (t, 2H), 4.34 (t, 2H), 6.71 (d, 1H), 8.20 (dd, 1H), 8.69 (d, 1H).

EXAMPLE 61

Synthesis of hydrochloride salt of 6-[4-[[N-(8-guanidinooctyl)carbamimidoyl]amino]butoxy]pyridine-3-carboxamidine The title compound (compound No. 61) was obtained in the same manner as in Example 2.
$^1$H NMR (CD$_3$OD): 1.32-1.66 (m, 12H), 1.70-1.90 (m, 4H), 3.13-3.23 (m, 4H), 3.28 (t, 2H), 4.39-4.53 (m, 2H), 6.95-7.04 (m, 1H), 8.04-8.17 (m, 1H), 8.61-8.70 (m, 1H).

EXAMPLE 62

Synthesis of tert-butyl N-[N-tert-butoxycarbonyl-N-[3-[4-(N-tert-butoxycarbonyl carbamimidoyl)phenoxy]propyl]-N'-phenyl-carbamimidoyl]-N-[3-[4-(N-tert-butoxy carbonylcarbamimidoyl)phenoxy]propyl]carbamate

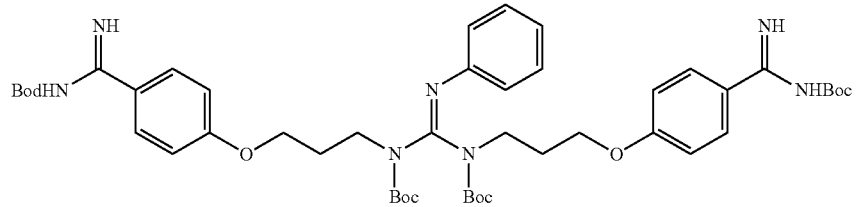

Tert-butyl N-[4-(3-bromopropoxy)benzenecarboximidoyl]carbamate (0.27 g) and tert-butyl N-(N-tert-butoxycarbonyl-N'-phenyl-carbamimidoyl)carbamate (0.60 g) were dissolved in N,N-dimethylformamide (5 mL). Potassium carbonate (0.56 g) was added to the solution, and then the mixture was stirred at 50° C. overnight. Then, the reaction mixture was cooled to room temperature, water was added thereto, and the resultant was subjected to extraction with chloroform. The resultant organic layer was dried over anhydrous magnesium sulfate and filtered. The filtrate was concentrated under reduced pressure and the resulting residue was purified by silica gel column chromatography to obtain the title compound (compound No. 62: 0.30 g, in a yield of 42%).

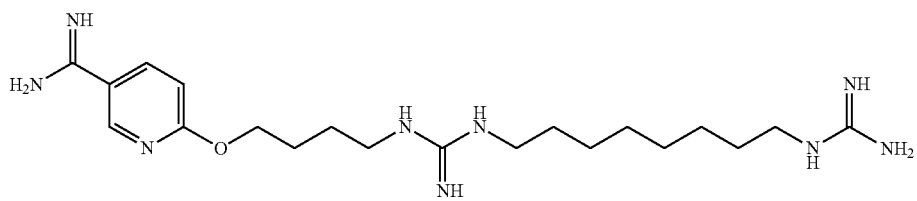 [SMILES: N=C(N)NCCCCCCCCNC(=N)NCCCCOc1ccc(C(=N)N)cn1]

$^1$H NMR (CDCl$_3$): 1.35-1.60 (m, 38H), 2.24 (tt, 2H), 3.25 (t, 2H), 3.71 (t, 2H), 3.99 (t, 2H), 4.11 (t, 2H), 6.74 (d, 2H), 6.80 (d, 2H), 6.86 (d, 2H), 7.02 (dd, 2H), 7.25 (dd, 2H), 7.77 (d, 2H).

EXAMPLE 63

Synthesis of hydrochloride salt of 4-[3-[[N-[3-(4-carbamimidoylphenoxy)propyl]-N'-phenyl-carbamimidoyl]amino]propoxy]benzamidine

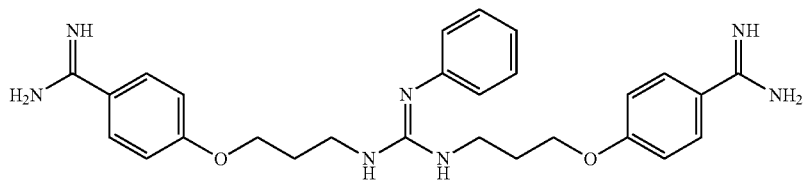 [SMILES: N=C(N)c1ccc(OCCCNC(=Nc2ccccc2)NCCCOc2ccc(C(=N)N)cc2)cc1]

The title compound (compound No. 63) was obtained in the same manner as in Example 2.

$^1$HNMR (CD$_3$OD): 2.02-2.26 (m, 4H), 3.50-3.62 (m, 4H), 4.20 (t, 2H), 7.11 (d, 2H), 7.23 (d, 2H), 7.33 (t, 1H), 7.43 (dd, 2H), 7.79 (d, 2H).

EXAMPLE 64

Synthesis of tert-Butyl N-[N,N'-bis(tert-butoxycarbonyl)-N-[3-[4-(N-tert-butoxycarbonyl carbamimidoyl)phenyl]propyl]carbamimidoyl]-N-[3-[4-(N-tert-butoxycarbonyl carbamimidoyl)phenyl]propyl]carbamate

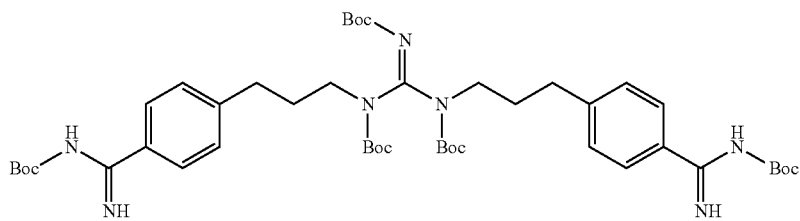 [SMILES: CC(C)(C)OC(=O)N=C(N(CCCc1ccc(C(=N)NC(=O)OC(C)(C)C)cc1)C(=O)OC(C)(C)C)N(CCCc1ccc(C(=N)NC(=O)OC(C)(C)C)cc1)C(=O)OC(C)(C)C]

Tert-butyl N-[N, N'-bis(tert-butoxycarbonyl)-N-[3-[4-(N-tert-butoxycarbonyl carbamimidoyl)phenyl]prop-2-ynyl]carbamimidoyl]-N-[3-[4-(N-tert-butoxycarbonyl carbamimidoyl)phenyl]prop-2-ynyl]carbamate (450 mg) was dissolved in methanol (5 mL), and palladium on carbon (45 mg) was added thereto at room temperature. The mixture was stirred under a hydrogen atmosphere at the same temperature overnight. The reaction mixture was filtered and concentrated under reduced pressure to obtain the title compound (compound No. 64: 90.8 mg, in a yield of 20%).

$^1$H NMR (CDCl$_3$): 1.43-1.56 (m, 45H), 1.87-1.98 (m, 4H), 2.62 (t, 4H), 3.52 (dd, 4H), 7.17 (d, 2H), 7.71 (d, 2H).

EXAMPLE 65

Synthesis of hydrochloride salt of 4-[3-[[N-[3-(4-carbamimidoylphenyl)propyl]carbamimidoyl]amino]propyl]benzamidine

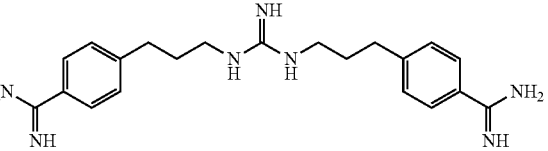

The title compound (compound No. 65) was obtained in the same manner as in Example 2.

$^1$HNMR (CD$_3$OD): 1.95 (dt, 4H), 2.83 (dd, 4H), 3.27 (dd, 4H), 7.51 (d, 4H), 7.75 (d, 4H)

EXAMPLE 66

Synthesis of di-tert-butyl [[[[2-[[2,2,2-trifluoroacetyl]imino]-1H-imidazole-1,3 [2H]-diyl]bis[propane-3,1-diylsulfonyl]]bis[4,1-phenylene]]bis[iminomethylene]]dicarbamate

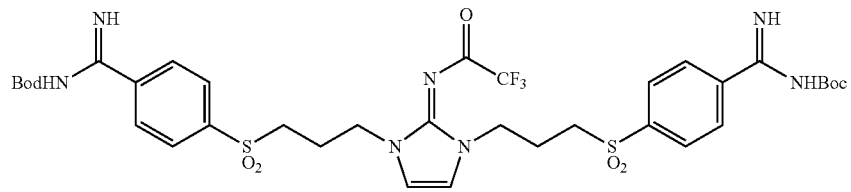

Di-tert-butyl [[[[2-[[2,2,2-trifluoroacetyl]imino]-1H-imidazole-1,3[2H]-diyl]bis[propane-3,1-diyl]]bis[sulfanediyl]]bis[4,1-phenylene]]bis[iminomethylene]]dicarbamate (168 mg) was dissolved in dichloromethane (5 mL). 3-chloroperbenzoic acid (268 mg) was added to the solution at room temperature. The mixture was stirred for 1.5 hours, and the resultant was poured into water to conduct extraction with ethyl acetate. The resultant organic layer was washed sequentially with saturated aqueous sodium thiosulfate solution, saturated aqueous sodium hydrogen carbonate solution, and saturated saline solution, and then dried over anhydrous sodium sulfate, followed by filtering. The filtrate was concentrated under reduced pressure, and the resulting residue was purified by silica gel column chromatography to obtain the title compound (compound No. 66: 116 mg).

$^1$H NMR (CDCl$_3$): 1.56 (s, 18H), 2.22 (tt, 4H), 3.12 (t, 4H), 4.03 (t, 4H), 6.86 (s, 2H), 7.85 (d, 4H), 7.91 (d, 4H).

EXAMPLE 67

Synthesis of hydrochloride salt of 4-[3-[3-[3-(4-carbamimidoylphenyl)sulfonylpropyl]-2-imino-imidazol-1-yl]propylsulfonyl]benzamidine

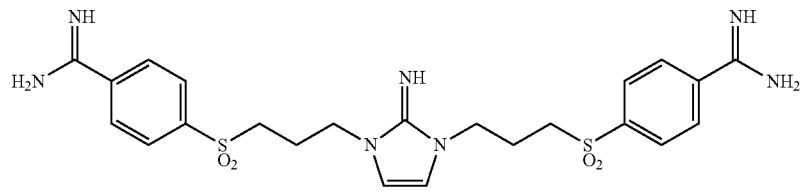 [SMILES: N=C(N)c1ccc(S(=O)(=O)CCCn2ccn(CCCS(=O)(=O)c3ccc(C(=N)N)cc3)c2=N)cc1]

The title compound (compound No. 67) was obtained in the same manner as in Example 52.

$^1$HNMR (CD$_3$OD): 2.11-2.26 (m, 4H), 3.42 (t, 4H), 4.05 (t, 4H), 6.99 (s, 2H), 8.05 (d, 4H), 8.18 (d, 4H).

EXAMPLE 68

Synthesis of tert-butyl N-[N-tert-butoxycarbonyl-N-[4-[4-(N-tert-butoxycarbonyl carbamimidoyl)phenoxy]butyl]-N'-phenyl-carbamimidoyl]-N-[4-[4-(N-tert-butoxycarbonylcarbamimidoyl)phenoxy]butyl] carbamate (compound No. 68-1) and tert-butyl N-[N'-tert-butoxycarbonyl-N-[4-[4-(N-tert-butoxycarbonylcarbamimidoyl)phenoxy]butyl]-N-phenyl-carbamimidoyl]-N-[4-[4-(N-tert-butoxycarbonylcarbamimidoyl)phenoxy]butyl]carbamate (compound No. 68-2)

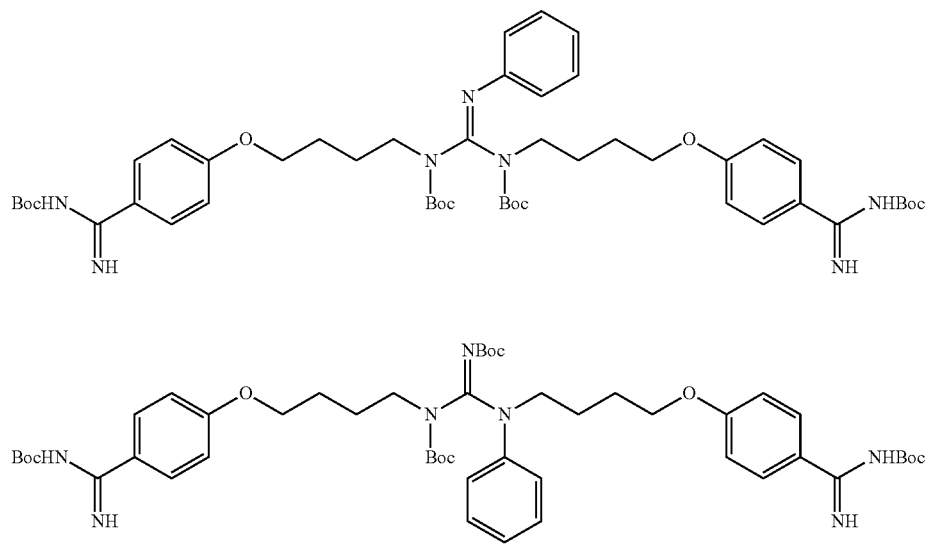

Tert-butyl N-[4-(4-bromobutoxy)benzenecarboximidoyl]carbamate (3.03 g) and tert-butyl N-(N-tert-butoxycarbonyl-N'-phenyl-carbamimidoyl)carbamate (1.25 g) were dissolved in N,N-dimethylformamide (5 mL), potassium carbonate (2.06 g) was added thereto, and the mixture was stirred at 60° C. overnight. Then, the reaction mixture was cooled to room temperature, water was added thereto, and the resultant was subjected to extraction with ethyl acetate. The resultant organic layer was dried over anhydrous magnesium sulfate, filtered, and then concentrated under reduced pressure. The resulting residue was purified by silica gel column chromatography to obtain the title compound (compound No. 68-1: 590 mg, in a yield of 17%) and the title compound (compound No. 68-2: 152 mg, in a yield of 4.5%).

Compound No. 68-1:
$^1$H NMR (CDCl$_3$): 1.37 (s, 9H), 1.43-1.68 (m, 31H), 1.75-1.98 (m, 4H), 3.16 (t, 2H), 3.79 (t, 2H), 3.85 (t, 2H), 3.99 (t, 2H), 6.75-6.88 (m, 6H), 7.03 (dd, 2H), 7.26 (d, 2H), 7.72-7.82 (m, 4H).

Compound No. 68-2:
$^1$H NMR (CDCl$_3$): 1.41-1.72 (m, 40H), 1.73-1.91 (m, 4H), 2.89-3.15 (m, 2H), 3.71-4.08 (m, 6H), 6.80 (d, 2H), 6.82 (d, 2H), 7.20-7.36 (m, 5H), 7.73-7.84 (m, 4H).

EXAMPLE 69

Synthesis of hydrochloride salt of 4-[4-[[N-[4-(4-carbamimidoylphenoxy)butyl]-N'-phenyl-carbamimidoyl]amino]butoxy]benzamidine

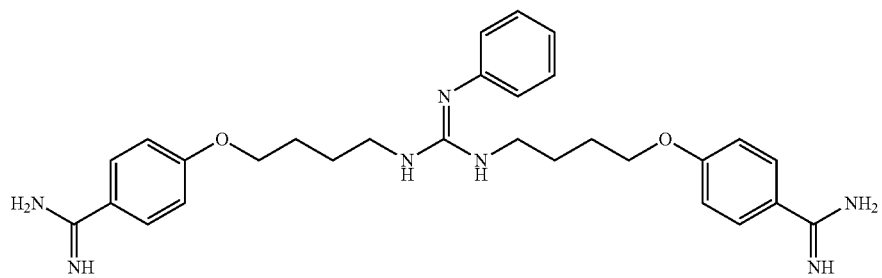 [SMILES: N=C(N)c1ccc(OCCCCNC(=Nc2ccccc2)NCCCCOc2ccc(C(=N)N)cc2)cc1]

The title compound (compound No. 69) was obtained in the same manner as in Example 2.
¹HNMR (CD₃OD): 1.77-1.97 (m, 8H), 3.36-3.47 (m, 4H), 4.14 (t, 4H), 7.12 (d, 4H), 7.28 (d, 2H), 7.34 (dd, 1H), 7.47 (dd, 2H), 7.79 (d, 4H).

EXAMPLE 70

Synthesis of hydrochloride salt of 4-[4-[[N-[4-(4-carbamimidoylphenoxy)butyl]-N-phenyl-carbamimidoyl]amino]butoxy]benzamidine

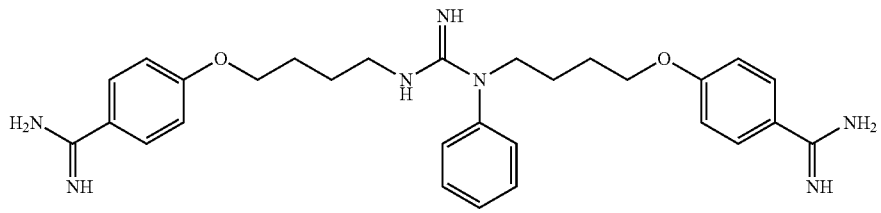 [SMILES: N=C(N)c1ccc(OCCCCNC(=N)N(CCCCOc2ccc(C(=N)N)cc2)c2ccccc2)cc1]

The title compound (compound No. 70) was obtained in the same manner as in Example 2.
¹HNMR (CD₃OD): 1.71-1.93 (m, 8H), 3.63-3.69 (m, 2H), 3.80 (t, 2H), 4.08 (t, 2H), 4.12 (t, 2H), 7.07 (d, 2H), 7.12 (d, 2H), 7.37 (d, 2H), 7.49 (dd, 1H), 7.56 (dd, 2H), 7.72-7.84 (m, 4H).

EXAMPLE 71

(Step 1) Synthesis of 2,2,2-trifluoro-N-[3-[8-[2-(2,2,2-trifluoroacetyl)imino-1H-imidazol-3-yl]octyl]-1H-imidazol-2-ylidene]acetamide

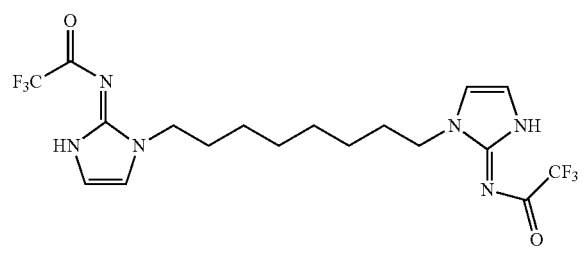 [SMILES: O=C(/N=c1\[nH]ccn1CCCCCCCCn1cc[nH]/c1=N\C(=O)C(F)(F)F)C(F)(F)F]

N-(1,3-dihydroimidazol-2-ylidene)-2,2,2-trifluoro-acetamide (5 g) was dissolved in acetonitrile (50 mL) and benzene (15 mL). Potassium carbonate (3.86 g) and dibromooctane (2.53 g) were added to the solution at room temperature. The reaction mixture was heated to 60° C., and stirred at the same temperature overnight. The reaction mixture was cooled to room temperature, water was added thereto, and the resultant was subjected to extraction with ethyl acetate. The resultant organic layer was dried over anhydrous sodium sulfate, filtered, and concentrated under reduced pressure. The resulting residue was purified by silica gel column chromatography to obtain the title compound (3.27 g, in a yield of 75.0%).
¹NMR (CDCl₃): 1.24-1.37 (m, 8H), 1.76 (tt, 4H), 3.99 (dd, 4H), 6.65 (d, 2H), 6.81 (d, 2H).

(Step 2) Synthesis of tert-butyl 2-[4-[3-[2-(2,2,2-trifluoroacetyl)imino-3-[8-[2-(2,2,2-trifluoroacetyl)imino-1H-imidazol-3-yl]octyl]imidazol-1-yl]propoxy]phenyl]-5,6-dihydro-4H-pyrimidine-1-carboxylate

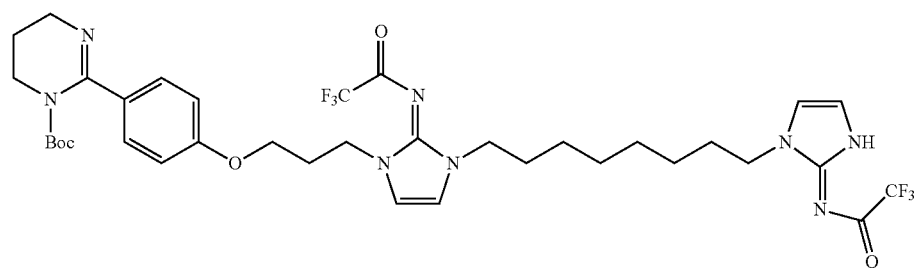 [SMILES: CC(C)(C)OC(=O)N1CCCN=C1c1ccc(OCCCn2ccn(CCCCCCCCn3cc[nH]/c3=N\C(=O)C(F)(F)F)/c2=N/C(=O)C(F)(F)F)cc1]

2,2,2-trifluoro-N-[3-[8-[2-(2,2,2-trifluoroacetypimino-1H-imidazol-3-yl]octyl]-1H- imidazol-2-ylidene]acetamide (943 mg) obtained in the step 1 was dissolved in acetonitrile (10 mL) and benzene (3 mL). Potassium carbonate (417 mg) and tert-butyl 2-[4(3bromopropoxy)phenyl]-5,6-dihydro-4H-pyrimidine-1 -carboxylate (800 mg) were added to the solution at room temperature. The reaction mixture was heated to 50° C. and stirred at the same temperature overnight. The reaction mixture was cooled to room temperature, water was added thereto, and the resultant was subjected to extraction with ethyl acetate. The resultant organic layer was dried over anhydrous sodium sulfate, filtered, and concentrated under reduced pressure. The resulting residue was purified by silica gel column chromatography to obtain the title compound (compound No. 282: 337 mg, in a yield of 21.0%).

$^1$H NMR (CDCl$_3$): 1.16 (s, 9H), 1.24-1.36 (m, 8H), 1.69-1.79 (m, 4H), 1.92 (dt, 2H), 2.24 (tt, 2H), 3.60 (dd, 2H), 3.70 (dd, 2H), 3.83 (dd, 2H), 3.95 (dd, 2H), 3.98 (dd, 2H), 4.12 (dd, 2H), 6.67-6.71 (m, 3H), 6.80 (d, 1H), 6.83 (d, 2H), 7.42 (d, 2H).

EXAMPLE 72

Synthesis of tert-butyl 2-[42-[3-[[N,N '-bis(tert-butoxycarbonyl)carbamimidoyl]amino]octyl]-2-imino-imidazolidin-1-yl]ethoxy]phenyl]-5,6-dihydro-4H-pyrimidine-1-carboxlate

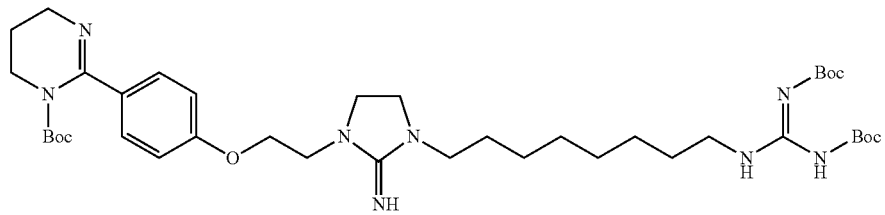 [SMILES: CC(C)(C)OC(=O)/N=C(/NCCCCCCCCN1CCN(CCOc2ccc(C3=NCCCN3C(=O)OC(C)(C)C)cc2)C1=N)NC(=O)OC(C)(C)C]

Tert-butyl 2-[4-[2-(2-iminoimidazolidin-1-yl)ethoxy]phenyl]-5,6-dihydro-4H- pyrimidine-1-carboxylate (140 mg) was dissolved in N, N-dimethylformamide (5 mL). Potassium carbonate (153 mg) and tert-butyl N-[(8-bromooctylamino)-(tert-butoxy carbonylamino)methylene]carbamate (333 mg) were added to the solution at room temperature.

The reaction mixture was stirred at the same temperature overnight. Water was added to the reaction mixture, and the mixture was subjected to extraction with ethyl acetate. The resultant organic layer was dried over anhydrous sodium sulfate, filtered, and concentrated under reduced pressure. The resulting residue was purified by silica gel column chromatography to obtain the title compound (compound No. 315: 119 mg, in a yield of 42.5%).

$^1$H NMR (CDCl$_3$): 1.16 (s, 9H), 1.24-1.36 (m, 8H), 1.47-1.54 (m, 20H), 1.59-1.72 (m, 2H), 1.94 (tt, 2H), 3.02-3.17 (m, 2H), 3.24 (dd, 2H), 3.42 (dd, 2H), 3.56-3.65 (m, 4H), 3.69 (dd, 2H), 3.88 (dd, 2H), 4.16 (dd, 2H), 6.89 (d, 2H), 7.41 (d, 2H)

The following compounds were synthesized taking into account Examples 1 to 72 and Synthesis Examples 1 to 9.

TABLE 74

| Compound No. | Structure |
|---|---|
| 71 | 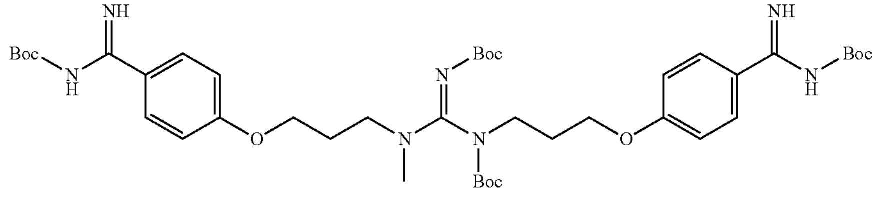 [SMILES: CN(CCCOc1ccc(C(=N)NC(=O)OC(C)(C)C)cc1)/C(=N/C(=O)OC(C)(C)C)N(CCCOc1ccc(C(=N)NC(=O)OC(C)(C)C)cc1)C(=O)OC(C)(C)C] |

TABLE 74-continued
| | |
|---|---|
| 72 | 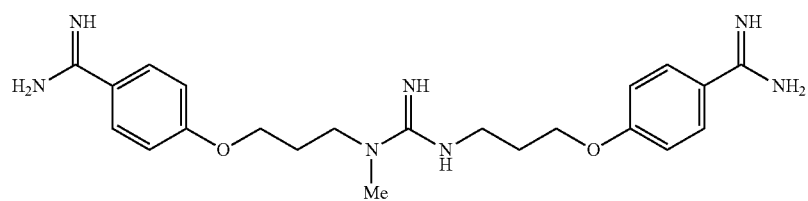 [SMILES: CN(CCCOc1ccc(C(=N)N)cc1)C(=N)NCCCOc1ccc(C(=N)N)cc1] |
| 73 | 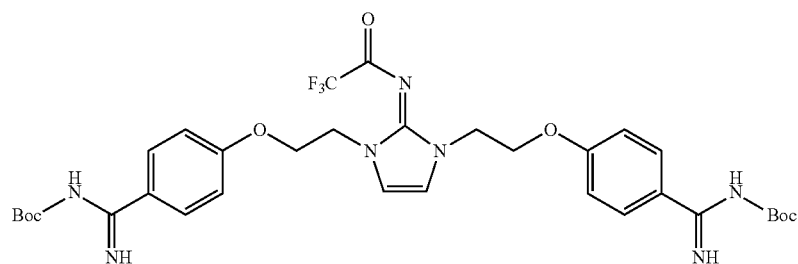 [SMILES: CC(C)(C)OC(=O)NC(=N)c1ccc(OCCn2ccn(CCOc3ccc(C(=N)NC(=O)OC(C)(C)C)cc3)c2=NC(=O)C(F)(F)F)cc1] |
| 74 | 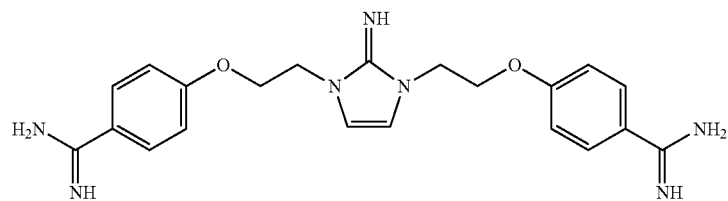 [SMILES: N=C(N)c1ccc(OCCn2ccn(CCOc3ccc(C(=N)N)cc3)c2=N)cc1] |
| 75 | 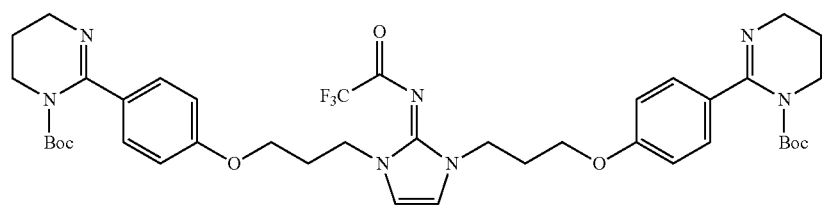 [SMILES: CC(C)(C)OC(=O)N1CCCN=C1c1ccc(OCCCn2ccn(CCCOc3ccc(C4=NCCCN4C(=O)OC(C)(C)C)cc3)c2=NC(=O)C(F)(F)F)cc1] |
| 76 | 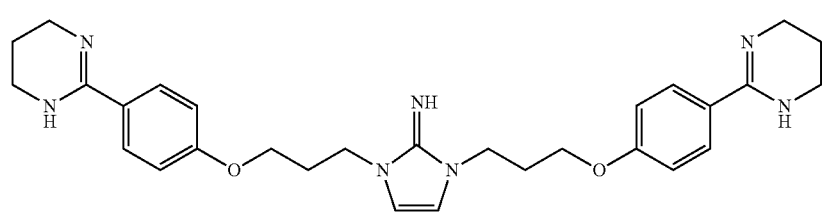 [SMILES: N=c1n(CCCOc2ccc(C3=NCCCN3)cc2)ccn1CCCOc1ccc(C2=NCCCN2)cc1] |
| 77 | 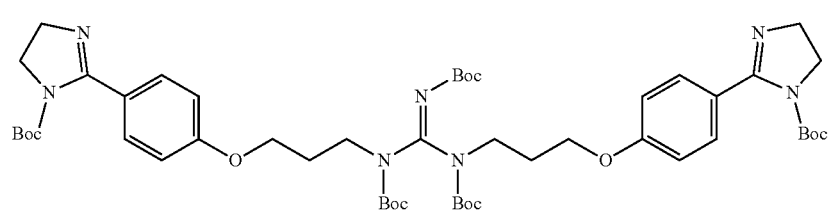 [SMILES: CC(C)(C)OC(=O)N=C(N(CCCOc1ccc(C2=NCCN2C(=O)OC(C)(C)C)cc1)C(=O)OC(C)(C)C)N(CCCOc1ccc(C2=NCCN2C(=O)OC(C)(C)C)cc1)C(=O)OC(C)(C)C] |
| 78 | 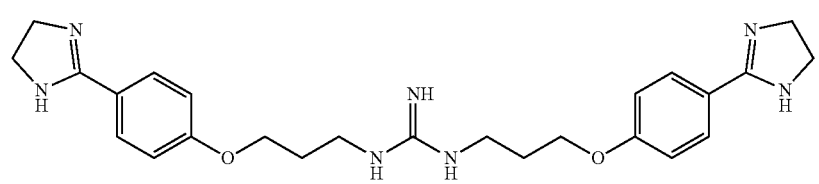 [SMILES: N=C(NCCCOc1ccc(C2=NCCN2)cc1)NCCCOc1ccc(C2=NCCN2)cc1] |

TABLE 74-continued

| Compound No. | Salt form | Physical property |
|---|---|---|
| 71 | — | ¹HNMR (CDCl₃): 1.44-1.60 (m, 36H), 2.02-2.19 (m, 4H), 3.00 (s, 3H), 3.24-3.49 (m, 2H), 3.51-3.69 (m, 2H), 3.83-4.04 (m, 4H), 6.69-6.93 (m, 4H), 7.64-7.84 (m, 4H) |
| 72 | hydrochloride | ¹HNMR (CD₃OD): 2.13 (dt, 4H), 3.08 (s, 3H), 3.43-3.49 (m, 2H), 3.62 (dd, 2H), 4.15-4.21 (m, 4H), 7.16 (dd, 4H), 7.80 (dd, 4H) |
| 73 | — | ¹HNMR (CDCl₃): 1.55 (s, 18H), 4.27 (dd, 4H), 4.33 (dd, 4H), 6.85 (d, 4H), 6.91 (s, 2H), 7.76 (d, 4H) |
| 74 | hydrochloride | ¹HNMR (CD₃OD): 4.34-4.43 (m, 8H), 7.09 (s, 2H), 7.17 (d, 4H), 7.79 (d, 4H) |
| 75 | — | ¹HNMR (CDCl₃): 1.16 (s, 18H), 1.92 (dt, 4H), 2.29 (dt, 4H), 3.60 (dd, 4H), 3.70 (dd, 4H), 3.99 (t, 4H), 4.22 (t, 4H), 6.74 (s, 2H), 6.84 (d, 4H), 7.43 (d, 4H) |
| 76 | hydrochloride | ¹HNMR (CD₃OD): 2.10 (dt, 4H), 2.26 (dt, 4H), 3.57 (dd, 8H), 4.11 (dd, 4H), 4.15 (dd, 4H), 6.97 (s, 2H), 7.13 (d, 4H), 7.67 (d, 4H) |
| 77 | — | ¹HNMR (CDCl₃): 1.31 (s, 18H), 1.46-1.53 (m, 27H), 2.16 (dd, 4H), 3.73 (dd, 4H), 3.90 (dd, 4H), 3.95 (dd, 4H), 4.02 (t, 4H), 6.85 (d, 4H), 7.45 (d, 4H) |
| 78 | hydrochloride | ¹HNMR (CD₃OD): 2.11 (dd, 4H), 2.55-2.92 (m, 4H), 3.35-3.49 (m, 8H), 4.20 (t, 4H), 7.18 (d, 4H), 7.84 (d, 4H) |
| 79 | — | ¹HNMR (CDCl₃): 1.44 (s, 18H), 1.50 (s, 9H), 1.57 (s, 18H), 2.09 (tt, 4H), 2.78 (t, 4H), 3.62 (t, 4H), 6.36 (s, 2H), 7.29 (d, 2H), 7.64 (dd, 2H), 7.97 (d, 2H). |
| 80 | hydrochloride | Melting point 174-182° C. |

In the table, Boc or BOC indicates a t-butoxycarbonyl group. In the table, "-" means that a compound was synthesized as free form.

TABLE 75

| Compound No. | Structure |
|---|---|
| 81 | 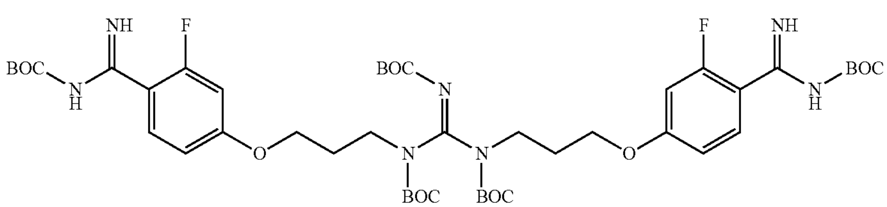 [SMILES: CC(C)(C)OC(=O)N=C(N(CCCOc1ccc(C(=N)NC(=O)OC(C)(C)C)c(F)c1)C(=O)OC(C)(C)C)N(CCCOc1ccc(C(=N)NC(=O)OC(C)(C)C)c(F)c1)C(=O)OC(C)(C)C] |

TABLE 75-continued
| | |
|---|---|
| 82 | 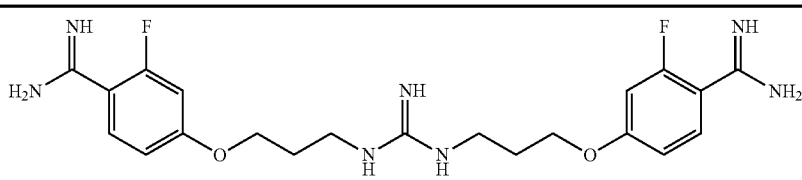 |
| 83 | 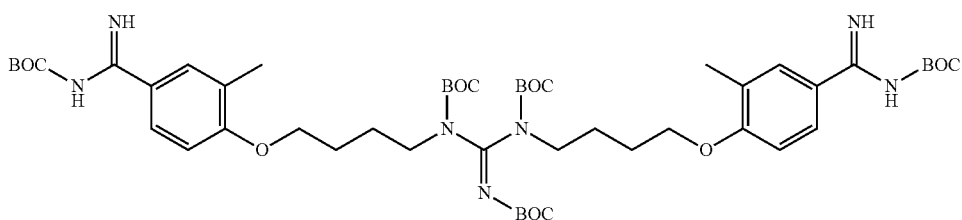 [SMILES: Cc1cc(C(=N)NC(=O)OC(C)(C)C)ccc1OCCCCN(C(=O)OC(C)(C)C)C(=NC(=O)OC(C)(C)C)N(CCCCOc1ccc(C(=N)NC(=O)OC(C)(C)C)cc1C)C(=O)OC(C)(C)C] |
| 84 | 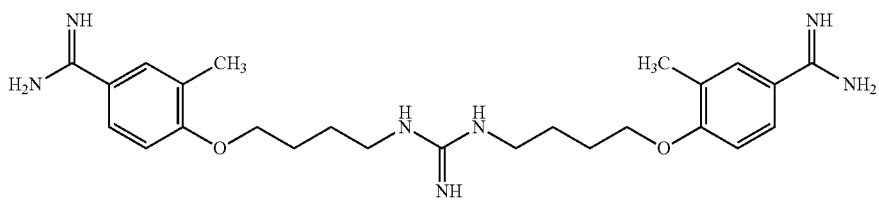 [SMILES: Cc1cc(C(=N)N)ccc1OCCCCNC(=N)NCCCCOc1ccc(C(=N)N)cc1C] |
| 85 | 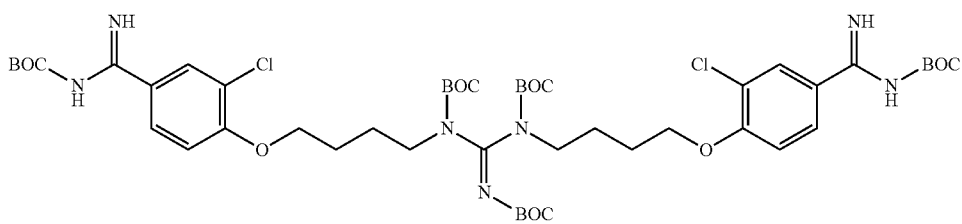 [SMILES: CC(C)(C)OC(=O)N=C(N(CCCCOc1ccc(C(=N)NC(=O)OC(C)(C)C)cc1Cl)C(=O)OC(C)(C)C)N(CCCCOc1ccc(C(=N)NC(=O)OC(C)(C)C)cc1Cl)C(=O)OC(C)(C)C] |
| 86 | 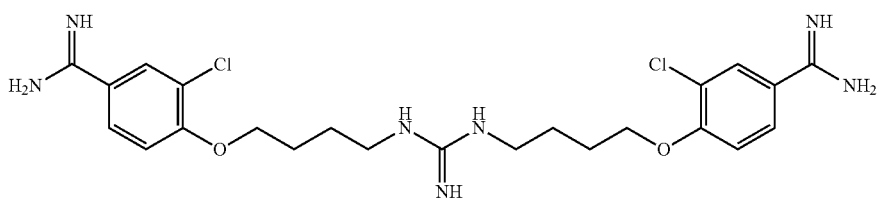 [SMILES: N=C(NCCCCOc1ccc(C(=N)N)cc1Cl)NCCCCOc1ccc(C(=N)N)cc1Cl] |
| 87 | 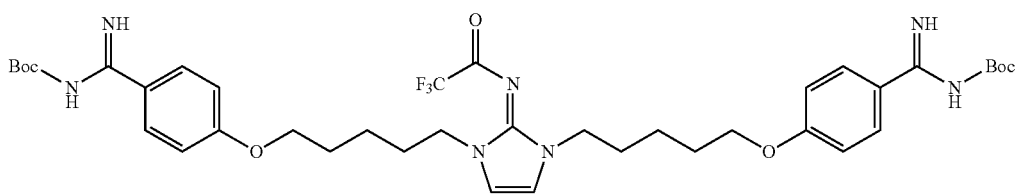 [SMILES: CC(C)(C)OC(=O)NC(=N)c1ccc(OCCCCCn2ccn(CCCCCOc3ccc(C(=N)NC(=O)OC(C)(C)C)cc3)c2=NC(=O)C(F)(F)F)cc1] |
| 88 | 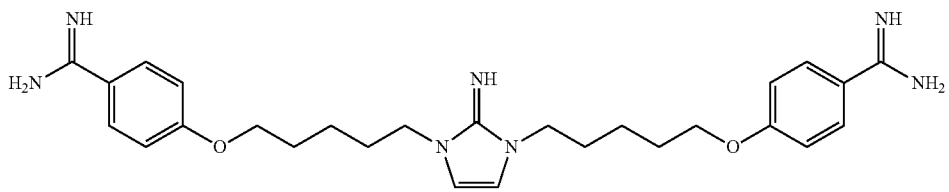 [SMILES: N=C(N)c1ccc(OCCCCCn2ccn(CCCCCOc3ccc(C(=N)N)cc3)c2=N)cc1] |
| 89 | 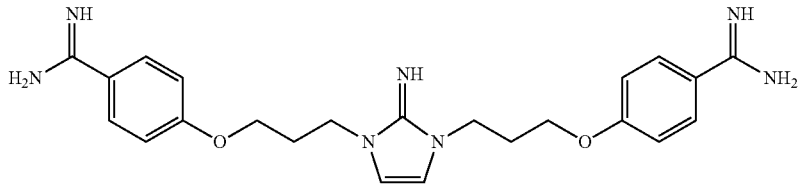 |

TABLE 75-continued

90

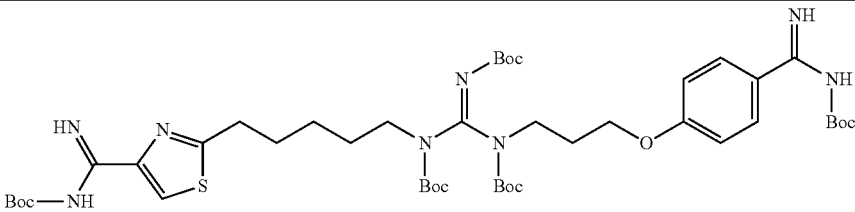

| Compound No. | Salt form | Physical property |
| --- | --- | --- |
| 81 | — | $^1$HNMR (CDCl$_3$): 1.44 (s, 18H), 1.50 (s, 9H), 1.57 (s, 18H), 2.09 (tt, 4H), 2.78 (t, 4H), 3.62 (t, 4H), 6.36 (s, 2H), 7.29 (d, 2H), 7.64 (dd, 2H), 7.97 (d, 2H). |
| 82 | hydrochloride | Melting point 181-185° C. |
| 83 | — | $^1$HNMR (CDCl$_3$): 1.46 (s, 18H), 1.49 (s, 9H), 1.56 (s, 18H), 1.77-1.90 (m, 8H), 3.62 (t, 4H), 3.94 (t, 4H), 6.67 (d, 2H), 7.59 (dd, 2H), 7.66 (d, 2H). |
| 84 | hydrochloride | Melting point 171-180° C. |
| 85 | — | $^1$HNMR (CDCl$_3$): 1.47 (s, 18H), 1.50 (s, 9H), 1.56 (s, 18H), 1.79-1.95 (m, 8H), 3.66 (t, 4H), 3.96 (t, 4H), 6.62 (d, 2H), 7.53 (dd, 2H), 7.86 (d, 2H). |
| 86 | hydrochloride | $^1$HNMR (CD$_3$OD): 1.80-2.01 (m, 8H), 3.33 (m, 4H), 4.24 (t, 4H), 7.31 (d, 2H), 7.78 (dd, 2H), 7.91 (d, 2H). |
| 87 | — | $^1$HNMR (CDCl$_3$): 1.46-1.56 (m, 22H), 1.76-1.87 (m, 8H), 3.90 (t, 4H), 3.97 (t, 4H), 6.73 (s, 2H), 6.87 (d, 4H), 7.80 (d, 4H) |
| 88 | hydrochloride | $^1$HNMR (CD$_3$OD): 1.52-1.61 (m, 4H), 1.79-1.93 (m, 8H), 3.90 (t, 4H), 4.11 (t, 4H), 6.99 (s, 2H), 7.12 (d, 4H), 7.77 (d, 4H) |
| 89 | acetate | Melting point 190-195° C. |
| 90 | — | $^1$HNMR (CDCl$_3$): 1.33-1.41 (m, 2H), 1.44-158 (m, 45H), 1.71 (dt, 2H),1.79 (dt, 2H), 2.16 (dd, 2H), 2.96 (dd, 2H), 3.49 (dd, 2H), 3.72 (dd, 2H), 4.06 (t, 2H), 6.88 (d, 2H), 7.80 (dt 2H), 8.21 (s, 1 H) |

In the table, Boc or BOC indicates a t-butoxycarbonyl group. In the table, "-" means that a compound was synthesized as free form.

TABLE 76

| Compound No. | Structure |
| --- | --- |
| 91 | 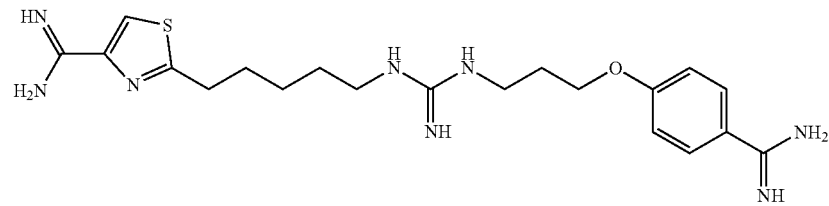 [SMILES: N=C(NCCCCCc1nc(C(=N)N)cs1)NCCCOc1ccc(C(=N)N)cc1] |
| 92 | 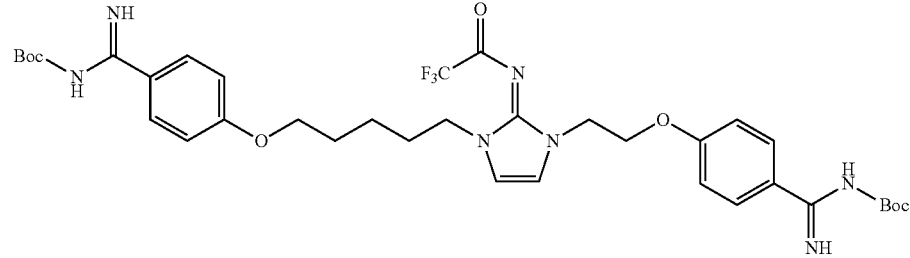 [SMILES: CC(C)(C)OC(=O)NC(=N)c1ccc(OCCCCCn2ccn(CCOc3ccc(C(=N)NC(=O)OC(C)(C)C)cc3)/c2=N/C(=O)C(F)(F)F)cc1] |

TABLE 76-continued
93 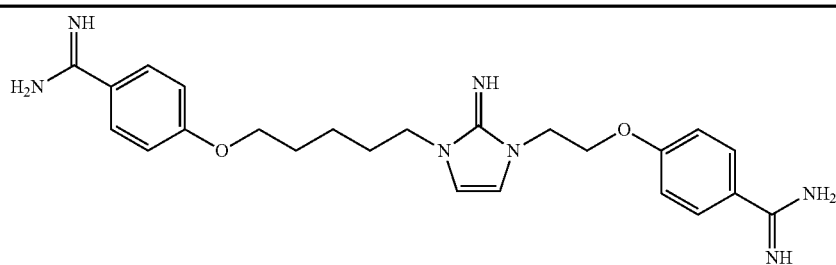
94 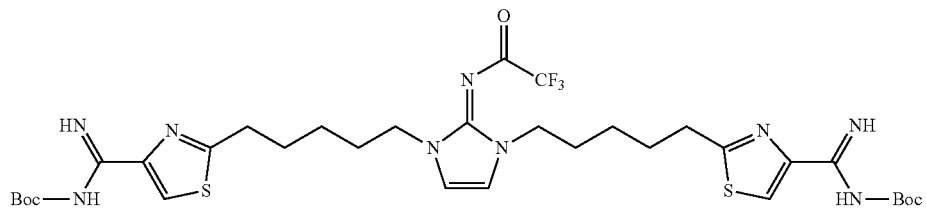 [SMILES: CC(C)(C)OC(=O)NC(=N)c1csc(CCCCCn2ccn(CCCCCc3nc(C(=N)NC(=O)OC(C)(C)C)cs3)c2=NC(=O)C(F)(F)F)n1]
95 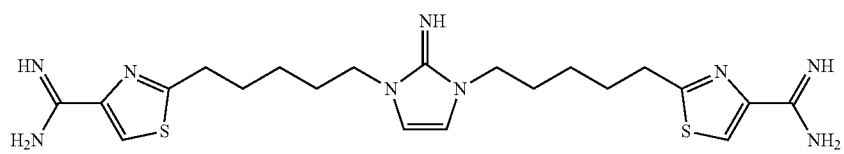 [SMILES: N=C(N)c1csc(CCCCCn2ccn(CCCCCc3nc(C(=N)N)cs3)c2=N)n1]
96 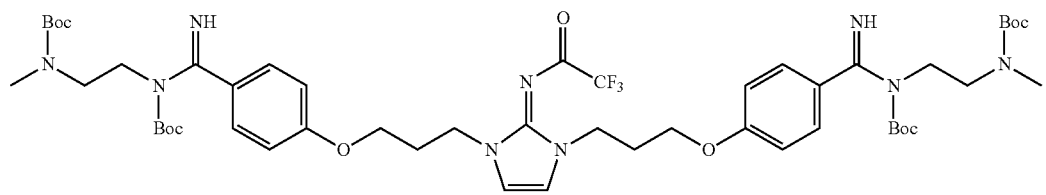
97 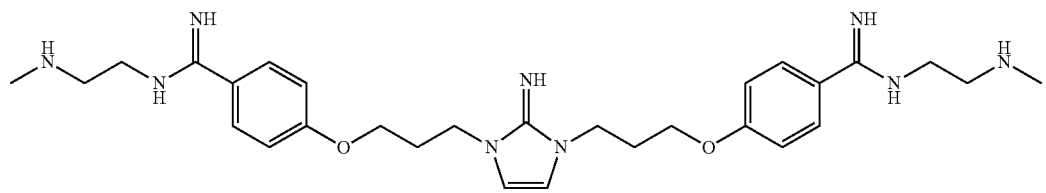
98 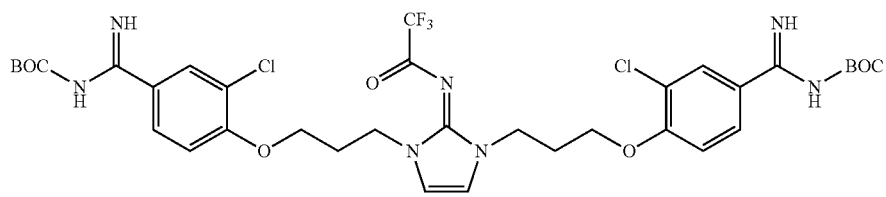 [SMILES: CC(C)(C)OC(=O)NC(=N)c1ccc(OCCCn2ccn(CCCOc3ccc(C(=N)NC(=O)OC(C)(C)C)cc3Cl)c2=NC(=O)C(F)(F)F)c(Cl)c1]
99 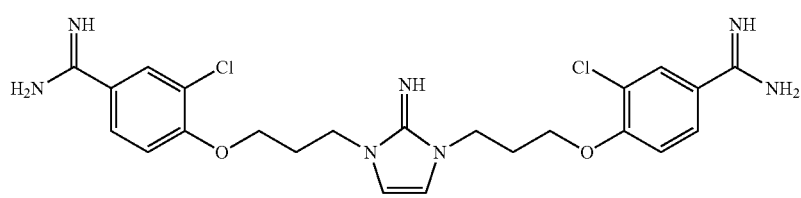 [SMILES: N=C(N)c1ccc(OCCCn2ccn(CCCOc3ccc(C(=N)N)cc3Cl)c2=N)c(Cl)c1]
100 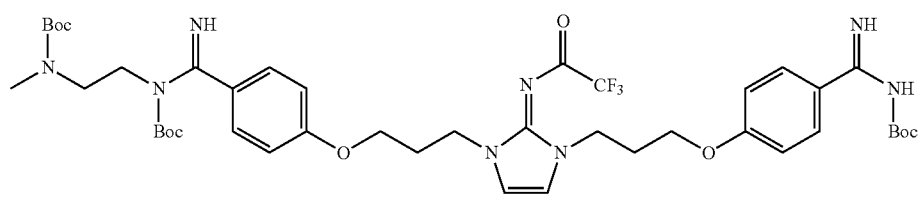 [SMILES: CN(CCN(C(=N)c1ccc(OCCCn2ccn(CCCOc3ccc(C(=N)NC(=O)OC(C)(C)C)cc3)/c2=N\C(=O)C(F)(F)F)cc1)C(=O)OC(C)(C)C)C(=O)OC(C)(C)C]

TABLE 76-continued

| Compound No. | Salt form | Physical property |
|---|---|---|
| 91 | hydrochloride | $^1$HNMR (CD$_3$OD): 1.50 (dt, 2H), 1.66 (dt, 2H), 1.88 (dt, 2H), 2.11 (dt, 2H), 3.11 (t, 2H), 3.17-3.24 (m, 2H), 3.40-3.47 (m, 2H), 4.18 (t, 2H), 7.12 (d, 2H), 7.80 (d, 2H), 8.56 (s, 1 H) |
| 92 | — | $^1$HNMR (CDCl$_3$): 1.52-1.58 (m, 20H), 1.74-1.86 (m, 4H), 3.88-3.98 (m, 4H), 4.24-4.37 (m, 4H), 6.73 (d, 1H), 6.82 (d, 2H), 6.87 (d, 2H), 6.98 (d, 1H), 7.75-7.83 (m, 4H) |
| 93 | hydrochloride | Melting point 183-187° C. |
| 94 | — | $^1$HNMR (CDCl$_3$): 1.41 (dt, 4H), 1.55 (s, 18H), 1.82 (dt, 8H), 2.99 (t, 4H), 3.87 (t, 4H), 6.70 (s, 2H), 8.20 (s, 2H) |
| 95 | hydrochloride | $^1$HNMR (CD$_3$OD): 1.48 (dt, 4H), 1.81 (dt, 4H), 1.91 (dt, 4H), 3.12 (t, 4H), 3.88 (t, 4H), 6.97 (s, 2H), 8.57 (s, 2H) |
| 96 | — | $^1$HNMR (CDCl$_3$): 1.34-1.48 (m, 36H), 2.24 (dt, 4H), 2.90 (s, 6H), 3.42-3.58 (m, 8H), 3.96 (1, 4H), 4.11 (t, 4H), 6.70 (s, 2H), 6.80-6.89 (m, 4H), 7.40 (d, 4H) |
| 97 | hydrochloride | $^1$HNMR (CD$_3$OD): 2.25 (dt, 4H), 2.91 (s, 6H), 3.46-3.54 (m, 8H), 3.92 (dd, 4H), 4.08 (dd, 4H), 6.95 (s, 2H), 6.84-6.92 (m, 4H), 7.82 (d, 4H) |
| 98 | — | $^1$HNMR (CD$_3$OD): 1.51 (s, 18H), 2.29 (tt, 4H), 4.08-4.17 (m, 8H), 7.07 (d, 2H), 7.20 (s, 2H), 7.75 (dd, 2H), 7.90 (d, 2H). |
| 99 | hydrochloride | Melting point 184-190° C. |
| 100 | — | $^1$HNMR (CDCl$_3$): 1.35-1.47 (m, 18H), 1.55 (s, 9H), 2.24 (dd, 4H), 2.90 (s, 3H), 3.44-3.58 (m, 4H), 3.91-3.99 (m, 4H), 4.08-4.17 (m, 4H), 6.69 (s, 2H), 6.78-6.87 (m, 4H), 7.38 (d, 2H), 7.82 (d, 2H) |

In the table, Boc or BOC indicates a t-butoxycarbonyl group. In the table, "-" means that a compound was synthesized as free form.

TABLE 77

| Compound No. | Structure |
|---|---|
| 101 | (structure: bis-amidine compound with imidazol-2-imine core linked via propoxy-phenyl groups; one end bears an N-(2-methylaminoethyl)amidine, the other a primary amidine) |
| 102 | (structure: BOC-protected bis-amidine with 2-fluorophenyl groups, linked via propoxy chains to an imidazole core bearing an N-trifluoroacetyl imine) |
| 103 | (structure: bis(2-fluoro-4-(3-aminoimidazolyl-propoxy)phenyl)amidine with imidazol-2-imine core) |

TABLE 77-continued
104 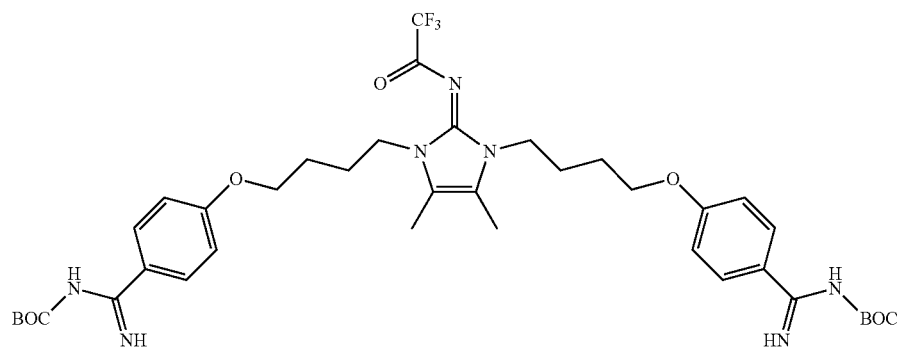 [SMILES: Cc1c(C)n(CCCCOc2ccc(C(=N)NC(=O)OC(C)(C)C)cc2)c(=NC(=O)C(F)(F)F)n1CCCCOc1ccc(C(=N)NC(=O)OC(C)(C)C)cc1]
105 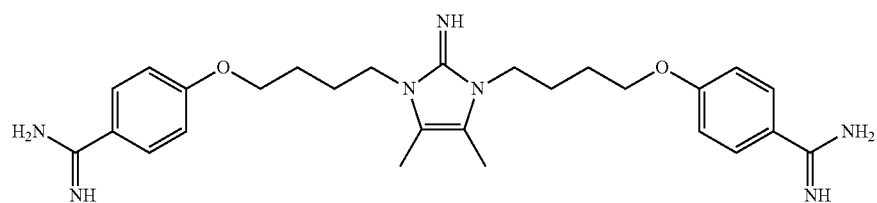 [SMILES: Cc1c(C)n(CCCCOc2ccc(C(=N)N)cc2)c(=N)n1CCCCOc1ccc(C(=N)N)cc1]
106 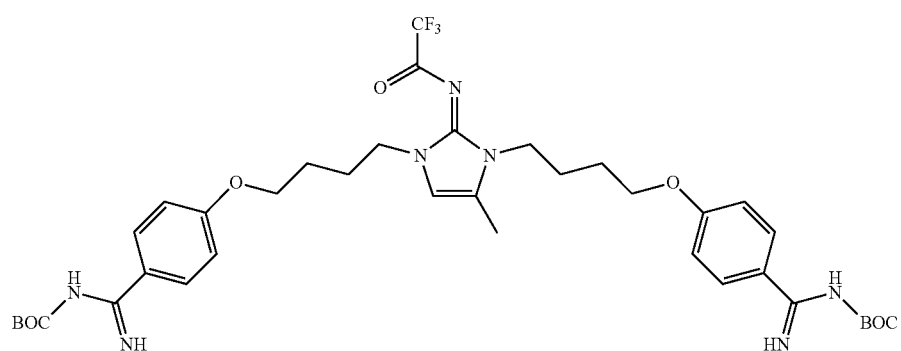 [SMILES: Cc1cn(CCCCOc2ccc(C(=N)NC(=O)OC(C)(C)C)cc2)/c(=N\C(=O)C(F)(F)F)n1CCCCOc1ccc(C(=N)NC(=O)OC(C)(C)C)cc1]
107 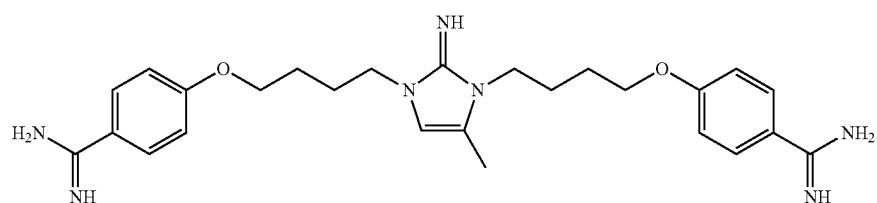 [SMILES: Cc1cn(CCCCOc2ccc(C(=N)N)cc2)c(=N)n1CCCCOc1ccc(C(=N)N)cc1]
108 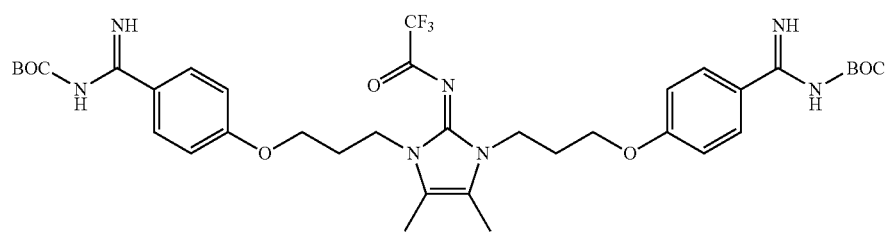 [SMILES: Cc1c(C)n(CCCOc2ccc(C(=N)NC(=O)OC(C)(C)C)cc2)c(=NC(=O)C(F)(F)F)n1CCCOc1ccc(C(=N)NC(=O)OC(C)(C)C)cc1]
109 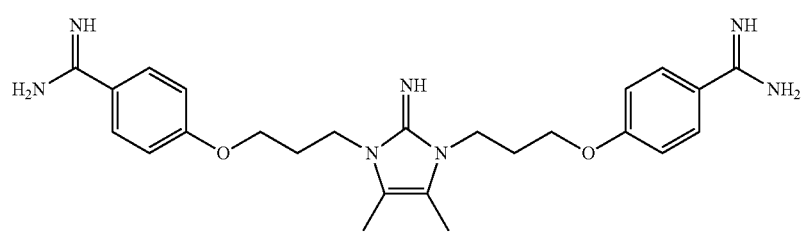 [SMILES: Cc1c(C)n(CCCOc2ccc(C(=N)N)cc2)c(=N)n1CCCOc1ccc(C(=N)N)cc1]

TABLE 77-continued

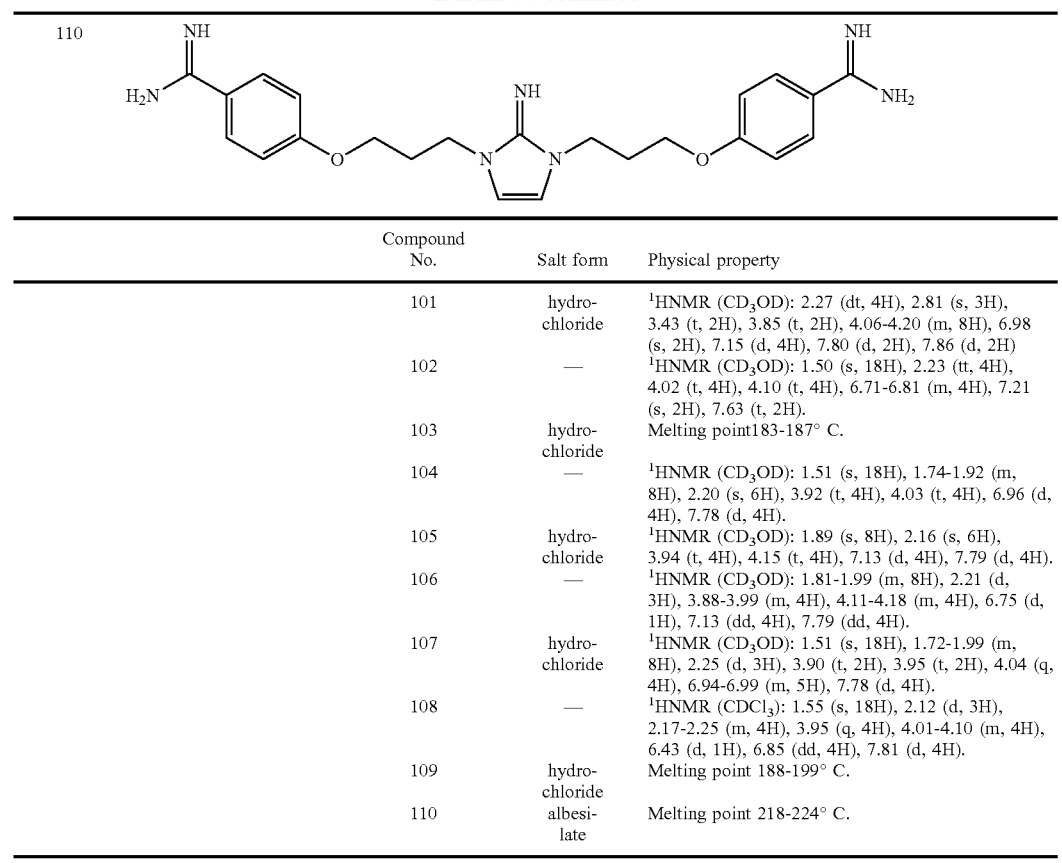

| Compound No. | Salt form | Physical property |
| --- | --- | --- |
| 101 | hydrochloride | ¹HNMR (CD$_3$OD): 2.27 (dt, 4H), 2.81 (s, 3H), 3.43 (t, 2H), 3.85 (t, 2H), 4.06-4.20 (m, 8H), 6.98 (s, 2H), 7.15 (d, 4H), 7.80 (d, 2H), 7.86 (d, 2H) |
| 102 | — | ¹HNMR (CD$_3$OD): 1.50 (s, 18H), 2.23 (tt, 4H), 4.02 (t, 4H), 4.10 (t, 4H), 6.71-6.81 (m, 4H), 7.21 (s, 2H), 7.63 (t, 2H). |
| 103 | hydrochloride | Melting point183-187° C. |
| 104 | — | ¹HNMR (CD$_3$OD): 1.51 (s, 18H), 1.74-1.92 (m, 8H), 2.20 (s, 6H), 3.92 (t, 4H), 4.03 (t, 4H), 6.96 (d, 4H), 7.78 (d, 4H). |
| 105 | hydrochloride | ¹HNMR (CD$_3$OD): 1.89 (s, 8H), 2.16 (s, 6H), 3.94 (t, 4H), 4.15 (t, 4H), 7.13 (d, 4H), 7.79 (d, 4H). |
| 106 | — | ¹HNMR (CD$_3$OD): 1.81-1.99 (m, 8H), 2.21 (d, 3H), 3.88-3.99 (m, 4H), 4.11-4.18 (m, 4H), 6.75 (d, 1H), 7.13 (dd, 4H), 7.79 (dd, 4H). |
| 107 | hydrochloride | ¹HNMR (CD$_3$OD): 1.51 (s, 18H), 1.72-1.99 (m, 8H), 2.25 (d, 3H), 3.90 (t, 2H), 3.95 (t, 2H), 4.04 (q, 4H), 6.94-6.99 (m, 5H), 7.78 (d, 4H). |
| 108 | — | ¹HNMR (CDCl$_3$): 1.55 (s, 18H), 2.12 (d, 3H), 2.17-2.25 (m, 4H), 3.95 (q, 4H), 4.01-4.10 (m, 4H), 6.43 (d, 1H), 6.85 (dd, 4H), 7.81 (d, 4H). |
| 109 | hydrochloride | Melting point 188-199° C. |
| 110 | albesilate | Melting point 218-224° C. |

In the table, Boc or BOC indicates a t-butoxycarbonyl group. In the table, "-" means that a compound was synthesized as free form.

TABLE 78

| Compound No. | Structure |
| --- | --- |

TABLE 78-continued
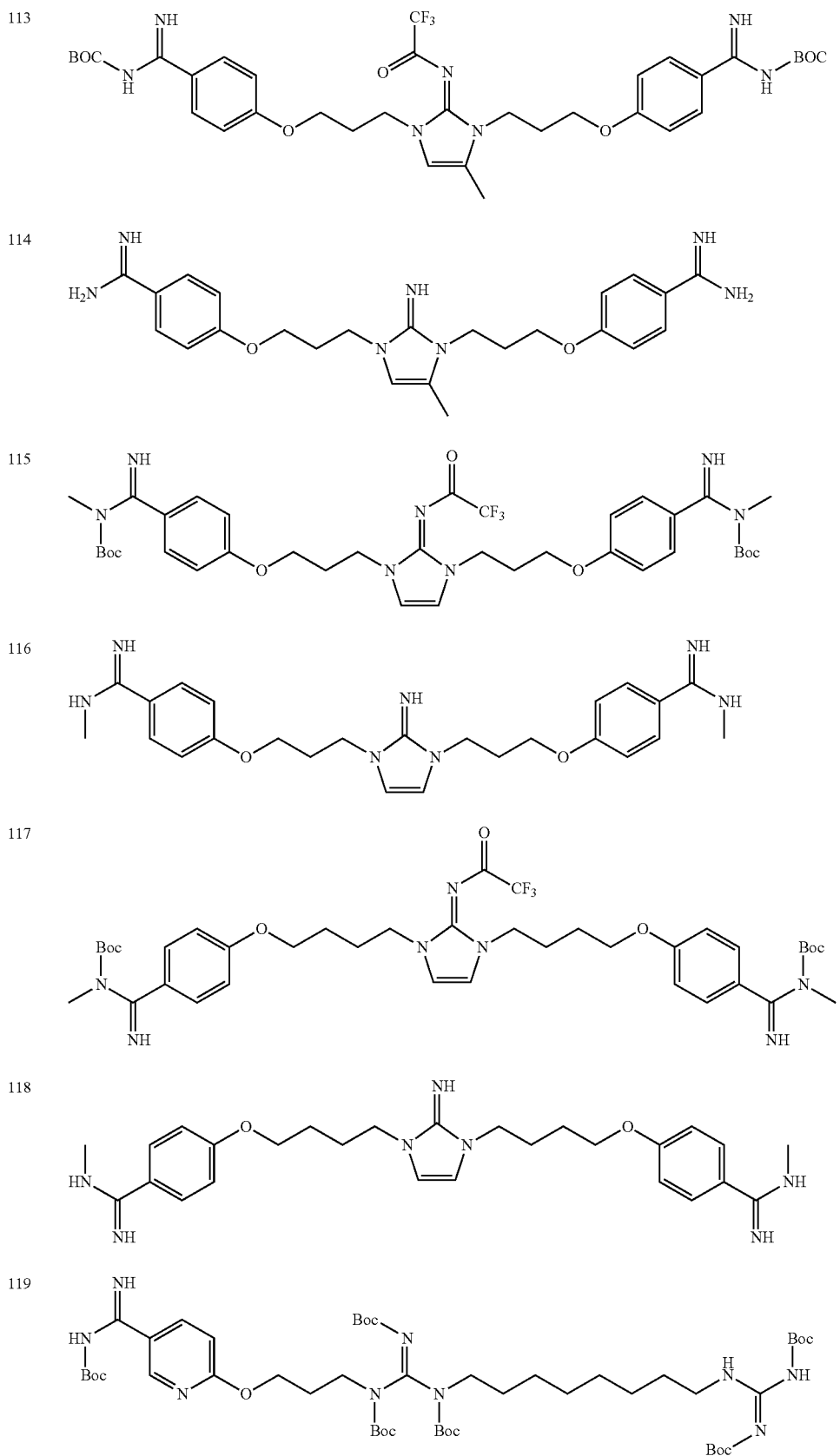

TABLE 78-continued

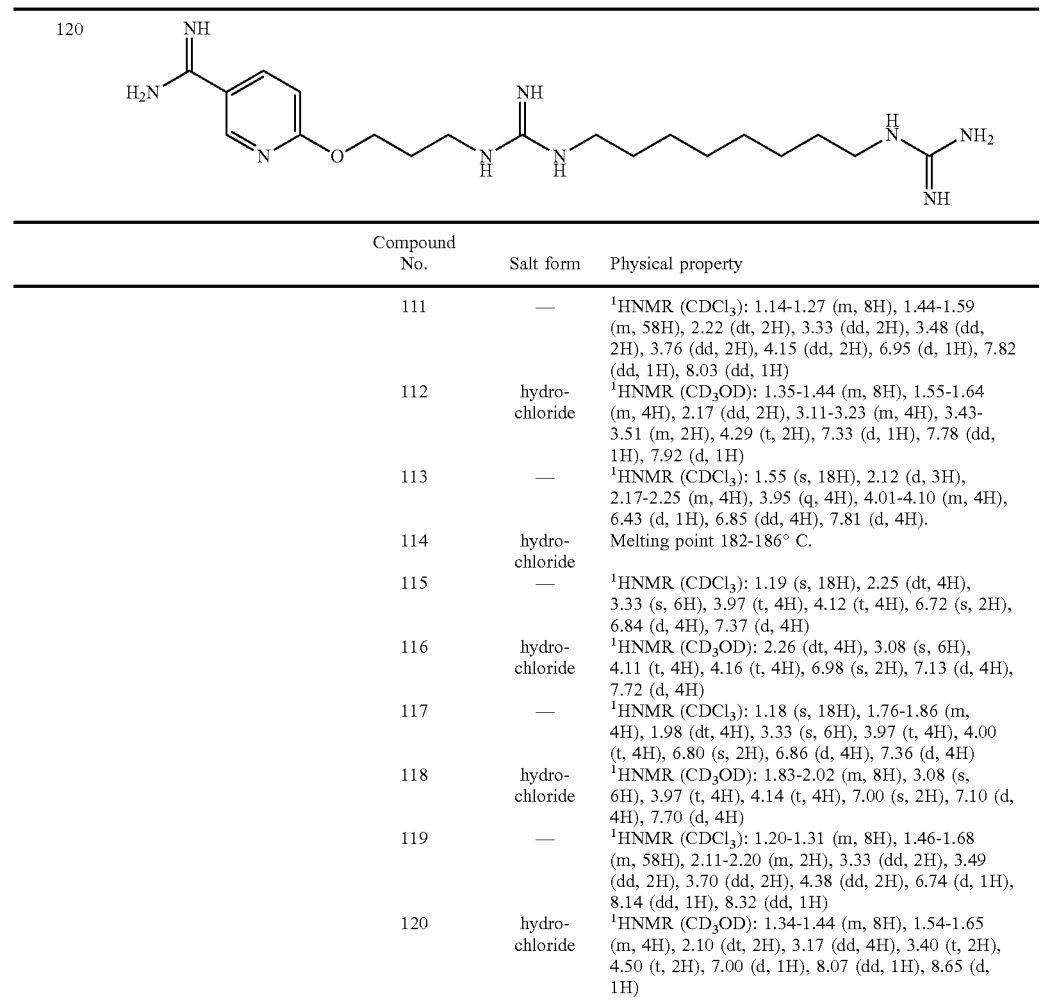

| Compound No. | Salt form | Physical property |
| --- | --- | --- |
| 111 | — | ¹HNMR (CDCl₃): 1.14-1.27 (m, 8H), 1.44-1.59 (m, 58H), 2.22 (dt, 2H), 3.33 (dd, 2H), 3.48 (dd, 2H), 3.76 (dd, 2H), 4.15 (dd, 2H), 6.95 (d, 1H), 7.82 (dd, 1H), 8.03 (dd, 1H) |
| 112 | hydrochloride | ¹HNMR (CD₃OD): 1.35-1.44 (m, 8H), 1.55-1.64 (m, 4H), 2.17 (dd, 2H), 3.11-3.23 (m, 4H), 3.43-3.51 (m, 2H), 4.29 (t, 2H), 7.33 (d, 1H), 7.78 (dd, 1H), 7.92 (d, 1H) |
| 113 | — | ¹HNMR (CDCl₃): 1.55 (s, 18H), 2.12 (d, 3H), 2.17-2.25 (m, 4H), 3.95 (q, 4H), 4.01-4.10 (m, 4H), 6.43 (d, 1H), 6.85 (dd, 4H), 7.81 (d, 4H). |
| 114 | hydrochloride | Melting point 182-186° C. |
| 115 | — | ¹HNMR (CDCl₃): 1.19 (s, 18H), 2.25 (dt, 4H), 3.33 (s, 6H), 3.97 (t, 4H), 4.12 (t, 4H), 6.72 (s, 2H), 6.84 (d, 4H), 7.37 (d, 4H) |
| 116 | hydrochloride | ¹HNMR (CD₃OD): 2.26 (dt, 4H), 3.08 (s, 6H), 4.11 (t, 4H), 4.16 (t, 4H), 6.98 (s, 2H), 7.13 (d, 4H), 7.72 (d, 4H) |
| 117 | — | ¹HNMR (CDCl₃): 1.18 (s, 18H), 1.76-1.86 (m, 4H), 1.98 (dt, 4H), 3.33 (s, 6H), 3.97 (t, 4H), 4.00 (t, 4H), 6.80 (s, 2H), 6.86 (d, 4H), 7.36 (d, 4H) |
| 118 | hydrochloride | ¹HNMR (CD₃OD): 1.83-2.02 (m, 8H), 3.08 (s, 6H), 3.97 (t, 4H), 4.14 (t, 4H), 7.00 (s, 2H), 7.10 (d, 4H), 7.70 (d, 4H) |
| 119 | — | ¹HNMR (CDCl₃): 1.20-1.31 (m, 8H), 1.46-1.68 (m, 58H), 2.11-2.20 (m, 2H), 3.33 (dd, 2H), 3.49 (dd, 2H), 3.70 (dd, 2H), 4.38 (dd, 2H), 6.74 (d, 1H), 8.14 (dd, 1H), 8.32 (dd, 1H) |
| 120 | hydrochloride | ¹HNMR (CD₃OD): 1.34-1.44 (m, 8H), 1.54-1.65 (m, 4H), 2.10 (dt, 2H), 3.17 (dd, 4H), 3.40 (t, 2H), 4.50 (t, 2H), 7.00 (d, 1H), 8.07 (dd, 1H), 8.65 (d, 1H) |

In the table, Boc or BOC indicates a t-butoxycarbonyl group. In the table, "-" means that a compound was synthesized as free form.

TABLE 79

| Compound No. | Structure |
| --- | --- |
| 121 | 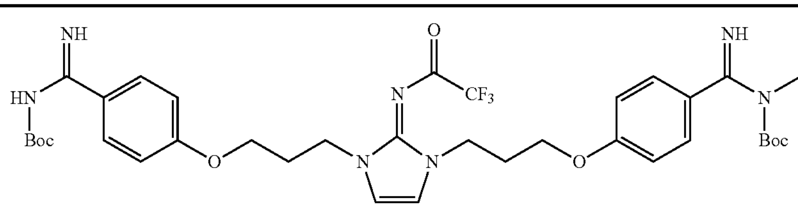 |
| 122 | 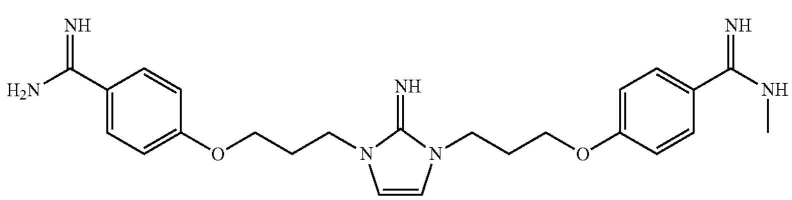 [SMILES: CNC(=N)c1ccc(OCCCn2ccn(CCCOc3ccc(C(=N)N)cc3)c2=N)cc1] |

TABLE 79-continued
| 123 | 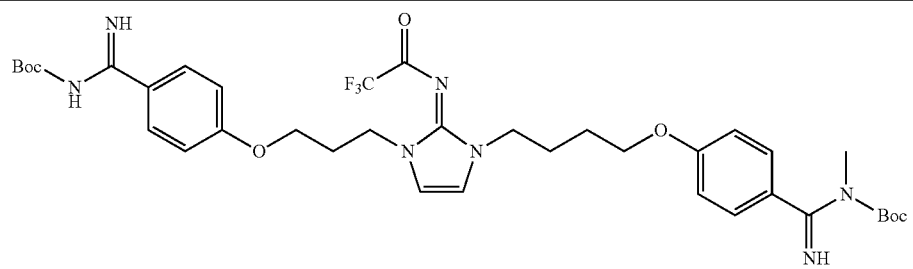 |
| --- | --- |
| 124 | 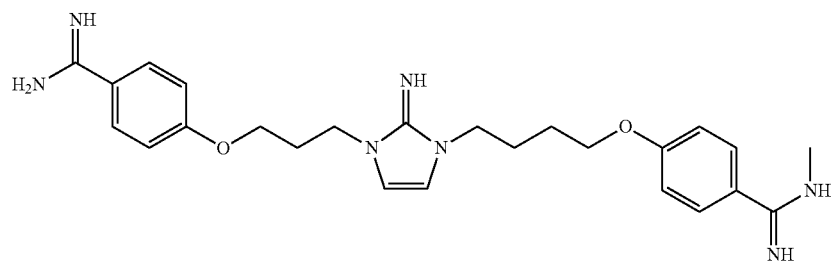 [SMILES: CNC(=N)c1ccc(OCCCCn2ccn(CCCOc3ccc(C(=N)N)cc3)c2=N)cc1] |
| 125 | 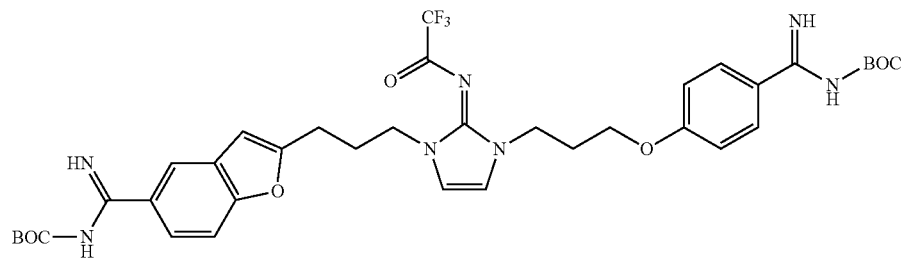 [SMILES: CC(C)(C)OC(=O)NC(=N)c1ccc(OCCCn2ccn(CCCc3cc4cc(C(=N)NC(=O)OC(C)(C)C)ccc4o3)/c2=N\C(=O)C(F)(F)F)cc1] |
| 126 | 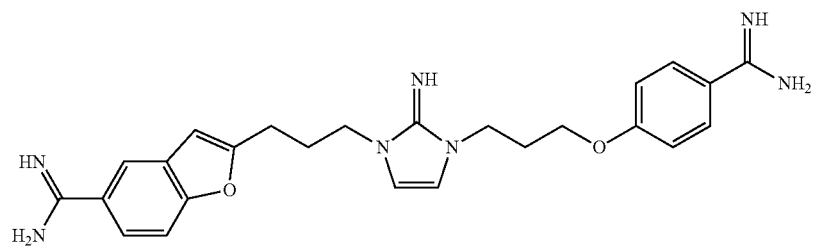 [SMILES: N=C(N)c1ccc(OCCCn2ccn(CCCc3cc4cc(C(=N)N)ccc4o3)c2=N)cc1] |
| 127 | 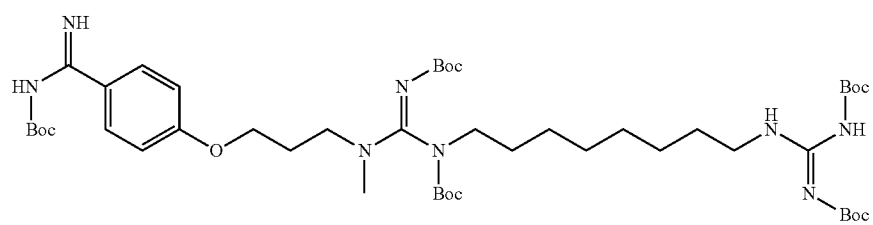 [SMILES: CN(CCCOc1ccc(C(=N)NC(=O)OC(C)(C)C)cc1)/C(=N/C(=O)OC(C)(C)C)N(CCCCCCCCN/C(=N/C(=O)OC(C)(C)C)NC(=O)OC(C)(C)C)C(=O)OC(C)(C)C] |
| 128 | 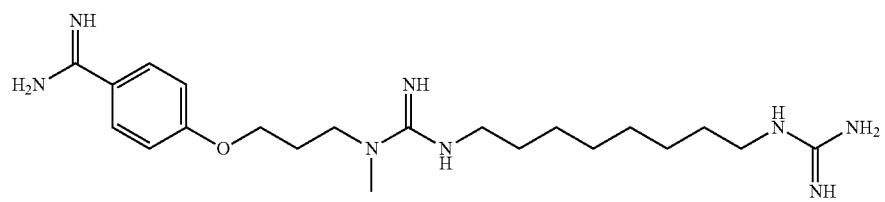 [SMILES: CN(CCCOc1ccc(C(=N)N)cc1)C(=N)NCCCCCCCCNC(=N)N] |
| 129 | 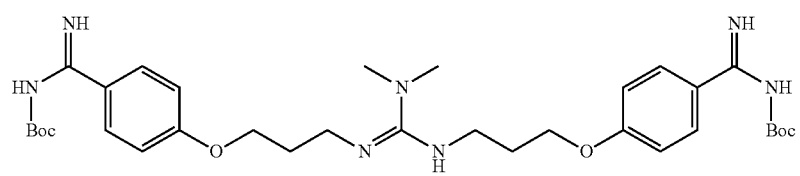 [SMILES: CN(C)/C(=N\CCCOc1ccc(C(=N)NC(=O)OC(C)(C)C)cc1)NCCCOc1ccc(C(=N)NC(=O)OC(C)(C)C)cc1] |

TABLE 79-continued

130

| Compound No. | Salt form | Physical property |
|---|---|---|
| 121 | — | ¹HNMR (CDCl₃): 1.19 (s, 9H), 1.55 (s, 9H), 2.19-2.28 (m, 4H), 3.33 (s, 3H), 3.97 (dd, 4H), 4.12 (t, 4H), 6.70 (dd, 2H), 6.82-6.91 (m, 4H), 7.37 (d, 2H), 7.82 (d, 2H) |
| 122 | hydro-chloride | ¹HNMR (CD₃OD): 2.23-2.32 (m, 4H), 3.08 (s, 3H), 4.08-4.20 (m, 8H), 6.98 (s, 2H), 7.11-7.18 (m, 4H), 7.72 (d, 2H), 7.80 (d, 2H) |
| 123 | — | ¹HNMR (CDCl₃): 1.18 (s, 9H), 1.55 (s, 9H), 1.80-1.85 (m, 2H), 1.97 (dt, 2H), 2.25 (dt, 2H), 3.33 (s, 3H), 3.93-4.02 (m, 6H), 4.12 (t, 2H), 6.75 (d, 2H), 6.85 (d, 2H), 6.89 (d, 2H), 7.36 (d, 2H), 7.81 (d, 2H) |
| 124 | hydro-chloride | ¹HNMR (CDOD): 1.84-2.00 (m, 4H), 2.28 (dt, 2H), 3.07 (s, 3H), 3.96 (t, 2H), 4.12 (t, 4H), 4.17 (t, 2H), 7.00 (d, 2H), 7.11 (d, 2H), 7.15 (d, 2H), 7.70 (d, 2H), 7.80 (d, 2H) |
| 125 | — | ¹HNMR (CDCl₃): 1.55 (s, 9H), 1.56 (s, 9H), 2.17-2.27 (m, 4H), 2.81 (t, 2H), 3.93-3.99 (m, 4H), 4.10 (t, 2H), 6.45 (s, 1H), 6.70 (dd, 2H), 6.86 (d, 2H), 7.40 (d, 1H), 7.73 (dd, 1H), 7.81 (d, 2H), 8.02 (d, 1H). |
| 126 | hydro-chloride | Melting point 227-236° C. |
| 127 | — | ¹HNMR (CDCl₃): 1.19-1.32 (m, 8H), 1.42-1.54 (m, 47H), 1.57-1.64 (m, 2H), 2.02 (dt, 2H), 3.01 (s, 3H), 3.42 (dd, 2H), 3.50 (dd, 2H), 3.63 (t, 2H), 4.11 (t, 2H), 6.86 (d, 2H), 7.42 (d, 2H) |
| 128 | hydro-chloride | ¹HNMR (CD₃OD): 1.18-1.33 (m, 8H), 1.36-1.47 (m, 2H), 1.55-1.62 (m, 2H), 2.00-2.06 (m, 2H), 3.02 (s, 3H), 3.39 (dd, 2H), 3.44-3.52 (m, 2H), 3.61 (t, 2H), 4.02 (t, 2H), 6.82 (d, 2H), 7.39 (d, 2H) |
| 129 | — | ¹HNMR (CDCl₃): 1.55 (s, 18H), 2.03-2.09 (m, 4H), 2.83 (s, 6H), 3.34 (t, 4H), 4.00 (t, 4H), 5.77 (d, 4H), 7.73 (d, 4H) |
| 1.30 | hydro-chloride | ¹HNMR (CD₃OD): 2.01-2.12 (m, 4H), 2.81 (s, 6H), 3.30 (t, 4H), 4.05 (t, 4H), 6.80 (d, 4H), 7.75 (d, 4H) |

In the table, Boc or BOC indicates a t-butoxycarbonyl group. In the table, "-" means that a compound was synthesized as free form.

TABLE 80

| Compound No. | Structure |
|---|---|
| 131 | 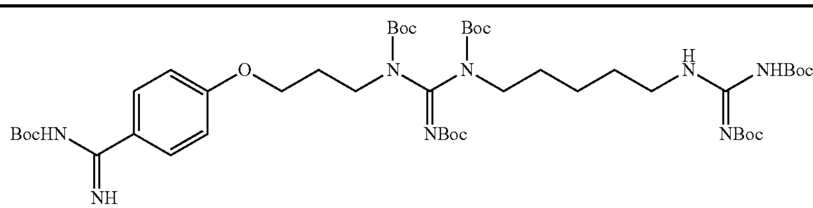 |
| 132 | 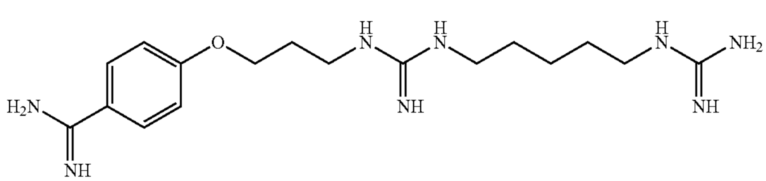 [SMILES: N=C(N)NCCCCCNC(=N)NCCCOc1ccc(C(=N)N)cc1] |

TABLE 80-continued
133 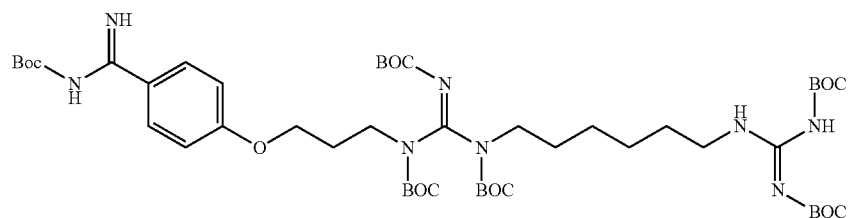 [SMILES: CC(C)(C)OC(=O)/N=C(/NCCCCCCN(C(=O)OC(C)(C)C)/C(=N/C(=O)OC(C)(C)C)N(CCCOc1ccc(C(=N)NC(=O)OC(C)(C)C)cc1)C(=O)OC(C)(C)C)NC(=O)OC(C)(C)C]
134 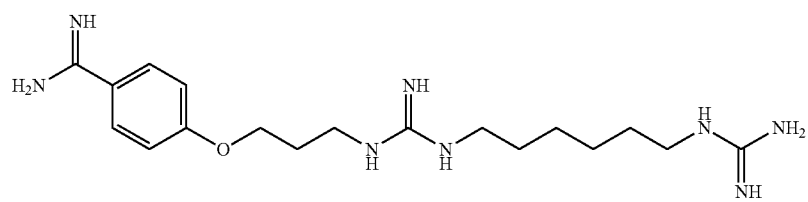 [SMILES: N=C(N)NCCCCCCNC(=N)NCCCOc1ccc(C(=N)N)cc1]
135 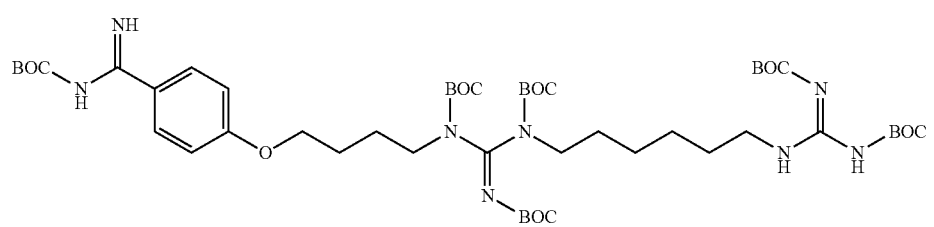 [SMILES: CC(C)(C)OC(=O)/N=C(\NCCCCCCN(C(=O)OC(C)(C)C)/C(=N\C(=O)OC(C)(C)C)N(CCCCOc1ccc(C(=N)NC(=O)OC(C)(C)C)cc1)C(=O)OC(C)(C)C)NC(=O)OC(C)(C)C]
136 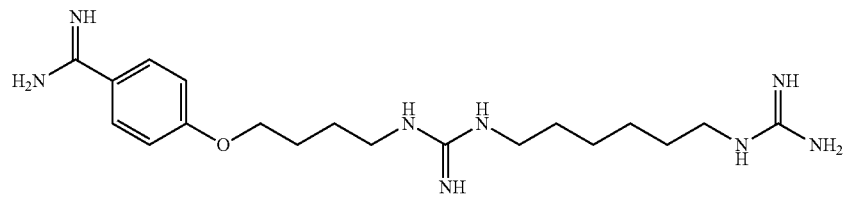 [SMILES: N=C(N)NCCCCCCNC(=N)NCCCCOc1ccc(C(=N)N)cc1]
137 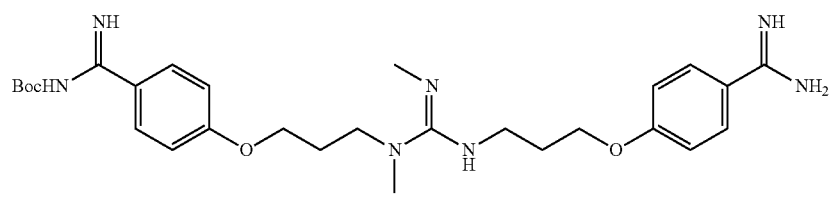 [SMILES: C/N=C(/NCCCOc1ccc(C(=N)N)cc1)N(C)CCCOc1ccc(C(=N)NC(=O)OC(C)(C)C)cc1]
138 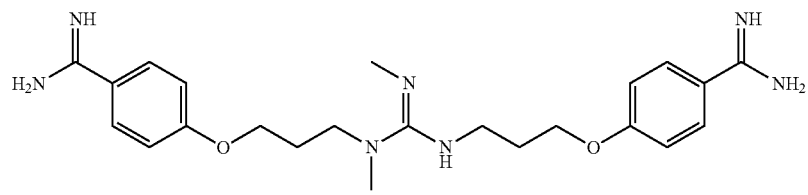 [SMILES: C/N=C(/NCCCOc1ccc(C(=N)N)cc1)N(C)CCCOc1ccc(C(=N)N)cc1]
139 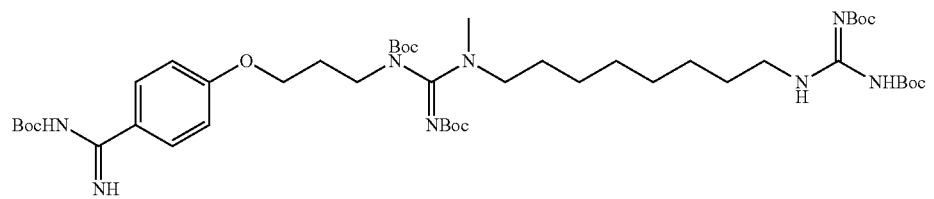

TABLE 80-continued

140 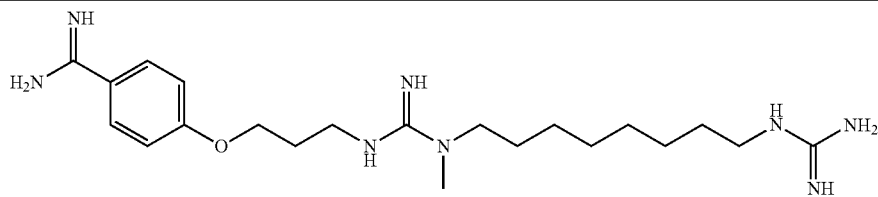

| Compound No. | Salt form | Physical property |
|---|---|---|
| 131 | — | ¹HNMR (CDCl₃): 1.40-1.61 (m, 60H), 2.15 (tt, 2H), 3.27 (q, 2H), 3.44 (dd, 2H), 3.71 (t, 2H), 4.10 (t, 2H), 6.90 (d, 2H), 7.90 (d, 2H). |
| 132 | hydro-chloride | ¹HNMR (CD₃OD): 1.41-1.50 (m, 2H), 1.58-1.68 (m, 4H), 2.12 (tt, 2H), 3.16-3.25 (m, 4H), 3.44 (t, 2H), 4.20 (t, 2H), 7.17 (d, 2H), 7.81 (d, 2H). |
| 133 | — | ¹HNMR (CDCl₃): 1.19-1.27 (m, 4H), 1.40-1.63 (m, 58H), 2.16 (tt, 2H), 3.31 (q, 2H), 3.45 (dd, 2H), 3.73 (t, 2H), 4.08 (t, 2H), 6.90 (d, 2H), 7.88 (d, 2H). |
| 134 | hydro-chloride | ¹HNMR (CD₃OD): 1.35-1.48 (m, 4H), 1.54-1.68 (m, 4H), 2.12 (tt, 2H), 3.19 (q, 4H), 3.44 (t, 2H), 4.20 (t, 2H), 7.17 (d, 2H), 7.81 (d, 2H). |
| 135 | — | ¹HNMR (CDCl₃): 1.24-1.68 (m, 62H), 1.75-1.91 (m, 4H), 3.32 (q, 2H), 3.44-3.52 (m, 2H), 3.59 (t, 2H), 4.00 (t, 2H), 6.88 (d, 2H), 7.85 (d, 2H). |
| 136 | hydro-chloride | ¹HNMR (CD₃OD): 1.39-1.50 (m, 4H), 1.56-1.67 (m, 4H), 1.74-1.85 (m, 2H), 1.85-1.95 (m, 2H), 3.20 (q, 4H), 3.29 (t, 2H), 4.14 (t, 2H), 7.13 (d, 2H), 7.79 (d, 2H). |
| 137 | — | ¹HNMR (CDCl₃): 1.55 (s, 9H), 1.96-2.06 (m, 4H), 2.94 (s, 3H), 2.97 (s, 3H), 3.56 (dd, 2H), 3.62 (dd, 2H), 3.95 (dt, 2H), 4.05 (t, 2H), 6.79-6.89 (m, 4H), 7.46 (d, 2H), 7.78 (d, 2H) |
| 138 | hydro-chloride | ¹HNMR (CD₃OD): 2.15-2.29 (m, 4H), 2.56 (s, 3H), 3.08 (s, 3H), 3.89 (dd, 2H), 4.05 (dd, 2H), 4.19 (dd, 4H), 7.11-7.19 (m, 4H), 7.72 (d, 2H), 7.82 (d, 2H) |
| 139 | — | ¹HNMR (CDCl₃): 1.11-1.31 (m, 8H), 1.46-1.59 (m, 51H), 2.04-2.16 (m, 2H), 2.93-3.03 (m, 3H), 3.72-3.89 (m, 4H), 4.01 (t, 2H), 6.88 (d, 2H), 7.84-7.94 (m, 2H) |
| 140 | hydro-chloride | ¹HNMR (CD₃OD): 1.31-1.48 (m, 10H), 1.54-1.69 (m, 4H), 2.10-2.22 (m, 2H), 3.00-3.09 (m, 3H), 3.14-3.22 (m, 2H), 3.45-3.55 (m, 2H), 4.14-4.27 (m, 2H), 7.13-7.22 (m, 2H), 7.76-7.86 (m, 2H) |

In the table, Boc or BOC indicates a t-butoxycarbonyl group. In the table, "-" means that a compound was synthesized as free form.

TABLE 81

| Compound No. | Structure |
|---|---|
| 141 | 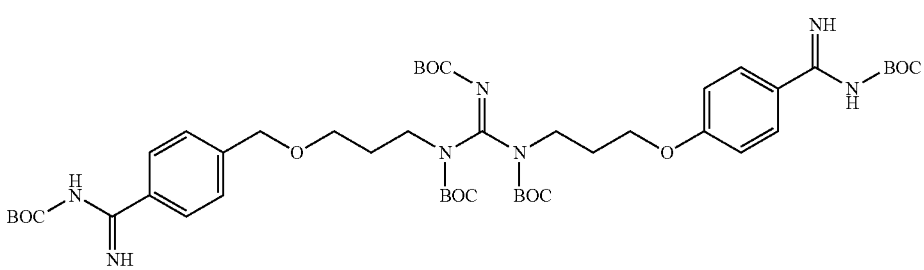 [SMILES: CC(C)(C)OC(=O)/N=C(\N(CCCOCc1ccc(C(=N)NC(=O)OC(C)(C)C)cc1)C(=O)OC(C)(C)C)N(CCCOc1ccc(C(=N)NC(=O)OC(C)(C)C)cc1)C(=O)OC(C)(C)C] |

TABLE 81-continued
142
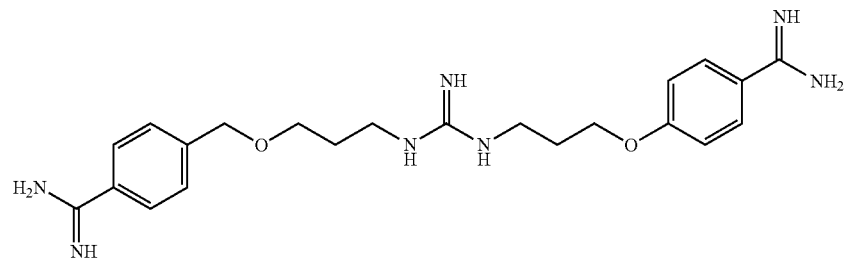 [SMILES: N=C(NCCCOCc1ccc(C(=N)N)cc1)NCCCOc1ccc(C(=N)N)cc1]
143
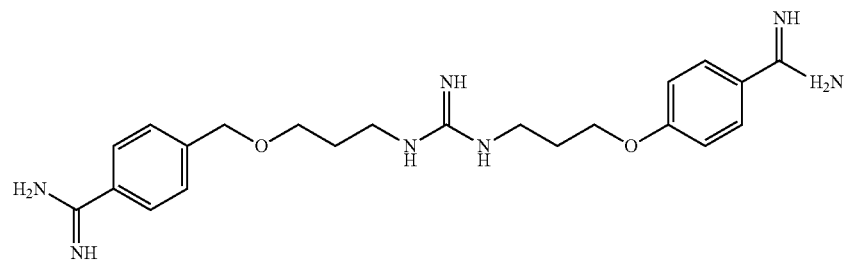 [SMILES: N=C(NCCCOCc1ccc(C(=N)N)cc1)NCCCOc1ccc(C(=N)N)cc1]
144
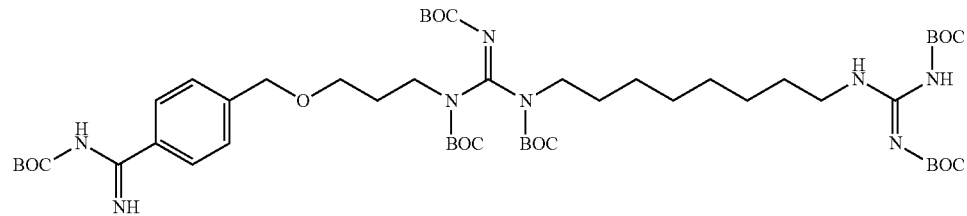 [SMILES: CC(C)(C)OC(=O)/N=C(/NCCCCCCCCN(C(=O)OC(C)(C)C)/C(=N/C(=O)OC(C)(C)C)N(CCCOCc1ccc(C(=N)NC(=O)OC(C)(C)C)cc1)C(=O)OC(C)(C)C)NC(=O)OC(C)(C)C]
145
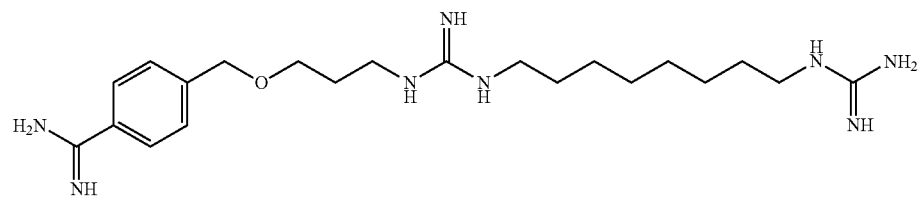 [SMILES: N=C(N)NCCCCCCCCNC(=N)NCCCOCc1ccc(C(=N)N)cc1]
146
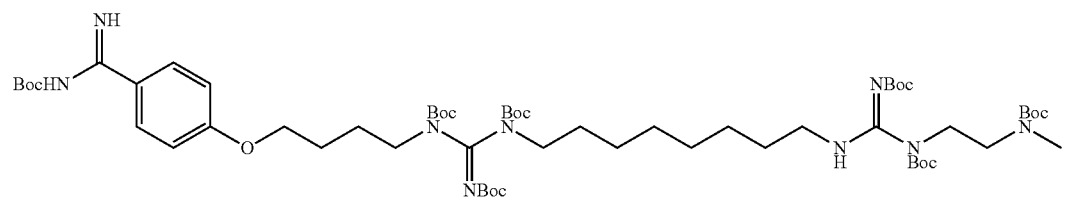
147
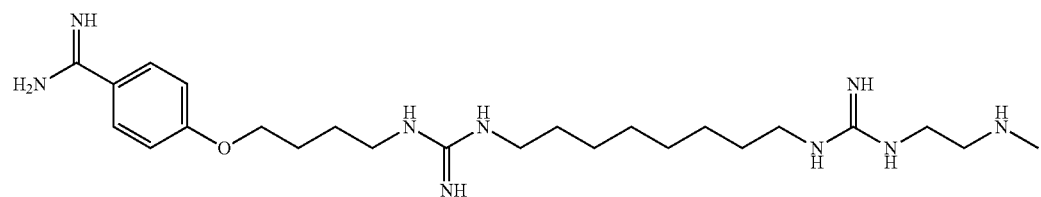 [SMILES: CNCCNC(=N)NCCCCCCCCNC(=N)NCCCCOc1ccc(C(=N)N)cc1]

TABLE 81-continued

148 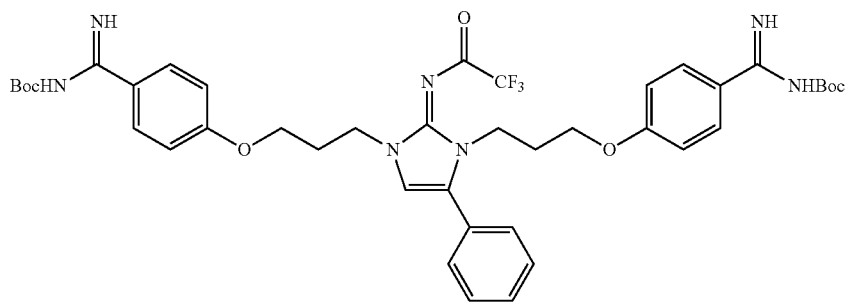 [SMILES: CC(C)(C)OC(=O)NC(=N)c1ccc(OCCCn2cc(-c3ccccc3)n(CCCOc3ccc(C(=N)NC(=O)OC(C)(C)C)cc3)/c2=N\C(=O)C(F)(F)F)cc1]

149 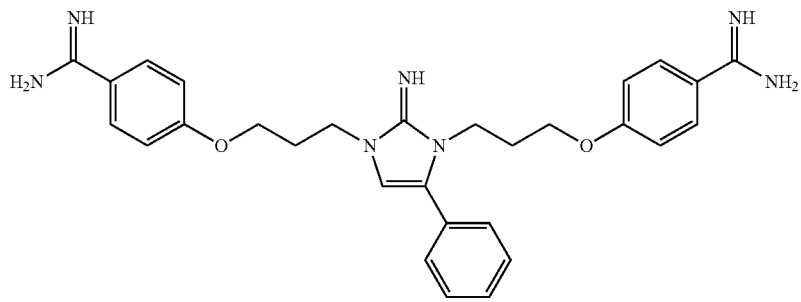 [SMILES: N=C(N)c1ccc(OCCCn2cc(-c3ccccc3)n(CCCOc3ccc(C(=N)N)cc3)c2=N)cc1]

150 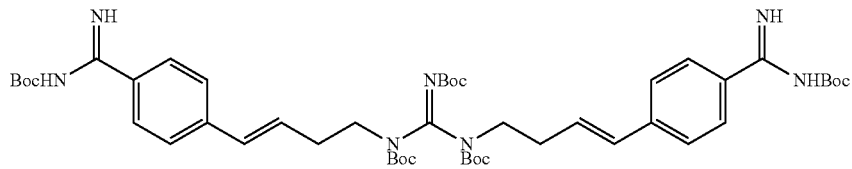

| Compound No. | Salt form | Physical property |
|---|---|---|
| 141 | — | ¹HNMR (CDCl₃): 1.46 (s, 9H), 1.47 (s, 9H), 1.49 (s, 9H), 1.55 (s, 9H), 1.56 (s, 9H), 1.96 (tt, 2H), 2.13 (tt, 2H), 3.49 (t, 2H), 3.63 (t, 2H), 3.72 (t, 2H), 4.02 (t, 2H), 4.49 (s, 2H), 6.82 (d, 2H), 7.32 (d, 2H), 7.71-7.81 (m, 4H). |
| 142 | hydrochloride | ¹HNMR (CD₃OD): 1.92 (tt, 2H), 2.11 (tt, 2H), 3.35 (t, 2H), 3.42 (t, 2H), 3.64 (t, 2H), 4.19 (t, 2H), 4.65 (s, 2H), 7.16 (d, 2H), 7.60 (d, 2H), 7.80 (d, 4H). |
| 143 | trifluoroacetate | Melting point 192-197° C. |
| 144 | — | ¹HNMR (CDCl₃): 1.20-1.35 (m, 8H), 1.43-1.65 (m, 58H), 1.94-2.04 (m, 2H), 3.36 (q, 2H), 3.48 (t, 2H), 3.53 (t, 2H), 3.65 (t, 2H), 4.53 (s, 2H), 7.38 (d, 2H), 7.85 (d, 2H). |
| 145 | hydrochloride | ¹HNMR (CD₃OD): 1.33-1.45 (m, 8H), 1.53-1.63 (m, 4H), 1.92 (tt, 2H), 3.16 (t, 4H), 3.34 (t, 2H), 3.64 (t, 2H), 4.65 (s, 2H), 7.60 (d, 2H), 7.80 (d, 2H). |
| 146 | — | ¹HNMR (CDCl₃): 1.23-1.33 (m, 10H), 1.43-1.51 (m, 63H), 1.75-1.86 (m, 4H), 2.87 (s, 3H), 3.10-3.26 (m, 2H), 3.37 (dd, 2H), 3.49 (dd, 2H), 3.59 (dd, 2H), 3.65-3.82 (m, 2H), 4.00 (dd, 2H), 4.12 (dd, 2H), 6.87 (d, 2H), 7.83 (d, 2H) |
| 147 | hydrochloride | ¹HNMR (CD₃OD): 1.36-1.45 (m, 8H), 1.55-1.66 (m, 4H), 1.70-1.77 (m, 2H), 1.80-1.89 (m, 2H), 3.75 (s, 3H), 3.15-3.26 (m, 8H), 3.60 (dd, 2H), 4.14 (dt, 2H), 7.15 (d, 2H), 7.80 (d, 2H) |
| 148 | — | ¹HNMR (CDCl₃): 1.54 (s, 18H), 2.06 (tt, 2H), 2.29 (tt, 2H), 3.78 (t, 2H), 3.99 (t, 2H), 4.09-4.21 (m, 4H), 6.63 (d, 2H), 6.68 (s, 1H), 6.83 (d, 2H), 7.20 (dd, 2H), 7.33-7.46 (m, 3H), 7.76 (d, 2H), 7.81 (d, 2H). |

TABLE 81-continued

| | 149 | hydro-chloride | $^1$HNMR (CD$_3$OD): 2.06 (tt, 2H), 2.34 (tt, 2H), 3.93 (t, 2H), 4.15-4.26 (m, 6H), 6.89 (d, 2H), 7.05 (s, 1H), 7.16 (d, 2H), 7.34-7.42 (m, 5H), 7.75 (d, 2H), 7.81 (d, 2H). |
| | 150 | — | $^1$HNMR (CDCl$_3$): 1.47 (s, 18H), 1.54-1.57 (m, 27H), 2.55 (dd, 4H), 3.66 (dd, 4H), 6.19 (dt, 2H), 6.35 (d, 2H), 7.23 (d, 2H), 7.71 (d, 2H) |

In the table, Boc or BOC indicates a t-butoxycarbonyl group. In the table, "-" means that a compound was synthesized as free form.

TABLE 82

| Compound No. | Structure |
| --- | --- |
| 151 | 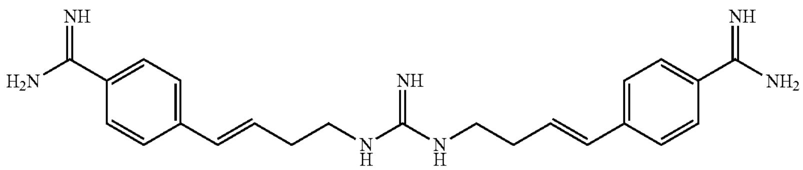 [SMILES: N=C(NCC/C=C/c1ccc(C(=N)N)cc1)NCC/C=C/c1ccc(C(=N)N)cc1] |
| 152 | 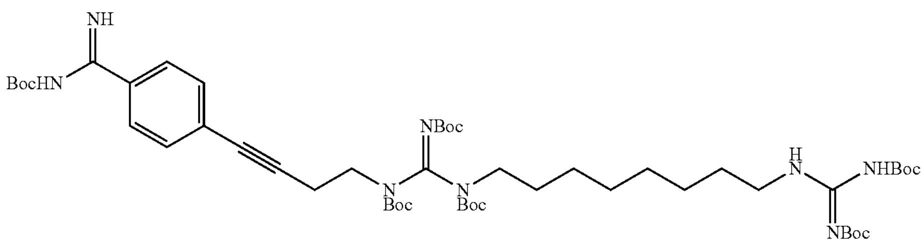 |
| 153 | 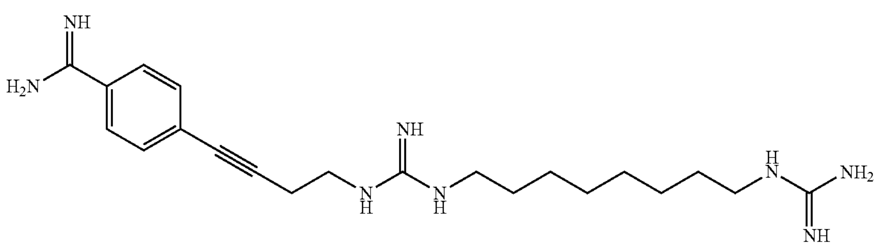 [SMILES: N=C(N)NCCCCCCCCNC(=N)NCCC#Cc1ccc(C(=N)N)cc1] |
| 154 | 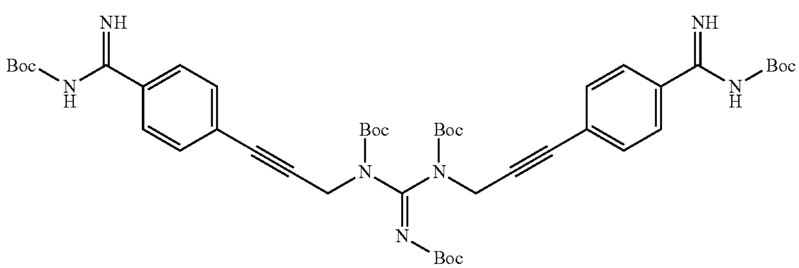 [SMILES: CC(C)(C)OC(=O)N=C(N(CC#Cc1ccc(C(=N)NC(=O)OC(C)(C)C)cc1)C(=O)OC(C)(C)C)N(CC#Cc1ccc(C(=N)NC(=O)OC(C)(C)C)cc1)C(=O)OC(C)(C)C] |
| 155 | 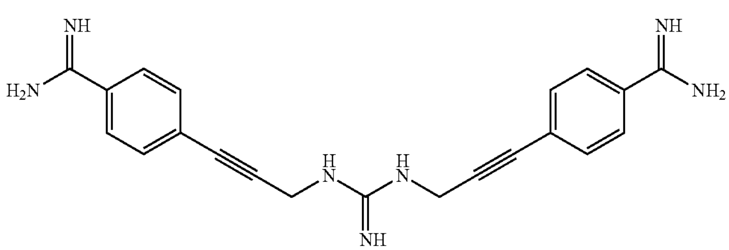 [SMILES: N=C(NCC#Cc1ccc(C(=N)N)cc1)NCC#Cc1ccc(C(=N)N)cc1] |

TABLE 82-continued
156 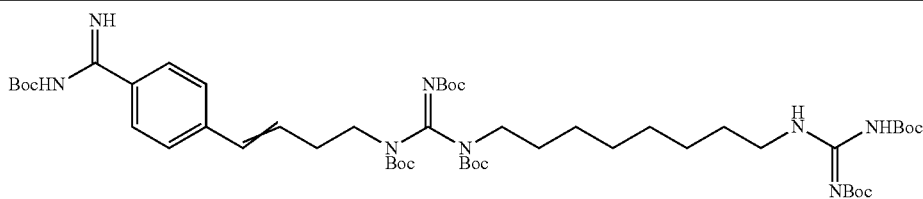
157 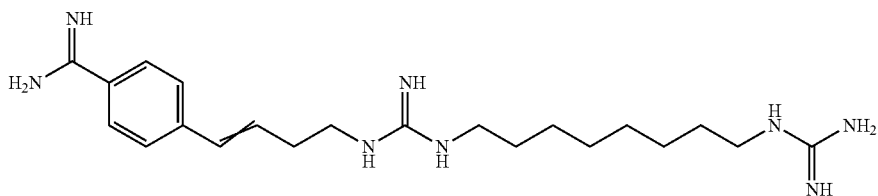 [SMILES: N=C(N)NCCCCCCCCNC(=N)NCCC=Cc1ccc(C(=N)N)cc1]
158 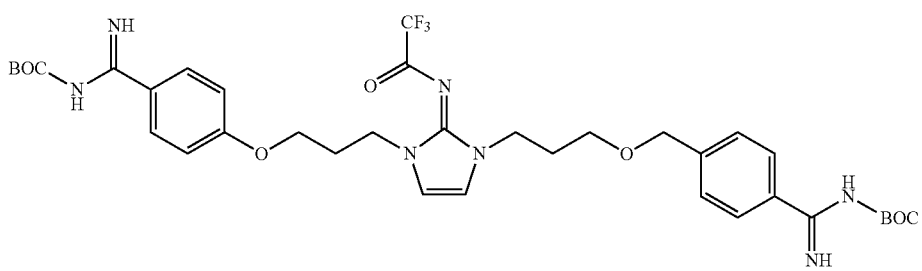 [SMILES: CC(C)(C)OC(=O)NC(=N)c1ccc(COCCCn2ccn(CCCOc3ccc(C(=N)NC(=O)OC(C)(C)C)cc3)/c2=N\C(=O)C(F)(F)F)cc1]
159 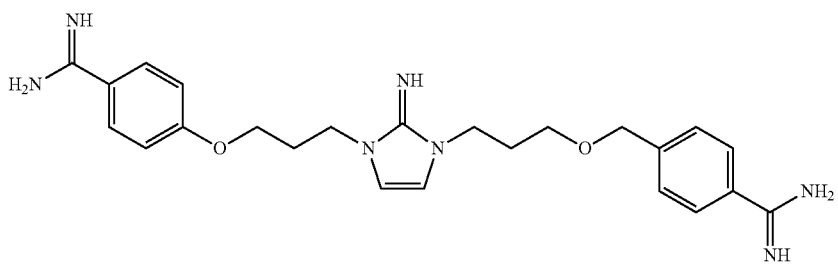 [SMILES: N=C(N)c1ccc(COCCCn2ccn(CCCOc3ccc(C(=N)N)cc3)c2=N)cc1]
160 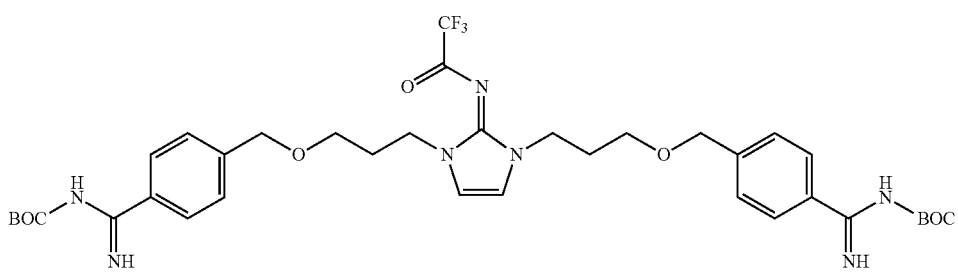 [SMILES: CC(C)(C)OC(=O)NC(=N)c1ccc(COCCCn2ccn(CCCOCc3ccc(C(=N)NC(=O)OC(C)(C)C)cc3)c2=NC(=O)C(F)(F)F)cc1]
| Compound No. | Salt form | Physical property |
|---|---|---|
| 151 | hydro-chloride | Melting point 179-181° C. |
| 152 | — | ¹HNMR(CDCl₃): 1.14-1.23 (m, 8H), 1.46-1.53 (m, 49H), 1.55 (s, 9H), 2.81 (dd, 2H), 3.30 (dd, 2H), 3.48 (dd, 2H), 3.83 (dd, 2H), 7.44 (d, 2H), 7.58 (d, 2H) |
| 153 | hydro-chloride | ¹H NMR (CD₃OD): 1.34-1.44 (m, 8H), 1.54-1.65 (m, 4H), 2.78 (t, 2H), 3.14-3.23 (m, 4H), 3.46-3.53 (m, 2H), 7.64 (d, 2H), 7.77 (d, 2H) |
| 154 | — | ¹HNMR (CDCl₃): 1.48-1.57 (m, 45H), 4.81 (s, 4H), 7.45 (d, 4H), 7.78 (d, 4H) |
| 155 | hydro-chloride | Melting point 220° C. UP |
| 156 | — | ¹HNMR (CDCl₃): 113-1.33 (m, 8H), 1.45-1.57 (m, 58H), 2.60 (dd, 2H), 3.30-3.39 (m, 2H), 3.41-3.48 (m, 2H), 3.70 (t, 2H), 6.31-6.39 (m, 1H), 6.45 (d, 1H), 7.38 (d, 2H), 7.85 (d, 2H) |

TABLE 82-continued

| | | |
|---|---|---|
| 157 | hydrochloride | $^1$HNMR (CD$_3$OD): 1.25-1.44 (m, 8H), 1.49-1.65 (m, 4H), 3.07-3.21 (m, 4H), 3.58-3.74 (m, 4H), 6.45-6.70 (m, 2H), 7.59-7.83 (m, 4H), |
| 158 | — | $^1$HNMR (CDCl$_3$): 1.55 (s, 9H), 1.56 (s, 9H), 2.03 (tt, 2H), 2.23 (tt, 2H), 3.46 (t, 2H), 3.96 (t, 2H), 3.99 (t, 2H), 4.10 (t, 2H), 4.50 (s, 2H), 6.65 (s, 2H), 6.87 (d, 2H), 7.35 (d. 2H), 7.82 (d, 4H). |
| 159 | hydrochloride | $^1$HNMR (CD$_3$OD): 2.07 (tt, 2H), 2.26 (tt, 2H), 3.60 (t, 2H), 4.03 (t, 2H), 4.10 (t, 2H), 4.16 (t, 2H), 4.62 (s, 2H), 6.96 (q, 2H), 7.14 (d, 2H), 7.60 (d, 2H), 7.81 (dd, 2H). |
| 160 | — | $^1$HNMR (CDCl$_3$): 1.55 (s, 18H), 2.01 (tt, 4H), 3.45 (t, 4H), 3.96 (t, 4H), 4.50 (s, 4H), 6.61 (s, 2H), 7.36 (d, 4H), 7.84 (d, 4H). |

In the table, Boc or BOC indicates a t-butoxycarbonyl group. In the table, "-" means that a compound was synthesized as free form.

TABLE 83

| Compound No. | Structure |
|---|---|
| 161 | 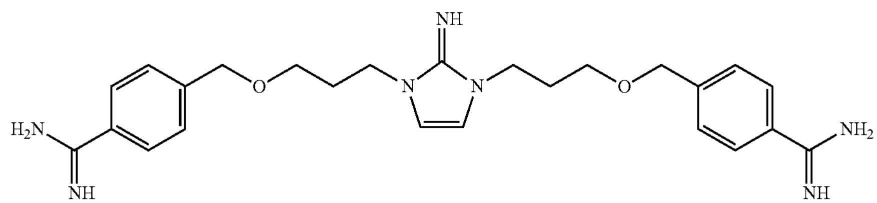 [SMILES: N=C(N)c1ccc(COCCCn2ccn(CCCOCc3ccc(C(=N)N)cc3)c2=N)cc1] |
| 162 | 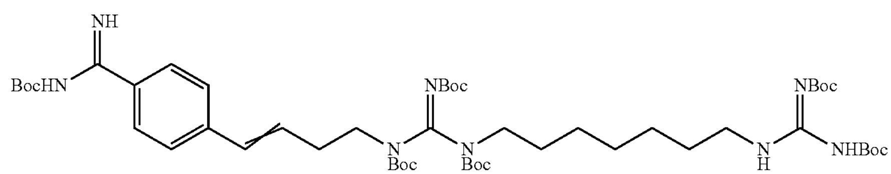 |
| 163 | 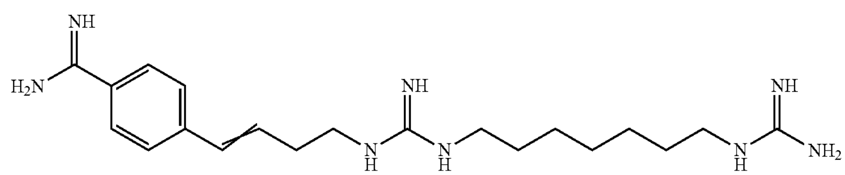 [SMILES: N=C(N)NCCCCCCCNC(=N)NCCC=Cc1ccc(C(=N)N)cc1] |
| 164 | 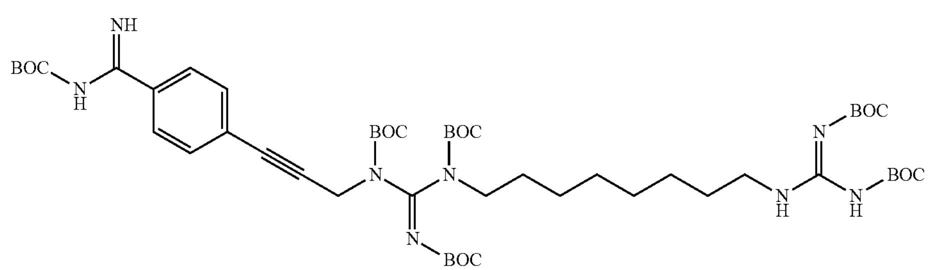 [SMILES: CC(C)(C)OC(=O)/N=C(/NCCCCCCCCN(C(=O)OC(C)(C)C)/C(=N\C(=O)OC(C)(C)C)N(CC#Cc1ccc(C(=N)NC(=O)OC(C)(C)C)cc1)C(=O)OC(C)(C)C)NC(=O)OC(C)(C)C] |
| 165 | 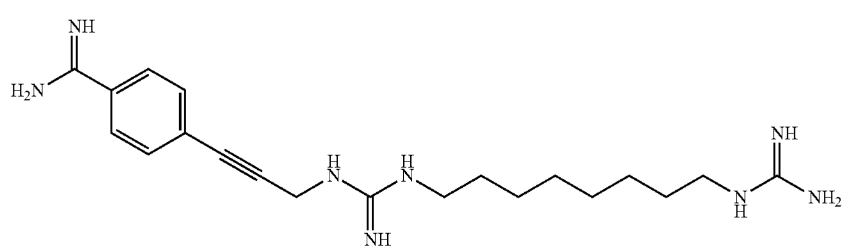 [SMILES: N=C(N)NCCCCCCCCNC(=N)NCC#Cc1ccc(C(=N)N)cc1] |

TABLE 83-continued
166 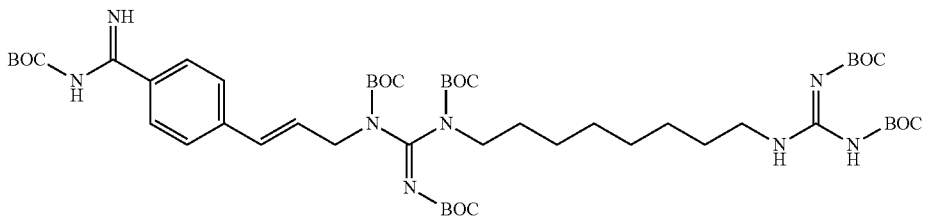 [SMILES: CC(C)(C)OC(=O)/N=C(/NCCCCCCCCN(C(=O)OC(C)(C)C)/C(=N\C(=O)OC(C)(C)C)N(C/C=C/c1ccc(C(=N)NC(=O)OC(C)(C)C)cc1)C(=O)OC(C)(C)C)NC(=O)OC(C)(C)C]
167 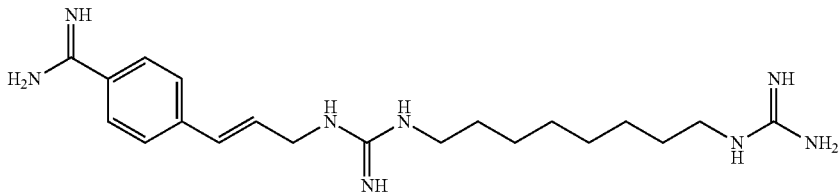 [SMILES: N=C(N)NCCCCCCCCNC(=N)NC/C=C/c1ccc(C(=N)N)cc1]
168 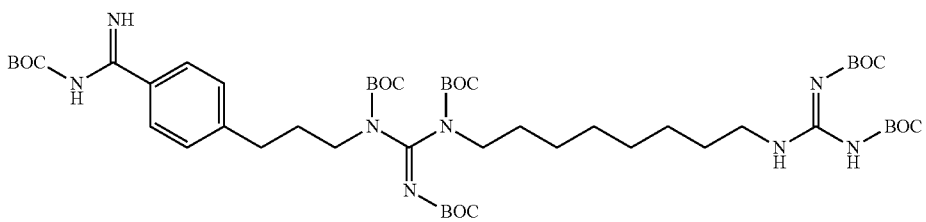 [SMILES: CC(C)(C)OC(=O)/N=C(/NCCCCCCCCN(C(=O)OC(C)(C)C)/C(=N\C(=O)OC(C)(C)C)N(CCCc1ccc(C(=N)NC(=O)OC(C)(C)C)cc1)C(=O)OC(C)(C)C)NC(=O)OC(C)(C)C]
169 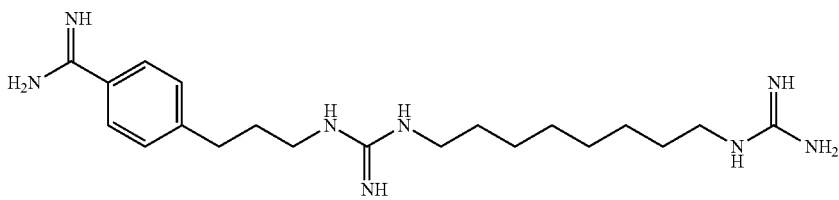 [SMILES: N=C(N)NCCCCCCCCNC(=N)NCCCc1ccc(C(=N)N)cc1]
170 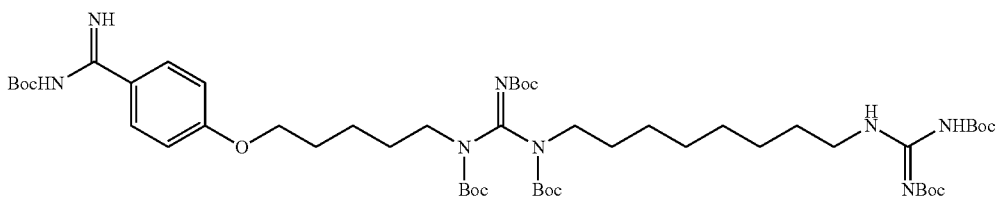
| Compound No. | Salt form | Physical property |
| --- | --- | --- |
| 161 | hydrochloride | ¹HNMR (CD₃OD): 2.06 (tt, 4H), 3.59 (t, 4H), 4.01 (t 4H) 4.63 (s 4H) 6.94 (s 2H) 7.60 (d 4H), 7.81 (d, 4H). |
| 162 | — | ¹HNMR (CDCl₃): 0.82-1.01 (m, 4H), 1.02-1.11 (m, 2H), 1.18-1.32 (m, 20H), 1.44-1.54 (m, 58H), 2.59 (dd, 2H), 3.31-3.39 (m, 2H), 3.73-3.81 (m, 2H), 6.37-6.49 (m, 2H), 7.38 (d, 2H), 7.97 (d, 2H) |
| 163 | hydrochloride | ¹HNMR (CD₃OD): 1.33-1.44 (m, 6H),1.53-1.65 (m, 4H), 2.55 (dd, 2H), 3.14-3.22 (m, 4H), 3.36-3.42 (m, 2H), 6.47-6.56 (m, 1H), 6.65 (d, 1H), 7.64 (d, 2H), 7.77 (d, 2H) |
| 164 | — | ¹HNMR (CDCl₃): 1.03-1.21 (m, 6H), 1.35-1.43 (m, 2H), 1.47-1.59 (m, 56H), 1.61-1.69 (m, 2H), 3.22 (dd, 2H), 3.49 (dd, 2H), 4.64 (s, 2H), 7.41 (d, 2H), 7.94 (d, 2H) |
| 165 | hydrochloride | ¹HNMR(CD₃OD): 1.32-1.46 (m, 8H), 1.53-1.67 (m, 4H), 3.16 (t, 2H), 3.23 (t, 2H), 4.35 (s, 2H), 7.66 (d, 2H), 7.79 (d, 2H) |
| 166 | — | ¹HNMR(CDCl₃): 0.98-1.21 (m, 8H), 1.45-1.59 (m, 58H), 3.29 (dd, 2H), 3.47 (dd, 2H), 4.33 (d, 2H), 6.40 (dt, 1H), 6.58 (d, 1H), 7.40 (d, 2H), 7.91 (d, 2H) |

TABLE 83-continued

| | | | |
|---|---|---|---|
| | 167 | hydro-chloride | $^1$HNMR(CD$_3$OD): 1.33-1.46 (m, 8H), 1.54-1.67 (m, 4H), 3.13-3.19 (m, 2H), 3.22 (t, 2H), 4.08 (d, 2H), 6.50 (dt, 1H), 6.72 (d, 1H), 7.67 (d, 2H), 7.79 (d, 2H) |
| | 168 | — | $^1$HNMR(CDCl$_3$): 1.20-1.31 (m, 8H), 1.44-1.62 (m, 58H), 1.91-2.04 (m, 2H), 2.67 (t, 2H), 3.41 (dd, 2H), 3.47 (dd, 2H), 3.54 (dd, 2H), 7.20-7.25 (m, 2H), 7.81 (d, 2H) |
| | 169 | hydro-chloride | $^1$HNMR(CD$_3$OD): 1.35-1.44 (m, 8H), 1.54-1.67 (m, 4H), 1.94 (dt, 2H), 2.82 (dd, 2H), 3.14-3.22 (m, 4H), 3.26 (t, 2H), 7.50 (d, 2H), 7.76 (d, 2H) |
| | 170 | — | $^1$HNMR(CDCl$_3$): 1 22-1.34 (m, 10H), 1.43-1.54 (m, 58H), 1.68-1.87 (m, 4H), 3.35 (dd, 2H), 3.48 (dt, 2H), 3.53 (dt, 2H), 3.98 (t, 2H), 6.89 (d, 2H), 7.84 (d, 2H) |

In the table, Boc or BOC indicates a t-butoxycarbonyl group. In the table, "-" means that a compound was synthesized as free form.

TABLE 84

| Compound No. | Structure |
|---|---|
| 171 | [chemical structure] |
| 172 | [chemical structure] |
| 173 | [chemical structure] |
| 174 | [chemical structure] |
| 175 | [chemical structure] |

TABLE 84-continued

176 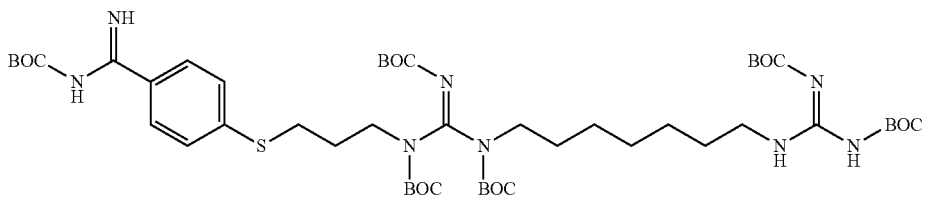 [SMILES: CC(C)(C)OC(=O)/N=C(/N(CCCCCCCN/C(=N\C(=O)OC(C)(C)C)NC(=O)OC(C)(C)C)C(=O)OC(C)(C)C)N(CCCSc1ccc(C(=N)NC(=O)OC(C)(C)C)cc1)C(=O)OC(C)(C)C]

177 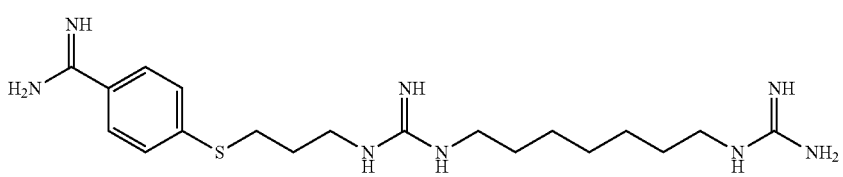

178 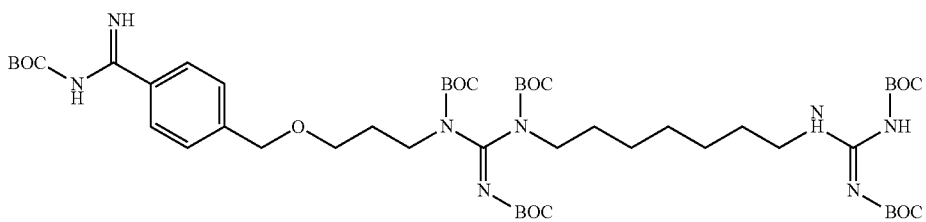 [SMILES: CC(C)(C)OC(=O)/N=C(/NCCCCCCCN(C(=O)OC(C)(C)C)/C(=N\C(=O)OC(C)(C)C)N(CCCOCc1ccc(C(=N)NC(=O)OC(C)(C)C)cc1)C(=O)OC(C)(C)C)NC(=O)OC(C)(C)C]

179 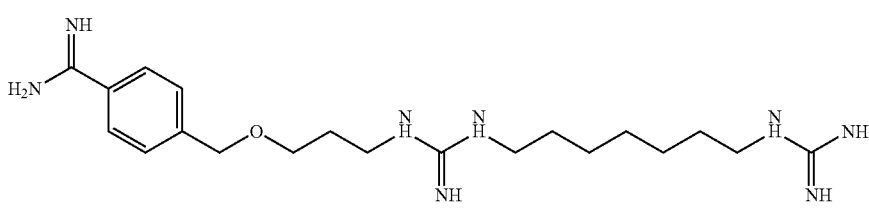

180 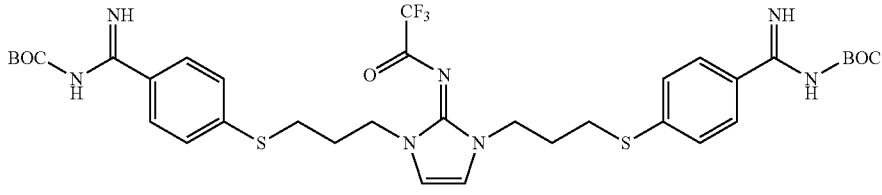 [SMILES: CC(C)(C)OC(=O)NC(=N)c1ccc(SCCCn2ccn(CCCSc3ccc(C(=N)NC(=O)OC(C)(C)C)cc3)c2=NC(=O)C(F)(F)F)cc1]

| Compound No. | Salt form | Physical property |
|---|---|---|
| 171 | hydro-chloride | $^1$HNMR (CD$_3$OD): 1.32-1.41 (m, 8H), 1.46-1.76 (m, 8H), 1.85 (dt, 2H), 3.10-3.21 (m, 6H), 4.01 (t, 2H), 7.38 (d, 2H), 7.75 (d, 2H) |
| 172 | — | $^1$HNMR (CDCl$_3$): 1.55 (s, 18H), 2.07 (tt, 2H), 2.25 (tt, 2H), 2.93 (t, 2H), 3.96 (t, 2H), 4.01 (t, 2H), 4.12 (t, 2H), 6.68 (dd, 2H), 6.84 (d, 2H), 7.26 (d, 2H), 7.77 (dd, 4H). |
| 173 | hydro-chloride | Melting point 168-171° C. |
| 174 | — | $^1$HNMR (CDCl$_3$): 1.46 (s, 18H), 1.49 (s, 9H), 1.55 (s, 18H), 1.96 (tt, 4H), 3.50 (t, 4H), 3.63 (t, 4H), 4.49 (s, 4H), 7.32 (d, 4H), 7.77 (d, 4H). |
| 175 | hydro-chloride | $^1$HNMR (CD$_3$OD): 1.91 (tt, 4H), 3.34 (t, 4H), 3.63 (t, 4H), 4.65 (s, 4H), 7.60 (d, 4H), 7.81 (d, 4H). |
| 176 | — | $^1$HNMR (CDCl$_3$): 1.09-1.24 (m, 6H), 1.40-1.67 (m, 58H), 2.02 (tt, 2H), 3.02 (t, 2H), 3.42 (t, 2H), 3.68 (t, 2H), 3.82 (t, 2H), 7.29 (d, 2H), 7.86 (d, 2H). |
| 177 | hydro-chloride | $^1$HNMR (CD$_3$OD): 1.35-1.47 (m, 6H), 1.55-1.65 (m, 4H), 1.98 (tt, 2H), 3.14-3.23 (m, 6H), 3.37 (t, 2H), 7.52 (d, 2H), 7.74 (d, 2H). |
| 178 | — | $^1$HNMR (CDCl$_3$): 1.16-1.30 (m, 6H), 1.43-1.67 (m, 58H), 1.98 (tt, 2H), 3.47 (t, 2H), 3.53 (t, 2H), 3.63 (t, 2H), 3.84 (t, 2H), 4.53 (s, 2H), 7.38 (d, 2H), 7.87 (d, 2H). |

TABLE 84-continued

| | | |
|---|---|---|
| 179 | hydrochloride | $^1$HNMR (CD$_3$OD): 1.33-1.49 (m, 6H), 1.53-1.65 (m, 4H), 1.92 (tt, 2H), 3.17 (t, 4H), 3.35 (t, 2H), 3.64 (t, 2H), 4.65 (s. 2H), 7.61 (d, 2H), 7.81 (d, 2H). |
| 180 | — | $^1$HNMR (CDCl$_3$): 1.55 (s, 18H), 2.09 (tt, 4H), 2.94 (tt, 4H), 4.02 (t, 2H), 8.88 (dd, 2H), 8.71 (s, 4H), 7.25 (d, 4H), 7.73 (d, 4H). |

In the table, Boc or BOC indicates a t-butoxycarbonyl group. In the table, "-" means that a compound was synthesized as free form.

TABLE 85

| Compound No. | Structure |
|---|---|
| 181 | 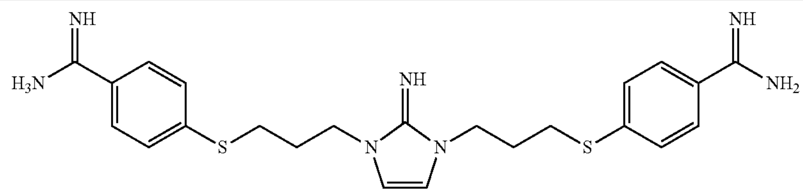 [SMILES: N=C(N)c1ccc(SCCCn2ccn(CCCSc3ccc(C(=N)N)cc3)c2=N)cc1] |
| 182 | 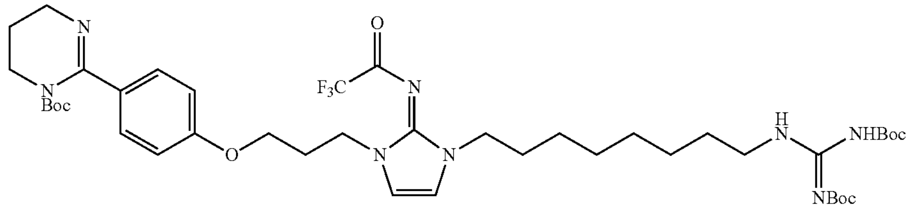 |
| 183 | 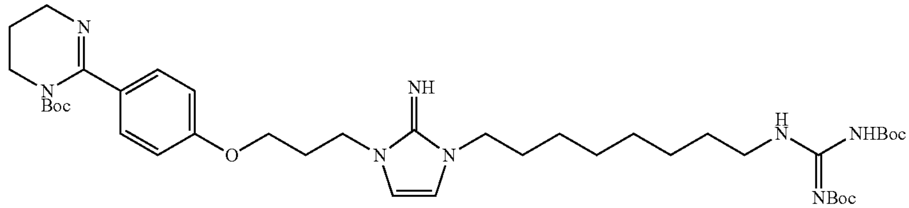 |
| 184 | 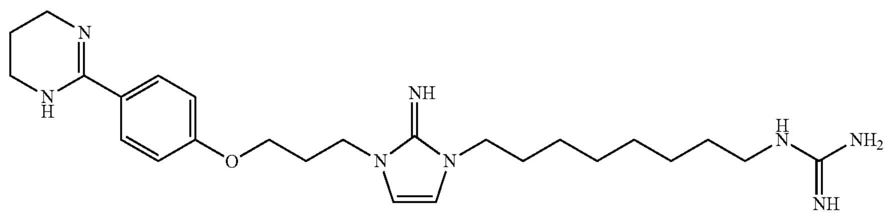 [SMILES: N=C(N)NCCCCCCCCn1ccn(CCCOc2ccc(C3=NCCCN3)cc2)c1=N] |
| 185 | 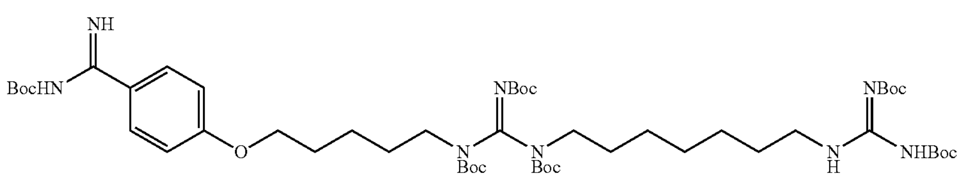 |
| 186 | 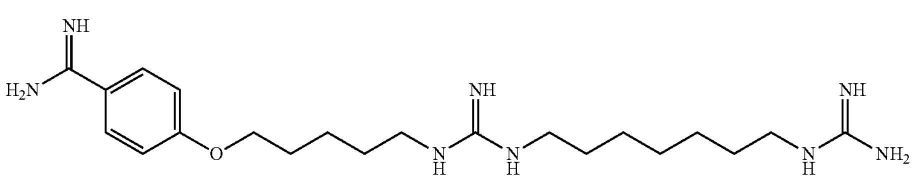 [SMILES: N=C(N)NCCCCCCCNC(=N)NCCCCCOc1ccc(C(=N)N)cc1] |

TABLE 85-continued

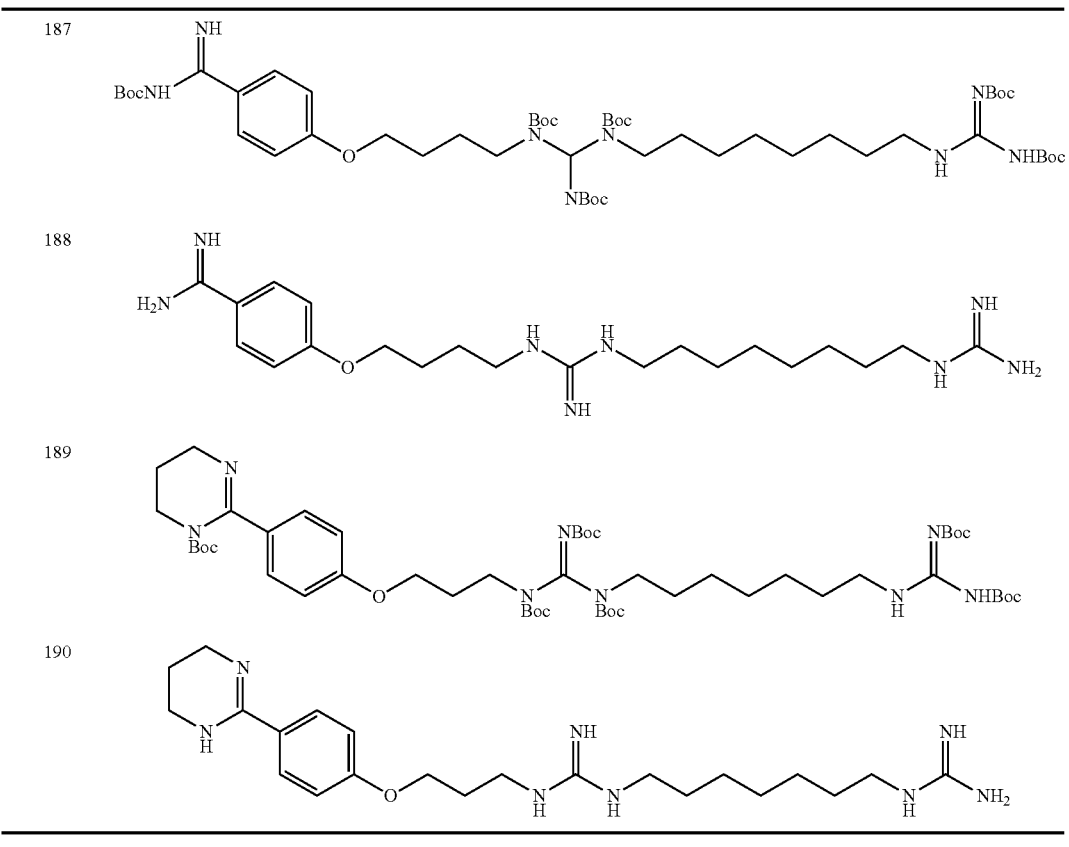

| Compound No. | Salt form | Physical property |
|---|---|---|
| 181 | hydro-chloride | Melting point 169-172° C. |
| 182 | — | ¹HNMR(CDCl₃): 1.16 (s, 9H), 1.92 (dt, 2H), 2.28 (dt, 2H), 3.60 (t, 2H), 3.70 (t, 2H), 3.99 (t, 2H), 4.23 (t, 2H), 6.62 (d, 1H), 6.75 (d, 1H), 6.83 (d, 2H), 7.43 (d, 2H) |
| 183 | — | ¹HNMR (CDCl₃): 1.16 (s, 9H), 1.23-1.35 (m, 8H), 1.46-1.55 (m, 20H), 1.67-1.78 (m, 2H), 1.92 (dt, 2H), 2.23 (dt, 2H), 3.60 (t, 2H), 3.69 (t, 2H), 3.81-3.91 (m, 4H), 3.95 (t, 2H), 4.12 (t, 2H), 6.81 (s, 2H), 6.83 (d, 2H), 7.48 (d, 2H) |
| 184 | hydro-chloride | ¹HNMR (CD₃OD): 1.33-1.44 (m, 8H), 1.54-1.63 (m, 2H), 1.69-1.79 (m, 2H), 2.1 0 (dt, 2H), 2.27 (dt, 2H), 3.16 (t, 2H), 353-3.62 (m, 4H), 3.86 (t, 2H), 4.09-4.18 (m, 4H), 6.96 (s, 2H), 7.12 (d, 2H), 7.62 (d, 2H) |
| 185 | — | ¹HNMR (CDCl₃): 1.15-1.32 (m, 6H), 1.44-1.53 (m, 49H), 1.58-1.66 (m, 2H), 1.67-1.76 (m, 2H), 1.82 (dt, 2H), 3.47 (dd, 2H), 3.53 (dd, 2H), 3.83 (dd, 2H), 3.99 (t, 2H), 6.90 (d, 2H), 7.87 (d, 2H) |
| 186 | hydro-chloride | ¹HNMR (CD₃OD): 1.36-1.44 (m, 6H), 1.49-1.73 (m, 8H), 1.87 (dt, 2H), 3.15-3.24 (m, 6H), 4.11 (t, 2H), 7.11 (d, 2H), 7.78 (d, 2H) |
| 187 | — | ¹HNMR (CDCl₃): 1.19-1.29 (m, 8H), 1.42-1.52 (m, 45H), 1.55 (s, 9H), 1.57-1.68 (m, 4H), 1.75-1.89 (m, 4H), 3.23-3.38 (m, 2H), 3.48 (t, 2H), 3.60 (t, 2H), 4.00 (t, 2H), 6.88 (d, 2H), 7.87 (d, 2H). |
| 188 | hydro-chloride | ¹HNMR (CD₃OD): 1.33-1.47 (m, 8H), 1.52-1.61 (m, 4H), 1.73-1.97 (m, 4H), 3.12-3.24 (m, 4H), 3.26-3.33 (m, 2H), 4.15 (t, 2H), 7.14 (d, 2H), 7.81 (d, 2H). |
| 189 | — | ¹HNMR (CDCl₃): 1.15 (s, 9H), 1.22-1.38 (m, 6H), 1.45-1.53 (m, 47H), 1.63-1.71 (m, 2H), 1.92 (tt, 2H), 2.18 (dt, 2H), 3.49 (dd, 2H), 3.59 (t, 2H), 3.67 (t, 2H), 3.72 (t, 2H), 3.87 (dt, 2H), 4.01 (t, 2H), 6.83 (d, 2H), 7.40 (d, 2H) |

TABLE 85-continued
| | | | |
|---|---|---|---|
| 190 | hydro-chloride | ¹HNMR (CD₃OD): 1.36-1.46 (m, 6H), 1.53-1.68 (m, 4H), 2.05-2.16 (m, 4H), 3.19 (dd, 4H), 3.42 (t, 2H), 3.54-3.61 (m, 4H), 4.18 (t, 2H), 7.15 (d, 2H), 7.67 (d, 2H) | |
In the table, Boc or BOC indicates a t-butoxycarbonyl group. In the table, "-" means that a compound was synthesized as free form.
TABLE 86
| Compound No. | Structure |
|---|---|
| 191 | 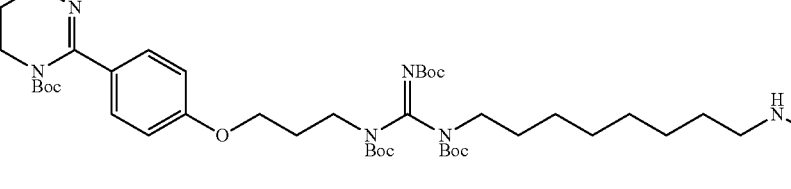 |
| 192 | 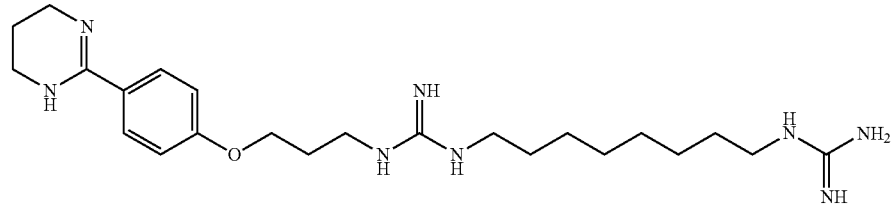 [SMILES: N=C(N)NCCCCCCCCNC(=N)NCCCOc1ccc(C2=NCCCN2)cc1] |
| 193 | 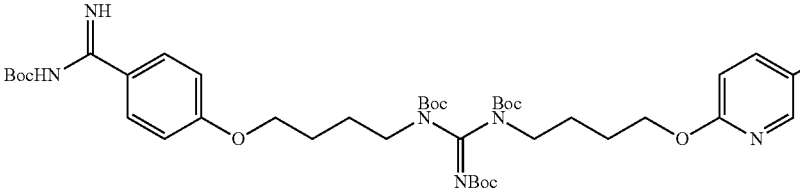 |
| 194 | 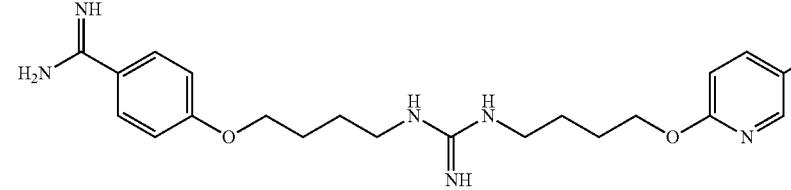 |
| 195 | 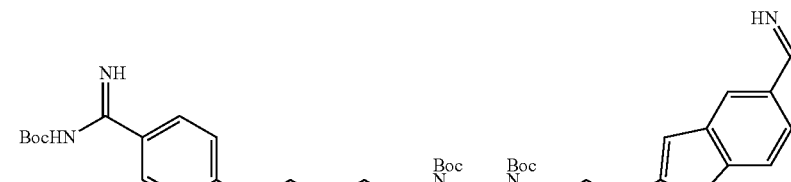 |

TABLE 86-continued
196 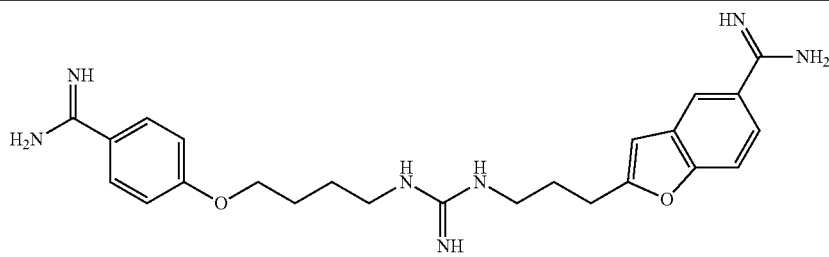
197 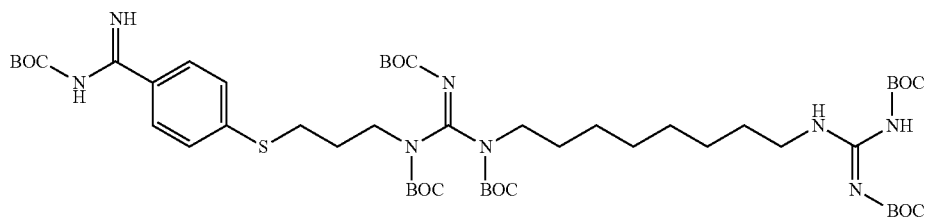 [SMILES: CC(C)(C)OC(=O)/N=C(/NCCCCCCCCN(C(=O)OC(C)(C)C)/C(=N/C(=O)OC(C)(C)C)N(CCCSc1ccc(C(=N)NC(=O)OC(C)(C)C)cc1)C(=O)OC(C)(C)C)NC(=O)OC(C)(C)C]
198 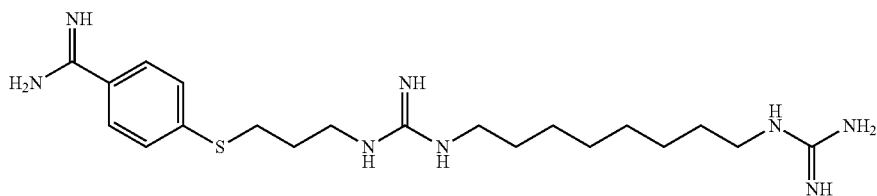 [SMILES: N=C(N)NCCCCCCCCNC(=N)NCCCSc1ccc(C(=N)N)cc1]
199 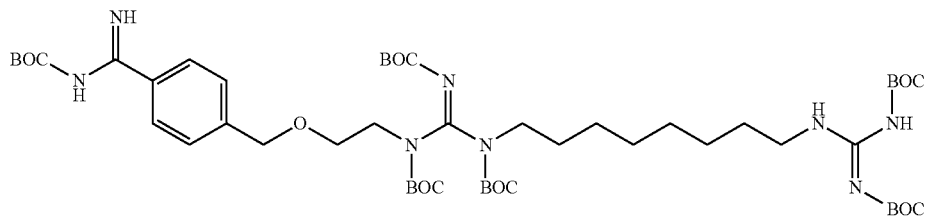 [SMILES: CC(C)(C)OC(=O)/N=C(/NCCCCCCCCN(C(=O)OC(C)(C)C)/C(=N/C(=O)OC(C)(C)C)N(CCOCc1ccc(C(=N)NC(=O)OC(C)(C)C)cc1)C(=O)OC(C)(C)C)NC(=O)OC(C)(C)C]
200 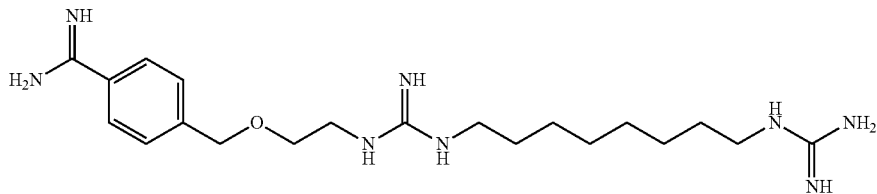 [SMILES: N=C(N)NCCCCCCCCNC(=N)NCCOCc1ccc(C(=N)N)cc1]
| Compound No. | Salt form | Physical property |
|---|---|---|
| 191 | — | $^1$HNMR (CDCl$_3$): 1.15 (s, 9H), 1.20-1.37 (m, 8H), 1.46-1.55 (m, 47H), 1.60-1.70 (m, 2H), 1.92 (tt, 2H), 2.16 (dt, 2H), 3.38 (dd, 2H), 3.48 (dd, 2H), 3.59 (t, 2H), 3.66-3.76 (m, 4H), 4.01 (t, 2H), 6.85 (d, 2H), 7.40 (d, 2H) |
| 192 | hydro-chloride | $^1$HNMR (CD$_3$OD): 1.35-1.43 (m, 8H), 1.54-1.64 (m, 4H), 2.05-2.15 (m, 4H), 3.17 (dd, 4H), 3.42 (t, 2H), 3.54-3.61 (m, 4H), 4.18 (t, 2H), 7.15 (d, 2H), 7.67 (d, 2H) |
| 193 | — | $^1$HNMR (CDCl$_3$): 1.43-1.58 (m, 45H), 1.69-1.89 (m, 8H), 3.51-3.67 (m, 4H), 3.94 (t, 2H), 4.26 (t, 2H), 6.61 (dd, 1H), 6.78 (d, 2H), 7.74 (d, 2H), 8.03 (ddd, 1H), 8.52 (d, 1H). |
| 194 | hydro-chloride | $^1$HNMR (CD$_3$OD): 1.69-1.99 (m, 8H), 3.27-3.34 (m, 4H), 4.05-4.24 (m, 2H), 4.40-4.53 (m, 2H), 6.88 (d, 1H), 7.14 (d, 2H), 7.50-7.69 (m, 1H), 7.79 (d, 1H), 8.07 (d, 1H). |
| 195 | — | $^1$HNMR (CDCl$_3$): 1.42-1.60 (m, 45H), 1.70-1.86 (m, 4H), 2.10 (tt, 2H), 2.79 (t, 2H), 3.60 (t, 2H), 3.65 (t, 2H), 3.88 (t, 2H), 6.38 (s, 1H), 6.72 (d, 2H), 7.30 (d, 1H), 7.66 (dd, 1H), 7.73 (d, 2H), 7.96 (d, 1H). |

TABLE 86-continued

| | | |
|---|---|---|
| 196 | hydro-chloride | $^1$HNMR (D$_2$O): 1.36-1.48 (m, 2H), 1.51-1.62 (m, 2H), 1.88 (tt, 2H), 2.73 (t, 2H), 2.88-2.99 (m, 2H), 3.15 (t, 2H), 3.91 (t, 2H), 6.52 (s, 1H), 6.91 (d, 2H), 7.44 (d, 2H), 7.53 (d, 2H), 7.78 (dd, 1H). |
| 197 | — | $^1$HNMR (CDCl$_3$): 1.19-1.31 (m, 8H), 1.40-1.65 (m, 58H), 2.03 (tt, 2H), 3.02 (t, 2H), 3.35 (q, 2H), 3.45 (t, 2H), 3.67 (t, 2H), 7.29 (d, 2H), 7.80 (d, 2H). |
| 198 | hydro-chloride | $^1$HNMR (CD$_3$OD): 1.35-1.44 (m, 8H), 1.53-1.65 (m, 4H), 1.98 (tt, 2H), 3.13-3.22 (m, 6H), 3.37 (t, 2H), 7.52 (d, 2H), 7.74 (d, 2H). |
| 199 | — | $^1$HNMR (CDCl$_3$): 1.09-1.30 (m, 8H), 1.43-1.62 (m, 58H), 3.33 (q, 2H), 3.43 (t, 2H), 3.71 (t, 2H), 3.84 (t, 2H), 4.55 (s, 2H), 7.38 (d, 2H), 7.88 (d, 2H). |
| 200 | hydro-chloride | $^1$HNMR (CD$_3$OD): 1.31-1.44 (m, 8H), 1.52-1.64 (m, 4H), 3.13-3.22 (m, 4H), 3.47 (t, 2H), 3.69 (t, 2H), 4.70 (s, 2H), 7.62 (d, 2H), 7.82 (d, 2H). |

In the table, Boc or BOC indicates a t-butoxycarbonyl group. In the table, "-" means that a compound was synthesized as free form.

TABLE 87

| Compound No. | Structure |
|---|---|
| 201 | 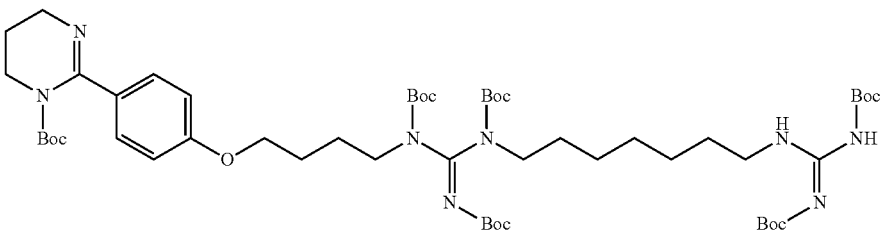 [SMILES: CC(C)(C)OC(=O)/N=C(\NCCCCCCCN(C(=O)OC(C)(C)C)/C(=N\C(=O)OC(C)(C)C)N(CCCCOc1ccc(C2=NCCCN2C(=O)OC(C)(C)C)cc1)C(=O)OC(C)(C)C)NC(=O)OC(C)(C)C] |
| 202 | 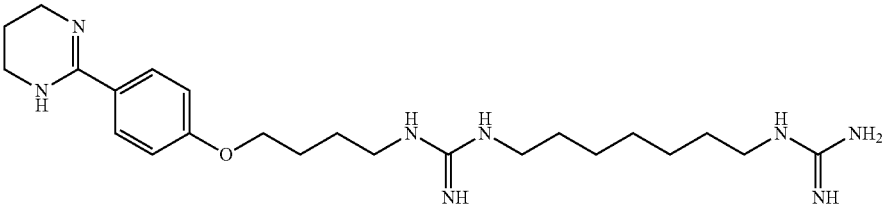 [SMILES: N=C(N)NCCCCCCCNC(=N)NCCCCOc1ccc(C2=NCCCN2)cc1] |
| 203 | 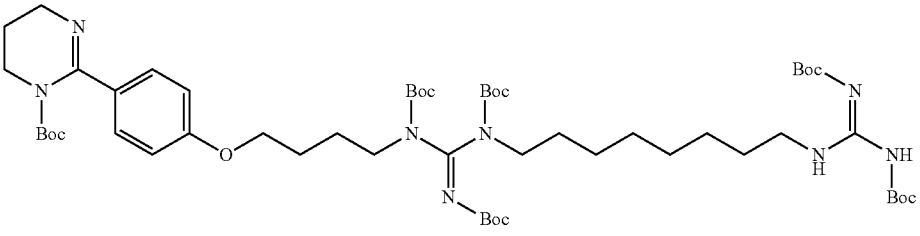 [SMILES: CC(C)(C)OC(=O)/N=C(\NCCCCCCCCN(C(=O)OC(C)(C)C)/C(=N\C(=O)OC(C)(C)C)N(CCCCOc1ccc(C2=NCCCN2C(=O)OC(C)(C)C)cc1)C(=O)OC(C)(C)C)NC(=O)OC(C)(C)C] |
| 204 | 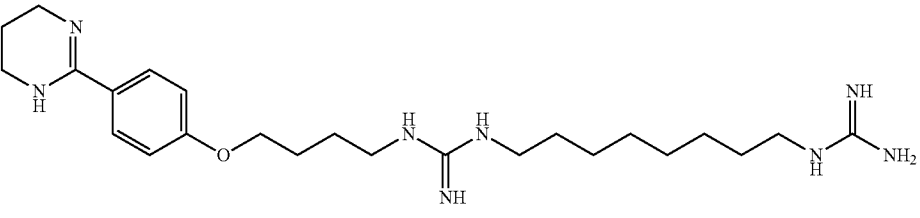 [SMILES: N=C(N)NCCCCCCCCNC(=N)NCCCCOc1ccc(C2=NCCCN2)cc1] |

TABLE 87-continued
205 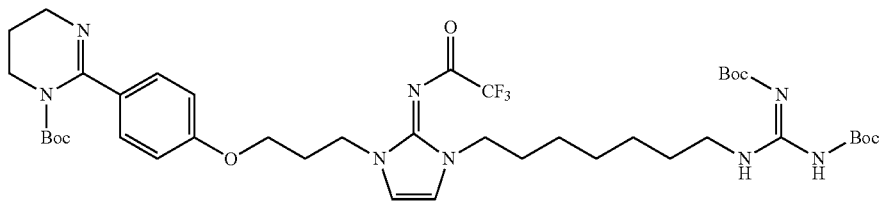 [SMILES: CC(C)(C)OC(=O)/N=C(\NCCCCCCCn1ccn(CCCOc2ccc(C3=NCCCN3C(=O)OC(C)(C)C)cc2)/c1=N/C(=O)C(F)(F)F)NC(=O)OC(C)(C)C]
206 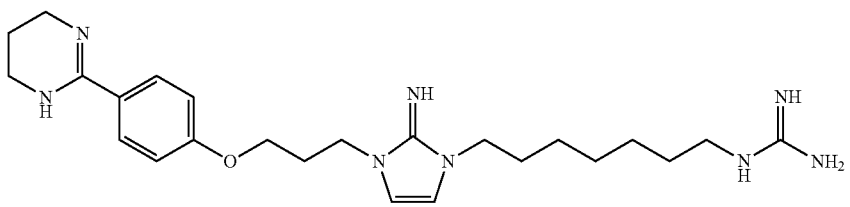 [SMILES: N=C(N)NCCCCCCCn1ccn(CCCOc2ccc(C3=NCCCN3)cc2)c1=N]
207 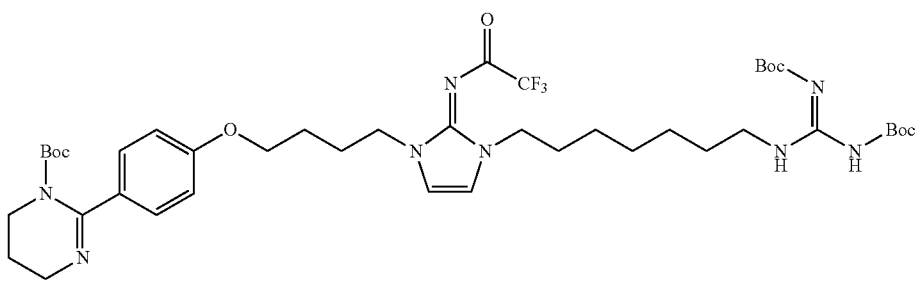 [SMILES: CC(C)(C)OC(=O)/N=C(\NCCCCCCCn1ccn(CCCCOc2ccc(C3=NCCCN3C(=O)OC(C)(C)C)cc2)/c1=N/C(=O)C(F)(F)F)NC(=O)OC(C)(C)C]
208 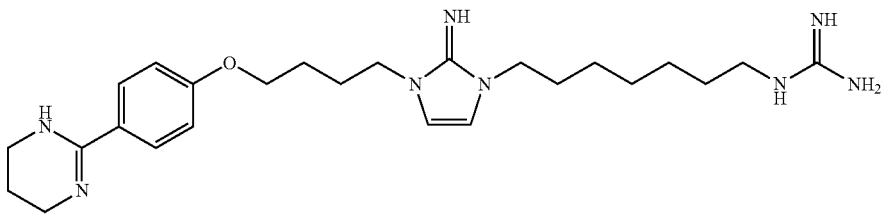 [SMILES: N=C(N)NCCCCCCCn1ccn(CCCCOc2ccc(C3=NCCCN3)cc2)c1=N]
209 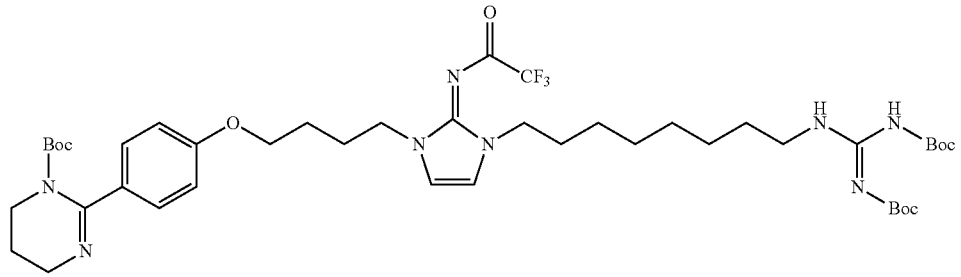 [SMILES: CC(C)(C)OC(=O)/N=C(/NCCCCCCCCn1ccn(CCCCOc2ccc(C3=NCCCN3C(=O)OC(C)(C)C)cc2)/c1=N/C(=O)C(F)(F)F)NC(=O)OC(C)(C)C]
210 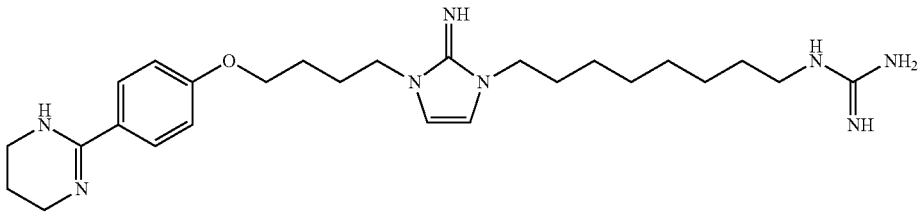 [SMILES: N=C(N)NCCCCCCCCn1ccn(CCCCOc2ccc(C3=NCCCN3)cc2)c1=N]
| Compound No. | Salt form | Physical property |
|---|---|---|
| 201 | — | ¹HNMR (CDCl$_3$): 1.15 (s, 9H), 1.24-1.38 (m, 6H), 1.44-1.57 (m, 47H), 1.62-1.70 (m, 2H), 1.74-1.87 (m, 4H), 1.92 (tt, 2H), 3.49 (dt, 2H), 3.54-3.61 (m, 4H), 3.69 (t, 2H), 3.87 (dt, 2H), 3.98 (t, 2H), 6.82 (d, 2H), 7.40 (d, 2H) |

TABLE 87-continued

| | | |
|---|---|---|
| 202 | hydro-chloride | ¹HNMR (CD₃OD): 1.37-1.45 (m, 6H), 1.54-1.68 (m, 4H), 1.75-1.83 (m, 2H), 1.83-1.88 (m, 2H), 2.10 (tt, 2H), 3.14-3.22 (m, 4H), 3.33-3.40 (m, 2H), 3.57 (t, 4H), 4.12 (t, 2H), 7.12 (d, 2H), 7.66 (d, 2H) |
| 203 | — | ¹HNMR (CDCl₃): 1.14 (s, 9H), 1.23-1.35 (m, 8H), 1.45-1.55 (m, 47H), 1.62-1.69 (m, 2H), 1.70-1.81 (m, 4H), 1.92 (tt, 2H), 3.39 (tt, 2H), 3.49 (dt, 2H), 3.55-3.63 (m, 4H), 3.69 (t, 2H), 3.98 (t, 2H), 6.82 (d, 2H), 7.40 (d, 2H) |
| 204 | hydro-chloride | ¹HNMR (CD₃OD): 1.35-1.44 (m, 8H), 1.54-1.66 (m, 4H), 1.69-1.79 (m, 2H), 1.80-1.88 (m, 2H), 2.10 (tt, 2H), 3.17 (tt, 4H), 3.32-3.39 (m, 2H), 3.57 (t, 4H), 4.12 (t, 2H), 7.14 (d, 2H), 7.67 (d, 2H) |
| 205 | — | ¹HNMR (CDCl₃): 1.16 (s, 9H), 1.24-1.39 (m, 6H), 1.46-1.63 (m, 20H), 1.69-1.79 (m, 2H), 1.92 (tt, 2H), 2.23 (tt, 2H), 3.60 (t, 2H), 3.69 (t, 2H), 3.80-3.79 (m, 4H), 3.95 (t, 2H), 4.12 (t, 2H), 6.69 (s, 2H), 6.84 (d, 2H), 7.42 (d, 2H) |
| 206 | hydro-chloride | ¹HNMR (CD₃OD): 1.34-1.44 (m, 6H), 1.54-1.67 (m, 2H), 1.69-1.80 (m, 2H), 2.10 (tt, 2H), 2.26 (tt, 2H), 3.17 (t, 2H), 3.54-3.61 (m, 4H), 3.86 (t, 2H), 4.09-4.18 (m, 4H), 6.97 (d, 2H), 7.12 (d, 2H), 7.68 (d, 2H) |
| 207 | — | ¹HNMR (CDCl₃): 1.16 (s, 9H), 1.19-1.33 (m, 6H), 1.47-1.58 (m, 20H), 1.70-1.83 (m, 4H), 1.86-2.02 (m, 4H), 3.60 (t, 2H), 3.69 (t, 2H), 3.82-3.90 (m, 4H), 3.95 (t, 2H), 3.99 (t, 2H), 6.76 (d, 2H), 6.83 (d, 2H), 7.41 (d, 2H) |
| 208 | hydro-chloride | ¹HNMR (CD₃OD): 1.35-1.46 (m, 6H), 1.54-1.66 (m, 2H), 1.72-1.81 (m, 2H), 1.82-2.01 (m, 4H), 2.09 (tt, 2H), 3.17 (t, 2H), 3.53-3.61 (m, 4H), 3.88 (t, 2H), 3.97 (t, 2H), 4.13 (t, 2H), 6.99 (d, 2H), 7.12 (d, 2H), 7.66 (d, 2H) |
| 209 | — | ¹HNMR (CDCl₃): 1.16 (s, 9H), 1.24-1.34 (m, 8H), 1.43-1.57 (m, 20H), 1.69-1.84 (m, 4H), 1.84-2.03 (m, 4H), 3.59 (t, 2H), 3.69 (t, 2H), 3.83-3.91 (m, 4H), 3.95 (t, 2H), 3.99 (t, 2H), 6.75 (d, 2H), 6.83 (d, 2H), 7.41 (d, 2H) |
| 210 | hydro-chloride | ¹HNMR (CD₃OD): 1.33-1.43 (m, 8H), 1.54-1.63 (m, 2H), 1.69-1.80 (m, 2H), 1.83-2.00 (m, 4H), 2.09 (tt, 2H), 3.17 (t, 2H), 3.54-3.51 (m, 4H), 3.85 (t, 2H), 3.97 (t, 2H), 4.13 (t, 2H), 6.99 (d, 2H), 7.11 (d, 2H), 7.67 (d, 2H) |

In the table, Boc or BOC indicates a t-butoxycarbonyl group. In the table, "-" means that a compound was synthesized as free form.

TABLE 88

| Compound No. | Structure |
|---|---|
| 211 | 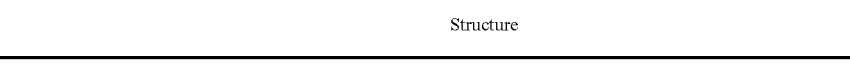 |

US 10,111,437 B2
257                                                                     258
TABLE 88-continued
212 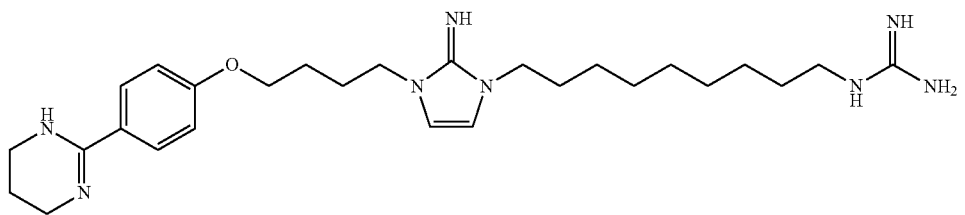 [SMILES: N=C(N)NCCCCCCCCCn1ccn(CCCCOc2ccc(C3=NCCCN3)cc2)c1=N]
213 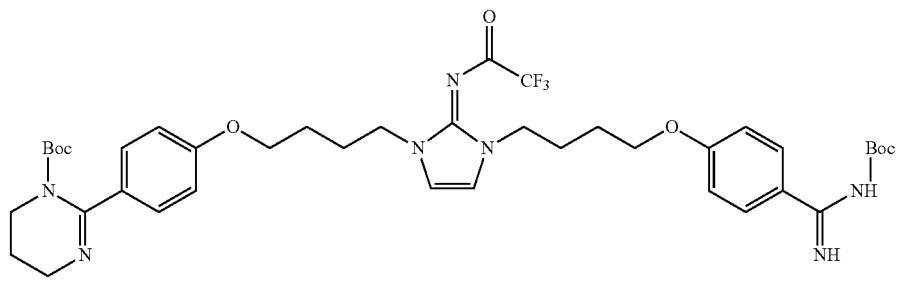 [SMILES: CC(C)(C)OC(=O)NC(=N)c1ccc(OCCCCn2ccn(CCCCOc3ccc(C4=NCCCN4C(=O)OC(C)(C)C)cc3)/c2=N/C(=O)C(F)(F)F)cc1]
214 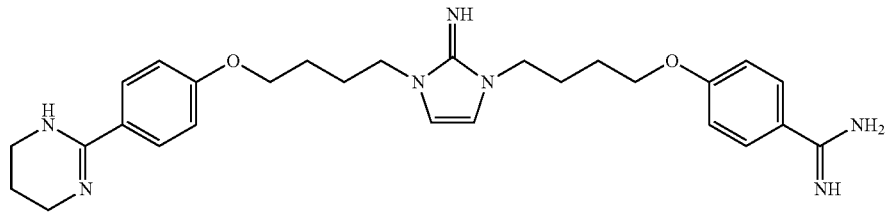 [SMILES: N=C(N)c1ccc(OCCCCn2ccn(CCCCOc3ccc(C4=NCCCN4)cc3)c2=N)cc1]
215 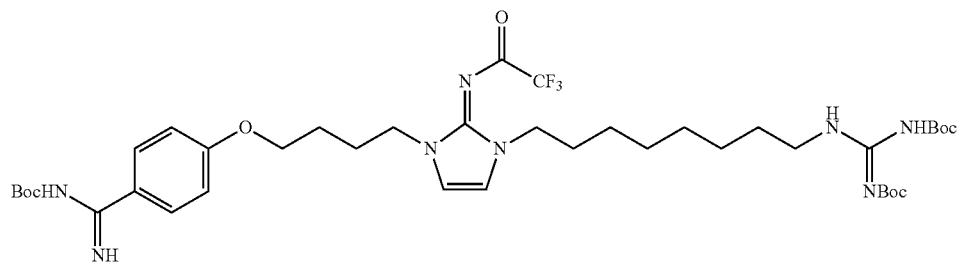
216 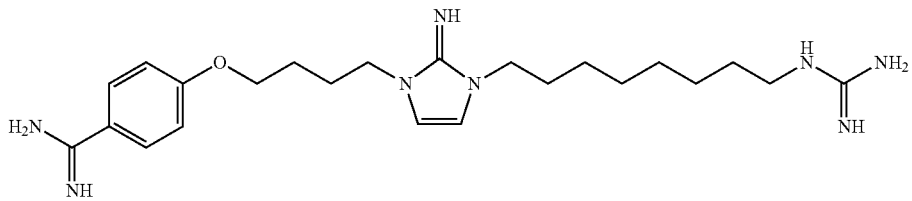 [SMILES: N=C(N)NCCCCCCCCn1ccn(CCCCOc2ccc(C(=N)N)cc2)c1=N]
217 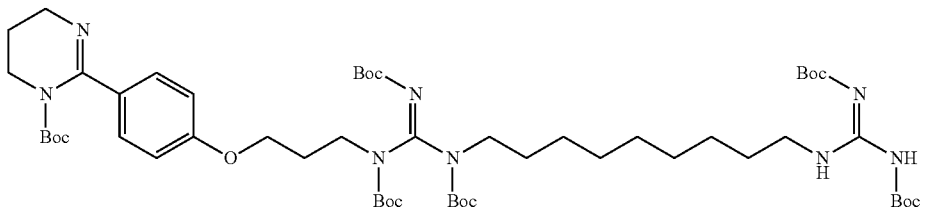 [SMILES: CC(C)(C)OC(=O)/N=C(/N(CCCCCCCCCN/C(=N\C(=O)OC(C)(C)C)NC(=O)OC(C)(C)C)C(=O)OC(C)(C)C)N(CCCOc1ccc(C2=NCCCN2C(=O)OC(C)(C)C)cc1)C(=O)OC(C)(C)C]
218 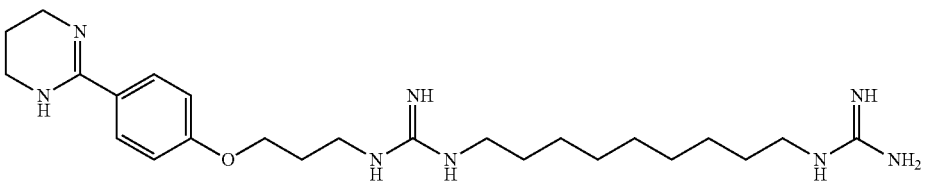 [SMILES: N=C(N)NCCCCCCCCCNC(=N)NCCCOc1ccc(C2=NCCCN2)cc1]

TABLE 88-continued

219 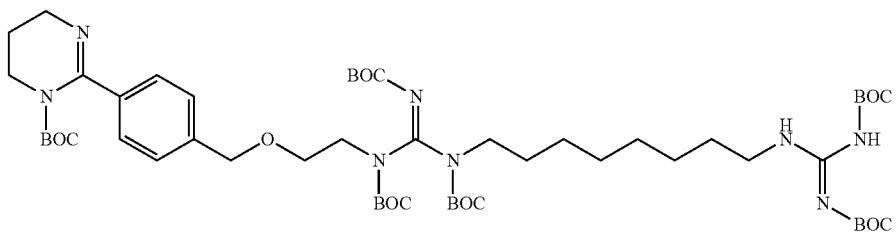 [SMILES: CC(C)(C)OC(=O)/N=C(/NCCCCCCCCN(C(=O)OC(C)(C)C)/C(=N/C(=O)OC(C)(C)C)N(CCOCc1ccc(C2=NCCCN2C(=O)OC(C)(C)C)cc1)C(=O)OC(C)(C)C)NC(=O)OC(C)(C)C]

220 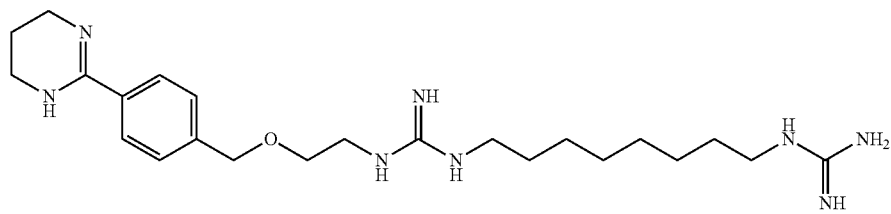 [SMILES: N=C(N)NCCCCCCCCNC(=N)NCCOCc1ccc(C2=NCCCN2)cc1]

| Compound No. | Salt form | Physical property |
|---|---|---|
| 211 | — | ¹HNMR (CDCl₃): 1.16 (s, 9H), 1.22-1.35 (m, 10H), 1.45-1.57 (m, 20H), 1.71-1.84 (m, 4H), 1.89-2.02 (m, 4H), 3.59 (t, 2H), 3.69 (t, 2H), 3.83-3.90 (m, 4H), 3.92-4.02 (m, 4H), 6.75 (d, 2H), 6.33 (d, 2H), 7 41 (d, 2H) |
| 212 | hydro-chloride | ¹HNMR (CD₃OD): 1.30-1.42 (m, 10H), 1.52-1.63 (m, 2H), 1.69-1.80 (m, 2H), 1.82-2.00 (m, 4H), 2.09 (tt, 2H), 3.16 (t, 2H), 3.54-3.60 (m, 4H), 3.87 (t, 2H), 3.97 (t, 2H), 4.13 (t, 2H), 6.99 (d, 2H), 7.19 (d, 2H), 7.66 (d, 2H) |
| 213 | — | ¹HNMR (CDCl₃): 1.16 (s, 9H), 1.55 (s, 9H), 1.74-1.87 (m, 4H), 1.88-2.02 (m, 6H), 3.59 (t, 2H), 3.69 (t, 2H), 3.93-4.04 (m, 8H), 6.78 (s, 2H), 6.85 (d, 2H), 6.89 (d, 2H), 7.41 (d, 2H), 7.82 (d, 2H) |
| 214 | hydro-chloride | ¹HNMR (CD₃OD): 1.84-2.03 (m, 8H), 2.06-2.14 (m, 2H), 3.54-3.62 (m, 4H), 3.93-4.03 (m, 4H), 4.10-4.20 (m, 4H), 7.02 (s, 2H), 7.13 (dd, 4H), 7.70 (d, 2H), 7.80 (d, 2H) |
| 215 | — | ¹HNMR (CDCl₃): 1.21-1.35 (m, 8H), 1.47-1.59 (m, 29H), 1.67-1.85 (m, 4H), 1.97 (tt, 2H), 3.80-3.90 (m, 4H), 3.95 (t, 2H), 4.01 (t, 2H), 6.74 (d, 1H), 6.77 (d, 1H), 6.88 (d, 2H), 7.84 (d, 2H). |
| 216 | hydro-chloride | ¹HNMR (CD₃OD): 1.31-1.45 (m, 8H), 1.59 (tt, 2H), 1.75 (tt, 2H), 1.83-2.03 (m, 4H), 3.16 (t, 2H), 3.88 (t, 2H), 3.98 (t, 2H), 4.15 (t, 2H), 6.78 (d, 1H), 7.01 (d, 1H), 7.13 (d, 2H), 7.80 (d, 2H). |
| 217 | — | ¹HNMR (CDCl₃): 1.65 (s, 9H), 1.20-1.30 (m, 12H), 1.45-1.54 (m, 45H), 1.64-1.70 (m, 2H), 1.91 (tt, 2H), 2.16 (tt, 2H), 3.49 (dd, 2H), 3.58 (dd, 2H), 3.69 (t, 2H), 3.73 (t, 2H), 3.88 (dd, 2H), 4.01 (t, 2H), 6.83 (d, 2H), 7.40 (d, 2H) |
| 218 | hydro-chloride | ¹HNMR (CD₃OD): 1.32-1.44 (m, 10H), 1.53-1.65 (m, 4H), 2.06-2.11 (m, 4H), 3.13-3.21 (m, 4H), 3.42 (t, 2H), 3.57 (t, 4H), 4.17 (t, 2H), 7.15 (d, 2H), 7.67 (d, 2H) |
| 219 | — | ¹HNMR (CDCl₃): 1.11 (s, 9H), 1.18-1.35 (m, 8H), 1.41-1.68 (m, 49H), 1.92 (tt, 2H), 3.35-3.42 (m, 2H), 3.46 (dd, 2H), 3.62 (t, 2H), 3.65-3.73 (m, 4H), 3.81 (dd, 2H), 4.53 (s, 2H), 7.29 (d, 2H), 7.44 (d, 2H). |
| 220 | hydro-chloride | ¹HNMR (CD₃OD): 1.33-1.44 (m, 8H), 1.53-1.64 (m, 4H), 2.12 (tt, 2H), 3.14-3.22 (m, 4H), 3.46 (t, 2H), 357-3.63 (m, 4H), 3.68 (t, 2H), 4.69 (s, 2H), 7.60 (d, 2H), 7.72 (d, 2H). |

In the table, Boc or BOC indicates a t-butoxycarbonyl group. In the table, "-" means that a compound was synthesized as free form.
TABLE 89
| Compound No. | Structure |
|---|---|
| 221 | 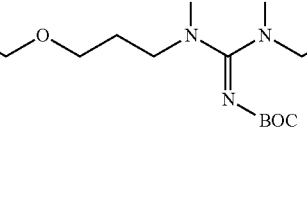 |
| 222 | 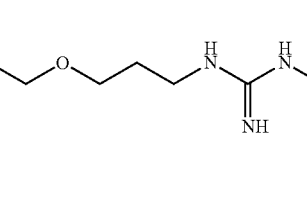 |
| 223 | 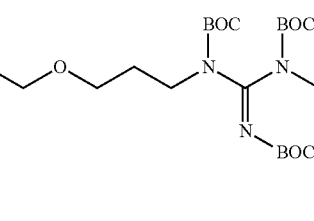 |
| 224 | 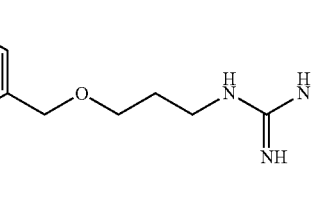 |
| 225 | 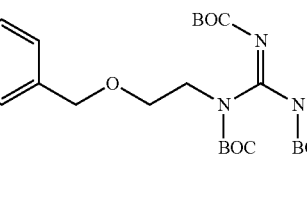 |
| 226 | 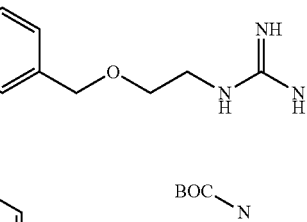 |
| 227 | 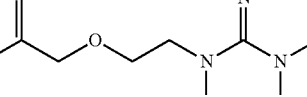 |

| | |
|---|---|
| 228 | 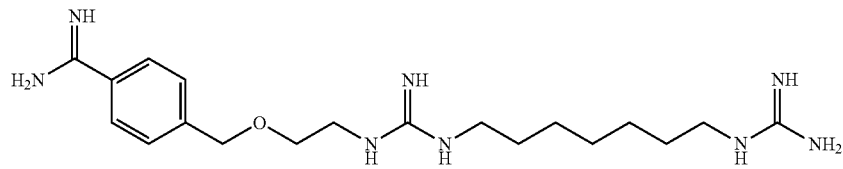 [SMILES: N=C(N)NCCCCCCCNC(=N)NCCOCc1ccc(C(=N)N)cc1] |
| 229 | 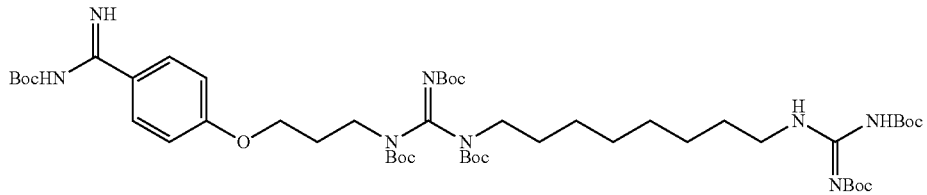 |
| 230 | 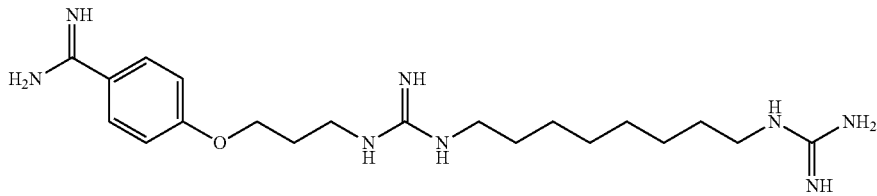 |

| Compound No. | Salt form | Physical property |
|---|---|---|
| 221 | — | ¹HNMR (CDCl₃): 1.11 (s, 9H), 1.22-1.35 (m, 8H), 1.43-1.69 (m, 49H), 1.88-2.01 (m, 4H), 3.39 (q, 2H), 3.44-3.51 (m, 4H), 3.59-3.66 (m, 4H), 3.71 (t, 2H), 4.51 (s, 2H), 7.28 (d, 2H), 7.44 (d, 2H). |
| 222 | hydrochloride | ¹HNMR (CD₃OD): 1.35-1.44 (m, 8H), 1.53-1.63 (m, 4H), 1.91 (tt, 2H), 2.12 (tt, 2H), 3.17 (t, 4H), 3.34 (t, 2H), 3.56-3.65 (m, 6H), 4.64 (s, 2H), 7.59 (d, 2H), 7.71 (d, 2H). |
| 223 | — | ¹HNMR (CDCl₃): 1.11 (s, 9H), 1.21-1.35 (m, 6H), 1.44-1.70 (m, 49H), 1.87-2.01 (m, 4H), 3.44-3.51 (m, 4H), 3.59-3.65 (m, 4H), 3.71 (t, 2H), 3.87 (dd, 2H), 4.51 (s, 2H), 7.28 (d, 2H), 7.44 (d, 2H). |
| 224 | hydrochloride | ¹HNMR (CD₃OD): 1.37-1.44 (m, 6H), 1.54-1.64 (m, 4H), 1.91 (tt, 2H), 2.12 (tt, 2H), 3.14-3.20 (m, 4H), 3.34 (t, 2H), 3.58-3.65 (m, 6H), 4.64 (s, 2H), 7.59 (d, 2H), 7.71 (d, 2H). |
| 225 | — | ¹HNMR (CDCl₃): 1.46 (s, 18H), 1.51 (s, 9H), 1.56 (s, 18H), 3.66 (t, 4H), 3.79 (t, 4H), 4.44 (s, 4H), 7.22 (d, 4H), 7.71 (d, 4H). |
| 226 | hydrochloride | Melting point 262-267° C. |
| 227 | — | ¹HNMR (CDCl₃): 0.88-1.08 (m, 6H), 1.38-1.58 (m, 58H), 3.51 (dd, 2H), 3.73 (t, 2H), 3.77 (dd, 2H), 3.87 (t, 2H), 4.54 (s, 2H), 7.37 (d, 2H), 8.00 (d, 2H). |
| 228 | hydrochloride | ¹HNMR (CD₃OD): 1.36-1.43 (m, 6H), 1.55-1.65 (m, 4H), 3.14-3.22 (m, 4H), 3.47 (t, 2H), 3.69 (t, 2H), 4.70 (s, 2H), 7.62 (d, 2H), 7.82 (d, 2H). |
| 229 | — | ¹HNMR (CDCl₃): 1.16-1.31 (m, 8H), 1.42-1.57 (m, 58H), 2.16 (tt, 2H), 3.30-3.40 (m, 2H), 3.47 (t, 2H), 3.73 (t, 2H), 4.06 (t, 2H), 6.90 (d, 2H), 7.87 (d, 2H). |
| 230 | hydrochloride | ¹HNMR (CD₃OD): 1.31-1.45 (m, 8H), 1.50-1.68 (m, 4H), 2.11 (tt, 2H), 3.10-3.27 (m, 4H), 3.44 (t, 2H), 4.20 (t, 2H), 7.17 (d, 2H), 7.81 (d, 2H). |

In the table, Boc or BOC indicates a t-butoxycarbonyl group. In the table, "-" means that a compound was synthesized as free form.

TABLE 90

| Compound No. | Structure |
|---|---|
| 231 | 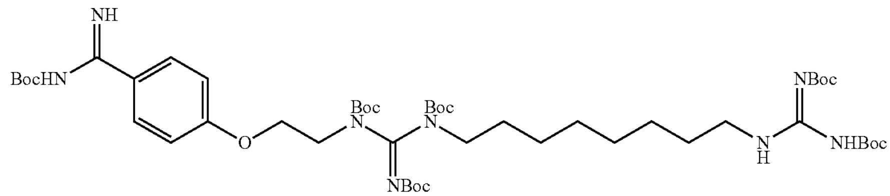 |
| 232 | 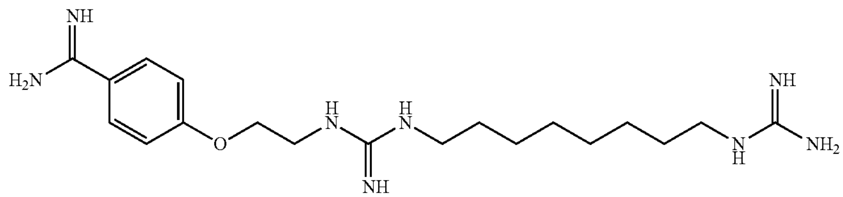 [SMILES: N=C(N)NCCCCCCCCNC(=N)NCCOc1ccc(C(=N)N)cc1] |
| 233 | 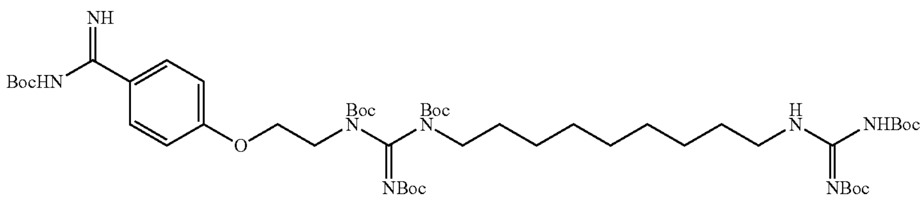 |
| 234 | 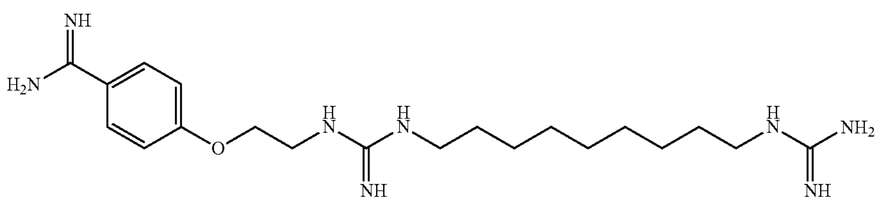 [SMILES: N=C(N)NCCCCCCCCCNC(=N)NCCOc1ccc(C(=N)N)cc1] |
| 235 | 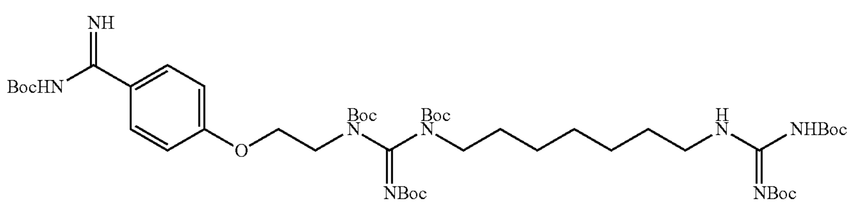 |
| 236 | 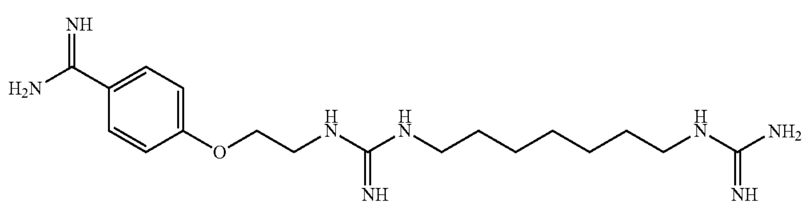 [SMILES: N=C(N)NCCCCCCCNC(=N)NCCOc1ccc(C(=N)N)cc1] |
| 237 | 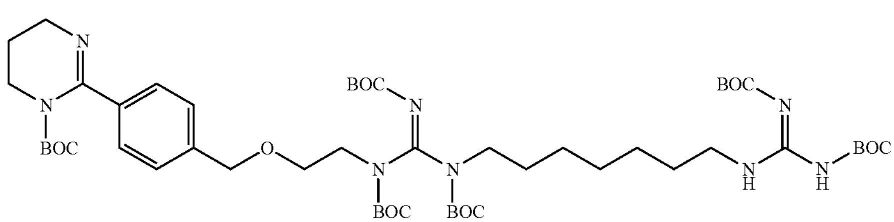 [SMILES: CC(C)(C)OC(=O)/N=C(/N(CCCCCCCN/C(=N\C(=O)OC(C)(C)C)NC(=O)OC(C)(C)C)C(=O)OC(C)(C)C)N(CCOCc1ccc(C2=NCCCN2C(=O)OC(C)(C)C)cc1)C(=O)OC(C)(C)C] |

TABLE 90-continued

| | Compound No. | Salt form | Physical property |
|---|---|---|---|
| | 231 | — | ¹HNMR (CDCl₃): 1.09 (m, 8H), 1.40-1.65 (m, 58H), 3.30 (td, 2H), 3.46 (t, 2H), 4.03 (t, 2H), 4.20 (t, 2H), 6.91 (d, 2H), 7.93 (d, 2H). |
| | 232 | hydro-chloride | ¹HNMR (CD₃OD): 1.31-1.46 (m, 8H), 1.50-1.67 (m, 4H), 3.17 (t, 2H), 3.21 (t, 2H), 3.69 (t, 2H), 4.25 (t, 2H), 7.19 (d, 2H), 7.45 (d, 2H). |
| | 233 | — | ¹HNMR (CDCl₃): 1.07 (m, 10H), 1.40-1.57 (m, 58H), 3.47 (t, 2H), 3.84 (t, 2H), 4.02 (t, 2H), 4.21 (t, 2H), 6.91 (d, 2H), 7.92 (d, 2H). |
| | 234 | hydro-chloride | ¹HNMR (CD₃OD): 1.30-1.45 (m, 20H), 1.51-1.67 (m, 4H), 3.16 (t, 2H), 3.21 (t, 2H), 3.69 (t, 2H), 4.25 (t, 2H), 7.19 (d, 2H), 7.82 (d, 2H). |
| | 235 | — | ¹HNMR (CDCl₃): 0.93 (m, 6H), 1.33-1.68 (m, 58H), 3.41 (t, 2H), 3.76 (t, 2H), 4.08 (t, 2H), 4.19 (t, 2H), 6.90 (d, 2H), 7.99 (d, 2H). |
| | 236 | hydro-chloride | ¹HNMR (CD₃OD): 1.34-1.47 (m, 6H), 1.53-1.68 (m, 4H), 3.11-3.27 (m, 4H), 3.67 (t, 2H), 4.25 (t, 2H), 7.19 (d, 2H), 7.83 (d, 2H). |
| | 237 | — | ¹HNMR (CDCl₃): 1.11 (s, 9H), 1.20-1.36 (m, 6H, 1.44-1.69 (m, 49H), 1.92 (tt, 2H), 3.47 (dd, 2H), 3.62 (t, 2H), 3.65-3.73 (m, 4H), 3.80 (t, 2H), 3.87 (t, 2H), 4.53 (s, 2H), 7.29 (d, 2H), 7.44 (d, 2H). |
| | 238 | hydro-chloride | ¹HNMR (CD₃OD): 1.37-1.45 (m, 6H), 1.54-1.65 (m, 4H), 2.12 (tt, 2H), 3.14-3.22 (m, 4H), 3.46 2H), 3.57-3.63 (m, 4H), 3.68 (t, 2H), 4.69 (s, 2H), 7.60 (d, 2H), 7.71 (d, 2H). |
| | 239 | — | ¹HNMR (CDCl₃): 1.14 (s, 9H), 1.20-1.38 (m, 8H), 1.44-1.52 (m, 47H), 1.62-1.70 (m, 2H), 1.88-1.95 (m, 2H), 3.34-3.42 (m, 2H), 3.45-3.54 (m, 2H), 3.58 (t, 2H), 3.68 (t, 2H), 3.96 (dd, 2H), 4.20 (dd, 2H), 6.85 (d, 2H), 7.40 (d, 2H) |
| | 240 | hydro-chloride | ¹HNMR (CD₃OD): 1.35-1.44 (m, 8H), 1.54-1.68 (m, 4H), 2.10 (tt, 2H), 3.14-3.24 (m, 4H), 3.58 (dd, 4H), 3.68 (t, 2H), 4.22 (t, 2H), 7.17 (d, 2H), 7.69 (d, 2H) |

In the table, Boc or BOC indicates a t-butoxycarbonyl group. In the table, "-" means that a compound was synthesized as free form.

TABLE 91

| Compound No. | Structure |
| --- | --- |
| 241 | 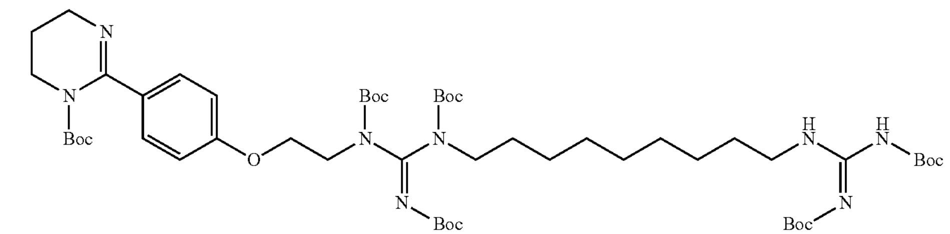 [SMILES: CC(C)(C)OC(=O)/N=C(\NCCCCCCCCCN(C(=O)OC(C)(C)C)/C(=N\C(=O)OC(C)(C)C)N(CCOc1ccc(C2=NCCCN2C(=O)OC(C)(C)C)cc1)C(=O)OC(C)(C)C)NC(=O)OC(C)(C)C] |
| 242 | 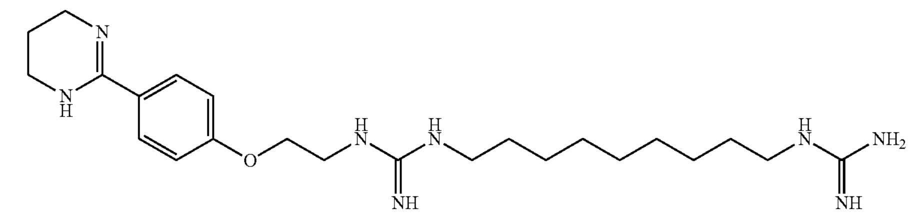 [SMILES: N=C(N)NCCCCCCCCCNC(=N)NCCOc1ccc(C2=NCCCN2)cc1] |
| 243 | 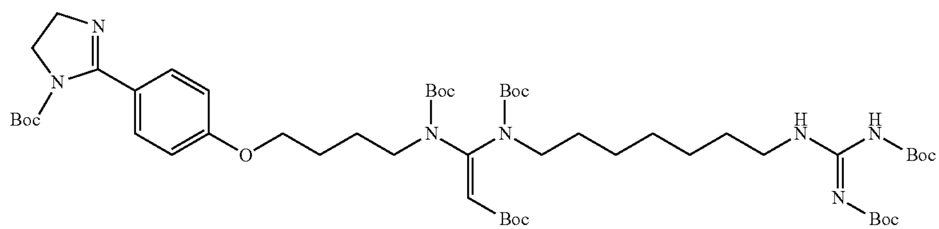 [SMILES: CC(C)(C)OC(=O)/C=C(\N(CCCCCCCN/C(=N/C(=O)OC(C)(C)C)NC(=O)OC(C)(C)C)C(=O)OC(C)(C)C)N(CCCCOc1ccc(C2=NCCN2C(=O)OC(C)(C)C)cc1)C(=O)OC(C)(C)C] |
| 244 | 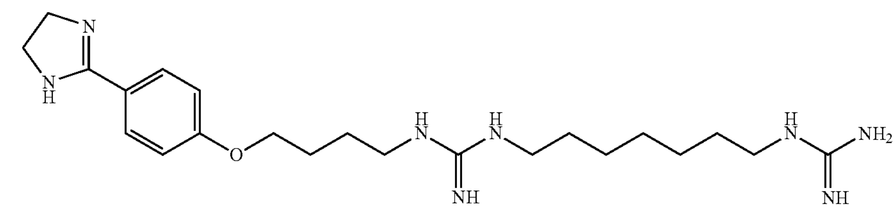 [SMILES: N=C(N)NCCCCCCCNC(=N)NCCCCOc1ccc(C2=NCCN2)cc1] |
| 245 | 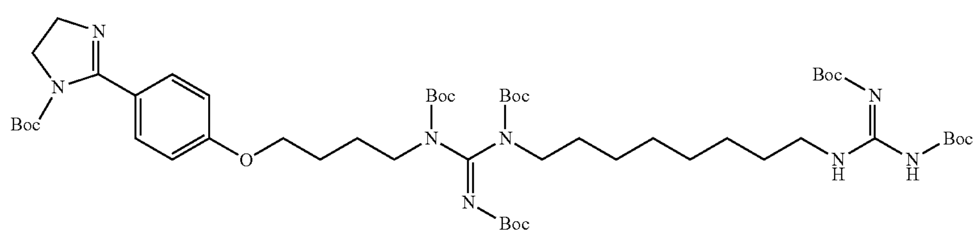 [SMILES: CC(C)(C)OC(=O)/N=C(\NCCCCCCCCN(C(=O)OC(C)(C)C)/C(=N\C(=O)OC(C)(C)C)N(CCCCOc1ccc(C2=NCCN2C(=O)OC(C)(C)C)cc1)C(=O)OC(C)(C)C)NC(=O)OC(C)(C)C] |
| 246 | 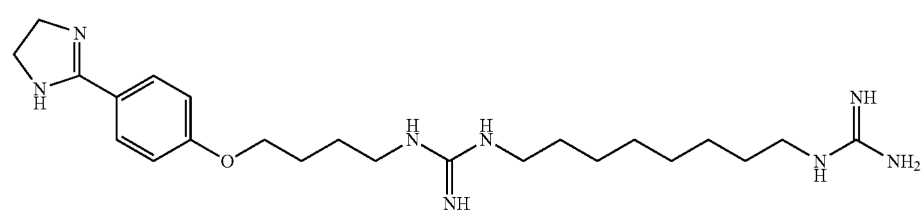 [SMILES: N=C(N)NCCCCCCCCNC(=N)NCCCCOc1ccc(C2=NCCN2)cc1] |

TABLE 91-continued

247 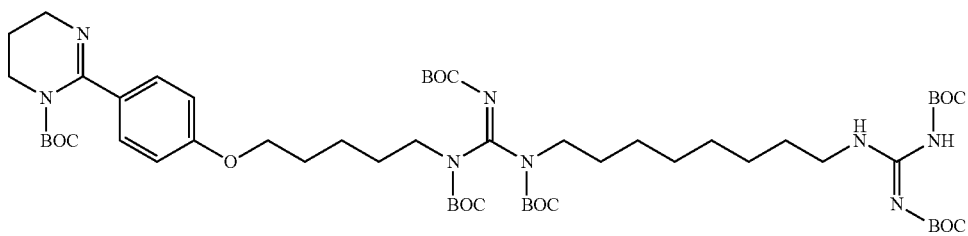 [SMILES: CC(C)(C)OC(=O)/N=C(/NCCCCCCCCN(C(=O)OC(C)(C)C)/C(=N/C(=O)OC(C)(C)C)N(CCCCCOc1ccc(C2=NCCCN2C(=O)OC(C)(C)C)cc1)C(=O)OC(C)(C)C)NC(=O)OC(C)(C)C]

248 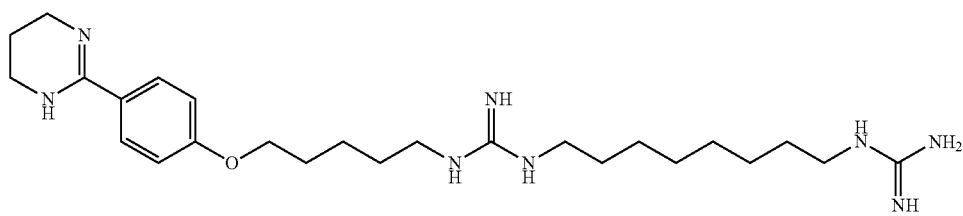 [SMILES: N=C(N)NCCCCCCCCNC(=N)NCCCCCOc1ccc(C2=NCCCN2)cc1]

249 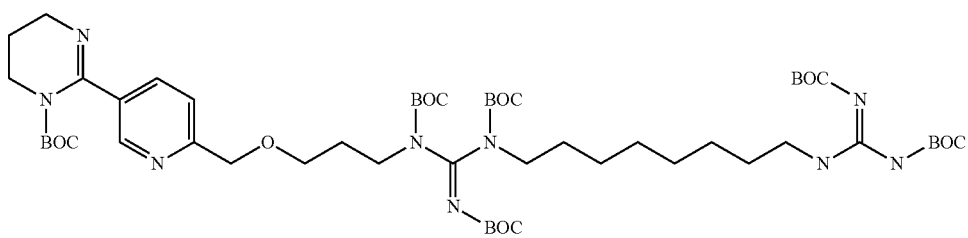 [SMILES: CC(C)(C)OC(=O)/N=C(\NCCCCCCCCN(C(=O)OC(C)(C)C)/C(=N\C(=O)OC(C)(C)C)N(CCCOCc1ccc(C2=NCCCN2C(=O)OC(C)(C)C)cn1)C(=O)OC(C)(C)C)NC(=O)OC(C)(C)C]

250 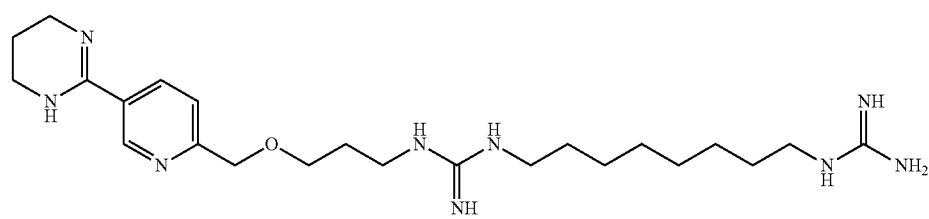 [SMILES: N=C(N)NCCCCCCCCNC(=N)NCCCOCc1ccc(C2=NCCCN2)cn1]

| Compound No. | Salt form | Physical property |
|---|---|---|
| 241 | — | $^1$HNMR (CDCl$_3$): 1.15 (s, 9H), 1.23-1.34 (m, 10H), 1.44-1.54 (m, 47H), 1.62-1.72 (m, 2H), 1.91 (tt, 2H), 3.45-3.53 (m, 2H), 3.59 (dd, 2H), 3.68 (t, 2H), 3.88 (dd, 2H), 3.95 (dd, 2H), 4.19 (t, 2H), 6.85 (d, 2H), 7.40 (d, 2H) |
| 242 | hydrochloride | $^1$HNMR (CD$_3$OD): 1.34-1.42 (m, 10H), 1.55-1.66 (m, 4H), 2.10 (tt, 2H), 3.14-3.22 (m, 4H), 3.58 (dd, 4H), 3.69 (t, 2H), 4.22 (dd, 2H), 7.17 (d, 2H), 7.69 (d, 2H) |
| 243 | — | $^1$HNMR (CDCl$_3$): 1.25-1.34 (m, 15H), 1.46-1.54 (m, 45H), 1.52-1.72 (m, 2H), 1.76-1.90 (m, 4H), 3.49 (dd, 2H), 3.57 (dd, 2H), 3.85-4.03 (m, 8H), 6.84 (d, 2H), 7.45 (d, 2H) |
| 244 | hydrochloride | $^1$HNMR (CD$_3$OD): 1.32-1.50 (m, 6H), 1.52-1.64 (m, 4H), 1.76-1.98 (m, 4H), 3.25-332 (m, 4H), 4.26-4.32 (m, 2H), 4.06 (s, 4H), 4.15 (t, 2H), 7.15 (d, 2H), 7.84 (d, 2H) |
| 245 | — | $^1$HNMR (CDCl$_3$): 1.25-1.34 (m, 18H), 1.46-1.54 (m, 45H), 1.55-1.64 (m, 4H), 1.76-1.90 (m, 4H), 3.39 (dd, 2H), 3.49 (dd, 2H), 3.58 (dd, 2H), 3.88-4.02 (m, 6H), 6.84 (d, 2H), 7.45 (d, 2H) |
| 246 | hydrochloride | $^1$HNMR (CD$_3$OD): 1.32-1.54 (m, 8H), 1.51-1.61 (m, 4H), 1.75-1.97 (m, 4H), 3.25-3.29 (m, 4H), 4.23-4.30 (m, 2H), 4.05 (s, 4H), 4.14 (t, 2H), 7.15 (d, 2H), 7.84 (d, 2H) |
| 247 | — | $^1$HNMR (CDCl$_3$): 1.15 (s, 9H), 1.21-1.36 (m, 8H), 1.40-1.85 (m, 55H), 1.91 (tt, 2H), 3.39 (q, 2H), 3.44-3.56 (m, 4H), 3.59 (t, 2H), 3.69 (t, 2H), 3.96 (t, 2H), 6.84 (d, 2H), 7.41 (d, 2H) |

TABLE 91-continued

| | | |
|---|---|---|
| 248 | hydro-chloride | $^1$HNMR (CD$_3$OD): 1.34-1.45 (m, 8H), 1.52-1.73 (m, 8H), 1.85 (tt, 2H), 2.09 (tt, 2H), 3.13-3.25 (m, 6H), 3.55-3.61 (m, 4H), 4.10 (t, 2H), 7.11 (d, 2H), 7.66 (d, 2H). |
| 249 | — | $^1$HNMR (CDCl$_3$): 1.16 (s, 9H), 1.22-1.33 (m, 8H), 1.44-1.70 (m, 49H), 1.91-2.06 (m, 4H), 3.48 (t, 2H), 3.59 (t, 2H), 3.64-3.69 (m, 4H), 3.74 (t, 2H), 3.38 (t, 2H), 4.64 (s, 2H), 7.43 (d, 1H), 7.79 (dd, 1H), 8.61 (d, 1H). |
| 250 | hydro-chloride | $^1$HNMR (CD$_3$OD): 1.34-1.44 (m, 8H), 1.54-1.65 (m, 4H), 1.93 (tt, 2H), 2.12 (tt, 2H), 3.14-3.22 (m, 4H), 3.40 (t, 2H), 3.63-3.69 (m, 4H), 3.80 (t, 2H), 4.98 (s, 2H), 8.12 (d, 1H), 8.66 (dd, 1H), 9.13 (d, 1H). |

In the table, Boc or BOC indicates a t-butoxycarbonyl group. In the table, "-" means that a compound was synthesized as free form.

TABLE 92

| Compound No. | Structure |
|---|---|
| 251 | 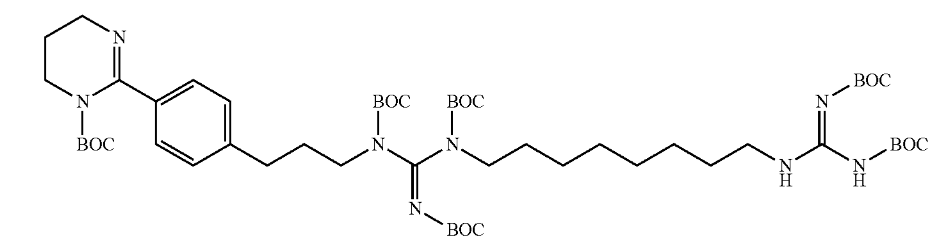 [SMILES: CC(C)(C)OC(=O)/N=C(/NCCCCCCCCN(C(=O)OC(C)(C)C)/C(=N\C(=O)OC(C)(C)C)N(CCCc1ccc(C2=NCCCN2C(=O)OC(C)(C)C)cc1)C(=O)OC(C)(C)C)NC(=O)OC(C)(C)C] |
| 252 | 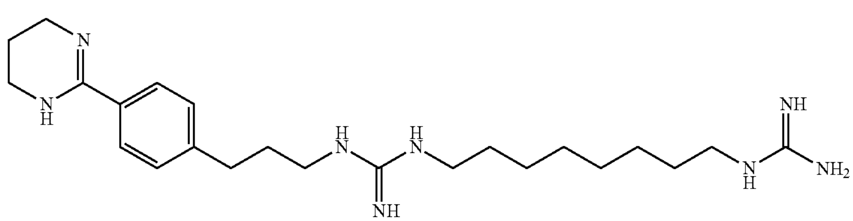 [SMILES: N=C(N)NCCCCCCCCNC(=N)NCCCc1ccc(C2=NCCCN2)cc1] |
| 253 | 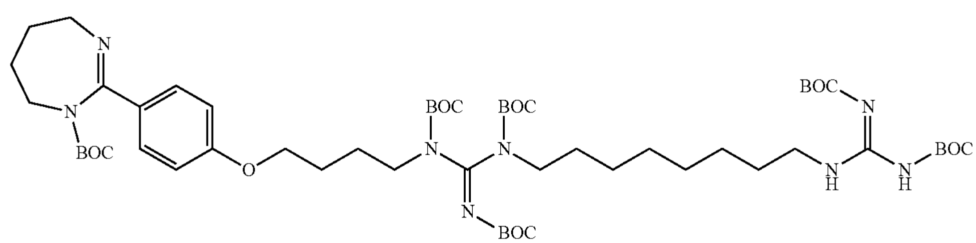 [SMILES: CC(C)(C)OC(=O)/N=C(\NCCCCCCCCN(C(=O)OC(C)(C)C)/C(=N\C(=O)OC(C)(C)C)N(CCCCOc1ccc(C2=NCCCCN2C(=O)OC(C)(C)C)cc1)C(=O)OC(C)(C)C)NC(=O)OC(C)(C)C] |
| 254 | 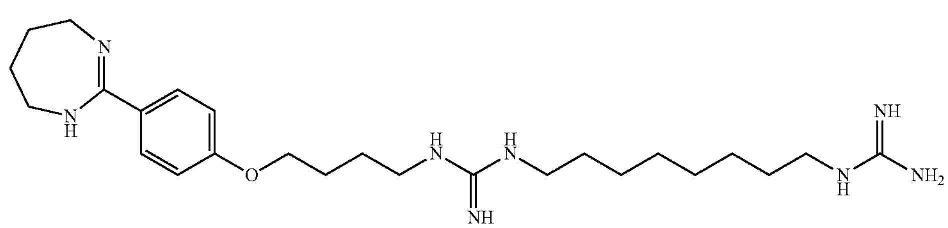 [SMILES: N=C(N)NCCCCCCCCNC(=N)NCCCCOc1ccc(C2=NCCCCN2)cc1] |

TABLE 92-continued
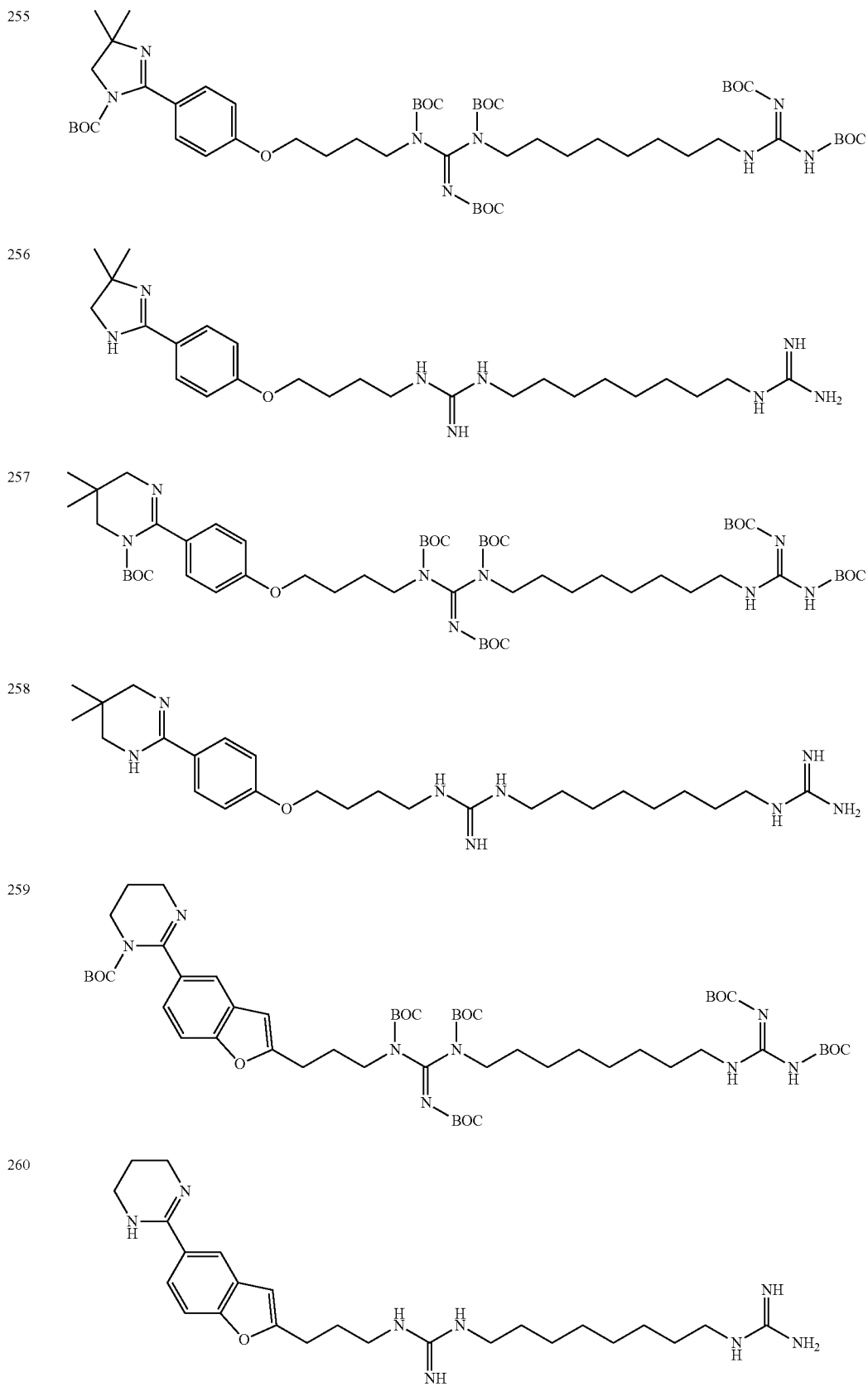

TABLE 92-continued

| Compound No. | Salt form | Physical property |
|---|---|---|
| 251 | — | $^1$HNMR (CDCl$_3$): 1.10 (s, 9H), 1.19-1.38 (m, 8H), 1.42-1.69 (m, 49H), 1.87-2.04 (m, 4H), 2.64 (t, 2H), 3.39 (tt, 2H), 3.47 (dd, 2H), 3.55 (dd, 2H), 3.60 (t, 2H), 3.70 (t, 2H), 7.16 (d, 2H), 7.38 (d, 2H). |
| 252 | trifluoro-acetate | $^1$HNMR (CD$_3$OD): 1.10 (s, 9H), 1.19-1.38 (m, 8H), 1.42-1.69 (m, 49H), 1.87-2.04 (m, 4H), 2.64 (t, 2H), 3.39 (tt, 2H), 3.47 (dd, 2H), 3.55 (dd, 2H), 3.60 (t, 2H), 3.70 (t, 2H), 7.16 (d, 2H), 7.38 (d, 2H) |
| 253 | — | $^1$HNMR (CD$_3$OD): 1.06-1.89 (m, 74H), 3.37-4.08 (m, 12H), 6.95 (d, 2H), 7.55 (d, 2H) |
| 254 | hydro-chloride | $^1$HNMR (CD$_3$OD): 1.34-1.45 (m, 8H), 1.54-1.65 (m, 4H), 1.74-1.93 (m, 4H), 2.04-2.10 (m, 4H), 3.14-3.21 (m, 4H), 3.28 (t, 2H), 3.69-3.77 (m, 4H), 4.13 (t, 2H), 7.11 (d, 2H), 7.63 (d, 2H). |
| 255 | — | $^1$HNMR (CD$_3$OD): 1.26-1.38 (m, 23H), 1.43-1.69 (m, 45H), 1.75-1.89 (m, 4H), 3.49 (t, 2H), 3.58 (t, 2H), 3.72 (s, 2H), 3.85 (t, 2H), 4.04 (t, 2H), 3.73 (t, 2H), 338 (t, 2H), 6.94 (d, 2H), 7.41 (d, 2H). |
| 256 | hydro-chloride | $^1$HNMR (CD$_3$OD): 1.34-1.45 (m, 8H), 1.53 (s, 6H), 1.55-1.65 (m, 4H), 1.75-1.94 (m, 4H), 3.14-3.21 (m, 4H), 3.28 (t, 2H), 3.82 (s, 2H), 4.16 (t, 2H), 7.16 (d, 2H), 7.85 (d, 2H). |
| 257 | — | $^1$HNMR (CD$_3$OD): 1.00 (s, 6H), 1.13 (s, 9H), 1.25-1.38 (m, 8H), 1.44-1.69 (m, 49H), 3.45 (s, 2H), 3.46-3.53 (m, 2H), 3.58 (t, 2H), 3.85 (t, 2H), 4.04 (t, 2H), 3.73 (t, 2H), 3.88 (t, 2H), 6.93 (d, 2H), 7.36 (d, 2H). |
| 258 | hydro-chloride | $^1$HNMR (CD$_3$OD): 1.13 (s, 6H), 1.35-1.43 (m, 8H), 1.54-1.65 (m, 4H), 1.75-1.93 (m, 4H), 3.14-3.21 (m, 4H), 3.25-3.29 (m, 6H), 4.13 (t, 2H), 7.13 (d, 2H), 7.69 (d, 2H) |
| 259 | — | $^1$HNMR (CDCl$_3$): 1.06 (s, 9H), 1.23-1.33 (m, 8H), 1.42-1.69 (m, 53H), 1.94 (tt, 2H), 2.12 (tt, 2H), 2.79 (t, 2H), 3.48 (t, 2H), 3.59-3.65 (m, 4H), 3.73 (t, 2H), 3.88 (t, 2H), 6.40 (s, 1H), 7.30-7.38 (m, 2H), 7.51 (d, 1H). |
| 260 | hydro-chloride | $^1$HNMR (CD$_3$OD): 1.33-1.46 (m, 8H), 1.53-1.64 (m, 4H), 2.06 (tt, 2H), 2.13 (tt, 2H), 2.94 (t, 2H), 3.12-3.21 (m, 4H), 3.58-3.64 (m, 4H), 6.73 (s, 1H), 7.56 (dd, 1H), 7.63 (d, 1H), 7.92 (d, 1H). |

In the table, Boc or BOC indicates a t-butoxycarbonyl group. In the table, "-" means that a compound was synthesized as free form.

TABLE 93

| Compound No. | Structure |
|---|---|
| 261 | ![structure 261] |
| 262 | ![structure 262] |

TABLE 93-continued
263 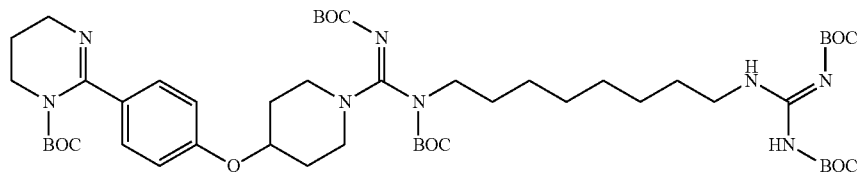 [SMILES: CC(C)(C)OC(=O)/N=C(\NCCCCCCCCN(C(=O)OC(C)(C)C)/C(=N/C(=O)OC(C)(C)C)N1CCC(Oc2ccc(C3=NCCCN3C(=O)OC(C)(C)C)cc2)CC1)NC(=O)OC(C)(C)C]
264 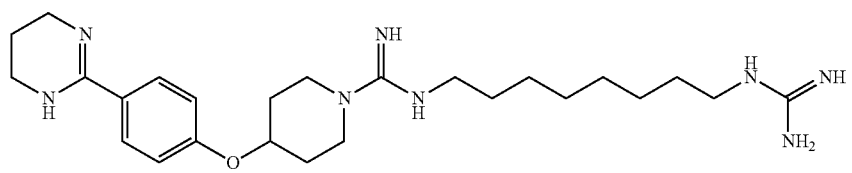 [SMILES: N=C(N)NCCCCCCCCNC(=N)N1CCC(Oc2ccc(C3=NCCCN3)cc2)CC1]
265 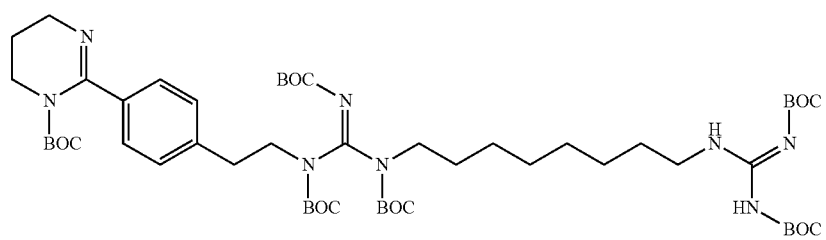 [SMILES: CC(C)(C)OC(=O)/N=C(/N(CCCCCCCCN/C(=N\C(=O)OC(C)(C)C)NC(=O)OC(C)(C)C)C(=O)OC(C)(C)C)N(CCc1ccc(C2=NCCCN2C(=O)OC(C)(C)C)cc1)C(=O)OC(C)(C)C]
266 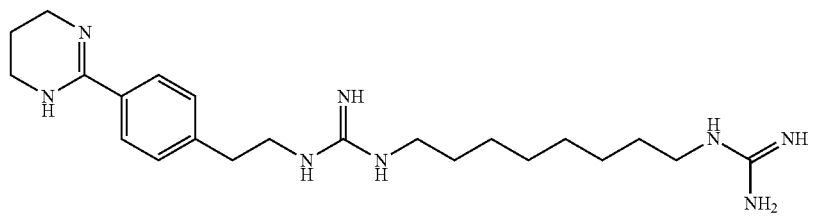 [SMILES: N=C(N)NCCCCCCCCNC(=N)NCCc1ccc(C2=NCCCN2)cc1]
267 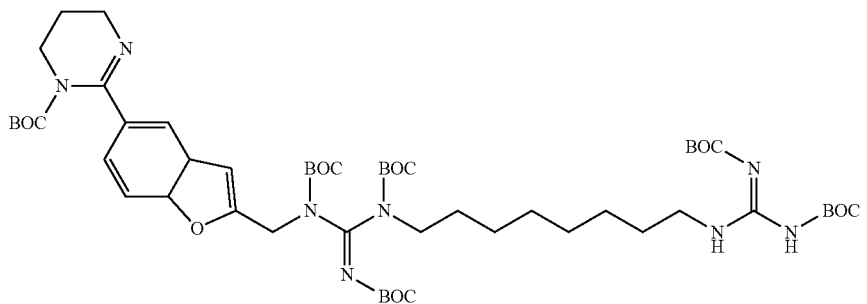 [SMILES: CC(C)(C)OC(=O)/N=C(\NCCCCCCCCN(C(=O)OC(C)(C)C)/C(=N\C(=O)OC(C)(C)C)N(CC1=CC2C=C(C3=NCCCN3C(=O)OC(C)(C)C)C=CC2O1)C(=O)OC(C)(C)C)NC(=O)OC(C)(C)C]
268 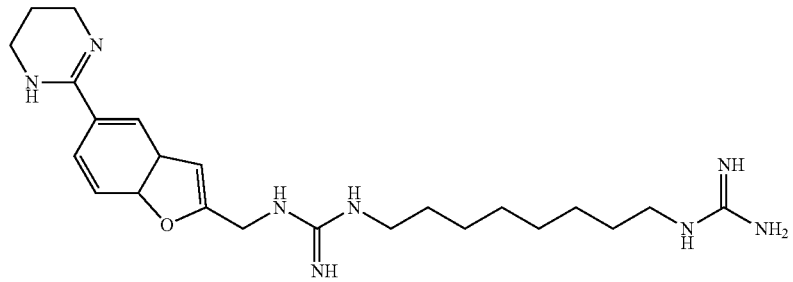 [SMILES: N=C(N)NCCCCCCCCNC(=N)NCC1=CC2C=C(C3=NCCCN3)C=CC2O1]

TABLE 93-continued

269 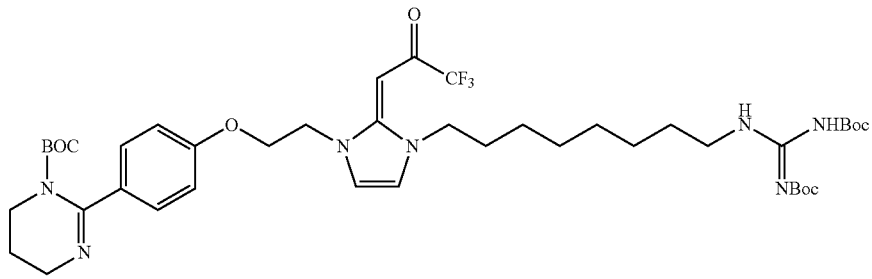

270 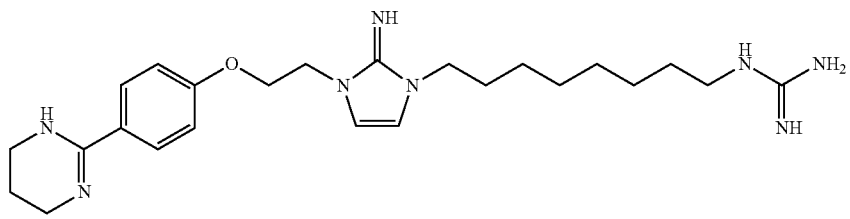 [SMILES: N=C(N)NCCCCCCCCn1ccn(CCOc2ccc(C3=NCCCN3)cc2)c1=N]

| | Compound No. | Salt form | Physical property |
|---|---|---|---|
| | 261 | — | ¹HNMR (CDCl₃): 1.11 (s, 9H), 1.14-1.29 (m, 8H), 1.38 (s, 9H), 1.45-1.62 (m, 40H), 1.92 (tt, 2H), 3.30 (m, 2H), 3.61 (t, 2H), 3.70 (t, 2H), 3.86 (t, 2H), 4.86 (s, 2H), 7.35 (d, 2H), 7.43 (d, 2H) |
| | 262 | hydro-chloride | ¹HNMR (CD₃OD): 1.34-1.45 (m, 8H), 1.54-1.67 (m, 4H), 2.12 (tt, 2H), 3.17 (t, 2H), 3.22 (t, 2H), 3.60 (t, 4H), 4.57 (s, 2H), 7.57 (d, 2H), 7.75 (d, 2H). |
| | 263 | — | ¹HNMR (CDCl₃): 1.15 (s, 9H), 1.20-1.39 (m, 8H), 1.45-2.10 (m, 46H), 3.35-3.90 (m, 12H), 4.61 (m, 1H), 6.88 (d, 2H), 7.43 (d, 2H) |
| | 264 | hydro-chloride | ¹HNMR (CD₃OD): 1.35-1.44 (m, 8H), 1.50-1.69 (m, 4H), 1.79-1.99 (m, 2H), 2.05-2.16 (m, 4H), 3.13-3.20 (m, 2H), 3.21-3.29 (m, 2H), 3.45-3.53 (m, 2H), 3.55-3.60 (m, 4H), 3.65-3.74 (m, 2H), 4.81-4.89 (m, 1H), 7.18 (d, 2H), 7.68 (d, 2H) |
| | 265 | — | ¹HNMR (CDCl₃): 1.09 (s, 9H), 1.22-1.35 (m, 8H), 1.44-1.69 (m, 49H), 1.92 (tt, 2H), 2.99 (dd, 2H), 3.53 (t, 2H), 3.58-3.68 (m, 4H), 3.70 (t, 2H), 3.88 (t, 2H), 7.19 (d, 2H), 7.40 (d, 2H) |
| | 266 | hydro-chloride | ¹HNMR (CD₃OD): 1.33-1.43 (m, 8H), 1.50-1.64 (m, 4H), 2.11 (tt, 2H), 3.00 (t, 2H), 3.10-3.20 (m, 4H), 3.51 (t, 2H), 3.56-3.62 (m, 4H), 7.52 (d, 2H), 7.68 (d, 2H) |
| | 267 | — | ¹HNMR (CDCl₃): 1.05 (s, 9H), 1.10-1.65 (m, 57H), 1.94 (tt, 2H), 3.33-3.43 (m, 4H), 3.63 (t, 2H), 3.73 (t, 2H), 4.96 (s, 2H), 6.73 (s, 1H), 7.34-7.42 (m, 2H), 7.66 (d, 1H) |
| | 268 | hydro-chloride | ¹HNMR (CDCl₃): 1.17 (s, 9H), 1.22-1.37 (m, 8H), (m, 4H), 2.13 (tt, 2H), 3.13-3.19 (m, 2H), 3.20-3.27 (m, 2H), 3.59-3.65 (m, 4H), 4.66-4.69 (m, 2H), 6.97 (s, 1H), 7.63-7.73 (m, 2H). 8.00 (d, 1H) |
| | 269 | — | ¹HNMR (CDCl₃): 1.17 (s, 9H), 1.23-1.37 (m, 8H), 1.44-1.61 (m, 20H), 1.67-1.80 (m, 2H), 1.92 (tt, 2H), 3.60 (t, 2H), 3.69 (t, 2H), 3.81-3.93 (m, 4H), 4.25 (t, 2H), 4.32 (t, 2H), 6.73 (d, 1H), 6.65 (d, 2H), 6.99 (d, 1H), 7.43 (d, 2H). |
| | 270 | hydro-chloride | ¹HNMR (CD₃OD): 1.30-1.43 (m, 8H), 1.57 (tt, 2H), 1.74 (tt, 2H), 2.09 (tt, 2H), 3.16 (t, 2H), 3.54-3.61 (m, 4H), 3.88 (t, 2H), 4.32-4.43 (m, 4H), 6.98 (d, 1H), 7.06 (d, 1H), 7.13 (d, 2H), 7.69 (d, 2H). |

In the table, Boc or BOC indicates a t-butoxycarbonyl group. In the table, "-" means that a compound was synthesized as free form.

TABLE 94

| Compound No. | Structure |
|---|---|
| 271 | 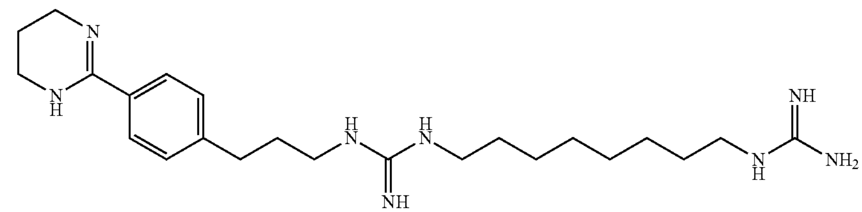 [SMILES: N=C(N)NCCCCCCCCNC(=N)NCCCc1ccc(C2=NCCCN2)cc1] |
| 272 | 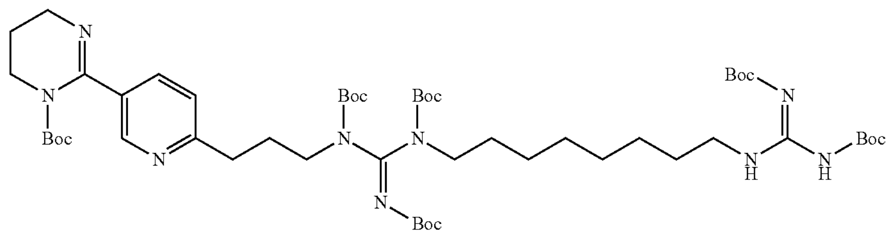 [SMILES: CC(C)(C)OC(=O)/N=C(\NCCCCCCCCN(C(=O)OC(C)(C)C)/C(=N\C(=O)OC(C)(C)C)N(CCCc1ccc(C2=NCCCN2C(=O)OC(C)(C)C)cn1)C(=O)OC(C)(C)C)NC(=O)OC(C)(C)C] |
| 273 | 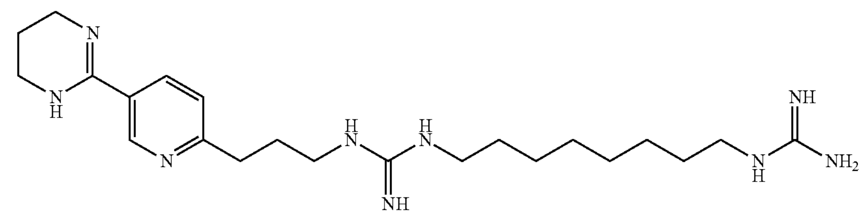 [SMILES: N=C(N)NCCCCCCCCNC(=N)NCCCc1ccc(C2=NCCCN2)cn1] |
| 274 | 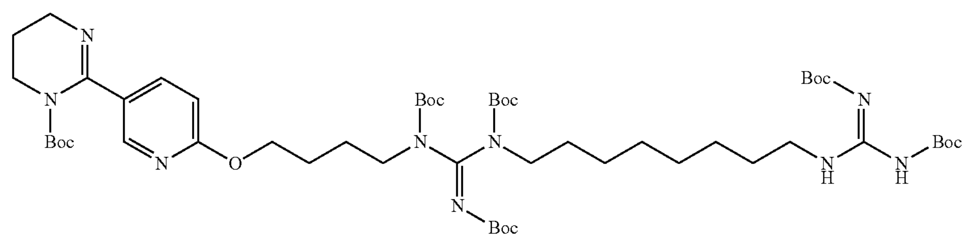 [SMILES: CC(C)(C)OC(=O)/N=C(\NCCCCCCCCN(C(=O)OC(C)(C)C)/C(=N\C(=O)OC(C)(C)C)N(CCCCOc1ccc(C2=NCCCN2C(=O)OC(C)(C)C)cn1)C(=O)OC(C)(C)C)NC(=O)OC(C)(C)C] |
| 275 | 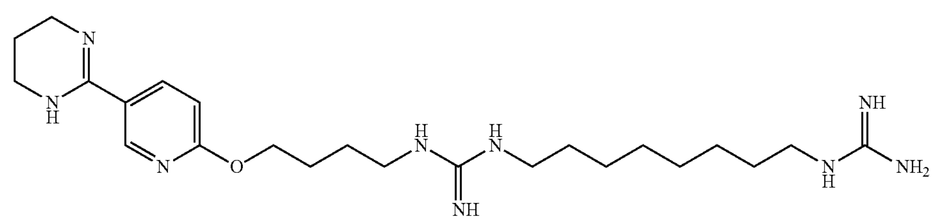 [SMILES: N=C(N)NCCCCCCCCNC(=N)NCCCCOc1ccc(C2=NCCCN2)cn1] |
| 276 | 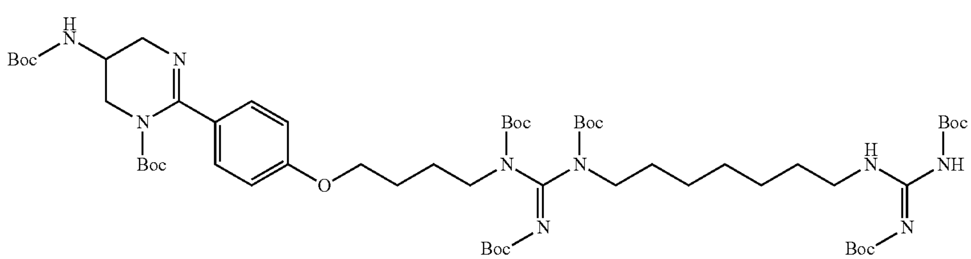 [SMILES: CC(C)(C)OC(=O)/N=C(/N(CCCCCCCN/C(=N\C(=O)OC(C)(C)C)NC(=O)OC(C)(C)C)C(=O)OC(C)(C)C)N(CCCCOc1ccc(C2=NCC(NC(=O)OC(C)(C)C)CN2C(=O)OC(C)(C)C)cc1)C(=O)OC(C)(C)C] |

TABLE 94-continued

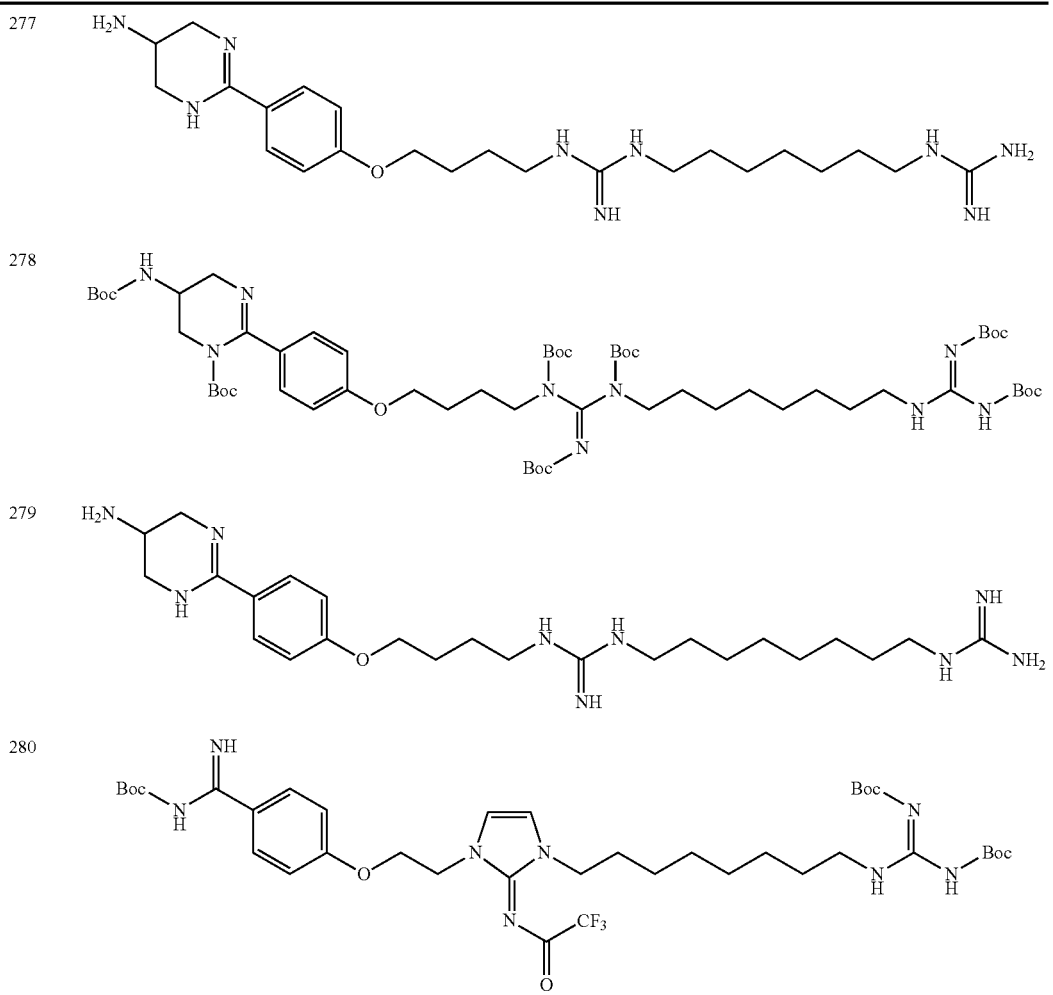

| Compound No. | Salt form | Physical property |
|---|---|---|
| 271 | hydrochloride | ¹HNMR (CD$_3$OD): 1.32-1.46 (m, 8H), 1.53-1.67 (m, 4H), 1.93 (tt, 2H), 2.11 (tt, 2H), 2.80 (t, 2H), 3.12-3.22 (m, 4H), 3.25 (t, 2H), 3.54-3.63 (m, 4H), 7.49 (d, 2H), 7.65 (d, 2H). |
| 272 | — | ¹HNMR (CDCl$_3$): 1.14 (s, 9H), 1.21-1.34 (m, 8H), 1.45-1.57 (m, 47H), 1.61-1.70 (m, 2H), 1.94 (dt, 2H), 2.08 (dt, 2H), 2.83 (dd, 2H), 3.46 (dd, 2H), 3.56-3.66 (m, 4H), 3.73 (dd, 2H), 3.87 (dd, 2H), 7.21 (d, 1H), 7.69 (dd, 1H), 8.57 (d, 1H) |
| 273 | hydrochloride | ¹HNMR (CD$_3$OD): 1.33-1.44 (m, 10H), 1.54-1.67 (m, 4H), 2.05 (dt, 2H), 2.14 (dt, 2H), 3.02 (dd, 2H), 3.13-3.22 (m, 4H), 3.60-3.65 (m, 4H), 7.69 (d, 1H), 8.20 (dd, 1H), 8.88 (d, 1H) |
| 274 | — | ¹HNMR (CDCl$_3$): 1.20 (s, 9H), 1.21-1.35 (m, 8H), 1.44-1.58 (m, 47H), 1.62-1.66 (m, 2H), 1.74-1.85 (m, 4H), 1.93 (dt, 2H), 3.49 (dd, 2H), 3.58 (dd, 2H), 3.62 (t, 2H), 3.71 (t, 2H), 3.88 (dd, 2H), 4.30 (dd, 2H), 3.68 (d, 1H), 7.68 (dd, 1H), 8.22 (d, 1H) |
| 275 | hydrochloride | ¹HNMR (CD$_3$OD): 1.35-1.44 (m, 8H), 1.53-1.65 (m, 4H), 1.72-1.79 (m, 2H), 1.84-1.90 (m, 2H), 2.11 (dt, 2H), 3.17 (dd, 4H), 3.27 (dd, 2H), 3.59 (dd, 4H), 4.43 (t, 2H), 6.96 (d, 1H), 7.95 (dd, 1H), 8.52 (d, 1H) |
| 276 | — | ¹HNMR (CDCl$_3$): 1.17 (s, 9H), 1.23-1.36 (m, 6H), 1.41-1.53 (m, 58H), 1.62-1.71 (m, 2H), 1.75-1.87 (m, 4H), 3.46-3.61 (m, 3H), 3.69-3.74 (m, 1H), 3.80-389 (m, 4H), 3.98 (dd, 2H), 4.68-4.73 (m, 1H), 6.84 (d, 2H), 7.42 (d, 2H) |

TABLE 94-continued

| | | |
|---|---|---|
| 277 | hydro-chloride | $^1$HNMR (CD$_3$OD): 1.36-1.45 (m, 6H), 1.55-1.65 (m, 4H), 1.75-1.94 (m, 4H), 3.14-3.24 (m, 4H), 3.44 (t, 2H), 3.77 (dd, 2H), 3.96 (dd, 2H), 4.11-4.17 (m, 3H), 7.14 (d, 2H), 7.76 (d, 2H) |
| 278 | — | $^1$HNMR (CDCl$_3$): 1.17 (s, 9H), 1.21-1.37 (m, 8H), 1.39-1.55 (m, 58H), 1.61-1.71 (m, 2H), 1.75-1.85 (m, 4H), 3.40-3.59 (m, 3H), 3.67-3.77 (m, 1H), 3.80-3.89 (m, 4H), 3.99 (dd, 2H), 4.69-4.72 (m, 1H), 6.84 (d, 2H), 7.43 (d, 2H) |
| 279 | hydro-chloride | $^1$HNMR (CD$_3$OD): 1.36-1.43 (m, 8H), 1.55-1.65 (m, 4H), 1.75-1.94 (m, 4H), 3.29-3.34 (m, 4H), 3.44 (dd, 2H), 3.74 (dd, 2H), 3.95 (dd, 2H), 4.12-4.19 (m, 3H), 7.15 (d, 2H), 7.76 (d, 2H) |
| 280 | — | $^1$HNMR (CDCl$_3$): 1.19-1.31 (m, 8H), 1.47-1.53 (m, 29H), 1.69-1.76 (m, 2H), 3.82-3.88 (m, 4H), 4.25 (dd, 2H), 4.35 (dd, 2H), 6.72 (d, 1H), 6.89 (d, 2H), 6.98 (d, 1H), 7.85 (d, 2H) |

In the table, Boc or BOC indicates a t-butoxycarbonyl group. In the table, "-" means that a compound was synthesized as free form.

TABLE 95

| Compound No. | Structure |
|---|---|
| 281 | 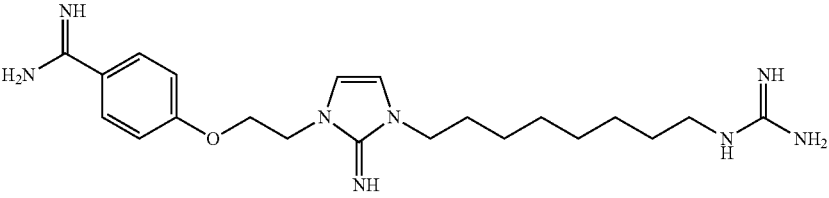 [SMILES: N=C(N)NCCCCCCCCn1ccn(CCOc2ccc(C(=N)N)cc2)c1=N] |
| 282 | 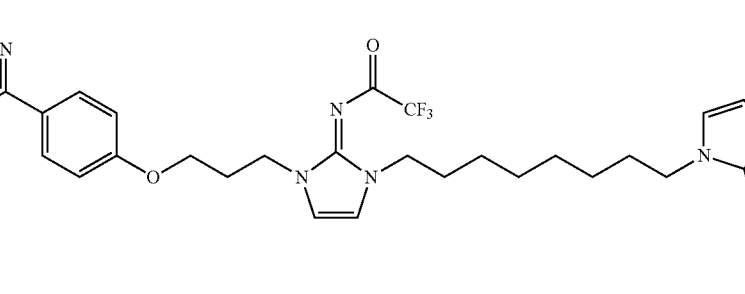 |
| 283 | 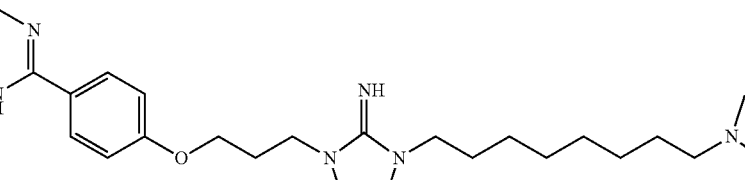 |
| 284 | 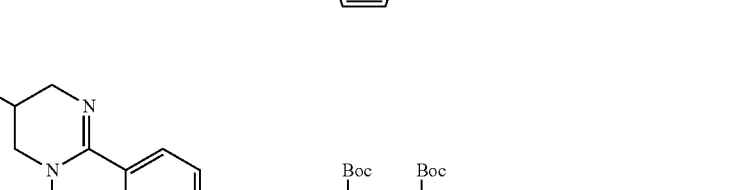 |

TABLE 95-continued
| | | |
|---|---|---|
| 285 | 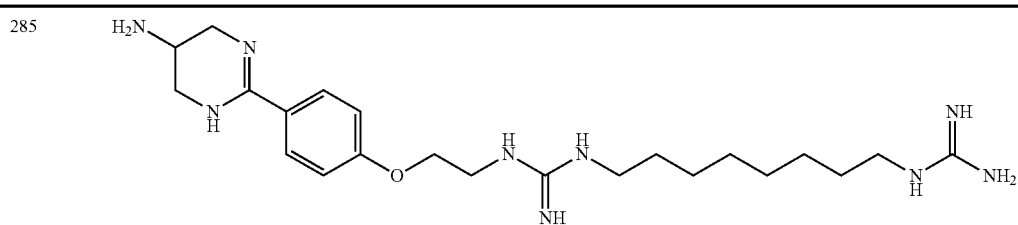 | |
| 286 | 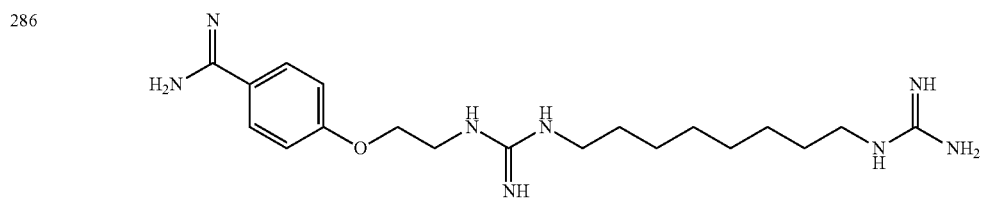 | |
| 287 | 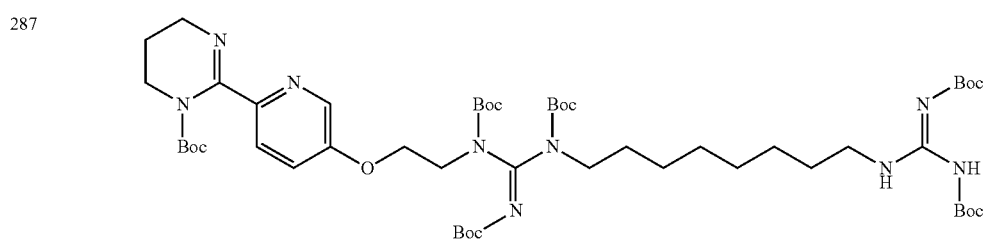 | |
| 288 | 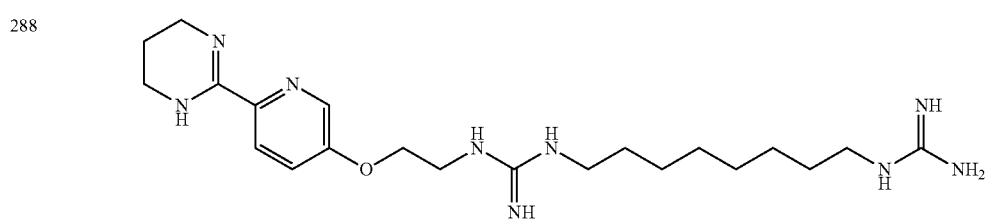 | |
| 289 | 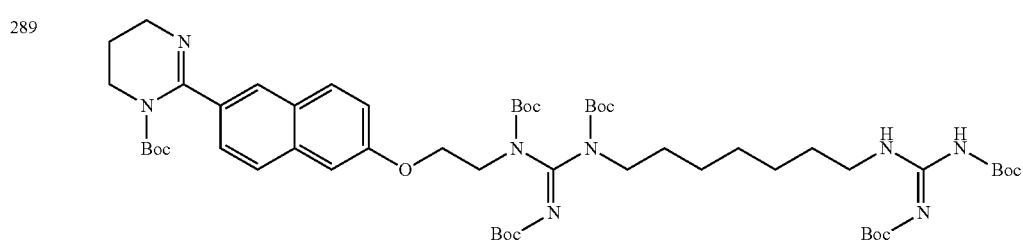 | |
| 290 | 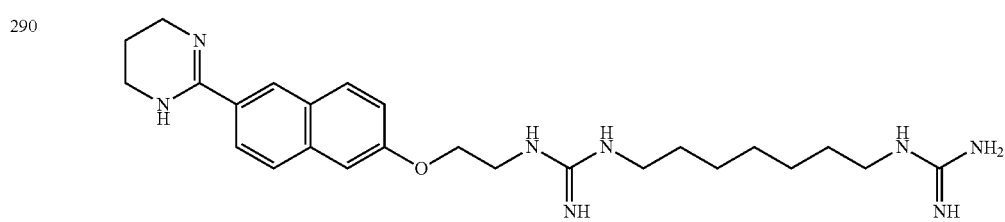 | |
| Compound No. | Salt form | Physical property |
|---|---|---|
| 281 | hydro-chloride | $^1$HNMR (CD$_3$OD): 1.34-1.39 (m, 8H), 1.54-1.61 (m, 2H), 1.70-1.79 (m, 2H), 3.15 (dd, 2H), 3.87 (dd, 2H), 4.35-4.42 (m, 4H), 6.98 (d, 1H), 7.06 (d, 1H), 7.14 (d, 2H), 7.81 (d, 2H) |
| 282 | — | $^1$HNMR (CDCl$_3$): 1.16 (s, 9H), 1.24-1.36 (m, 8H), 1.69-1.79 (m, 4H), 1.92 (dt, 2H), 2.24 (tt, 2H), 3.60 (dd, 2H), 3.70 (dd, 2H), 3.83 (dd, 2H), 3.95 (dd, 2H), 3.98 (dd, 2H), 4.12 (dd, 2H), 6.67-6.71 (m, 3H), 6.80 (d, 1H), 6.83 (d, 2H), 7.42 (d, 2H) |

TABLE 95-continued

| | | |
|---|---|---|
| 283 | hydro-chloride | $^1$HNMR (CD$_3$OD): 1.34-1.39 (m, 8H), 1.71-1.78 (m, 4H), 2.09 (dt, 2H), 2.27 (dt, 2H), 3.57 (dd, 4H), 3.85 (dd, 4H), 4.09-4.17 (m, 4H), 6.84 (d, 1H), 6.89 (d, 1H), 7.14 (d, 2H), 7.67 (d, 2H) |
| 284 | — | $^1$HNMR (CDCl$_3$): 1.17 (s, 9H), 1.20-1.37 (m, 8H), 1.42-1.55 (m, 54H), 1.60-1.68 (m, 4H), 3.38 (dd, 2H), 3.46-3.61 (m, 2H), 3.67-3.76 (m, 1H), 3.86 (dd, 2H), 3.96 (dd, 2H), 3.98-4.07 (m, 1H), 4.21 (dd, 2H), 4.71-4.80 (m, 1H), 6.85 (d, 2H), 7.45 (d, 2H) |
| 285 | hydro-chloride | $^1$HNMR (CD$_3$OD): 1.36-1.44 (m, 8H), 1.54-1.66 (m, 4H), 3.14-3.24 (m, 4H), 3.67 (dd, 2H), 3.75 (dd, 2H), 3.96 (dd, 2H), 4.15 (dd, 1H), 4.24 (dd, 2H), 7.19 (d, 2H), 7.80 (d, 2H) |
| 286 | 4-dodecyl-benzene sulfonate | $^1$HNMR (CD$_3$OD): 0.75-0.92 (m, 21H), 1.05-1.37 (m, 40H), 1.50-1.71 (m, 10H), 2.42-2.49 (m, 2H), 2.53-2.62 (m, 12H), 2.73 (dd, 2H), 3.12-3.21 (m, 4H), 3.68 (dd, 2H), 4.22 (dd, 2H), 7.16 (d, 2H), 7.22 (d, 6H), 7.75 (d, 6H), 7.81 (d, 1H) |
| 287 | — | $^1$HNMR (CD$_3$OD): 1.16 (s, 9H), 1.23-1.36 (m, 8H), 1.46-1.62 (m, 49H), 1.89-2.00 (m, 2H), 3.38 (dd, 2H), 3.50 (dd, 2H), 3.61 (dd, 2H), 3.73 (dd, 2H), 3.96 (dd, 2H), 4.27 (dd, 2H) 7.50-7.59 (m, 1H), 8.22 (d, 1H), 8.22-8.25 (m, 1H) |
| 288 | hydro-chloride | $^1$HNMR (CD$_3$OD): 1.35-1.44 (m, 8H), 1.54-1.67 (m, 4H), 2.12 (dt, 2H), 3.16 (t, 2H), 3.21 (t, 2H), 3.63 (dd, 2H), 3.71 (dd, 2H), 4.32 (dd, 2H), 7.62 (dd, 1H), 8.05 (d, 1H), 8.49 (d, 1H) |
| 289 | — | $^1$HNMR (CDCl$_3$): 1.01 (s, 9H), 1.16-1.33 (m, 6H), 1.39-1.58 (m, 47H), 1.63-1.74 (m, 4H), 1.97 (tt, 2H), 3.46-3.55 (m, 2H), 3.67 (dd, 2H), 3.76 (dd, 2H), 3.85 (dd, 2H), 4.03-4.10 (m, 2H), 4.27-4.34 (m, 2H), 7.08-7.17 (m, 2H), 7.52-7.58 (m, 1H), 7.69 (dd, 2H), 7.87 (d, 1H) |
| 290 | hydro-chloride | $^1$HNMR (CD$_3$OD): 1.34-1.44 (m, 6H), 1.55-1.67 (m, 4H), 2.15 (tt, 2H), 3.16 (dd, 2H), 3.22 (dd, 2H), 3.62-3.66 (m, 4H), 3.70-3.75 (m, 2H), 4.30 (dd, 2H), 7.32 (dd, 1H), 7.42 (d, 1H), 7.66 (dd, 1H), 8.00 (dd, 2H), 8.24 (d, 1H) |

In the table, Boc or BOC indicates a t-butoxycarbonyl group. In the table, "-" means that a compound was synthesized as free form.

TABLE 96

| Compound No. | Structure |
|---|---|
| 291 | 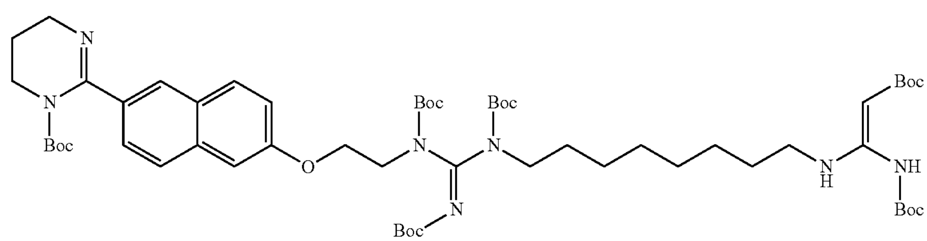 [SMILES: CC(C)(C)OC(=O)/C=C(/NCCCCCCCCN(C(=O)OC(C)(C)C)/C(=N/C(=O)OC(C)(C)C)N(CCOc1ccc2cc(C3=NCCCN3C(=O)OC(C)(C)C)ccc2c1)C(=O)OC(C)(C)C)NC(=O)OC(C)(C)C] |
| 292 | 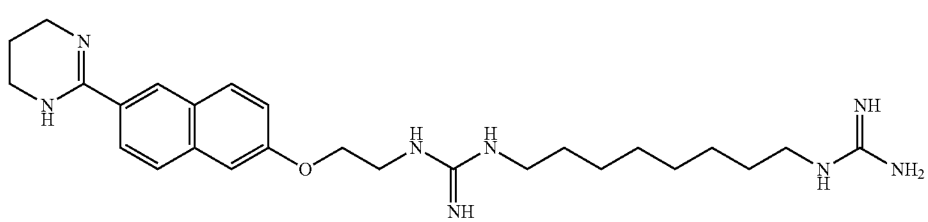 [SMILES: N=C(N)NCCCCCCCCNC(=N)NCCOc1ccc2cc(C3=NCCCN3)ccc2c1] |

TABLE 96-continued
293 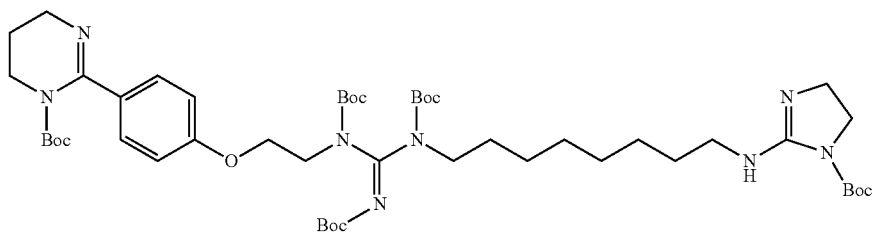 [SMILES: CC(C)(C)OC(=O)/N=C(/N(CCCCCCCCNC1=NCCN1C(=O)OC(C)(C)C)C(=O)OC(C)(C)C)N(CCOc1ccc(C2=NCCCN2C(=O)OC(C)(C)C)cc1)C(=O)OC(C)(C)C]
294 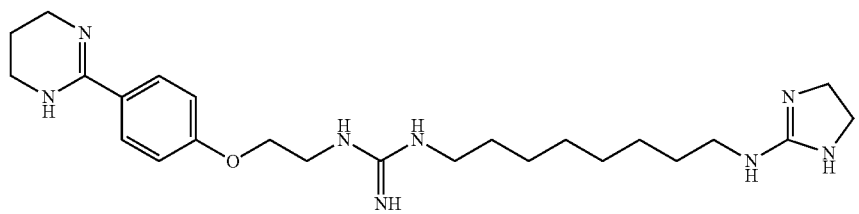 [SMILES: N=C(NCCCCCCCCNC1=NCCN1)NCCOc1ccc(C2=NCCCN2)cc1]
295 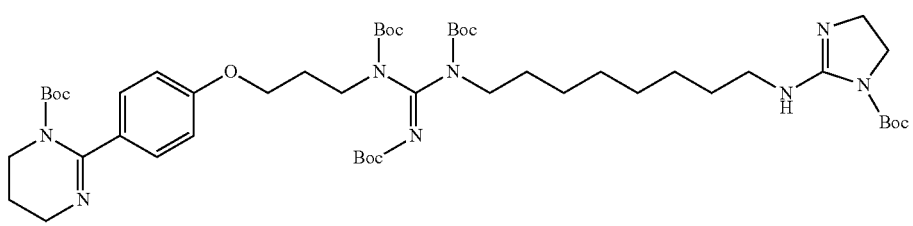 [SMILES: CC(C)(C)OC(=O)/N=C(/N(CCCCCCCCNC1=NCCN1C(=O)OC(C)(C)C)C(=O)OC(C)(C)C)N(CCCOc1ccc(C2=NCCCN2C(=O)OC(C)(C)C)cc1)C(=O)OC(C)(C)C]
296 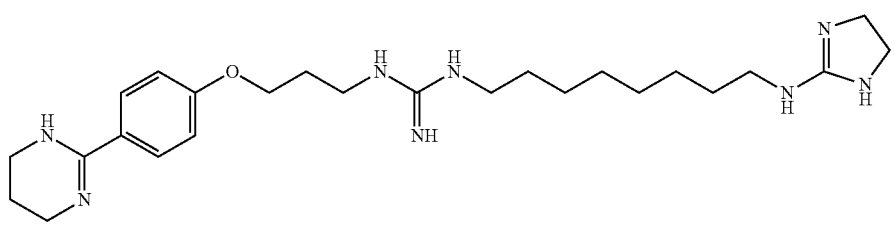 [SMILES: N=C(NCCCCCCCCNC1=NCCN1)NCCCOc1ccc(C2=NCCCN2)cc1]
297 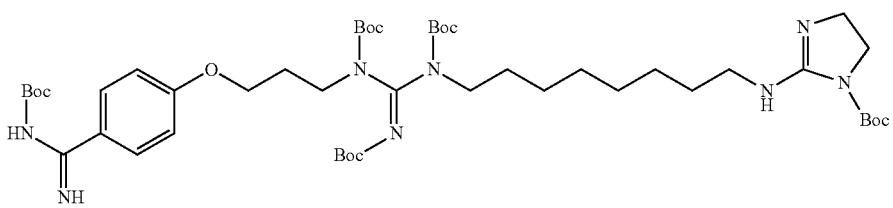 [SMILES: CC(C)(C)OC(=O)/N=C(/N(CCCCCCCCNC1=NCCN1C(=O)OC(C)(C)C)C(=O)OC(C)(C)C)N(CCCOc1ccc(C(=N)NC(=O)OC(C)(C)C)cc1)C(=O)OC(C)(C)C]
298 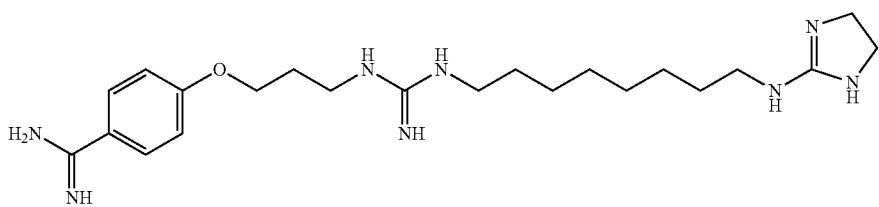 [SMILES: N=C(NCCCCCCCCNC1=NCCN1)NCCCOc1ccc(C(=N)N)cc1]
299 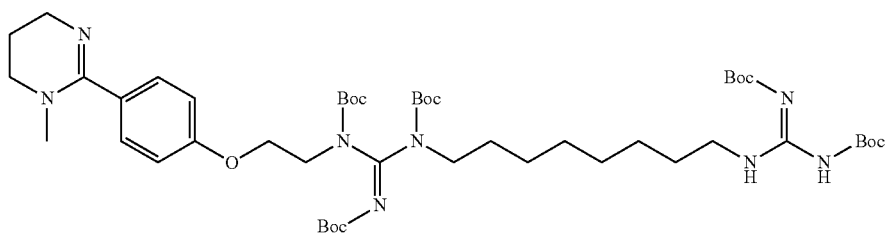 [SMILES: CN1CCCN=C1c1ccc(OCCN(C(=O)OC(C)(C)C)/C(=N\C(=O)OC(C)(C)C)N(CCCCCCCCN/C(=N\C(=O)OC(C)(C)C)NC(=O)OC(C)(C)C)C(=O)OC(C)(C)C)cc1]

TABLE 96-continued

300 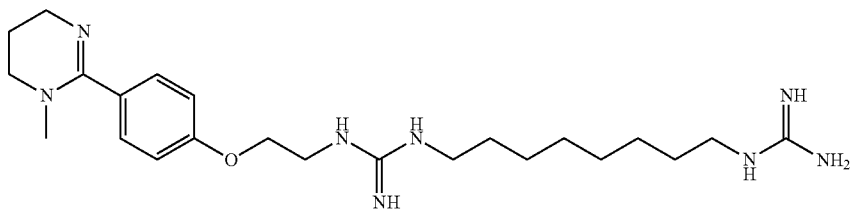 [SMILES: CN1CCCN=C1c1ccc(OCCNC(=N)NCCCCCCCCNC(=N)N)cc1]

| Compound No. | Salt form | Physical property |
|---|---|---|
| 291 | — | ¹HNMR (CDCl$_3$): 1.01 (s, 9H), 1.16-1.30 (m, 8H), 1.41-1.57 (m, 47H), 1.62-1.71 (m, 2H), 1.97 (tt, 2H), 3.37 (dd, 2H), 3.50 (dd, 2H), 3.67 (t, 2H), 3.76 (tt, 2H), 4.07 (dd, 2H), 4.30 (dd, 2H), 7.09-7.18 (m, 2H), 7.57 (dd, 1H), 7.69 (dd, 2H), 7.88 (d, 1H) |
| 292 | hydrochloride | ¹HNMR (CD$_3$OD): 1.35-1.44 (m, 8H), 1.54-1.66 (m, 4H), 2.15 (tt, 2H), 3.15 (dd, 2H), 3.22 (dd, 2H), 3.63-3.66 (m, 4H), 3.71-3.74 (m, 2H), 4.29 (dd, 2H), 7.34 (dd, 1H), 7.42 (d, 1H), 7.69 (dd, 1H), 7.95-8.02 (m, 2H), 8.24 (d, 1H) |
| 293 | — | ¹HNMR (CDCl$_3$): 1.14 (s, 9H), 1.19-1.27 (m, 8H), 1.43-1.57 (m, 42H), 1.60-1.69 (m, 2H), 1.91 (tt, 2H), 3.03-3.10 (m, 2H), 3.48 (dd, 2H), 3.59 (t, 2H), 3.68 (t, 2H), 3.96 (dd, 2H), 4.20 (dd, 2H), 6.87 (d, 2H), 7.40 (d, 2H) |
| 294 | hydrochloride | ¹HNMR (CD$_3$OD): 1.36-1.44 (m, 8H), 1.58-1.70 (m, 4H), 2.09 (tt, 2H), 2.91 (dd, 2H), 3.21 (dd, 2H), 3.35-3.42 (m, 2H), 3.57 (dd, 4H), 3.68 (dd, 4H), 4.23 (dd, 2H), 7.18 (d, 2H), 7.68 (d, 2H) |
| 295 | — | ¹HNMR (CDCl$_3$): 1.15 (s, 9H), 1.24-1.32 (m, 8H), 1.44-1.58 (m, 42H), 1.61-1.69 (m, 2H), 1.94 (tt, 2H), 2.15 (dd, 2H), 3.02-3.12 (m, 2H), 3.49 (dd, 2H), 3.59 (dd, 2H), 3.66-3.76 (m, 4H), 4.02 (dd, 2H), 6.85 (d, 2H), 7.40 (d, 2H) |
| 296 | hydrochloride | ¹HNMR (CD$_3$OD): 1.36-1.44 (m, 8H), 1.58-1.74 (m, 4H), 2.09-2.16 (m, 4H), 2.90-2.96 (m, 2H), 3.17-3.21 (m, 2H), 3.34-3.40 (m, 4H), 3.41-3.51 (m, 2H), 3.54-3.62 (m, 4H), 4.13-4.21 (m, 2H), 7.14 (d, 2H), 7.64 (d, 2H) |
| 297 | — | ¹HNMR (CDCl$_3$): 1.22-1.28 (m, 8H), 1.44-1.56 (m, 49H), 1.59-1.68 (m, 2H), 2.16 (tt, 2H), 3.04-3.10 (m, 2H), 3.48 (dd, 2H), 3.69-3.78 (m, 4H), 4.06 (dd, 2H), 6.88 (d, 2H), 7.85 (d, 2H) |
| 298 | hydrochloride | ¹HNMR (CD$_3$OD): 1.36-1.44 (m, 8H), 1.55-1.70 (m, 4H), 2.11 (tt, 2H), 2.91 (dd, 2H), 3.18 (dd, 2H), 3.29-3.38 (m, 4H), 3.43 (dd, 2H), 4.18 (dd, 2H), 7.18 (d, 2H), 7.80 (d, 2H) |
| 299 | — | ¹HNMR (CDCl$_3$): 1.20-1.32 (m, 8H), 1.43-1.59 (m, 47H), 1.63-1.71 (m, 2H), 1.93 (tt, 2H), 2.74 (s, 3H), 3.25 (dd, 2H), 3.44-3.52 (m, 4H), 3.87 (dd, 2H), 3.96 (dd, 2H), 4.18 (dd, 2H), 6.85 (d, 2H), 7.30 (d, 2H) |
| 300 | hydrochloride | ¹HNMR (CD$_3$OD): 1.35-1.44 (m, 8H), 1.53-1.65 (m, 4H), 2.18 (tt, 2H), 3.08 (s, 3H), 3.16 (dd, 2H), 3.21 (dd, 2H), 3.50 (dd, 2H), 3.62-3.69 (m, 4H), 4.21 (dd, 2H), 7.16 (d, 2H), 7.53 (d, 2H) |

In the table, Boc or BOC indicates a t-butoxycarbonyl group. In the table, "-" means that a compound was synthesized as free form.

TABLE 97

| Compound No. | Structure |
|---|---|
| 301 | 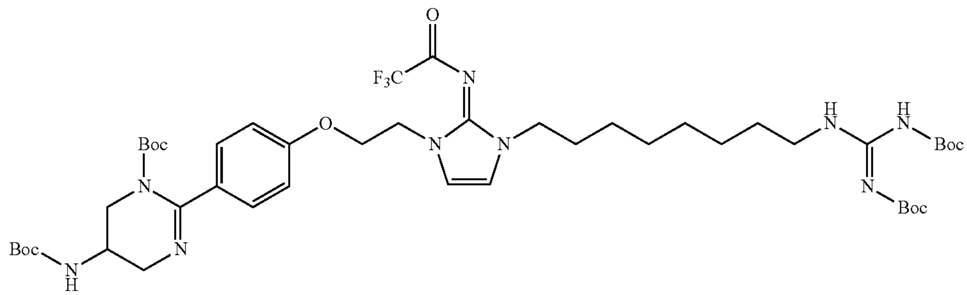 [SMILES: CC(C)(C)OC(=O)/N=C(/NCCCCCCCCn1ccn(CCOc2ccc(C3=NCC(NC(=O)OC(C)(C)C)CN3C(=O)OC(C)(C)C)cc2)/c1=N\C(=O)C(F)(F)F)NC(=O)OC(C)(C)C] |
| 302 | 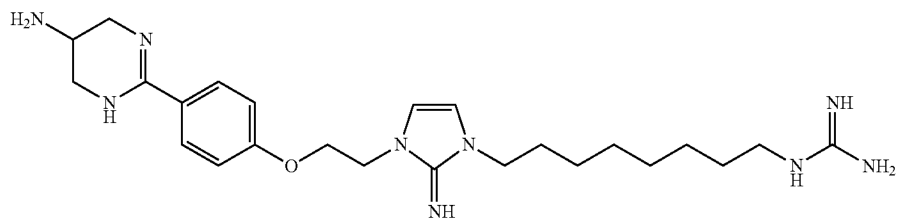 [SMILES: N=C(N)NCCCCCCCCn1ccn(CCOc2ccc(C3=NCC(N)CN3)cc2)c1=N] |
| 303 | 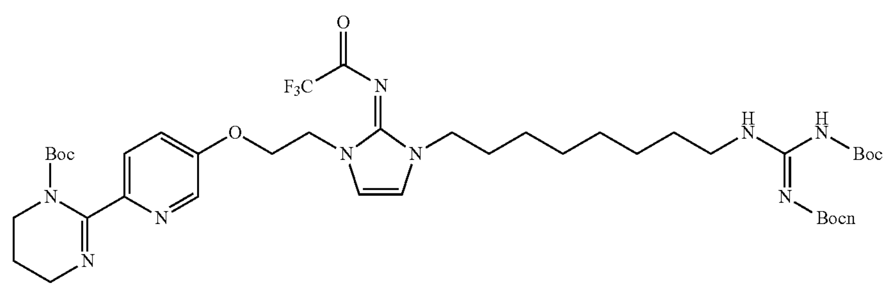 |
| 304 | 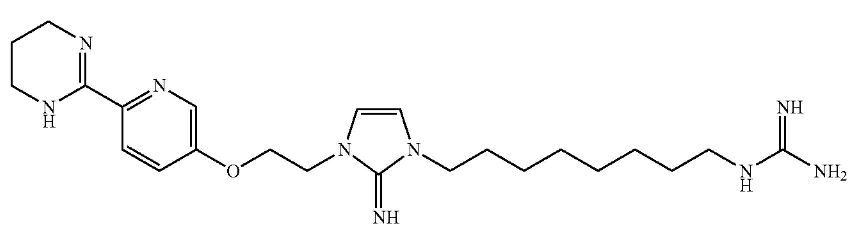 [SMILES: N=C(N)NCCCCCCCCn1ccn(CCOc2ccc(C3=NCCCN3)nc2)c1=N] |
| 305 | 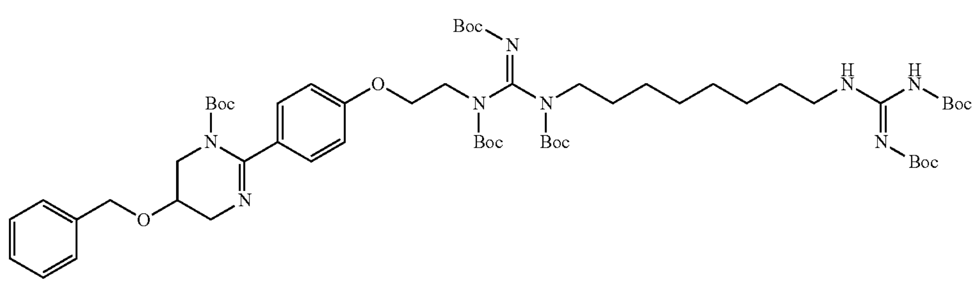 [SMILES: CC(C)(C)OC(=O)/N=C(/NCCCCCCCCN(C(=O)OC(C)(C)C)/C(=N/C(=O)OC(C)(C)C)N(CCOc1ccc(C2=NCC(OCc3ccccc3)CN2C(=O)OC(C)(C)C)cc1)C(=O)OC(C)(C)C)NC(=O)OC(C)(C)C] |

TABLE 97-continued
306 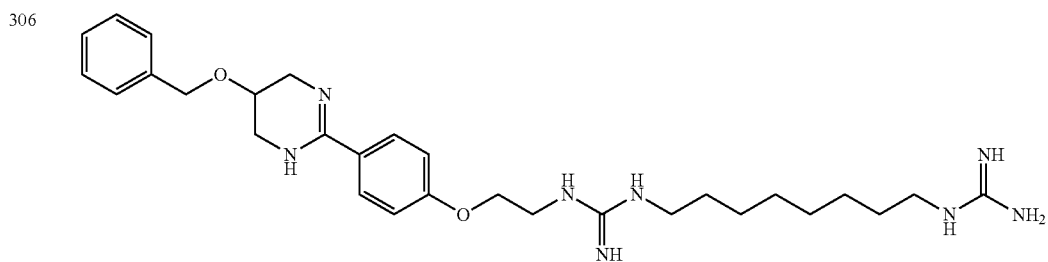
307 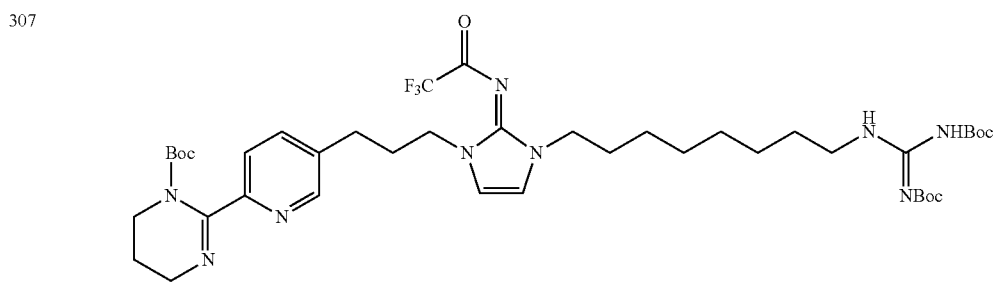
308 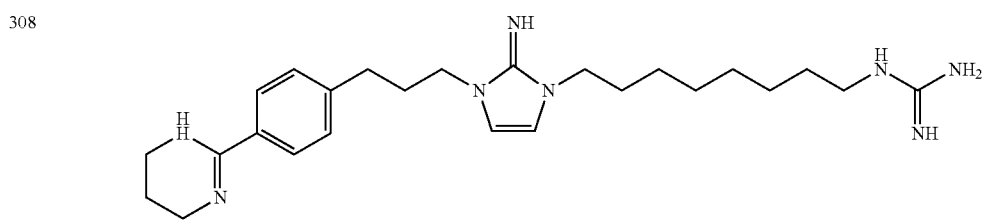
309 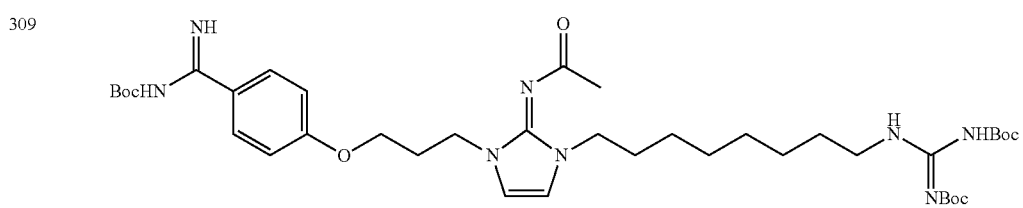
310 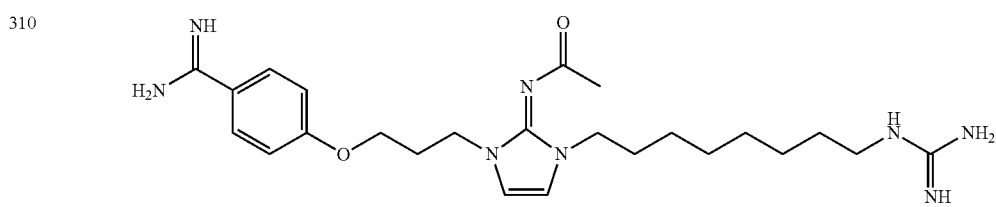
| Compound No. | Salt form | Physical property |
| --- | --- | --- |
| 301 | — | $^1$HNMR (CDCl$_3$): 1.19 (s, 9H), 1.23-1.34 (m, 8H), 1.42-1.57 (m, 29H), 1.71-1.77 (m, 2H), 3.52-3.60 (m, 1H), 3.65-3.73 (m, 1H), 3.82-3.89 (m, 6H), 4.24 (dd, 2H), 4.32 (dd, 2H), 4.64-4.72 (m, 1H), 6.72 (d, 1H), 6.85 (d, 2H), 6.99 (d, 1H), 7.45 (d, 2H) |
| 302 | hydrochloride | $^1$HNMR (CD$_3$OD): 1.33-1.44 (m, 8H), 1.54-1.63 (m, 2H), 1.72-1.81 (m, 2H), 3.13-3.20 (m, 2H), 3.70-3.78 (m, 2H), 3.88 (dd, 2H), 3.92-3.98 (m, 2H), 4.14-4.19 (m, 1H), 4.34-4.42 (m, 4H), 6.98 (s, 1H), 7.06 (s, 1H), 7.17 (d, 2H), 7.79 (d, 2H) |
| 303 | — | $^1$HNMR (CDCl$_3$): 1.18 (s, 9H), 1.24-1.37 (m, 8H), 1.47-1.53 (m, 20H), 1.70-1.79 (m, 2H), 1.93 (dt, 2H), 3.61 (dd, 2H), 3.72 (dd, 2H), 3.83-3.91 (m, 4H), 4.28 (dd, 2H), 4.38 (dd, 2H), 6.75 (d, 1H), 6.97 (d, 1H), 7.23 (dd, 1H), 7.56 (d, 1H), 8.21 (d, 1H) |

TABLE 97-continued

| | | |
|---|---|---|
| 304 | hydrochloride | $^1$HNMR (CD$_3$OD): 1.34-1.42 (m, 8H), 1.57 (dd, 2H), 1.71-1.80 (m, 2H), 2.11 (dd, 2H), 3.15 (dd, 2H), 3.58-3.65 (m, 4H), 3.88 (dd, 2H), 4.38-4.43 (m, 2H), 4.46-4.52 (m, 2H), 6.99 (s, 1H), 7.07 (s, 1H), 7.63 (d, 1H), 8.05 (d, 1H), 8.45 (s, 1H) |
| 305 | — | $^1$HNMR (CDCl$_3$): 1.12 (s, 9H), 1.19-1.36 (m, 8H), 1.43-1.56 (m, 47H), 1.64-1.71 (m, 2H), 3.38 (dd, 2H), 3.45-3.58 (m, 3H), 3.68-3.76 (m, 1H), 3.84-3.92 (m, 2H), 3.94-4.00 (m, 2H), 4.12-4.26 (m, 2H), 4.29-4.39 (m, 1H), 4.54 (d, 1H), 4.67 (d, 1H), 6.86 (d, 2H), 7.30-7.37 (m, 5H), 7.46 (d, 2H) |
| 306 | hydrochloride | $^1$HNMR (CD$_3$OD): 1.35-1.42 (m, 8H), 1.54-1.65 (m, 4H), 3.16 (dd, 2H), 3.21 (dd, 2H), 3.60-3.78 (m, 5H), 4.19-4.31 (m, 4H), 4.63 (s, 2H), 7.18 (d, 2H), 7.29-7.38 (m, 5H), 7.69 (d, 2H) |
| 307 | — | $^1$HNMR (CDCl$_3$): 1.11 (s, 9H), 1.21-1.37 (m, 8H), 1.49 (s, 9H), 1.50-1.60 (m, 11H), 1.67-1.79 (m, 2H), 1.92 (dt, 2H), 2.06 (dt, 2H), 2.65 (t, 2H), 3.61 (t, 2H), 3.70 (t, 2H), 3.80-3.93 (m, 6H), 6.67 (d, 1H), 6.73 (d, 1H), 7.14 (d, 2H), 7.41 (d, 2H). |
| 308 | hydrochloride | $^1$HNMR (CD$_3$OD): 1.30-1.46 (m, 8H), 1.59 (dt, 2H), 1.75 (dt, 2H), 2.04-2.16 (m, 4H), 2.79 (t, 2H), 3.16 (t, 2H), 3.56-3.54 (m, 4H), 3.87 (t, 2H), 3.97 (t, 2H), 6.93-7.02 (m, 2H), 7.48 (d, 2H), 7.67 (d, 2H). |
| 309 | — | $^1$HNMR (CDCl$_3$): 1.10-1.25 (m, 8H), 1.43-1.67 (m, 31H), 1.76 (s, 3H), 2.27 (dt, 2H), 3.83 (t, 2H), 3.90-4.09 (m, 4H), 6.88 (d, 2H), 6.95 (s, 1H), 7.03 (s, 1H), 7.93 (d, 2H) |
| 310 | trifluoroacetate | $^{13}$CNMR (D$_2$O) 20.9 (CH3), 25.5 (CH2), 25.6 (CH2), 26.9 (CH2), 27.8 (CH2), 28.0 (CH2), 28.1 (CH2), 41.1 (CH2), 44.1 (CH2), 48.7 (CH2), 48.9 (CH2), 51.3 (CH2), 64.4 (CH2), 64.7 (CH2), 115, 119, 130, 138, 157, 163, 166, 173 (C=O) |

In the table, Boc or BOC indicates a t-butoxycarbonyl group. In the table, "-" means that a compound was synthesized as free form.

TABLE 98

| Compound No. | Structure |
|---|---|
| 311 | 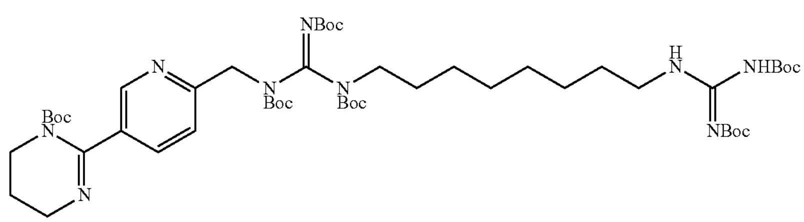 |
| 312 | 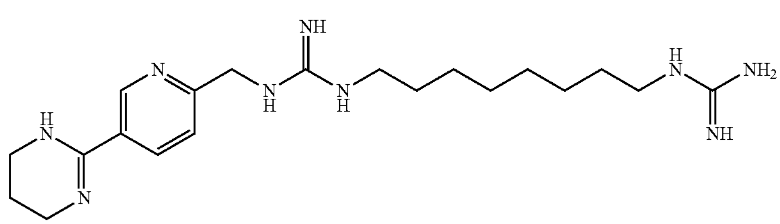 [SMILES: N=C(N)NCCCCCCCCNC(=N)NCc1ccc(C2=NCCCN2)cn1] |

TABLE 98-continued
313 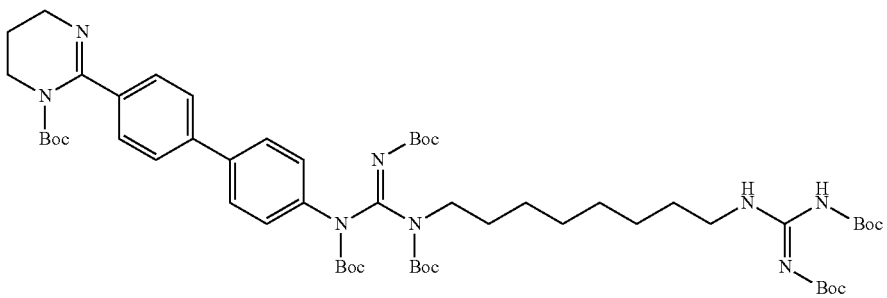 [SMILES: CC(C)(C)OC(=O)/N=C(/NCCCCCCCCN(C(=O)OC(C)(C)C)/C(=N\C(=O)OC(C)(C)C)N(C(=O)OC(C)(C)C)c1ccc(-c2ccc(C3=NCCCN3C(=O)OC(C)(C)C)cc2)cc1)NC(=O)OC(C)(C)C]
314 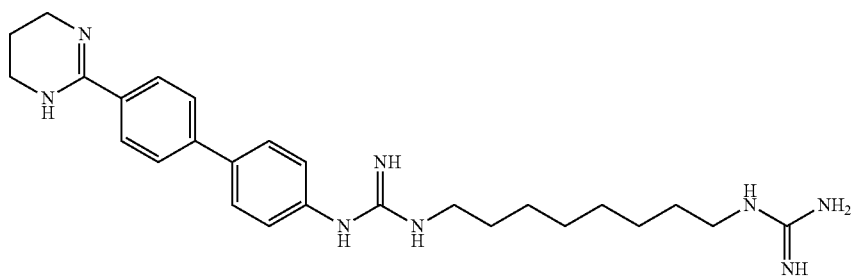 [SMILES: N=C(N)NCCCCCCCCNC(=N)Nc1ccc(-c2ccc(C3=NCCCN3)cc2)cc1]
315 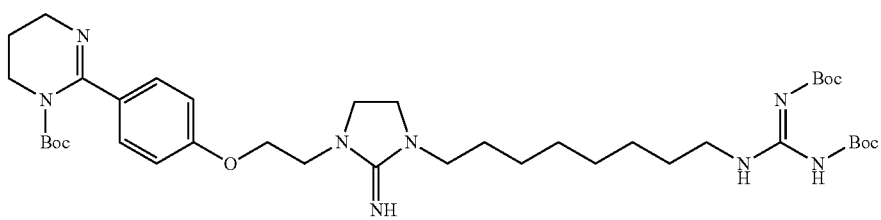 [SMILES: CC(C)(C)OC(=O)/N=C(/NCCCCCCCCN1CCN(CCOc2ccc(C3=NCCCN3C(=O)OC(C)(C)C)cc2)C1=N)NC(=O)OC(C)(C)C]
316 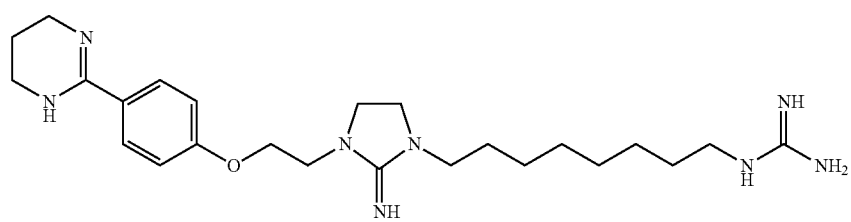 [SMILES: N=C(N)NCCCCCCCCN1CCN(CCOc2ccc(C3=NCCCN3)cc2)C1=N]
| Compound No. | Salt form | Physical property |
| --- | --- | --- |
| 311 | — | ¹HNMR (CDCl₃): 1.16 (s, 9H), 1.22-1.32 (m, 8H), 1.36 (s, 9H), 1.44-1.60 (m, 38H), 1.61-1.69 (m, 2H), 1.94 (dt, 2H), 33.46 (t, 2H), 3.65 (t, 2H), 3.72 (t, 2H), 3.88 (t, 2H), 4.96 (s, 2H), 7.43 (dd, 1H), 7.75 (dd, 1H), 8.59 (d, 1H) |
| 312 | hydro-chloride | ¹HNMR (CD₃OD): 1.34-1.49 (m, 8H), 1.54-1.69 (m, 4H), 2.15 (t, 2H), 3.18 (t, 2H), 3.26 (t, 2H), 3.61-3.69 (m, 4H), 4.75 (s, 2H), 7.77 (d, 1H), 8.31 (d, 1H), 9.01 (m, 1H) |
| 313 | — | ¹HNMR (CDCl₃): 1.13 (s, 9H), 1.33-1.39 (m, 17H), 1.48-1.59 (m, 38H), 1.69-1.79 (m, 2H), 1.95 (tt, 2H), 3.38 (dd, 2H), 3.54-3.69 (m, 4H), 3.73 (dd, 2H), 7.22 (d, 2H), 7.54 (s, 4H), 7.57 (d, 2H) |
| 314 | hydro-chloride | ¹HNMR (CD₃OD): 1.38-1.46 (m, 8H), 1.56-1.75 (m, 4H), 2.14 (tt, 2H), 3.17 (dd, 2H), 3.30-3.36 (m, 4H), 3.53 (dd, 2H), 7.43 (d, 2H), 7.84 (d, 2H), 7.86-7.94 (m, 4H) |
| 315 | — | ¹HNMR (CDCl₃): 1.16 (s, 9H), 1.24-1.36 (m, 8H), 1.47-1.54 (m, 20H), 1.59-1.72 (m, 2H), 1.94 (tt, 2H), 3.02-3.17 (m, 2H), 3.24 (dd, 2H), 3.42 (dd, 2H), 3.56-3.65 (m, 4H), 3.69 (dd, 2H), 3.88 (dd, 2H), 4.16 (dd, 2H), 6.89 (d, 2H), 7.41 (d, 2H) |

TABLE 98-continued

| | | | |
|---|---|---|---|
| 316 | | hydrochloride | $^1$HNMR (CD$_3$OD): 1.33-1.44 (m, 8H), 1.54-1.67 (m, 4H), 2.10 (tt, 2H), 3.17 (dd, 2H), 3.34 (dd, 2H), 3.56-3.61 (m, 4H), 3.65-3.72 (m, 2H), 3.77-3.84 (m, 4H), 4.29 (dd, 2H), 7.15 (d, 2H), 7.69 (d, 2H) |

In the table, Boc or BOC indicates a t-butoxycarbonyl group. In the table, "-" means that a compound was synthesized as free form.

SYNTHESIS EXAMPLE 1

Synthesis of tert-butyl 2-(4-hydroxyphenyl)-5,6-dihydro-4H-pyrimidine-1-carboxylate

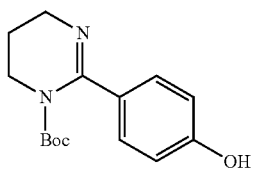 [SMILES: CC(C)(C)OC(=O)N1CCCN=C1c1ccc(O)cc1]

4-(1,4,5,6-tetrahydropyrimidin-2-yl)phenol (20 g) was dissolved in N, N-dimethylformamide (200 mL). Triethylamine (45.7 g) and di-tert-butyl dicarbonate (74 g) were added to the resultant under ice-cooling. The reaction mixture was warmed to room temperature and stirred at the same temperature overnight. Water was added to the reaction mixture, and the mixture was subjected to extraction with ethyl acetate. The resultant organic layer was dried over anhydrous sodium sulfate and filtered. Then, the filtrate was concentrated under reduced pressure. The resulting residue was dissolved in methanol (300 mL). 10% aqueous solution of sodium hydroxide (150 mL) was added to the solution at room temperature and the resultant was stirred at the same temperature for 6 hours. The reaction mixture was concentrated under reduced pressure, and the resulting residue was purified by silica gel column chromatography to obtain the title compound (22.0 g, in a yield of 71%).

$^1$H NMR (CDCl$_3$): 1.14 (s, 9H), 1.93 (dt, 2H), 3.56 (dd, 2H), 3.70 (t, 2H), 6.58 (d, 2H), 7.23 (d, 2H).

SYNTHESIS EXAMPLE 2

(Step 1) Synthesis of tert-butyl 2-(4-iodophenyl)-5,6-dihydro-4H-pyrimidine-1-carboxylate

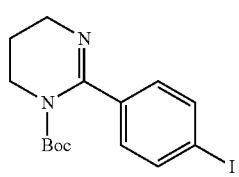 [SMILES: CC(C)(C)OC(=O)N1CCCN=C1c1ccc(I)cc1]

A toluene solution of 2M trimethylaluminum (27 mL), 1,3-propanediamine (2.30 mL), and a toluene solution (10 mL) of ethyl 4-iodobenzoate (5.00 g) were added sequentially to toluene (145 mL) under a nitrogen atmosphere at room temperature, and the mixture was heated to 130° C. and stirred overnight. Then, the resultant was cooled to room temperature, followed by adding chloroform (36 mL), methanol (36 mL) and water (7.5 mL) sequentially thereto, and stirring the mixture at room temperature for 1 hour. Then, the reaction mixture was filtered with Celite (trademark) while washing with a mixture solvent composed of chloroform/methanol=9/1. The filtrate was concentrated under reduced pressure and the residue was dissolved in methanol. The resultant was dried over anhydrous sodium sulfate and filtered. The filtrate was concentrated under reduced pressure to obtain a residue (5.77 g). Then, the residue was dissolved in N, N-dimethylformamide (91 mL). Di-tert-butyl dicarbonate (12.15 g) and triethylamine (6.76 g) were added to the solution, and stirred at room temperature overnight. The reaction mixture was poured into water, and the resultant was subjected to extraction with ethyl acetate. The resultant organic layer was dried over anhydrous magnesium sulfate and filtered. The filtrate was concentrated under reduced pressure. The resulting residue was purified by silica gel column chromatography to obtain the title compound (7.28 g, quantitative).

$^1$H NMR (CDCl$_3$): 1.15 (s, 9H), 1.92 (tt, 2H), 3.62 (t, 2H), 3.70 (t, 2H), 7.22 (d, 2H), 7.69 (d, 2H).

(Step 2) Synthesis of tert-butyl 2-[4-(3-hydroxy-prop-1-ynyl)phenyl]-5,6-dihydro-4H-pyrimidine-1-carboxylate

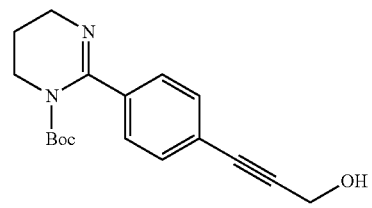 [SMILES: CC(C)(C)OC(=O)N1CCCN=C1c1ccc(C#CCO)cc1]

Tert-butyl 2-(4-iodophenyl)-5,6-dihydro-4H-pyrimidine-1-carboxylate (3.60 g) obtained in the step 1 was dissolved in triethylamine (10 mL), and propargyl alcohol (0.58 g), bis(triphenylphosphine)palladium (II) dichloride (65 mg) and copper iodide (I) (36 mg) were added to the solution, nitrogen purge was conducted, and the resultant was stirred at 80° C. for 40 minutes. Then, the resultant was cooled to room temperature, and poured into water to conduct extraction with ethyl acetate. The resultant organic layer was dried over anhydrous magnesium sulfate and filtered. Then, the filtrate was concentrated under reduced pressure. The resulting residue was purified by silica gel column chromatography to obtain the title compound (1.94 g, in a yield of 66%).

$^1$H NMR (CDCl$_3$): 1.11 (s, 9H), 1.92 (tt, 2H), 3.63 (t, 2H), 3.70 (t, 2H), 4.49 (s, 2H), 7.36-7.50(m, 4H).

SYNTHESIS EXAMPLE 3

(Step 1) synthesis of [4-(1,4,5,6-tetrahydropyrimidin-2-yl)phenyl]methanol

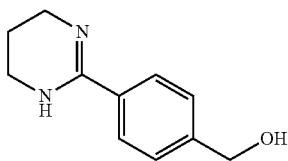 [SMILES: OCc1ccc(C2=NCCCN2)cc1]

Ethyl 4-(hydroxymethyl) benzene-1-carboxyimidate hydrochloride salt (7.68 g) was dissolved in ethanol (36 mL). 1,3-propanediamine (2.64 g) was added to the solution and the mixture was heated under reflux overnight. Then, the resultant was cooled to room temperature and concentrated under reduced pressure. The precipitated solid was filtered while conducting washing with ethanol to obtain the title compound (2.78 g, in a yield of 41%).

$^1$H NMR (CD$_3$OD): 2.12 (tt, 2H), 3.60 (t, 4H), 4.71 (s, 2H), 7.58 (d, 2H), 7.68 (d, 2H).

(Step 2) Synthesis of tert-butyl 2-(4-(hydroxymethyl)phenyl)-5,6-dihydropyrimidine-1 (4H)-carboxylate

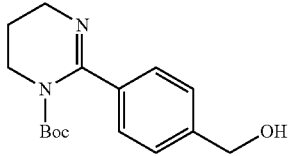 [SMILES: CC(C)(C)OC(=O)N1CCCN=C1c1ccc(CO)cc1]

[4-(1,4,5,6-tetrahydropyrimidin-2-yl)phenyl]methanol (4.52 g) obtained in the step 1 was dissolved in N, N-dimethylformamide (500 mL). At room temperature, triethylamine (16 mL) and N, N-dimethyl-4-aminopyridine (0.29 g) were added to the solution, and then di-tert-butyl dicarbonate (15.71 g) was added thereto. The reaction mixture was stirred at room temperature overnight and then concentrated under reduced pressure. The resulting residue was purified by silica gel column chromatography to obtain the title compound (4.57 g).

$^1$H NMR (CD$_3$OD): 1.10 (s, 9H), 1.94 (tt, 2H), 3.52 (t, 2H), 3.71 (t, 2H), 4.64 (s, 2H), 7.36-7.43 (m, 4H).

SYNTHESIS EXAMPLE 4

Synthesis of 4-[[3-[[tert-butyldimethylsilyl]oxy]propyl]thio]benzonitrile

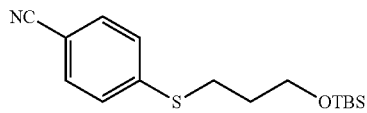 [SMILES: CC(C)(C)[Si](C)(C)OCCCSc1ccc(C#N)cc1]

4-[3-[tert-butyl(dimethyl)silyl]oxypropylsulfanyl]benzonitrile (5.73 g) was dissolved in N, N-dimethylformamide (100 mL). At room temperature, imidazole (3.55 g) and tert-butyl dimethylchlorosilane (5.53 g) were added to the solution. The mixture was stirred for 1 hour, the resultant was poured into water, and the mixture was subjected to extraction with ethyl acetate. The resultant organic layer was washed with saturated saline solution, dried over anhydrous sodium sulfate, and then filtered. The filtrate was concentrated under reduced pressure, and the resulting residue was purified by silica gel column chromatography to obtain the title compound (9.77 g).

$^1$HNMR(CDCl$_3$): 0.07 (s, 6H), 0.91 (s, 9H), 1.88 (t t, 2H), 3.08 (t, 2H), 3.73 (t, 2H), 7.32 (d, 2H), 7.52 (d, 2H).

SYNTHESIS EXAMPLE 5

Synthesis of tert-butyl 2-(6-(hydroxymethyl)pyridin-3-yl)-5,6-dihydropyrimidine-1(4H)-carboxylate

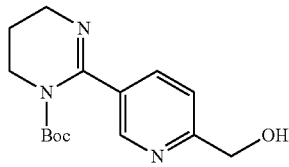 [SMILES: CC(C)(C)OC(=O)N1CCCN=C1c1ccc(CO)nc1]

1,3-diaminopropane (4.91 g) was dissolved in toluene (90 mL) under a nitrogen atmosphere. Trimethylaluminum (21 mL, 2.0M in a toluene solution) was added to the resultant while conducting cooling in an ice bath. The mixture was stirred for 1 hour at the same temperature, methyl 6-hydroxymethylpyridine-3-carboxylate (3.52 g) and toluene (100 mL) were added to the resultant at room temperature, and then the mixture was stirred at 80° C. overnight. Then, methanol was added to the resultant while conducting cooling in an ice bath and the mixture was filtered. The filtrate was concentrated under reduced pressure and the resulting residue was dissolved in N, N-dimethylformamide (200 mL). At room temperature, triethylamine (6 mL) was added to the solution, and then di-tert-butyl dicarbonate (7.09 g) and N,N-dimethyl-4-aminopyridine (0.29 g) were added thereto. At room temperature, the reaction mixture was stirred overnight and then filtered. The resultant was poured into water, and the mixture was subjected to extraction with ethyl acetate. The resultant organic layer was combined, dried over anhydrous sodium sulfate, and then filtered. The filtrate was concentrated under reduced pressure and the resulting residue was purified by silica gel column chromatography to obtain the title compound (0.86 g).

$^1$H NMR (CDCl$_3$): 1.16 (s, 9H), 1.95 (tt, 2H), 3.67 (t, 2H), 3.74 (t, 2H), 4.79 (s, 2H), 7.25 (d, 1H), 7.80 (dd, 1H), 8.63 (d, 1H).

SYNTHESIS EXAMPLE 6

Synthesis of tert-Butyl N-[4-[3-[[N,N'-bis(tert-butoxycarbonyl)carbamimidoyl]-methyl amino] propoxy]benzenecarboximidoyl]carbamate

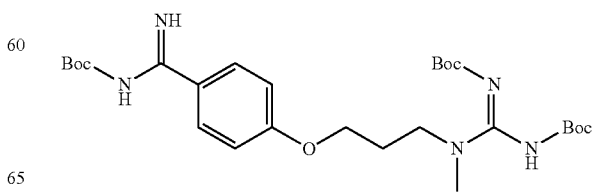

Tert-butyl N-[4-[3-(methylamino)propoxy]benzenecarboximidoyl]carbamate (254 mg) was dissolved in tetrahydrofuran (4 mL). Triethylamine (250 mg), silver trifluoromethanesulfonate (255 mg) and tert-butyl-N-[(tert-butoxycarbonylamino)-methylsulfanyl-methylene]carbamate (240 mg) were added to the solution under ice-cooling. The reaction mixture was warmed to room temperature and stirred at the same temperature overnight. The reaction mixture was filtered, and then the filtrate was concentrated under reduced pressure. The resulting residue was purified by silica gel column chromatography to obtain the title compound (301 mg, in a yield of 66%).

$^{1}$H NMR (CDCl$_{3}$): 1.46-1.59 (m, 27H), 2.14 (dt, 2H), 3.02 (s, 3H), 3.61-3.76 (m, 2H), 4.08 (t, 2H), 6.92 (d, 2H), 7.82 (d, 2H).

SYNTHESIS EXAMPLE 7

Synthesis of tert-Butyl N-[8-[[N,N'-bis(tert-butoxycarbonyl)carbamimidoyl]amino]octyl]-N-[N-tert-butoxycarbonyl-C-(4-hydroxy-1-piperidyl)carbonimidoyl]carbamate

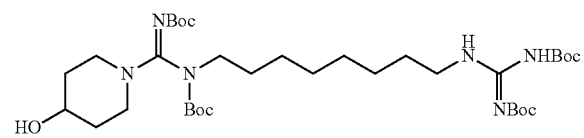

Tert-butyl (((tert-butoxycarbonyl)amino)(4-hydroxypiperidin-1-yl)methylene) carbamate (0.53 g) was dissolved in tetrahydrofuran (10 mL). Tert-butyl N-[(tert-butoxycarbonylamino)-(8-hydroxyoctylamino)methylene]carbamate (1.02 g) was added to the solution at room temperature. Triphenylphosphine (0.62 g) and bis(2-methoxyethyl)azodicarboxylate (0.58 g) were added to the mixture at room temperature. The resultant was stirred overnight, poured into water, and then subjected to extraction with ethyl acetate. The resultant organic layer was washed with saturated saline solution, dried over anhydrous sodium sulfate, and then filtered. The filtrate was concentrated under reduced pressure and the resulting residue was purified by silica gel column chromatography to obtain the title compound (0.64 g).

$^{1}$H NMR (CDCl$_{3}$): 1.20-1.38 (m, 8H), 1.40-2.00 (m, 44H), 3.15-4.33 (m, 9H).

SYNTHESIS EXAMPLE 8

Synthesis of tert-butyl 2-(8-hydroxyoctylamino)-4,5-dihydroimidazole-1-carboxylate

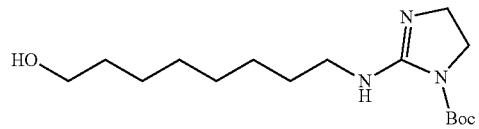 [SMILES: CC(C)(C)OC(=O)N1CCN=C1NCCCCCCCCO]

2-(methylsulfanyl)-4,5-dihydro-1H-imidazole hydroiodide (4 g) was dissolved in methanol (50 mL). 1-amino-8-octanol (3.57 g) was added to the solution at room temperature. The reaction mixture was heated to 60° C., and stirred at the same temperature overnight. The reaction mixture was cooled to room temperature and then concentrated under reduced pressure. The resulting residue was dissolved in N,N-dimethylformamide (50 mL), and triethylamine (9.96 g) and di-tert-butyl dicarbonate (12.52 g) were added thereto under ice-cooling. The reaction mixture was warmed to room temperature and stirred at the same temperature overnight. Water was added to the reaction mixture, and the mixture was subjected to extraction with ethyl acetate. The resultant organic layer was dried over anhydrous sodium sulfate, filtered, and then concentrated under reduced pressure. The resulting residue was purified by silica gel column chromatography to obtain the title compound (1.86 g, in a yield of 36.2%).

$^{1}$H NMR (CDCl$_{3}$): 1.27-1.36 (m, 8H), 1.44-1.58 (m, 17H), 3.07-3.14 (m, 2H), 3.63 (dd, 2H).

SYNTHESIS EXAMPLE 9

(Step 1) Synthesis of tert-butyl 2-[4-[2-[2-(2,2,2-trifluoroacetyl)iminoimidazolidin-1-yl]ethoxy]phenyl]-5,6-dihydro-4H-pyrimidine-1-carboxylate

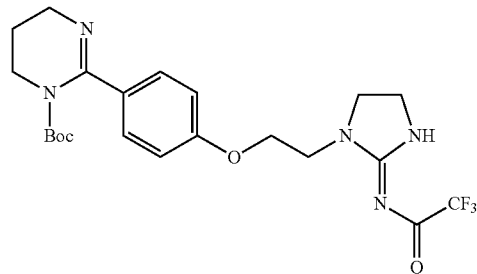 [SMILES: CC(C)(C)OC(=O)N1CCCN=C1c1ccc(OCCN2CCN/C2=N\C(=O)C(F)(F)F)cc1]

Tert-butyl 2[4(2-bromoethoxy)phenyl]-5,6-dihydro-4H-pyrimidine-1-carboxylate (698 mg) was dissolved in N,N-dimethylformamide (8 mL). Potassium carbonate (344 mg) and 2,2,2-trifluoro-N-imidazolidin-2-ylidene-acetamide (300 mg) were added to the solution at room temperature. The reaction mixture was heated to 50° C. and stirred at the same temperature overnight. The reaction mixture was cooled to room temperature, water was added thereto, and the mixture was subjected to extraction with ethyl acetate. The organic layer was dried over anhydrous sodium sulfate, filtered, and then concentrated under reduced pressure. The resulting residue was purified by silica gel column chromatography to obtain the title compound (219 mg, in a yield of 27.3%).

$^{1}$H NMR (CDCl$_{3}$): 1.12 (s, 9H), 1.92 (tt, 2H), 3.60 (dd, 2H), 3.69 (dd, 2H), 3.73-3.82 (m, 4H), 3.82 (dd, 2H), 4.19 (dd, 2H), 6.85 (d, 2H), 7.43 (d, 2H)

(Step 2) Synthesis of tert-butyl 2-[4-[2-(2-iminoimidazolidin-1-yl)ethoxy]phenyl]-5,6-dihydro-4H-pyrimidine-1-carboxylate

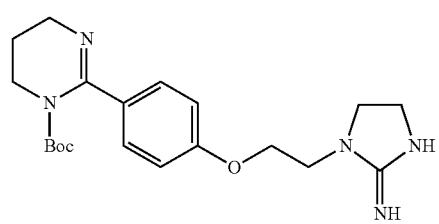 [SMILES: CC(C)(C)OC(=O)N1CCCN=C1c1ccc(OCCN2CCNC2=N)cc1]

Tert-butyl 2-[4-[2-[2-(2,2,2-trifluoroacetyl)iminoimidazolidin-1-yl]ethoxy]phenyl]-5,6-dihydro-4H-pyrimidine-1-carboxylate (185 mg) obtained in the step 1 was dissolved in methanol (5 mL). Potassium carbonate (61 mg) was added to the solution at room temperature, and then the mixture was stirred at the same temperature overnight. The reaction mixture was concentrated under reduced pressure, water was added to the resulting residue, and then the mixture was subjected to extraction with ethyl acetate. The resultant organic layer was dried over anhydrous sodium sulfate and filtered. The filtrate was concentrated under reduced pressure to obtain the title compound (140 mg, in a yield of 97.9%).

$^1$H NMR (CD$_3$OD): 1.13 (s, 9H), 1.92 (tt, 2H), 3.43-3.52 (m, 4H), 3.64-3.68 (m, 4H), 3.69 (dd, 2H), 4.19 (dd, 2H), 6.98 (d, 2H), 7.37 (d, 2H)

FORMULATION EXAMPLE (EMULSION)

| | |
|---|---|
| Compound according to the present invention | 5.62 parts by mass |
| Surfactant | 4.49 parts by mass |
| Dimethylformamide | 89.89 parts by mass |

The above components were mixed and dissolved to obtain each emulsion containing 5.62% of an active ingredient.

TEST EXAMPLE 1

(Apple Scab Control Test)

Each emulsion prepared in accordance with the formulation of the Formulation Example was diluted with water to contain 125 ppm of the active ingredient. The dilution was sprayed to apple seedlings (variety "Orin", 3 to 4 leaf stage) grown in clay pots. The leaves were air-dried at room temperature. Then, the apple seedlings were inoculated with conidia of Apple scab fungus (*Venturia inaequalis*), and then held in a room at 20° C. under a high humidity with light and darkness being repeated every 12 hours. Control effects were examined by comparing lesion appearance state of the apple seedlings with that of untreated apple seedlings. The control value was calculated by the following equation.

$$\text{Control value (\%)} = 100 - \frac{\text{lesion appearance on treated apple seedlings}}{\text{lesion appearance on untreated apple seedlings}} \times 100$$

Compounds represented by compound No. 2, 4, 6, 8, 10, 12, 16, 17, 20, 22, 25, 27, 29, 30, 32, 34, 36, 38, 40, 42, 44, 48, 50, 52, 57, 59, 61, 63, 65, 72, 73, 76, 78, 80, 82, 84, 86, 88, 89, 91, 93, 95, 97, 99, 101, 103, 105, 107, 109, 110, 112, 114, 116, 118, 120, 122, 124, 126, 128, 130, 132, 134, 136, 138, 140, 142, 143, 145, 147, 149, 151, 153, 155, 157, 159, 161, 163, 165, 167, 169, 171, 173, 175, 177, 179, 181, 184, 186, 188, 190, 192, 194, 196, 198, 200, 202, 206, 208, 210, 212, 214, 220, 222, 224, 226, 228, 230, 232, 234, 236, 238, 240, 242, 244, 246, 250, 254, 256, 262, 264, 266, 270, 271, 273, 275, 277, 279, 283, 285, 288, 290, 292, 294, 296, 298, 300, and 302 were subjected to the apple scab control test. All of the compounds showed at least 75% control value.

TEST EXAMPLE 2

(Cucumber Gray Mold Control Test)

Each emulstion prepared in accordance with the formulation of the Formulation Example was diluted with water to contain 125 ppm of the active ingredient. The dilution was sprayed to cucumber seedlings (variety "*Cucumis sativus*", cotyledon stage) grown in clay pots. The leaves were air-dried at room temperature. Then, a conidia suspension of cucumber gray mold fungus (*Botrytis cinerea*) was dropped on the cucumber seedlings to inoculate the cucumber seedlings therewith, and then the cucumber seedlings were held in a dark room at 20° C. under a high humidity for 4 days. Control effects were examined by comparing lesion appearance state on leaves of the cucumber seedlings with that of untreated cucumber seedlings in the same manner as Example 1.

Compounds represented by compound No. 2, 4, 6, 8, 10, 12, 14, 16, 17, 20, 22, 25, 27, 29, 30, 32, 34, 36, 38, 40, 42, 44, 46, 48, 50, 52, 54, 57, 59, 61, 63, 65, 72, 76, 78, 80, 82, 84, 86, 88, 89, 91, 93, 95, 99, 101, 103, 105, 107, 109, 110, 112, 114, 116, 118, 120, 122, 124, 126, 128, 130, 132, 134, 136, 138, 140, 142, 143, 145, 147, 149, 151, 153, 155, 157, 159, 161, 163, 165, 167, 169, 171, 173, 175, 177, 179, 181, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 273, 275, 277, 279, 281, 283, 285, 286, 288, 296, 298, 300, and 302 were subjected to the cucumber gray mold control test. All of the compounds showed at least 75% control value.

TEST EXAMPLE 3

(Wheat Powdery Mildew Control Test)

Each emulstion prepared in accordance with the formulation of the Formulation Example was diluted with water to contain 125 ppm of the active ingredient. The dilution was sprayed to wheat seedlings (variety "Chihoku", 1.0 to 1.2 leaf stage) grown in clay pots. The leaves were air-dried at room temperature. Then, conidia of wheat powdery mildew fungus (*Blumeria graminis* f. sp. *tritici*) was sprinkled on the wheat seedlings to inoculate the wheat seedlings therewith, and then the wheat seedlings were held in a greenhouse at 22 to 25° C. for 7 days. Control effects were examined by comparing lesion appearance state on the wheat leaves with that of untreated wheat leaves in the same manner as Example 1.

Compounds represented by compound No. 2, 6, 8, 10, 12, 16, 17, 20, 22, 25, 29, 30, 32, 34, 36, 40, 42, 44, 46, 50, 52, 57, 59, 61, 63, 65, 72, 82, 89, 93, 99, 101, 103, 105, 107, 109, 110, 112, 114, 120, 122, 126, 128, 130, 132, 134, 136, 138, 140, 142, 143, 145, 147, 149, 151, 153, 155, 157, 159, 161, 163, 165, 167, 169, 171, 173, 175, 177, 179, 181, 184, 186, 188, 190, 192, 194, 196, 198, 200, 202, 204, 206, 208, 210, 212, 214, 216, 218, 220, 222, 224, 228, 230, 232, 234, 236, 238, 240, 242, 246, 248, 250, 252, 254, 256, 258, 260, 262, 264, 266, 268, 270, 271, 273, 275, 277, 279, 281, 283, 285, 286, 288, and 300 were subjected to the wheat powdery mildew control test. All of the compounds showed at least 75% control value.

TEST EXAMPLE 4

(Tomato Late Blight Control Test)

Each emulstion prepared in accordance with the formulation of the Formulation Example was diluted with water to contain 125 ppm of the active ingredient. The dilution was sprayed to tomato seedlings (variety "Regina", 4 to 5 leaf stage) grown in clay pots. The leaves were air-dried, and a zoosporangia suspension of Tomato late blight fungus (*Phytophthora infestans*) was sprayed on the tomato seedlings to inoculate the tomato seedlings therewith, and then the tomato seedlings were held in a thermostatic chamber (20° C.) under a high humidity with light and darkness being repeated every 12 hours for 4 days. The lesion appearance state on the leaves was compared with that of untreated leaves in the same manner as Example 1 to obtain the control value.

Compounds represented by compound No. 2, 6, 8, 10, 16, 20, 22, 25, 27, 29, 30, 32, 34, 36, 40, 42, 44, 52, 54, 57, 61, 76, 80, 82, 84, 86, 88, 89, 91, 93, 99, 101, 103, 105, 107, 109, 110, 112, 114, 116, 118, 120, 122, 124, 126, 128, 130, 132, 134, 136, 138, 140, 142, 143, 145, 147, 149, 151, 153, 155, 157, 159, 163, 165, 167, 169, 171, 173, 177, 179, 181, 184, 186, 188, 190, 192, 194, 196, 198, 200, 202, 204, 206, 208, 210, 212, 214, 216, 218, 220, 222, 224, 228, 230, 232, 234, 240, 242, 246, 248, 250, 252, 254, 256, 258, 260, 264, 266, 268, 270, 271, 273, 275, 277, 279, 281, 285, 288, 290, 292, 298, 300, and 302 were subjected to the tomato late blight control test. All of the compounds showed at least 75% control value.

TEST EXAMPLE 5

(Wheat Leaf Rust Control Test)

Each emulstion prepared in accordance with the formulation of the Formulation Example was diluted with water to contain 125 ppm of the active ingredient. The dilution was sprayed to wheat seedlings (variety "Norin 61", 1.0 to 1.2 leaf stage) grown in clay pots. The leaves were air-dried, uredospores of wheat leaf rust fungus (*Puccinia recondita*) were sprinkled thereon to inoculate the leaves therewith, and then the wheat seedlings were held in a greenhouse at 22 to 25° C. for 10 days. The lesion appearance state on the leaves was compared with that of untreated leaves in the same manner as Example 1 to obtain the control value.

Compounds represented by compound No. 6, 8, 10, 16, 20, 22, 25, 29, 32, 34, 40, 42, 48, 50, 52, 57, 59, 61, 72, 89, 103, 107, 109, 110, 112, 114, 120, 122, 124, 126, 128, 130, 136, 140, 142, 143, 145, 151, 153, 157, 163, 165, 167, 169, 171, 173, 177, 179, 184, 186, 188, 192, 194, 200, 204, 206, 216, 218, 220, 222, 228, 230, 232, 234, 236, 238, 240, 242, 244, 246, 248, 252, 254, 256, 258, 260, 262, 264, 266, 268, 270, 271, 273, 275, 277, 279, 281, 285, 286, 288, 292, 298, 300, and 302 were subjected to the wheat leaf rust control test. All of the compounds showed at least 75% control value.

INDUSTRIAL APPLICABILITY

The guanidine compound (the compound of formula [I] or the salt thereof) according to the present invention has excellent fungicidal activity, is safe to use, and can be industrially advantageously synthesized. The fungicide or the plant disease-controlling agent containing the guanidine compound as an active ingredient thereof is particularly excellent in controlling plant diseases such as apple scab, cucumber gray mold, wheat powdery mildew, tomato late blight, and wheat leaf rust.

The invention claimed is:

1. A compound of formula [I]:

[I]

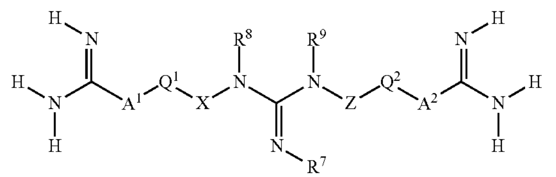

or a salt thereof, wherein:

$A^1$ represents heterocyclyl, arylene optionally substituted with $C_{1-6}$ alkyl or halogeno, or —N(H)—;

$A^2$ represents heterocyclyl, arylene optionally substituted with $C_{1-6}$ alkyl or halogeno, or —N(H)—;

$Q^1$ represents a single bond, phenylene, —CH═CH—, —C≡C—, —O—, —S —, —S(O)—, —$S(O)_2$—, or —N(H)—;

$Q^2$ represents a single bond, phenylene, —CH═CH—, —C≡C—, —O—, —S —,S(O)—, —$S(O)_2$—, or —N(H)—;

X represents alkylene, alkenylene, alkynylene, -$T^a$-O-$T^b$, -$T^a$-S-$T^b$, or -$T^a$-N(H)-$T^b$-;

Z represents alkylene, alkenylene, alkynylene, -$T^a$-O-$T^b$, -$T^a$-S-$T^b$, or -$T^a$-N(H)-$T^b$-;

$T^a$ represents a single bond or alkylene optionally substituted with $C_{1-6}$ alkyl, halogeno, or oxo;

$T^b$ represents a single bond or alkylene optionally substituted with $C_{1-6}$ alkyl, halogeno, or oxo;

$R^7$ represents hydrogen or hydrocarbon;

$R^8$ represents hydrogen or hydrocarbon; and $R^9$ represents hydrogen or hydrocarbon; or $R^8$ and $R^9$, bonded together, form a divalent organic group; or $R^8$ and a substituent on X, bonded together, form a divalent organic group.

2. A fungicide comprising, as an active ingredient thereof, at least one selected from a compound of formula [I]:

[I]

or a salt thereof, wherein:

$A^1$ represents heterocyclyl, arylene optionally substituted with $C_{1-6}$ alkyl or halogeno, or —N(H)—;

$A^2$ represents heterocyclyl, arylene optionally substituted with $C_{1-6}$ alkyl or halogeno, or —N(H)—;

$Q^1$ represents a single bond, phenylene, —CH═CH—, —C≡C—, —O—, —S —, —S(O)—, —$S(O)_2$—, or —N(H)—;

$Q^2$ represents a single bond, phenylene, —CH═CH—, —C≡C—, —O—, —S —,S(O)—, —$S(O)_2$—, or —N(H)—;

X represents alkylene, alkenylene, alkynylene, -$T^a$-O-$T^b$, -$T^a$-S-$T^b$, or -$T^a$-N(H)-$T^b$-;

Z represents alkylene, alkenylene, alkynylene, -$T^a$-O-$T^b$, -$T^a$-S-$T^b$, or -$T^a$-N(H)-$T^b$-;

$T^a$ represents a single bond or alkylene optionally substituted with $C_{1-6}$ alkyl, halogeno, or oxo;

$T^b$ represents a single bond or alkylene optionally substituted with $C_{1-6}$ alkyl, halogeno, or oxo;

$R^7$ represents hydrogen or hydrocarbon;

$R^8$ represents hydrogen or hydrocarbon; and $R^9$ represents hydrogen or hydrocarbon; or $R^8$ and $R^9$, bonded together, form a divalent organic group; or $R^8$ and a substituent on X, bonded together, form a divalent organic group.

3. A plant disease-controlling agent comprising, as an active ingredient thereof, at least one selected from a compound of formula [I]:

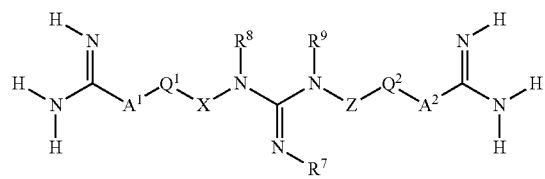

[I]

or a salt thereof, wherein:

$A^1$ represents heterocyclyl, arylene optionally substituted with $C_{1-6}$ alkyl or halogeno, or —N(H)—;

$A^2$ represents heterocyclyl, arylene optionally substituted with $C_{1-6}$ alkyl or halogeno, or —N(H)—;

$Q^1$ represents a single bond, phenylene, —CH=CH—, —C≡C—, —O—, —S—, —S(O)—, —S(O)$_2$—, or —N(H)—;

$Q^2$ represents a single bond, phenylene, —CH=CH—, —C≡C—, —O—, —S—, S(O)—, —S(O)$_2$—, or —N(H)—;

X represents alkylene, alkenylene, alkynylene, -$T^a$-O-$T^b$, -$T^a$-S-$T^b$, or -$T^a$-N(H)-$T^b$-;

Z represents alkylene, alkenylene, alkynylene, -$T^a$-O-$T^b$, -$T^a$-S-$T^b$, or -$T^a$-N(H)-$T^b$-;

$T^a$ represents a single bond or alkylene optionally substituted with $C_{1-6}$ alkyl, halogeno, or oxo;

$T^b$ represents a single bond or alkylene optionally substituted with $C_{1-6}$ alkyl, halogeno, or oxo;

$R^7$ represents hydrogen or hydrocarbon;

$R^8$ represents hydrogen or hydrocarbon; and $R^9$ represents hydrogen or hydrocarbon; or $R^8$ and $R^9$, bonded together, form a divalent organic group; or $R^8$ and a substituent on X, bonded together, form a divalent organic group.

* * * * *